| (12) | United States Patent | (10) Patent No.: | US 7,842,291 B1 |
|---|---|---|---|
| | Ruben et al. | (45) Date of Patent: | Nov. 30, 2010 |

(54) METHODS AND COMPOSITIONS FOR DIAGNOSING AND TREATING DISEASES

(75) Inventors: Steve Ruben, Brookeville, MD (US); Paul A. Moore, North Bethesda, MD (US); Tao He, North Potomac, MD (US); Candy N. Lee, Bethesda, MD (US); Karen Van Orden, Gaithersburg, MD (US); Charles E. Birse, North Potomac, MD (US); Mehdi Mesri, North Potomac, MD (US); Elizabeth G. Joseloff, Silver Spring, MD (US)

(73) Assignee: Celera Corporation, Alameda, CA (US)

( * ) Notice: Subject to any disclaimer, the term of this patent is extended or adjusted under 35 U.S.C. 154(b) by 661 days.

(21) Appl. No.: 11/802,321

(22) Filed: May 22, 2007

Related U.S. Application Data

(60) Provisional application No. 60/835,419, filed on Aug. 4, 2006, provisional application No. 60/833,471, filed on Jul. 27, 2006, provisional application No. 60/833,470, filed on Jul. 27, 2006, provisional application No. 60/819,611, filed on Jul. 11, 2006, provisional application No. 60/819,612, filed on Jul. 11, 2006, provisional application No. 60/819,616, filed on Jul. 11, 2006, provisional application No. 60/810,179, filed on Jun. 2, 2006, provisional application No. 60/810,180, filed on Jun. 2, 2006, provisional application No. 60/810,183, filed on Jun. 2, 2006, provisional application No. 60/802,151, filed on May 22, 2006, provisional application No. 60/802,153, filed on May 22, 2006, provisional application No. 60/802,152, filed on May 22, 2006.

(51) Int. Cl.
*A16K 39/395* (2006.01)
(52) U.S. Cl. ................................. 424/130.1; 530/387.1
(58) Field of Classification Search ....................... None
See application file for complete search history.

(56) References Cited

U.S. PATENT DOCUMENTS

2006/0275794 A1* 12/2006 Carrino et al. ................. 435/6

FOREIGN PATENT DOCUMENTS

| WO | 00/26245 A2 | 5/2000 |
| WO | 03/024392 A2 | 3/2003 |

* cited by examiner

*Primary Examiner*—Larry R. Helms
*Assistant Examiner*—Meera Natarajan

(57) ABSTRACT

Methods and compositions are provided for assessing, treating, and preventing diseases, especially cancer, using cancer-associated targets (CAT). Methods and compositions are also provided for determining or predicting the effectiveness of a treatment for these diseases or for selecting a treatment, using CAT. Methods and compositions are further provided for modulating cell function using CAT. Also provided are compositions that modulate CAT (e.g., antagonists or agonists), such as antibodies, proteins, small molecule compounds, and nucleic acid agents (e.g., RNAi and antisense agents), as well as pharmaceutical compositions thereof. Further provided are methods of screening for agents that modulate CAT, and agents identified by these screening methods.

4 Claims, 92 Drawing Sheets

FIGURE 1
TMPRSS4 is Over-Expressed in Multiple Tumor Types

| | Tumor Expression (% tumors) Δ+2 |
|---|---|
| Kidney | 100% |
| Brain, Glioblastoma | 85% |
| Lung, Adenocarcinoma | 70% |
| Melanoma, Node | 60% |
| Liver | 50% |
| Pancreas | 43% |
| Lung, Squamous | 40% |
| Pancreas, Metastatic | 33% |
| Colon | 20% |

Knockdown of TMPRSS4 (0212) mRNA Inhibits Proliferation in Multiple Cancer Cells

* Reproducible 35% (except 25% for Calu-1) or greater decrease in proliferation

Knockdown of TMPRSS4 (0212) mRNA Inhibits Proliferation in H1299 Lung Cancer Cells

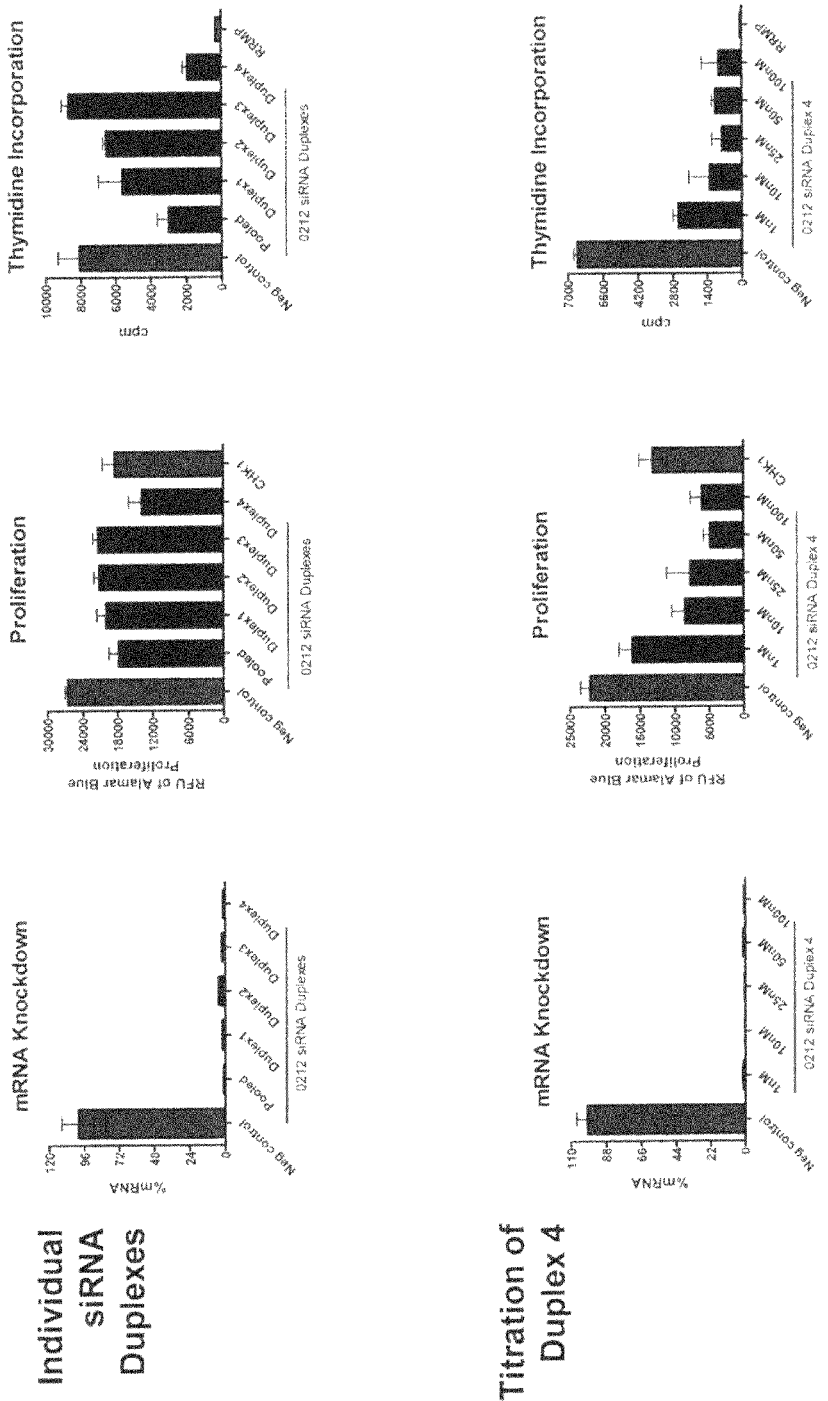

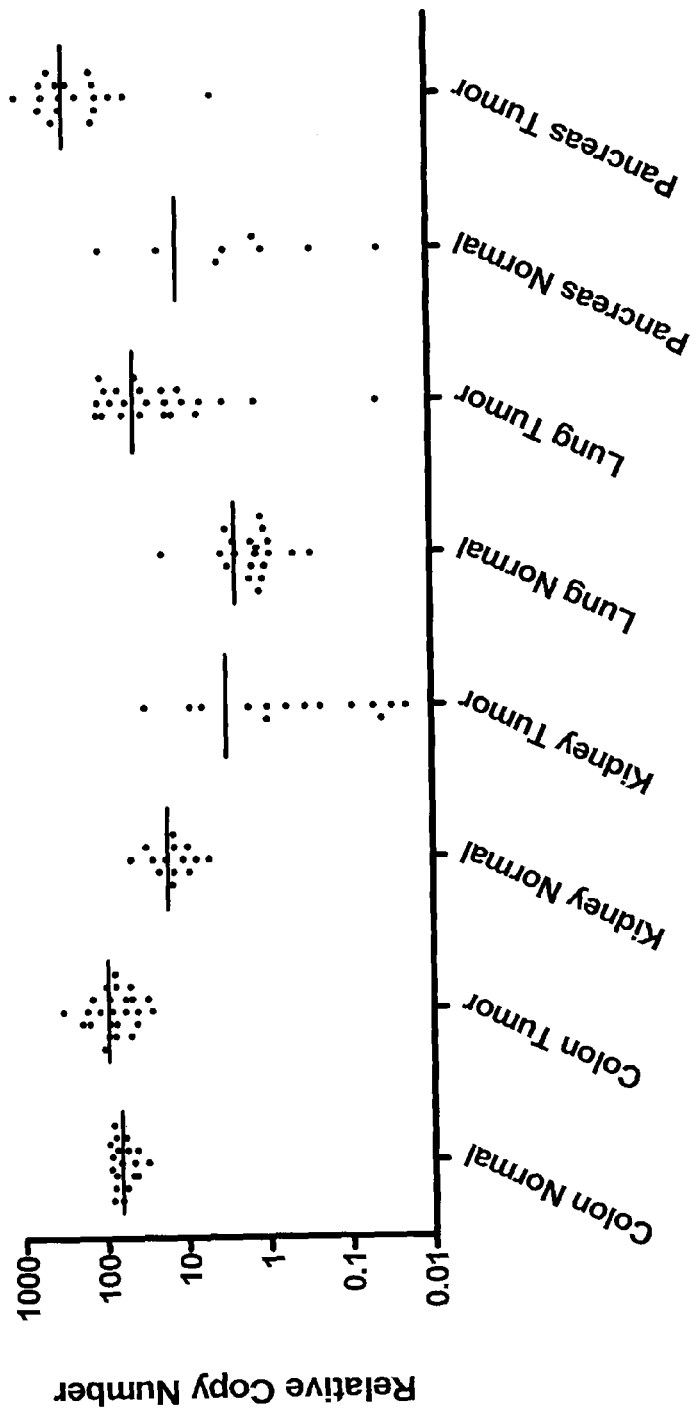

FIGURE 6
mRNA sequence of TMPRSS4

AATCAAGCTGCCCAAAGTCCCCCAATCACTCCTGGAATACACAGAGAGAGGCAGCAGCTTGCTCAGCGGACAAGGATGCTGG
GCGTGAGGGACCAAGGCCTGCCCTGCCACTGCCCTCGGGCCTCCTCCAGCAGGACCAGTCCTGACCAGGGACTTCTGACCTGCTGGCCAGCC
AGGACCTGTGTGGGGAGGCCCTCCTGCTGCCTGGGGTGACAATCTCAGCTCCAGCTCAGCGGAGACCGGGAGGATCACA
GAGCCAGCATGTTACAGGATCCTGACAGTGATCAACCTCTGAACAGCCTCGATGTCAAACCCTGCGCAAACCCGTATCCC
CATGGAGACCCTTCAGAAAGGTGGGGATCCCCATCATCATAGCACTACTGAGCCTGGCGAGTATCATCATTGTGTTGTCCTCA
TCAAGGTGATTCTGGATAAATATACTTCCTCTGCGGGCAGCCTCTCAAGAGCTTCCCAAGGGCCTGCAGTGGCAGTCCGCCTCTC
GCTGGACTGTCCCTTGGGGAGGACGAGGAGCACTGTGTCAACAGGCACTCGGCCACACAGCAGCAAACCCACTTTCAGAGCTGTGGGCCCCTGT
CAAGGACCGATCACACTGCAGGTGCTGGACTCGGCCACAGCAGCAAACCCACTTTCAGAGCTGTGGGCCCCAGACCAGGATC
CTCGCTGAGACAGCCTGTAGGCAGATGGGCTACAGAGAGCTTCGCATGCGGAACTCAAGTGGTGGGTGGGGAGGAGCCCTCTGTGGATTCTTG
TGGATGTTGTTGAAATCACAGAAACAGCAGGAGCTTGAAGACCCTCTGTGGAAGAGCCTGAAGACCACTGTGACCCCCACTGGTCCTCACGGC
GCCTTGGCAGGTCAGCATCCAGTACGACAAACAGCACGTCTGAGGGAGCATCCTGAGACTCAGACAACTGGGCAGCTTCCCATCC
AGCCACTGCTTCAGGAAACATACCGATGTTCAACTGGAAGGTCGGGCAGGCTCAGACAACATGACATCGCCCTCATGAAGCTGCAGT
CTGGGCTGTGGGCCAAGATCATCATCAGTACCCCAAAGACAATGAGGACTCACTCCAGGCACCCACTCTGGA
CCCACTCCACTTTCTCAGGCACGTCAGGCAGAATGGAGGGAAGAGTGTCTGACATACTGCTGCAGGCGTCAGTCCCGGAAGGGGTGT
TCATTGGATGGGCTTTACGAACGATGCAATGCTACCAGGGCCCCTGATGTACCAAGTCTCGACCAGTGCCATGTGGCATGTGTTAGCTGGGG
CACACGGTGCAATGCCAGGGTGACAGTGGTGGGCCCAGAGTATACACCAAGGTCTCAACTTCTCAACTGGATCTACAATGTCTGGAAG
GGACACCTGCGCAGGGTGACAGTGGTGGGCCCAGAGTATACACCAAGGTCTCAACTTCTCAACTGGATCTACAATGTCTGGAAG
CTATGGCTGCGGGGGGCGAGCCCGAGCACCCAGAGCCCCTTTGCAGTGCTGCCCCTTTGCAGCTGAGGCCGCTTCCTGCCCATCTGCTCCCCAGCGCCTTCTTGGAGCGCATTCTTGGAGCAGCAAAGGGCCTCAATT
GCTGAGCTGTAATGCTGCCCCTTTGGGTACACCCCTGCCCACCTGGAGGCACACTTGGTGCTGCCAGCAT
CAGACACAGAAGAGTCTCGCAGACCCTCGCAGCCCACTGAACAAGGCTCTGCCCAGAGGGCCCAGAAGTCAGCAGCCCTAGCTGGGGCACAACTTCCCCACACTACTGAATGG
CCCAGGGAGAGACACACCCGAGCAAGCCCACTGAACAAGGCTCTGGGCTGGAGAGGAAACCAGTTGTAATATAAATGCCCTACTGTTGGTATGACTACCGTTACCTA
AAGCAGGCTGTCTCTTGTAAAGCCTACTAGAGCAAGAAACCAGTTGTAATATAAATGCCCTACTGTTGGTATGACTACCGTTACCTA
ACCATCCCCAAGCCTACTAGAGCAAGAAACCAGTTGTAATATAAATGCCCTACTGTTGGTATGACTACCGTTACCTA
CTGTTGTCATTGTTATTACAGCTATGCCCACTATATTATTAAAGAGCTGTAACATCTCTGAAAAAAAAAAAAAAA (SEQ ID NO:76)

Bold underline indicates siRNA target region

FIGURE 7
SLC5A6 is Overexpressed in Multiple Tumor Types

|  | Overexpression (% tumors) | |
|---|---|---|
|  | Δ+1 | Δ+2 |
| Renal | 100 | 100 |
| Breast | 90 | 90 |
| Lung (Squamous) | 70 | 70 |
| Liver | 63 | 63 |
| Lung (Non-Squamous) | 60 | 60 |
| Met. Pancreas | 50 | 50 |
| Colon | 30 | 30 |
| Ovary | 20 | 20 |

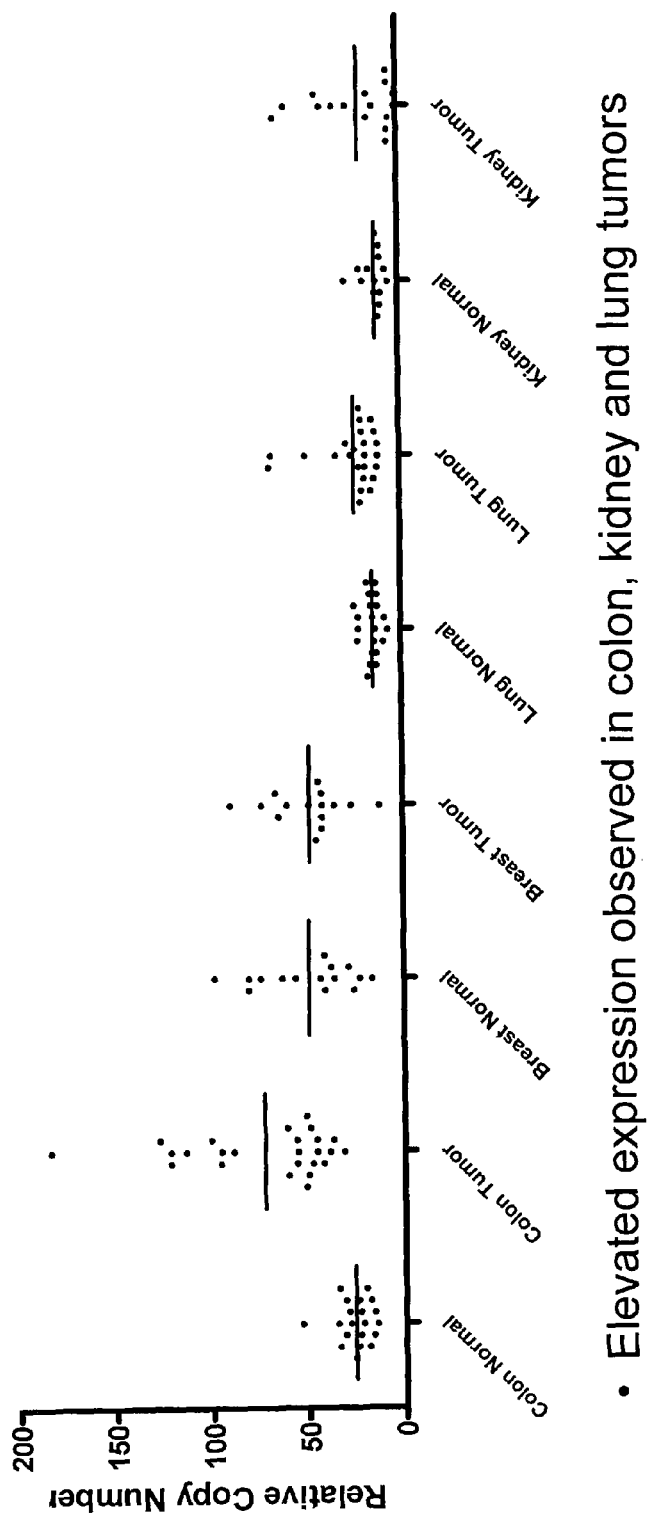

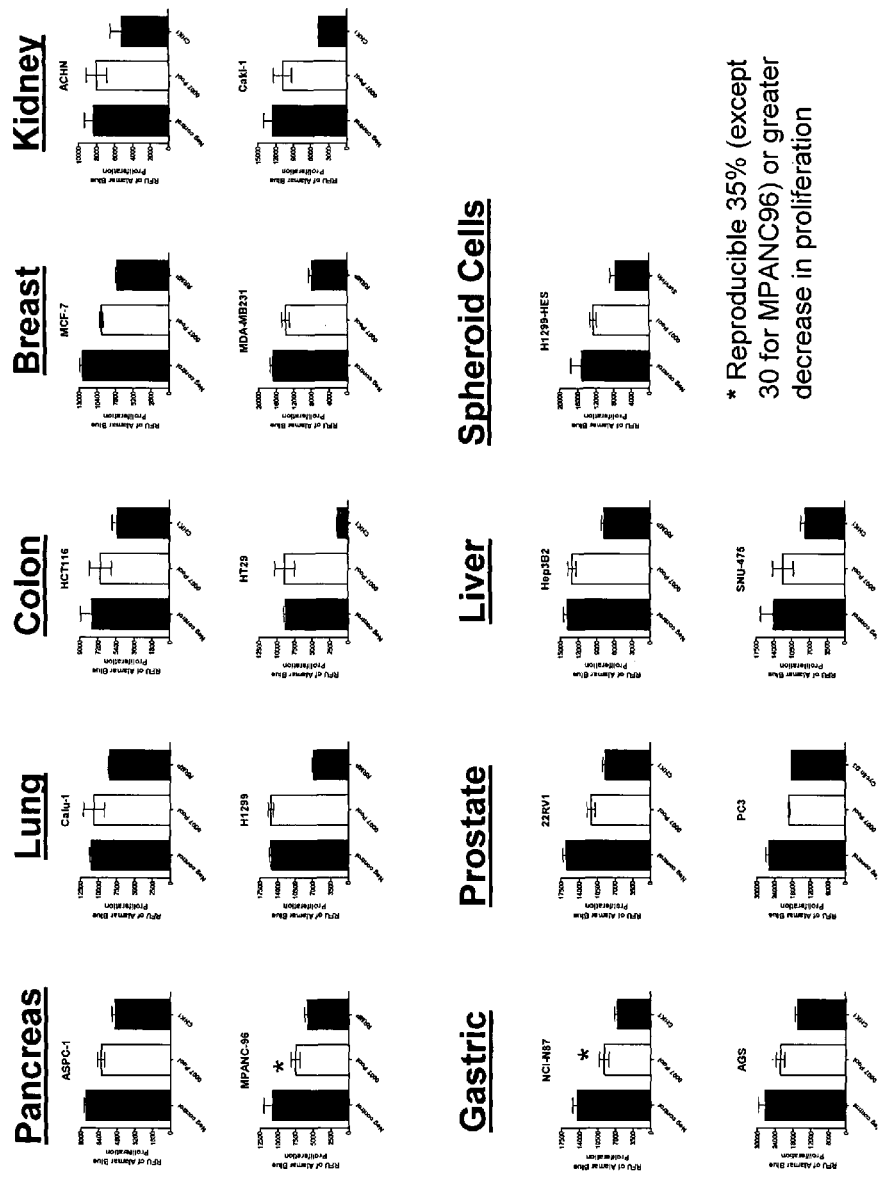

FIGURE 10
mRNA sequence of SLC5A6

GCGCCCTAGCCCTCTTTCGGGGATACTGGCCGACCCCTCTTCCTTTCCCCTTTAGTGAAGGCCTCCCCGTCGCGCGGCTTCCCGGAGCCGACTGCAGACT
CCCTCAGCCCGGTGTTCCCCGGTCCGGAGACGCCGAGGTCGCGGCGTTCGCAGAAACTCGGGCCCCTCAGAAAGGGAGCGATGTTGATCTCAGGA
AGCACAAAGGGACCTTCCTAGCTCTGACTGAACCACGGAGCTCACCCTGGAGACTGTGAGACTGTGGCTGGAAGCCAGATTGTAG
CCACACATCCGCCCCTCGGGCACAAGCTGGGCATGTGTCCCATCACAGAGACAGTGAGGATATGAGTGTTGCTCTCTGCCATTGGCCTCTACCCTCT
TCCCAACCTCGGCTGGGCGGCCATGTCGTGAGCTGCTGGCGACCGCCAATATTGGTTCCTGGGCTGCTGATACCTGCACACATCTTCAT
TGTCGTGGCCATCCTGGGTGTGCCGCTGACATCCTGCATCTACCAGTGCCTATGGCCTATGGAGCTGCCGTATGAGTCAGAGATCTACCGATTTGGGACCAGTTGTGCTCTATGCTCCGTCATGGGACTGCCTATGAGTCAGGTACCTGGAGCTTCGATTCAATAAAACTGTGGAACTGTGACCTTCATCTTTCAGATGGT
CCCCGTTTTCTACCGCTGAGTTGTGCTCTATGCTCCGTCATGGGACTGCCTATGAGTCAGGTACCTGGAGCTTCGATTCAATAAAACTGTGGAACTGTGACCTTCATCTTTCAGATGGT
TACAGCTCTGGGCTGAGGCCGTCATCTGAAGCGCATCTGGACAGATGTTCCAGACGCCATCTGGTTCAGTGCAGGATCCAGACCCTTTGTGCGACGAGTCAGCCAAGGTG
GCGCGTTTGGGCGTGTGGGGCATCCTTCATGATGCTCCTCTCCTGATGGGCTGGGCATGGCCTCAGCTGTGCCTCTCTCCATGAGGCTCAGGCA
TTCGGGGGGTGTCTCATGATGCTCCTCTTAATACGGGGTGAACCAGGCTCAGGTGCAGCCTCCAGTGCCAGTGCCAGTGCCTCAGGCA
CAGTGTTCCCCTTCCCCAGTGCTGTCCCTGTACTTGTGATGGCCTATATTCCCCAGATGGACCCAGCAATCAGCATCTTGGCCTCTGATTGGCATCGGGGACCGCTGC
GCCCAGACCAGTGCGTCGTCGTACTTGTGATGGCCTATATTCCCCAGATGGACCCAGCAATCAGCATCTTGGCCTCTGATTGGCATCGGGGAGC
ATCCTCTGCTTTAATTCATTGCAACTGTTACGATGGCTATTGTTCTAGAATGGCTTCCATGTCTTCCACCACCCCAATCTAACCGTTGCCACTGTGACCACACTGATGCCCTT
CTTGGCTATGGGCTGCTTGTCTGCTGAATGTCTTCCATGTCTTCCACCACCCCAATCTAACCGTTGCCACTGTGACCACACTGATGCCCTT
TGGGACTCTCTGCCTTGGAATGCCAACGCTCCAGCATGCCAAGCCACAGAGGCTGCAGGATCAGGGCTACTGTTGCCACTGTTGGATTGCACCAAGTGATTGTGTGGGCCTGATTGTCAG
ATCGTGACCAGCAGCATGGCCTCAGCATGCCAAGGCACAGAGGCTGCAGGATCAGGGCTACTGTTGCCACTGTTGGATTGCACCAAGTGATTGTGTGGGCCTGATTGTCAG
TACTACTCACTGGGAGAATGCAGGACCAGGCCGGTCCCTGAACCCTGCAAACATTACCCAGTGCCAAAGCTCCTGTCCCTCTTCCGTTGTCCTGTCAGAAGCGGCTCC
ACTGCAGAGCTACGGCCAGGAGGTCACGTGACCTCCAGGAGACCTCCCTGTATGTTGACTCAGGAGCCCCTGAAATGGTGTGCTCCTCACTGTCCAGGCCATAGC
CAGAGGCCACCACCCTAGTACAGGAGCAGGGCTACATCCTCAAGCATGTGAGGAGAGGCTGTTGGGTCGCGGATGATCTGCAGGAGCAGGACCTTGTTCTGAGAGGTTCTTGCCTG
CAGGAGAAGCTGTCACATCTCAAGCATGTGAAGGCTGTTGGGTCGCGGATGATCTGCAGGAGCAGGACCTTGTTCTGAGAGGTTCTTGCCTG
CAGGAGAAGCTGTCACATCTCAAGCATGTGAAGGCTGCCAATCTGTTTTCTCGCCTTGCCAATATGGCTCTGATTCAACATAGCCATAGCCAAGATAATGGCTCGTAGAAACAGCACTCTGTTATAATTGCCCC
AGGGATGGAAGTGCATCGGGAACTGACTCTGGAAAAAGATAATAAACTCATTTATCTGCTCCATGCTTCCCCTGTAGTCCCGTAGTCTGAAGAGGAGGTTTTGGTCTGGGAAATAGAAGATCCATTTG
AGGGCCTGATTGTCTGTGAGCAACTCAAGCACGTTTCCACCTCAGTGTCCAATCCATTTTATCTGTCTCCATCCTGACTGTCCTGACTGTCCAGAAACCAGGCCATG
TCTTGTGTAGAGCACTGTGGACAAGCACGTTTCCACCTCAGTGTCCAATCCATTTTATCTGTCTCCATCCTGACTGTCCTGACTGTCCAGAAACCAGGCCATG
ACCAGGTCCACTGTTCCTGGGGAATAAAAACTACCATTGGACCTAAAAAAAAAAAAAAAA (SEQ ID NO:77)
CATTATCTTTGTTCCTGGGGAATAAAAACTACCATTGGACCTAAAAAAAAAAAAAAAA (SEQ ID NO:77)

Bold underline indicates siRNA target region

FIGURE 11
ITGB6 is Over-expressed in Multiple Tumor Types, as indicated by IHC

| | Overexpression Δ+1 (% tumors) | Overexpression Δ+2 (% tumors) |
|---|---|---|
| Pancreas (metastatic) | 67 | 67 |
| Pharyngeal | 60 | 60 |
| Pancreas | 57 | 57 |
| Lung (NSC) | 50 | 50 |
| Skin, Melanoma | 40 | 40 |
| Melanoma, Lymph node | 40 | 40 |
| Liver | 38 | 38 |
| Breast | 30 | 30 |
| Lung, Squamous | 40 | 10 |
| Esophageal | 40 | - |

Knockdown of ITGB6 (0213) mRNA Induces Apoptosis in Multiple Cancer Cells

* Reproducible 50% or greater increase in apoptosis

Knockdown of ITGB6 (0213) mRNA Inhibits Proliferation and Induces Apoptosis in MPANC96 Pancreatic Cancer Cells Knockdown of ITGB6 (0213) mRNA Inhibits Proliferation and Induces Apoptosis in HT29 Colon Cancer Cells Knockdown of ITGB6 (0213) mRNA Induces Apoptosis in Caki-1 Kidney Cancer Cells

Knockdown of ITGB6 (0213) mRNA Inhibits Proliferation in H1299 Lung Cancer Cells Knockdown of ITGB6 (0213) mRNA Inhibits Proliferation in H1299-HES Spheroid Cancer Cells Knockdown of ITGB6 (0213) mRNA Inhibits Proliferation in NCI-N87 Gastric Cancer Cells Knockdown of ITGB6 (0213) mRNA Inhibits Proliferation in HUVEC Endothelial Cells

Knockdown of ITGB6 (0213) mRNA Inhibits Proliferation and Induces Apoptosis in HMVEC Endothelial Cells

Knockdown of ITGB6 (0213) mRNA in Combination with Gemzar Increases Apoptosis in Calu-1 Lung Cancer Cells

ITGB6 mRNA in Pancreatic Tumor

Knockdown of ITGB63 Inhibits Proliferation in H1299 Lung Cancer cells (Normalized over 3 Experiments)

FIGURE 27
GLG1 is Overexpressed in Multiple Tumor Types

| | Overexpression (% tumors) | |
|---|---|---|
| | Δ+1 | Δ+2 |
| Breast | 30% | 10% |
| Bladder | 20% | 10% |
| Glioblastoma | 17% | 0 |
| Colon | 10% | 0 |
| Lung (Adenocarcinoma) | 50% | 10% |
| Lung (Squamous) | 30% | 30% |
| Ovary | 10% | 0 |
| Melanoma | 80% | 80% |
| Melanoma, Lymph Nodes | 50% | 50% |
| Non-Hodgkin's Lymphoma | 17% | 17% |
| Pharyngeal | 10% | 0 |
| Pancreas | 43% | 43% |

CONFIDENTIAL

GLG1 mRNA Expression Analysis in Multiple Tumor Tissues

Knockdown of GLG1 (0041) mRNA Inhibits Proliferation in SNU-475 Kidney Cancer Cells

FIGURE 31 mRNA sequence of GLG1

Ggtcgagctcgcgcggactcaagatggcggcgtgtgacgtgtacggagagatgttccgcttgtcgcgcgctgcatctgctcgtcgtattcgcggccggggccgagaaactcccgcggccagggcgtccacgccagggcca
gggtcccgggccaacctttggtcctctgtagggcggcaggccgggagcgcggccgggagctcgcccgggggcgggccggagttcagcagctgccccagcttcagcagcagcgtcagcagcagcagcagcagcctcagccg
ccgagccgcctttccggcgggtggcctccgccccgggggaggagcgggggctgtgggggctgaaggcgcgaggaagagtccgcaggggagacgtgaccccgtgccctaagcacacctggagcaacaa
ccggcggtgctgagtgcctgcaggatgtgaggagctgaaatgaaaattttcagactgcaatcattgttgtggaattaagctgaactaactacgatcccaaatttgaatctgtgccagagaggttgcaaatctactata
acagagattaagaaatgtctgatgaaccggttgaaagttcctgcttggtggatcaccgaggcaacatcactgagtatcagttcagtgcaccagatgaccgccatcattttagtgattaccgtttaatctg
tggcttcatggatgactgcaaaaatgcaacaactctgaaatggcagttctcggggtgctgagctgtcatcggtgagccatcttacttagaccggcatttatattctgccccagatgcgggtggtatcatcttggagaaggcctggtgaaggaagcagagaaccc
aagattcaagttttctgaactctgcaagaaagccatttcccggtgctgaactcatcgaatgatgcaaaaagtgtcgagaagcacttacaacccgccaaaagctgattgcccaggattataaagttcagttactttcgccaaatcgtaaaagtcgggagaaataac
gtaaagtgcctcttaaccataaattgaagaatccatgaatgtgcgagagcacttacaacccgccaaaagctgattgcccaggattataaagttcagttattcattggccaaatcgtaaaagtcagttaccgacgcatgttgatggaa
gactttcctgagccctgagatcatcctaagctgtcggggggagattgaacaccattgttccggattacatacatgaaaagggcgacctacactgtgatgaaagtaagttcgagggggagagaagggggaacctggaatgaactgccag
caggcgctcaaacactgattcaggagactgacccgtgcagattaccgcattgacgagttcatctccggattggaagctgaacgtcctgatcctagagcgcaaggtgagagagcgtctcgtcttgcacaccaccggttgga
acattataccagagaagatgggagactgtgaacaccgtctctgttatacagacacgctcaggaaacagggaacaagggaggctcccaggggagtgccgagttccaaggatccaaaggatctcaccagcgtgccatggatgtc
aagctgatctgccctccaggataagtgccgattgatctggaaatggcagtgagaaaaacagagaactgaacaggagcagcaggaagcagccccgctcggaaggagttgcttgagtgtgtagatgttgcaacct
cactgagttagaatcagaggatattcaaatagaaagccttgctgatgagcctgagagctgcagatgaaggatttcggtttctacaagtttaaaatgcctgcaaggagcgactgttgaagcttgccccaaacataaaaagaaggtggacg
agaaggacatgaacagaagtgtgccatcggagttcaccttccagctgggtcgagaagagacaagcagcaaggagcacaggtgtcctgaagtgccaggcaagcccctcggtgtggaggagtggagaatgacggaggaacatccgcttgagccagatcctatac
tggtgatctgccctgagccaccgtccaatgacactctgcaggaaccgccaaggagcacactctgttccgctgcaatgcagcctcagattacgcctgcaatatgactccgattatgaatgtctgaaagaaacaagagaacagcagcaccaccgaggagagatgt
gaagctgcaagagtgacatcaaaacttctgccgtgcaatatcttgcctgcaggttgagcggctgcagatgcctcagatctgcaggagagttctccggaagcagattcaaaaccatttgcagtgcttgaagcaaataaaaacagtgaattgatgccaaatgcaaacaga
atgaccagagctagactacacccccatgaggtctcaagcagatgatgataaagaggttctccggaagcagattcaaaaccattctcacgtatcctaaattctgactaaggccaaggatgattcagaattaggacagtcat
tgataaccaagcccgatacccagaacacagattaccgcttaaaaccctgttaaaaccctgttgaaaggatcgaatcattatccaggagtccgccctgactaccgcctgatcctcagctccgctgactccgctcgcagagagatctcagtctagtg
ctcttgctgaagctgagatatgctgaccagcagcagcagcctgctcagactgtgaaggagttgcttcaaggtcaacctcttcaagatcaaacagaatgtgtaaaaagaagtgctaaacatgtgaaggagaacaaagcagacatctttggaccc
ggtactcatactgcttgcccggacattaaacaacactgcgcagccaccctgccgcgccaatgtctgtcatgaaggctgcatgaaggctggaagcatctctgctatgaaggcaggtggatcaccgcagcatccgcgctaagg
accggattgaatgttaatacgcagcaaaggtgcccagcagatggtctcctgatctggcaaggaagttctgagatgacaaagaatctgtaaaaggtttggtgtctcaggattgtgcctggagatggagcatcgtatcagtgggagcatcgtatattgttcctgattggcctgatg
tgtggacggatcaccaagccagtgaccagagctcaaggacaggctcaatacaggtcagagacaatgctataaaaaggtgaagagaaaaaaaaaaaaaaa (SEQ ID NO:78)
cccagacaagctcctttgtcctctacgtgagagggtggaagttacattaaaagatggaggattaaaaaaaaaaaaaaaaaaa

*Bold italics* indicates siRNA target region with biological activity
<u>Bold underlined</u> indicates siRNA target region with dose-dependent biological activity

FIGURE 32
KIAA0152 is Over-Expressed in Multiple Tumor Types, as indicated by IHC

| | Overexpression Δ+1 (% tumors) | Overexpression Δ+2 (% tumors) |
|---|---|---|
| Brain, Glioblastoma | 100 | 100 |
| Pancreas | 86 | 57 |
| Liver | 75 | 38 |
| Pancreas (Metastatic) | 66 | 33 |
| Bladder | 60 | 30 |
| Melanoma, Lymph node | 80 | 10 |
| Skin, Melanoma | 50 | 10 |
| Ovary | 50 | 0 |
| Lung, Squamous | 70 | 0 |
| Breast | 30 | 0 |
| Lung, NSC | 20 | 0 |
| Kidney | 10 | 0 |

KIAA0152 mRNA Expression Analysis in Multiple Tumor Tissues

Knockdown of KIAA0152 (0009) mRNA Inhibits Proliferation in Multiple Cancer Cells Knockdown of KIAA0152 (03-0009) mRNA Inhibits Proliferation in HCT116 Colon Cancer Cells Knockdown of KIAA0152 (03-0009) mRNA Inhibits Proliferation in H1299 Lung Cancer Cells Knockdown of KIAA0152 (03-0009) mRNA Inhibits Proliferation in MPANC96 Pancreatic Cancer Cells Knockdown of KIAA0152 (0009) mRNA Inhibits Proliferation in NCI-N87 Gastric Cancer Cells

Knockdown of KIAA0152 (0009) mRNA Inhibits Proliferation in SK-MEL-2 Melanoma Cancer Cells Knockdown of KIAA0152 (0009) mRNA Inhibits Proliferation in SNU-475 Liver Cancer Cells Knockdown of KIAA0152 Inhibits Proliferation in HCT116 Colon Cancer Cells
(Normalized over 3 Experiments)

Knockdown of KIAA0152 Inhibits Proliferation in H1299 Lung Cancer cells (Normalized over 3 Experiments)

KIAA0152 mRNA Expression Analysis in Multiple Tumor Tissues

KIAA0152 mRNA Expression Analysis in Multiple Tumor Tissues

KIAA0152 mRNA Expression in Colon Tumor Tissues

FIGURE 46
mRNA sequence of KIAA0152

[mRNA nucleotide sequence] (SEQ ID NO:79)

*Bold italics* indicates siRNA target region with biological activity

<u>Bold underlined</u> indicates siRNA target region with dose-dependent biological activity

FIGURE 47
Matriptase is Overexpressed in Multiple Tumor Types, as indicated by IHC

|  | Overexpression (% tumors) | |
| --- | --- | --- |
|  | Δ+1 | Δ+2 |
| Non-Hodgkin's Lymphoma (LN) | 83 | 83 |
| Colon | 70 | 70 |
| Ovary | 60 | 60 |
| Pancreas | 50 | 38 |
| Lung (Squamous) | 40 | 20 |

Matriptase mRNA Expression Analysis Multiple Tumor Tissues

- Elevated mRNA expression observed in pancreatic, lung and ovarian tumors

Knockdown of Matriptase Inhibits Proliferation in H1299 Lung Cancer cells (Normalized over 3 Experiments)

Knockdown of Matriptase Inhibits Proliferation in HCT116 Colon Cancer cells (Normalized over 3 Experiments)

Knockdown of Matriptase mRNA Inhibits Proliferation in Multiple Cancer Cells

* Reproducible 35% (except 25% for Calu-1) or greater decrease in proliferation

Knockdown of Matriptase (0010) mRNA Inhibits Proliferation in HCT116 Colon Cancer Cells

Knockdown of Matriptase (0010) mRNA Inhibits Proliferation in H1299 Lung Cancer Cells

Knockdown of Matriptase (0010) mRNA Inhibits Proliferation in ASPC-1 Pancreatic Cancer Cells

FIGURE 55
mRNA sequence of Matriptase

AGCGGAGCTGCAGCCGGAGAAAGAGGAAGAGAGAGACCGGAGGGCGAGGGCACCGGCTGGGCGCGCGGTCTGGGCGCGCCGGCCTGCCCGGAATCCCGCCG
CCTGCGCCCCGCGCCCCCGCGCCCCATGGAGCCCTGCGCGGGCCATGGGAGCCGGCCCCGCCCGCGGGGCGGCAGGGACGACGCCTGTGAGACCCGAGCGA
TCGGGCCCCGCAAGGGCGGAGGGGCCCGAAGGACTTCGGCCGCGGGGCGCCGGGGACTCAAGTACAACTCCCGGCACGAGAAAGTGAATGGCCTTGGAGAAGGCCGTGGAGTTCC
TGCCAGTCAACAACGTCAAGAAGGTGAAAAGCATGGCCGGGACGTGCGTGTCAGAGGTCTTCAATGGCTACAGCGAAGGATCACAAATGAGAATTTTGTGGATGCCTACGAGAACTCCAACT
TCCTGGTGTGGACCATTGCAGCCTTGTAAGCCTGGCCAGCAGCGGTGCTGTCAGAGGACGGCAAGGTGAAGGATGACGCGTCATGCGCTACTACTGCGTCGAGTTCTGAGTTCACAGCTGTACAGCGAAGCAGGTGCCGCGAGTCA
CCTTCAGCGAGGGCAGCGTCATCGCCTACTACTGCGTCGAGTTCTGCACCTCACCTCACCGACACGCCCGGGTGTGAGCCTCACCTTCTTCACCTGCCCCCGGCGCGGCCGTTCACCTTCACCCTCACCGCGGGTGTGAGCCTCAGTGCTGAGCCTCAGTGCTGAGCCTCACCTTCACCGCGGGTGTGAGCCTCAGTGCTGAGCCTCAGTGCTGTGGCCACACTTCCTTCCTGCCCCCGCGGGTGTGAGCCTCAGTGCTGAGCCTCACCGGGCATCCCGGCTTTGAGGCCACCTTCCCAACCTCTCGAGATGAACATTGAGGTGCCAACAACCAGCATGTGCAGCCTGGGTGCTTTCAAATTCTTCTACCTGCTGAGCCCGCCGAGCCCGGCG
AGCGGCGGCACTACCCACCCAAGGACTACGTGCCCAAGGACTGCGAGATCAACGGGGAGATCAACGGGAGATCAACGGGTCCCAGTGACCAACAGATCACAG
CCCAAGGCCACTGCCCCCAAGGACGACTACCGCTGAGACATCAACGGGGATCAACGGGTGCGTCGTCAGCTCAAGTGACCCATCCAAGTGACCCAGTGACCCATGTCCCGGGGCAGTTCACGTCGCCACCAGTTCACGTGCAAG
TGCCCTGCGGGACACCTGCCCCAAGGACTACGGCAGGGCTGGAGACACGGGGATCAACGCGGTCTACACGGACTGAGCTCAACTGAGCTCAACTGACACGATGACACGAAGCAACAGCAGCAACAGATGACCGATGAGCTCAAGCGATGACAGGAGCACCCCCTGGGGCAGTTCACGTCCAGGACCCAGCGCCCCCAGTTCACGTCGCCACCAGTTCACGTGCAAG
TTCGCTTCCACTCAGATACAGTCCTACACCGACACAGTCCTACACCGACACAGCGGCTTCTTAGCTGAGCCGACTGCACCGACCAGCACTGAGCTCAACTGAGCGACAACAGCGACGATGAGCTGAACAGCGACGACAGCGACGATGAGCTGAACAGCGACGACAGCAGTTCACGTCACGTGCAAG
CGGTGTATCCGGAAGGAGCTGCGCTGTGATGGCTGCGACAGTCTCGGGTCTCGCAGTGCAATGGGACAGTGCAATGGGACAGTGCAGTTGTCCGGCCCAGACCTTCAGTGTT
AACAAGTTCTGCAAGCCCCTCTCGGTCTCGCAGTGCAATGGGACAGTGCAATGGGACAGTGCAATGGGACAGTGAGCTCCGACAGCAGGGTGCAGTTGTCCGGCCCAGACCTTCAGTGTT
CCAATGGAAGTGCCTCTCGAAAAGCCAGCAGTGCAATGGGACAGTGCAATGGGACAGCAGTGCAATGGGACAGGAGAGCAGCGAGGCAGCCGACAGCAGCCGAGAGCTCCGACAGCAGGGTGCAGTTGTCCGGCCCAGACCTTCAGTGTT
ACACGCAGCCACTACCGCTGCCTCAATGGGCTCTGCTTGAGCAAGCAACCCCTGAGTGCAATGGGACAGTGCAATGGGACAGCAGAGCAGCGAGGCAGCCGACAGCAGCCGAGAGCTCCGACAGCAGCAGTTCACGTCACGTGCAGTGCAGTGCAGG
ACTGTGGCTGCGGTCATTCACGAGACAGGCTGCCTCATCTCTCCCAACTGGCTGTCTCTGCCGCACACTGGCTACATCGATGAGGACAGCAGAGCGCATCATCTCCCAACTGCCTGCCGGACGCCTCAATGACTCTTCACCTTCG
GCCACATCTGCGGTGTTGCACGAGACCAGAGCAGACAGGAGCTGGAGGTGCAGGGTACAGCTGCCGCCGCCCAGCAGTTCAGGTACTCAGGTACTCAGGACTACATCGATGAGGACAGCAGCGCATCATCTCCCAACTGGACG
GCCTTCCTGGGCTTGCACGAGACCAGAGCAGGAGCTGGAGGTGCAGGGTACAGCTGGCAGGTGCCAAAAGGGGTGATCTGCAAAAGGGTGATCTCAACCAGACCACCTGCGAGAACC
ACTATGACATCCGCTGCTGAGCTGGGACACCAGTATGGAGGCACTGGCGCGCGATCCTGCAAAAGGGTGATCTGCAAAAGGGTGATCTCAACCAGACCACCTGCGAGAACC
CCATCTGGGCTACGGCGATCACGCCGCATGATGTCGGTGGTGAGCTGGGGACCTCGCCGAGCTGAGCCAGGTGATTCCGGGGACCCCTGTCCAGCGTGACTG
GGCGATGGGGATCTTCCAGCCGCGGTATAGGGCCCCCAGAACATACACTGTCCAGAGAACCTCTCGCTTCCTCAGCCTCCAAAGTGGAG
GGAGGAGTAGAAACACTGGGTATAGGGAGGACAGCGGGGAACAGCAGCAGCAGCTTCGGGGCCTCCCTGAAGGTGGTGAGCTGAAGGTGCCGCGGGATCTGCGCAGCCCAAGCTGGGCCGAGGCGC
GTTTGTGCATATCTGCCTCTCTAAGGACAGCAGCAGCAGCAGTGACCTCCCTCAGTGAAGGTGGTGGGCTGCGGGATCTGGGCTGGGGCCC
TTGGGCCACGCTCTTGAGGAAGCCCAGGCTCGGAGGACCCTGGAAAAACAGAAGCCCTGGAAATTGTTTTACCAGGTGGACTTCAGTGTGT
ATTTGTGTAAATGAGTAAAACATTTTATTTCTTTTAAAAAAAAAAAAAAAAAA   (SEQ ID NO:80)

*Bold italics* indicates siRNA target region with biological activity
<u>Bold underlined</u> indicates siRNA target region with dose-dependent biological activity

FIGURE 56
AADACL1 is Over-Expressed in Multiple Tumor Types, as Indicated by IHC

| | Overexpression Δ+1 (% tumors) | Overexpression Δ+2 (% tumors) |
|---|---|---|
| Pancreas | 100% | 100% |
| Melanoma, lymph node | 80% | 80% |
| Melanoma | 80% | 80% |
| Metastatic Pancreas | 75% | 75% |
| Colon | 60% | 60% |
| NHL | 33% | 33% |

AADACL1 mRNA Expression Analysis in Pancreatic and Lung Tumor Tissues

FIGURE 58
Podocalyxin is Overexpressed in Multiple Tumor Types, as Indicated by IHC

|  | Overexpression Δ+1 (% tumors) | Overexpression Δ+2 (% tumors) |
|---|---|---|
| Pancreas | 40% | 40% |
| Ovary | 20% | 20% |
| Breast | 10% | 10% |
| Colon | 10% | 10% |

Knockdown of Podocalyxin (0112) mRNA Inhibits Proliferation in Lung Cancer Cells Knockdown of Podocalyxin (0112) mRNA Increases Apoptosis in Lung Cancer Cells

Knockdown of Podocalyxin (0112) mRNA Inhibits Proliferation and induces apoptosis in Lung Cancer Cells

Knockdown of Podocalyxin (0112) mRNA Inhibits Proliferation in H1299 Lung Cancer Cells

Knockdown of Podocalyxin (0112) mRNA Induces Apoptosis H1229 Lung Cancer Cells

Knockdown of Podocalyxin (O112) mRNA Induces Apoptosis in H358 Lung Cancer Cells Synergy of Podocalyxin (0112) siRNA with EGFR siRNA

FIGURE 66
mRNA sequence of Podocalyxin

*Bold italics* indicates siRNA target region with biological activity
Bold underlined indicates siRNA target region with dose-dependent biological activity

FIGURE 67
CD90 is Over-expressed in Multiple Tumor Types, as indicated by IHC

|  | Overexpression Δ+1 (% tumors) | Overexpression Δ+2 (% tumors) |
|---|---|---|
| Pancreas | 38 | 38 |
| Liver | 25 | 25 |
| Prostate | 20 | 20 |
| Skin, Melanoma | 20 | 20 |
| Gastric | 20 | 20 |
| Breast | 20 | 20 |
| Bladder | 20 | 20 |
| Non-Hodgkin's Lymphoma | 17 | 17 |

FIGURE 68
CD90 is Over-expressed in Multiple Tumor Types, as indicated by IHC

|  | Overexpression Δ+1 (% tumors) | Overexpression Δ+2 (% tumors) |
|---|---|---|
| Liver | 38 | 38 |
| Skin, Melanoma | 30 | - |
| Pancreas | 25 | 25 |
| Lung, NSC | 20 | 20 |
| Breast | 20 | 10 |
| Colon | 20 | - |
| Non-Hodgkin's Lymphoma | 17 | - |

CD90 mRNA Expression Analysis in Multiple Tumor Tissues

CD90 (0077) mRNA Expression Analysis in Kidney Tumor Tissue Endothelial Cells

CD90 mRNA Expression Analysis in Pancreas Tumor Tissues

CD90 mRNA Expression Analysis in Lung Tumor Tissues

Knockdown of CD90 (0077) mRNA Inhibits Proliferation in Multiple Cancer Cells

Knockdown of CD90 (0077) mRNA Inhibits Proliferation in Caki-1 Kidney Cancer Cells Knockdown of CD90 (0077) mRNA Inhibits Proliferation in SK-MEL-2 Melanoma Cancer Cells

Knockdown of CD90 (0077) mRNA Inhibits Proliferation in Caco-2 Colon Cancer Cells

FIGURE 77
mRNA sequence of CD90

GGAGGCTGCAGCAGCGGAAGACCCCAGTCCAGGACTGAGATCCAGAACCATGAACCTGGCCATCAG
CATCGCTCCTGCTAACAGTCTTGCAGGTCTCCGAGGGCAGAAGGTGACCAGCTAAGGCCTGCCTAGTGG
ACCAGAGCCTTCGTC*GACTGCCGCCATG**GAGAATA*CCAGCAGTTCACCCATCCAGTACGAGTTCAGCCTGACC
CGTGAGACAAAGAAGCACGTGCTCTTTGGCACTGTGGGGTGCCTGAGCACACATACCGCTCCCGAAC**CAACTT
CACCAGCAAATACAACATGAAGGTCCTCTACT**TATCGCGCTTCTACTAGCAAGGACGAGGCACCTACACGTGTG
CACTCCACCACTCTGGCCATTCCCCACCCATCTCCTCCCAGAACGTCACAGTGCT**CAGAGACAAACTGGTCAAG
TGT**GAGGGCATCAGCCTGCTGGCTCAGAACACCTCGTGGCTGCTGCTCCTCTCCCTCCTCCA
GGCCACGGATTTCATGTCCCTGTGACTGGTGGGGCCCATGGAGGAGACAGGAAGCCTCAAGTTCCAGTGCAGA
GATCCTACTTCTCTGAGTCAGTGCTGCATGCGATTATCTACCCACGTCTCCCGCGCCACCTCACCCTCTCCGCACAC
CCTCATCAGGAGTTCCAGTGCTCAGTGGTCCTTCTGTGTATACTGGTTTATGGTTTATCCTTCCTTTCTTT
CTCTGGCTGTCTTTTTGTACTTTTGTTCCAGAGCTGCTTCTGTCTGTTATTAGTTTATCCTTCCTTTCTTT
GAGAGTTCGTGAAGAGGAAGCCAGGATTGGGGACTTGCCCATCCTTGCCCATCGTGAGAGCATGTGAGGGTAGTGGGAT
GGTGGGTACCAGCCACTGCCGAGGGGTCCTAGCCGGACATGGTCTGTCCTGACAGAAACCTGGGAGAGACTTGGATGAGG
AGTGGTTGGGCTGTGCCTGGGCCCAGATGTGAGGGCACCACCAAGAATTTGTGGCCTACCTCTCGGCAGGCATC
TGCCTGAAGACCCAGATGTGAGGGCACCACCAAGAATTTGTGGCCACCTGCATGTGAGGGTCCCTCAGAGG
TCCAGCATTCTCAGCCACAAACCAAAAAAAATAAAAAGGCAGCCCTCTTACCACTGTAGTGGAAGGTTGGAGAAGGAGG
CCTTGGGCATGACCAGTGAAGATGCAGGTTTGACCAGGAAAGCAGCGTAGTGGAGCCCCTGCTGCCCCTGCCTCC
TAAGGATGAGGGTTCATCATCCCTGCTAAGGAAGCTAAAAGCATGCCCTGTGCCAAGCTCCCAAGAGCTTCCAGA
ACCACAGTGGAGAGGGCTACAAAGGAGGACAAGAACCCCTCTCAGCTGTCCCAGAGCTCCCAAGAGCTTCCAGA
GCTCTGACCCACAGCCTCAGGTGGGGTGGGGAGTCCAGGAGCTGCAGGGTTTGGCCACAGGGTTTGGCCCAAGTTTCTAAG
GGAGGCACTTCCTCCCCTCGCCCATCAGTGCCAAGGACTTCTGCAGCCTGAGGCAAGCCATGGAGTGAGACCCAGGAGCC
TGCCCCGCAGGCCTGCCTTCTGCGGAATGGCTTCCAACCCCCAGCCCCACCCGTGTTCTTCCTGTTCTGTGACTGTGTA
GGACACTTTCAGGAATGGCTTATGCCATCTCATTGAGGACAACAGGAAAACTGCACAATAAAACCAAGCCTGTGAATCTA
AAAAAAAAAAAAAAAAAAAAAA (SEQ ID NO:82)

*Bold italics* indicates siRNA target region with biological activity
<u>Bold underlined</u> indicates siRNA target region with dose-dependent biological activity

FIGURE 78
ISGF4 is Over-Expressed in
Multiple Tumor Types, as indicated by IHC

| | Overexpression (% tumors) | |
|---|---|---|
| | Δ+1 | Δ+2 |
| Kidney | 100 | 100 |
| Ovary | 80 | 80 |
| Bladder | 60 | 60 |
| Lung, NSC | 50 | 50 |
| Lung, Squamous | 50 | 50 |
| Liver | 50 | 50 |
| Stomach | 50 | 50 |
| Breast | 40 | 10 |
| Panc, Metastatic | 33 | 33 |
| Colon | 30 | 30 |
| Prostate | 20 | 20 |

ISGF4 mRNA Expression is Elevated in Breast Tumor Tissues

Knockdown of ISGF4 (0011) mRNA Inhibits Proliferation in Multiple Cancer Cells

* Reproducible 35% (except 25% for Calu-1 and H1299) or greater decrease in proliferation Knockdown of ISGF4 (0011) mRNA Inhibits Proliferation in NCI-N87 Gastric Cancer Cells Knockdown of ISGF4 (0011) mRNA Inhibits Proliferation in 22RV1 Prostate Cancer Cells

FIGURE 83
mRNA sequence of IGSF4

```
GACATGGGGAGTGTAGTGCTGCCAGAGCGGATCCCAGTGTGCGGGCGAGCGGGCAGCGCGGGGCGGGCCCTCCGGCTTCCGGCTTCTGTGTTGCTCTTC
TCCGCCGGGCACTGATCCCACAGAGTGTGGGCAGAGATCTGTTACGAAAGACGACGACAGTGACAGTGCCAGACCATCAGTTGCCAAGTCAATAA
GAGTGACGACTCTGTGATTCAGCTACTGAATCCCAACAGGCAGCAGCCATTATTTTCAGGGACTTCAGGGCCTTTGAAGGACAGCAGGTTCAGTTGCTGAATTTTCTA
GCAGTGAACTCAAAGTATCATTGACAAAGCTCTCAATTTCTGATGAAGATACTTTTGCCAGCTCTATACCGATCCCCACAGGAAAGTTACACCACCATCACA
GTCCTGGTCCCACCACGTAATCTGATGATCGAGATATCCAGAGACAACTGCGGTGGAAGGTGAAGAGTGTCAGAGAAGTACACTGTGACCAGTGATGCTGAAGGT
CACGACTATCAGGTGGTTCAAAGGAACACAGAGCTAAAAGGCAAATCGGAGGTGGAGCACCTGCCGGTCACTGGAAACCTGCAGACGCGTATCTAGAAGTACAGTATAAGCCAC
GCACAAGGAGGACGATGGGGTCCCAGTGATCTGGAGCACCTGCCGGTCACTGGAAACCTGCAGACGCGTATCTAGAAGTACAGTATAAGCCAC
AAGTGCACATTCAGATGACTTATCCTCTACAAGGCTTAACGCGTACTGTCGGGCCCAACCTGTTGAGTTAACATGTGAAGCCATCGGGAAGCCCCAGCTGTGATGGTAA
CTTGGGTGAGAGTCGATGAATGCTCAACACGTCGTGATGAAATGCTGGGGCCAACCTGTTGAGTTAACATGTGAAGCCATCGGGAAGCCCCAGCTGTGATGGTAA
AGCTTCAAACATAGTGGGGAAAGCTCACTGTGTATATCTATATGATCCCCCACAACCTAAACAAAACAGATAATGGTACATACCGCTGTGA
ACCACCACCATCTTACCATCATCACAGATTCCCGAGCAGGTGAAAGAAGGCTCAGGGCAGCATAAAGGTACATACTTCACTCATGAAGCCAAAGGAGCCCGATGACGCAGCAGA
GGTGTTCGCCATGCTGTGCTTGCTCATCATTCTGGGGCGCTATTTGCCAGACATAAAGGTACATACTTCACTCATGAAGCCAAAGGAGCCCGATGACGCAGCAGA
CGCAGACACAGCTATAATCAATGCAAGGAGGACAGAACAACTCCGAAGAAAGAGATACTTCATCTAGATCAGCCTTTTGTTCAATGAGGTGTCCAACT
GGCCCTATTTAGATGATAAAGAGACAGTGATATTGAACTTGCGAGAAATTCGTGTGTTTTGTTGTCCTCTCTTTTCTTGTTGTGCGTTCCTCTTTTTCTGTTTCGTCAAGTCAA
TGCTGTGTGTAAAAAAAAATGTCTTTGGAAAGTACACTCTGTCTGTTGACACCTCTCTTTTGTTGTGCCGTTCCTCTTTTCTTGTTGTGCGTTCCTCTTTCTAGTTTTTACTTTGT
ACTTGGATACTTGGATTAGTTCAGTAGATTGCAGAAAATTGCAGAAATTCGTGGTGCCAATTCGTGTATATGGACTGTGATTCA
CCTCTACCCCAATTCGGATTTTCCAAATCTCCCCATTTGGAATTTGCTGTGTAACAATACATTAGTCAGTTCCAAATCTCTTAATCTGATCTAGAGACTAGAAAATTAGACTGTGATTCA
TTATTTATGGTAACTGCTTTCGTGTTCGTAACATACCATTCCAGAAAGGTTTGGGCAGAAAAGGTTGGGCAGAAAGGACACCTGACAGGTGAGGTCTGTTCCTTTT
CTCTGTGTAAAGATTTGCTGTGGAACTACATTACTGTCGTCCAGAAAGGTTTGGGCAGAAAAGGTTGGGCAGAAAGGACACCTGACAGGTGAGGTCTGTTCCTTTT
CGGCTCAGTATAGATACCGCTGTCCAGAAAGGTTTGGGCAGAAAAGGTAGGGGGAAGTAGGGGAAAAGCAAGTTCGTCTGTTGTGCGAATGACTGACAGAGTTGATTTTTTTTCCTTTGTGCTTAG
ATATAAGTGGACAAATTTTGAGTTGCCACAGGAGGGGAAGTTGCAATGCAACTACACAGGAAGTGTGCAATGACAGGTTCGTCTGTTGTGCGAATGACTGACAGAGTTGATTTTTTTTCCTTTGTGCTTAG
CAATCGGCCTTACTTCCTCACTAATTTGTAGGAAAAAGCAAGTTCGTCTGTTGTGCGAATGCAATGACAGAGTTGATTTTTTTTCCTTTGTGCTTAG
TTAGGAAGGCAGTAGGATGGCCTGCATGTATGTATATTACAGATATTGTATGCTGGGATTTCGTCTGAAACTTCATTCCTTCAGATTTG
GCTTGACAAAGGCAGGAGGTACAAAAGAGAAGGCTGTTATTGTCTCACACTGGTCTGCGCTCAGTTGCTCGATAGGTCAGAGCAGAGGTGGAAAAACAGC
ATGTACGGATTTACTGATCTCGATGATGGCATGATTTAAAGAAAAGAAGTGTGGGGAATGCCCTATGGAAGCTGGAAATCTCAGAAGATTTTTCAGTGAGT
CAAAAATTACCAGCTTAATCAAAAACTTAGTGGCTCCAGCTAACAGTGCCATATTATCTCTGAAAAGCATCCCAGTGAAGCTGGAAATCTCAGAAGTACATCTGC
CACGTTACCATTTACATGTTTAAGAAAACATTGATAGAACCATTGCAATATGGGGACCGCTTGGAGCCTGTATGTAAAAGAAAATCCATTATCGCAGCAGCATTT
GTTGGTAAGACTCCAGACTCCAGCTAACAGTCCCATATGGAAAGATATGGCATCAAAAAGATAGATCTATATATATTATATGGAAGTCTCTGTATTACATTTCAGTGAG
TAATTTTGGATTTCAAGGTGCATTTTACTATTGTTACATTAGTGCTGATTTATTAAGGGGAAAGTGTCAACTCTTGTTATTGAAACAT
GTTTATTTCTGTCTTATTTAACCTTTGATAGAACCATTGCAATATGGGGACCGCTTGTATGTAAAAGAAAATCCATTATCGCAGCAGCATTT
ATTTACCCCTCCCCTATCCCCTAGCCACTTAACCAAGACAAAAAGCACCAATGAACATCCCTTTATAATCTGTGAGAATTTTATAATCTCGACTCTATTCCGAGCCCTTAGCA
CCCATTCCGACCATAGTATAATCATATCAAGGGTGAGAATCATTTTGGAGGTGTAGCATGTTAGCATCATTTAGCATGTTTTCAGTGTTGTTGAAGGTTTTTTCAGTTCTTTTAGAAAAAAG (SEQ ID NO:83)
```

Bold underline indicates siRNA target region with biological activity

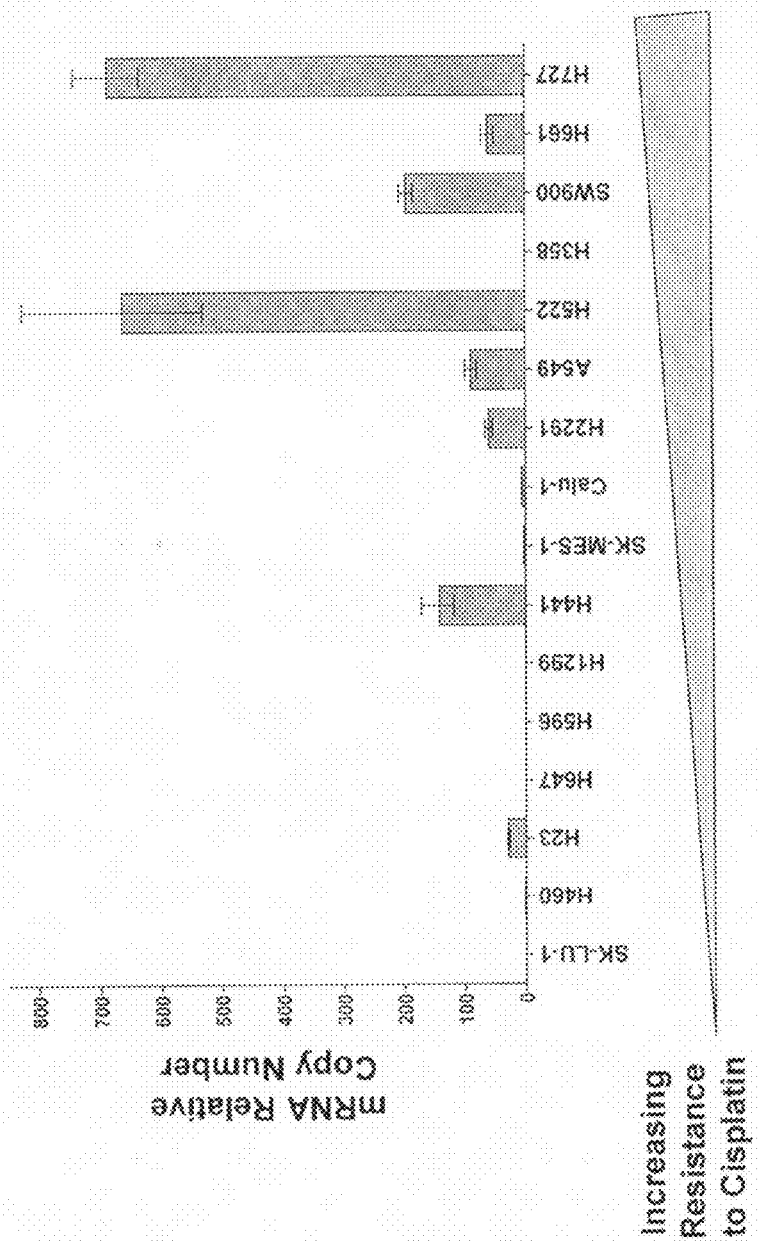

FIGURE 85
DB83 is Over-expressed in Multiple Tumor Types

|  | Overexpression (% tumors) | |
|---|---|---|
|  | Δ+1 | Δ+2 |
| Kidney | 100% | 100% |
| Melanoma | 80% | 80% |
| Lung, Adeno | 80% | 80% |
| Brain, Glioblastoma | 66% | 66% |
| Lung, Squamous | 50% | 50% |
| Metastatic Pancreas | 33% | 33% |
| Pancreas | 29% | 29% |
| Colon | 20% | 20% |
| Bladder | 60% | -- |
| Melanoma, Lymh Node | 30% | -- |
| Prostate | 30% | -- |
| Gastric | 30% | -- |
| Liver | 25% | -- |
| Ovary | 20% | -- |

DB83 Cell Surface Expression in Colon Cancer Cells by FACS

Knockdown of DB83 (0106) mRNA Inhibits Proliferation in Multiple Cancer Cells

* Reproducible 35% (except 25% for Calu-1) or greater decrease in proliferation

Knockdown of DB83 (0106) mRNA Induces Apoptosis in Multiple Cancer Cells

* Reproducible 50% or greater increase in proliferation

Knockdown of DB83 (02-0106) mRNA Inhibits Proliferation and Induces Apoptosis in ACHN Kidney Cancer Cells Knockdown of DB83 (02-0106) mRNA Induces Apoptosis in HT29 Colon Cancer Cells Knockdown of DB83 (0106) mRNA Inhibits Proliferation in Calu-1 Lung Cancer Cells Knockdown of DB83 (02-0106) mRNA Inhibits Proliferation and Induces Apoptosis in SK-N-SH Neuroblastoma Cancer Cells

US 7,842,291 B1

SEQUENCE LISTING

```
<160> NUMBER OF SEQ ID NOS: 83

<210> SEQ ID NO 1
<211> LENGTH: 435
<212> TYPE: PRT
<213> ORGANISM: Homo sapiens

<400> SEQUENCE: 1

Met Asp Pro Asp Ser Asp Gln Pro Leu Asn Ser Leu Asp Val Lys Pro
1               5                   10                  15

Leu Arg Lys Pro Arg Ile Pro Met Glu Thr Phe Arg Lys Val Gly Ile
                20                  25                  30

Pro Ile Ile Ile Ala Leu Leu Ser Leu Ala Ser Ile Ile Ile Val Val
            35                  40                  45

Val Leu Ile Lys Val Ile Leu Asp Lys Tyr Tyr Phe Leu Cys Gly Gln
        50                  55                  60

Pro Leu His Phe Ile Pro Arg Lys Gln Leu Cys Asp Gly Glu Leu Asp
65                  70                  75                  80

Cys Pro Leu Gly Glu Asp Glu Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

Phe Thr Glu Ala Leu Ala Glu Thr Ala Cys Arg Gln Met Gly Tyr Ser
    130                 135                 140

Ser Lys Pro Thr Phe Arg Ala Val Glu Ile Gly Pro Asp Gln Asp Leu
145                 150                 155                 160

Asp Val Val Glu Ile Thr Glu Asn Ser Gln Glu Leu Arg Met Arg Asn
                165                 170                 175

Ser Ser Gly Pro Cys Leu Ser Gly Ser Leu Val Ser Leu His Cys Leu
            180                 185                 190

Ala Cys Gly Lys Ser Leu Lys Thr Pro Arg Val Val Gly Val Glu Glu
        195                 200                 205

Ala Ser Val Asp Ser Trp Pro Trp Gln Val Ser Ile Gln Tyr Asp Lys
    210                 215                 220
```

```
Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                245                 250                 255

Arg Ala Gly Ser Asp Lys Leu Gly Ser Phe Pro Ser Leu Ala Val Ala
            260                 265                 270

Lys Ile Ile Ile Glu Phe Asn Pro Met Tyr Pro Lys Asp Asn Asp
        275                 280                 285

Ile Ala Leu Met Lys Leu Gln Phe Pro Leu Thr Phe Ser Gly Thr Val
    290                 295                 300

Arg Pro Ile Cys Leu Pro Phe Phe Asp Glu Glu Leu Thr Pro Ala Thr
305                 310                 315                 320

Pro Leu Trp Ile Ile Gly Trp Gly Phe Thr Lys Gln Asn Gly Gly Lys
                325                 330                 335

Met Ser Asp Ile Leu Leu Gln Ala Ser Val Gln Val Ile Asp Ser Thr
            340                 345                 350

Arg Cys Asn Ala Asp Asp Ala Tyr Gln Gly Glu Val Thr Glu Lys Met
        355                 360                 365

Met Cys Ala Gly Ile Pro Glu Gly Gly Val Asp Thr Cys Gln Gly Asp
    370                 375                 380

Ser Gly Gly Pro Leu Met Tyr Gln Ser Asp Gln Trp His Val Val Gly
385                 390                 395                 400

Ile Val Ser Trp Gly Tyr Gly Cys Gly Gly Pro Ser Thr Pro Gly Val
                405                 410                 415

Tyr Thr Lys Val Ser Ala Tyr Leu Asn Trp Ile Tyr Asn Val Trp Lys
            420                 425                 430

Ala Glu Leu
        435

<210> SEQ ID NO 2
<211> LENGTH: 437
<212> TYPE: PRT
<213> ORGANISM: Homo sapiens

<400> SEQUENCE: 2

Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
            20                  25                  30

Gly Ile Pro Ile Ile Ile Ala Leu Leu Ser Leu Ala Ser Ile Ile Ile
        35                  40                  45

Val Val Val Leu Ile Lys Val Ile Leu Asp Lys Tyr Tyr Phe Leu Cys
    50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu His Cys Val Lys Ser Phe
                85                  90                  95

Pro Glu Gly Pro Ala Val Ala Val Arg Leu Ser Lys Asp Arg Ser Thr
            100                 105                 110

Leu Gln Val Leu Asp Ser Ala Thr Gly Asn Trp Phe Ser Ala Cys Phe
        115                 120                 125

Asp Asn Phe Thr Glu Ala Leu Ala Glu Thr Ala Cys Arg Gln Met Gly
    130                 135                 140

Tyr Ser Ser Lys Pro Thr Phe Arg Ala Val Glu Ile Gly Pro Asp Gln
145                 150                 155                 160
```

```
Asp Leu Asp Val Val Glu Ile Thr Glu Asn Ser Gln Glu Leu Arg Met
                165                 170                 175

Arg Asn Ser Ser Gly Pro Cys Leu Ser Gly Ser Leu Val Ser Leu His
            180                 185                 190

Cys Leu Ala Cys Gly Lys Ser Leu Lys Thr Pro Arg Val Val Gly Gly
        195                 200                 205

Glu Glu Ala Ser Val Asp Ser Trp Pro Trp Gln Val Ser Ile Gln Tyr
    210                 215                 220

Asp Lys Gln His Val Cys Gly Gly Ser Ile Leu Asp Pro His Trp Val
225                 230                 235                 240

Leu Thr Ala Ala His Cys Phe Arg Lys His Thr Asp Val Phe Asn Trp
                245                 250                 255

Lys Val Arg Ala Gly Ser Asp Lys Leu Gly Ser Phe Pro Ser Leu Ala
            260                 265                 270

Val Ala Lys Ile Ile Ile Ile Glu Phe Asn Pro Met Tyr Pro Lys Asp
        275                 280                 285

Asn Asp Ile Ala Leu Met Lys Leu Gln Phe Pro Leu Thr Phe Ser Gly
    290                 295                 300

Thr Val Arg Pro Ile Cys Leu Pro Phe Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335

Gly Lys Met Ser Asp Ile Leu Leu Gln Ala Ser Val Gln Val Ile Asp
            340                 345                 350

Ser Thr Arg Cys Asn Ala Asp Asp Ala Tyr Gln Gly Glu Val Thr Glu
        355                 360                 365

Lys Met Met Cys Ala Gly Ile Pro Glu Gly Gly Val Asp Thr Cys Gln
    370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
            420                 425                 430

Trp Lys Ala Glu Leu
        435

<210> SEQ ID NO 3
<211> LENGTH: 437
<212> TYPE: PRT
<213> ORGANISM: Homo sapiens

<400> SEQUENCE: 3

Met Val Ser Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
            20                  25                  30

Gly Ile Pro Ile Ile Ile Ala Leu Ser Leu Ala Ser Ile Ile Ile
        35                  40                  45

Val Val Val Leu Ile Lys Val Ile Leu Asp Lys Tyr Tyr Phe Leu Cys
    50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu Glu His Cys Val Lys Ser Phe
```

```
                85                  90                  95
Pro Glu Gly Pro Ala Val Ala Val Arg Leu Ser Lys Asp Arg Ser Thr
            100                 105                 110
Leu Gln Val Leu Asp Ser Ala Thr Gly Asn Trp Phe Ser Ala Cys Phe
        115                 120                 125
Asp Asn Phe Thr Glu Ala Leu Ala Glu Thr Ala Cys Arg Gln Met Gly
    130                 135                 140
Tyr Ser Ser Lys Pro Thr Phe Arg Ala Val Glu Ile Gly Pro Asp Gln
145                 150                 155                 160
Asp Leu Asp Val Val Glu Ile Thr Glu Asn Ser Gln Glu Leu Arg Met
                165                 170                 175
Arg Asn Ser Ser Gly Pro Cys Leu Ser Gly Ser Leu Val Ser Leu His
            180                 185                 190
Cys Leu Ala Cys Gly Lys Ser Leu Lys Thr Pro Arg Val Val Gly Val
        195                 200                 205
Glu Glu Ala Ser Val Asp Ser Trp Pro Trp Gln Val Ser Ile Gln Tyr
    210                 215                 220
Asp Lys Gln His Val Cys Gly Gly Ser Ile Leu Asp Pro His Trp Val
225                 230                 235                 240
Leu Thr Ala Ala His Cys Phe Arg Lys His Thr Asp Val Phe Asn Trp
                245                 250                 255
Lys Val Arg Ala Gly Ser Asp Lys Leu Gly Ser Phe Pro Ser Leu Ala
            260                 265                 270
Val Ala Lys Ile Ile Ile Glu Phe Asn Pro Met Tyr Pro Lys Asp
        275                 280                 285
Asn Asp Ile Ala Leu Met Lys Leu Gln Phe Pro Leu Thr Phe Ser Gly
    290                 295                 300
Thr Val Arg Pro Ile Cys Leu Pro Phe Phe Asp Glu Glu Leu Thr Pro
305                 310                 315                 320
Ala Thr Pro Leu Trp Ile Ile Gly Trp Gly Phe Thr Lys Gln Asn Gly
                325                 330                 335
Gly Lys Met Ser Asp Ile Leu Leu Gln Ala Ser Val Gln Val Ile Asp
            340                 345                 350
Ser Thr Arg Cys Asn Ala Asp Asp Ala Tyr Gln Gly Glu Val Thr Glu
        355                 360                 365
Lys Met Met Cys Ala Gly Ile Pro Glu Gly Gly Val Asp Thr Cys Gln
    370                 375                 380
Gly Asp Ser Gly Gly Pro Leu Met Tyr Gln Ser Asp Gln Trp His Val
385                 390                 395                 400
Val Gly Ile Val Ser Trp Gly Tyr Gly Cys Gly Gly Pro Ser Thr Pro
                405                 410                 415
Gly Val Tyr Thr Lys Val Ser Ala Tyr Leu Asn Trp Ile Tyr Asn Val
            420                 425                 430
Trp Lys Ala Glu Leu
        435

<210> SEQ ID NO 4
<211> LENGTH: 2590
<212> TYPE: DNA
<213> ORGANISM: Homo sapiens

<400> SEQUENCE: 4
actcctggaa tacacagaga gaggcagcag cttgctcagc ggacaaggat gctgggcgtg      60
agggaccaag gcctgccctg cactcgggcc tcctccagcc agtgctgacc agggacttct     120
```

-continued

```
gacctgctgg ccagccagga cctgtgtggg gaggccctcc tgctgccttg gggtgacaat      180
ctcagctcca ggctacaggg agaccgggag gatcacagag ccagcatgga tcctgacagt      240
gatcaacctc tgaacagcct cgatgtcaaa cccctgcgca aacccgtat ccccatggag       300 accttcagaa aggtggggat ccccatcatc atagcactac tgagcctggc gagtatcatc      360
attgtggttg tcctcatcaa ggtgattctg gataaatact acttcctctg cgggcagcct      420
ctccacttca tcccgaggaa gcagctgtgt gacggagagc tggactgtcc cttgggggag      480
gacgaggagc actgtgtcaa gagcttcccc gaagggcctg cagtggcagt ccgcctctcc      540
aaggaccgat ccacactgca ggtgctggac tcggccacag gaactggtt ctctgcctgt       600 ttcgacaact tcacagaagc tctcgctgag acagcctgta ggcagatggg ctacagcagc      660
aaacccactt tcagagctgt ggagattggc ccagaccagg atctggatgt tgttgaaatc      720
acagaaaaca gccaggagct tcgcatgcgg aactcaagtg gccctgtct ctcaggctcc       780 ctggtctccc tgcactgtct tgcctgtggg aagagcctga agacccccg tgtggtgggt       840 gtggaggagg cctctgtgga ttcttggcct tggcaggtca gcatccagta cgacaaacag      900
cacgtctgtg gagggagcat cctggacccc cactgggtcc tcacggcagc ccactgcttc      960
aggaaacata ccgatgtgtt caactggaag gtgcgggcag gctcagacaa actgggcagc      1020
ttcccatccc tggctgtggc caagatcatc atcattgaat caaccccat gtaccccaaa       1080 gacaatgaca tcgccctcat gaagctgcag ttcccactca ctttctcagg cacagtcagg      1140
cccatctgtc tgccccttctt tgatgaggag ctcactccag ccacccact ctggatcatt      1200 ggatggggct ttacgaagca gaatggaggg aagatgtctg acatactgct gcaggcgtca      1260
gtccaggtca ttgacagcac acggtgcaat gcagacgatg cgtaccaggg ggaagtcacc      1320
gagaagatga tgtgtgcagg catcccggaa gggggtgtgg acacctgcca gggtgacagt      1380
ggtgggcccc tgatgtacca atctgaccag tggcatgtgg tgggcatcgt tagttggggc      1440
tatggctgcg ggggcccgag cacccccagga gtatacacca aggtctcagc ctatctcaac      1500
tggatctaca atgtctggaa ggctgagctg taatgctgct gccccttgc agtgctggga      1560 gccgcttcct tcctgccctg cccacctggg gatccccccaa agtcagacac agagcaagag      1620
tccccttggg tacacccctc tgcccacagc ctcagcattt cttggagcag caaagggcct      1680
caattcctat aagagaccct cgcagcccag aggcgcccag aggaagtcag cagccctagc      1740
tcggccacac ttggtgctcc cagcatccca gggagagaca cagcccactg aacaaggtct      1800 cagggggtatt gctaagccaa gaaggaactt tcccacacta ctgaatggaa gcaggctgtc      1860
ttgtaaaagc ccagatcact gtgggctgga ggagagaagg aaagggtctg cgccagccct      1920
gtccgtcttc acccatcccc aagcctacta gagcaagaaa ccagttgtaa tataaaatgc      1980
actgccctac tgttggtatg actaccgtta cctactgttg tcattgttat tacagctatg      2040
gccactatta ttaaagagct gtgtaacatc tctggcatag gctagctgga atgcttgata      2100
agaactgagc tgggatgatt gaactttcat tctttggctt ggggagaaaa gaagtcctgg      2160
ggaagcaatt gagtctcaaa gtagaggcag gggaaaaaag agttagggag accagatctg      2220
ctgagtggca gcaagagtga gctgcagatt acagaaacca gggtgagcaa gtttgagtcc      2280
cacacagggc cttctcccctt tgcctctttc cctccctccc tgcctgtgat aatcagccag      2340
gagccaggga taacctatga cttgggaaag agatgagtta ggcagtcaag ggtgacattc      2400
aatcagggat ccacaagtgg ctggaaagaa atgctggtcc tgtgtcctaa cttttttccgc      2460
```

-continued

| | |
|---|---|
| ctggagagcc ctcagtgtgg cttcttacat ttaaaaaaca aaaaggatca gctgccaggt | 2520 |
| gtgaggcagt ccccaagctg agttgtgagg atgtaagcat gaataagtcc ctgcactcaa | 2580 |
| aatggtcaaa | 2590 |

<210> SEQ ID NO 5
<211> LENGTH: 2021
<212> TYPE: DNA
<213> ORGANISM: Homo sapiens

<400> SEQUENCE: 5

| | |
|---|---|
| ctgcactcgg gcctcctcca gccagtgctg accagggact tctgacctgc tggcagccag | 60 |
| gacctgtgtg gggaggccct cctgctgcct tggggtgaca atctcagctc caggctacag | 120 |
| ggagaccggg aggatcacag agccagcatg ttacaggatc ctgacagtga tcaacctctg | 180 |
| aacagcctcg atgtcaaacc cctgcgcaaa ccccgtatcc ccatggagac cttcagaaag | 240 |
| gtggggatcc ccatcatcat agcactactg agcctggcga gtatcatcat tgtggttgtc | 300 |
| ctcatcaagg tgattctgga taaatactac ttcctctgcg ggcagcctct ccacttcatc | 360 |
| ccgaggaagc agctgtgtga cggagagctg gactgtccct gggggagga cgaggagcac | 420 |
| tgtgtcaaga gcttccccga agggcctgca gtggcagtcc gcctctccaa ggaccgatcc | 480 |
| acactgcagg tgctggactc ggccacaggg aactggttct ctgcctgttt cgacaacttc | 540 |
| acagaagctc tcgctgagac agcctgtagg cagatgggct acagcagcaa acccactttc | 600 |
| agagctgtgg agattggccc agaccaggat ctggatgttg ttgaaatcac agaaaacagc | 660 |
| caggagcttc gcatgcggaa ctcaagtggg ccctgtctct caggctccct ggtctccctg | 720 |
| cactgtcttg cctgtgggaa gagcttgaag acccccgtg tggtgggtgg ggaggaggcc | 780 |
| tctgtggatt cttggccttg gcaggtcagc atccagtacg acaaacagca cgtctgtgga | 840 |
| gggagcatcc tggaccccca ctgggtcctc acggcagccc actgcttcag gaaacatacc | 900 |
| gatgtgttca ctggaaggt gcgggcaggc tcagacaaac tgggcagctt cccatccctg | 960 |
| gctgtggcca agatcatcat cattgaattc aaccccatgt accccaaaga caatgacatc | 1020 |
| gccctcatga agctgcagtt cccactcact ttctcaggca cagtcaggcc catctgtctg | 1080 |
| cccttctttg atgaggagct cactccagcc accccactct ggatcattgg atggggcttt | 1140 |
| acgaagcaga atggagggaa gatgtctgac atactgctgc aggcgtcagt ccaggtcatt | 1200 |
| gacagcacac ggtgcaatgc agacgatgcg taccagggg aagtcaccga gaagatgatg | 1260 |
| tgtgcaggca tcccggaagg gggtgtggac acctgccagg gtgacagtgg tgggcccctg | 1320 |
| atgtaccaat ctgaccagtg gcatgtggtg ggcatcgtta gttggggcta tggctgcggg | 1380 |
| ggcccgagca ccccaggagt atacaccaag gtctcagcct atctcaactg gatctacaat | 1440 |
| gtctggaagg ctgagctgta atgctgctgc ccctttgcag tgctgggagc cgcttccttc | 1500 |
| ctgccctgcc cacctgggga tccccccaaag tcagacacag agcaagagtc cccttgggta | 1560 |
| caccctctg cccacagcct cagcatttct tggagcagca agggcctca attcctgtaa | 1620 |
| gagaccctcg cagcccagag gcgcccgagag gaagtcagca gccctagctc ggccacactt | 1680 |
| ggtgctccca gcatcccagg gagagacaca gcccactgaa caaggtctca ggggtattgc | 1740 |
| taagccaaga aggaactttc ccacactact gaatggaagc aggctgtctt gtaaaagccc | 1800 |
| agatcactgt gggctggaga ggagaaggaa agggtctgcg ccagccctgt ccgtcttcac | 1860 |
| ccatccccaa gcctactaga gcaagaaacc agttgtaata taaatgcac tgccctactg | 1920 |
| ttggtatgac taccgttacc tactgttgtc attgttatta cagctatggc cactattatt | 1980 | aaagagctgt gtaacatctc tggaaaaaaa aaaaaaaaa a           2021

<210> SEQ ID NO 6
<211> LENGTH: 2627
<212> TYPE: DNA
<213> ORGANISM: Homo sapiens

<400> SEQUENCE: 6

| | | | | | |
|---|---|---|---|---|---|
| ttttaatcaa | gctgcccaaa | gtcccccaat | cactcctgga | atacacagag | agaggcagca | 60 |
| gcttgctcag | cggacaagga | tgctgggcgt | gagggaccaa | ggcctgccct | gcactcgggc | 120 |
| ctcctccagc | cagtgctgac | cagggacttc | tgacctgctg | gccagccagg | acctgtgtgg | 180 |
| ggaggccctc | ctgctgcctt | ggggtgacaa | tctcagctcc | aggctacagg | agaccgggga | 240 |
| ggatcacaga | gccagcatgg | tgagtgatcc | tgacagtgat | caacctctga | acagcctcga | 300 |
| tgtcaaaccc | ctgcgcaaac | cccgtatccc | catggagacc | ttcagaaagg | tggggatccc | 360 |
| catcatcata | gcactactga | gcctggcgag | tatcatcatt | gtggttgtcc | tcatcaaggt | 420 |
| gattctggat | aaatactact | tcctctgcgg | gcagcctctc | cacttcatcc | cgaggaagca | 480 |
| gctgtgtgac | ggagagctgg | actgtccctt | ggggaggac | gaggagcact | gtgtcaagag | 540 |
| cttccccgaa | gggcctgcag | tggcagtccg | cctctccaag | gaccgatcca | cactgcaggt | 600 |
| gctggactcg | gccacaggga | actggttctc | tgcctgtttc | gacaacttca | cagaagctct | 660 |
| cgctgagaca | gcctgtaggc | agatgggcta | cagcagcaaa | cccactttca | gagctgtgga | 720 |
| gattggccca | gaccaggatc | tggatgttgt | tgaaatcaca | gaaaacagcc | aggagcttcg | 780 |
| catgcggaac | tcaagtgggc | cctgtctctc | aggctccctg | gtctccctgc | actgtcttgc | 840 |
| ctgtgggaag | agcctgaaga | ccccccgtgt | ggtgggtgtg | gaggaggcct | ctgtggattc | 900 |
| ttggccttgg | caggtcagca | tccagtacga | caaacagcac | gtctgtggag | ggagcatcct | 960 |
| ggaccccac | tgggtcctca | cggcagccca | ctgcttcagg | aaacataccg | atgtgttcaa | 1020 |
| ctggaaggtg | cgggcaggct | cagacaaact | gggcagcttc | ccatccctgg | ctgtggccaa | 1080 |
| gatcatcatc | attgaattca | ccccatgta | ccccaaagac | aatgcatcg | ccctcatgaa | 1140 |
| gctgcagttc | ccactcactt | tctcaggcac | agtcaggccc | atctgtctgc | ccttctttga | 1200 |
| tgaggagctc | actccagcca | ccccactctg | gatcattgga | tggggctta | cgaagcagaa | 1260 |
| tggagggaag | atgtctgaca | tactgctgca | ggcgtcagtc | caggtcattg | acagcacacg | 1320 |
| gtgcaatgca | gacgatgcgt | accaggggga | agtcaccgag | aagatgatgt | gtgcaggcat | 1380 |
| cccggaaggg | ggtgtggaca | cctgccaggg | tgacagtggt | gggccctga | tgtaccaatc | 1440 |
| tgaccagtgg | catgtggtgg | gcatcgttag | ttggggctat | ggctgcgggg | gcccgagcac | 1500 |
| cccaggagta | tacaccaagg | tctcagccta | tctcaactgg | atctacaatg | tctggaaggc | 1560 |
| tgagctgtaa | tgctgctgcc | cctttgcagt | gctgggagcc | gcttccttcc | tgccctgccc | 1620 |
| acctggggat | ccccaaagt | cagacacaga | gcaagagtcc | ccttgggtac | accctctgc | 1680 |
| ccacagcctc | agcatttctt | ggagcagcaa | agggcctcaa | ttcctataag | agaccctcgc | 1740 |
| agcccagagg | cgcccagagg | aagtcagcag | ccctagctcg | gccacacttg | gtgctcccag | 1800 |
| catcccaggg | agacacacag | cccactgaac | aaggtctcag | gggtattgct | aagccaagaa | 1860 |
| ggaactttcc | cacactactg | aatggaagca | ggctgtcttg | taaaagccca | gatcactgtg | 1920 |
| ggctggagag | gagaaggaaa | gggtctgcgc | cagccctgtc | cgtcttcacc | catcccaag | 1980 |
| cctactagag | caagaaacca | gttgtaatat | aaaatgcact | gccctactgt | tggtatgact | 2040 |

```
accgttacct actgttgtca ttgttattac agctatggcc actattatta aagagctgtg    2100
taacatctct ggcataggct agctggaatg cttgataaga actgagctgg gatgattgaa    2160
ctttcattct ttggcttggg gagaaaagaa gtcctgggga agcaattgag tctcaaagta    2220
gaggcagggg aaaaaagagt tagggagacc agatctgctg agtggcagca agagtgagct    2280
gcagattaca gaaaccaggg tgagcaagtt tgagtcccac acagggcctt ctccctttgc    2340
ctctttccct ccctccctgc ctgtgataat cagccaggag ccaggataa cctatgactt     2400 gggaaagaga tgagttaggc agtcaagggt gacattcaat cagggatcca caagtggctg    2460
gaaagaaatg ctggtcctgt gtcctaactt tttccgcctg gagagccctc agtgtggctt    2520
cttacattta aaaacaaaa aggatcagct gccaggtgtg aggcagtccc caagctgagt     2580
tgtgaggatg taagcatgaa taagtccctg cactcaaaat ggtcaaa                  2627
```

<210> SEQ ID NO 7
<211> LENGTH: 635
<212> TYPE: PRT
<213> ORGANISM: Homo sapiens

<400> SEQUENCE: 7

```
Met Ser Val Gly Val Ser Thr Ser Ala Pro Leu Ser Pro Thr Ser Gly
 1               5                  10                  15

Thr Ser Val Gly Met Ser Thr Phe Ser Ile Met Asp Tyr Val Phe
            20                  25                  30

Val Leu Leu Leu Val Leu Ser Leu Ala Ile Gly Leu Tyr His Ala Cys
        35                  40                  45

Arg Gly Trp Gly Arg His Thr Val Gly Glu Leu Leu Met Ala Asp Arg
    50                  55                  60

Lys Met Gly Cys Leu Pro Val Ala Leu Ser Leu Leu Ala Thr Phe Gln
65                  70                  75                  80

Ser Ala Val Ala Ile Leu Gly Val Pro Ser Glu Ile Tyr Arg Phe Gly
                85                  90                  95

Thr Gln Tyr Trp Phe Leu Gly Cys Cys Tyr Phe Leu Gly Leu Leu Ile
            100                 105                 110

Pro Ala His Ile Phe Ile Pro Val Phe Tyr Arg Leu His Leu Thr Ser
        115                 120                 125

Ala Tyr Glu Tyr Leu Glu Leu Arg Phe Asn Lys Thr Val Arg Val Cys
    130                 135                 140

Gly Thr Val Thr Phe Ile Phe Gln Met Val Ile Tyr Met Gly Val Val
145                 150                 155                 160

Leu Tyr Ala Pro Ser Leu Ala Leu Asn Ala Val Thr Gly Phe Asp Leu
                165                 170                 175

Trp Leu Ser Val Leu Ala Leu Gly Ile Val Cys Thr Val Tyr Thr Ala
            180                 185                 190

Leu Gly Gly Leu Lys Ala Val Ile Trp Thr Asp Val Phe Gln Thr Leu
        195                 200                 205

Val Met Phe Leu Gly Gln Leu Ala Val Ile Val Gly Ser Ala Lys
    210                 215                 220

Val Gly Gly Leu Gly Arg Val Trp Ala Val Ala Ser Gln His Gly Arg
225                 230                 235                 240

Ile Ser Gly Phe Glu Leu Asp Pro Asp Pro Phe Val Arg His Thr Phe
                245                 250                 255

Trp Thr Leu Ala Phe Gly Gly Val Phe Met Met Leu Ser Leu Tyr Gly
            260                 265                 270
```

```
Val Asn Gln Ala Gln Val Gln Arg Tyr Leu Ser Ser Arg Thr Glu Lys
        275                 280                 285

Ala Ala Val Leu Ser Cys Tyr Ala Val Phe Pro Phe Gln Gln Val Ser
    290                 295                 300

Leu Cys Val Gly Cys Leu Ile Gly Leu Val Met Phe Ala Tyr Tyr Gln
305                 310                 315                 320

Glu Tyr Pro Met Ser Ile Gln Gln Ala Gln Ala Pro Asp Gln Phe
                325                 330                 335

Val Leu Tyr Phe Val Met Asp Leu Leu Lys Gly Leu Pro Gly Leu Pro
            340                 345                 350

Gly Leu Phe Ile Ala Cys Leu Phe Ser Gly Ser Leu Ser Thr Ile Ser
            355                 360                 365

Ser Ala Phe Asn Ser Leu Ala Thr Val Thr Met Glu Asp Leu Ile Arg
    370                 375                 380

Pro Trp Phe Pro Glu Phe Ser Glu Ala Arg Ala Ile Met Leu Ser Arg
385                 390                 395                 400

Gly Leu Ala Phe Gly Tyr Gly Leu Leu Cys Leu Gly Met Ala Tyr Ile
                405                 410                 415

Ser Ser Gln Met Gly Pro Val Leu Gln Ala Ala Ile Ser Ile Phe Gly
            420                 425                 430

Met Val Gly Gly Pro Leu Leu Gly Leu Phe Cys Leu Gly Met Phe Phe
            435                 440                 445

Pro Cys Ala Asn Pro Pro Gly Ala Val Val Gly Leu Leu Ala Gly Leu
            450                 455                 460

Val Met Ala Phe Trp Ile Gly Ile Gly Ser Ile Val Thr Ser Met Gly
465                 470                 475                 480

Ser Ser Met Pro Pro Ser Pro Ser Asn Gly Ser Ser Phe Ser Leu Pro
                485                 490                 495

Thr Asn Leu Thr Val Ala Thr Val Thr Thr Leu Met Pro Leu Thr Thr
            500                 505                 510

Phe Ser Lys Pro Thr Gly Leu Gln Arg Phe Tyr Ser Leu Ser Tyr Leu
            515                 520                 525

Trp Tyr Ser Ala His Asn Ser Thr Thr Val Ile Val Val Gly Leu Ile
530                 535                 540

Val Ser Leu Leu Thr Gly Arg Met Arg Gly Arg Ser Leu Asn Pro Ala
545                 550                 555                 560

Thr Ile Tyr Pro Val Leu Pro Lys Leu Leu Ser Leu Pro Leu Ser
            565                 570                 575

Cys Gln Lys Arg Leu His Cys Arg Ser Tyr Gly Gln Asp His Leu Asp
            580                 585                 590

Thr Gly Leu Phe Pro Glu Lys Pro Arg Asn Gly Val Leu Gly Asp Ser
            595                 600                 605

Arg Asp Lys Glu Ala Met Ala Leu Asp Gly Thr Ala Tyr Gln Gly Ser
610                 615                 620

Ser Ser Thr Cys Ile Leu Gln Glu Thr Ser Leu
625                 630                 635

<210> SEQ ID NO 8
<211> LENGTH: 257
<212> TYPE: PRT
<213> ORGANISM: Homo sapiens

<400> SEQUENCE: 8

Met Glu Asp Leu Ile Arg Pro Trp Phe Pro Glu Phe Ser Glu Ala Arg
1               5                   10                  15
```

```
Ala Ile Met Leu Ser Arg Gly Leu Ala Phe Gly Tyr Gly Leu Leu Cys
            20                  25                  30

Leu Gly Met Ala Tyr Ile Ser Ser Gln Met Gly Pro Val Leu Gln Ala
            35                  40                  45

Ala Ile Ser Ile Phe Gly Met Val Gly Gly Pro Leu Leu Gly Leu Phe
 50                  55                  60

Cys Leu Gly Met Phe Phe Pro Cys Ala Asn Pro Pro Gly Ala Val Val
 65                  70                  75                  80

Gly Leu Leu Ala Gly Leu Val Met Ala Phe Trp Ile Gly Ile Gly Ser
                85                  90                  95

Ile Val Thr Ser Met Gly Phe Ser Met Pro Pro Ser Pro Ser Asn Gly
            100                 105                 110

Ser Ser Phe Ser Leu Pro Thr Asn Leu Thr Val Ala Thr Val Thr Thr
            115                 120                 125

Leu Met Pro Leu Thr Thr Phe Ser Lys Pro Thr Gly Leu Gln Arg Phe
            130                 135                 140

Tyr Ser Leu Ser Tyr Leu Trp Tyr Ser Ala His Asn Ser Thr Thr Val
145                 150                 155                 160

Ile Val Val Gly Leu Ile Val Ser Leu Leu Thr Gly Arg Met Arg Gly
                165                 170                 175

Arg Ser Leu Asn Pro Ala Thr Ile Tyr Pro Val Leu Pro Lys Leu Leu
            180                 185                 190

Ser Leu Leu Pro Leu Ser Cys Gln Lys Arg Leu His Cys Arg Ser Tyr
            195                 200                 205

Gly Gln Asp His Leu Asp Thr Gly Leu Phe Pro Glu Lys Pro Arg Asn
            210                 215                 220

Gly Val Leu Gly Asp Ser Arg Asp Lys Glu Ala Met Ala Leu Asp Gly
225                 230                 235                 240

Thr Ala Tyr Gln Gly Ser Ser Ser Thr Cys Ile Leu Gln Glu Thr Ser
            245                 250                 255

Leu

<210> SEQ ID NO 9
<211> LENGTH: 635
<212> TYPE: PRT
<213> ORGANISM: Homo sapiens

<400> SEQUENCE: 9

Met Ser Val Gly Val Ser Thr Ser Ala Pro Leu Ser Pro Thr Ser Gly
 1               5                  10                  15

Thr Ser Val Gly Met Ser Thr Phe Ser Ile Met Asp Tyr Val Val Phe
            20                  25                  30

Val Leu Leu Leu Val Leu Ser Leu Ala Ile Gly Leu Tyr His Ala Cys
            35                  40                  45

Arg Gly Trp Gly Arg His Thr Val Gly Glu Leu Leu Met Ala Asp Arg
 50                  55                  60

Lys Met Gly Cys Leu Pro Val Ala Leu Ser Leu Leu Ala Thr Phe Gln
 65                  70                  75                  80

Ser Ala Val Ala Ile Leu Gly Val Pro Ser Glu Ile Tyr Arg Phe Gly
                85                  90                  95

Thr Gln Tyr Trp Phe Leu Gly Cys Cys Tyr Phe Leu Gly Leu Leu Ile
            100                 105                 110

Pro Ala His Ile Phe Ile Pro Val Phe Tyr Arg Leu His Leu Thr Ser
            115                 120                 125
```

```
Ala Tyr Glu Tyr Leu Glu Leu Arg Phe Asn Lys Thr Val Arg Val Cys
    130                 135                 140

Gly Thr Val Thr Phe Ile Phe Gln Met Val Ile Tyr Met Gly Val Val
145                 150                 155                 160

Leu Tyr Ala Pro Ser Leu Ala Leu Asn Ala Val Thr Gly Phe Asp Leu
                165                 170                 175

Trp Leu Ser Val Leu Ala Leu Gly Ile Val Cys Thr Val Tyr Thr Ala
            180                 185                 190

Leu Gly Gly Leu Lys Ala Val Ile Trp Thr Asp Val Phe Gln Thr Leu
        195                 200                 205

Val Met Phe Leu Gly Gln Leu Ala Val Ile Ile Val Gly Ser Ala Lys
    210                 215                 220

Val Gly Gly Leu Gly Arg Val Trp Ala Val Ala Ser Gln His Gly Arg
225                 230                 235                 240

Ile Ser Gly Phe Glu Leu Asp Pro Asp Pro Phe Val Arg His Thr Phe
                245                 250                 255

Trp Thr Leu Ala Phe Gly Gly Val Phe Met Met Leu Ser Leu Tyr Gly
            260                 265                 270

Val Asn Gln Ala Gln Val Gln Arg Tyr Leu Ser Ser Arg Thr Glu Lys
        275                 280                 285

Ala Ala Val Leu Ser Cys Tyr Ala Val Phe Pro Phe Gln Gln Val Ser
    290                 295                 300

Leu Cys Val Gly Cys Leu Ile Gly Leu Val Met Phe Ala Tyr Tyr Gln
305                 310                 315                 320

Glu Tyr Pro Met Ser Ile Gln Gln Ala Gln Ala Ala Pro Asp Gln Phe
                325                 330                 335

Val Leu Tyr Phe Val Met Asp Leu Leu Lys Gly Leu Pro Gly Leu Pro
            340                 345                 350

Gly Leu Phe Ile Ala Cys Leu Phe Ser Gly Ser Leu Ser Thr Ile Ser
        355                 360                 365

Ser Ala Phe Asn Ser Leu Ala Thr Val Thr Met Glu Asp Leu Ile Arg
    370                 375                 380

Pro Trp Phe Pro Glu Phe Ser Glu Ala Arg Ala Ile Met Leu Ser Arg
385                 390                 395                 400

Gly Leu Ala Phe Gly Tyr Gly Leu Leu Cys Leu Gly Met Ala Tyr Ile
                405                 410                 415

Ser Ser Gln Met Gly Pro Val Leu Gln Ala Ala Ile Ser Ile Phe Gly
            420                 425                 430

Met Val Gly Gly Pro Leu Leu Gly Leu Phe Cys Leu Gly Met Phe Phe
        435                 440                 445

Pro Cys Ala Asn Pro Pro Gly Ala Val Val Gly Leu Leu Ala Gly Leu
    450                 455                 460

Val Met Ala Phe Trp Ile Gly Ile Gly Ser Ile Val Thr Ser Met Gly
465                 470                 475                 480

Phe Ser Met Pro Pro Ser Pro Ser Asn Gly Ser Ser Phe Ser Leu Pro
                485                 490                 495

Thr Asn Leu Thr Val Ala Thr Val Thr Thr Leu Met Pro Leu Thr Thr
            500                 505                 510

Phe Ser Lys Pro Thr Gly Leu Gln Arg Phe Tyr Ser Leu Ser Tyr Leu
        515                 520                 525

Trp Tyr Ser Ala His Asn Ser Thr Thr Val Ile Val Val Gly Leu Ile
    530                 535                 540
```

```
Val Ser Leu Leu Thr Gly Arg Met Arg Gly Arg Ser Leu Asn Pro Ala
545                 550                 555                 560

Thr Ile Tyr Pro Val Leu Pro Lys Leu Leu Ser Leu Leu Pro Leu Ser
                565                 570                 575

Cys Gln Lys Arg Leu His Cys Arg Ser Tyr Gly Gln Asp His Leu Asp
            580                 585                 590

Thr Gly Leu Phe Pro Glu Lys Pro Arg Asn Gly Val Leu Gly Asp Ser
        595                 600                 605

Arg Asp Lys Glu Ala Met Ala Leu Asp Gly Thr Ala Tyr Gln Gly Ser
    610                 615                 620

Ser Ser Thr Cys Ile Leu Gln Glu Thr Ser Leu
625                 630                 635

<210> SEQ ID NO 10
<211> LENGTH: 3031
<212> TYPE: DNA
<213> ORGANISM: Homo sapiens

<400> SEQUENCE: 10
atatcgcaca gggaaggtcc tcatctctga agatcactat tcgaacttat ttattatgct      60
ttctgcagag acttctcaat ctgacagccc tagtttggcg cggtgtaaaa cgaccgcagg     120
aaaagggagc gatgttgatc tcaggaagca caaagggacc ttcctagctc tgactgaacc     180
acggagctca ccctggacag tatcactccg tggaggaaga ctgtgagact gtggctggaa     240
gccagattgt agccacacat ccgcccctgc cctaccccag agccctggag cagcaactgg     300
ctgcagatca cagacacagt gaggatatga gtgtaggggt gagcacctca gcccctcttt     360
ccccaacctc gggcacaagc gtgggcatgt ctaccttctc catcatggac tatgtggtgt     420 cgtcctgct gctggttctc tctcttgcca ttgggctcta ccatgcttgt cgtggctggg     480
gccggcatac tgttggtgag ctgctgatgg cggaccgcaa atgggctgc cttccggtgg      540 cactgtccct gctggccacc ttccagtcag ccgtggccat cctgggtgtg ccgtcagaga     600
tctaccgatt tgggacccaa tattggttcc tgggctgctg ctactttctg ggctgctga      660 tacctgcaca catcttcatc cccgttttct accgcctgca tctcaccagt gcctatgagt     720
acctggagct tcgattcaat aaaactgtgc gagtgtgtgg aactgtgacc ttcatctttc     780
agatggtgat ctacatggga gttgtgctct atgctccgtc attggctctc aatgcagtga     840
ctggctttga tctgtggctg tccgtgctgg ccctgggcat tgtctgtacc gtctatacag     900
ctctgggtgg gctgaaggcc gtcatctgga cagatgtgtt ccagacactg gtcatgttcc     960
tcgggcagct ggcagttatc atcgtggggt cagccaaggt gggcggcttg ggcgtgtgt    1020 gggccgtggc ttcccagcac ggccgcatct ctgggtttga gctggatcca gacccctttg    1080
tgcggcacac cttctggacc ttggccttcg ggggtgtctt catgatgctc tccttatacg    1140
gggtgaacca ggctcaggtg cagcggtacc tcagttcccg cacggagaag ctgctgtgc    1200 tctcctgtta tgcagtgttc ccccttccagc aggtgtccct ctgcgtgggc tgcctcattg    1260
gcctggtcat gttcgcgtat taccaggagt atcccatgag cattcagcag gctcaggcag    1320
ccccagacca gttcgtcctg tactttgtga tggatctcct gaagggcctg ccaggcctgc    1380
cagggctctt cattgcctgc ctcttcagcg gctctctcag cactatatcc tctgcttta    1440 attcattggc aactgttacg atggaagacc tgattcgacc ttggttccct gagttctctg    1500
aagcccgggc catcatgctt tccagaggcc ttgcctttgg ctatgggctg ctttgtctag    1560
gaatggccta tatttcctcc cagatgggac ctgtgctgca ggcagcaatc agcatctttg    1620
```

```
gcatggttgg gggaccgctg ctgggactct tctgccttgg aatgttcttt ccatgtgcta    1680
accctcctgg tgctgttgtg ggcctgttgg ctgggctcgt catggccttc tggattggca    1740
tcgggagcat cgtgaccagc atgggcttca gcatgccacc ctctccctct aatgggtcca    1800
gcttctccct gcccaccaat ctaaccgttg ccactgtgac cacactgatg cccttgacta    1860
ccttctccaa gcccacaggg ctgcagcggt tctattcctt gtcttactta tggtacagtg    1920
ctcacaactc caccacagtg attgtggtgg gcctgattgt cagtctactc actgggagaa    1980
tgcgaggccg gtccctgaac cctgcaacca tttacccagt gttgccaaag ctcctgtccc    2040
tccttccgtt gtcctgtcag aagcggctcc actgcaggag ctacggccag gaccacctcg    2100
acactggcct gtttcctgag aagccgagga atggtgtgct gggggacagc agagacaagg    2160
aggccatggc cctggatggc acagcctatc aggggagcag ctccacctgc atcctccagg    2220
agacctccct gtgatgttga ctcaggaccc cgcctctgtc ctcacttgtg ttctgcaggg    2280
acaggcctgg atgatctagc tcataccaaa ggaccttgtt ctgagaggtt cttgcctgca    2340
ggagaagctg tcacatctca agcatgtgag gcaccgtttt tctcgtcgct tgccaatctg    2400 tttttttaaag gatcaggctc gtagggagca ggatcatgcc agaaatagggg atggaagtgc    2460 atcctctggg aaaagataaa tggcttctga ttcaacatag ccatagtcct ttgaagtaag    2520
tggctagaaa cagcactctg gttataattg ccccagggcc tgattcagga ctgactctcc    2580
accataaaac tggaagctgc ttcccctgta gtccccattt cagtaccagt tctgccagcc    2640
acagtgagcc cctattatta cttttcagatt gtctgtgaca ctcaagcccc tctcattttt    2700
atctgtctac ctccattctg aagagggagg ttttggtgtc cctggtcctc tgggaataga    2760
agatccattt gtctttgtgt agagcaagca cgttttccac ctcactgtct ccatcctcca    2820
cctctgagat ggacacttaa gagacggggc aaatgtggat ccaagaaacc agggccatga    2880
ccaggtccac tgtggagcag ccatctatct acctgactcc tgagccaggc tgccgtggtg    2940
tcatttctgt catccgtgct ctgtttcctt ttggagtttc ttctccacat tatctttgtt    3000
cctggggaat aaaaactacc attggaccta g                                   3031
```

<210> SEQ ID NO 11
<211> LENGTH: 3031
<212> TYPE: DNA
<213> ORGANISM: Homo sapiens

<400> SEQUENCE: 11

```
atatcgcaca gggaaggtcc tcatctctga agatcactat tcgaacttat ttattatgct    60
ttctgcagag acttctcaat ctgacagccc tagtttggcg cggtgtaaaa cgaccgcagg    120
aaaagggagc gatgttgatc tcaggaagca caagggacc ttcctagctc tgactgaacc    180
acggagctca ccctggacag tatcactccg tggaggaaga ctgtgagact gtggctggaa    240
gccagattgt agccacacat ccgcccctgc cctacccag agccctggag cagcaactgg    300
ctgcagatca cagacacagt gaggatatga gtgtaggggt gagcacctca gcccctcttt    360
ccccaacctc gggcacaagc gtgggcatgt ctaccttctc catcatggac tatgtggtgt    420
tcgtcctgct gctggttctc tctcttgcca ttgggctcta ccatgcttgt cgtggctggg    480
gccggcatac tgttggtgag ctgctgatgg cggaccgcaa aatgggctgc ttccggtgg    540 cactgtccct gctggccacc ttccagtcag ccgtggccat cctgggtgtg ccgtcagaga    600
tctaccgatt tgggacccaa tattggttcc tgggctgctg ctactttctg gggctgctga    660
```

```
tacctgcaca catcttcatc cccgttttct accgcctgca tctcaccagt gcctatgagt    720
acctggagct tcgattcaat aaaactgtgc gagtgtgtgg aactgtgacc ttcatctttc    780
agatggtgat ctacatggga gttgtgctct atgctccgtc attggctctc aatgcagtga    840
ctggctttga tctgtggctg tccgtgctgg ccctgggcat tgtctgtacc gtctatacag    900
ctctgggtgg gctgaaggcc gtcatctgga cagatgtgtt ccagacactg gtcatgttcc    960
tcgggcagct ggcagttatc atcgtggggt cagccaaggt gggcggcttg gggcgtgtgt   1020
gggccgtggc ttcccagcac ggccgcatct ctgggtttga gctggatcca gacccctttg   1080
tgcggcacac cttctggacc ttggccttcg ggggtgtctt catgatgctc tccttatacg   1140
gggtgaacca ggctcaggtg cagcggtacc tcagttcccg cacggagaag gctgctgtgc   1200
tctcctgtta tgcagtgttc cccttccagc aggtgtccct ctgcgtgggc tgcctcattg   1260
gcctggtcat gttcgcgtat taccaggagt atcccatgag cattcagcag gctcaggcag   1320
ccccagacca gttcgtcctg tactttgtga tggatctcct gaagggcctg ccaggcctgc   1380
cagggctctt cattgcctgc ctcttcagcg gctctctcag cactatatcc tctgctttta   1440
attcattggc aactgttacg atggaagacc tgattcgacc ttggttccct gagttctctg   1500
aagcccgggc catcatgctt tccagaggcc ttgcctttgg ctatgggctg ctttgtctag   1560
gaatggccta tatttcctcc cagatgggac ctgtgctgca ggcagcaatc agcatctttg   1620
gcatggttgg gggaccgctg ctgggactct tctgccttgg aatgttcttt ccatgtgcta   1680
accctcctgg tgctgttgtg ggcctgttgg ctgggctcgt catggccttc tggattggca   1740
tcgggagcat cgtgaccagc atgggcttca gcatgccacc ctctccctct aatgggtcca   1800
gcttctccct gcccaccaat ctaaccgttg ccactgtgac cacactgatg cccttgacta   1860
ccttctccaa gcccacaggg ctgcagcggt tctattcctt gtcttactta tggtacagtg   1920
ctcacaactc caccacagtg attgtggtgg gcctgattgt cagtctactc actgggagaa   1980
tgcgaggccg gtccctgaac cctgcaacca tttacccagt gttgccaaag ctcctgtccc   2040
tccttccgtt gtcctgtcag aagcggctcc actgcaggag ctacggccag gaccacctcg   2100
acactggcct gtttcctgag aagccgagga atggtgtgct gggggacagc agagacaagg   2160
aggccatggc cctggatggc acagcctatc aggggagcag ctccacctgc atcctccagg   2220
agacctccct gtgatgttga ctcaggaccc cgcctctgtc ctcacttgtg ttctgcaggg   2280
acaggcctgg atgatctagc tcataccaaa ggaccttgtt ctgagaggtt cttgcctgca   2340
ggagaagctg tcacatctca agcatgtgag gcaccgtttt tctcgtcgct tgccaatctg   2400
ttttttaaag gatcaggctc gtagggagca ggatcatgcc agaaatagg g atggaagtgc   2460
atcctctggg aaaaagataa tggcttctga ttcaacatag ccatagtcct ttgaagtaag   2520
tggctagaaa cagcactctg gttataattg ccccagggcc tgattcagga ctgactctcc   2580
accataaaac tggaagctgc ttcccctgta gtccccattt cagtaccagt tctgccagcc   2640
acagtgagcc cctattatta ctttcagatt gtctgtgaca ctcaagcccc tctcattttt   2700
atctgtctac ctccattctg aagagggagg ttttggtgtc cctggtcctc tgggaataga   2760
agatccattt gtctttgtgt agagcaagca cgttttccac ctcactgtct ccatcctcca   2820
cctctgagat ggacacttaa gagacggggc aaatgtggat ccaagaaacc agggccatga   2880
ccaggtccac tgtggagcag ccatctatct acctgactcc tgagccaggc tgccgtggtg   2940
tcatttctgt catccgtgct ctgtttcctt ttggagtttc ttctccacat tatctttgtt   3000
cctggggaat aaaaactacc attggaccta g                                 3031
```

<210> SEQ ID NO 12
<211> LENGTH: 3031
<212> TYPE: DNA
<213> ORGANISM: Homo sapiens

<400> SEQUENCE: 12

```
atatcgcaca gggaaggtcc tcatctctga agatcactat tcgaacttat ttattatgct      60
ttctgcagag acttctcaat ctgacagccc tagtttggcg cggtgtaaaa cgaccgcagg     120
aaaagggagc gatgttgatc tcaggaagca caaagggacc ttcctagctc tgactgaacc     180
acggagctca ccctggacag tatcactccg tggaggaaga ctgtgagact gtggctggaa     240
gccagattgt agccacacat ccgcccctgc cctaccccag agccctggag cagcaactgg     300
ctgcagatca cagacacagt gaggatatga gtgtaggggt gagcacctca gcccctcttt     360
ccccaacctc gggcacaagc gtgggcatgt ctaccttctc catcatggac tatgtggtgt     420
tcgtcctgct gctggttctc tctcttgcca ttgggctcta ccatgcttgt cgtggctggg     480
gccggcatac tgttggtgag ctgctgatgg cggaccgcaa aatgggctgc cttccggtgg     540
cactgtccct gctggccacc ttccagtcag ccgtggccat cctgggtgtg ccgtcagaga     600
tctaccgatt tgggacccaa tattggttcc tgggctgctg ctactttctg ggctgctga      660 tacctgcaca catcttcatc cccgttttct accgcctgca tctcaccagt gcctatgagt     720
acctggagct tcgattcaat aaaactgtgc gagtgtgtgg aactgtgacc ttcatctttc     780
agatggtgat ctacatggga gttgtgctct atgctccgtc attggctctc aatgcagtga     840
ctggctttga tctgtggctg tccgtgctgg ccctgggcat tgtctgtacc gtctatacag     900
ctctgggtgg gctgaaggcc gtcatctgga cagatgtgtt ccagacactg gtcatgttcc     960
tcgggcagct ggcagttatc atcgtggggt cagccaaggt gggcggcttg gggcgtgtgt    1020
gggccgtggc ttcccagcac ggccgcatct ctgggtttga gctggatcca gaccccttg     1080 tgcggcacac cttctggacc ttggccttcg ggggtgtctt catgatgctc tccttatacg    1140
gggtgaacca ggctcaggtg cagcggtacc tcagttcccg cacggagaag gctgctgtgc    1200
tctcctgtta tgcagtgttc cccttccagc aggtgtccct ctgcgtgggc tgcctcattg    1260
gcctggtcat gttcgcgtat taccaggagt atcccatgag cattcagcag gctcaggcag    1320
ccccagacca gttcgtcctg tactttgtga tggatctcct gaagggcctg ccaggcctgc    1380
cagggctctt cattgcctgc ctcttcagcg gctctctcag cactatatcc tctgctttta    1440
attcattggc aactgttacg atggaagacc tgattcgacc ttggttccct gagttctctg    1500
aagcccgggc catcatgctt tccagaggcc ttgcctttgg ctatgggctg ctttgtctag    1560
gaatggccta tatttcctcc cagatgggac ctgtgctgca ggcagcaatc agcatctttg    1620
gcatggttgg gggaccgctg ctgggactct tctgccttgg aatgttcttt ccatgtgcta    1680
accctcctgg tgctgttgtg ggcctgttgg ctgggctcgt catggccttc tggattggca    1740
tcgggagcat cgtgaccagc atgggcttca gcatgccacc ctctccctct aatgggtcca    1800
gcttctccct gcccaccaat ctaaccgttg ccactgtgac cacactgatg cccttgacta    1860
ccttctccaa gcccacaggg ctgcagcggt tctattcctt gtcttactta tggtacagtg    1920
ctcacaactc caccacagtg attgtggtgg gcctgattgt cagtctactc actgggagaa    1980
tgcgaggccg gtccctgaac cctgcaacca tttaccagt gttgccaaag ctcctgtccc     2040
tccttccgtt gtcctgtcag aagcggctcc actgcaggag ctacggccag gaccacctcg    2100
```

-continued

```
acactggcct gtttcctgag aagccgagga atggtgtgct ggggacagc agagacaagg    2160 aggccatggc cctggatggc acagcctatc aggggagcag ctccacctgc atcctccagg    2220
agacctccct gtgatgttga ctcaggaccc cgcctctgtc ctcacttgtg ttctgcaggg    2280
acaggcctgg atgatctagc tcataccaaa ggaccttgtt ctgagaggtt cttgcctgca    2340
ggagaagctg tcacatctca agcatgtgag gcaccgtttt tctcgtcgct tgccaatctg    2400 tttttaaag gatcaggctc gtaggagca ggatcatgcc agaaataggg atggaagtgc    2460
atcctctggg aaaagataa tggcttctga ttcaacatag ccatagtcct ttgaagtaag    2520
tggctagaaa cagcactctg gttataattg ccccagggcc tgattcagga ctgactctcc    2580
accataaaac tggaagctgc ttcccctgta gtccccattt cagtaccagt tctgccagcc    2640
acagtgagcc cctattatta ctttcagatt gtctgtgaca ctcaagcccc tctcattttt    2700
atctgtctac ctccattctg aagagggagg ttttggtgtc cctggtcctc tgggaataga    2760
agatccattt gtctttgtgt agagcaagca cgttttccac ctcactgtct ccatcctcca    2820
cctctgagat ggacacttaa gagacggggc aaatgtggat ccaagaaacc agggccatga    2880
ccaggtccac tgtggagcag ccatctatct acctgactcc tgagccaggc tgccgtggtg    2940
tcatttctgt catccgtgct ctgtttcctt ttggagtttc ttctccacat tatctttgtt    3000
cctggggaat aaaaactacc attggaccta g                                   3031
```

<210> SEQ ID NO 13
<211> LENGTH: 414
<212> TYPE: PRT
<213> ORGANISM: Homo sapiens

<400> SEQUENCE: 13

```
Met Ala Ser Val Val Leu Pro Ser Gly Ser Gln Cys Ala Ala Ala
  1               5                  10                  15

Ala Ala Ala Pro Pro Gly Leu Arg Leu Arg Leu Leu Leu Leu
                 20                  25                  30

Phe Ser Ala Ala Ala Leu Ile Pro Thr Gly Asp Gly Gln Asn Leu Phe
             35                  40                  45

Thr Lys Asp Val Thr Val Ile Glu Gly Glu Val Ala Thr Ile Ser Cys
         50                  55                  60

Gln Val Asn Lys Ser Asp Asp Ser Val Ile Gln Leu Leu Asn Pro Asn
     65                  70                  75                  80

Arg Gln Thr Ile Tyr Phe Arg Asp Phe Arg Pro Leu Lys Asp Ser Arg
                 85                  90                  95

Phe Gln Leu Leu Asn Phe Ser Ser Glu Leu Lys Val Ser Leu Thr
                100                 105                 110

Asn Val Ser Ile Ser Asp Glu Gly Arg Tyr Phe Cys Gln Leu Tyr Thr
             115                 120                 125

Asp Pro Pro Gln Glu Ser Tyr Thr Thr Ile Thr Val Leu Val Pro Pro
         130                 135                 140

Arg Asn Leu Met Ile Asp Ile Gln Lys Asp Thr Ala Val Glu Gly Glu
    145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205
```

```
Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Ser Arg Ala Gly
                325                 330                 335

Glu Glu Gly Ser Ile Arg Ala Val Asp His Ala Val Ile Gly Gly Val
            340                 345                 350

Val Ala Val Val Val Phe Ala Met Leu Cys Leu Leu Ile Ile Leu Gly
        355                 360                 365

Arg Tyr Phe Ala Arg His Lys Gly Thr Tyr Phe Thr His Glu Ala Lys
    370                 375                 380

Gly Ala Asp Asp Ala Ala Asp Ala Asp Thr Ala Ile Ile Asn Ala Glu
385                 390                 395                 400

Gly Gly Gln Asn Asn Ser Glu Glu Lys Lys Glu Tyr Phe Ile
                405                 410

<210> SEQ ID NO 14
<211> LENGTH: 442
<212> TYPE: PRT
<213> ORGANISM: Homo sapiens

<400> SEQUENCE: 14

Met Ala Ser Val Val Leu Pro Ser Gly Ser Gln Cys Ala Ala Ala Ala
  1               5                  10                  15

Ala Ala Ala Ala Pro Pro Gly Leu Arg Leu Arg Leu Leu Leu Leu Leu
                 20                  25                  30

Phe Ser Ala Ala Ala Leu Ile Pro Thr Gly Asp Gly Gln Asn Leu Phe
             35                  40                  45

Thr Lys Asp Val Thr Val Ile Glu Gly Glu Val Ala Thr Ile Ser Cys
 50                  55                  60

Gln Val Asn Lys Ser Asp Asp Ser Val Ile Gln Leu Leu Asn Pro Asn
65                  70                  75                  80

Arg Gln Thr Ile Tyr Phe Arg Asp Phe Arg Pro Leu Lys Asp Ser Arg
                 85                  90                  95

Phe Gln Leu Leu Asn Phe Ser Ser Ser Glu Leu Lys Val Ser Leu Thr
            100                 105                 110

Asn Val Ser Ile Ser Asp Glu Gly Arg Tyr Phe Cys Gln Leu Tyr Thr
        115                 120                 125

Asp Pro Pro Gln Glu Ser Tyr Thr Thr Ile Thr Val Leu Val Pro Pro
    130                 135                 140

Arg Asn Leu Met Ile Asp Ile Gln Arg Asp Thr Ala Val Glu Gly Glu
145                 150                 155                 160

Glu Ile Glu Val Asn Cys Thr Ala Met Ala Ser Lys Pro Ala Thr Thr
                165                 170                 175
```

-continued

```
Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Pro Pro Thr Thr
                325                 330                 335

Ile Pro Pro Pro Thr Thr Thr Thr Thr Thr Thr Thr Thr Thr Thr Thr
            340                 345                 350

Thr Ile Leu Thr Ile Ile Thr Asp Ser Arg Ala Gly Glu Glu Gly Ser
        355                 360                 365

Ile Arg Ala Val Asp His Ala Val Ile Gly Gly Val Val Ala Val Val
    370                 375                 380

Val Phe Ala Met Leu Cys Leu Leu Ile Ile Leu Gly Arg Tyr Phe Ala
385                 390                 395                 400

Arg His Lys Gly Thr Tyr Phe Thr His Glu Ala Lys Gly Ala Asp Asp
                405                 410                 415

Ala Ala Asp Ala Asp Thr Ala Ile Ile Asn Ala Glu Gly Gly Gln Asn
            420                 425                 430

Asn Ser Glu Glu Lys Lys Glu Tyr Phe Ile
        435                 440

<210> SEQ ID NO 15
<211> LENGTH: 333
<212> TYPE: PRT
<213> ORGANISM: Homo sapiens

<400> SEQUENCE: 15

Met Ala Ser Val Val Leu Pro Ser Gly Ser Gln Cys Ala Ala Ala Ala
  1               5                  10                  15

Ala Ala Ala Ala Pro Pro Gly Leu Arg Leu Arg Leu Leu Leu Leu Leu
                 20                  25                  30

Phe Ser Ala Ala Ala Leu Ile Pro Thr Gly Asp Gly Gln Asn Leu Phe
             35                  40                  45

Thr Lys Asp Val Thr Val Ile Glu Gly Glu Val Ala Thr Ile Ser Cys
         50                  55                  60

Gln Val Asn Lys Ser Asp Asp Ser Val Ile Gln Leu Leu Asn Pro Asn
 65                  70                  75                  80

Arg Gln Thr Ile Tyr Phe Arg Asp Phe Arg Pro Leu Lys Asp Ser Arg
                 85                  90                  95

Phe Gln Leu Leu Asn Phe Ser Ser Ser Glu Leu Lys Val Ser Leu Thr
```

```
                    100                 105                 110
Asn Val Ser Ile Ser Asp Glu Gly Arg Tyr Phe Cys Gln Leu Tyr Thr
                115                 120                 125
Asp Pro Pro Gln Glu Ser Tyr Thr Thr Ile Thr Val Leu Val Pro Pro
            130                 135                 140
Arg Asn Leu Met Ile Asp Ile Gln Lys Asp Thr Ala Val Glu Gly Glu
145                 150                 155                 160
Glu Ile Glu Val Asn Cys Thr Ala Met Ala Ser Lys Pro Ala Thr Thr
                165                 170                 175
Ile Arg Trp Phe Lys Gly Asn Thr Glu Leu Lys Gly Lys Ser Glu Val
                180                 185                 190
Glu Glu Trp Ser Asp Met Tyr Thr Val Thr Ser Gln Leu Met Leu Lys
            195                 200                 205
Val His Lys Glu Asp Asp Gly Val Pro Val Ile Cys Gln Val Glu His
            210                 215                 220
Pro Ala Val Thr Gly Asn Leu Gln Thr Gln Arg Tyr Leu Glu Val Gln
225                 230                 235                 240
Tyr Lys Pro Gln Val His Ile Gln Met Thr Tyr Pro Leu Gln Gly Leu
                245                 250                 255
Thr Arg Glu Gly Asp Ala Leu Glu Leu Thr Cys Glu Ala Ile Gly Lys
                260                 265                 270
Pro Gln Pro Val Met Val Thr Trp Val Arg Val Asp Asp Glu Met Pro
            275                 280                 285
Gln His Ala Val Leu Ser Gly Pro Asn Leu Phe Ile Asn Asn Leu Asn
            290                 295                 300
Lys Thr Asp Asn Gly Thr Tyr Arg Cys Glu Ala Ser Asn Ile Val Gly
305                 310                 315                 320
Lys Ala His Ser Asp Tyr Met Leu Tyr Val Tyr Gly Thr
                325                 330

<210> SEQ ID NO 16
<211> LENGTH: 443
<212> TYPE: PRT
<213> ORGANISM: Homo sapiens

<400> SEQUENCE: 16

Met Ala Ser Val Val Leu Pro Ser Gly Ser Gln Cys Ala Ala Ala Ala
  1               5                  10                  15
Ala Ala Ala Ala Pro Pro Gly Leu Arg Leu Arg Leu Leu Leu Leu Leu
                20                  25                  30
Phe Ser Ala Ala Ala Leu Ile Pro Thr Gly Asp Gly Gln Asn Leu Phe
            35                  40                  45
Thr Lys Asp Val Thr Val Ile Glu Gly Glu Val Ala Thr Ile Ser Cys
 50                  55                  60
Gln Val Asn Lys Ser Asp Asp Ser Val Ile Gln Leu Leu Asn Pro Asn
 65                  70                  75                  80
Arg Gln Thr Ile Tyr Phe Arg Asp Phe Arg Pro Leu Lys Asp Ser Arg
                85                  90                  95
Phe Gln Leu Leu Asn Phe Ser Ser Glu Leu Lys Val Ser Leu Thr
                100                 105                 110
Asn Val Ser Ile Ser Asp Glu Gly Arg Tyr Phe Cys Gln Leu Tyr Thr
                115                 120                 125
Asp Pro Pro Gln Glu Ser Tyr Thr Thr Ile Thr Val Leu Val Pro Pro
            130                 135                 140
```

```
Arg Asn Leu Met Ile Asp Ile Gln Lys Asp Thr Ala Val Glu Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
        195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
        275                 280                 285

Gln His Ala Val Leu Ser Gly Pro Asn Leu Phe Ile Asn Asn Leu Asn
    290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Thr Thr Ala Thr
                325                 330                 335

Thr Glu Pro Ala Val His Gly Leu Thr Gln Leu Pro Asn Ser Ala Glu
            340                 345                 350

Glu Leu Asp Ser Glu Asp Leu Ser Asp Ser Arg Ala Gly Glu Glu Gly
        355                 360                 365

Ser Ile Arg Ala Val Asp His Ala Val Ile Gly Gly Val Val Ala Val
    370                 375                 380

Val Val Phe Ala Met Leu Cys Leu Leu Ile Ile Leu Gly Arg Tyr Phe
385                 390                 395                 400

Ala Arg His Lys Gly Thr Tyr Phe Thr His Glu Ala Lys Gly Ala Asp
                405                 410                 415

Asp Ala Ala Asp Ala Asp Thr Ala Ile Ile Asn Ala Glu Gly Gly Gln
            420                 425                 430

Asn Asn Ser Glu Glu Lys Lys Glu Tyr Phe Ile
        435                 440

<210> SEQ ID NO 17
<211> LENGTH: 425
<212> TYPE: PRT
<213> ORGANISM: Homo sapiens

<400> SEQUENCE: 17

Met Ala Ser Val Val Leu Pro Ser Gly Ser Gln Cys Ala Ala Ala Ala
 1               5                  10                  15

Ala Ala Ala Ala Pro Pro Gly Leu Arg Leu Arg Leu Leu Leu Leu Leu
                20                  25                  30

Phe Ser Ala Ala Ala Leu Ile Pro Thr Gly Asp Gly Gln Asn Leu Phe
            35                  40                  45

Thr Lys Asp Val Thr Val Ile Glu Gly Glu Val Ala Thr Ile Ser Cys
        50                  55                  60

Gln Val Asn Lys Ser Asp Asp Ser Val Ile Gln Leu Leu Asn Pro Asn
65                  70                  75                  80
```

```
Arg Gln Thr Ile Tyr Phe Arg Asp Phe Arg Pro Leu Lys Asp Ser Arg
                85                  90                  95

Phe Gln Leu Leu Asn Phe Ser Ser Glu Leu Lys Val Ser Leu Thr
            100                 105                 110

Asn Val Ser Ile Ser Asp Glu Gly Arg Tyr Phe Cys Gln Leu Tyr Thr
            115                 120                 125

Asp Pro Pro Gln Glu Ser Tyr Thr Thr Ile Thr Val Leu Val Pro Pro
        130                 135                 140

Arg Asn Leu Met Ile Asp Ile Gln Lys Asp Thr Ala Val Gly Glu
145                 150                 155                 160

Glu Ile Glu Val Asn Cys Thr Ala Met Ala Ser Lys Pro Ala Thr Thr
                165                 170                 175

Ile Arg Trp Phe Lys Gly Asn Thr Glu Leu Lys Gly Lys Ser Glu Val
            180                 185                 190

Glu Glu Trp Ser Asp Met Tyr Thr Val Thr Ser Gln Leu Met Leu Lys
            195                 200                 205

Val His Lys Glu Asp Asp Gly Val Pro Val Ile Cys Gln Val Glu His
    210                 215                 220

Pro Ala Val Thr Gly Asn Leu Gln Thr Gln Arg Tyr Leu Glu Val Gln
225                 230                 235                 240

Tyr Lys Pro Gln Val His Ile Gln Met Thr Tyr Pro Leu Gln Gly Leu
                245                 250                 255

Thr Arg Glu Gly Asp Ala Leu Glu Leu Thr Cys Glu Ala Ile Gly Lys
            260                 265                 270

Pro Gln Pro Val Met Val Thr Trp Val Arg Val Asp Asp Glu Met Pro
            275                 280                 285

Gln His Ala Val Leu Ser Gly Pro Asn Leu Phe Ile Asn Asn Leu Asn
        290                 295                 300

Lys Thr Asp Asn Gly Thr Tyr Arg Cys Glu Ala Ser Asn Ile Val Gly
305                 310                 315                 320

Lys Ala His Ser Asp Tyr Met Leu Tyr Val Tyr Asp Thr Thr Ala Thr
                325                 330                 335

Thr Glu Pro Ala Val His Asp Ser Arg Ala Gly Glu Glu Gly Ser Ile
            340                 345                 350

Arg Ala Val Asp His Ala Val Ile Gly Gly Val Val Ala Val Val Val
            355                 360                 365

Phe Ala Met Leu Cys Leu Leu Ile Ile Leu Gly Arg Tyr Phe Ala Arg
        370                 375                 380

His Lys Gly Thr Tyr Phe Thr His Glu Ala Lys Gly Ala Asp Asp Ala
385                 390                 395                 400

Ala Asp Ala Asp Thr Ala Ile Ile Asn Ala Glu Gly Gly Gln Asn Asn
                405                 410                 415

Ser Glu Glu Lys Lys Glu Tyr Phe Ile
            420                 425

<210> SEQ ID NO 18
<211> LENGTH: 2940
<212> TYPE: DNA
<213> ORGANISM: Homo sapiens

<400> SEQUENCE: 18
cgccgaacgc cagcgccagg gggcggggtg ggggagggag cgaggccctc cgagagccgg     60
gttgggctcg cggcgctgtg attggtctgc ccggactccg cctccagcgc atgtcattag    120
```

-continued

```
catctcatta gctgtccgct cgggctccgg aggcagccaa cgccgccagt ctgaggcagg      180
tgcccgacat ggcgagtgta gtgctgccga gcggatccca gtgtgcggcg gcagcggcgg      240
cggcggcgcc tcccgggctc cggctccggc ttctgctgtt gctcttctcc gccgcggcac      300
tgatccccac aggtgatggg cagaatctgt ttacgaaaga cgtgacagtg atcgagggag      360
aggttgcgac catcagttgc caagtcaata gagtgacga ctctgtgatt cagctactga       420
atcccaacag gcagaccatt tatttcaggg acttcaggcc tttgaaggac agcaggtttc      480
agttgctgaa ttttctagc agtgaactca aagtatcatt gacaaacgtc tcaatttctg       540
atgaaggaag atacttttgc cagctctata ccgatccccc acaggaaagt tacaccacca      600
tcacagtcct ggtcccacca cgtaatctga tgatcgatat ccagaaagac actgcggtgg      660
aaggtgagga gattgaagtc aactgcactg ctatggccag caagccagcc acgactatca      720
ggtggttcaa agggaacaca gagctaaaag gcaaatcgga ggtggaagag tggtcagaca      780
tgtacactgt gaccagtcag ctgatgctga aggtgcacaa ggaggacgat ggggtcccag      840
tgatctgcca ggtggagcac cctgcggtca ctggaaacct gcagacccag cggtatctag      900
aagtacagta taagcctcaa gtgcacattc agatgactta tcctctacaa ggcttaaccc      960
gggaagggga cgcgcttgag ttaacatgtg aagccatcgg gaagcccag cctgtgatgg      1020 taacttgggt gagagtcgat gatgaaatgc ctcaacacgc cgtactgtct gggcccaacc      1080
tgttcatcaa taacctaaac aaaacagata atggtacata ccgctgtgaa gcttcaaaca      1140
tagtggggaa agctcactcg gattatatgc tgtatgtata cgacacaacg gcgacgacag      1200
aaccagcagt tcacgattcc cgagcaggtg aagaaggctc gatcagggca gtggatcatg      1260
ccgtgatcgg tggcgtcgtg gcggtggtgg tgttcgccat gctgtgcttg ctcatcattc      1320
tggggcgcta ttttgccaga cataaaggta catacttcac tcatgaagcc aaaggagccg      1380
atgacgcagc agacgcagac acagctataa tcaatgcaga aggaggacag aacaactccg      1440 aagaaagaa agagtacttc atctagatca gccttttgt ttcaatgagg tgtccaactg       1500
gccctattta gatgataaag agacagtgat attggaactt gcgagaaatt cgtgtgtttt      1560
tttatgaatg ggtggaaagg tgtgagactg ggaaggcttg ggatttgctg tgtaaaaaaa      1620
aaaaaaatgt tctttggaaa gtacactctg ctgtttgaca cctctttttt cgtttgtttg      1680
tttgtttaat ttttatttct tcctaccaag tcaaacttgg atacttggat ttagtttcag      1740
tagattgcag aaaattctgt gccttgtttt ttgtttgttt gttgcgttcc tttcttttcc      1800 cccttgtgc acatttattt cctccctcta ccccaatttc ggatttttc caaaatctcc        1860 cattttggaa tttgcctgct gggattcctt agactctttt ccttcccttt tctgttctag      1920
ttttttactt ttgtttattt ttatggtaac tgctttctgt tccaaattca gtttcataaa      1980
aggagaacca gcacagctta gatttcatag ttcagaattt agtgtatcca taatgcattc      2040
ttctctgttg tcgtaaagat ttgggtgaac aaacaatgaa aactctttgc tgctgcccat      2100
gtttcaaata cttagagcag tgaagactag aaaattagac tgtgattcag aaaatgttct      2160
gtttgctgtg gaactacatt actgtacagg ttatctgca agtgaggtgt gtcacaatga       2220
gattgaattt cactgtcttt aattctgtat ctgtagacgg ctcagtatag atacccctacg     2280 ctgtccagaa aggtttgggg cagaaaggac tcctcctttt tccatgccct aaacagacct     2340
gacaggtgag gtctgttcct tttatataag tggacaaatt ttgagttgcc acaggagggg      2400
aagtagggag gggggaaata cagttctgct ctggttgttt ctgttccaaa tgattccatc      2460
cacctttccc aatcggcctt acttctcact aatttgtagg aaaaagcaag ttcgtctgtt      2520
```

| | | | | |
|---|---|---|---|---|
| gtgcgaatga | ctgaatggga | cagagttgat | tttttttttt | tttcctttgt | gcttagttag | 2580 |
| gaaggcagta | ggatgtggcc | tgcatgtact | gtatattaca | gatatttgtc | atgctgggat | 2640 |
| ttccaactcg | aatctgtgtg | aaactttcat | tccttcagat | ttggcttgac | aaaggcagga | 2700 |
| ggtacaaaag | aagggctggt | attgttctca | cactggtctg | ctgtcgctct | cagttctcga | 2760 |
| taggtcagag | cagaggtgga | aaaacagcat | gtacggattt | tcagttactt | aatcaaaact | 2820 |
| caaatgtgag | tgtttttatc | tttttacctt | tcatacacta | gccttggcct | ctttcctcag | 2880 |
| ccatagtgca | tagctactaa | aatcagtgac | cttgaacata | tcttagatgg | ggagcctcgg | 2940 |

<210> SEQ ID NO 19
<211> LENGTH: 3512
<212> TYPE: DNA
<213> ORGANISM: Homo sapiens

<400> SEQUENCE: 19

| | | | | | | |
|---|---|---|---|---|---|---|
| gacatggcga | gtgtagtgct | gccgagcgga | tcccagtgtg | cggcggcagc | ggcggcggcg | 60 |
| gcgcctcccg | ggctccggct | ccggcttctg | ctgttgctct | tctccgccgc | ggcactgatc | 120 |
| cccacaggtg | atgggcagaa | tctgtttacg | aaagacgtga | cagtgatcga | gggagaggtt | 180 |
| gcgaccatca | gttgccaagt | caataagagt | gacgactctg | tgattcagct | actgaatccc | 240 |
| aacaggcaga | ccatttattt | cagggacttc | aggcctttga | aggacagcag | gtttcagttg | 300 |
| ctgaattttt | ctagcagtga | actcaaagta | tcattgacaa | acgtctcaat | ttctgatgaa | 360 |
| ggaagatact | tttgccagct | ctataccgat | cccccacagg | aaagttacac | caccatcaca | 420 |
| gtcctggtcc | caccacgtaa | tctgatgatc | gatatccaga | gagacactgc | ggtggaaggt | 480 |
| gaggagattg | aagtcaactg | cactgctatg | ccagcaagc | cagccacgac | tatcaggtgg | 540 |
| ttcaaaggga | acacagagct | aaaaggcaaa | tcggaggtgg | aagagtggtc | agacatgtac | 600 |
| actgtgacca | gtcagctgat | gctgaaggtg | cacaaggagg | acgatggggt | cccagtgatc | 660 |
| tgccaggtgg | agcaccctgc | ggtcactgga | aacctgcaga | cccagcggta | tctagaagta | 720 |
| cagtataagc | cacaagtgca | cattcagatg | acttatcctc | tacaaggctt | aacccgggaa | 780 |
| ggggacgcgc | ttgagttaac | atgtgaagcc | atcgggaagc | cccagcctgt | gatggtaact | 840 |
| tgggtgagag | tcgatgatga | aatgcctcaa | cacgccgtac | tgtctgggcc | caacctgttc | 900 |
| atcaataacc | taaacaaaac | agataatggt | acataccgct | gtgaagcttc | aaacatagtg | 960 |
| gggaaagctc | actcggatta | tatgctgtat | gtatacgatc | cccccacaac | tatccctcct | 1020 |
| cccacaacaa | ccaccaccac | caccaccacc | accaccacca | ccatccttac | catcatcaca | 1080 |
| gattcccgag | caggtgaaga | aggctcgatc | agggcagtgg | atcatgccgt | gatcggtggc | 1140 |
| gtcgtggcgg | tggtggtgtt | cgccatgctg | tgcttgctca | tcattctggg | gcgctatttt | 1200 |
| gccagacata | aagtacata | cttcactcat | gaagccaaag | gagccgatga | cgcagcagac | 1260 |
| gcagacacag | ctataatcaa | tgcagaagga | ggacagaaca | actccgaaga | aagaaagag | 1320 |
| tacttcatct | agatcagcct | ttttgtttca | atgaggtgtc | caactggccc | tatttagatg | 1380 |
| ataaagagac | agtgatattg | aacttgcga | gaaattcgtg | tgtttttta | tgaatgggtg | 1440 |
| gaaaggtgtg | agactgggaa | ggcttgggat | ttgctgtgta | aaaaaaaaaa | aaatgttct | 1500 |
| ttggaaagta | cactctgctg | tttgacacct | cttttttcgt | ttgtttgttt | gtttaatttt | 1560 |
| tatttcttcc | taccaagtca | aacttggata | cttggattta | gtttcagtag | attgcagaaa | 1620 |
| attctgtgcc | ttgttttttg | tttgtttgtt | gcgttccttt | cttttccccc | tttgtgcaca | 1680 |

```
tttatttcct ccctctaccc caatttcgga ttttttccaa aatctcccat tttggaattt      1740
gcctgctggg attccttaga ctcttttcct tcccttttct gttctagttt tttacttttg      1800
tttattttta tggtaactgc tttctgttcc aaattcagtt tcataaaagg agaaccagca      1860
cagcttagga tttcatagtt cagaatttag tgtatccata atgcattctt ctctgttgtc      1920
gtaaagattt gggtgaacaa acaatgaaaa ctctttgctg ctgcccatgt ttcaaatact      1980
tagagcagtg aagactagaa aattagactg tgattcagaa aatgttctgt ttgctgtgga      2040
actacattac tgtacagggt tatctgcaag tgaggtgtgt cacaatgaga ttgaatttca      2100
ctgtctttaa ttctgtatct gtagacggct cagtatagat accctacgct gtccagaaag      2160
gtttggggca gaaaggactc ctccttttc catgccctaa acagacctga caggtgaggt       2220
ctgttccttt tatataagtg gacaaatttt gagttgccac aggagggaa gtagggaggg       2280 gggaaataca gttctgctct ggttgtttct gttccaaatg attccatcca cctttcccaa      2340
tcggccttac ttctcactaa tttgtaggaa aaagcaagtt cgtctgttgt gcgaatgact      2400
gaatgggaca gagttgattt tttttttttt tttcctttgt gcttagttag aaggcagta       2460 ggatgtggcc tgcatgtact gtatattaca gatatttgtc atgctgggat ttccaactcg      2520
aatctgtgtg aaactttcat tccttcagat ttggcttgac aaaggcagga ggtacaaaag      2580
aagggctggt attgttctca cactggtctg ctgtcgctct cagttctcga taggtcagag      2640
cagaggtgga aaaacagcat gtacggattt tcagttactt aatcaaaact caaatgtgag      2700 tgttttatc tttttaccctt tcatacacta gccttggcct ctttcctcag ccttaagaac       2760
catctgccaa aaattactga tcctcgcatg atggcagcca tagtgcatag ctactaaaat      2820
cagtgacctt gaacatatct tagatgggga gcctcgggaa aagtagagg agtcacgtta       2880 ccatttacat gttttaaaga aagaagtgtg gggattttca ctgaaacgtc taggaaatct      2940
agaagtagtc ctgaaggaca gaaactaaac tcttaccata tgtttggtaa gactccagac      3000
tccagctaac agtccctatg gaaagatggc atcaaaaaag atagatctat atatatatat      3060
aaatatatat tctattacat tttcagtgag taattttgga ttttgcaagg tgcatttta       3120 ctattgttac attatgtgga aaacttatgc tgatttattt aagggggaaa aagtgtcaac      3180
tctttgttat ttgaaaacat gtttatttt cttgtcttta ttttaacctt tgatagaacc       3240
attgcaatat gggggccttt tgggaacgga ctggtatgta aagaaaatc cattatcgag       3300 cagcatttta tttaccccctc ccctatccct aggcacttaa ccaagacaaa agccacaat      3360 gaacatccct ttttcaatga attttataat ctgcagctct attccgagcc cttagcaccc      3420
attccgacca tagtataatc atatcaaagg gtgagaatca tttagcatgt tgttgaaagg      3480
ttttttttca gttgttcttt ttagaaaaaa ag                                    3512

<210> SEQ ID NO 20
<211> LENGTH: 2940
<212> TYPE: DNA
<213> ORGANISM: Homo sapiens

<400> SEQUENCE: 20
cgccgaacgc cagcgccagg gggcggggtg ggggagggag cgaggccctc cgagagccgg        60
gttgggctcg cggcgctgtg attggtctgc ccggactccg cctccagcgc atgtcattag       120
catctcatta gctgtccgct cgggctccgg aggcagccaa cgccgccagt ctgaggcagg       180
tgcccgacat ggcgagtgta gtgctgccga gcggatccca gtgtgcggcg gcagcggcgg       240
cggcggcgcc tcccgggctc cggctccggc ttctgctgtt gctcttctcc gccgcggcac       300
```

-continued

| | | |
|---|---|---|
| tgatccccac aggtgatggg cagaatctgt ttacgaaaga cgtgacagtg atcgagggag | 360 |
| aggttgcgac catcagttgc caagtcaata agagtgacga ctctgtgatt cagctactga | 420 |
| atcccaacag gcagaccatt tatttcaggg acttcaggcc tttgaaggac agcaggtttc | 480 |
| agttgctgaa ttttctagc agtgaactca agtatcatt gacaaacgtc tcaatttctg | 540 |
| atgaaggaag atacttttgc cagctctata ccgatccccc acaggaaagt tacaccacca | 600 |
| tcacagtcct ggtcccacca cgtaatctga tgatcgatat ccagaaagac actgcggtgg | 660 |
| aaggtgagga gattgaagtc aactgcactg ctatggccag caagccagcc acgactatca | 720 |
| ggtggttcaa agggaacaca gagctaaaag gcaaatcgga ggtggaagag tggtcagaca | 780 |
| tgtacactgt gaccagtcag ctgatgctga aggtgcacaa ggaggacgat ggggtcccag | 840 |
| tgatctgcca ggtggagcac cctgcggtca ctggaaaccct gcagacccag cggtatctag | 900 |
| aagtacagta taagcctcaa gtgcacattc agatgactta tcctctacaa ggcttaaccc | 960 |
| gggaagggga cgcgcttgag ttaacatgtg aagccatcgg gaagcccag cctgtgatgg | 1020 |
| taacttgggt gagagtcgat gatgaaatgc ctcaacacgc cgtactgtct gggcccaacc | 1080 |
| tgttcatcaa taacctaaac aaaacagata atggtacata ccgctgtgaa gcttcaaaca | 1140 |
| tagtggggaa agctcactcg gattatatgc tgtatgtata cgacacaacg gcgacgacag | 1200 |
| aaccagcagt tcacgattcc cgagcaggtg aagaaggctc gatcagggca gtggatcatg | 1260 |
| ccgtgatcgg tggcgtcgtg gcggtggtgg tgttcgccat gctgtgcttg ctcatcattc | 1320 |
| tggggcgcta ttttgccaga cataaaggta catacttcac tcatgaagcc aaaggagccg | 1380 |
| atgacgcagc agacgcagac acagctataa tcaatgcaga aggaggacag aacaactccg | 1440 |
| aagaaaagaa agagtacttc atctagatca gcctttttgt ttcaatgagg tgtccaactg | 1500 |
| gccctattta gatgataaag agacagtgat attggaactt gcgagaaatt cgtgtgtttt | 1560 |
| tttatgaatg ggtggaaagg tgtgagactg ggaaggcttg ggatttgctg tgtaaaaaaa | 1620 |
| aaaaaaatgt tctttggaaa gtacactctg ctgtttgaca cctctttttt cgtttgtttg | 1680 |
| tttgtttaat ttttattct tcctaccaag tcaaacttgg atacttggat ttagtttcag | 1740 |
| tagattgcag aaaattctgt gccttgtttt ttgtttgttt gttgcgttcc tttctttttcc | 1800 |
| cccttttgtgc acatttattt cctccctcta ccccaatttc ggattttttc caaaatctcc | 1860 |
| cattttggaa tttgcctgct gggattcctt agactctttt ccttcccttt tctgttctag | 1920 |
| ttttttactt ttgtttattt ttatggtaac tgctttctgt tccaaattca gtttcataaa | 1980 |
| aggagaacca gcacagctta gatttcatag ttcagaattt agtgtatcca taatgcattc | 2040 |
| ttctctgttg tcgtaaagat ttgggtgaac aaacaatgaa aactctttgc tgctgcccat | 2100 |
| gtttcaaata cttagagcag tgaagactag aaaattagac tgtgattcag aaaatgttct | 2160 |
| gtttgctgtg gaactacatt actgtacagg gttatctgca agtgaggtgt gtcacaatga | 2220 |
| gattgaattt cactgtcttt aattctgtat ctgtagacgg ctcagtatag atacccctacg | 2280 |
| ctgtccagaa aggtttgggg cagaaaggac tcctccttt tccatgccct aaacagacct | 2340 |
| gacaggtgag gtctgttcct tttatataag tggacaaatt ttgagttgcc acaggagggg | 2400 |
| aagtagggag gggggaaata cagttctgct ctggttgttt ctgttccaaa tgattccatc | 2460 |
| cacctttccc aatcggcctt acttctcact aatttgtagg aaaaagcaag ttcgtctgtt | 2520 |
| gtgcgaatga ctgaatggga cagagttgat ttttttttt tttcctttgt gcttagttag | 2580 |
| gaaggcagta ggatgtggcc tgcatgtact gtatattaca gatatttgtc atgctgggat | 2640 |

-continued

| | | | | |
|---|---|---|---|---|
| ttccaactcg | aatctgtgtg | aaactttcat | tccttcagat | ttggcttgac | aaaggcagga | 2700 |
| ggtacaaaag | aagggctggt | attgttctca | cactggtctg | ctgtcgctct | cagttctcga | 2760 |
| taggtcagag | cagaggtgga | aaaacagcat | gtacggattt | tcagttactt | aatcaaaact | 2820 |
| caaatgtgag | tgttttatc | tttttacctt | tcatacacta | gccttggcct | ctttcctcag | 2880 |
| ccatagtgca | tagctactaa | aatcagtgac | cttgaacata | tcttagatgg | ggagcctcgg | 2940 |

<210> SEQ ID NO 21  
<211> LENGTH: 2940  
<212> TYPE: DNA  
<213> ORGANISM: Homo sapiens

<400> SEQUENCE: 21

| | | | | | |
|---|---|---|---|---|---|
| cgccgaacgc | cagcgccagg | gggcggggtg | ggggagggag | cgaggccctc | cgagagccgg | 60 |
| gttgggctcg | cggcgctgtg | attggtctgc | ccggactccg | cctccagcgc | atgtcattag | 120 |
| catctcatta | gctgtccgct | cgggctccgg | aggcagccaa | cgccgccagt | ctgaggcagg | 180 |
| tgcccgacat | ggcgagtgta | gtgctgccga | gcggatccca | gtgtgcggcg | gcagcggcgg | 240 |
| cggcggcgcc | tccgggctc | cggctccggc | ttctgctgtt | gctcttctcc | gccgcggcac | 300 |
| tgatccccac | aggtgatggg | cagaatctgt | ttacgaaaga | cgtgacagtg | atcgagggag | 360 |
| aggttgcgac | catcagttgc | caagtcaata | agagtgacga | ctctgtgatt | cagctactga | 420 |
| atcccaacag | gcagaccatt | tatttcaggg | acttcaggcc | tttgaaggac | agcaggtttc | 480 |
| agttgctgaa | tttttctagc | agtgaactca | agtatcatt | gacaaacgtc | tcaatttctg | 540 |
| atgaaggaag | atacttttgc | cagctctata | ccgatccccc | acaggaaagt | tacaccacca | 600 |
| tcacagtcct | ggtcccacca | cgtaatctga | tgatcgatat | ccagaaagac | actgcggtgg | 660 |
| aaggtgagga | gattgaagtc | aactgcactg | ctatggccag | caagccagcc | acgactatca | 720 |
| ggtggttcaa | agggaacaca | gagctaaaag | gcaaatcgga | ggtggaagag | tggtcagaca | 780 |
| tgtacactgt | gaccagtcag | ctgatgctga | aggtgcacaa | ggaggacgat | ggggtcccag | 840 |
| tgatctgcca | ggtggagcac | cctgcggtca | ctggaaaccct | gcagacccag | cggtatctag | 900 |
| aagtacagta | taagcctcaa | gtgcacattc | agatgactta | tcctctacaa | ggcttaaccc | 960 |
| gggaagggga | cgcgcttgag | ttaacatgtg | aagccatcgg | gaagcccccag | cctgtgatgg | 1020 |
| taacttgggt | gagagtcgat | gatgaaatgc | ctcaacacgc | cgtactgtct | gggcccaacc | 1080 |
| tgttcatcaa | taacctaaac | aaaacagata | atggtacata | ccgctgtgaa | gcttcaaaca | 1140 |
| tagtggggaa | agctcactcg | gattatatgc | tgtatgtata | cgacacaacg | gcgacgacag | 1200 |
| aaccagcagt | tcacgattcc | cgagcaggtg | aagaaggctc | gatcagggca | gtggatcatg | 1260 |
| ccgtgatcgg | tggcgtcgtg | gcggtggtgg | tgttcgccat | gctgtgcttg | ctcatcattc | 1320 |
| tggggcgcta | ttttgccaga | cataaaggta | catacttcac | tcatgaagcc | aaaggagccg | 1380 |
| atgacgcagc | agacgcagac | acagctataa | tcaatgcaga | aggaggacag | aacaactccg | 1440 |
| aagaaagaa | agagtacttc | atctagatca | gccttttgt | ttcaatgagg | tgtccaactg | 1500 |
| gccctattta | gatgataaag | agacagtgat | attggaactt | gcgagaaatt | cgtgtgtttt | 1560 |
| tttatgaatg | ggtggaaagg | tgtgagactg | ggaaggcttg | ggatttgctg | tgtaaaaaaa | 1620 |
| aaaaaaatgt | tctttggaaa | gtacactctg | ctgtttgaca | cctcttttt | cgttgtttg | 1680 |
| tttgtttaat | tttatttct | tcctaccaag | tcaaacttgg | atacttggat | ttagtttcag | 1740 |
| tagattgcag | aaaattctgt | gccttgtttt | ttgtttgttt | gttgcgttcc | tttctttcc | 1800 |
| ccctttgtgc | acatttattt | cctccctcta | ccccaatttc | ggattttttc | caaaatctcc | 1860 |

```
catttggaa tttgcctgct gggattcctt agactctttt ccttcccttt tctgttctag    1920 tttttactt tgtttattt ttatggtaac tgctttctgt tccaaattca gtttcataaa     1980
aggagaacca gcacagctta gatttcatag ttcagaattt agtgtatcca taatgcattc   2040
ttctctgttg tcgtaaagat ttgggtgaac aaacaatgaa aactctttgc tgctgcccat   2100
gtttcaaata cttagagcag tgaagactag aaaattagac tgtgattcag aaaatgttct   2160
gtttgctgtg gaactacatt actgtacagg gttatctgca agtgaggtgt gtcacaatga   2220
gattgaattt cactgtcttt aattctgtat ctgtagacgg ctcagtatag atacctacg    2280 ctgtccagaa aggtttgggg cagaaaggac tcctcctttt tccatgccct aaacagacct   2340
gacaggtgag gtctgttcct tttatataag tggacaaatt ttgagttgcc acaggagggg   2400
aagtagggag gggggaaata cagttctgct ctggttgttt ctgttccaaa tgattccatc   2460
cacctttccc aatcggcctt acttctcact aatttgtagg aaaaagcaag ttcgtctgtt   2520
gtgcgaatga ctgaatggga cagagttgat tttttttttt tttcctttgt gcttagttag   2580
gaaggcagta ggatgtggcc tgcatgtact gtatattaca gatatttgtc atgctgggat   2640
ttccaactcg aatctgtgtg aaactttcat tccttcagat ttggcttgac aaaggcagga   2700
ggtacaaaag aagggctggt attgttctca cactggtctg ctgtcgctct cagttctcga   2760
taggtcagag cagaggtgga aaaacagcat gtacggattt tcagttactt aatcaaaact   2820
caaatgtgag tgttttatc tttttacctt tcatacacta gccttggcct ctttcctcag    2880
ccatagtgca tagctactaa aatcagtgac cttgaacata tcttagatgg ggagcctcgg   2940

<210> SEQ ID NO 22
<211> LENGTH: 2940
<212> TYPE: DNA
<213> ORGANISM: Homo sapiens

<400> SEQUENCE: 22
cgccgaacgc cagcgccagg gggcggggtg ggggagggag cgaggccctc cgagagccgg     60
gttgggctcg cggcgctgtg attggtctgc ccggactccg cctccagcgc atgtcattag    120
catctcatta gctgtccgct cgggctccgg aggcagccaa cgccgccagt ctgaggcagg    180
tgcccgacat ggcgagtgta gtgctgccga gcggatccca gtgtgcggcg gcagcggcgg    240
cggcggcgcc tcccgggctc cggctccggc ttctgctgtt gctcttctcc gccgcggcac    300
tgatccccac aggtgatggg cagaatctgt ttacgaaaga cgtgacagtg atcgagggag    360
aggttgcgac catcagttgc caagtcaata agagtgacga ctctgtgatt cagctactga   420
atcccaacag gcagaccatt tatttcaggg acttcaggcc tttgaaggac agcaggtttc    480
agttgctgaa ttttctagc agtgaactca agtatcatt gacaaacgtc tcaatttctg     540
atgaaggaag atacttttgc cagctctata ccgatccccc acaggaaagt tacaccacca    600
tcacagtcct ggtcccacca cgtaatctga tgatcgatat ccagaaagac actgcggtgg   660
aaggtgagga gattgaagtc aactgcactg ctatggccag caagccagcc acgactatca    720
ggtggttcaa agggaacaca gagctaaaag gcaaatcgga ggtggaagag tggtcagaca   780
tgtacactgt gaccagtcag ctgatgctga aggtgcacaa ggaggacgat ggggtcccag   840
tgatctgcca ggtggagcac cctgcggtca ctggaaacct gcagacccag cggtatctag    900
aagtacagta taagcctcaa gtgcacattc agatgactta tcctctacaa ggcttaaccc    960
gggaagggga cgcgcttgag ttaacatgtg aagccatcgg gaagcccag cctgtgatgg    1020
```

```
taacttgggt gagagtcgat gatgaaatgc ctcaacacgc cgtactgtct gggcccaacc    1080
tgttcatcaa taacctaaac aaaacagata atggtacata ccgctgtgaa gcttcaaaca    1140
tagtggggaa agctcactcg gattatatgc tgtatgtata cgacacaacg gcgacgacag    1200
aaccagcagt tcacgattcc cgagcaggtg aagaaggctc gatcagggca gtggatcatg    1260
ccgtgatcgg tggcgtcgtg gcggtggtgg tgttcgccat gctgtgcttg ctcatcattc    1320
tggggcgcta ttttgccaga cataaaggta catacttcac tcatgaagcc aaaggagccg    1380
atgacgcagc agacgcagac acagctataa tcaatgcaga aggaggacag aacaactccg    1440
aagaaaagaa agagtacttc atctagatca gccttttgt ttcaatgagg tgtccaactg    1500
gccctattta gatgataaag agacagtgat attggaactt gcgagaaatt cgtgtgtttt    1560
tttatgaatg ggtggaaagg tgtgagactg gaaggcttg ggatttgctg tgtaaaaaaa    1620
aaaaaaatgt tctttggaaa gtacactctg ctgtttgaca cctctttttt cgtttgtttg    1680
tttgtttaat tttatttct tcctaccaag tcaaacttgg atacttggat ttagtttcag    1740
tagattgcag aaaattctgt gccttgtttt ttgtttgttt gttgcgttcc tttctttcc    1800 cccttttgtgc acatttattt cctccctcta ccccaatttc ggattttttc caaaatctcc    1860
cattttggaa tttgcctgct gggattcctt agactctttt ccttcccttt tctgttctag    1920
ttttttactt ttgtttattt ttatggtaac tgctttctgt tccaaattca gttttcataaa    1980 aggagaacca gcacagctta gatttcatag ttcagaattt agtgtatcca taatgcattc    2040
ttctctgttg tcgtaaagat ttgggtgaac aaacaatgaa aactctttgc tgctgcccat    2100
gtttcaaata cttagagcag tgaagactag aaaattagac tgtgattcag aaaatgttct    2160
gtttgctgtg gaactacatt actgtacagg gttatctgca agtgaggtgt gtcacaatga    2220
gattgaattt cactgtcttt aattctgtat ctgtagacgg ctcagtatag atatccctacg    2280 ctgtccagaa aggtttgggg cagaaaggac tcctccttt tccatgccct aaacagacct    2340
gacaggtgag gtctgttcct tttatataag tggacaaatt ttgagttgcc acaggagggg    2400
aagtagggag gggggaaata cagttctgct ctggttgttt ctgttccaaa tgattccatc    2460
cacctttccc aatcggcctt acttctcact aatttgtagg aaaaagcaag ttcgtctgtt    2520
gtgcgaatga ctgaatggga cagagttgat tttttttttt tttcctttgt gcttagttag    2580
gaaggcagta ggatgtggcc tgcatgtact gtatattaca gatatttgtc atgctgggat    2640
ttccaactcg aatctgtgtg aaactttcat tccttcagat ttggcttgac aaaggcagga    2700
ggtacaaaag aagggctggt attgttctca cactggtctg ctgtcgctct cagttctcga    2760
taggtcagag cagaggtgga aaaacagcat gtacggattt tcagttactt aatcaaaact    2820
caaatgtgag tgtttttatc ttttaccttt catacacta gccttggcct ctttcctcag    2880
ccatagtgca tagctactaa aatcagtgac cttgaacata tcttagatgg ggagcctcgg    2940
```

<210> SEQ ID NO 23
<211> LENGTH: 788
<212> TYPE: PRT
<213> ORGANISM: Homo sapiens

<400> SEQUENCE: 23

```
Met Gly Ile Glu Leu Leu Cys Leu Phe Phe Leu Phe Leu Gly Arg Asn
 1               5                  10                  15

Asp His Val Gln Gly Gly Cys Ala Leu Gly Gly Ala Glu Thr Cys Glu
            20                  25                  30

Asp Cys Leu Leu Ile Gly Pro Gln Cys Ala Trp Cys Ala Gln Glu Asn
```

-continued

```
                35                  40                  45
Phe Thr His Pro Ser Gly Val Gly Glu Arg Cys Asp Thr Pro Ala Asn
 50                  55                  60

Leu Leu Ala Lys Gly Cys Gln Leu Asn Phe Ile Glu Asn Pro Val Ser
 65                  70                  75                  80

Gln Val Glu Ile Leu Lys Asn Lys Pro Leu Ser Val Gly Arg Gln Lys
                 85                  90                  95

Asn Ser Ser Asp Ile Val Gln Ile Ala Pro Gln Ser Leu Ile Leu Lys
                100                 105                 110

Leu Arg Pro Gly Gly Ala Gln Thr Leu Gln Val His Val Arg Gln Thr
                115                 120                 125

Glu Asp Tyr Pro Val Asp Leu Tyr Tyr Leu Met Asp Leu Ser Ala Ser
130                 135                 140

Met Asp Asp Asp Leu Asn Thr Ile Lys Glu Leu Gly Ser Arg Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
                180                 185                 190

Ile Ala Asn Pro Cys Ser Ser Ile Pro Tyr Phe Cys Leu Pro Thr Phe
                195                 200                 205

Gly Phe Lys His Ile Leu Pro Leu Thr Asn Asp Ala Glu Arg Phe Asn
210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255

Gly Trp Arg Asn Asp Ser Leu His Leu Leu Val Phe Val Ser Asp Ala
                260                 265                 270

Asp Ser His Phe Gly Met Asp Ser Lys Leu Ala Gly Ile Val Ile Pro
                275                 280                 285

Asn Asp Gly Leu Cys His Leu Asp Ser Lys Asn Glu Tyr Ser Met Ser
                290                 295                 300

Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
                340                 345                 350

Leu Gln Lys Asp Ser Gly Asn Ile Leu Gln Leu Ile Ile Ser Ala Tyr
                355                 360                 365

Glu Glu Leu Arg Ser Glu Val Glu Leu Glu Val Leu Gly Asp Thr Glu
                370                 375                 380

Gly Leu Asn Leu Ser Phe Thr Ala Ile Cys Asn Asn Gly Thr Leu Phe
385                 390                 395                 400

Gln His Gln Lys Lys Cys Ser His Met Lys Val Gly Asp Thr Ala Ser
                405                 410                 415

Phe Ser Val Thr Val Asn Ile Pro His Cys Glu Arg Arg Ser Arg His
                420                 425                 430

Ile Ile Ile Lys Pro Val Gly Leu Gly Asp Ala Leu Glu Leu Leu Val
                435                 440                 445

Ser Pro Glu Cys Asn Cys Asp Cys Gln Lys Glu Val Glu Val Asn Ser
450                 455                 460
```

```
Ser Lys Cys His His Gly Asn Gly Ser Phe Gln Cys Gly Val Cys Ala
465                 470                 475                 480

Cys His Pro Gly His Met Gly Pro Arg Cys Glu Cys Gly Glu Asp Met
            485                 490                 495

Leu Ser Thr Asp Ser Cys Lys Glu Ala Pro Asp His Pro Ser Cys Ser
                500                 505                 510

Gly Arg Gly Asp Cys Tyr Cys Gly Gln Cys Ile Cys His Leu Ser Pro
            515                 520                 525

Tyr Gly Asn Ile Tyr Gly Pro Tyr Cys Gln Cys Asp Asn Phe Ser Cys
            530                 535                 540

Val Arg His Lys Gly Leu Leu Cys Gly Gly Asn Gly Asp Cys Asp Cys
545                 550                 555                 560

Gly Glu Cys Val Cys Arg Ser Gly Trp Thr Gly Glu Tyr Cys Asn Cys
                565                 570                 575

Thr Thr Ser Thr Asp Ser Cys Val Ser Glu Asp Gly Val Leu Cys Ser
                580                 585                 590

Gly Arg Gly Asp Cys Val Cys Gly Lys Cys Val Cys Thr Asn Pro Gly
            595                 600                 605

Ala Ser Gly Pro Thr Cys Glu Arg Cys Pro Thr Cys Gly Asp Pro Cys
610                 615                 620

Asn Ser Lys Arg Ser Cys Ile Glu Cys His Leu Ser Ala Ala Gly Gln
625                 630                 635                 640

Ala Arg Glu Glu Cys Val Asp Lys Cys Lys Leu Ala Gly Ala Thr Ile
                645                 650                 655

Ser Glu Glu Glu Asp Phe Ser Lys Asp Gly Ser Val Ser Cys Ser Leu
                660                 665                 670

Gln Gly Glu Asn Glu Cys Leu Ile Thr Phe Leu Ile Thr Thr Asp Asn
            675                 680                 685

Glu Gly Lys Thr Ile Ile His Ser Ile Asn Glu Lys Asp Cys Pro Lys
690                 695                 700

Pro Pro Asn Ile Pro Met Ile Met Leu Gly Val Ser Leu Ala Ile Leu
705                 710                 715                 720

Leu Ile Gly Val Val Leu Leu Cys Ile Trp Lys Leu Leu Val Ser Phe
                725                 730                 735

His Asp Arg Lys Glu Val Ala Lys Phe Glu Ala Glu Arg Ser Lys Ala
            740                 745                 750

Lys Trp Gln Thr Gly Thr Asn Pro Leu Tyr Arg Gly Ser Thr Ser Thr
            755                 760                 765

Phe Lys Asn Val Thr Tyr Lys His Arg Glu Lys Gln Lys Val Asp Leu
770                 775                 780

Ser Thr Asp Cys
785

<210> SEQ ID NO 24
<211> LENGTH: 2932
<212> TYPE: DNA
<213> ORGANISM: Homo sapiens

<400> SEQUENCE: 24
cacagcaaga actgaaacga atggggattg aactgctttg cctgttcttt ctatttctag     60
gaaggaatga tcacgtacaa ggtggctgtg ccctgggagg tgcagaaacc tgtgaagact    120
gcctgcttat tggaccctcag tgtgcctggt gtgctcagga gaattttact catccatctg    180
gagttggcga aggtgtgat accccagcaa acctttttagc taaaggatgt caattaaact    240
```

-continued

```
tcatcgaaaa ccctgtctcc caagtagaaa tacttaaaaa taagcctctc agtgtaggca     300
gacagaaaaa tagttctgac attgttcaga ttgcgcctca aagcttgatc cttaagttga     360
gaccaggtgg tgcgcagact ctgcaggtgc atgtccgcca gactgaggac tacccggtgg     420
atttgtatta cctcatggac ctctccgcct ccatggatga cgacctcaac acaataaagg     480
agctgggctc ccggctttcc aaagagatgt ctaaattaac cagcaacttt agactgggct     540
tcggatcttt tgtggaaaaa cctgtatccc cttttgtgaa aacaacacca gaagaaattg     600
ccaacccttg cagtagtatt ccatacttct gtttacctac atttggattc aagcacattt     660
tgccattgac aaatgatgct gaaagattca atgaaattgt gaagaatcag aaaatttctg     720
ctaatattga cacacccgaa ggtggatttg atgcaattat gcaagctgct gtgtgtaagg     780
aaaaaattgg ctggcggaat gactccctcc acctcctggt ctttgtgagt gatgctgatt     840
ctcattttgg aatggacagc aaactagcag gcatcgtcat tcctaatgac gggctctgtc     900
acttggacag caagaatgaa tactccatgt caactgtctt ggaatatcca acaattggac     960
aactcattga taaactggta caaaacaacg tgttattgat cttcgctgta acccaagaac    1020
aagttcattt atatgagaat tacgcaaaac ttattcctgg agctacagta ggtctacttc    1080
agaaggactc cggaaacatt ctccagctga tcatctcagc ttatgaagaa ctgcggtctg    1140
aggtggaact ggaagtatta ggagacactg aaggactcaa cttgtcattt acagccatct    1200
gtaacaacgg taccctcttc caacaccaaa agaaatgctc tcacatgaaa gtgggagaca    1260
cagcttcctt cagcgtgact gtgaatatcc cacactgcga gagaagaagc aggcacatta    1320
tcataaagcc tgtggggctg ggggatgccc tggaattact tgtcagccca gaatgcaact    1380
gcgactgtca gaaagaagtg gaagtgaaca gctccaaatg tcaccacggg aacggctctt    1440
tccagtgtgg ggtgtgtgcc tgccaccctg ccacatgggc gctcgctgt gagtgtggcg    1500
aggacatgct gagcacagat tcctgcaagg aggcccaga tcatccctcc tgcagcggaa    1560
ggggtgactg ctactgtggg cagtgtatct gccacttgtc tccctatgga acatttatg    1620
ggccttattg ccagtgtgac aatttctcct gcgtgagaca caaagggctg ctctgcggag    1680
gtaacggcga ctgtgactgt ggtgaatgtg tgtgcaggag cggctggact ggcgagtact    1740
gcaactgcac caccagcacg gactcctgcg tctctgaaga tggagtgctc tgcagcgggc    1800
gcggggactg tgtttgtggc aagtgtgttt gcacaaaccc tggagcctca ggaccaacct    1860
gtgaacgatg tcctacctgt ggtgacccct gtaactctaa acggagctgc attgagtgcc    1920
acctgtcagc agctggccaa gcccgagaag aatgtgtgga caagtgcaaa ctagctggtg    1980
cgaccatcag tgaagaagaa gatttctcaa aggatggttc tgtttcctgc tctctgcaag    2040
gagaaaatga atgtcttatt acattcctaa taactacaga taatgagggg aaaaccatca    2100
ttcacagcat caatgaaaaa gattgtccga agcctccaaa cattcccatg atcatgttag    2160
gggtttccct ggctattctt ctcatcgggg ttgtcctact gtgcatctgg aagctactgg    2220
tgtcatttca tgatcgtaaa gaagttgcca aatttgaagc agaacgatca aaagccaagt    2280
ggcaaacggg aaccaatcca ctctacagag gatccacaag tactttaaa aatgtaactt    2340
ataaacacag ggaaaaacaa aaggtagacc tttccacaga ttgctagaac tactttatgc    2400
atgaaaaag tctgtttcac tgatatgaaa tgttaatgca ctatttaatt ttttctctt    2460
tgttgcttca aaatgaggtt ggtttaagat aataatagga catctgcaga taagtcatcc    2520
tctacatgaa ggtgacagac tgttggcagt ttcaaaataa tcaagaagag aaatatcctt    2580
```

```
agcaaagaga tgactttggg gatcatttga ggaatactaa ctctgttgca ttaatgcttc    2640
aaaaaatcat caaatgattc atgggggcct gatttgcatt tgaaaaatgt ttgaaattag    2700
agtctcattt gtttcaggaa tgcagctacc tgagttttt gtctcggcaa agtcacaaag     2760
cccatatact cacattgtgt gtctatactt gccaattaat tctaaacttg taggaaatat    2820
gccctctctt aaaggagaat ttttttaaa tctctgagaa atgagattct gagtttattt     2880
cagctaaaag gttgcaattc ttctgaagat atctcaaata taaggttgaa ag            2932
```

<210> SEQ ID NO 25
<211> LENGTH: 1179
<212> TYPE: PRT
<213> ORGANISM: Homo sapiens

<400> SEQUENCE: 25

```
Met Ala Ala Cys Gly Arg Val Arg Arg Met Phe Arg Leu Ser Ala Ala
 1               5                   10                  15

Leu His Leu Leu Leu Leu Phe Ala Ala Gly Ala Glu Lys Leu Pro Gly
                20                  25                  30

Gln Gly Val His Ser Gln Gly Gln Gly Pro Gly Ala Asn Phe Val Ser
            35                  40                  45

Phe Val Gly Gln Ala Gly Gly Gly Pro Ala Gly Gln Gln Leu Pro
        50                  55                  60

Gln Leu Pro Gln Ser Ser Gln Leu Gln Gln Gln Gln Gln Gln Gln Gln
65                  70                  75                  80

Gln Gln Gln Gln Pro Gln Pro Pro Gln Pro Pro Phe Pro Ala Gly Gly
                85                  90                  95

Pro Pro Ala Arg Arg Gly Gly Ala Gly Ala Gly Gly Gly Trp Lys Leu
            100                 105                 110

Ala Glu Glu Glu Ser Cys Arg Glu Asp Val Thr Arg Val Cys Pro Lys
        115                 120                 125

His Thr Trp Ser Asn Asn Leu Ala Val Leu Glu Cys Leu Gln Asp Val
    130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
            180                 185                 190

Glu Pro Val Gly Lys Gly Tyr Met Val Ser Cys Leu Val Asp His Arg
        195                 200                 205

Gly Asn Ile Thr Glu Tyr Gln Cys His Gln Tyr Ile Thr Lys Met Thr
    210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
            260                 265                 270

Gly Leu Val Lys Glu Ala Glu Arg Glu Pro Lys Ile Gln Val Ser
        275                 280                 285

Glu Leu Cys Lys Lys Ala Ile Leu Arg Val Ala Glu Leu Ser Ser Asp
    290                 295                 300

Asp Phe His Leu Asp Arg His Leu Tyr Phe Ala Cys Arg Asp Asp Arg
305                 310                 315                 320
```

```
Glu Arg Phe Cys Glu Asn Thr Gln Ala Gly Glu Gly Arg Val Tyr Lys
                325                 330                 335

Cys Leu Phe Asn His Lys Phe Glu Glu Ser Met Ser Glu Lys Cys Arg
            340                 345                 350

Glu Ala Leu Thr Thr Arg Gln Lys Leu Ile Ala Gln Asp Tyr Lys Val
        355                 360                 365

Ser Tyr Ser Leu Ala Lys Ser Cys Lys Ser Asp Leu Lys Lys Tyr Arg
    370                 375                 380

Cys Asn Val Glu Asn Leu Pro Arg Ser Arg Glu Ala Arg Leu Ser Tyr
385                 390                 395                 400

Leu Leu Met Cys Leu Glu Ser Ala Val His Arg Gly Arg Gln Val Ser
                405                 410                 415

Ser Glu Cys Gln Gly Glu Met Leu Asp Tyr Arg Arg Met Leu Met Glu
            420                 425                 430

Asp Phe Ser Leu Ser Pro Glu Ile Ile Leu Ser Cys Arg Gly Glu Ile
        435                 440                 445

Glu His His Cys Ser Gly Leu His Arg Lys Gly Arg Thr Leu His Cys
    450                 455                 460

Leu Met Lys Val Val Arg Gly Glu Lys Gly Asn Leu Gly Met Asn Cys
465                 470                 475                 480

Gln Gln Ala Leu Gln Thr Leu Ile Gln Glu Thr Asp Pro Gly Ala Asp
                485                 490                 495

Tyr Arg Ile Asp Arg Ala Leu Asn Glu Ala Cys Glu Ser Val Ile Gln
            500                 505                 510

Thr Ala Cys Lys His Ile Arg Ser Gly Asp Pro Met Ile Leu Ser Cys
        515                 520                 525

Leu Met Glu His Leu Tyr Thr Glu Lys Met Val Glu Asp Cys Glu His
    530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
                565                 570                 575

Thr His Gly Trp Asn Glu Thr Ser Glu Phe Met Pro Gln Gly Ala Val
            580                 585                 590

Phe Ser Cys Leu Tyr Arg His Ala Tyr Arg Thr Glu Glu Gln Gly Arg
        595                 600                 605

Arg Leu Ser Arg Glu Cys Arg Ala Glu Val Gln Arg Ile Leu His Gln
    610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
                645                 650                 655

Leu Glu Cys Leu Gln Asp His Leu Asp Asp Leu Val Val Glu Cys Arg
            660                 665                 670

Asp Ile Val Gly Asn Leu Thr Glu Leu Glu Ser Glu Asp Ile Gln Ile
        675                 680                 685

Glu Ala Leu Leu Met Arg Ala Cys Glu Pro Ile Ile Gln Asn Phe Cys
    690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
                725                 730                 735
```

```
Gly Val Thr His Phe Gln Leu Val Gln Met Lys Asp Phe Arg Phe Ser
            740                 745                 750
Tyr Lys Phe Lys Met Ala Cys Lys Glu Asp Val Leu Lys Leu Cys Pro
        755                 760                 765
Asn Ile Lys Lys Val Asp Val Ile Cys Leu Ser Thr Thr Val
770                 775                 780
Arg Asn Asp Thr Leu Gln Glu Ala Lys Glu His Arg Val Ser Leu Lys
785                 790                 795                 800
Cys Arg Arg Gln Leu Arg Val Glu Glu Leu Glu Met Thr Glu Asp Ile
            805                 810                 815
Arg Leu Glu Pro Asp Leu Tyr Glu Ala Cys Lys Ser Asp Ile Lys Asn
            820                 825                 830
Phe Cys Ser Ala Val Gln Tyr Gly Asn Ala Gln Ile Ile Glu Cys Leu
        835                 840                 845
Lys Glu Asn Lys Lys Gln Leu Ser Thr Arg Cys His Gln Lys Val Phe
850                 855                 860
Lys Leu Gln Glu Thr Glu Met Met Asp Pro Glu Leu Asp Tyr Thr Leu
865                 870                 875                 880
Met Arg Val Cys Lys Gln Met Ile Lys Arg Phe Cys Pro Glu Ala Asp
            885                 890                 895
Ser Lys Thr Met Leu Gln Cys Leu Lys Gln Asn Lys Asn Ser Glu Leu
        900                 905                 910
Met Asp Pro Lys Cys Lys Gln Met Ile Thr Lys Arg Gln Ile Thr Gln
            915                 920                 925
Asn Thr Asp Tyr Arg Leu Asn Pro Met Leu Arg Lys Ala Cys Lys Ala
930                 935                 940
Asp Ile Pro Lys Phe Cys His Gly Ile Leu Thr Lys Ala Lys Asp Asp
945                 950                 955                 960
Ser Glu Leu Glu Gly Gln Val Ile Ser Cys Leu Lys Leu Arg Tyr Ala
            965                 970                 975
Asp Gln Arg Leu Ser Ser Asp Cys Glu Asp Gln Ile Arg Ile Ile Ile
            980                 985                 990
Gln Glu Ser Ala Leu Asp Tyr Arg Leu Asp Pro Gln Leu Gln Leu His
            995                 1000                1005
Cys Ser Asp Glu Ile Ser Ser Leu Cys Ala Glu Glu Ala Ala Gln
    1010                1015                1020
Glu Gln Thr Gly Gln Val Glu Glu Cys Leu Lys Val Asn Leu Leu Lys
1025                1030                1035                1040
Ile Lys Thr Glu Leu Cys Lys Lys Glu Val Leu Asn Met Leu Lys Glu
                1045                1050                1055
Ser Lys Ala Asp Ile Phe Val Asp Pro Val Leu His Thr Ala Cys Ala
                1060                1065                1070
Leu Asp Ile Lys His His Cys Ala Ala Ile Thr Pro Gly Arg Gly Arg
        1075                1080                1085
Gln Met Ser Cys Leu Met Glu Ala Leu Glu Asp Lys Arg Val Arg Leu
    1090                1095                1100
Gln Pro Glu Cys Lys Lys Arg Leu Asn Asp Arg Ile Glu Met Trp Ser
1105                1110                1115                1120
Tyr Ala Ala Lys Val Ala Pro Ala Asp Gly Phe Ser Asp Leu Ala Met
                1125                1130                1135
Gln Val Met Thr Ser Pro Ser Lys Asn Tyr Ile Leu Ser Val Ile Ser
            1140                1145                1150
Gly Ser Ile Cys Ile Leu Phe Leu Ile Gly Leu Met Cys Gly Arg Ile
```

```
             1155                1160                1165
Thr Lys Arg Val Thr Arg Glu Leu Lys Asp Arg
    1170                1175

<210> SEQ ID NO 26
<211> LENGTH: 756
<212> TYPE: PRT
<213> ORGANISM: Homo sapiens

<400> SEQUENCE: 26

Met Ser Arg Pro Gly Thr Ala Thr Pro Ala Leu Ala Leu Val Leu Leu
 1               5                  10                  15

Ala Val Thr Leu Ala Gly Val Gly Ala Gln Gly Ala Ala Leu Glu Asp
             20                  25                  30

Pro Asp Tyr Tyr Gly Gln Glu Ile Trp Ser Arg Glu Pro Tyr Tyr Ala
         35                  40                  45

Arg Pro Glu Pro Glu Leu Glu Thr Phe Ser Pro Pro Leu Pro Ala Gly
     50                  55                  60

Pro Gly Glu Glu Trp Glu Arg Arg Pro Gln Glu Pro Arg Pro Pro Lys
 65                  70                  75                  80

Arg Ala Thr Lys Pro Lys Lys Ala Pro Lys Arg Glu Lys Ser Ala Pro
                 85                  90                  95

Glu Pro Pro Pro Gly Lys His Ser Asn Lys Lys Val Met Arg Thr
            100                 105                 110

Lys Ser Ser Glu Lys Ala Ala Asn Asp Asp His Ser Val Arg Val Ala
            115                 120                 125

Arg Glu Asp Val Arg Glu Ser Cys Pro Pro Leu Gly Leu Glu Thr Leu
        130                 135                 140

Lys Ile Thr Asp Phe Gln Leu His Ala Ser Thr Val Lys Arg Tyr Gly
145                 150                 155                 160

Leu Gly Ala His Arg Gly Arg Leu Asn Ile Gln Ala Gly Ile Asn Glu
                165                 170                 175

Asn Asp Phe Tyr Asp Gly Ala Trp Cys Ala Gly Arg Asn Asp Leu Gln
            180                 185                 190

Gln Trp Ile Glu Val Asp Ala Arg Arg Leu Thr Arg Phe Thr Gly Val
        195                 200                 205

Ile Thr Gln Gly Arg Asn Ser Leu Trp Leu Ser Asp Trp Val Thr Ser
    210                 215                 220

Tyr Lys Val Met Val Ser Asn Asp Ser His Thr Trp Val Thr Val Lys
225                 230                 235                 240

Asn Gly Ser Gly Asp Met Ile Phe Glu Gly Asn Ser Glu Lys Glu Ile
                245                 250                 255

Pro Val Leu Asn Glu Leu Pro Val Pro Met Val Ala Arg Tyr Ile Arg
            260                 265                 270

Ile Asn Pro Gln Ser Trp Phe Asp Asn Gly Ser Ile Cys Met Arg Met
        275                 280                 285

Glu Ile Leu Gly Cys Pro Leu Pro Asp Pro Asn Asn Tyr Tyr His Arg
    290                 295                 300

Arg Asn Glu Met Thr Thr Thr Asp Asp Leu Asp Phe Lys His His Asn
305                 310                 315                 320

Tyr Lys Glu Met Arg Gln Leu Met Lys Val Val Asn Glu Met Cys Pro
                325                 330                 335

Asn Ile Thr Arg Ile Tyr Asn Ile Gly Lys Ser His Gln Gly Leu Lys
            340                 345                 350
```

```
Leu Tyr Ala Val Glu Ile Ser Asp His Pro Gly Glu His Glu Val Gly
            355                 360                 365
Glu Pro Glu Phe His Tyr Ile Ala Gly Ala His Gly Asn Glu Val Leu
        370                 375                 380
Gly Arg Glu Leu Leu Leu Leu Val Gln Phe Val Cys Gln Glu Tyr
385                 390                 395                 400
Leu Ala Arg Asn Ala Arg Ile Val His Leu Val Glu Glu Thr Arg Ile
                405                 410                 415
His Val Leu Pro Ser Leu Asn Pro Asp Gly Tyr Glu Lys Ala Tyr Glu
            420                 425                 430
Gly Gly Ser Glu Leu Gly Gly Trp Ser Leu Gly Arg Trp Thr His Asp
        435                 440                 445
Gly Ile Asp Ile Asn Asn Asn Phe Pro Asp Leu Asn Thr Leu Leu Trp
    450                 455                 460
Glu Ala Glu Asp Arg Gln Asn Val Pro Arg Lys Val Pro Asn His Tyr
465                 470                 475                 480
Ile Ala Ile Pro Glu Trp Phe Leu Ser Glu Asn Ala Thr Val Ala Ala
                485                 490                 495
Glu Thr Arg Ala Val Ile Ala Trp Met Glu Lys Ile Pro Phe Val Leu
            500                 505                 510
Gly Gly Asn Leu Gln Gly Gly Glu Leu Val Val Ala Tyr Pro Tyr Asp
        515                 520                 525
Leu Val Arg Ser Pro Trp Lys Thr Gln Glu His Thr Pro Thr Pro Asp
    530                 535                 540
Asp His Val Phe Arg Trp Leu Ala Tyr Ser Tyr Ala Ser Thr His Arg
545                 550                 555                 560
Leu Met Thr Asp Ala Arg Arg Val Cys His Thr Glu Asp Phe Gln
                565                 570                 575
Lys Glu Glu Gly Thr Val Asn Gly Ala Ser Trp His Thr Val Ala Gly
            580                 585                 590
Ser Leu Asn Asp Phe Ser Tyr Leu His Thr Asn Cys Phe Glu Leu Ser
        595                 600                 605
Ile Tyr Val Gly Cys Asp Lys Tyr Pro His Glu Ser Gln Leu Pro Glu
    610                 615                 620
Glu Trp Glu Asn Asn Arg Glu Ser Leu Ile Val Phe Met Glu Gln Val
625                 630                 635                 640
His Arg Gly Ile Lys Gly Leu Val Arg Asp Ser His Gly Lys Gly Ile
                645                 650                 655
Pro Asn Ala Ile Ile Ser Val Glu Gly Ile Asn His Asp Ile Arg Thr
            660                 665                 670
Ala Asn Asp Gly Asp Tyr Trp Arg Leu Leu Asn Pro Gly Glu Tyr Val
        675                 680                 685
Val Thr Ala Lys Ala Glu Gly Phe Thr Ala Ser Thr Lys Asn Cys Met
    690                 695                 700
Val Gly Tyr Asp Met Gly Ala Thr Arg Cys Asp Phe Thr Leu Ser Lys
705                 710                 715                 720
Thr Asn Met Ala Arg Ile Arg Glu Ile Met Glu Lys Phe Gly Lys Gln
                725                 730                 735
Pro Val Ser Leu Pro Ala Arg Arg Leu Lys Leu Arg Gly Arg Lys Arg
            740                 745                 750
Arg Gln Arg Gly
        755
```

<210> SEQ ID NO 27
<211> LENGTH: 1203
<212> TYPE: PRT
<213> ORGANISM: Homo sapiens

<400> SEQUENCE: 27

```
Met Ala Ala Cys Gly Arg Val Arg Arg Met Phe Arg Leu Ser Ala Ala
 1               5                  10                  15

Leu His Leu Leu Leu Leu Phe Ala Ala Gly Ala Glu Lys Leu Pro Gly
            20                  25                  30

Gln Gly Val His Ser Gln Gly Gln Gly Pro Gly Ala Asn Phe Val Ser
        35                  40                  45

Phe Val Gly Gln Ala Gly Gly Gly Pro Ala Gly Gln Gln Leu Pro
    50                  55                  60

Gln Leu Pro Gln Ser Ser Gln Leu Gln Gln Gln Gln Gln Gln Gln Gln
 65                  70                  75                  80

Gln Gln Gln Gln Pro Gln Pro Pro Gln Pro Pro Phe Pro Ala Gly Gly
                85                  90                  95

Pro Pro Ala Arg Arg Gly Gly Ala Gly Ala Gly Gly Gly Trp Lys Leu
            100                 105                 110

Ala Glu Glu Glu Ser Cys Arg Glu Asp Val Thr Arg Val Cys Pro Lys
            115                 120                 125

His Thr Trp Ser Asn Asn Leu Ala Val Leu Glu Cys Leu Gln Asp Val
        130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
            180                 185                 190

Glu Pro Val Gly Lys Gly Tyr Met Val Ser Cys Leu Val Asp His Arg
        195                 200                 205

Gly Asn Ile Thr Glu Tyr Gln Cys His Gln Tyr Ile Thr Lys Met Thr
    210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
            260                 265                 270

Gly Leu Val Lys Glu Ala Glu Arg Glu Pro Lys Ile Gln Val Ser
        275                 280                 285

Glu Leu Cys Lys Lys Ala Ile Leu Arg Val Ala Glu Leu Ser Ser Asp
    290                 295                 300

Asp Phe His Leu Asp Arg His Leu Tyr Phe Ala Cys Arg Asp Asp Arg
305                 310                 315                 320

Glu Arg Phe Cys Glu Asn Thr Gln Ala Gly Glu Gly Arg Val Tyr Lys
                325                 330                 335

Cys Leu Phe Asn His Lys Phe Glu Glu Ser Met Ser Glu Lys Cys Arg
            340                 345                 350

Glu Ala Leu Thr Thr Arg Gln Lys Leu Ile Ala Gln Asp Tyr Lys Val
        355                 360                 365

Ser Tyr Ser Leu Ala Lys Ser Cys Lys Ser Asp Leu Lys Lys Tyr Arg
    370                 375                 380
```

-continued

```
Cys Asn Val Glu Asn Leu Pro Arg Ser Arg Glu Ala Arg Leu Ser Tyr
385                 390                 395                 400

Leu Leu Met Cys Leu Glu Ser Ala Val His Arg Gly Arg Gln Val Ser
            405                 410                 415

Ser Glu Cys Gln Gly Glu Met Leu Asp Tyr Arg Arg Met Leu Met Glu
        420                 425                 430

Asp Phe Ser Leu Ser Pro Glu Ile Ile Leu Ser Cys Arg Gly Glu Ile
    435                 440                 445

Glu His His Cys Ser Gly Leu His Arg Lys Gly Arg Thr Leu His Cys
450                 455                 460

Leu Met Lys Val Val Arg Gly Glu Lys Gly Asn Leu Gly Met Asn Cys
465                 470                 475                 480

Gln Gln Ala Leu Gln Thr Leu Ile Gln Glu Thr Asp Pro Gly Ala Asp
            485                 490                 495

Tyr Arg Ile Asp Arg Ala Leu Asn Glu Ala Cys Glu Ser Val Ile Gln
        500                 505                 510

Thr Ala Cys Lys His Ile Arg Ser Gly Asp Pro Met Ile Leu Ser Cys
    515                 520                 525

Leu Met Glu His Leu Tyr Thr Glu Lys Met Val Glu Asp Cys Glu His
530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
            565                 570                 575

Thr His Gly Trp Asn Glu Thr Ser Glu Phe Met Pro Gln Gly Ala Val
        580                 585                 590

Phe Ser Cys Leu Tyr Arg His Ala Tyr Arg Thr Glu Glu Gln Gly Arg
    595                 600                 605

Arg Leu Ser Arg Glu Cys Arg Ala Glu Val Gln Arg Ile Leu His Gln
610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
            645                 650                 655

Leu Glu Cys Leu Gln Asp His Leu Asp Asp Leu Val Val Glu Cys Arg
        660                 665                 670

Asp Ile Val Gly Asn Leu Thr Glu Leu Glu Ser Glu Asp Ile Gln Ile
    675                 680                 685

Glu Ala Leu Leu Met Arg Ala Cys Glu Pro Ile Ile Gln Asn Phe Cys
690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
            725                 730                 735

Gly Val Thr His Phe Gln Leu Val Gln Met Lys Asp Phe Arg Phe Ser
        740                 745                 750

Tyr Lys Phe Lys Met Ala Cys Lys Glu Asp Val Leu Lys Leu Cys Pro
    755                 760                 765

Asn Ile Lys Lys Lys Val Asp Val Val Ile Cys Leu Ser Thr Thr Val
770                 775                 780

Arg Asn Asp Thr Leu Gln Glu Ala Lys Glu His Arg Val Ser Leu Lys
785                 790                 795                 800

Cys Arg Arg Gln Leu Arg Val Glu Glu Leu Glu Met Thr Glu Asp Ile
```

```
                    805                 810                 815
Arg Leu Glu Pro Asp Leu Tyr Glu Ala Cys Lys Ser Asp Ile Lys Asn
                820                 825                 830
Phe Cys Ser Ala Val Gln Tyr Gly Asn Ala Gln Ile Ile Glu Cys Leu
            835                 840                 845
Lys Glu Asn Lys Lys Gln Leu Ser Thr Arg Cys His Gln Lys Val Phe
        850                 855                 860
Lys Leu Gln Glu Thr Glu Met Met Asp Pro Glu Leu Asp Tyr Thr Leu
865                 870                 875                 880
Met Arg Val Cys Lys Gln Met Ile Lys Arg Phe Cys Pro Glu Ala Asp
                885                 890                 895
Ser Lys Thr Met Leu Gln Cys Leu Lys Gln Asn Lys Asn Ser Glu Leu
            900                 905                 910
Met Asp Pro Lys Cys Lys Gln Met Ile Thr Lys Arg Gln Ile Thr Gln
        915                 920                 925
Asn Thr Asp Tyr Arg Leu Asn Pro Met Leu Arg Lys Ala Cys Lys Ala
    930                 935                 940
Asp Ile Pro Lys Phe Cys His Gly Ile Leu Thr Lys Ala Lys Asp Asp
945                 950                 955                 960
Ser Glu Leu Glu Gly Gln Val Ile Ser Cys Leu Lys Leu Arg Tyr Ala
                965                 970                 975
Asp Gln Arg Leu Ser Ser Asp Cys Glu Asp Gln Ile Arg Ile Ile Ile
            980                 985                 990
Gln Glu Ser Ala Leu Asp Tyr Arg Leu Asp Pro Gln Leu Gln Leu His
        995                 1000                1005
Cys Ser Asp Glu Ile Ser Ser Leu Cys Ala Glu Glu Ala Ala Gln
    1010                1015                1020
Glu Gln Thr Gly Gln Val Glu Glu Cys Leu Lys Val Asn Leu Leu Lys
1025                1030                1035                1040
Ile Lys Thr Glu Leu Cys Lys Lys Glu Val Leu Asn Met Leu Lys Glu
                1045                1050                1055
Ser Lys Ala Asp Ile Phe Val Asp Pro Val Leu His Thr Ala Cys Ala
            1060                1065                1070
Leu Asp Ile Lys His His Cys Ala Ala Ile Thr Pro Gly Arg Gly Arg
        1075                1080                1085
Gln Met Ser Cys Leu Met Glu Ala Leu Glu Asp Lys Arg Val Arg Leu
    1090                1095                1100
Gln Pro Glu Cys Lys Lys Arg Leu Asn Asp Arg Ile Glu Met Trp Ser
1105                1110                1115                1120
Tyr Ala Ala Lys Val Ala Pro Ala Asp Gly Phe Ser Asp Leu Ala Met
                1125                1130                1135
Gln Val Met Thr Ser Pro Ser Lys Asn Tyr Ile Leu Ser Val Ile Ser
            1140                1145                1150
Gly Ser Ile Cys Ile Leu Phe Leu Ile Gly Leu Met Cys Gly Arg Ile
        1155                1160                1165
Thr Lys Arg Val Thr Arg Glu Leu Lys Asp Arg Leu Gln Tyr Arg Ser
    1170                1175                1180
Glu Thr Met Ala Tyr Lys Gly Leu Val Trp Ser Gln Asp Val Thr Gly
1185                1190                1195                1200

Ser Pro Ala

<210> SEQ ID NO 28
<211> LENGTH: 1177
```

<210> TYPE: PRT
<213> ORGANISM: Homo sapiens

<400> SEQUENCE: 28

```
Met Ala Ala Cys Gly Arg Val Arg Arg Met Phe Arg Leu Ser Ala Ala
1               5                   10                  15

Leu His Leu Leu Leu Leu Phe Ala Ala Gly Gly Arg Asn Ser Pro Ala
            20                  25                  30

Arg Ala Ser His Ser Gln Gly Gln Gly Pro Gly Ala Asn Phe Val Ser
        35                  40                  45

Phe Val Gly Gln Ala Gly Gly Gly Pro Ala Gly Gln Gln Leu Pro
    50                  55                  60

Gln Leu Pro Gln Ser Ser Gln Leu Gln Gln Gln Gln Gln Gln Gln Gln
65                  70                  75                  80

Gln Gln Gln Gln Pro Gln Pro Pro Gln Pro Pro Phe Pro Ala Gly Gly
                85              90                  95

Pro Pro Arg Arg Gly Gly Ala Gly Ala Gly Gly Gly Trp Lys Leu Ala
            100                 105                 110

Glu Glu Glu Ser Cys Arg Glu Asp Val Thr Arg Val Cys Pro Lys His
            115                 120                 125

Thr Trp Ser Asn Asn Leu Ala Val Leu Glu Cys Leu Gln Asp Val Arg
        130                 135                 140

Glu Pro Glu Asn Glu Ile Ser Ser Asp Cys Asn His Leu Leu Trp Asn
145                 150                 155                 160

Tyr Lys Leu Asn Leu Thr Thr Asp Pro Lys Phe Glu Ser Val Ala Arg
                165                 170                 175

Glu Val Cys Lys Ser Thr Ile Thr Glu Ile Lys Glu Cys Ala Asp Glu
            180                 185                 190

Pro Val Gly Lys Gly Tyr Met Val Ser Cys Leu Val Asp His Arg Gly
        195                 200                 205

Asn Ile Thr Glu Tyr Gln Cys His Gln Tyr Ile Thr Lys Met Thr Ala
    210                 215                 220

Ile Ile Phe Ser Asp Tyr Arg Leu Ile Cys Gly Phe Met Asp Asp Cys
225                 230                 235                 240

Lys Asn Asp Ile Asn Ile Leu Lys Cys Gly Ser Ile Arg Leu Gly Glu
                245                 250                 255

Lys Asp Ala His Ser Gln Gly Glu Val Val Ser Cys Leu Glu Lys Gly
            260                 265                 270

Leu Val Lys Glu Ala Glu Arg Glu Pro Lys Ile Gln Val Ser Glu
        275                 280                 285

Leu Cys Lys Lys Ala Ile Leu Arg Val Ala Glu Leu Ser Ser Asp Asp
    290                 295                 300

Phe His Leu Asp Arg His Leu Tyr Phe Ala Cys Arg Asp Asp Arg Glu
305                 310                 315                 320

Arg Phe Cys Glu Asn Thr Gln Ala Gly Glu Gly Arg Val Tyr Lys Cys
                325                 330                 335

Leu Phe Asn His Lys Phe Glu Ser Met Ser Glu Lys Cys Arg Glu
            340                 345                 350

Ala Leu Thr Thr Arg Gln Lys Leu Ile Ala Gln Asp Tyr Lys Val Ser
        355                 360                 365

Tyr Ser Leu Ala Lys Ser Cys Lys Ser Asp Leu Lys Lys Tyr Arg Cys
    370                 375                 380

Asn Val Glu Asn Leu Pro Arg Ser Arg Glu Ala Arg Leu Ser Tyr Leu
385                 390                 395                 400
```

-continued

```
Leu Met Cys Leu Glu Ser Ala Val His Arg Gly Arg Gln Val Ser Ser
            405                 410                 415
Glu Cys Gln Gly Glu Met Leu Asp Tyr Arg Arg Met Leu Met Glu Asp
            420                 425                 430
Phe Ser Leu Ser Pro Glu Ile Ile Leu Ser Cys Arg Gly Glu Ile Glu
            435                 440                 445
His His Cys Ser Gly Leu His Arg Lys Gly Arg Thr Leu His Cys Leu
            450                 455                 460
Met Lys Val Val Arg Gly Glu Lys Gly Asn Leu Gly Met Asn Cys Gln
465                 470                 475                 480
Gln Ala Leu Gln Thr Leu Ile Gln Glu Thr Asp Pro Gly Ala Asp Tyr
            485                 490                 495
Arg Ile Asp Arg Ala Leu Asn Glu Ala Cys Glu Ser Val Ile Gln Thr
            500                 505                 510
Ala Cys Lys His Ile Arg Ser Gly Asp Pro Met Ile Ser Ser Cys Leu
            515                 520                 525
Met Glu His Leu Tyr Thr Glu Lys Met Val Glu Asp Cys Glu His Arg
            530                 535                 540
Leu Leu Glu Leu Gln Tyr Phe Ile Ser Arg Asp Trp Lys Leu Asp Pro
545                 550                 555                 560
Val Leu Tyr Arg Lys Cys Gln Gly Asp Ala Ser Arg Leu Cys His Thr
            565                 570                 575
His Gly Trp Asn Glu Thr Ser Glu Phe Met Pro Gln Gly Ala Val Phe
            580                 585                 590
Ser Cys Leu Tyr Arg His Ala Tyr Arg Thr Glu Glu Gln Gly Arg Arg
            595                 600                 605
Leu Ser Arg Glu Cys Arg Ala Glu Val Gln Arg Ile Leu His Gln Arg
            610                 615                 620
Ala Met Asp Val Lys Leu Asp Pro Ala Leu Gln Asp Lys Cys Leu Ile
625                 630                 635                 640
Asp Leu Gly Lys Trp Cys Ser Glu Lys Thr Glu Thr Gly Gln Glu Leu
            645                 650                 655
Glu Cys Leu Gln Asp His Leu Asp Asp Leu Val Val Glu Cys Arg Asp
            660                 665                 670
Ile Val Gly Asn Leu Thr Glu Leu Glu Ser Glu Asp Ile Gln Ile Glu
            675                 680                 685
Ala Leu Leu Met Arg Ala Cys Glu Pro Ile Ile Gln Thr Phe Cys His
            690                 695                 700
Asp Ala Asp Asn Gln Ile Asp Ser Gly Asp Leu Met Glu Cys Leu Ile
705                 710                 715                 720
Gln Asn Lys His Gln Lys Asp Met Asn Glu Lys Cys Ala Ile Gly Val
            725                 730                 735
Thr His Phe Gln Leu Val Gln Met Lys Asp Phe Arg Phe Ser Tyr Lys
            740                 745                 750
Phe Lys Met Ala Cys Lys Glu Asp Val Leu Lys Leu Cys Pro Asn Ile
            755                 760                 765
Lys Lys Lys Val Asp Val Val Ile Cys Leu Ser Thr Thr Val Arg Asn
            770                 775                 780
Asp Thr Leu Gln Glu Ala Lys Glu His Arg Val Ser Leu Lys Cys Arg
785                 790                 795                 800
Arg Gln Leu Arg Val Glu Glu Leu Glu Met Thr Glu Asp Ile Arg Leu
            805                 810                 815
```

-continued

```
Glu Pro Asp Leu Tyr Glu Ala Cys Lys Ser Asp Ile Lys Asn Phe Cys
            820                 825                 830

Ser Ala Val Gln Tyr Gly Asn Ala Gln Ile Ile Glu Cys Leu Lys Glu
        835                 840                 845

Asn Lys Lys Gln Leu Ser Thr Arg Cys His Gln Lys Val Phe Lys Leu
    850                 855                 860

Gln Glu Thr Glu Met Met Asp Pro Glu Leu Asp Tyr Thr Leu Met Arg
865                 870                 875                 880

Val Cys Lys Gln Met Ile Lys Arg Phe Cys Pro Glu Ala Asp Ser Lys
                885                 890                 895

Thr Met Leu Gln Cys Leu Lys Gln Asn Lys Asn Ser Glu Leu Met Asp
            900                 905                 910

Pro Lys Cys Lys Gln Met Ile Thr Lys Arg Gln Ile Thr Gln Asn Thr
        915                 920                 925

Asp Tyr Arg Leu Asn Pro Met Leu Arg Lys Ala Cys Lys Ala Asp Ile
    930                 935                 940

Pro Lys Phe Cys His Gly Ile Leu Thr Lys Ala Lys Asp Asp Ser Glu
945                 950                 955                 960

Leu Glu Gly Gln Val Ile Ser Cys Leu Lys Leu Arg Tyr Ala Asp Gln
                965                 970                 975

Arg Leu Ser Ser Asp Cys Glu Asp Gln Ile Arg Ile Ile Gln Glu
            980                 985                 990

Ser Ala Leu Asp Tyr Arg Leu Asp Pro Gln Leu Gln Leu His Cys Ser
        995                 1000                1005

Asp Glu Ile Ser Ser Leu Cys Ala Glu Glu Ala Ala Gln Glu Gln
    1010                1015                1020

Thr Gly Gln Val Glu Glu Cys Leu Lys Val Asn Leu Leu Lys Ile Lys
1025                1030                1035                1040

Thr Glu Leu Cys Lys Lys Glu Val Leu Asn Met Leu Lys Glu Ser Lys
                1045                1050                1055

Ala Asp Ile Phe Val Asp Pro Val Leu His Thr Ala Cys Ala Leu Asp
            1060                1065                1070

Ile Lys His His Cys Ala Ala Leu Thr Pro Gly Arg Gly Arg Gln Met
        1075                1080                1085

Ser Cys Leu Met Glu Ala Leu Glu Asp Lys Arg Val Arg Leu Gln Pro
    1090                1095                1100

Glu Cys Lys Lys Arg Leu Asn Asp Arg Ile Glu Met Trp Ser Tyr Ala
1105                1110                1115                1120

Ala Lys Val Ala Pro Ala Asp Gly Phe Ser Asp Leu Ala Met Gln Val
                1125                1130                1135

Met Thr Ser Pro Ser Lys Asn Tyr Ile Leu Ser Val Ile Ser Gly Ser
            1140                1145                1150

Ile Cys Ile Leu Phe Leu Ile Gly Leu Met Cys Gly Arg Ile Thr Lys
        1155                1160                1165

Arg Val Thr Arg Glu Leu Lys Asp Arg
    1170                1175

<210> SEQ ID NO 29
<211> LENGTH: 442
<212> TYPE: PRT
<213> ORGANISM: Homo sapiens

<400> SEQUENCE: 29

Met Ser Ala Ala Gln Gly Trp Asp Arg Asn Arg Arg Gly Gly Gly
1               5                   10                  15
```

-continued

```
Ala Ala Gly Ala Gly Gly Gly Ser Gly Ala Gly Gly Ser Gly
         20                  25                  30

Gly Ser Gly Gly Arg Gly Thr Gly Gln Leu Asn Arg Phe Val Gln Leu
         35                  40                  45

Ser Gly Arg Pro His Leu Pro Gly Lys Lys Ile Arg Trp Asp Pro
    50                  55                  60

Val Arg Arg Arg Phe Ile Gln Ser Cys Pro Ile Ile Arg Ile Pro Asn
65                  70                  75                  80

Arg Phe Leu Arg Gly His Arg Pro Pro Ala Arg Ser Gly His Arg
                85                  90                  95

Cys Val Ala Asp Asn Thr Asn Leu Tyr Val Phe Gly Gly Tyr Asn Pro
                100                 105                 110

Asp Tyr Asp Glu Ser Gly Gly Pro Asp Asn Glu Asp Tyr Pro Leu Phe
                115                 120                 125

Arg Glu Leu Trp Arg Tyr His Phe Ala Thr Gly Val Trp His Gln Met
        130                 135                 140

Gly Thr Asp Gly Tyr Met Pro Arg Glu Leu Ala Ser Met Ser Leu Val
145                 150                 155                 160

Leu His Gly Asn Asn Leu Leu Val Phe Gly Gly Thr Gly Ile Pro Phe
                165                 170                 175

Gly Glu Ser Asn Gly Asn Asp Val His Val Cys Asn Val Lys Tyr Lys
                180                 185                 190

Arg Trp Ala Leu Leu Ser Cys Arg Gly Lys Lys Pro Ser Arg Ile Tyr
        195                 200                 205

Gly Gln Ala Met Ala Ile Ile Asn Gly Ser Leu Tyr Val Phe Gly Gly
        210                 215                 220

Thr Thr Gly Tyr Ile Tyr Ser Thr Asp Leu His Lys Leu Asp Leu Asn
225                 230                 235                 240

Thr Arg Glu Trp Thr Gln Leu Lys Pro Asn Asn Leu Ser Cys Asp Leu
            245                 250                 255

Pro Glu Glu Arg Tyr Arg His Glu Ile Ala His Asp Gly Gln Arg Ile
            260                 265                 270

Tyr Ile Leu Gly Gly Gly Thr Ser Trp Thr Ala Tyr Ser Leu Asn Lys
        275                 280                 285

Ile His Ala Tyr Asn Leu Glu Thr Asn Ala Trp Glu Glu Ile Ala Thr
        290                 295                 300

Lys Pro His Glu Lys Ile Gly Phe Pro Ala Ala Arg Arg Cys His Ser
305                 310                 315                 320

Cys Val Gln Ile Lys Asn Asp Val Phe Ile Cys Gly Gly Tyr Asn Gly
            325                 330                 335

Glu Val Ile Leu Gly Asp Ile Trp Lys Leu Asn Leu Gln Thr Phe Gln
            340                 345                 350

Trp Val Lys Leu Pro Ala Thr Met Pro Glu Pro Val Tyr Phe His Cys
        355                 360                 365

Ala Ala Val Thr Pro Ala Gly Cys Met Tyr Ile His Gly Gly Val Val
        370                 375                 380

Asn Ile His Glu Asn Lys Arg Thr Gly Ser Leu Phe Lys Ile Trp Leu
385                 390                 395                 400

Val Val Pro Ser Leu Leu Glu Leu Ala Trp Glu Lys Leu Leu Ala Ala
                405                 410                 415

Phe Pro Asn Leu Ala Asn Leu Ser Arg Thr Gln Leu Leu His Leu Gly
            420                 425                 430
```

```
Leu Thr Gln Gly Leu Ile Glu Arg Leu Lys
        435                 440

<210> SEQ ID NO 30
<211> LENGTH: 698
<212> TYPE: PRT
<213> ORGANISM: Homo sapiens

<400> SEQUENCE: 30

Met Ala Ala Cys Gly Arg Val Arg Arg Met Phe Arg Leu Ser Ala Ala
1               5                   10                  15

Leu His Leu Leu Leu Phe Ala Ala Gly Ala Glu Lys Leu Pro Gly
            20                  25                  30

Gln Gly Val His Ser Gln Gly Gln Gly Pro Gly Ala Asn Phe Val Ser
        35                  40                  45

Phe Val Gly Gln Ala Gly Gly Gly Pro Ala Gly Gln Gln Leu Pro
    50                  55                  60

Gln Leu Pro Gln Ser Ser Gln Leu Gln Gln Gln Gln Gln Gln Gln
65                  70                  75                  80

Gln Gln Gln Gln Pro Gln Pro Pro Gln Pro Pro Phe Pro Ala Gly Gly
                85                  90                  95

Pro Pro Ala Arg Arg Gly Gly Ala Gly Ala Gly Gly Gly Trp Lys Leu
            100                 105                 110

Ala Glu Glu Glu Ser Cys Arg Glu Asp Val Thr Arg Val Cys Pro Lys
            115                 120                 125

His Thr Trp Ser Asn Asn Leu Ala Val Leu Glu Cys Leu Gln Asp Val
    130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
            180                 185                 190

Glu Pro Val Gly Lys Gly Tyr Met Val Ser Cys Leu Val Asp His Arg
        195                 200                 205

Gly Asn Ile Thr Glu Tyr Gln Cys His Gln Tyr Ile Thr Lys Met Thr
    210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
            260                 265                 270

Gly Leu Val Lys Glu Ala Glu Glu Arg Glu Pro Lys Ile Gln Val Ser
        275                 280                 285

Glu Leu Cys Lys Lys Ala Ile Leu Arg Val Ala Glu Leu Ser Ser Asp
    290                 295                 300

Asp Phe His Leu Asp Arg His Leu Tyr Phe Ala Cys Arg Asp Asp Arg
305                 310                 315                 320

Glu Arg Phe Cys Glu Asn Thr Gln Ala Gly Glu Gly Arg Val Tyr Lys
                325                 330                 335

Cys Leu Phe Asn His Lys Phe Glu Glu Ser Met Ser Glu Lys Cys Arg
            340                 345                 350

Glu Ala Leu Thr Thr Arg Gln Lys Leu Ile Ala Gln Asp Tyr Lys Val
        355                 360                 365
```

-continued

```
Ser Tyr Ser Leu Ala Lys Ser Cys Lys Ser Asp Leu Lys Lys Tyr Arg
    370                 375                 380

Cys Asn Val Glu Asn Leu Pro Arg Ser Arg Glu Ala Arg Leu Ser Tyr
385                 390                 395                 400

Leu Leu Met Cys Leu Glu Ser Ala Val His Arg Gly Arg Gln Val Ser
                405                 410                 415

Ser Glu Cys Gln Gly Glu Met Leu Asp Tyr Arg Arg Met Leu Met Glu
            420                 425                 430

Asp Phe Ser Leu Ser Pro Glu Ile Ile Leu Ser Cys Arg Gly Glu Ile
            435                 440                 445

Glu His His Cys Ser Gly Leu His Arg Lys Gly Arg Thr Leu His Cys
        450                 455                 460

Leu Met Lys Val Val Arg Gly Glu Lys Gly Asn Leu Gly Met Asn Cys
465                 470                 475                 480

Gln Gln Ala Leu Gln Thr Leu Ile Gln Glu Thr Asp Pro Gly Ala Asp
                485                 490                 495

Tyr Arg Ile Asp Arg Ala Leu Asn Glu Ala Cys Glu Ser Val Ile Gln
            500                 505                 510

Thr Ala Cys Lys His Ile Arg Ser Gly Asp Pro Met Ile Leu Ser Cys
        515                 520                 525

Leu Met Glu His Leu Tyr Thr Glu Lys Met Val Glu Asp Cys Glu His
    530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
                565                 570                 575

Thr His Gly Trp Asn Glu Thr Ser Glu Phe Met Pro Gln Gly Ala Val
            580                 585                 590

Phe Ser Cys Leu Tyr Arg His Ala Tyr Arg Thr Glu Glu Gln Gly Arg
        595                 600                 605

Arg Leu Ser Arg Glu Cys Arg Ala Glu Val Gln Arg Ile Leu His Gln
    610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
                645                 650                 655

Leu Glu Cys Leu Gln Asp His Leu Asp Asp Leu Val Val Glu Cys Arg
            660                 665                 670

Asp Ile Val Gly Asn Leu Thr Glu Leu Glu Ser Glu Ala Glu Arg Glu
        675                 680                 685

Tyr Val Phe Lys Asn Leu Pro Phe Lys Val
    690                 695

<210> SEQ ID NO 31
<211> LENGTH: 299
<212> TYPE: PRT
<213> ORGANISM: Homo sapiens

<400> SEQUENCE: 31

Met Gly Thr Asp Gly Tyr Met Pro Arg Glu Leu Ala Ser Met Ser Leu
1               5                   10                  15

Val Leu His Gly Asn Asn Leu Leu Val Phe Gly Gly Thr Gly Ile Pro
                20                  25                  30

Phe Gly Glu Ser Asn Gly Asn Asp Val His Val Cys Asn Val Lys Tyr
```

-continued

```
            35                  40                  45
Lys Arg Trp Ala Leu Leu Ser Cys Arg Gly Lys Lys Pro Ser Arg Ile
 50                  55                  60

Tyr Gly Gln Ala Met Ala Ile Ile Asn Gly Ser Leu Tyr Val Phe Gly
 65                  70                  75                  80

Gly Thr Thr Gly Tyr Ile Tyr Ser Thr Asp Leu His Lys Leu Asp Leu
                     85                  90                  95

Asn Thr Arg Glu Trp Thr Gln Leu Lys Pro Asn Asn Leu Ser Cys Asp
                100                 105                 110

Leu Pro Glu Glu Arg Tyr Arg His Glu Ile Ala His Asp Gly Gln Arg
            115                 120                 125

Ile Tyr Ile Leu Gly Gly Gly Thr Ser Trp Thr Ala Tyr Ser Leu Asn
130                 135                 140

Lys Ile His Ala Tyr Asn Leu Glu Thr Asn Ala Trp Glu Glu Ile Ala
145                 150                 155                 160

Thr Lys Pro His Glu Lys Ile Gly Phe Pro Ala Ala Arg Arg Cys His
                165                 170                 175

Ser Cys Val Gln Ile Lys Asn Asp Val Phe Ile Cys Gly Gly Tyr Asn
                180                 185                 190

Gly Glu Val Ile Leu Gly Asp Ile Trp Lys Leu Asn Leu Gln Thr Phe
            195                 200                 205

Gln Trp Val Lys Leu Pro Ala Thr Met Pro Glu Pro Val Tyr Phe His
210                 215                 220

Cys Ala Ala Val Thr Pro Ala Gly Cys Met Tyr Ile His Gly Gly Val
225                 230                 235                 240

Val Asn Ile His Glu Asn Lys Arg Thr Gly Ser Leu Phe Lys Ile Trp
                245                 250                 255

Leu Val Val Pro Ser Leu Leu Glu Leu Ala Trp Glu Lys Leu Leu Ala
                260                 265                 270

Ala Phe Pro Asn Leu Ala Asn Leu Ser Arg Thr Gln Leu Leu His Leu
            275                 280                 285

Gly Leu Thr Gln Gly Leu Ile Glu Arg Leu Lys
290                 295
```

<210> SEQ ID NO 32
<211> LENGTH: 906
<212> TYPE: PRT
<213> ORGANISM: Homo sapiens

<400> SEQUENCE: 32

```
Met Thr Ser His Lys Ser Gly Arg Asp Gln Arg His Val Thr Gln Ser
 1               5                  10                  15

Gly Cys Asn Arg Lys Phe Lys Cys Thr Glu Cys Gly Lys Ala Phe Lys
                 20                  25                  30

Tyr Lys His His Leu Lys Glu His Leu Arg Ile His Ser Gly Glu Lys
             35                  40                  45

Pro Tyr Glu Cys Pro Asn Cys Lys Lys Arg Phe Ser His Ser Gly Ser
 50                  55                  60

Tyr Ser Ser His Ile Ser Ser Lys Lys Cys Ile Ser Leu Ile Pro Val
 65                  70                  75                  80

Asn Gly Arg Pro Arg Thr Gly Leu Lys Thr Ser Gln Cys Ser Ser Pro
                 85                  90                  95

Ser Leu Ser Ala Ser Pro Gly Ser Pro Thr Arg Pro Gln Ile Arg Gln
                100                 105                 110
```

-continued

```
Lys Ile Glu Asn Lys Pro Leu Gln Glu Gln Leu Ser Val Asn Gln Ile
            115                 120                 125
Lys Thr Glu Pro Val Asp Tyr Glu Phe Lys Pro Ile Val Val Ala Ser
        130                 135                 140
Gly Ile Asn Cys Ser Thr Pro Leu Gln Asn Gly Val Phe Thr Gly Gly
145                 150                 155                 160
Gly Pro Leu Gln Ala Thr Ser Ser Pro Gln Gly Met Val Gln Ala Val
                165                 170                 175
Val Leu Pro Thr Val Gly Leu Val Ser Pro Ile Ser Ile Asn Leu Ser
            180                 185                 190
Asp Ile Gln Asn Val Leu Lys Val Ala Val Asp Gly Asn Val Ile Arg
        195                 200                 205
Gln Val Leu Glu Asn Asn Gln Ala Asn Leu Ala Ser Lys Glu Gln Glu
    210                 215                 220
Thr Ile Asn Ala Ser Pro Ile Gln Gln Gly Gly His Ser Val Ile Ser
225                 230                 235                 240
Ala Ile Ser Leu Pro Leu Val Asp Gln Asp Gly Thr Thr Lys Ile Ile
                245                 250                 255
Ile Asn Tyr Ser Leu Glu Gln Pro Ser Gln Leu Gln Val Val Pro Gln
            260                 265                 270
Asn Leu Lys Lys Glu Asn Pro Val Ala Thr Asn Ser Cys Lys Ser Glu
        275                 280                 285
Lys Leu Pro Glu Asp Leu Thr Val Lys Ser Glu Lys Asp Lys Ser Phe
    290                 295                 300
Glu Gly Gly Val Asn Asp Ser Thr Cys Leu Leu Cys Asp Asp Cys Pro
305                 310                 315                 320
Gly Asp Ile Asn Ala Leu Pro Glu Leu Lys His Tyr Asp Leu Lys Gln
                325                 330                 335
Pro Thr Gln Pro Pro Leu Pro Ala Ala Glu Ala Glu Lys Pro Glu
            340                 345                 350
Ser Ser Val Ser Ser Ala Thr Gly Asp Gly Asn Leu Ser Pro Ser Gln
        355                 360                 365
Pro Pro Leu Lys Asn Leu Leu Ser Leu Leu Lys Ala Tyr Tyr Ala Leu
    370                 375                 380
Asn Ala Gln Pro Ser Ala Glu Glu Leu Ser Lys Ile Ala Asp Ser Val
385                 390                 395                 400
Asn Leu Pro Leu Asp Val Val Lys Lys Trp Phe Glu Lys Met Gln Ala
                405                 410                 415
Gly Gln Ile Ser Val Gln Ser Ser Glu Pro Ser Ser Glu Pro Gly
            420                 425                 430
Lys Val Asn Ile Pro Ala Lys Asn Asn Asp Gln Pro Gln Ser Ala Asn
        435                 440                 445
Ala Asn Glu Pro Gln Asp Ser Thr Val Asn Leu Gln Ser Pro Leu Lys
    450                 455                 460
Met Thr Asn Ser Pro Val Leu Pro Val Gly Ser Thr Asn Gly Ser
465                 470                 475                 480
Arg Ser Ser Thr Pro Ser Pro Leu Asn Leu Ser Ser Ser Arg
                485                 490                 495
Asn Thr Gln Gly Tyr Leu Tyr Thr Ala Glu Gly Ala Gln Glu Glu Pro
            500                 505                 510
Gln Val Glu Pro Leu Asp Leu Ser Leu Pro Lys Gln Gln Gly Glu Leu
        515                 520                 525
Leu Glu Arg Ser Thr Ile Thr Ser Val Tyr Gln Asn Ser Val Tyr Ser
```

-continued

```
                530                 535                 540
Val Gln Glu Glu Pro Leu Asn Leu Ser Cys Ala Lys Lys Glu Pro Gln
545                 550                 555                 560

Lys Asp Ser Cys Val Thr Asp Ser Glu Pro Val Val Asn Val Ile Pro
                565                 570                 575

Pro Ser Ala Asn Pro Ile Asn Ile Ala Ile Pro Thr Val Thr Ala Gln
                580                 585                 590

Leu Pro Thr Ile Val Ala Ile Ala Asp Gln Asn Ser Val Pro Cys Leu
                595                 600                 605

Arg Ala Leu Ala Ala Asn Lys Gln Thr Ile Leu Ile Pro Gln Val Ala
610                 615                 620

Tyr Thr Tyr Ser Thr Thr Val Ser Pro Ala Val Gln Glu Pro Pro Leu
625                 630                 635                 640

Lys Val Ile Gln Pro Asn Gly Asn Gln Asp Glu Arg Gln Asp Thr Ser
                645                 650                 655

Ser Glu Gly Val Ser Asn Val Glu Asp Gln Asn Asp Ser Asp Ser Thr
                660                 665                 670

Pro Pro Lys Lys Lys Met Arg Lys Thr Glu Asn Gly Met Tyr Ala Cys
                675                 680                 685

Asp Leu Cys Asp Lys Ile Phe Gln Lys Ser Ser Ser Leu Leu Arg His
                690                 695                 700

Lys Tyr Glu His Thr Gly Lys Arg Pro His Glu Cys Gly Ile Cys Lys
705                 710                 715                 720

Lys Ala Phe Lys His Lys His His Leu Ile Glu His Met Arg Leu His
                725                 730                 735

Ser Gly Glu Lys Pro Tyr Gln Cys Asp Lys Cys Gly Lys Arg Phe Ser
                740                 745                 750

His Ser Gly Ser Tyr Ser Gln His Met Asn His Arg Tyr Ser Tyr Cys
                755                 760                 765

Lys Arg Glu Ala Glu Glu Arg Asp Ser Thr Glu Gln Glu Glu Ala Gly
                770                 775                 780

Pro Glu Ile Leu Ser Asn Glu His Val Gly Ala Arg Ala Ser Pro Ser
785                 790                 795                 800

Gln Gly Asp Ser Asp Glu Arg Glu Ser Leu Thr Arg Glu Glu Asp Glu
                805                 810                 815

Asp Ser Glu Lys Glu Glu Glu Glu Asp Lys Glu Met Glu Glu Leu
                820                 825                 830

Gln Glu Glu Lys Glu Cys Glu Lys Pro Gln Gly Asp Glu Glu Glu Glu
                835                 840                 845

Glu Glu Glu Glu Glu Val Glu Glu Glu Val Glu Glu Ala Glu Asn
850                 855                 860

Glu Gly Glu Glu Ala Lys Thr Glu Gly Leu Met Lys Asp Asp Arg Ala
865                 870                 875                 880

Glu Ser Gln Ala Ser Ser Leu Gly Gln Lys Val Gly Glu Ser Ser Glu
                885                 890                 895

Gln Val Ser Glu Glu Lys Thr Asn Glu Ala
                900                 905

<210> SEQ ID NO 33
<211> LENGTH: 1179
<212> TYPE: PRT
<213> ORGANISM: Homo sapiens

<400> SEQUENCE: 33
```

-continued

```
Met Ala Ala Cys Gly Arg Val Arg Arg Met Phe Arg Leu Ser Ala Ala
 1               5                  10                  15

Leu His Leu Leu Leu Leu Phe Ala Ala Gly Ala Glu Lys Leu Pro Gly
            20                  25                  30

His Gly Val His Ser Gln Gly Gln Gly Pro Ala Asn Phe Val Ser
            35                  40                  45

Phe Val Gly Gln Ala Gly Gly Gly Pro Ala Gly Gln Gln Leu Pro
     50                  55                  60

Gln Leu Leu Gln Ser Ser Gln Leu Gln Gln Gln Gln Gln Gln Gln Gln
65                  70                  75                  80

Gln Gln Gln Gln Leu Gln Pro Pro Gln Pro Phe Pro Ala Gly Gly
                85                  90                  95

Pro Pro Ala Arg Arg Gly Gly Ala Gly Ala Gly Gly Trp Lys Leu
            100                 105                 110

Ala Glu Glu Glu Ser Cys Arg Glu Asp Val Thr Arg Val Cys Pro Lys
            115                 120                 125

His Thr Trp Ser Asn Asn Leu Ala Val Leu Glu Cys Leu Gln Asp Val
            130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
            180                 185                 190

Glu Pro Val Gly Lys Gly Tyr Met Val Ser Cys Leu Val Asp His Arg
            195                 200                 205

Gly Asn Ile Thr Glu Tyr Gln Cys His Gln Tyr Ile Thr Lys Met Thr
210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
            260                 265                 270

Gly Leu Val Lys Glu Ala Glu Glu Arg Glu Pro Lys Ile Gln Val Ser
            275                 280                 285

Glu Leu Cys Lys Lys Ala Ile Leu Arg Val Ala Glu Leu Ser Ser Asp
            290                 295                 300

Asp Phe His Leu Asp Arg His Leu Tyr Phe Ala Cys Arg Asp Asp Arg
305                 310                 315                 320

Glu Arg Phe Cys Glu Asn Thr Gln Ala Gly Glu Gly Arg Val Tyr Lys
                325                 330                 335

Cys Leu Phe Asn His Lys Phe Glu Glu Ser Met Ser Glu Lys Cys Arg
            340                 345                 350

Glu Ala Leu Thr Thr Arg Gln Lys Leu Ile Ala Gln Asp Tyr Lys Val
            355                 360                 365

Ser Tyr Ser Leu Ala Lys Ser Cys Lys Ser Asp Leu Lys Lys Tyr Arg
370                 375                 380

Cys Asn Val Glu Asn Leu Pro Arg Ser Arg Glu Ala Arg Leu Ser Tyr
385                 390                 395                 400

Leu Leu Met Cys Leu Glu Ser Ala Val His Arg Gly Arg Gln Val Ser
                405                 410                 415

Ser Glu Cys Gln Gly Glu Met Leu Asp Tyr Arg Arg Met Leu Met Glu
```

-continued

```
                420                 425                 430
Asp Phe Ser Leu Ser Pro Glu Ile Ile Leu Ser Cys Arg Gly Glu Ile
            435                 440                 445
Glu His His Cys Ser Gly Leu His Arg Lys Gly Arg Thr Leu His Cys
450                 455                 460
Leu Met Lys Val Val Arg Gly Glu Lys Gly Asn Leu Gly Met Asn Cys
465                 470                 475                 480
Gln Gln Ala Leu Gln Thr Leu Ile Gln Glu Thr Asp Pro Gly Ala Asp
                485                 490                 495
Tyr Arg Ile Asp Arg Ala Leu Asn Glu Ala Cys Glu Ser Val Ile Gln
            500                 505                 510
Thr Ala Cys Lys His Ile Arg Ser Gly Asp Pro Met Ile Leu Ser Cys
        515                 520                 525
Leu Met Glu His Leu Tyr Thr Glu Lys Met Val Glu Asp Cys Glu His
    530                 535                 540
Arg Leu Leu Glu Leu Gln Tyr Phe Ile Ser Arg Asp Trp Lys Leu Asp
545                 550                 555                 560
Pro Val Leu Tyr Arg Lys Cys Gln Gly Asp Ala Ser Arg Leu Cys His
                565                 570                 575
Thr His Gly Trp Asn Glu Thr Ser Glu Phe Met Pro Gln Gly Ala Val
            580                 585                 590
Phe Ser Cys Leu Tyr Arg His Ala Tyr Arg Thr Glu Glu Gln Gly Arg
        595                 600                 605
Arg Leu Ser Arg Glu Cys Arg Ala Glu Val Gln Arg Ile Leu His Gln
    610                 615                 620
Arg Ala Met Asp Val Lys Leu Asp Pro Ala Leu Gln Asp Lys Cys Leu
625                 630                 635                 640
Ile Asp Leu Gly Lys Trp Cys Ser Glu Lys Thr Glu Thr Gly Gln Glu
                645                 650                 655
Leu Glu Cys Leu Gln Asp His Leu Asp Asp Leu Val Val Glu Cys Arg
            660                 665                 670
Asp Ile Val Gly Asn Leu Thr Glu Leu Glu Ser Glu Asp Ile Gln Ile
        675                 680                 685
Glu Ala Leu Leu Met Arg Ala Cys Glu Pro Ile Ile Gln Asn Phe Cys
    690                 695                 700
His Asp Val Ala Asp Asn Gln Ile Asp Ser Gly Asp Leu Met Glu Cys
705                 710                 715                 720
Leu Ile Gln Asn Lys His Gln Lys Asp Met Asn Glu Lys Cys Ala Ile
                725                 730                 735
Gly Val Thr His Phe Gln Leu Val Gln Met Lys Asp Phe Arg Phe Ser
            740                 745                 750
Tyr Lys Phe Lys Met Ala Cys Lys Glu Asp Val Leu Lys Leu Cys Pro
        755                 760                 765
Asn Ile Lys Lys Lys Val Asp Val Val Ile Cys Leu Ser Thr Thr Val
    770                 775                 780
Arg Asn Asp Thr Leu Gln Glu Ala Lys Glu His Arg Val Ser Leu Lys
785                 790                 795                 800
Cys Arg Arg Gln Leu Arg Val Glu Glu Leu Glu Met Thr Glu Asp Ile
                805                 810                 815
Arg Leu Glu Pro Asp Leu Tyr Glu Ala Cys Lys Ser Asp Ile Lys Asn
            820                 825                 830
Phe Cys Ser Ala Val Gln Tyr Gly Asn Ala Gln Ile Ile Glu Cys Leu
        835                 840                 845
```

Lys Glu Asn Lys Lys Gln Leu Ser Thr Arg Cys His Gln Lys Val Phe
850                 855                 860

Lys Leu Gln Glu Thr Glu Met Met Asp Pro Glu Leu Asp Tyr Thr Leu
865                 870                 875                 880

Met Arg Val Cys Lys Gln Met Ile Lys Arg Phe Cys Pro Glu Ala Asp
                885                 890                 895

Ser Lys Thr Met Leu Gln Cys Leu Lys Gln Asn Lys Asn Ser Glu Leu
            900                 905                 910

Met Asp Pro Lys Cys Lys Gln Met Ile Thr Lys Arg Gln Ile Thr Gln
            915                 920                 925

Asn Thr Asp Tyr Arg Leu Asn Pro Met Leu Arg Lys Ala Cys Lys Ala
        930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
                965                 970                 975

Asp Gln Arg Leu Ser Ser Asp Cys Glu Asp Gln Ile Arg Ile Ile Ile
            980                 985                 990

Gln Glu Ser Ala Leu Asp Tyr Arg Leu Asp Pro Gln Leu Gln Leu His
        995                 1000                1005

Cys Ser Asp Glu Ile Ser Ser Leu Cys Ala Glu Ala Ala Ala Gln
    1010                1015                1020

Glu Gln Thr Gly Gln Val Glu Glu Cys Leu Lys Val Asn Leu Leu Lys
1025                1030                1035                1040

Ile Lys Thr Glu Leu Cys Lys Lys Glu Val Leu Asn Met Leu Lys Glu
                1045                1050                1055

Ser Lys Ala Asp Ile Phe Val Asp Pro Val Leu His Thr Ala Cys Ala
            1060                1065                1070

Leu Asp Ile Lys His His Cys Ala Ala Ile Thr Pro Gly Arg Gly Arg
            1075                1080                1085

Gln Met Ser Cys Leu Met Glu Ala Leu Glu Asp Lys Arg Val Arg Leu
        1090                1095                1100

Gln Pro Glu Cys Lys Lys Arg Leu Asn Asp Arg Ile Glu Met Trp Ser
1105                1110                1115                1120

Tyr Ala Ala Lys Val Ala Pro Ala Asp Gly Phe Ser Asp Leu Ala Met
                1125                1130                1135

Gln Val Met Thr Ser Pro Ser Lys Asn Tyr Ile Leu Ser Val Ile Ser
            1140                1145                1150

Gly Ser Ile Cys Ile Leu Phe Leu Ile Gly Leu Met Cys Gly Arg Ile
        1155                1160                1165

Thr Lys Arg Val Thr Arg Glu Leu Lys Asp Arg
    1170                1175

<210> SEQ ID NO 34
<211> LENGTH: 5191
<212> TYPE: DNA
<213> ORGANISM: Homo sapiens

<400> SEQUENCE: 34
ggcgagtgcg tcgagctcgc cgcggactca agatggcggc gtgtggacgt gtacggagga      60
tgttccgctt gtcggcggcg ctgcatctgc tgctgctatt cgcggccggg gccgagaaac     120
tccccggcca gggcgtccac agccagggcc agggtcccgg ggccaacttt gtgtccttcg     180
tagggcaggc cggaggcggc ggcccggcgg gtcagcagct gccccagctg cctcagtcat     240

-continued

```
cgcagcttca gcagcaacag cagcagcagc aacagcaaca gcagcctcag ccgccgcagc    300
cgcctttccc ggcgggtggg cctccggccc ggcggggagg agcgggggct ggtgggggct    360
ggaagctggc ggaggaagag tcctgcaggg aggacgtgac ccgcgtgtgc cctaagcaca    420
cctggagcaa caacctggcg gtgctcgagt gcctgcagga tgtgagggag cctgaaaatg    480
aaatttcttc agactgcaat catttgttgt ggaattataa gctgaaccta actacagatc    540
ccaaatttga atctgtggcc agagaggttt gcaaatctac tataacagag attaaagaat    600
gtgctgatga accggttgga aaaggttaca tggtttcctg cttggtggat caccgaggca    660
acatcactga gtatcagtgt caccagtaca ttaccaagat gacggccatc attttagtg    720
attaccgttt aatctgtggc ttcatggatg actgcaaaaa tgacatcaac attctgaaat    780
gtggcagtat tcggcttgga gaaaaggatg cacattcaca aggtgaggtg gtatcatgct    840
tggagaaagg cctggtgaaa gaagcagaag aaagagaacc caagattcaa gtttctgaac    900
tctgcaagaa agccattctc cgggtggctg agctgtcatc ggatgacttt cacttagacc    960
ggcatttata ttttgcttgc cgagatgatc gggagcgttt ttgtgaaaat acacaagctg   1020
gtgagggcag agtgtataag tgcctctttta accataaatt tgaagaatcc atgagtgaaa   1080
agtgtcgaga agcacttaca acccgccaaa agctgattgc ccaggattat aaagtcagtt   1140
attcattggc caaatcctgt aaaagtgact gaagaaata ccggtgcaat gtggaaaacc   1200
ttccgcgatc gcgtgaagcc aggctctcct acttgttaat gtgcctggag tcagctgtac   1260
acagagggcg acaagtcagc agtgagtgcc aggggagat gctggattac cgacgcatgt   1320
tgatggaaga cttttctctg agccctgaga tcatcctaag ctgtcggggg gagattgaac   1380
accattgttc cggattacat cgaaaagggc ggacccctaca ctgtctgatg aaagtagttc   1440
gaggggagaa ggggaacctt ggaatgaact gccagcaggc gcttcaaaca ctgattcagg   1500
agactgaccc tggtgcagat taccgcattg atcgagcttt gaatgaagct tgtgaatctg   1560
taatccagac agcctgcaaa catataagat ctggagaccc aatgatcttg tcgtgcctga   1620
tggaacattt atacacagag aagatggtag aagactgtga acaccgtctc ttagagctgc   1680
agtatttcat ctcccgggat tggaagctgg accctgtcct gtaccgcaag tgccagggag   1740
acgcttctcg tctttgccac acccacggtt ggaatgagac cagtgaattt atgcctcagg   1800
gagctgtgtt ctcttgttta tacagacacg cctaccgcac tgaggaacag ggaaggaggc   1860
tctcacggga gtgccgagct gaagtccaaa ggatcctaca ccagcgtgcc atggatgtca   1920
agctggatcc tgccctccag gataagtgcc tgattgatct gggaaaatgg tgcagtgaga   1980
aaacagagac tggacaggag ctggagtgcc ttcaggacca tctggatgac ttggtggtgg   2040
agtgtagaga tatagttggc aacctcactg agttagaatc agaggatatt caaatagaag   2100
ccttgctgat gagagcctgt gagcccataa ttcagaactt ctgccacgat gtggcagata   2160
accagataga ctctggggac ctgatggagt gtctgataca gaacaaacac cagaaggaca   2220
tgaacgagaa gtgtgccatc ggagttaccc acttccagct ggtgcagatg aaggattttc   2280
ggttttctta caagtttaaa atggcctgca aggaggacgt gttgaagctt tgcccaaaca   2340
taaaaaagaa ggtggacgtg gtgatctgcc tgagcacgac cgtgcgcaat gacactctgc   2400
aggaagccaa ggagcacagg gtgtccctga agtgccgcag gcagctccgt gtggaggagc   2460
tggagatgac ggaggacatc cgcttggagc cagatctata cgaagcctgc aagagtgaca   2520
tcaaaaactt ctgttccgct gtgcaatatg gcaacgctca gattatcgaa tgtctgaaag   2580
```

```
aaaacaagaa gcagctaagc acccgctgcc accaaaaagt atttaagctg caggagacag   2640
agatgatgga cccagagcta gactacaccc tcatgagggt ctgcaagcag atgataaaga   2700
ggttctgtcc ggaagcagat tctaaaacca tgttgcagtg cttgaagcaa aataaaaaca   2760
gtgaattgat ggatcccaaa tgcaaacaga tgataaccaa gcgccagatc acccagaaca   2820
cagattaccg cttaaacccc atgttaagaa aagcctgtaa agctgacatt cctaaattct   2880
gtcacggtat cctgactaag gccaaggatg attcagaatt agaaggacaa gtcatctctt   2940
gcctgaagct gagatatgct gaccagcgcc tgtcttcaga ctgtgaagac cagatccgaa   3000
tcattatcca ggagtccgcc ctggactacc gcctggatcc tcagctccag ctgcactgct   3060
cagacgagat ctccagtcta tgtgctgaag aagcagcagc caagagcag acaggtcagg   3120 tggaggagtg cctcaaggtc aacctgctca agatcaaaac agaattgtgt aaaaaggaag   3180
tgctaaacat gctgaaggaa agcaaagcag acatctttgt tgacccggta cttcatactg   3240
cttgtgccct ggacattaaa caccactgcg cagccatcac ccctggccgc gggcgtcaaa   3300
tgtcctgtct catggaagca ctggaggata gcgggtgag gttacagccc gagtgcaaaa   3360
agcgcctcaa tgaccggatt gagatgtgga gttacgcagc aaaggtggcc ccagcagatg   3420
gcttctctga tcttgccatg caagtaatga cgtctccatc taagaactac attctctctg   3480
tgatcagtgg gagcatctgt atattgttcc tgattggcct gatgtgtgga cggatccacca   3540 agcgagtgac acgagagctc aaggacaggt agagccacct tgaccaccaa aggaactacc   3600
tatccagtgc ccagtttgta cagccctctt gtatagcatc cccactcacc tcgctcttct   3660
cagaagtgac accaaccccg tgttagagca ttagcagatg tccactgcgt tgtcccatcc   3720
agcctccact cgtgtccatg gtgtcctcct cctcctcacc gtgcagcagc agcagctggt   3780
cgctggggtt actgcctttg tttggcaaac ttgggtttac ctgcctgtag acaagtctct   3840
ctcataccaa cagaacttcc ggtacttcca gaaccaactc acctgacctg caactcaaag   3900
gcttttttaa gaaaaccacc aaaaaaaaaa atttttttaa agaaaaaaat gtatatagta   3960
acgcatctcc tccaggcttg atttgggcaa tggggttatg tctttcatat gactgtgtaa   4020
aacaaagaca ggacttggag gggaagcaca ccacccagtg tgccatgact gaggtgtctc   4080
gttcatctct cagaagcacc ttgggccctc gccagggccg tggtcttcac cgaggcgtgg   4140
gtgggcagcc gttccccagg ctgtgtgggg tcctgctttc ttctgctgag acagtgacgc   4200
tttccagttt ccaccctaat cagccactgc tggtcacagc cccacagcca tgggtatttc   4260
tgtggtctcc tcgcttcatt gaagcaaagc atgagccttc ctagacaagg gcagctgggg   4320
aggggaaggg accggaagtt tgtgaagttg aacagtccat ccatctgcac tgagaggctg   4380
gatcctgagt cccggggcag caggatccca ggaaccttcc tcctccaggg cagcacagga   4440
ctcagccatg tctggaccgg ccctgctgag gctacagtca ctctggaagc tctgcgcttc   4500
atcaggaggc aggactgtgg cgggaggggt ccttgaagat gggtgtgggg agcagtgggt   4560
caggaagtgg gagccagagg tttgactcac tttgctttat ttttcaggct acaatacagg   4620
tcagagacaa tggcttataa aggtttagtg tggtctcagg atgtgacagg cagtccagcc   4680
tgacctttct gcacactcca gacaaacttc ccagacaagc tcctttgtgc ctctacgtgg   4740
agagggtgtg gaaagttatc acattaaaag atggaggatt tgctctgttt ttttctttc   4800 tgtccatttg ctgcgtgtac ccactctagt aggcattggc taaatgttgt attttggcga   4860
ttcatcaacc tttgcagaat atgggcttta tagaagcaat attcttggcc atcccgcctc   4920
attcctccag tgtggagatg acaagtctgg gtgtgagagg gaggggtccg ggcatcatgg   4980
```

| | |
|---|---|
| ttcagcgtgg cactcctttg gttgagtttg gggcatgaga tcacagtggc tgcacaagag | 5040 |
| agcagtgtgt acagtaggag agacatttat gtaatatata ttttattaac ctgttagatg | 5100 |
| tccacaaagt attataaatc acgtgcctaa aactgtccat gtagaccaag gcctgccctc | 5160 |
| ggcgcccccc actcttgcct ctgctctgca c | 5191 |

<210> SEQ ID NO 35
<211> LENGTH: 3556
<212> TYPE: DNA
<213> ORGANISM: Homo sapiens

<400> SEQUENCE: 35

| | |
|---|---|
| cgggccggtc acacgcgcag ccagccggcc gccctcccgc gcccaagcgc gccgctctag | 60 |
| ctgtgccctg cgcccttgcc ccgcgccagc ttctgcgccc gcagcccgcc cggcgccccc | 120 |
| ggtgaccgtg accctgccct gggcgcgggg cggagcaggc atgtcccgcc cggggaccgc | 180 |
| taccccagcg ctggccctgg tgctcctggc agtgaccctg gccggggtcg agcccaggg | 240 |
| cgcagccctc gaggaccctg attattacgg gcaggagatc tggagccggg agccctacta | 300 |
| cgcgcgcccg gagcccgagc tcgagacctt ctctccgccg ctgcctgcgg ggcccgggga | 360 |
| ggagtgggag cggcgcccgc aggagcccag gccgcccaag agggccacca agcccaagaa | 420 |
| agctcccaag agggagaagt cggctccgga gccgcctcca ccaggtaaac acagcaacaa | 480 |
| aaaagttatg agaaccaaga gctctgagaa ggctgccaac gatgatcaca gtgtccgtgt | 540 |
| ggcccgtgaa gatgtcagag agagttgccc acctcttggt ctggaaacct taaaaatcac | 600 |
| agacttccag ctccatgcct ccacggtgaa gcgctatggc ctggggcac atcgagggag | 660 |
| actcaacatc caggcgggca ttaatgaaaa tgatttttat gacggagcgt ggtgcgcggg | 720 |
| aagaaatgac ctccagcagt ggattgaagt ggatgctcgg cgcctgacca gattcactgg | 780 |
| tgtcatcact caagggagga actccctctg gctgagtgac tgggtgacat cctataaggt | 840 |
| catggtgagc aatgacagcc acacgtgggt cactgttaag aatggatctg agacatgat | 900 |
| atttgaggga aacagtgaga aggagatccc tgttctcaat gagctacccg tccccatggt | 960 |
| ggcccgctac atccgcataa accctcagtc ctggtttgat aatgggagca tctgcatgag | 1020 |
| aatggagatc ctgggctgcc cactgccaga tcctaataat tattatcacc gccgaacga | 1080 |
| gatgaccacc actgatgacc tggattttaa gcaccacaat tataaggaaa tgcgccagtt | 1140 |
| gatgaaagtt gtgaatgaaa tgtgtcccaa tatcaccaga atttacaaca ttggaaaaag | 1200 |
| ccaccagggc ctgaagctgt atgctgtgga gatctcagat caccctgggg agcatgaagt | 1260 |
| cggtgagccc gagttccact acatcgcggg ggcccacggc aatgaggtgc tgggccggga | 1320 |
| gctgctgctg ctgctggtgc agttcgtgtg tcaggagtac ttggcccgga atgcgcgcat | 1380 |
| cgtccacctg gtgaggaga gcggattca cgtcctcccc tccctcaacc ccgatggcta | 1440 |
| cgagaaggcc tatgaagggg gctcggagct gggaggctgg tccctgggac gctggaccca | 1500 |
| cgatggaatt gacatcaaca caacctttcc tgatttaaac acgctgctct gggaggcaga | 1560 |
| ggatcgacag aatgtcccca ggaaagttcc caatcactat attgcaatcc ctgagtggtt | 1620 |
| tctgtcggaa aatgccacgg tggctgccga gaccagagca gtcatagcct ggatggaaaa | 1680 |
| aatccctttt gtgctgggcg gcaacctgca gggcggcgag ctggtggtgg cgtaccccta | 1740 |
| cgacctggtg cggtccccct ggaagacgca ggaacacacc cccacccccg acgaccacgt | 1800 |
| gttccgctgg ctggccctact cctatgcctc cacacaccgc ctcatgacag acgcccggag | 1860 |

-continued

```
gagggtgtgc cacacggagg acttccagaa ggaggagggc actgtcaatg gggcctcctg    1920
gcacaccgtc gctggaagtc tgaacgattt cagctaccct catacaaact gcttcgaact    1980
gtccatctac gtgggctgtg ataaatacccc acatgagagc cagctgcccg aggagtggga   2040
gaataaccgg gaatctctga tcgtgttcat ggagcaggtt catcgtggca ttaaaggctt    2100
ggtgagagat tcacatggaa aaggaatccc aaacgccatt atctccgtag aaggcattaa    2160
ccatgacatc cgaacagcca acgatgggga ttactggcgc ctcctgaacc ctggagagta    2220
tgtggtcaca gcaaaggccg aaggtttcac tgcatccacc aagaactgta tggttggcta    2280
tgacatgggg gccacaaggt gtgacttcac acttagcaaa accaacatgg ccaggatccg    2340
agagatcatg gagaagtttg ggaagcagcc cgtcagcctg ccagccaggc ggctgaagct    2400
gcggggggcg aagagacgac agcgtgggtg accctcctgg gcccttgaga ctcgtctggg    2460
acccatgcaa attaaaccaa cctggtagta gctccatagt ggactcactc actgttgttt    2520
cctctgtaat tcaagaagtg cctggaagag agggtgcatt tgaggcagg tcccaaaagg    2580 gaaggctgga ggctgaggct gttttctttt ctttgttccc atttatccaa ataacttgga    2640
cagagcagca gagaaaagct gatgggagtg agagaactca gcaagccaac ctgggaatca    2700
gagagagaag gagaaggagg ggagcctgtc cgttcagagc ctctggctgc atagaaaagg    2760
attctggtgc ttcccctgtt tgcgtggcag caagggttcc acgtgcattt gcaatttgca    2820
cagctaaaat tgcagcattt ccccagctgg gctgtcccaa atgttaccat ttgagatgct    2880
cccaggcgtc ctaagagaat ccaccctctc tggccctggg acattgcaag ctgctacaaa    2940
taaattctgt gttcttttga caatagcgtc attgccaagt gcacatcagt gagcctcttg    3000
aatctgttta gtctccttttt tcaacaaagg agtgtgttca gaaaggaga gagaggctga    3060 gatcattcag gagtttgttg ggcagcaagc atggagcttc ttgcacaaat tctgggtcca    3120
taaacaaccc ccaaagtccc tgctgatcca gtagccctgg aggttcccca ggtagggaga    3180
gccagaggtg ccagccttcc tgaagggcca gaaaatttag cctggatctc ctcttttacc    3240
tgctaggact ggaaagagcc agaagtgggg tggcctgaag ccctctctct gcttgaggta    3300
ttgcccctgt gtggaattga gtgctcatgg gttggcctca tatcagcctg ggagttattt    3360
ttgatatgta gaatgccaga tcttccagat taggctaaat gtaatgaaaa cctcttagga    3420
ttatctgtgg agcatcagtt tgggaagaat tattgaatta tcttgcaaga aaaaagtatg    3480
tctcactttt tgttaatgtt gctgcctcat tgacctggga aaaatgaaaa aaaaaaataa    3540
agcaaatggt aagacc                                                    3556
```

<210> SEQ ID NO 36
<211> LENGTH: 5191
<212> TYPE: DNA
<213> ORGANISM: Homo sapiens

<400> SEQUENCE: 36

```
ggcgagtgcg tcgagctcgc cgcggactca agatggcggc gtgtggacgt gtacggagga      60
tgttccgctt gtcggcggcg ctgcatctgc tgctgctatt cgcggccggg gccgagaaac     120
tccccggcca gggcgtccac agccagggcc agggtcccgg ggccaacttt gtgtccttcg     180
tagggcaggc cggaggcggc ggcccggcgg gtcagcagct gccccagctg cctcagtcat     240
cgcagcttca gcagcaacag cagcagcagc aacagcaaca gcagcctcag ccgccgcagc     300
cgcctttccc ggcgggtggg cctccggccc ggcggggagg agcgggggct ggtggggct      360 ggaagctggc ggaggaagag tcctgcaggg aggacgtgac ccgcgtgtgc cctaagcaca     420
```

-continued

```
cctggagcaa caacctggcg gtgctcgagt gcctgcagga tgtgagggag cctgaaaatg    480
aaatttcttc agactgcaat catttgttgt ggaattataa gctgaaccta actacagatc    540
ccaaatttga atctgtggcc agagaggttt gcaaatctac tataacagag attaaagaat    600
gtgctgatga accggttgga aaaggttaca tggtttcctg cttggtggat caccgaggca    660
acatcactga gtatcagtgt caccagtaca ttaccaagat gacggccatc attttttagtg   720
attaccgttt aatctgtggc ttcatggatg actgcaaaaa tgacatcaac attctgaaat    780
gtggcagtat tcggcttgga gaaaaggatg cacattcaca aggtgaggtg gtatcatgct    840
tggagaaagg cctggtgaaa gaagcagaag aaagagaacc caagattcaa gtttctgaac    900
tctgcaagaa agccattctc cgggtggctg agctgtcatc ggatgacttt cacttagacc    960
ggcatttata ttttgcttgc cgagatgatc gggagcgttt ttgtgaaaat acacaagctg   1020
gtgagggcag agtgtataag tgcctctttta accataaatt tgaagaatcc atgagtgaaa   1080
agtgtcgaga agcacttaca acccgccaaa agctgattgc ccaggattat aaagtcagtt   1140
attcattggc caaatcctgt aaaagtgact gaagaaata ccggtgcaat gtggaaaacc    1200
ttccgcgatc gcgtgaagcc aggctctcct acttgttaat gtgcctggag tcagctgtac   1260
acagagggcg acaagtcagc agtgagtgcc aggggagat gctggattac cgacgcatgt    1320
tgatggaaga cttttctctg agccctgaga tcatcctaag ctgtcggggg gagattgaac   1380
accattgttc cggattacat cgaaaagggc ggaccctaca ctgtctgatg aaagtagttc    1440
gagggggagaa ggggaacctt ggaatgaact gccagcaggc gcttcaaaca ctgattcagg   1500
agactgaccc tggtgcagat taccgcattg atcgagcttt gaatgaagct tgtgaatctg   1560
taatccgac agcctgcaaa catataagat ctggagaccc aatgatcttg tcgtgcctga    1620
tggaacattt atacacagag aagatggtag aagactgtga acaccgtctc ttagagctgc   1680
agtatttcat ctcccgggat tggaagctgg accctgtcct gtaccgcaag tgccagggag   1740
acgcttctcg tctttgccac acccacggtt ggaatgagac cagtgaattt atgcctcagg   1800
gagctgtgtt ctcttgttta tacagacacg cctaccgcac tgaggaacag ggaaggaggc    1860
tctcacggga gtgccgagct gaagtccaaa ggatcctaca ccagcgtgcc atggatgtca   1920
agctggatcc tgccctccag gataagtgcc tgattgatct gggaaaatgg tgcagtgaga   1980
aaacagagac tggacaggag ctggagtgcc ttcaggacca tctggatgac ttggtggtgg   2040
agtgtagaga tatagttggc aacctcactg agttagaatc agaggatatt caaatagaag   2100
ccttgctgat gagagcctgt gagcccataa ttcagaactt ctgccacgat gtggcagata   2160
accagataga ctctggggac ctgatggagt gtctgataca gaacaaacac cagaaggaca   2220
tgaacgagaa gtgtgccatc ggagttaccc acttccagct ggtgcagatg aaggattttc   2280
ggttttctta caagttttaaa atggcctgca aggaggacgt gttgaagctt tgcccaaaca   2340
taaaaaagaa ggtggacgtg gtgatctgcc tgagcacgac cgtgcgcaat gacactctgc   2400
aggaagccaa ggagcacagg gtgtccctga agtgccgcag gcagctccgt gtggaggagc    2460
tggagatgac ggaggacatc cgcttggagc cagatctata cgaagcctgc aagagtgaca   2520
tcaaaaactt ctgttccgct gtgcaatatg gcaacgctca gattatcgaa tgtctgaaag   2580
aaaacaagaa gcagctaagc acccgctgcc accaaaaagt atttaagctg caggagacag    2640
agatgatgga cccagagcta gactacaccc tcatgagggt ctgcaagcag atgataaaga   2700
ggttctgtcc ggaagcagat tctaaaacca tgttgcagtg cttgaagcaa aataaaaaca    2760
```

```
gtgaattgat ggatcccaaa tgcaaacaga tgataaccaa gcgccagatc acccagaaca    2820
cagattaccg cttaaacccc atgttaagaa aagcctgtaa agctgacatt cctaaattct    2880
gtcacggtat cctgactaag gccaaggatg attcagaatt agaaggacaa gtcatctctt    2940
gcctgaagct gagatatgct gaccagcgcc tgtcttcaga ctgtgaagac cagatccgaa    3000
tcattatcca ggagtccgcc ctggactacc gcctggatcc tcagctccag ctgcactgct    3060
cagacgagat ctccagtcta tgtgctgaag aagcagcagc caagagcag acaggtcagg     3120 tggaggagtg cctcaaggtc aacctgctca agatcaaaac agaattgtgt aaaaaggaag    3180
tgctaaacat gctgaaggaa agcaaagcag acatctttgt tgacccggta cttcatactg    3240
cttgtgccct ggacattaaa caccactgcg cagccatcac ccctggccgc gggcgtcaaa    3300
tgtcctgtct catggaagca ctggaggata agcgggtgag gttacagccc gagtgcaaaa    3360
agcgcctcaa tgaccggatt gagatgtgga gttacgcagc aaaggtggcc ccagcagatg    3420
gcttctctga tcttgccatg caagtaatga cgtctccatc taagaactac attctctctg    3480
tgatcagtgg gagcatctgt atattgttcc tgattggcct gatgtgtgga cggatcacca    3540
agcgagtgac acgagagctc aaggacaggt agagccacct tgaccaccaa aggaactacc    3600
tatccagtgc ccagtttgta cagccctctt gtatagcatc cccactcacc tcgctcttct    3660
cagaagtgac accaaccccg tgttagagca ttagcagatg tccactgcgt tgtcccatcc    3720
agcctccact cgtgtccatg gtgtcctcct cctcctcacc gtgcagcagc agcagctggt    3780 cgctgggggtt actgcctttg tttggcaaac ttgggtttac ctgcctgtag acaagtctct    3840
ctcataccaa cagaacttcc ggtacttcca gaaccaactc acctgacctg caactcaaag    3900 gctttttaa gaaaaccacc aaaaaaaaaa atttttttaa agaaaaaaat gtatatagta     3960
acgcatctcc tccaggcttg atttgggcaa tggggttatg tctttcatat gactgtgtaa    4020
aacaaagaca ggacttggag gggaagcaca ccacccagtg tgccatgact gaggtgtctc    4080
gttcatctct cagaagcacc ttggggcctc gccagggccg tggtcttcac cgaggcgtgg    4140
gtgggcagcc gttccccagg ctgtgtgggg tcctgctttc ttctgctgag acagtgacgc    4200
tttccagttt ccaccctaat cagccactgc tggtcacagc cccacagcca tgggtatttc    4260
tgtggtctcc tcgcttcatt gaagcaaagc atgagcctcc ctagacaagg gcagctgggg    4320
aggggaaggg accggaagtt tgtgaagttg aacagtccat ccatctgcac tgagaggctg    4380
gatcctgagt cccggggcag caggatccca ggaaccttcc tcctccaggg cagcacagga    4440
ctcagccatg tctggaccgg ccctgctgag gctacagtca ctctggaagc tctgcgcttc    4500
atcaggaggc aggactgtgg cgggaggggt ccttgaagat gggtgtgggg agcagtgggt    4560
caggaagtgg gagccagagg tttgactcac tttgctttat ttttcaggct acaatacagg    4620
tcagagacaa tggcttataa aggtttagtg tggtctcagg atgtgacagg cagtccagcc    4680
tgacctttct gcacactcca gacaaacttc ccagacaagc tcctttgtgc ctctacgtgg    4740
agagggtgtg gaaagttatc acattaaaag atggaggatt tgctctgttt tttttctttc    4800
tgtccatttg ctgcgtgtac ccactctagt aggcattggc taaatgttgt attttggcga    4860
ttcatcaacc tttgcagaat atgggcttta tagaagcaat attcttggcc atcccgcctc    4920
attcctccag tgtggagatg acaagtctgg gtgtgagagg gaggggtccg ggcatcatgg    4980
ttcagcgtgg cactcctttg gttgagtttg gggcatgaga tcacagtggc tgcacaagag    5040
agcagtgtgt acagtaggag agacatttat gtaatatata ttttattaac ctgttagatg    5100
tccacaaagt attataaatc acgtgcctaa aactgtccat gtagaccaag gcctgccctc    5160
```

```
ggcgcccccc actcttgcct ctgctctgca c                                     5191

<210> SEQ ID NO 37
<211> LENGTH: 5191
<212> TYPE: DNA
<213> ORGANISM: Homo sapiens

<400> SEQUENCE: 37
ggcgagtgcg tcgagctcgc cgcggactca agatggcggc gtgtggacgt gtacggagga       60
tgttccgctt gtcggcggcg ctgcatctgc tgctgctatt cgcggccggg gccgagaaac      120
tccccggcca gggcgtccac agccagggcc agggtcccgg ggccaacttt gtgtccttcg      180
tagggcaggc cggaggcggc ggccggcgg gtcagcagct gccccagctg cctcagtcat       240
cgcagcttca gcagcaacag cagcagcagc aacagcaaca gcagcctcag ccgccgcagc      300
cgcctttccc ggcgggtggg cctccggcc ggcggggagg agcgggggct ggtgggggct       360
ggaagctggc ggaggaagag tcctgcaggg aggacgtgac ccgcgtgtgc cctaagcaca      420
cctggagcaa caacctggcg gtgctcgagt gcctgcagga tgtgagggag cctgaaaatg      480
aaatttcttc agactgcaat catttgttgt ggaattataa gctgaaccta actacagatc      540
ccaaatttga atctgtggcc agagaggttt gcaaatctac tataacagag attaaagaat      600
gtgctgatga accggttgga aaaggttaca tggtttcctg cttggtggat caccgaggca      660
acatcactga gtatcagtgt caccagtaca ttaccaagat gacggccatc attttttagtg     720 attaccgttt aatctgtggc ttcatggatg actgcaaaaa tgacatcaac attctgaaat      780
gtggcagtat tcggcttgga gaaaaggatg cacattcaca aggtgaggtg gtatcatgct      840
tggagaaagg cctggtgaaa gaagcagaag aaagagaacc caagattcaa gtttctgaac      900
tctgcaagaa agccattctc cgggtggctg agctgtcatc ggatgacttt cacttagacc      960
ggcatttata ttttgcttgc cgagatgatc gggagcgttt ttgtgaaaat acacaagctg     1020
gtgagggcag agtgtataag tgcctcttta accataaatt tgaagaatcc atgagtgaaa     1080
agtgtcgaga agcacttaca acccgccaaa agctgattgc ccaggattat aaagtcagtt     1140
attcattggc caaatcctgt aaaagtgact gaagaaata ccggtgcaat gtggaaaacc      1200
ttccgcgatc gcgtgaagcc aggctctcct acttgttaat gtgcctggag tcagctgtac     1260
acagagggcg acaagtcagc agtgagtgcc aggggagat gctggattac cgacgcatgt      1320
tgatggaaga cttttctctg agccctgaga tcatcctaag ctgtcggggg agattgaac      1380 accattgttc cggattacat cgaaagggc ggaccctaca ctgtctgatg aaagtagttc      1440 gagggagaa gggaacctt ggaatgaact gccagcaggc gcttcaaaca ctgattcagg      1500
agactgaccc tggtgcagat taccgcattg atcgagcttt gaatgaagct tgtgaatctg     1560
taatccagac agcctgcaaa catataagat ctggagaccc aatgatcttg tcgtgcctga     1620
tggaacattt atacacagag aagatggtag aagactgtga acaccgtctc ttagagctgc      1680
agtatttcat ctcccgggat tggaagctgg accctgtcct gtaccgcaag tgccagggag     1740
acgcttctcg tctttgccac acccacggtt ggaatgagac cagtgaattt atgcctcagg     1800
gagctgtgtt ctcttgttta tacagacacg cctaccgcac tgaggaacag ggaaggaggc     1860
tctcacggga gtgccgagct gaagtccaaa ggatcctaca ccagcgtgcc atggatgtca     1920
agctggatcc tgccctccag gataagtgcc tgattgatct gggaaaatgg tgcagtgaga     1980
aaacagagac tggacaggag ctggagtgcc ttcaggacca tctggatgac ttggtggtgg     2040
```

```
agtgtagaga tatagttggc aacctcactg agttagaatc agaggatatt caaatagaag    2100
ccttgctgat gagagcctgt gagcccataa ttcagaactt ctgccacgat gtggcagata    2160
accagataga ctctggggac ctgatggagt gtctgataca gaacaaacac cagaaggaca    2220
tgaacgagaa gtgtgccatc ggagttaccc acttccagct ggtgcagatg aaggattttc    2280
ggttttctta caagtttaaa atggcctgca aggaggacgt gttgaagctt tgcccaaaca    2340
taaaaaagaa ggtggacgtg gtgatctgcc tgagcacgac cgtgcgcaat gacactctgc    2400
aggaagccaa ggagcacagg gtgtccctga agtccgcag gcagctccgt gtggaggagc     2460
tggagatgac ggaggacatc cgcttggagc cagatctata cgaagcctgc aagagtgaca    2520
tcaaaaactt ctgttccgct gtgcaatatg gcaacgctca gattatcgaa tgtctgaaag    2580
aaaacaagaa gcagctaagc acccgctgcc accaaaaagt atttaagctg caggagacag    2640
agatgatgga cccagagcta gactacaccc tcatgagggt ctgcaagcag atgataaaga    2700
ggttctgtcc ggaagcagat tctaaaacca tgttgcagtg cttgaagcaa aataaaaaca    2760
gtgaattgat ggatcccaaa tgcaaacaga tgataaccaa gcgccagatc acccagaaca    2820
cagattaccg cttaaacccc atgttaagaa aagcctgtaa agctgacatt cctaaattct    2880
gtcacggtat cctgactaag gccaaggatg attcagaatt agaaggacaa gtcatctctt    2940
gcctgaagct gagatatgct gaccagcgcc tgtcttcaga ctgtgaagac cagatccgaa    3000
tcattatcca ggagtccgcc ctggactacc gcctggatcc tcagctccag ctgcactgct    3060
cagacgagat ctccagtcta tgtgctgaag aagcagcagc ccaagagcag acaggtcagg    3120
tggaggagtg cctcaaggtc aacctgctca agatcaaaac agaattgtgt aaaaaggaag    3180
tgctaaacat gctgaaggaa agcaaagcag acatctttgt tgacccggta cttcatactg    3240
cttgtgccct ggacattaaa caccactgcg cagccatcac ccctggccgc gggcgtcaaa    3300
tgtcctgtct catggaagca ctggaggata agcgggtgag gttacagccc gagtgcaaaa    3360
agcgcctcaa tgaccggatt gagatgtgga gttacgcagc aaaggtggcc ccagcagatg    3420
gcttctctga tcttgccatg caagtaatga cgtctccatc taagaactac attctctctg    3480
tgatcagtgg gagcatctgt atattgttcc tgattggcct gatgtgtgga cggatcacca    3540
agcgagtgac acgagagctc aaggacaggt agagccacct tgaccaccaa aggaactacc    3600
tatccagtgc ccagtttgta cagccctctt gtatagcatc cccactcacc tcgctcttct    3660
cagaagtgac accaaccccg tgttagagca ttagcagatg tccactgcgt tgtcccatcc    3720
agcctccact cgtgtccatg gtgtcctcct cctcctcacc gtgcagcagc agcagctggt    3780
cgctggggtt actgcctttg tttggcaaac ttgggtttac ctgcctgtag acaagtctct    3840
ctcataccaa cagaacttcc ggtacttcca gaaccaactc acctgacctg caactcaaag    3900
gcttttttaa gaaaccacc aaaaaaaaaa atttttttaa agaaaaaaat gtatatagta     3960
acgcatctcc tccaggcttg atttgggcaa tggggttatg tctttcatat gactgtgtaa    4020
aacaaagaca ggacttggag gggaagcaca ccacccagtg tgccatgact gaggtgtctc    4080
gttcatctct cagaagcacc ttggggcctc gccaggccg tggtcttcac cgaggcgtgg      4140
gtgggcagcc gttccccagg ctgtgtgggg tcctgctttc ttctgctgag acagtgacgc    4200
tttccagttt ccaccctaat cagccactgc tggtcacagc cccacagcca tgggtatttc    4260
tgtggtctcc tcgcttcatt gaagcaaagc atgagccttc ctagacaagg gcagctgggg    4320
aggggaaggg accggaagtt tgtgaagttg aacagtccat ccatctgcac tgagaggctg    4380
gatcctgagt cccggggcag caggatccca ggaaccttcc tcctccaggg cagcacagga    4440
```

| | |
|---|---|
| ctcagccatg tctggaccgg ccctgctgag gctacagtca ctctggaagc tctgcgcttc | 4500 |
| atcaggaggc aggactgtgg cgggaggggt ccttgaagat gggtgtgggg agcagtgggt | 4560 |
| caggaagtgg gagccagagg tttgactcac tttgctttat ttttcaggct acaatacagg | 4620 |
| tcagagacaa tggcttataa aggtttagtg tggtctcagg atgtgacagg cagtccagcc | 4680 |
| tgacctttct gcacactcca gacaaacttc ccagacaagc tcctttgtgc ctctacgtgg | 4740 |
| agagggtgtg gaaagttatc acattaaaag atggaggatt tgctctgttt ttttctttc | 4800 |
| tgtccatttg ctgcgtgtac ccactctagt aggcattggc taaatgttgt attttggcga | 4860 |
| ttcatcaacc tttgcagaat atgggcttta tagaagcaat attcttggcc atcccgcctc | 4920 |
| attcctccag tgtggagatg acaagtctgg gtgtgagagg gaggggtccg ggcatcatgg | 4980 |
| ttcagcgtgg cactcctttg gttgagtttg gggcatgaga tcacagtggc tgcacaagag | 5040 |
| agcagtgtgt acagtaggag agacatttat gtaatatata ttttattaac ctgttagatg | 5100 |
| tccacaaagt attataaatc acgtgcctaa aactgtccat gtagaccaag gcctgccctc | 5160 |
| ggcgcccccc actcttgcct ctgctctgca c | 5191 |

<210> SEQ ID NO 38
<211> LENGTH: 6437
<212> TYPE: DNA
<213> ORGANISM: Homo sapiens

<400> SEQUENCE: 38

| | |
|---|---|
| agtcattggt ctctggtggg accgggcgct gcccccttcc cctgtctcct gggtctctgg | 60 |
| aggagcccag gaaggaggct ccgctggttc cgctgggtca ggcgctgacg ggaccgggct | 120 |
| gcggcaatcg ttagcgggtc atgtcggccg cccaggggctg gacaggaac cgccggaggg | 180 |
| gaggaggcgc cgccggcgct ggtggcggag gtagcggggc cggcggggc agtgggggca | 240 |
| gcggggggtcg ggggactggc cagctcaacc gcttcgtgca actctccggg cggccgcacc | 300 |
| tgccaggtaa gaagaaaata cgatgggacc cagttaggag gcgcttcatt cagtcctgtc | 360 |
| ccatcataag gatccctaac aggttttttga gaggccacag acctccacca gcacgaagtg | 420 |
| gacatcgttg tgtggcagat aataccaacc tatatgtgtt tggaggttat aacccagatt | 480 |
| atgatgaatc ggggagggcct gataatgaag actatcctct cttcagggaa ctctggaggt | 540 |
| atcattttgc tacaggagta tggcaccaga tgggcacaga tggctacatg ccccgggaat | 600 |
| tggcatctat gtcacttgtg ctgcatgaa acaacctgtt agtatttgga ggtacgggca | 660 |
| tcccatttgg agagagcaac ggcaatgacg tccatgtgtg taatgtgaag tataagagat | 720 |
| gggctttgct cagctgtcgg gggaagaaac ccagtcgtat atatgacag gctatggcca | 780 |
| tcatcaatgg ctcccttat gtctttggag gtacaaccgg ctatatttac agcacagacc | 840 |
| tgcacaagtt agatctcaat accagagagt ggacacaact gaaaccaaac aacctatcct | 900 |
| gtgatctacc agaagagaga taccgacatg aaattgcaca tgacgggcag aggatttaca | 960 |
| tcttgggagg tggtacttcc tggacagcat attccttaaa caagatccat gcatacaacc | 1020 |
| ttgaaacgaa tgcctgggag gaaattgcaa caaaccccca tgaaaaaata ggctttcctg | 1080 |
| cagcccgaag gtgtcacagt tgtgttcaaa taaaaaatga tgtatttatt tgtggggct | 1140 |
| ataatggaga ggtgatcctg ggagatatct ggaagttgaa tctgcagact ttccaatggg | 1200 |
| tgaagctccc agctaccatg ccagagccag tttatttca ctgtgcagct gttacaccag | 1260 |
| ctggttgcat gtacacattcat ggaggagtgg tgaacatcca tgaaaacaaa cggactgggt | 1320 |

```
cattgtttaa gatctggctg gtggtaccta gcctgctgga actggcatgg gagaagctgc    1380
ttgcggcctt ccctaacctt gcaaacctct cccgaacaca acttctgcac cttggactca    1440
cacagggact catcgaacgc ttgaaatgag gatttctgga ctgttcattg atactggaaa    1500
tgttaattta aagagactcc tttatttatg ggcagtgtag aatgtgctac aaagaggatt    1560
ggttaccctg atcaaggcct tatttagaaa atacatcaga tgcctttctg taaattggtt    1620
tttcagttta tggacatctc actttcccac gtgcttcctt ctttgcttct gttcctcctg    1680
acccattaca tgcacatgta ctcacatact ccctcttcct tctcgatgga gttaagggaa    1740
agcctgaaag taccttaata atgttattaa tcaagacaga ttcctttta aaggaattct     1800 gaatagttcc atgtcataca atattctaga aattaaaaca tcatcaacat aaagaaaaat    1860
gaaattaaaa aattttaca tctagcaaca gcaacaacca caaatttagg ggaagctgag      1920
aaggctaacc ttgggaatct tgcaggttat acttaaacct agatgtttaa cttagtgttt    1980
tcaagatgtg tctaactgag tagtagctgg gtctgatggc agcagtgctt gccatcttgt    2040
tgcacagata actcaaacct acccttggc tttgaaggaa ggttaagcag cccagcaact       2100
cttggttagt gatttcttc tcatcctcat ggtgccagca gtggttagag ttggtttgtc       2160
aaaagactta cgtgtgtgtc gtggtcgtgc tctttgttgt tgctcttaga aattatggca    2220
ccaagaatgt ttcaaacgga aaaacttgtg gtggccaaag ttcttcattc tggcagtttt    2280
gaaactctct tatgcttatt aatggtttta aatatctctt tgacttcttc atggggaatt    2340
gtagacccta gtatgtggt gtaaatgcca tgtaacatga acacaagctc ccgagggagg     2400
ccagagaaga gccaggcaga gaaaacctgc atcctctggg cttgttaact tggcttccac    2460
tcgggctgtg gtctttggct atcatcttgg ccatttcctt ttgagaactt gtttcttttc    2520
taatctctgg gccaggtacc tgccattttc tcaggcagtt ggtccttgat ttttccctta    2580
gcttgttgcc ttcttttccg tctgctttaa tgtgcatggt gctgtgaata attgtctagt    2640
aattggatac aaggtcttgg gggtaaagcc acaggtcatc cttcctgaag aaccaagtat    2700
catttaaaaa ctagcatgag gaaggaatga aactgagtag cattcatttt gtgtgtgtga    2760
aattttagtt ctggtttgtt tgatttgttt ttttttttaat tctaaaaaga atgacataaa    2820
ttttcactcg ctttgccatc tggctgctag gggagctgag caagaggctc accatgcgca    2880
tgtgtaagcc gcaggtgtac tcaaggtgct gaaggcgtgc aaggggcagc gctggtcctc    2940
ccggggccaa ctcacagcag gagactcgca tgggagagtt ggaacacatc tttcctttaa    3000
gtgcctcttt tttcacctag cttttaaagt tattctttgt ccttcatctc agaagggatc    3060
tctttagctt atgtgtggat ttaaaatgac ctttgagcta cggttaaaaa gctaccatct    3120
ggtgttcagt tctgggaaag agaaaaccgt agcctccaga catgctcctg atttctaggc    3180
cttatcatac catcccctct gtgatgggtt gagttcatgg agcctgtatt ctgggaagtc    3240
ttataataac cacgcacctg tgaacgtggg tcctttctgg ggagtgagga atgtgggaga    3300
gaggcagaaa aaggagcagc tcctctaggg gcccatcctc ccacatcttg ccattaccag    3360
tctgtgtagc acttaacctc ctgccaccac tgccaggctt gctcctccgt tctctcccag    3420
agcaagtcag tctgagcagc tccattagtc caaaacagag cttgctgca tgacttcagc       3480 ctggcctctg gatatttggt ggaaatatat tctaaattga acaagccagg ctgtccaggg    3540
tggcaagagg atttttgacc tggatttata cagggaccaa agactgaatg ctcagcctct    3600
gtgcttagac tttcatggtc cttaggatag aagtgagtct ctagccctgc tacaccagag    3660
agctgaagag agatgtggtc tggttccatc catacttgct ggcatccttt gttaagccct    3720
```

```
ctgagggcag tcttctttga ggtagacctt ggaggcctga catcgaagac ctgtgtgttt    3780
tattttcata aaagtatata tccttggtct aaagtgtctt cttttaatat aacactagta    3840
aaaatgacat ggtatgacca gcactgagtg ctatagaacc acacatgtgt acatgttctg    3900
gatgccaaat gagactgtgt gtaaatgact aagtgtagat aactagaaat tagataggggg   3960 tcatcaggcg tttcggtata cctataacca gcactcggaa ttcctgacac tgtttacttg    4020
atttaggaaa gtttatgcct gctgcttctc tgcctctttg aggtactccc agccgtctta    4080
ctacagtcct gtaaatttaa gtgcaatata tagaaacata tggatatata cagattatat    4140
atagggtgta actataaagc aggtagacta cttttttgca tcttgggaa gtgagctcat      4200 tactttaggt tcaaattatg ccaagaattt tagatgtgat cagctggctt aagccaactc    4260
atgtcatgat aaagctggat tttcaagtcc atgttttctt actccaactc ttagagactc    4320
attgttcctt aggtttgtta gagttgagat ttttttttctc cctgtcatct ttgtactctc    4380
tcatgtttgc atgtcttaca ttttgttgcc ggagaacaag gaagtccatc tgtaaggagt    4440
ttcctaaacg gagaattaaa acctagtatt taacactaac cattctccta tgtatatact    4500
aatttatctg ggaatgtaat actttattaa atgaagaaaa tgatgctttc ttcatttaat    4560
attttccaca tcctggaaaa actataaact gacacagaat agattgaaat cttaactggg    4620
gctaaacaaa ccctttcca ttggcagaat ctcctttttt cagggccata atgacatgat     4680
gtaaaatttt gctttaaacc attcatgccc ttaaatagct agattttaaa gcataataag    4740
catattaaca tttttaagca aaagatacgt taacagtgac ctttggttat ccacagtagc    4800
aagagtaaag cacagatcat tgaaatccat agataatcag tgaatcaact ttcctaccaa    4860
acaatagatt catttacatt tcttttttcct ccctatcctt tcctgtaagc acctgttttt    4920
ccatggaatg gggttaatga gtaggtagaa aaggaaaagg aataatcagt aggagctgac    4980
aaccagtgac catataagca gctgattgcc tgtaattagt caggctgaac aattagagtt    5040
gaatgctgaa attaggaacc acaggtggta atcctgagta gatgtagctc ttcagcgtca    5100
tctcctgccc tgagctccag gccatctctc taaccaccaa agaactctta gtacctacgg    5160
gaaggaaaag ctgtgtgcga cacagaggaa actccattat ttgaacacat ttctttggct    5220
cttgacaaat acttgctttt cctctaatct tgcaagagct atggctcttc tattttccaa    5280
tcacacagct tggcatgtag gaaaggttga atgatcctct aagactgtgt tggtcttcgt    5340
attctgtaaa accccatttttt tttttgtggt cttacagatg tttagaaagt ggcacaggtt    5400
actgaattgt ctacctgcca gcattctgat atagcacaaa aagctatttt cctttatttt    5460
ttgtattatt ttttattttt ctggcattga gctctagggt ggatgagggt ttatggtcct    5520
ctgatcataa gctccattct aaaaactggt cactgttagc tgaaattgct ttggttcccc    5580
aaatgccttg gaactccaga cgcacccgca gggcctgagg taggcttcat agagttctag    5640
gacttccgtg tgcgttgcca ccagatcctg cccagcaatg gcctttccct tctaaggtca    5700
ttagattcag ccaaaagcga cctcttctct agtccggtgt tacgaacaga agttctgagt    5760
tgtgctacaa aagtagttcc atcttttttgg tgtaatttttc atgttttttaa tttgaaaaaa    5820 aaaaaaaaaa aaaacaactt tttataagtt ttttaagggc cctgcttagt cagtgtacag    5880
ggtggagtca gaggcagttt tcagaaaaaa acaaaaaaca aaaaaatttt caccaagcgg    5940
tagtaattgt tgttttacta gttatacatt tagaatataa aggaggcatc agaaaacaca    6000
ctctctaaag ccacttcctt gtgcacagag tctgcacagg gagagcacag gcatctccct    6060
```

```
ggaaaagcac ctgccaatga cgaatttcat ggaagaacct aggcaagaaa ggaagcctct    6120
ttctgagaca cagtctctga gaggtgagcc tagctttgct cttcctacag ggtatgcttg    6180
ggccatacac aatgctcgcc ttactttaaa gctattttgc cacagtcctg ttaaatagtg    6240
tggacgtcct tttgcagtct ggtgtgcatg ccatatgatc aggacagctt ttccacttta    6300
ctcggtttcc tacaagcaag taggaaatac agtgaattta ccctaaaatg tccaatctgt    6360
atttatgtac cttgtcagtg ttttgctgtt ggttttctaa acaatctga tcaataaatc     6420 ttatccaaat caatttg                                                   6437

<210> SEQ ID NO 39
<211> LENGTH: 5191
<212> TYPE: DNA
<213> ORGANISM: Homo sapiens

<400> SEQUENCE: 39
ggcgagtgcg tcgagctcgc cgcggactca agatggcggc gtgtggacgt gtacggagga      60
tgttccgctt gtcggcggcg ctgcatctgc tgctgctatt cgcggccggg gccgagaaac     120
tccccggcca gggcgtccac agccagggcc agggtcccgg ggccaacttt gtgtccttcg     180
tagggcaggc cggaggcggc ggcccggcgg gtcagcagct gccccagctg cctcagtcat     240
cgcagcttca gcagcaacag cagcagcagc aacagcaaca gcagcctcag ccgccgcagc     300
cgcctttccc ggcgggtggg cctccggccc ggcggggagg agcggggggct ggtgggggct    360 ggaagctggc ggaggaagag tcctgcaggg aggacgtgac ccgcgtgtgc cctaagcaca    420
cctggagcaa caacctggcg gtgctcgagt gcctgcagga tgtgagggag cctgaaaatg    480
aaatttcttc agactgcaat catttgttgt ggaattataa gctgaaccta actacagatc    540
ccaaatttga atctgtggcc agagaggttt gcaaatctac tataacagag attaaagaat    600
gtgctgatga accggttgga aaaggttaca tggtttcctg cttggtggat caccgaggca    660
acatcactga gtatcagtgt caccagtaca ttaccaagat gacggccatc attttttagtg    720 attaccgttt aatctgtggc ttcatggatg actgcaaaaa tgacatcaac attctgaaat    780
gtggcagtat tcggcttgga gaaaaggatg cacattcaca aggtgaggtg gtatcatgct    840
tggagaaagg cctggtgaaa gaagcagaag aaagagaacc caagattcaa gtttctgaac    900
tctgcaagaa agccattctc cgggtggctg agctgtcatc ggatgacttt cacttagacc    960
ggcatttata ttttgcttgc cgagatgatc gggagcgttt ttgtgaaaat acacaagctg   1020
gtgagggcag agtgtataag tgcctctta accataaatt tgaagaatcc atgagtgaaa    1080
agtgtcgaga agcacttaca acccgccaaa agctgattgc ccaggattat aaagtcagtt    1140
attcattggc caaatcctgt aaaagtgact gaagaaata ccggtgcaat gtggaaaacc    1200
ttccgcgatc gcgtgaagcc aggctctcct acttgttaat gtgcctggag tcagctgtac    1260
acagagggcg acaagtcagc agtgagtgcc aggggagat gctggattac cgacgcatgt    1320
tgatggaaga cttttctctg agccctgaga tcatcctaag ctgtcggggg agattgaac    1380 accattgttc cggattacat cgaaaagggc ggacctaca ctgtctgatg aaagtagttc    1440
gaggggagaa ggggaaccct ggaatgaact gccagcaggc gcttcaaaca ctgattcagg   1500
agactgaccc tggtgcagat taccgcattg atcgagcttt gaatgaagct tgtgaatctg   1560
taatccagac agcctgcaaa catataagat ctggagaccc aatgatcttg tcgtgcctga   1620
tggaacattt atacacagag aagatggtag aagactgtga acaccgtctc ttagagctgc   1680
agtatttcat ctcccgggat tggaagctgg accctgtcct gtaccgcaag tgccaggag   1740
```

-continued

| | |
|---|---|
| acgcttctcg tctttgccac acccacggtt ggaatgagac cagtgaattt atgcctcagg | 1800 |
| gagctgtgtt ctcttgttta tacagacacg cctaccgcac tgaggaacag ggaaggaggc | 1860 |
| tctcacggga gtgccgagct gaagtccaaa ggatcctaca ccagcgtgcc atggatgtca | 1920 |
| agctggatcc tgccctccag gataagtgcc tgattgatct gggaaaatgg tgcagtgaga | 1980 |
| aaacagagac tggacaggag ctggagtgcc ttcaggacca tctggatgac ttggtggtgg | 2040 |
| agtgtagaga tatagttggc aacctcactg agttagaatc agaggatatt caaatagaag | 2100 |
| ccttgctgat gagagcctgt gagcccataa ttcagaactt ctgccacgat gtggcagata | 2160 |
| accagataga ctctggggac ctgatggagt gtctgataca gaacaaacac cagaaggaca | 2220 |
| tgaacgagaa gtgtgccatc ggagttaccc acttccagct ggtgcagatg aaggattttc | 2280 |
| ggttttctta caagttttaaa atggcctgca aggaggacgt gttgaagctt tgcccaaaca | 2340 |
| taaaaaagaa ggtggacgtg tgatctgcc tgagcacgac cgtgcgcaat gacactctgc | 2400 |
| aggaagccaa ggagcacagg gtgtccctga agtgccgcag gcagctccgt gtggaggagc | 2460 |
| tggagatgac ggaggacatc cgcttggagc cagatctata cgaagcctgc aagagtgaca | 2520 |
| tcaaaaactt ctgttccgct gtgcaatatg gcaacgctca gattatcgaa tgtctgaaag | 2580 |
| aaaacaagaa gcagctaagc acccgctgcc accaaaaagt atttaagctg caggagacag | 2640 |
| agatgatgga cccagagcta gactacaccc tcatgagggt ctgcaagcag atgataaaga | 2700 |
| ggttctgtcc ggaagcagat tctaaaacca tgttgcagtg cttgaagcaa aataaaaaca | 2760 |
| gtgaattgat ggatcccaaa tgcaaacaga tgataaccaa cgccagatc acccagaaca | 2820 |
| cagattaccg cttaaacccc atgttaagaa aagcctgtaa agctgacatt cctaaattct | 2880 |
| gtcacgtat cctgactaag gccaaggatg attcagaatt agaaggacaa gtcatctctt | 2940 |
| gcctgaagct gagatatgct gaccagcgcc tgtcttcaga ctgtgaagac cagatccgaa | 3000 |
| tcattatcca ggagtccgcc ctggactacc gcctggatcc tcagctccag ctgcactgct | 3060 |
| cagacgagat ctccagtcta tgtgctgaag aagcagcagc ccaagagcag acaggtcagg | 3120 |
| tggaggagtg cctcaaggtc aacctgctca agatcaaaac agaattgtgt aaaaaggaag | 3180 |
| tgctaaacat gctgaaggaa agcaaagcag acatctttgt tgacccggta cttcatactg | 3240 |
| cttgtgccct ggacattaaa caccactgcg cagccatcac ccctggccgc gggcgtcaaa | 3300 |
| tgtcctgtct catggaagca ctggaggata gcgggtgag gttacagccc gagtgcaaaa | 3360 |
| agcgcctcaa tgaccggatt gagatgtgga gttacgcagc aaaggtggcc ccagcagatg | 3420 |
| gcttctctga tcttgccatg caagtaatga cgtctccatc taagaactac attctctctg | 3480 |
| tgatcagtgg gagcatctgt atattgttcc tgattggcct gatgtgtgga cggatcacca | 3540 |
| agcgagtgac acgagagctc aaggacaggt agagccacct tgaccaccaa aggaactacc | 3600 |
| tatccagtgc ccagtttgta cagccctctt gtatagcatc cccactcacc tcgctcttct | 3660 |
| cagaagtgac accaccccg tgttagagca ttagcagatg tccactgcgt tgtcccatcc | 3720 |
| agcctccact cgtgtccatg gtgtcctcct cctcctcacc gtgcagcagc agcagctggt | 3780 |
| cgctgggtt actgcctttg tttggcaaac ttgggtttac ctgcctgtag acaagtctct | 3840 |
| ctcataccaa cagaacttcc ggtacttcca gaaccaactc acctgacctg caactcaaag | 3900 |
| gcttttttaa gaaaaccacc aaaaaaaaaa atttttttaa agaaaaaaat gtatatagta | 3960 |
| acgcatctcc tccaggcttg atttgggcaa tggggttatg tctttcatat gactgtgtaa | 4020 |
| aacaaagaca ggacttggag gggaagcaca ccacccagtg tgccatgact gaggtgtctc | 4080 |

```
gttcatctct cagaagcacc ttggggcctc gccagggccg tggtcttcac cgaggcgtgg      4140
gtgggcagcc gttccccagg ctgtgtgggg tcctgctttc ttctgctgag acagtgacgc      4200
tttccagttt ccaccctaat cagccactgc tggtcacagc cccacagcca tgggtatttc      4260
tgtggtctcc tcgcttcatt gaagcaaagc atgagccttc ctagacaagg gcagctgggg      4320
aggggaaggg accggaagtt tgtgaagttg aacagtccat ccatctgcac tgagaggctg      4380
gatcctgagt cccggggcag caggatccca ggaaccttcc tcctcagggc agcacagga      4440 ctcagccatg tctggaccgg ccctgctgag gctacagtca ctctggaagc tctgcgcttc      4500
atcaggaggc aggactgtgg cgggaggggt ccttgaagat gggtgtgggg agcagtgggt      4560
caggaagtgg gagccagagg tttgactcac tttgctttat ttttcaggct acaatacagg      4620
tcagagacaa tggcttataa aggtttagtg tggtctcagg atgtgacagg cagtccagcc      4680
tgacctttct gcacactcca gacaaacttc ccagacaagc tcctttgtgc ctctacgtgg      4740
agagggtgtg gaaagttatc acattaaaag atggaggatt tgctctgttt tttttctttc      4800
tgtccatttg ctgcgtgtac ccactctagt aggcattggc taaatgttgt attttggcga      4860
ttcatcaacc tttgcagaat atgggcttta tagaagcaat attcttggcc atcccgcctc      4920
attcctccag tgtggagatg acaagtctgg gtgtgagagg gaggggtccg ggcatcatgg      4980
ttcagcgtgg cactcctttg gttgagtttg gggcatgaga tcacagtggc tgcacaagag      5040
agcagtgtgt acagtaggag agacatttat gtaatatata ttttattaac ctgttagatg      5100
tccacaaagt attataaatc acgtgcctaa aactgtccat gtagaccaag gcctgccctc      5160
ggcgcccccc actcttgcct ctgctctgca c                                    5191

<210> SEQ ID NO 40
<211> LENGTH: 6090
<212> TYPE: DNA
<213> ORGANISM: Homo sapiens

<400> SEQUENCE: 40
cagctcaacc gcttcgtgca actctccggg cggccgcacc tgccaggcca cagacctcca        60
ccagcacgaa gtggacatcg ttgtgtggca gataatacca acctatatgt gtttggaggt       120
tataacccag attatgatga atcgggaggg cctgataatg aagctatacc tctcttcagg       180
gaactctgga ggtatcattt tgctacagga gtatggcacc agatgggcac agatggctac       240
atgccccggg aattggcatc tatgtcactt gtgctgcatg gaaacaacct gttagtattt       300
ggaggtacgg gcatcccatt tggagagagc aacggcaatg acgtccatgt gtgtaatgtg       360
aagtataaga gatgggcttt gctcagctgt cggggaagaa aacccagtcg tatatatgga       420
caggctatgg ccatcatcaa tggctccctt tatgtctttg gaggtacaac cggctatatt       480
tacagcacag acctgcacaa gttagatctc aataccagag agtggacaca actgaaacca       540
aacaacctat cctgtgatct accagaagag agataccgac atgaaattgc acatgacggg       600
cagaggattt acatcttggg aggtggtact tcctggacag catattcctt aaacaagatc       660
catgcataca accttgaaac gaatgcctgg gaggaaattg caacaaaacc ccatgaaaaa       720
ataggctttc ctgcagcccg aaggtgtcac agttgtgttc aaataaaaaa tgatgtattt       780
atttgtgggg gctataatgg agaggtgatc ctggagagata tctggaagtt gaatctgcag       840
actttccaat gggtgaagct cccagctacc atgccagagc cagtttattt tcactgtgca       900
gctgttacac cagctggttg catgtacatt catggaggag tggtgaacat ccatgaaaac       960
aaacggactg ggtcattgtt taagatctgg ctggtggtac ctagcctgct ggaactggca      1020
```

```
tgggagaagc tgcttgcggc cttccctaac cttgcaaacc tctcccgaac acaacttctg    1080
caccttggac tcacacaggg actcatcgaa cgcttgaaat gaggatttct ggactgttca    1140
ttgatactgg aaatgttaat ttaaagagac tcctttattt atgggcagtg tagaatgtgc    1200
tacaaagagg attggttacc ctgatcaagg ccttatttag aaaatacatc agatgccttt    1260
ctgtaaattg gttttcagt ttatggacat ctcactttcc cacgtgcttc cttctttgct     1320
tctgttcctc ctgacccatt acatgcacat gtactcacat actccctctt ccttctcgat    1380
ggagttaagg gaaagcctga agtaccctta ataatgttat taatcaagac agattccttt    1440
ttaaaggaat tctgaatagt tccatgtcat acaatattct agaaattaaa acatcatcaa    1500
cataaagaaa aatgaaatta aaaaatttt acatctagca acagcaacaa ccacaaattt     1560
aggggaagct gagaaggcta accttgggaa tcttgcaggt tatacttaaa cctagatgtt    1620
taacttagtg ttttcaagat gtgtctaact gagtagtagc tgggtctgat ggcagcagtg    1680
cttgccatct tgttgcacag ataactcaaa cctacccttt ggctttgaag gaaggttaag    1740
cagcccagca actcttggtt agtgatttct ttctcatcct catggtgcca gcagtggtta    1800
gagttggttt gtcaaaagac ttacgtgtgt gtcgtggtcg tgctctttgt tgttgctctt    1860
agaaattatg gcaccaagaa tgtttcaaac ggaaaaactt gtggtggcca aagttcttca    1920
ttctggcagt tttgaaactc tcttatgctt attaatggtt ttaaatatct ctttgacttc    1980
ttcatgggga attgtagacc ctaagtatgt ggtgtaaatg ccatgtaaca tgaacacaag    2040
ctcccgaggg aggccagaga agagccaggc agagaaaacc tgcatcctct gggcttgtta    2100
acttggcttc cactcgggct gtggtctttg gctatcatct tggccatttc cttttgagaa    2160
cttgtttctt ttctaatctc tgggccaggt acctgccatt ttctcaggca gttggtcctt    2220
gatttttccc ttagcttgtt gccttctttt ccgtctgctt taatgtgcat ggtgctgtga    2280
ataattgtct agtaattgga tacaaggtct tgggggtaaa gccacaggtc atccttcctg    2340
aagaaccaag tatcatttaa aaactagcat gaggaaggaa tgaaactgag tagcattcat    2400
tttgtgtgtg tgaaatttta gttctggttt gtttgatttg tttttttttt aattctaaaa    2460
agaatgacat aaatttcac tcgctttgcc atctggctgc taggggagct gagcaagagg     2520
ctcaccatgc gcatgtgtaa gccgcaggtg tactcaaggt gctgaaggcg tgcaagggc     2580 agcgctggtc ctcccggggc caactcacag caggagactc gcatgggaga gttggaacac    2640
atctttcctt taagtgcctc ttttttcacc tagcttttaa agttattctt tgtccttcat    2700
ctcagaaggg atctctttag cttatgtgtg gatttaaaat gacctttgag ctacggttaa    2760
aaagctacca tctggtgttc agttctggga aagagaaaac cgtagcctcc agacatgctc    2820
ctgatttcta ggccttatca taccatcccc tctgtgatgg gttgagttca tggagcctgt    2880
attctgggaa gtcttataat aaccacgcac ctgtgaacgt gggtcctttc tggggagtga    2940
ggaatgtggg agagaggcag aaaaaggagc agctcctcta ggggcccatc ctcccacatc    3000
ttgccattac cagtctgtgt agcacttaac ctcctgccac cactgccagg cttgctcctc    3060
cgttctctcc cagagcaagt cagtctgagc agctccatta gtccaaaaca gagctttgct    3120
gcatgacttc agcctggcct ctggatattt ggtggaaata tattctaaat tgaacaagcc    3180
aggctgtcca gggtggcaag aggattttg acctggattt atacagggac caaagactga    3240
atgctcagcc tctgtgctta gactttcatg gtccttagga tagaagtgag tctctagccc    3300
tgctacacca gagagctgaa gagagatgtg gtctggttcc atccatactt gctggcatcc    3360
```

```
tttgttaagc cttctgaggg cagtcttctt tgaggtagac cttggaggcc tgacatcgaa    3420
gacctgtgtg ttttatttc ataaaagtat atatccttgg tctaaagtgt cttctttaa     3480 tataacacta gtaaaaatga catggtatga ccagcactga gtgctataga accacacatg    3540
tgtacatgtt ctggatgcca aatgagactg tgtgtaaatg actaagtgta gataactaga   3600
aattagatag gggtcatcag gcgtttcggt atacctataa ccagcactcg gaattcctga    3660
cactgtttac ttgatttagg aaagtttatg cctgctgctt ctctgcctct ttgaggtact    3720
cccagccgtc ttactacagt cctgtaaatt taagtgcaat atatagaaac atatggatat    3780
atacagatta tatatagggt gtaactataa agcaggtaga ctactttttt gcatcttggg    3840
gaagtgagct cattacttta ggttcaaatt atgccaagaa ttttagatgt gatcagctgg    3900
cttaagccaa ctcatgtcat gataaagctg gattttcaag tccatgtttt cttactccaa   3960
ctcttagaga ctcattgttc cttaggtttg ttagagttga gattttttt ctccctgtca     4020 tctttgtact ctctcatgtt tgcatgtctt acattttgtt gccggagaac aaggaagtcc    4080
atctgtaagg agtttcctaa acggagaatt aaaacctagt atttaacact aaccattctc    4140
ctatgtatat actaatttat ctgggaatgt aatactttat taaatgaaga aaatgatgct    4200
ttcttcattt aatatttcc acatcctgga aaaactataa actgacacag aatagattga     4260
aatcttaact ggggctaaac aaaacccttt ccattggcag aatctccttt tttcagggcc    4320
ataatgacat gatgtaaaaa tttgctttaa accattcatg cccttaaata gctagatttt    4380
aaagcataat aagcatatta acattttaa gcaaaagata cgttaacagt gacctttggt     4440
tatccacagt agcaagagta aagcacagat cattgaaatc catagataat cagtgaatca    4500
actttcctac caaacaatag attcatttac atttcttttt cctccctatc ctttcctgta    4560
agcacctgtt tttccatgga atggggttaa tgagtaggta gaaaaggaaa aggaataatc    4620
agtaggagct gacaaccagt gaccatataa gcagctgatt gcctgtaatt agtcaggctg    4680
aacaattaga gttgaatgct gaaattagga accacaggtg gtaatcctga gtagatgtag    4740
ctcttcagcg tcatctcctg ccctgagctc caggccatct ctctaaccac caaagaactc    4800
ttagtaccta cgggaaggaa aagctgtgtg cgacacagag gaaactccat tatttgaaca    4860
catttctttg gctcttgaca aatacttgct tttcctctaa tcttgcaaga gctatggctc    4920
ttctattttc caatcacaca gcttggcatg taggaaaggt tgaatgatcc tctaagactg    4980
tgttggtctt cgtattctgt aaacccatt tttttttgt ggtcttacag atgtttagaa       5040
agtggcacag gttactgaat tgtctacctg ccagcattct gatatagcac aaaaagctat    5100
tttcctttat ttttgtatt attttttatt tttctggcat tgagctctag ggtggatgag     5160
ggtttatggt cctctgatca taagctccat tctaaaaact ggtcactgtt agctgaaatt    5220
gctttggttc cccaaatgcc ttggaactcc agacgcaccc gcagggcctg aggtaggctt    5280
catagagttc taggacttcc gtgtgcgttg ccaccagatc ctgcccagca atggccttc     5340 ccttctaagg tcattagatt cagccaaaag cgacctcttc tctagtccgg tgttacgaac    5400
agaagttctg agttgtgcta caaaagtagt tccatctttt tggtgtaatt ttcatgtttt    5460
taatttgaaa aaaaaaaaa aaaaaacaa cttttataa gttttttaag ggccctgctt        5520
agtcagtgta cagggtggag tcagaggcag ttttcagaaa aaacaaaaa acaaaaaaa        5580 tttcaccaag cggtagtaat tgttgtttta ctagttatac atttagaata taaggaggc     5640 atcagaaaac acactctcta aagccacttc cttgtgcaca gagtctgcac agggagcaga    5700
caggcatctc cctggaaaag cacctgccaa tgacgaattt catggaagaa cctaggcaag    5760
```

-continued

| | |
|---|---|
| aaaggaagcc tctttctgag acacagtctc tgagaggtga gcctagcttt gctcttccta | 5820 |
| cagggtatgc ttgggccata cacaatgctc gccttacttt aaagctattt tgccacagtc | 5880 |
| ctgttaaata gtgtggacgt ccttttgcag tctggtgtgc atgccatatg atcaggacag | 5940 |
| cttttccact ttactcggtt tcctacaagc aagtaggaaa tacagtgaat ttaccctaaa | 6000 |
| atgtccaatc tgtatttatg taccttgtca gtgttttgct gttggttttc taaaacaatc | 6060 |
| tgatcaataa atcttatcca aatcaatttg | 6090 |

<210> SEQ ID NO 41
<211> LENGTH: 5753
<212> TYPE: DNA
<213> ORGANISM: Homo sapiens

<400> SEQUENCE: 41

| | |
|---|---|
| atcatggcgg atggccccag gtgtaagcgc agaaagcagg cgaacccgcg gcgcaataac | 60 |
| gttacaaatt ataatactgt ggtagaaaca aattcagatt cagatgatga agacaaactg | 120 |
| catattgtgg aagaagaaag tgttacagat gcagctgact gtgaaggtgt accagaggat | 180 |
| gacctgccaa cagaccagac agtgttacca gggaggagca gtgaaagaga agggaatgct | 240 |
| aagaactgct gggaggatga cagaaaggaa gggcaagaaa tcctgggggcc tgaagctcag | 300 |
| gcagatgaag caggatgtac agtaaaagat gatgaatgcg agtcagatgc agaaaatgag | 360 |
| caaaaccatg atcctaatgt tgaagagttt ctacaacaac aagacactgc tgtcattttt | 420 |
| cctgaggcac ctgaagagga ccagaggcag ggcacaccag aagccagtgg tcatgatgaa | 480 |
| aatggaacac cagatgcatt ttcacaatta ctcacctgtc catattgtga tagaggctat | 540 |
| aaacgcttta cctctctgaa agaacacatt aaatatcgtc atgaaagaa tgaagataac | 600 |
| tttagttgct ccctgtgcag ttacaccttt gcatacagaa cccaacttga acgtcacatg | 660 |
| acatcacata aatcaggaag agatcaaaga catgtgacgc agtctgggtg taatcgtaaa | 720 |
| ttcaaatgca ctgagtgtgg aaaagctttc aaatacaaac atcacctaaa agagcactta | 780 |
| agaattcaca gtggagagaa gccatatgaa tgcccaaact gcaagaaacg cttttcccat | 840 |
| tctggctcct atagctcaca cataagcagt aagaaatgta tcagcttgat acctgtgaat | 900 |
| gggcgaccaa gaacaggact caagacatct cagtgttctt caccgtctct ttcagcatca | 960 |
| ccaggcagtc ccacacgacc acagatacgg caaaagatag agaataaacc ccttcaagaa | 1020 |
| caactttctg ttaaccaaat taaaactgaa cctgtggatt atgaattcaa acccatagtg | 1080 |
| gttgcttcag gaatcaactg ttcaacccct ttacaaaatg gggttttcac tggtggtggc | 1140 |
| ccattacagg caaccagttc tcctcagggc atggtgcaag ctgttgttct gccaacagtt | 1200 |
| ggtttggtgt ctcccataag tatcaattta agtgatattc agaatgtact taaagtggcg | 1260 |
| gtagatggta atgtaataag gcaagtgttg gagaataatc aagccaatct tgcatccaaa | 1320 |
| gaacaagaaa caatcaatgc ttcacccata caacaaggtg gccattctgt tatttcagcc | 1380 |
| atcagtcttc ctttggttga tcaagatgga acaaccaaaa ttatcatcaa ctacagtctt | 1440 |
| gagcagccta gccaacttca agttgttcct caaaatttaa aaaagaaaa tccagtcgct | 1500 |
| acaaacagtt gtaaaagtga aaagttacca gaagatctta ctgttaagtc tgagaaggac | 1560 |
| aaaagctttg aagggggggt gaatgatagc acttgtcttc tgtgtgatga ttgtccagga | 1620 |
| gatattaatg cacttccaga attaaagcac tatgacctaa agcagcctac tcagcctcct | 1680 |
| ccactccctg cagcagaagc tgagaagcct gagtcctctg tttcatcagc tactggagat | 1740 |

-continued

```
ggcaatttgt ctcctagtca gccaccttta aagaacctct tgtctctcct aaaagcatat    1800
tatgctttga atgcacaacc aagtgcagaa gagctctcaa aaattgctga ttcagtaaac    1860
ctaccactgg atgtagtaaa aaagtggttt gaaaagatgc aagctggaca gatttcagtg    1920
cagtcttctg aaccatcttc tcctgaacca ggcaaagtaa atatccctgc caagaacaat    1980
gatcagcctc aatctgcaaa tgcaaatgaa ccccaggaca gcacagtaaa tctacaaagt    2040
cctttgaaga tgactaactc cccagtttta ccagtgggat caaccaccaa tggttccaga    2100
agtagtacac catccccatc acctctaaac ctttcctcat ccagaaatac acagggttac    2160
ttgtacacag ctgagggtgc acaagaagag ccacaagtag aacctcttga tctttcacta    2220
ccaaagcaac agggagaatt attagaaagg tcaactatca ctagtgttta ccagaacagt    2280
gtttattctg tccaggaaga acccttgaac ttgtcttgcg caaaaaagga gccacaaaag    2340
gacagttgtg ttacagactc agaaccagtt gtaaatgtaa tcccaccaag tgccaacccc    2400
ataaatatcg ctatacctac agtcactgcc cagttaccca caatcgtggc cattgctgac    2460
cagaacagtg ttccatgctt aagagcgcta gctgccaata agcaaacgat tctgattccc    2520
caggtggcat acacctactc aactacggtc agccctgcag tccaagaacc acccttgaaa    2580
gtgatccagc caaatggaaa tcaggatgaa agacaagata ctagctcaga aggagtatca    2640
aatgtagagg atcagaatga ctctgattct acaccgccca aaaagaaaat gcggaagaca    2700
gaaaatggaa tgtatgcttg tgatttgtgt gacaagatat tccaaaagag tagttcatta    2760
ttgagacata aatatgaaca cacaggtaaa agacctcatg agtgtggaat ctgtaaaaag    2820
gcatttaaac acaaacatca tttgattgaa cacatgcgat acattctggg agaaaagccc    2880
tatcaatgtg acaaatgtgg aaagcgcttc tcacactctg ggtcttattc tcaacacatg    2940
aatcatcgct actcctactg taagagagaa gcggaagaac gtgacagcac agagcaggaa    3000
gaggcagggc ctgaaatcct ctcgaatgag cacgtgggtg ccagggcgtc tccctcacag    3060
ggcgactcgg acgagagaga gagtttgaca agggaagagg atgaagacag tgaaaaagag    3120
gaagaggagg aggataaaga gatggaagaa ttgcaggaag aaaagaatg tgaaaaacca    3180
caaggggatg aggaagagga ggaggaggag gaagaagtgg aagaagaaga ggtagaagag    3240
gcagagaatg agggagaaga agcaaaaact gaaggtctga tgaaggatga cagggctgaa    3300
agtcaagcaa gcagcttagg acaaaaagta ggcgagagta gtgagcaagt gtctgaagaa    3360
aagacaaatg aagcctaatc gttttctag aaggaaaata aattctaatt gataatgaat    3420
ttcgttcaat attatccttg ctttcatgg aaacacagta acctgtatgc tgtgattcct    3480
gttcactact gtgtaaagta aaaactaaaa aaatacaaaa tacaaaacac acacacac    3540
acacacacac acacacacac acacacaaaa taaatccggg tgtgcctgaa cctcagacct    3600
agtaatttt catgcagttt tcaaagttag gaacaagttt gtaacatgca gcagattaga    3660
aaaccttaat gactcagaga gcaacaatac aagaggttaa aggaagctga ttaattagat    3720
atgcatctgg cattgttta tcttatcagt attatcactc ttatgttggt ttattcttaa    3780
gctgtacaat tgggagaaat tttataattt tttattggta acatatgct aaatccgctt    3840
cagtatttta ttatgttttt taaatgtga gaacttctgc actacaaaat tcccttcaca    3900
gagaagtata atgtagttcc aacccgtgct aactaccttt tataaattca gtctagaagg    3960
tagtaatttc taatatttag atgtcttagt agagcgtatt atcatttaaa gtgtattgtt    4020
agccttaaga aagcagctga tagaagaact gaagtttctt actcacgtgg tttaaaatgg    4080
agttcaaaag attgccattg agttctgatt gcagggacta acaatgttaa tctgataagg    4140
```

```
acagcaaaat catcagaatc agtgtttgtg attgtgtttg aatatgtggt aacatatgaa    4200
ggatatgaca tgaagctttg tatctccttt ggccttaagc aagacctgtg tgctgtaagt    4260
gccatttctc agtattttca aggctctaac ccgccttcat ccaatgtgtg gcctacaata    4320
actagcattt gttgatttgt ctcttgtatc aaaattccca aataaaactt aaaaccactg    4380
actctgtcag agaaactgaa acactgggac atttcatcct tcaattcctc ggtattgatt    4440
ttatgttgat tgattttcag aatttctcta cagaaacgaa agggaaattt tctaatctgc    4500
tttatccatg tacttgcatt tcagacatgg acatgctatt gttatttggc tcataactgt    4560
ttccaaatgt tagttattat ggacccaatt tattaacaac attagctgat ttttacctat    4620
cagtattatt ttatttcttt tagtttatag atctgtgcaa cattttttgta ctgtatgtct    4680 tcaaacctgg cagtattaat acccttctta ctgacatatg tactttttagt tttagaaaac    4740 ttttatattt atgtgtctta tttttatatt tctttattta ttacacagtg tagtgtataa    4800
tactgtagtt tgtattaata caataatata ttttagtatg aaaatttgga aagttgataa    4860
gatttaaagt agagatgcaa ttggttctcc tgcattgaga tttgatttaa cagtgttatg    4920
ttaacattta tacttgcctt ggactgtaga acagaactta aatgggaatg tattagtttt    4980
acaactacaa tcaagtcatt ttaccttttac ccagttttta atataaaact taaattttga    5040
aattcactgt gtgactaata gcatgatgct ctgcagtttt attaagaaat cagcctaacc    5100
atacaactct catttcctta gtaagccaaa ttaggattaa cttctataaa cagtgttggg    5160
aacaatgttt aacattttgt gccaatttgt tcctgtattc atgtatgtaa gttacagatc    5220
tgactcttca ttttttaagtt ccttgttaca tcatggtcat tttctagttt tttaccagac    5280
tcccatctca caataaaatg catcaacaag cctgaactgc tgtcattctt ttcatcatta    5340
tcagtatttt ctttggaaaa ctgtgaaatg gggtacattg tcatcctgca tttgattcat    5400
cttgagctga atttgggtaa cactaaatgt tttagacatt ctccactaaa ttatggatttt    5460 tcttgtggct aaatgtttct ggagaggtca gagttgacaa aacctcttca caggttgctc    5520
cttcttcctg aaatccttaa tcctccgcat ttcatgcttc aggtcatttc agggaagcct    5580
gggtttagat gcctttctga ctctcagctc ctgcacttct gtcatcatac ctctgatact    5640
attatttata ttccttcccc actaggaaca ggaaccacat ttgtcatagt cactctcaca    5700
ttcctcactg cctaacaggg tgcctggcat aagttgggac aacagatatt tgt           5753
```

<210> SEQ ID NO 42
<211> LENGTH: 3901
<212> TYPE: DNA
<213> ORGANISM: Homo sapiens

<400> SEQUENCE: 42

```
aagatggcgg cgtgtggacg tgtacggagg atgttccgct tgtcggcggc gctgcatctg      60
ctgctgctat tcgcggccgg ggccgagaaa ctccccggcc atggcgtcca cagccagggc     120
cagggtcccg gggccaactt tgtgtccttc gtagggcagg ccggaggcgg cggcccggcg     180
ggtcagcagc tgccccagct gcttcagtca tcgcagcttc agcagcaaca gcagcagcag     240
caacagcaac agcagcttca gccgccgcag ccgccttttcc cggcgggtgg gcctccggcc     300
cggcggggag gagcggggc tggtgggggc tggaagctgg cggaggaaga gtcctgcagg     360
gaggacgtga cccgcgtgtg ccctaagcac acctggagca acaacctggc ggtgctcgag     420
tgcctgcagg atgtgaggga gcctgaaaat gaaatttctt cagactgcaa tcatttgttg     480
```

```
tggaattata agctgaacct aactacagat cccaaatttg aatctgtggc cagagaggtt      540
tgcaaatcta ctataacaga gattaaagaa tgtgctgatg aaccggttgg aaaaggttac      600
atggtttcct gcttagtgga tcaccgaggc aacatcactg agtatcagtg tcaccagtac      660
attaccaaga tgacggccat cattttagt gattaccgtt taatctgtgg cttcatggat       720
gactgcaaaa atgacatcaa cattctgaaa tgtggcagta ttcggcttgg agaaaaggat      780
gcacattcac aaggtgaggt ggtatcatgc ttggagaaag gcctggtgaa agaagcagaa      840
gaaagagaac ccaagattca gtttctgaa ctctgcaaga aagccattct ccgggtggct       900
gagctgtcat cggatgactt tcacttagac cggcatttat attttgcttg ccagagatgat    960 cgggagcgtt tttgtgaaaa tacacaagct ggtgagggca gagtgtataa gtgcctcttt     1020
aaccataaat ttgaagaatc catgagtgaa aagtgtcgag aagcacttac aacccgccaa     1080
aagctgattg cccaggatta taaagtcagt tattcattgg ccaaatcctg taaaagtgac     1140
ttgaagaaat accggtgcaa tgtggaaaac cttccgcgat cgcgtgaagc caggctctcc     1200
tacttgttaa tgtgcctgga gtcagctgta cacagagggc gacaagtcag cagtgagtgc     1260
cagggggaga tgctggatta ccgacgcatg ttgatggaag acttttctct gagccctgag     1320
atcatcctaa gctgtcgggg ggagattgaa caccattgtt ccggattaca tcgaaaaggg     1380
cggaccctac actgtctgat gaaagtagtt cgaggggaga aggggaacct tggaatgaac     1440
tgccagcagg cgcttcaaac actgattcag gagactgacc ctggtgcaga ttaccgcatt     1500
gatcgagctt tgaatgaagc ttgtgaatct gtaatccaga cagcctgcaa acatataaga     1560
tctggagacc caatgatctt gtcgtgcctg atggaacatt tatacacaga gaagatggta     1620
gaagactgtg aacaccgtct cttagagctg cagtatttca tctcccggga ttggaagctg     1680
gaccctgtcc tgtaccgcaa gtgccaggga gacgcttctc gtctttgcca cacccacggt     1740
tggaatgaga ccagtgaatt tatgcctcag ggagctgtgt tctcttgttt atacagacac     1800
gcctaccgca ctgaggaaca gggaaggagg ctctcacggg agtgccgagc tgaagtccaa     1860
aggatcctac accagcgtgc catggatgtc aagctggatc ctgccctcca ggataagtgc     1920
ctgattgatc tgggaaaatg gtgcagtgag aaaacagaga ctggacagga gctggagtgc     1980
cttcaggacc atctgatga cttggtggtg gagtgtagag atatagttgg caacctcact      2040
gagttagaat cagaggatat tcaaatagaa gccttgctga tgagagcctg tgagcccata     2100
attcagaact tctgccacga tgtggcagat aaccagatag actctgggga cctgatggag     2160
tgtctgatac agaacaaaca ccagaaggac atgaacgaga agtgtgccat cggagttacc     2220
cacttccagc tggtgcagat gaaggatttt cggttttctt acaagtttaa aatggcctgc     2280
aaggaggacg tgttgaagct tgccccaaac ataaaaaaga aggtggacgt ggtgatctgc     2340
ctgagcacga ccgtgcgcaa tgacactctg caggaagcca aggagcacag ggtgtccctg     2400
aagtgccgca ggcagctccg tgtggaggag ctggagtgga cggaggacat ccgcttggag     2460
ccagatctat acgaagcctg caagagtgac atcaaaaact tctgttccgc tgtgcaatat     2520
ggcaacgctc agattatcga atgtctgaaa gaaaacaaga agcagctaag cacccgctgc     2580
caccaaaaag tatttaagct gcaggagaca gagatgatgg acccagagct agactacacc     2640
ctcatgaggg tctgcaagca gatgataaag aggttctgtc cggaagcaga ttctaaaacc     2700
atgttgcagt gcttgaagca aaataaaaac agtgaattga tggatcccaa atgcaaacag     2760
atgataacca agcgccagat cacccagaac acagattacc gcttaaaccc catgttaaga     2820
aaagcctgta aagctgacat tcctaaattc tgtcacggta tcctgactaa ggccaaggat     2880
```

-continued

```
gattcagaat tagaaggaca agtcatctct tgcctgaagc tgagatatgc tgaccagcgc    2940
ctgtcttcag actgtgaaga ccagatccga atcattatcc aggagtccgc cctggactac    3000
cgcctggatc ctcagctcca gctgcactgc tcagacgaga tctccagtct atgtgctgaa    3060
gaagcagcag cccaagagca gacaggtcag gtggaggagt gcctcaaggt caacctgctc    3120
aagatcaaaa cagaattgtg taaaaaggaa gtgctaaaca tgctgaagga agcaaagca    3180 gacatctttg ttgacccggt acttcatact gcttgtgccc tggacattaa acaccactgc    3240
gcagccatca cccctggccg cgggcgtcaa atgtcctgtc tcatggaagc actggaggat    3300
aagcgggtga ggttacagcc cgagtgcaaa aagcgcctca atgaccggat tgagatgtgg    3360
agttacgcag caaaggtggc cccagcagat ggcttctctg atcttgccat gcaagtaatg    3420
acgtctccat ctaagaacta cattctctct gtgatcagtg ggagcatctg tatattgttc    3480
ctgattggcc tgatgtgtgg acggatcacc aagcgagtga cacgagagct caaggacagg    3540
tagagccacc ttgaccacca aggaactac ctatccagtg cccagtttgt acagccctct    3600
tgtatagcat ccccactcac ctcgctcttc tcagaagtga caccaacccc gtgttagagc    3660
attagcagat gtccactgcg ttgtcccatc cagcctccac tcgtgtccat ggtgtcctcc    3720
tcctcctcac cgtgcagcag cagcagctgg tcgctggggt tactgccttt gtttggcaaa    3780
cttgggttta cctgcctgta gacaagtctc tctcatacca acagaacttc cggtacttcc    3840
agaaccaact cacctgacct gcaactcaaa ggcttttta agaaaaccac caaaaaaaaa    3900
a                                                                   3901
```

<210> SEQ ID NO 43
<211> LENGTH: 247
<212> TYPE: PRT
<213> ORGANISM: Homo sapiens

<400> SEQUENCE: 43

```
Met Ala Asp Thr Thr Pro Ser Gly Pro Gln Gly Ala Gly Ala Val Gln
 1               5                  10                  15

Phe Met Met Thr Asn Lys Leu Asp Thr Ala Met Trp Leu Ser Arg Leu
                20                  25                  30

Phe Thr Val Tyr Cys Ser Ala Leu Phe Val Leu Pro Leu Leu Gly Leu
            35                  40                  45

His Glu Ala Ala Ser Phe Tyr Gln Arg Ala Leu Leu Ala Asn Ala Leu
        50                  55                  60

Thr Ser Ala Leu Arg Leu His Gln Arg Leu Pro His Phe Gln Leu Ser
65                  70                  75                  80

Arg Ala Phe Leu Ala Gln Ala Leu Leu Glu Asp Ser Cys His Tyr Leu
                85                  90                  95

Leu Tyr Ser Leu Ile Phe Val Asn Ser Tyr Pro Val Thr Met Ser Ile
            100                 105                 110

Phe Pro Val Leu Leu Phe Ser Leu Leu His Ala Ala Thr Tyr Thr Lys
        115                 120                 125

Lys Val Leu Asp Ala Arg Gly Ser Asn Ser Leu Pro Leu Leu Arg Ser
    130                 135                 140

Val Leu Asp Lys Leu Ser Ala Asn Gln Gln Asn Ile Leu Lys Phe Ile
145                 150                 155                 160

Ala Cys Asn Glu Ile Phe Leu Met Pro Ala Thr Val Phe Met Leu Phe
                165                 170                 175

Ser Gly Gln Gly Ser Leu Leu Gln Pro Phe Ile Tyr Tyr Arg Phe Leu
```

```
                      180                 185                 190
Thr Leu Arg Tyr Ser Ser Arg Arg Asn Pro Tyr Cys Arg Thr Leu Phe
                195                 200                 205

Asn Glu Leu Arg Ile Val Val Glu His Ile Ile Met Lys Pro Ala Cys
            210                 215                 220

Pro Leu Phe Val Arg Arg Leu Cys Leu Gln Ser Ile Ala Phe Ile Ser
225                 230                 235                 240

Arg Leu Ala Pro Thr Val Pro
                245

<210> SEQ ID NO 44
<211> LENGTH: 247
<212> TYPE: PRT
<213> ORGANISM: Homo sapiens

<400> SEQUENCE: 44

Met Ala Asp Thr Thr Pro Asn Gly Pro Gln Gly Ala Gly Ala Val Gln
  1               5                  10                  15

Phe Met Met Thr Asn Lys Leu Asp Thr Ala Met Trp Leu Ser Arg Leu
                 20                  25                  30

Phe Thr Val Tyr Cys Ser Ala Leu Phe Val Leu Pro Leu Leu Gly Leu
             35                  40                  45

His Glu Ala Ala Ser Phe Tyr Gln Arg Ala Leu Leu Asn Ala Leu
         50                  55                  60

Thr Ser Ala Leu Arg Leu His Gln Arg Leu Pro His Phe Gln Leu Ser
 65                  70                  75                  80

Arg Ala Phe Leu Ala Gln Ala Leu Leu Glu Asp Ser Cys His Tyr Leu
                 85                  90                  95

Leu Tyr Ser Leu Ile Phe Val Asn Ser Tyr Pro Val Thr Met Ser Ile
            100                 105                 110

Phe Pro Val Leu Leu Phe Ser Leu Leu His Ala Ala Thr Tyr Thr Lys
        115                 120                 125

Lys Val Leu Asp Ala Arg Gly Ser Asn Ser Leu Pro Leu Leu Arg Ser
130                 135                 140

Val Leu Asp Lys Leu Ser Ala Asn Gln Gln Asn Ile Leu Lys Phe Ile
145                 150                 155                 160

Ala Cys Asn Glu Ile Phe Leu Met Pro Ala Thr Val Phe Met Leu Phe
                165                 170                 175

Ser Gly Gln Gly Ser Leu Leu Gln Pro Phe Ile Tyr Tyr Arg Phe Leu
            180                 185                 190

Thr Leu Arg Tyr Ser Ser Arg Arg Asn Pro Tyr Cys Arg Thr Leu Phe
        195                 200                 205

Asn Glu Leu Arg Ile Val Val Glu His Ile Ile Met Lys Pro Ala Cys
    210                 215                 220

Pro Leu Phe Val Arg Arg Leu Cys Leu Gln Ser Ile Ala Phe Ile Ser
225                 230                 235                 240

Arg Leu Ala Pro Thr Val Pro
                245

<210> SEQ ID NO 45
<211> LENGTH: 1780
<212> TYPE: DNA
<213> ORGANISM: Homo sapiens

<400> SEQUENCE: 45
gtaggttggc tctttagggc ttcaccccga agctccacct tcgctcccgt ctttctggaa    60
```

```
acaccgcttt gatctcggcg gtgcgggaca ggtacctccc ggctgctgcg ggtgccctgg    120
atccagtcgg ctgcaccaga cgctagtgtg agccccatg  gcagatacga ccccgaacgg    180
cccccaaggg gcgggcgctg tgcaattcat gatgaccaat aaactggaca cggcaatgtg    240
gctttctcgc ttgttcacag tttactgctc tgctctgttt gttctgcctc ttcttgggtt    300
gcatgaagca gcaagctttt accaacgtgc tttgctggca aatgctctta ccagtgctct    360
gaggctgcat caaagattac cacacttcca gttaagcaga gcattcctgg cccaggcttt    420
gttagaggac agctgccact acctgttgta ttcactcatc tttgtaaatt cctatccagt    480
tacaatgagt atcttcccag tcttgttatt ctctttgctt catgctgcca catatacgaa    540
aaaggtcctt gacgcaaggg gctcaaatag tttacctctg ctgagatctg tcttggacaa    600
attaagtgct aatcaacaaa atattctgaa attcattgct gcaatgaaaa tattcctgat    660
gcctgcgaca gttttttatgc ttttttagtgg tcaaggaagt ttgctccaac cttttatata   720
ctatagattt cttacccttc gatattcgtc tcgaagaaac ccatattgtc ggaccttatt    780
taatgaactg aggattgttg ttgaaacacat aataatgaaa cctgcttgcc cactgtttgt    840
gagaagactt tgtctccaga gcattgcctt tataagcaga ttggcaccaa cagttccata    900
gtttaacatc tagttaagct acaaatatag tataagcatt attagcagct ggtacttctg    960
ctaggggttg taaattccag gtgttacact gacctcaatc caatttacat aatttacata   1020
aatgcatctc ggtggaaaaa taatcatttt cttggcatgt aaatcaagc  ttaaaaagtt   1080 ttgagaaaat tttactgtgc tgtgttgcta atggttaaag aagtctgtat ctagtgataa   1140
atataccagt ttttttaaaa agatgctgtt gtgcctatat catgaagtac attaatttct   1200
catgtaaaaa aaatagctct aaaatttcag tattctacca ttcagtaatt ttggttaatg   1260
attttaacac ttctcagtgt atttaatttc aaattgtttt tttaattggt tttatgctgc   1320
tttgttagga cagatgtgtt ttgaatgtac cattataaga agaattctat gtatcttaaa   1380
ctatgatctt ctaaaatttt atttccgtaa gtacttctgt ggccttgagt atttttttaaa  1440 aggctcaact gtaagcctct tagccagttg gataaatatt tggggtcacc tagccattga   1500
aagcagaaag cagtagtgac acagctttcc cttcaaagag ccattgagaa acatttctca   1560
aacaggaaat ccttcttta  ctaatgtgga catatagatt attcgtatta tagttttgtag  1620 aactacctag ttcagaatct tgactgccag ttttcttggt ttcttaggct tgaattttca   1680
tagacaattg caacagttta gatgcctttt gaaaggaatg taatgaagat tcagcatctg   1740
actatatgtg tgtctatcct gaaataataa tggagagtat                         1780
```

<210> SEQ ID NO 46
<211> LENGTH: 1780
<212> TYPE: DNA
<213> ORGANISM: Homo sapiens

<400> SEQUENCE: 46

```
gtaggttggc tctttagggc ttcaccccga agctccacct tcgctcccgt ctttctggaa     60
acaccgcttt gatctcggcg gtgcgggaca ggtacctccc ggctgctgcg ggtgccctgg    120
atccagtcgg ctgcaccaga cgctagtgtg agccccatg  gcagatacga ccccgaacgg    180
cccccaaggg gcgggcgctg tgcaattcat gatgaccaat aaactggaca cggcaatgtg    240
gctttctcgc ttgttcacag tttactgctc tgctctgttt gttctgcctc ttcttgggtt    300
gcatgaagca gcaagctttt accaacgtgc tttgctggca aatgctctta ccagtgctct    360
```

```
gaggctgcat caaagattac cacacttcca gttaagcaga gcattcctgg cccaggcttt    420
gttagaggac agctgccact acctgttgta ttcactcatc tttgtaaatt cctatccagt    480
tacaatgagt atcttcccag tcttgttatt ctctttgctt catgctgcca catatacgaa    540
aaaggtcctt gacgcaaggg gctcaaatag tttacctctg ctgagatctg tcttggacaa    600
attaagtgct aatcaacaaa atattctgaa attcattgct tgcaatgaaa tattcctgat    660
gcctgcgaca gtttttatgc ttttagtgg tcaaggaagt ttgctccaac cttttatata    720
ctatagattt cttacccttc gatattcgtc tcgaagaaac ccatattgtc ggaccttatt    780
taatgaactg aggattgttg ttgaacacat aataatgaaa cctgcttgcc cactgtttgt    840
gagaagactt tgtctccaga gcattgcctt tataagcaga ttggcaccaa cagttccata    900
gtttaacatc tagttaagct acaaatatag tataagcatt attagcagct ggtacttctg    960
ctaggggttg taaattccag gtgttacact gacctcaatc caatttacat aatttacata   1020
aatgcatctc ggtggaaaaa taatcatttt cttggcatgt taaatcaagc ttaaaaagtt   1080
ttgagaaaat tttactgtgc tgtgttgcta atggttaaag aagtctgtat ctagtgataa   1140
atataccagt ttttttaaaa agatgctgtt gtgcctatat catgaagtac attaatttct   1200
catgtaaaaa aaatagctct aaaatttcag tattctacca ttcagtaatt ttggttaatg   1260
attttaacac ttctcagtgt atttaatttc aaattgtttt tttaattggt tttatgctgc   1320
tttgttagga cagatgtgtt ttgaatgtac cattataaga agaattctat gtatcttaaa   1380
ctatgatctt ctaaaatttt atttccgtaa gtacttctgt ggccttgagt atttttttaaa   1440
aggctcaact gtaagcctct tagccagttg gataaatatt tggggtcacc tagccattga   1500
aagcagaaag cagtagtgac acagcttttcc cttcaaagag ccattgagaa acatttctca   1560
aacaggaaat ccttctttta ctaatgtgga catatagatt attcgtatta tagtttgtag   1620
aactacctag ttcagaatct tgactgccag ttttcttggt ttcttaggct tgaattttca   1680
tagacaattg caacagttta gatgcctttt gaaaggaatg taatgaagat tcagcatctg   1740
actatatgtg tgtctatcct gaaataataa tggagagtat                          1780
```

<210> SEQ ID NO 47
<211> LENGTH: 363
<212> TYPE: PRT
<213> ORGANISM: Homo sapiens

<400> SEQUENCE: 47

```
Met Leu Gly Ala Trp Ala Val Glu Gly Thr Ala Val Ala Leu Leu Arg
 1               5                  10                  15

Leu Leu Leu Leu Leu Pro Pro Ala Ile Arg Gly Pro Gly Leu Gly
            20                  25                  30

Val Ala Gly Val Ala Gly Ala Ala Gly Ala Gly Leu Pro Glu Ser Val
        35                  40                  45

Ile Trp Ala Val Asn Ala Gly Gly Glu Ala His Val Asp Val His Gly
    50                  55                  60

Ile His Phe Arg Lys Asp Pro Leu Glu Gly Arg Val Gly Arg Ala Ser
65                  70                  75                  80

Asp Tyr Gly Met Lys Leu Pro Ile Leu Arg Ser Asn Pro Glu Asp Gln
                85                  90                  95

Ile Leu Tyr Gln Thr Glu Arg Tyr Asn Glu Glu Thr Phe Gly Tyr Glu
            100                 105                 110

Val Pro Ile Lys Glu Glu Gly Asp Tyr Val Leu Val Leu Lys Phe Ala
        115                 120                 125
```

```
Glu Val Tyr Phe Ala Gln Ser Gln Gln Lys Val Phe Asp Val Arg Leu
        130                 135                 140

Asn Gly His Val Val Lys Asp Leu Asp Ile Phe Asp Arg Val Gly
145                 150                 155                 160

His Ser Thr Ala His Asp Glu Ile Ile Pro Met Ser Ile Arg Lys Gly
                165                 170                 175

Lys Leu Ser Val Gln Gly Glu Val Ser Thr Phe Thr Gly Lys Leu Tyr
                180                 185                 190

Ile Glu Phe Val Lys Gly Tyr Tyr Asp Asn Pro Lys Val Cys Ala Leu
            195                 200                 205

Tyr Ile Met Ala Gly Thr Val Asp Asp Val Pro Lys Leu Gln Pro His
        210                 215                 220

Pro Gly Leu Glu Lys Lys Glu Glu Glu Glu Glu Glu Tyr Asp
225                 230                 235                 240

Glu Gly Ser Asn Leu Lys Lys Gln Thr Asn Lys Asn Arg Val Gln Ser
                245                 250                 255

Gly Pro Arg Thr Pro Asn Pro Tyr Ala Ser Asp Asn Ser Ser Leu Met
                260                 265                 270

Phe Pro Ile Leu Val Ala Phe Gly Val Phe Ile Pro Thr Leu Phe Cys
            275                 280                 285

Leu Cys Arg Leu Ala Gly Trp Val Cys Phe Gly Leu Ser Pro Ser Val
        290                 295                 300

Ala Pro Glu Glu Gly Glu Thr Glu Ala Arg Gln Ser Asp Ser Thr Leu
305                 310                 315                 320

Lys Gln Asn Arg Lys His Pro Gly Thr Val Gln Lys Ser Gln Lys Lys
                325                 330                 335

Ser Ala Ser Leu Arg Trp Lys Asp Ile Ile Asn Asp Gln Arg Ala Phe
                340                 345                 350

Ser Leu Ser Val Gln Thr Lys Thr Leu Cys Ile
            355                 360

<210> SEQ ID NO 48
<211> LENGTH: 292
<212> TYPE: PRT
<213> ORGANISM: Homo sapiens

<400> SEQUENCE: 48

Met Leu Gly Ala Trp Ala Val Glu Gly Thr Ala Val Ala Leu Leu Arg
 1               5                  10                  15

Leu Leu Leu Leu Leu Leu Pro Pro Ala Ile Arg Gly Pro Gly Leu Gly
                20                  25                  30

Val Ala Gly Val Ala Gly Ala Ala Gly Ala Gly Leu Pro Glu Ser Val
            35                  40                  45

Ile Trp Ala Val Asn Ala Gly Gly Glu Ala His Val Asp Val His Gly
        50                  55                  60

Ile His Phe Arg Lys Asp Pro Leu Glu Gly Arg Val Gly Arg Ala Ser
65                  70                  75                  80

Asp Tyr Gly Met Lys Leu Pro Ile Leu Arg Ser Asn Pro Glu Asp Gln
                85                  90                  95

Ile Leu Tyr Gln Thr Glu Arg Tyr Asn Glu Glu Thr Phe Gly Tyr Glu
                100                 105                 110

Val Pro Ile Lys Glu Glu Gly Asp Tyr Val Leu Val Leu Lys Phe Ala
            115                 120                 125

Glu Val Tyr Phe Ala Gln Ser Gln Gln Lys Val Phe Asp Val Arg Leu
```

```
                130              135              140
Asn Gly His Val Val Lys Asp Leu Asp Ile Phe Asp Arg Val Gly
145                 150                  155                 160

His Ser Thr Ala His Asp Glu Ile Ile Pro Met Ser Ile Arg Lys Gly
                165                  170                 175

Lys Leu Ser Val Gln Gly Glu Val Ser Thr Phe Thr Gly Lys Leu Tyr
                180                  185                 190

Ile Glu Phe Val Lys Gly Tyr Tyr Asp Asn Pro Lys Val Cys Ala Leu
            195                  200                  205

Tyr Ile Met Ala Gly Thr Val Asp Asp Val Pro Lys Leu Gln Pro His
    210                  215                  220

Pro Gly Leu Glu Lys Lys Glu Glu Glu Glu Glu Glu Tyr Asp
225                  230                  235                 240

Glu Gly Ser Asn Leu Lys Lys Gln Thr Asn Lys Asn Arg Val Gln Ser
                245                  250                  255

Gly Pro Arg Thr Pro Asn Pro Tyr Ala Ser Asp Asn Ser Ser Leu Met
                260                  265                  270

Phe Pro Ile Leu Val Ala Phe Gly Val Phe Ile Pro Thr Leu Phe Cys
            275                  280                  285

Leu Cys Arg Leu
    290
```

<210> SEQ ID NO 49
<211> LENGTH: 1800
<212> TYPE: DNA
<213> ORGANISM: Homo sapiens

<400> SEQUENCE: 49

```
gtggctgaga agaaggaggc ctgagagcga catgtccccg gcggctcagg cggagcggcc      60
cgtggcgctg ttttctgag  tccggggtgg cctggcagcc ggccgaggac gagggtcggc     120
gggggctgcc cccgtggtgg tggccgccat gctgggagcc tgggcggttg agggaaccgc     180
tgtgcgcctc ctgcgactgc tgctgctgct gctgccgccg gcgatccggg acccgggct      240
cggcgtggcc ggcgtggccg gcgcggcggg ggccgggctg cccgagagcg tcatttgggc     300
ggtcaacgcg ggtggagagg cgcatgtgga cgtgcacggg atccacttcc gcaaggaccc     360
tttggaaggc cgggtgggcc gagcctcaga ctatggcatg aaactgccaa tcctgcgttc     420
caaccctgag gaccagatcc tgtatcaaac tgagcggtac aatgaggaga cctttggcta     480
cgaagtgccc atcaaagagg aggggggacta cgtgctggtc ttgaaatttg cagaggtcta     540
ctttgcacag tcccagcaaa aggtatttga tgtacgattg aatggccacg tcgtggtgaa     600
ggacttggat atctttgatc gtgttgggca tagcacagct cacgatgaaa ttatacctat     660
gagcatcaga aaggggaagc tgagtgtcca ggggggaggtg tccaccttca cagggaaact     720
ctacattgag tttgtcaagg gtactatga  caatcccaag gtctgtgcac tctacatcat     780
ggctgggaca gtggatgatg taccaaagct tcagcctcat ccgggattgg agaagaaaga     840
agaggaagaa gaagaagaag aatatgatga agggtctaat ctcaaaaaac agaccaataa     900
gaaccgggtg cagtcaggcc ccgcacacc  caacccctat gcctcggaca cagcagcct      960
catgtttccc atcctggtgg ccttcggagt cttcattcca accctcttct gcctctgccg    1020
gttggcagga tgggtatgct ttgggctttc tccttctgtg gccccggagg aaggagagac    1080
tgaggcaagg caaagtgata gtacactgaa gcagaaccgg aaacacccag gaactgttca    1140
gaaatctcag aagaaatctg cttctcttcg atggaaagat ataattaacg atcaaagagc    1200
```

```
ttttctctt tcagtccaaa ctaagactct ctgtatttaa atctctctgg ggcaagaggg    1260
ctagatttcc tcattttgtt atgagactag attggtacca gtagatcagc tgcctagcga    1320
gggcaggttt cttcttttgca tctgtgtggc ttgcttccag tctggcctgt cctttccagc    1380
tgccttttgt ctagcctgct atgggggggcc agattatctt gataagagca ggtgatttgg    1440
ggactagctg ggttggcagg aaaagagcag atggatctc ttgggacagg ttcccccagg    1500
agtataaaca caaggagcca ggattgtgct gtctattttg agcttcagtg ctttatttca    1560
gtatgaggaa aaacaacaac aaactgaagt gcgctttccg tcctttcaaa ggacaactgt    1620
cgggaaggga gagccgagtt gcgaggtagg aggggagcac tggcagggag agacattctt    1680
gactcctctc ttccctggtg tgttgtgatc cagggcaggc aaggaccagc tgcccattct    1740
gagcccaggg cagcctcttc aaccattatt ggtctaacct ggcttgtcag gaaaccaagc    1800

<210> SEQ ID NO 50
<211> LENGTH: 6340
<212> TYPE: DNA
<213> ORGANISM: Homo sapines

<400> SEQUENCE: 50
gtggctgaga agaaggaggc ctgagagcga catgtccccg gcggctcagg cggagcggcc      60
cgtggcgctg ttttttctgag tccggggtgg cctggcagcc ggccgaggac gagggtcggc     120
gggggctgcc cccgtggtgg tggccgccat gctgggagcc tgggcggttg agggaaccgc     180
tgtggcgctc ctgcgactgc tgctgctgct gctgccgccg cgatccgggg acccgggct     240 cggcgtggcc ggcgtggccg gcgcggcggg ggccgggctg cccgagagcg tcatttgggc     300
ggtcaacgcg ggtggagagg cgcatgtgga cgtgcacggg atccacttcc gcaaggaccc     360
tttggaaggc cgggtgggcc gagcctcaga ctatggcatg aaactgccaa tcctgcgttc     420
caaccctgag gaccagatcc tgtatcaaac tgagcggtac aatgaggaga cctttggcta     480
cgaagtgccc atcaaagagg aggggggacta cgtgctggtc ttgaaatttg cagaggtcta     540 cttttgcacag tcccagcaaa aggtatttga tgtacgattg aatggccacg tcgtggtgaa     600
ggacttggat atctttgatc gtgttgggca tagcacagct cacgatgaaa ttatacctat     660
gagcatcaga aaggggaagc tgagtgtcca gggggaggtg tccaccttca cagggaaact     720
ctacattgag tttgtcaagg ggtactatga caatcccaag gtctgtgcac tctacatcat     780
ggctgggaca gtggatgatg taccaaagct tcagcctcat ccgggattgg agaagaaga     840 agaggaagaa gaagaagaag aatatgatga agggtctaat ctcaaaaaac agaccaataa     900
gaaccgggtg cagtccaggcc cccgcacacc caacccctat gcctcggaca cagcagcct     960 catgtttccc atcctggtgg ccttcggagt cttcattcca accctcttct gcctctgccg    1020
gttgtgagaa caaatgacta tcctgaacag ggtggagggg tgtgggaaag aaaccagcca    1080
tattggtttt ggtttctgta ttttcacaa tgattaatga acaaaacaa agagaaaaaa    1140 acacacatca attaaaggag acaaaaagag gcagagcgag tagagagcag ccctcattca    1200
ccacctggtc ccagacgtgc ttcagtcctc gtcctctctt tgtggctggc tcccagcctt    1260
ctctttcctc ttgaggatac ttagggtaaa ctggatcctt cctgctcaag atcctcatt    1320 tgtataccta gtggaaagga ctctgaactc agaggagtca ctgttccttt ttttaggtta    1380
gaaattaaca gcagggaaat gccatcttat tacctgagac gaccagcact gggagttagg    1440
tacggtctga agttatgtct agataagact tcagacgtcc tgggattgaa agaatgtgtg    1500
```

```
tgaaggggta gaatttgtgc ggtaaagact taaaaaaaaa agtagggaga ttaaaaaaaa    1560
agaaagaaaa tgcttcctta tctggaagcc tttctggatt aatccagtga tggtcccacc    1620
tttagtgttt gagctttgtc attgcttgtc tccctggcat gtgccagtta tagactgtcc    1680
agcatccaag acgtttcggt tatgtcgggt cctcagatcg cctctgactt gttaccacaa    1740
caaatcattt tgatttcagt gcctgttggg gacttgattt cttctcagtt ttgtttgttt    1800
gtttgtttcc ttaatctggc tcatttgaaa tttcttctcc ctctcaacca tcccactaag    1860
ttatagccaa gaagggaagg agacacgggg atttggggtt ctctgcttga atgtcttctc    1920
ctttaccacc tcaccttgtt ggtacctccc tccctgatc tctgagccag cagccaggag     1980
gacctgaccc agcagttctt tactggcccc tttgtagggc cttgctgcca ggggcaggg     2040
atgctttcca gcctgcagca acagaacact tgaccttaaa agtctcttct ggtctttgga    2100
ttagaaaagg cttatgttag catagcttaa gagcaacctc agagatttga ccctactaa     2160
gtgactgacc actgtttaga gtgtctggta tctgatgttc atttattccc atgttcttgt    2220
gtgtcacagt tcagccagtt ttggtttatg cctagagcta cttcaaggaa ctagactaat    2280
tagctatata ggcccagcga tgcttcttat tgatcttaat agtatgcccc tccttcccct    2340
gtcctttcat ttctctatcc aagtagcagt caggttcttg gtgtgatggg actgaaagaa    2400
ttccagtcag ccagagcctt ggcagctctg aagctaacct tagcatctaa gtgtcgatct    2460
tgaattccct gaaaaatttt ctataggaaa tgaagcttcc ctggtcccct cctttctggc    2520
cattgtcatc catttcccag ttagggcaac aatgaaggag gacccagcca agctagaagg    2580
aattttgtgg atgggagaca gcaggattag cttcagcttg ggctggagca gtcaatatag    2640
gatctcaggc caggcccgct tttctagaat gtgtttaatt ttgagtttgc tttattagat    2700
atgttttta agagctctgt atatttgaac tgctccttat gtgacaaaat aggtagctct     2760
tgggctcatg tcctgggttt tggctccttta atgattactc caggccagca tttagtcgtt    2820
tgagaattgt agcctgttgt tttcgctgtg acttgggtct cagtgctagg gtattgagtc    2880
aggcagctgg agggttgtgg cccgaggctg cagtcagagg tatacttccc atagtgcttc    2940
acacagctcc cctgcttcta aaggataagg tactgtagcc ttggtcctgg ggaccacctg    3000
cctggggcag tggacatcct aactaaacag gcttctggca gtagctttgg ttccatcccc    3060
atcgaaattc cccaaagccc tgggccactg ccattgggtt agtcaagatg aaggaggagg    3120
actggctgcc tccatttttgc cttgtttgtt agtttgcctg ggtctgtctg aggaaggagg    3180
gggtcccgcc ttccacctca acacatccct tcagtgactc agagtctcag aaggaaaccc    3240
tgactcctgg ggccatttcc taatggtact gtaagccaag cagctttgct tctgcctctg    3300
tttccaagcc cacccttttc ccctgagctc agggttaggg atgggcgctt tcctctctgg    3360
ttgtgaacga aaggaaggaa catctttcta tggctaacaa aaactaaagg ggaagtgagg    3420
aaacaggaag aagtatggtg ggggctgggg tagactcccc tggagccaag cctatccagc    3480
taacaagagc tccctggggc tggtcacagc tggctcatga tgctgaactt gaaagttttt    3540
ttgttttttgt ttttgttttg tggctcctcc aagatatagg tacatgaagt ttaggttaaa    3600
ggggtgggat tctttatttt tattttttgta ttgtatgtgt caagaattac tctgttgttc    3660
accttttgct ttttgcactg tttgttctct tatctgtatt ttgagcttag tgctaggact    3720
gagaggctgc accatagggca atgtatggga gatggtgagg ggtgccagtg aggggtgcgt    3780
ggaggagagg cctgggctcc tctactggat ctacactctg tcccaggttt ttagatccca    3840
ctgagcccag ctgactgaaa acaaggacag tcagggtgaa acttcttttg ccagaagtgt    3900
```

```
ggcctgagtt gaatttctgg gaggatgacg cagatgtctg ctgcagagct gggctgagag    3960
ttctgcagtc tagctctgac ttaggtcagg ggcctgttgg tctctcattg gacgttttg     4020 ggtctcactc atgcttactg aaacattgtg ccaagaaact ctgtgggatt tgtgtcccct    4080
aaaccagact cacttttctg aaaaatctcc attgttgagg agaggctgct caatcgacac    4140
cccgagttct catgactggg aagatagttt tcttcaggtg tcaatggcgt tagactccca    4200
ggaagactag ccctgcccac agggccacct gttggtttga gagcgtgttc gtgttctctt    4260
gccctccctg cctaagagct actgggatca cgttagcggg catttaggct ttgatgagag    4320
ggcacagttt gagttaggtt tacctccccc tttctgtgcc tgggaactgt ttggtccagc    4380
tttagaactg tggttttgac ttccttatct cttgggagaa gcttctgttt taaggaattt    4440
ctcttccttc ttctcctgcc tctagcctct cctggaaagg cctggatatg gtttctaaaa    4500
tctcagctga gaacttcaga aaacagcagc agtattttcc ttttcctagt gctaaaatcc    4560 cttttccctag aaattggctc accttgggaa acccagggaa agaatcagca ggttctctgc    4620
cctccctagg ggttggggaa ggacccaccc cggtcagcac agtgccttt cctctcctgc     4680 tctgagccag ggtgggcat tccctctaga ttcaggtttg ggcaggggtc ctatagtccc     4740
tgccatgggg ctgcttccct gtcccttccc tcccctttgc tggcctactc tggcataatt    4800
caagtgtctt cttgccttgg ggatccttag tggcatcaaa tggcaacatg gaatattgtc    4860
ctccatgccc ctccagaagg acctaggaga gtaggtgagc tttccaaagt gagagacgaa    4920
tctttctttc tttttttttt taaagggcag gatgggtatg ctttgggctt tctccttctg    4980
tggccccgga ggaaggagag actgaggcaa ggcaaagtga tagtacactg aagcagaacc    5040
ggaaacaccc aggaactgtt cagaaatctc agaagaaatc tgcttctctt cgatggaaag    5100
atataattaa cgatcaaaga gctctaagaa aattgcaaag aagccttaat gttcaagctt    5160
tagaaagatc agagcaattt ttctctttca gtccaaacta agactctctg tatttaaatc    5220
tctctggggc aagagggcta gatttcctca ttttgttatg agactagatt ggtaccagta    5280
gatcagctgc ctagcgaggg caggtttctt ctttgcatct gtgtggcttg cttccagtct    5340
ggcctgtcct ttccagctgc cttttgtcta gcctgctatg gggggccaga ttatcttgat    5400
aagagcaggt gatttgggga ctagctgggt tggcaggaaa agagcaggat ggatctcttg    5460
ggacaggttc ccccaggagt ataaacacaa ggagccagga ttgtgctggc agccaaggaa    5520
acagtagtgc ctgtttgagt tggcagagag ggccttggca cctcttgcat ccaggcagtc    5580
ttgtgagatg ggggcacata gcactgggga aagcagaact ccattctcac ctctattttg    5640
agcttcagtc ctttatttca gtatgaggaa aaacaacaac aaactgaagt gcgctttccg    5700
tcctttcaaa ggacaactgt cgggaaggga gagccgagtt gcgaggtagg aggggagcac    5760
tggcagggag agacattctt gactcctctc ttccctggtg tgttgtgatc cagggaatga    5820
aaagaaattt gaccctggat tggttctctc cttggactta aggaatctta ccttttcctt    5880
ccacaaagtt ctcccaggca aggaccagct gcccattctg agcccagggc agcctcttca    5940
accattattg gtctaacctg gcttgtcagg aaaccaagcc caccctttcca cattgggcct    6000 ggctgctcta ttctgtacca agtactggag aaaaagcatc aagttcttag cccttgtagc    6060
ttctaccctg gtttcccatc ctctctctgt ggaggccaaa ccaactcttt gccagcagcc    6120
acaacatgca ttgacagcgg cacagtgaga tataactgat gggctttgaa cctggttggc    6180
cggggaagct gtaggggtgg atagagctgg ctttccttct gggctgtctc catctgaccc    6240
```

-continued

```
tacccctcc atgtcccacc ccactcccac caaaaagtac aaaatcagga tgtttttcac      6300
tgtccattgc tttgtgtttt aataaacaat ttgcagtgac                           6340
```

<210> SEQ ID NO 51
<211> LENGTH: 855
<212> TYPE: PRT
<213> ORGANISM: Homo sapiens

<400> SEQUENCE: 51

```
Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
            20                  25                  30

Glu Glu Gly Val Glu Phe Leu Pro Val Asn Asn Val Lys Lys Val Glu
        35                  40                  45

Lys His Gly Pro Gly Arg Trp Val Val Leu Ala Ala Val Leu Ile Gly
    50                  55                  60

Leu Leu Leu Val Leu Leu Gly Ile Gly Phe Leu Val Trp His Leu Gln
65              70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
        115                 120                 125

Ser Gly Val Pro Phe Leu Gly Pro Tyr His Lys Glu Ser Ala Val Thr
    130                 135                 140

Ala Phe Ser Glu Gly Ser Val Ile Ala Tyr Tyr Trp Ser Glu Phe Ser
145             150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
    210                 215                 220

Leu Met Arg Phe Thr Thr Pro Gly Phe Pro Asp Ser Pro Tyr Pro Ala
225             230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Thr Val Tyr Asn Thr Leu Ser Pro Met Glu Pro His
        275                 280                 285

Ala Leu Val Gln Leu Cys Gly Thr Tyr Pro Pro Ser Tyr Asn Leu Thr
    290                 295                 300

Phe His Ser Ser Gln Asn Val Leu Leu Ile Thr Leu Ile Thr Asn Thr
305             310                 315                 320

Glu Arg Arg His Pro Gly Phe Glu Ala Thr Phe Phe Gln Leu Pro Arg
                325                 330                 335

Met Ser Ser Cys Gly Gly Arg Leu Arg Lys Ala Gln Gly Thr Phe Asn
            340                 345                 350

Ser Pro Tyr Tyr Pro Gly His Tyr Pro Pro Asn Ile Asp Cys Thr Trp
```

-continued

```
              355                 360                 365
Asn Ile Glu Val Pro Asn Gln His Val Lys Val Arg Phe Lys Phe
        370                 375                 380
Phe Tyr Leu Leu Glu Pro Gly Val Pro Ala Gly Thr Cys Pro Lys Asp
385                 390                 395                 400
Tyr Val Glu Ile Asn Gly Glu Lys Tyr Cys Gly Arg Ser Gln Phe
            405                 410                 415
Val Val Thr Ser Asn Ser Asn Lys Ile Thr Val Arg Phe His Ser Asp
            420                 425                 430
Gln Ser Tyr Thr Asp Thr Gly Phe Leu Ala Glu Tyr Leu Ser Tyr Asp
            435                 440                 445
Ser Ser Asp Pro Cys Pro Gly Gln Phe Thr Cys Arg Thr Gly Arg Cys
450                 455                 460
Ile Arg Lys Glu Leu Arg Cys Asp Gly Trp Ala Asp Cys Thr Asp His
465                 470                 475                 480
Ser Asp Glu Leu Asn Cys Ser Cys Asp Ala Gly His Gln Phe Thr Cys
                485                 490                 495
Lys Asn Lys Phe Cys Lys Pro Leu Phe Trp Val Cys Asp Ser Val Asn
                500                 505                 510
Asp Cys Gly Asp Asn Ser Asp Glu Gln Gly Cys Ser Cys Pro Ala Gln
                515                 520                 525
Thr Phe Arg Cys Ser Asn Gly Lys Cys Leu Ser Lys Ser Gln Gln Cys
        530                 535                 540
Asn Gly Lys Asp Asp Cys Gly Asp Gly Ser Asp Glu Ala Ser Cys Pro
545                 550                 555                 560
Lys Val Asn Val Val Thr Cys Thr Lys His Thr Tyr Arg Cys Leu Asn
                    565                 570                 575
Gly Leu Cys Leu Ser Lys Gly Asn Pro Glu Cys Asp Gly Lys Glu Asp
            580                 585                 590
Cys Ser Asp Gly Ser Asp Glu Lys Asp Cys Asp Cys Gly Leu Arg Ser
                595                 600                 605
Phe Thr Arg Gln Ala Arg Val Val Gly Gly Thr Asp Ala Asp Glu Gly
        610                 615                 620
Glu Trp Pro Trp Gln Val Ser Leu His Ala Leu Gly Gln Gly His Ile
625                 630                 635                 640
Cys Gly Ala Ser Leu Ile Ser Pro Asn Trp Leu Val Ser Ala Ala His
                    645                 650                 655
Cys Tyr Ile Asp Asp Arg Gly Phe Arg Tyr Ser Asp Pro Thr Gln Trp
                660                 665                 670
Thr Ala Phe Leu Gly Leu His Asp Gln Ser Gln Arg Ser Ala Pro Gly
            675                 680                 685
Val Gln Glu Arg Arg Leu Lys Arg Ile Ile Ser His Pro Phe Phe Asn
        690                 695                 700
Asp Phe Thr Phe Asp Tyr Asp Ile Ala Leu Leu Glu Leu Glu Lys Pro
705                 710                 715                 720
Ala Glu Tyr Ser Ser Met Val Arg Pro Ile Cys Leu Pro Asp Ala Ser
                    725                 730                 735
His Val Phe Pro Ala Gly Lys Ala Ile Trp Val Thr Gly Trp Gly His
                740                 745                 750
Thr Gln Tyr Gly Gly Thr Gly Ala Leu Ile Leu Gln Lys Gly Glu Ile
            755                 760                 765
Arg Val Ile Asn Gln Thr Thr Cys Glu Asn Leu Leu Pro Gln Gln Ile
        770                 775                 780
```

```
Thr Pro Arg Met Met Cys Val Gly Phe Leu Ser Gly Val Asp Ser
785                 790                 795                 800

Cys Gln Gly Asp Ser Gly Pro Leu Ser Ser Val Glu Ala Asp Gly
            805                 810                 815

Arg Ile Phe Gln Ala Gly Val Val Ser Trp Gly Asp Gly Cys Ala Gln
            820                 825                 830

Arg Asn Lys Pro Gly Val Tyr Thr Arg Leu Pro Leu Phe Arg Asp Trp
            835                 840                 845

Ile Lys Glu Asn Thr Gly Val
    850                 855

<210> SEQ ID NO 52
<211> LENGTH: 422
<212> TYPE: PRT
<213> ORGANISM: Homo sapiens

<400> SEQUENCE: 52

Ser Tyr Thr Asp Thr Gly Phe Leu Ala Glu Tyr Leu Ser Tyr Asp Ser
1               5                   10                  15

Ser Asp Pro Cys Pro Gly Gln Phe Thr Cys Arg Thr Gly Arg Cys Ile
            20                  25                  30

Arg Lys Glu Leu Arg Cys Asp Gly Trp Ala Asp Cys Thr Asp His Ser
        35                  40                  45

Asp Glu Leu Asn Cys Ser Cys Asp Ala Gly His Gln Phe Thr Cys Lys
    50                  55                  60

Asn Lys Phe Cys Lys Pro Leu Phe Trp Val Cys Asp Ser Val Asn Asp
65                  70                  75                  80

Cys Gly Asp Asn Ser Asp Glu Gln Gly Cys Ser Cys Pro Ala Gln Thr
                85                  90                  95

Phe Arg Cys Ser Asn Gly Lys Cys Leu Ser Lys Ser Gln Gln Cys Asn
            100                 105                 110

Gly Lys Asp Asp Cys Gly Asp Gly Ser Asp Glu Ala Ser Cys Pro Lys
        115                 120                 125

Val Asn Val Val Thr Cys Thr Lys His Thr Tyr Arg Cys Leu Asn Gly
    130                 135                 140

Leu Cys Leu Ser Lys Gly Asn Pro Glu Cys Asp Gly Lys Glu Asp Cys
145                 150                 155                 160

Ser Asp Gly Ser Asp Glu Lys Asp Cys Asp Cys Gly Leu Arg Ser Phe
                165                 170                 175

Thr Arg Gln Ala Arg Val Val Gly Gly Thr Asp Ala Asp Glu Gly Glu
            180                 185                 190

Trp Pro Trp Gln Val Ser Leu His Ala Leu Gly Gln Gly His Ile Cys
        195                 200                 205

Gly Ala Ser Leu Ile Ser Pro Asn Trp Leu Val Ser Ala Ala His Cys
    210                 215                 220

Tyr Ile Asp Asp Arg Gly Phe Arg Tyr Ser Asp Pro Thr Gln Trp Thr
225                 230                 235                 240

Ala Phe Leu Gly Leu His Asp Gln Ser Gln Arg Ser Ala Pro Gly Val
                245                 250                 255

Gln Glu Arg Arg Leu Lys Arg Ile Ile Ser His Pro Phe Phe Asn Asp
            260                 265                 270

Phe Thr Phe Asp Tyr Asp Ile Ala Leu Leu Glu Leu Glu Lys Pro Ala
        275                 280                 285

Glu Tyr Ser Ser Met Val Arg Pro Ile Cys Leu Pro Asp Ala Ser His
```

|  |  |  |  |  |  |  |  |  |  |  |
|---|---|---|---|---|---|---|---|---|---|---|
| | | 290 | | | 295 | | | 300 | | |
| Val | Phe | Pro | Ala | Gly | Lys | Ala | Ile | Trp | Val | Thr | Gly | Trp | Gly | His | Thr |
| 305 | | | | | 310 | | | | | 315 | | | | | 320 |

Gln Tyr Gly Gly Thr Gly Ala Leu Ile Leu Gln Lys Gly Glu Ile Arg
                  325                    330                    335

Val Ile Asn Gln Thr Thr Cys Glu Asn Leu Leu Pro Gln Gln Ile Thr
            340                    345                    350

Pro Arg Met Met Cys Val Gly Phe Leu Ser Gly Val Asp Ser Cys
         355                    360                    365

Gln Gly Asp Ser Gly Pro Leu Ser Ser Val Glu Ala Asp Gly Arg
370                    375                    380

Ile Phe Gln Ala Gly Val Val Ser Trp Gly Asp Gly Cys Ala Gln Arg
385                    390                    395                    400

Asn Lys Pro Gly Val Tyr Thr Arg Leu Pro Leu Phe Arg Asp Trp Ile
            405                    410                    415

Lys Glu Asn Thr Gly Val
         420

```
<210> SEQ ID NO 53
<211> LENGTH: 3120
<212> TYPE: DNA
<213> ORGANISM: Homo sapiens

<400> SEQUENCE: 53
cgaggatcct gagacccgcg agcggcctcg gggaccatgg ggagcgatcg ggcccgcaag      60
ggcggagggg gcccgaagga cttcggcgcg ggactcaagt acaactcccg gcacgagaaa     120
gtgaatggct tggaggaagg cgtggagttc ctgccagtca caacgtcaa gaaggtggaa      180
aagcatggcc cggggcgctg ggtggtgctg gcagccgtgc tgatcggcct cctcttggtc     240
ttgctgggga tcggcttcct ggtgtggcat ttgcagtacc gggacgtgcg tgtccagaag     300
gtcttcaatg gctacatgag gatcacaaat gagaattttg tggatgccta cgagaactcc     360
aactccactg agtttgtaag cctggccagc aaggtgaagg acgcgctgaa gctgctgtac     420
agcggagtcc cattcctggg ccccctaccac aaggagtcgg ctgtgacggc cttcagcgag     480
ggcagcgtca tcgcctacta ctggtctgag ttcagcatcc gcagcacct ggtgaggag       540
gccgagcgcg tcatggccga ggagcgcgta gtcatgctgc cccgcgggc gcgctccctg      600
aagtcctttg tggtcacctc agtggtggct ttccccacgg actccaaaac agtacagagg     660
acccaggaca acagctgcag ctttggcctg cacgcccgcg gtgtggagct gatgcgcttc     720
accacgcccg gcttccctga cagcccctac cccgctcatg cccgctgcca gtgggccctg     780
cgggggggacg ccgactcagt gctgagcctc accttccgca gctttgacct tgcgtcctgc     840
gacgagcgcg gcagcgacct ggtgacggtg tacaacaccc tgagccccat ggagccccac     900
gccctggtgc agttgtgtgg cacctaccct ccctcctaca acctgacctt ccactcctcc     960
cagaacgtcc tgctcatcac actgataacc aacactgagc ggcggcatcc cggctttgag    1020
gccaccttct tccagctgcc taggatgagc agctgtggag gccgcttacg taaagcccag    1080
ggacattca acagccccta ctacccaggc cactacccac caacattga ctgcacatgg      1140
aacattgagg tgcccaacaa ccagcatgtg aaggtgcgct tcaaattctt ctacctgctg    1200
gagcccggcg tgcctgcggg cacctgcccc aaggactacg tggagatcaa tggggagaaa    1260
tactgcggag agaggtccca gttcgtcgtc accagcaaca gcaacaagat cacagttcgc    1320
ttccactcag atcagtccta caccgacacc ggcttcttag ctgaatacct ctcctacgac    1380
```

```
tccagtgacc catgcccggg gcagttcacg tgccgcacgg ggcggtgtat ccggaaggag    1440
ctgcgctgtg atggctgggc cgactgcacc gaccacagcg atgagctcaa ctgcagttgc    1500
gacgccggcc accagttcac gtgcaagaac aagttctgca agcccctctt ctgggtctgc    1560
gacagtgtga acgactgcgg agacaacagc gacgagcagg ggtgcagttg tccggcccag    1620
accttcaggt gttccaatgg gaagtgcctc tcgaaaagcc agcagtgcaa tgggaaggac    1680
gactgtgggg acgggtccga cgaggcctcc tgccccaagg tgaacgtcgt cacttgtacc    1740
aaacacacct accgctgcct caatgggctc tgcttgagca agggcaaccc tgagtgtgac    1800
gggaaggagg actgtagcga cggctcagat gagaaggact gcgactgtgg gctgcggtca    1860
ttcacgagac aggctcgtgt tgttgggggc acggatgcgg atgagggcga gtggccctgg    1920
caggtaagcc tgcatgctct gggccagggc cacatctgcg gtgcttccct catctctccc    1980
aactggctgg tctctgccgc acactgctac atcgatgaca gaggattcag gtactcagac    2040
cccacgcagt ggacggcctt cctgggcttg cacgaccaga gccagcgcag cgcccctggg    2100
gtgcaggagc gcaggctcaa gcgcatcatc tcccacccct tcttcaatga cttcaccttc    2160
gactatgaca tcgcgctgct ggagctggag aaaccggcag agtacagctc catggtgcgg    2220
cccatctgcc tgccggacgc ctcccatgtc ttccctgccg gcaaggccat ctgggtcacg    2280
ggctggggac acacccagta tggaggcact ggcgcgctga tcctgcaaaa gggtgagatc    2340
cgcgtcatca accagaccac ctgcgagaac ctcctgccgc agcagatcac gccgcgcatg    2400
atgtgcgtgg gcttcctcag cggcggcgtg gactcctgcc aggtgattc cggggggaccc    2460 ctgtccagcg tggaggcgga tgggcggatc ttccaggccg gtgtggtgag ctggggagac    2520
ggctgcgctc agaggaacaa gccaggcgtg tacacaaggc tccctctgtt tcgggactgg    2580
atcaaagaga acactggggt atagggccg gggcacccaa gatgtgtaca cctgcggggc    2640
cacccatcgt ccaccccagt gtgcacgcct gcaggctgga gactgaccg ctgactgcac    2700 cagcgccccc agaacataca ctgtgaactc aatctccagg gctccaaatc tgcctagaaa    2760
acctctcgct tcctcagcct ccaaagtgga gctgggaggg agaaggggag gacactggtg    2820
gttctactga cccaactggg ggcaaaggtt tgaagacaca gcctccccg ccagccccaa    2880 gctgggccga ggcgcgtttg tgtatatctg cctcccctgt ctgtaaggag cagcgggaac    2940
ggagcttcgg ggcctcctca gtgaaggtgg tggggctgcc ggatctgggc tgtggggccc    3000
ttgggccacg ctcttgagga agcccaggct cggaggaccc tggaaaacag acgggtctga    3060
gactgaaatt gttttaccag ctcccagggt ggacttcagt gtgtgtattt gtgtaaatga    3120
```

<210> SEQ ID NO 54
<211> LENGTH: 3305
<212> TYPE: DNA
<213> ORGANISM: Homo sapiens

<400> SEQUENCE: 54

```
agcggagctg cagccggaga aagaggaaga gggagagaga gcgcgccagg gcagggcac      60 cgccgccggt cgggcgcgct gggcctgccc ggaatcccgc cgcctgcgcc ccgcgccccg     120
cgccctgcgg gccatgggag ccggccgccg gcagggacga cgcctgtgag acccgcgagc     180
ggcctcgggg accatgggga gcgatcgggc ccgcaagggc ggaggggcc cgaaggactt     240 cggcgcggga ctcaagtaca actcccggca cgagaaagtg aatggcttgg aggaaggcgt     300
ggagttcctg ccagtcaaca acgtcaagaa ggtggaaaag catggcccgg ggcgctgggt     360
```

```
ggtgctggca gccgtgctga tcggcctcct cttggtcttg ctggggatcg gcttcctggt    420
gtggcatttg cagtaccggg acgtgcgtgt ccagaaggtc ttcaatggct acatgaggat    480
cacaaatgag aattttgtgg atgcctacga gaactccaac tccactgagt ttgtaagcct    540
ggccagcaag gtgaaggacg cgctgaagct gctgtacagc ggagtcccat tcctgggccc    600
ctaccacaag gagtcggctg tgacggcctt cagcgagggc agcgtcatcg cctactactg    660
gtctgagttc agcatcccgc agcacctggt ggaggaggcc gagcgcgtca tggccgagga    720
gcgcgtagtc atgctgcccc cgcgggcgcg ctccctgaag tcctttgtgg tcacctcagt    780
ggtggctttc cccacggact ccaaaacagt acagaggacc caggacaaca gctgcagctt    840
tggcctgcac gcccgcggtg tggagctgat gcgcttcacc acgcccggct ccctgacag    900 cccctacccc gctcatgccc gctgccagtg ggccctgcgg ggggacgccg actcagtgct    960
gagcctcacc ttccgcagct ttgaccttgc gtcctgcgac gagcgcggca gcgacctggt   1020
gacggtgtac aacaccctga gccccatgga gccccacgcc ctggtgcagt tgtgtggcac   1080
ctaccctccc tcctacaacc tgaccttcca ctcctcccag aacgtcctgc tcatcacact   1140
gataaccaac actgagcggc ggcatcccgg ctttgaggcc accttcttcc agctgcctag   1200
gatgagcagc tgtggaggcc gcttacgtaa agcccagggg acattcaaca gcccctacta   1260
cccaggccac tacccaccca acattgactg cacatggaac attgaggtgc caacaacca   1320 gcatgtgaag gtgcgcttca aattcttcta cctgctggag cccggcgtgc ctgcgggcac   1380
ctgccccaag gactacgtgg agatcaatgg ggagaaatac tgcggagaga ggtcccagtt   1440
cgtcgtcacc agcaacagca acaagatcac agttcgcttc cactcagatc agtcctacac   1500
cgacaccggc ttcttagctg aatacctctc ctacgactcc agtgaccat gcccggggca   1560 gttcacgtgc cgcacggggc ggtgtatccg gaaggagctg cgctgtgatg gctgggccga   1620
ctgcaccgac cacagcgatg agctcaactg cagttgcgac gccggccacc agttcacgtg   1680
caagaacaag ttctgcaagc ccctcttctg ggtctgcgac agtgtgaacg actgcggaga   1740
caacagcgac gagcaggggt gcagttgtcc ggcccagacc ttcaggtgtt ccaatgggaa   1800
gtgcctctcg aaaagccagc agtgcaatgg aaggacgac tgtggggacg gtccgacga   1860 ggcctcctgc cccaaggtga acgtcgtcac ttgtaccaaa cacacctacc gctgcctcaa   1920
tgggctctgc ttgagcaagg caaccctga gtgtgacggg aaggaggact gtagcgacgg   1980
ctcagatgag aaggactgcg actgtgggct gcggtcattc acgagacagg ctcgtgttgt   2040 tggggcacg gatgcggatg agggcgagtg gccctggcag gtaagcctgc atgctctggg   2100
ccagggccac atctgcggtg cttccctcat ctctcccaac tggctggtct ctgccgcaca   2160
ctgctacatc gatgacagag gattcaggta ctcagacccc acgcagtgga cggccttcct   2220
gggcttgcac gaccagagcc agcgcagcgc ccctggggtg caggagcgca ggctcaagcg   2280
catcatctcc caccccttct tcaatgactt caccttcgac tatgacatcg cgctgctgga   2340
gctggagaaa ccggcagagt acagctccat ggtgcggccc atctgcctgc cggacgcctc   2400
ccatgtcttc cctgccggca aggccatctg ggtcacgggc tggggacaca cccagtatgg   2460
aggcactggc gcgctgatcc tgcaaaaggg tgagatccgc gtcatcaacc agaccacctg   2520
cgagaacctc ctgccgcagc agatcacgcc gcgcatgatg tgcgtgggct tcctcagcgg   2580
cggcgtggac tcctgccagg gtgattccgg gggaccctg tccagcgtgg aggcggatgg   2640
gcggatcttc caggccggtg tggtgagctg gggagacggc tgcgctcaga ggaacaagcc   2700
aggcgtgtac acaaggctcc ctctgtttcg ggactggatc aaagagaaca ctgggggtata 2760
```

```
gggggccgggg ccacccaaat gtgtacacct gcggggccac ccatcgtcca ccccagtgtg    2820
cacgcctgca ggctggagac tggaccgctg actgcaccag cgcccccaga acatacactg    2880
tgaactcaat ctccagggct ccaaatctgc ctagaaaacc tctcgcttcc tcagcctcca    2940
aagtggagct gggaggtaga aggggaggac actggtggtt ctactgaccc aactgggggc    3000
aaaggtttga agacacagcc tcccccgcca gccccaagct gggccgaggc gcgtttgtgt    3060
atatctgcct cccctgtctg taaggagcag cgggaacgga gcttcggagc ctcctcagtg    3120
aaggtggtgg ggctgccgga tctgggctgt ggggcccttg ggccacgctc ttgaggaagc    3180
ccaggctcgg aggaccctgg aaaacagacg ggtctgagac tgaaattgtt ttaccagctc    3240
ccagggtgga cttcagtgtg tgtatttgtg taaatgagta aaacatttta tttctttttta   3300 ggtaa                                                                 3305

<210> SEQ ID NO 55
<211> LENGTH: 3305
<212> TYPE: DNA
<213> ORGANISM: Homo sapiens

<400> SEQUENCE: 55
agcggagctg cagccggaga aagaggaaga gggagagaga gcgcgccagg gcgagggcac      60
cgccgccggt cgggcgcgct gggcctgccc ggaatcccgc cgcctgcgcc ccgcgccccg     120
cgccctgcgg gccatgggag ccggccgccg gcagggacga cgcctgtgag acccgcgagc     180
ggcctcgggg accatgggga gcgatcgggc ccgcaagggc ggagggggcc cgaaggactt     240
cggcgcggga ctcaagtaca actcccggca cgagaaagtg aatggcttgg aggaaggcgt     300
ggagttcctg ccagtcaaca cgtcaagaa ggtggaaaag catggcccgg ggcgctgggt      360
ggtgctggca gccgtgctga tcggcctcct cttggtcttg ctgggatcg gcttcctggt      420 gtggcatttg cagtaccggg acgtgcgtgt ccagaaggtc ttcaatggct acatgaggat      480
cacaaatgag aattttgtgg atgcctacga gaactccaac tccactgagt ttgtaagcct      540
ggccagcaag gtgaaggacg cgctgaagct gctgtacagc ggagtcccat tcctgggccc      600
ctaccacaag gagtcggctg tgacggcctt cagcgagggc agcgtcatcg cctactactg      660
gtctgagttc agcatcccgc agcacctggt ggaggaggcc gagcgcgtca tggccgagga      720
gcgcgtagtc atgctgcccc cgcgggcgcg ctcccctgaag tcctttgtgg tcacctcagt      780
ggtggctttc cccacggact ccaaaacagt acagaggacc caggacaaca gctgcagctt      840
tggcctgcac gcccgcggtg tggagctgat gcgcttcacc acgcccggct tccctgacag      900
ccccctaccc cgctcatgcc cgctgccagtg ggccctgcgg ggggacgccg actcagtgct      960
gagcctcacc ttccgcagct ttgaccttgc gtcctgcgac gagcgcggca gcgacctggt     1020
gacggtgtac aacaccctga gccccatgga gccccacgcc ctggtgcagt tgtgtggcac     1080
ctaccctccc tcctacaacc tgaccttcca ctcctcccag aacgtcctgc tcatcacact     1140
gataaccaac actgagcggc ggcatcccgg ctttgaggcc accttcttcc agctgcctag     1200
gatgagcagc tgtggaggcc gcttacgtaa agcccagggg acattcaaca gcccctacta     1260
cccaggccac tacccacccca acattgactg cacatggaac attgaggtgc caacaaccca     1320
gcatgtgaag gtgcgcttca aattcttcta cctgctggag cccggcgtgc ctgcgggcac     1380
ctgccccaag gactacgtgg agatcaatgg ggagaaatac tgcggagaga ggtcccagtt     1440
cgtcgtcacc agcaacagca acaagatcac agttcgcttc cactcagatc agtcctacac     1500
```

-continued

```
cgacaccggc ttcttagctg aatacctctc ctacgactcc agtgacccat gcccggggca   1560
gttcacgtgc cgcacggggc ggtgtatccg gaaggagctg cgctgtgatg gctgggccga   1620
ctgcaccgac cacagcgatg agctcaactg cagttgcgac gccggccacc agttcacgtg   1680
caagaacaag ttctgcaagc ccctcttctg ggtctgcgac agtgtgaacg actgcggaga   1740
caacagcgac gagcagggt gcagttgtcc ggcccagacc ttcaggtgtt ccaatgggaa   1800
gtgcctctcg aaaagccagc agtgcaatgg aaggacgac tgtggggacg gtccgacga   1860
ggcctcctgc cccaaggtga acgtcgtcac ttgtaccaaa cacacctacc gctgcctcaa   1920
tgggctctgt tgagcaagg caaccctga gtgtgacggg aaggaggact gtagcgacgg   1980
ctcagatgag aaggactgcg actgtgggct gcggtcattc acgagacagg ctcgtgttgt   2040
tggggggcacg gatgcggatg agggcgagtg gccctggcag gtaagcctgc atgtctggg   2100
ccagggccac atctgcggtg cttccctcat ctctcccaac tggctggtct ctgccgcaca   2160
ctgctacatc gatgacagag gattcaggta ctcagacccc acgcagtgga cggccttcct   2220
gggcttgcac gaccagagcc agcgcagcgc ccctggggtg caggagcgca ggctcaagcg   2280
catcatctcc caccccttct tcaatgactt caccttcgac tatgacatcg cgctgctgga   2340
gctggagaaa ccggcagagt acagctccat ggtgcggccc atctgcctgc ggacgcctc   2400
ccatgtcttc cctgccggca aggccatctg ggtcacgggc tggggacaca cccagtatgg   2460
aggcactggc gcgctgatcc tgcaaaaggg tgagatccgc gtcatcaacc agaccacctg   2520
cgagaacctc ctgccgcagc agatcacgcc gcgcatgatg tgcgtgggct tcctcagcgg   2580
cggcgtggac tcctgccagg gtgattccgg gggacccctg tccagcgtgg aggcggatgg   2640
gcggatcttc caggccggtg tggtgagctg gggagacggc tgcgctcaga ggaacaagcc   2700
aggcgtgtac acaaggctcc ctctgtttcg ggactggatc aaagagaaca ctggggtata   2760
ggggccgggg ccacccaaat gtgtacacct gcggggccac ccatcgtcca ccccagtgtg   2820
cacgcctgca ggctggagac tggaccgctg actgcaccag cgcccccaga acatacactg   2880
tgaactcaat ctccagggct ccaaatctgc ctagaaaacc tctcgcttcc tcagcctcca   2940
aagtggagct gggaggtaga aggggaggac actggtggtt ctactgaccc aactgggggc   3000
aaaggtttga agacacagcc tcccccgcca gccccaagct gggccgaggc gcgtttgtgt   3060
atatctgcct ccctgtctg taaggagcag cgggaacgga gcttcggagc ctcctcagtg   3120
aaggtggtgg ggctgccgga tctgggctgt ggggcccttg ggccacgctc ttgaggaagc   3180
ccaggctcgg aggaccctgg aaaacagacg ggtctgagac tgaaattgtt ttaccagctc   3240
ccagggtgga cttcagtgtg tgtatttgtg taaatgagta aaacatttta tttctttta   3300
ggtaa                                                               3305
```

<210> SEQ ID NO 56
<211> LENGTH: 408
<212> TYPE: PRT
<213> ORGANISM: Homo sapiens

<400> SEQUENCE: 56

Met Arg Ser Ser Cys Val Leu Leu Thr Ala Leu Val Ala Leu Ala Ala
1               5                  10                  15

Tyr Tyr Val Tyr Ile Pro Leu Pro Gly Ser Val Ser Asp Pro Trp Lys
            20                  25                  30

Leu Met Leu Leu Asp Ala Thr Phe Arg Gly Ala Gln Gln Val Ser Asn
        35                  40                  45

```
Leu Ile His Tyr Leu Gly Leu Ser His His Leu Leu Ala Leu Asn Phe
 50                  55                  60

Ile Ile Val Ser Phe Gly Lys Lys Ser Ala Trp Ser Ser Ala Lys Val
 65                  70                  75                  80

Lys Val Thr Asp Thr Asp Phe Asp Gly Val Glu Val Arg Val Phe Glu
                 85                  90                  95

Gly Pro Pro Lys Pro Glu Glu Pro Leu Lys Arg Ser Val Val Tyr Ile
            100                 105                 110

His Gly Gly Gly Trp Ala Leu Ala Ser Ala Lys Ile Arg Tyr Tyr Asp
        115                 120                 125

Glu Leu Cys Thr Ala Met Ala Glu Glu Leu Asn Ala Val Ile Val Ser
130                 135                 140

Ile Glu Tyr Arg Leu Val Pro Lys Val Tyr Phe Pro Glu Gln Ile His
145                 150                 155                 160

Asp Val Val Arg Ala Thr Lys Tyr Phe Leu Lys Pro Glu Val Leu Gln
                165                 170                 175

Lys Tyr Met Val Asp Pro Gly Arg Ile Cys Ile Ser Gly Asp Ser Ala
            180                 185                 190

Gly Gly Asn Leu Ala Ala Ala Leu Gly Gln Gln Phe Thr Gln Asp Ala
        195                 200                 205

Ser Leu Lys Asn Lys Leu Lys Leu Gln Ala Leu Ile Tyr Pro Val Leu
210                 215                 220

Gln Ala Leu Asp Phe Asn Thr Pro Ser Tyr Gln Gln Asn Val Asn Thr
225                 230                 235                 240

Pro Ile Leu Pro Arg Tyr Val Met Val Lys Tyr Trp Val Asp Tyr Phe
                245                 250                 255

Lys Gly Asn Tyr Asp Phe Val Gln Ala Met Ile Val Asn Asn His Thr
            260                 265                 270

Ser Leu Asp Val Glu Glu Ala Ala Val Arg Ala Arg Leu Asn Trp
        275                 280                 285

Thr Ser Leu Leu Pro Ala Ser Phe Thr Lys Asn Tyr Lys Pro Val Val
290                 295                 300

Gln Thr Thr Gly Asn Ala Arg Ile Val Gln Glu Leu Pro Gln Leu Leu
305                 310                 315                 320

Asp Ala Arg Ser Ala Pro Leu Ile Ala Asp Gln Ala Val Leu Gln Leu
                325                 330                 335

Leu Pro Lys Thr Tyr Ile Met Thr Cys Glu His Asp Val Leu Arg Asp
            340                 345                 350

Asp Gly Ile Met Tyr Ala Lys Arg Leu Glu Ser Ala Gly Val Glu Val
        355                 360                 365

Thr Leu Asp His Phe Glu Asp Gly Phe His Gly Cys Met Ile Phe Thr
370                 375                 380

Ser Trp Pro Thr Asn Phe Ser Val Gly Ile Arg Thr Arg Asn Ser Tyr
385                 390                 395                 400

Ile Lys Trp Leu Asp Gln Asn Leu
                405

<210> SEQ ID NO 57
<211> LENGTH: 440
<212> TYPE: PRT
<213> ORGANISM: Homo sapiens

<400> SEQUENCE: 57

Met Ser Ser Cys Arg Gly Gln Lys Val Ala Gly Gly Leu Arg Val Val
 1               5                  10                  15
```

```
Ser Pro Phe Pro Leu Cys Gln Pro Ala Gly Glu Pro Ser Gln Gly Lys
            20                  25                  30

Met Arg Ser Ser Cys Val Leu Leu Thr Ala Leu Val Ala Leu Ala Ala
                35                  40                  45

Tyr Tyr Val Tyr Ile Pro Leu Pro Gly Ser Val Ser Asp Pro Trp Lys
            50                  55                  60

Leu Met Leu Leu Asp Ala Thr Phe Arg Gly Ala Gln Gln Val Ser Asn
 65                  70                  75                  80

Leu Ile His Tyr Leu Gly Leu Ser His His Leu Leu Ala Leu Asn Phe
                85                  90                  95

Ile Ile Val Ser Phe Gly Lys Lys Ser Ala Trp Ser Ser Ala Gln Val
            100                 105                 110

Lys Val Thr Asp Thr Asp Phe Asp Gly Val Glu Val Arg Val Phe Glu
            115                 120                 125

Gly Pro Pro Lys Pro Glu Glu Pro Leu Lys Arg Ser Val Val Tyr Ile
            130                 135                 140

His Gly Gly Gly Trp Ala Leu Ala Ser Ala Lys Ile Arg Tyr Tyr Asp
145                 150                 155                 160

Glu Leu Cys Thr Ala Met Ala Glu Glu Leu Asn Ala Val Ile Val Ser
                165                 170                 175

Ile Glu Tyr Arg Leu Val Pro Lys Val Tyr Phe Pro Glu Gln Ile His
            180                 185                 190

Asp Val Val Arg Ala Thr Lys Tyr Phe Leu Lys Pro Glu Val Leu Gln
            195                 200                 205

Lys Tyr Met Val Asp Pro Gly Arg Ile Cys Ile Ser Gly Asp Ser Ala
210                 215                 220

Gly Gly Asn Leu Ala Ala Ala Leu Gly Gln Gln Phe Thr Gln Asp Ala
225                 230                 235                 240

Ser Leu Lys Asn Lys Leu Lys Leu Gln Ala Leu Ile Tyr Pro Val Leu
                245                 250                 255

Gln Ala Leu Asp Phe Asn Thr Pro Ser Tyr Gln Gln Asn Val Asn Thr
            260                 265                 270

Pro Ile Leu Pro Arg Tyr Val Met Val Lys Tyr Trp Val Asp Tyr Phe
            275                 280                 285

Lys Gly Asn Tyr Asp Phe Val Gln Ala Met Ile Val Asn Asn His Thr
            290                 295                 300

Ser Leu Asp Val Glu Glu Ala Ala Ala Val Arg Ala Arg Leu Asn Trp
305                 310                 315                 320

Thr Ser Leu Leu Pro Ala Ser Phe Thr Lys Asn Tyr Lys Pro Val Val
                325                 330                 335

Gln Thr Thr Gly Asn Ala Arg Ile Val Gln Glu Leu Pro Gln Leu Leu
            340                 345                 350

Asp Ala Arg Ser Ala Pro Leu Ile Ala Asp Gln Ala Val Leu Gln Leu
            355                 360                 365

Leu Pro Lys Thr Tyr Ile Leu Thr Cys Glu His Asp Val Leu Arg Asp
            370                 375                 380

Asp Gly Ile Met Tyr Ala Lys Arg Leu Glu Ser Ala Gly Val Glu Val
385                 390                 395                 400

Thr Leu Asp His Phe Glu Asp Gly Phe His Gly Cys Met Ile Phe Thr
                405                 410                 415

Ser Trp Pro Thr Asn Phe Ser Val Gly Ile Arg Thr Arg Asn Ser Tyr
            420                 425                 430
```

```
Ile Lys Trp Leu Asp Gln Asn Leu
        435                 440

<210> SEQ ID NO 58
<211> LENGTH: 408
<212> TYPE: PRT
<213> ORGANISM: Homo sapiens

<400> SEQUENCE: 58

Met Arg Ser Ser Cys Val Leu Leu Thr Ala Leu Val Ala Leu Ala Ala
 1               5                  10                  15

Tyr Tyr Val Tyr Ile Pro Leu Pro Gly Ser Val Ser Asp Pro Trp Lys
            20                  25                  30

Leu Met Leu Leu Asp Ala Thr Phe Arg Gly Ala Gln Gln Val Ser Asn
        35                  40                  45

Leu Ile His Tyr Leu Gly Leu Ser His His Leu Leu Ala Leu Asn Phe
    50                  55                  60

Ile Ile Val Ser Phe Gly Lys Lys Ser Ala Trp Ser Ser Ala Gln Val
65                  70                  75                  80

Lys Val Thr Asp Thr Asp Phe Asp Gly Val Glu Val Arg Val Phe Glu
                85                  90                  95

Gly Pro Pro Lys Pro Glu Glu Pro Leu Lys Arg Ser Val Val Tyr Ile
            100                 105                 110

His Gly Gly Gly Trp Ala Leu Ala Ser Ala Lys Ile Arg Tyr Tyr Asp
        115                 120                 125

Glu Leu Cys Thr Ala Met Ala Glu Glu Leu Asn Ala Val Ile Val Ser
    130                 135                 140

Ile Glu Tyr Arg Leu Val Pro Lys Val Tyr Phe Pro Glu Gln Ile His
145                 150                 155                 160

Asp Val Val Arg Ala Thr Lys Tyr Phe Leu Lys Pro Glu Val Leu Gln
                165                 170                 175

Lys Tyr Met Val Asp Pro Gly Arg Ile Cys Ile Ser Gly Asp Ser Ala
            180                 185                 190

Gly Gly Asn Leu Ala Ala Ala Leu Gly Gln Gln Phe Thr Gln Asp Ala
        195                 200                 205

Ser Leu Lys Asn Lys Leu Lys Leu Gln Ala Leu Ile Tyr Pro Val Leu
    210                 215                 220

Gln Ala Leu Asp Phe Asn Thr Pro Ser Tyr Gln Gln Asn Val Asn Thr
225                 230                 235                 240

Pro Ile Leu Pro Arg Tyr Val Met Val Lys Tyr Trp Val Asp Tyr Phe
                245                 250                 255

Lys Gly Asn Tyr Asp Phe Val Gln Ala Met Ile Val Asn Asn His Thr
            260                 265                 270

Ser Leu Asp Val Glu Glu Ala Ala Val Arg Ala Arg Leu Asn Trp
    275                 280                 285

Thr Ser Leu Leu Pro Ala Ser Phe Thr Lys Asn Tyr Lys Pro Val Val
    290                 295                 300

Gln Thr Thr Gly Asn Ala Arg Ile Val Gln Glu Leu Pro Gln Leu Leu
305                 310                 315                 320

Asp Ala Arg Ser Ala Pro Leu Ile Ala Asp Gln Ala Val Leu Gln Leu
                325                 330                 335

Leu Pro Lys Thr Tyr Ile Leu Thr Cys Glu His Asp Val Leu Arg Asp
            340                 345                 350

Asp Gly Ile Met Tyr Ala Lys Arg Leu Glu Ser Ala Gly Val Glu Val
        355                 360                 365
```

```
Thr Leu Asp His Phe Glu Asp Gly Phe His Gly Cys Met Ile Phe Thr
    370                 375                 380

Ser Trp Pro Thr Asn Phe Ser Val Gly Ile Arg Thr Arg Asn Ser Tyr
385                 390                 395                 400

Ile Lys Trp Leu Asp Gln Asn Leu
                405

<210> SEQ ID NO 59
<211> LENGTH: 430
<212> TYPE: PRT
<213> ORGANISM: Homo sapiens

<400> SEQUENCE: 59

Gly Gly Leu Arg Val Val Ser Pro Phe Pro Leu Cys Gln Pro Ala Gly
1               5                   10                  15

Glu Pro Ser Arg Gly Lys Met Arg Ser Ser Cys Val Leu Leu Thr Ala
            20                  25                  30

Leu Val Ala Leu Ala Thr Tyr Tyr Val Tyr Ile Pro Leu Pro Gly Ser
        35                  40                  45

Val Ser Asp Pro Trp Lys Leu Met Leu Leu Asp Ala Thr Phe Arg Gly
50                  55                  60

Ala Gln Gln Val Ser Asn Leu Ile His Tyr Leu Gly Leu Ser His His
65                  70                  75                  80

Leu Leu Ala Leu Asn Phe Ile Ile Val Ser Phe Gly Lys Lys Ser Ala
                85                  90                  95

Trp Ser Ser Ala Gln Val Lys Val Thr Asp Thr Asp Phe Asp Gly Val
            100                 105                 110

Glu Val Arg Val Phe Glu Gly Pro Lys Pro Glu Glu Pro Leu Lys
        115                 120                 125

Arg Ser Val Val Tyr Ile His Gly Gly Gly Trp Ala Leu Ala Ser Ala
130                 135                 140

Lys Ile Arg Tyr Tyr Asp Glu Leu Cys Thr Ala Met Ala Glu Glu Leu
145                 150                 155                 160

Asn Ala Val Ile Val Ser Ile Glu Tyr Arg Leu Val Pro Lys Val Tyr
                165                 170                 175

Phe Pro Glu Gln Ile His Asp Val Val Arg Ala Thr Lys Tyr Phe Leu
            180                 185                 190

Lys Pro Glu Val Leu Gln Lys Tyr Met Val Asp Pro Gly Arg Ile Cys
        195                 200                 205

Ile Ser Gly Asp Ser Ala Gly Gly Asn Leu Ala Ala Ala Leu Gly Gln
210                 215                 220

Gln Phe Thr Gln Asp Ala Ser Leu Lys Asn Lys Leu Lys Leu Gln Ala
225                 230                 235                 240

Leu Ile Tyr Pro Val Leu Gln Ala Leu Asp Phe Asn Thr Pro Ser Tyr
                245                 250                 255

Gln Gln Asn Val Asn Thr Pro Ile Leu Pro Arg Tyr Val Met Val Lys
            260                 265                 270

Tyr Trp Val Asp Tyr Phe Lys Gly Asn Tyr Asp Phe Gln Ala Met
        275                 280                 285

Ile Val Asn Asn His Thr Ser Leu Asp Val Glu Glu Ala Ala Ala Val
290                 295                 300

Arg Ala Arg Leu Asn Trp Thr Ser Leu Leu Pro Ala Ser Phe Thr Lys
305                 310                 315                 320

Asn Tyr Lys Pro Val Val Gln Thr Thr Gly Asn Ala Arg Ile Val Gln
```

```
                      325                 330                 335
Glu Leu Pro Gln Leu Leu Asp Ala Arg Ser Ala Pro Leu Ile Ala Asp
        340                 345                 350

Gln Ala Val Leu Gln Leu Leu Pro Lys Thr Tyr Ile Leu Thr Cys Glu
        355                 360                 365

His Asp Val Leu Arg Asp Asp Gly Ile Met Tyr Ala Lys Arg Leu Glu
        370                 375                 380

Ser Ala Gly Val Glu Val Thr Leu Asp His Phe Glu Asp Gly Phe His
385                 390                 395                 400

Gly Cys Met Ile Phe Thr Ser Trp Pro Thr Asn Phe Ser Val Gly Ile
        405                 410                 415

Arg Thr Arg  Asn Ser Tyr Ile Lys Trp Leu Asp Gln Asn Leu
        420                 425                 430

<210> SEQ ID NO 60
<211> LENGTH: 4339
<212> TYPE: DNA
<213> ORGANISM: Homo sapiens

<400> SEQUENCE: 60
```

| | | | | | |
|---|---|---|---|---|---|
| atgcagtaca | aaccagtgtc | ctccagagtc | cgctgtgcct | acggccagag | cagcgacaga | 60 |
| gccttcctca | aacctgtagt | gactgccaca | ctttgcaagg | acaccgtaga | ggggggcatgt | 120 |
| ccgcgctcca | acttcctccc | gacgcagcct | ctgattggct | cctgggctta | taagaaacgc | 180 |
| gtgaatgagc | agctgccgcg | ggcagaaagt | tgccggaggt | ctccgggtgg | tatcgccctt | 240 |
| tcctctttgc | cagcccgctg | gcgagccgag | ccagggcaag | atgaggtcgt | cctgtgtcct | 300 |
| gctcaccgcc | ctggtggcgc | tggccgccta | ttacgtctac | atcccgctgc | ctggctccgt | 360 |
| gtccgacccc | tggaagctga | tgctgctgga | cgccactttc | cggggtgcac | agcaagtgag | 420 |
| taacctgatc | cactacctgg | gactgagcca | tcacctgctg | gcactgaatt | ttatcattgt | 480 |
| ttcttttggc | aaaaaaagcg | cgtggtcttc | tgcccaagtg | aaggtgaccg | acacagactt | 540 |
| tgatggtgtg | gaagtcagag | tgtttgaagg | ccctccgaag | cccgaagagc | cactgaaacg | 600 |
| cagcgtcgtt | tatatccacg | gaggaggctg | ggccttggca | agtgcaaaaa | tcaggtatta | 660 |
| tgatgagctg | tgtacagcaa | tggctgagga | attgaatgct | gtcattgttt | ccattgaata | 720 |
| caggctagtt | ccaaaggttt | attttcctga | gcaaattcat | gatgttgtac | gggccacaaa | 780 |
| gtatttcctg | aagccagaag | tcttacagaa | gtatatggtt | gatccaggca | gaatttgcat | 840 |
| ttctggtgac | agtgctggtg | gaaatctggc | tgctgccctt | ggacaacagt | ttactcaaga | 900 |
| tgccagccta | aaaaataagc | tcaaactaca | agctttaatt | tatccagttc | ttcaagcttt | 960 |
| agattttaac | acaccatctt | atcagcaaaa | tgtgaacacc | ccaatcctgc | cccgctatgt | 1020 |
| catggtgaag | tattgggtgg | actacttcaa | aggcaactat | gactttgtgc | aggcaatgat | 1080 |
| cgttaacaat | cacacttcac | ttgatgtgga | agaggctgct | gctgtcaggg | cccgtctaaa | 1140 |
| ctggacatcc | ctcttgcctg | catccttcac | aaagaactac | aagcctgttg | tacagaccac | 1200 |
| aggcaatgcc | aggattgtcc | aggagcttcc | tcagttgctg | atgcccgct | ccgcccact | 1260 |
| cattgcagac | caggcagtgc | tgcagctcct | cccaaagacc | tacattctga | cgtgtgagca | 1320 |
| tgatgtcctc | agagacgatg | gcatcatgta | tgccaagcgt | ttggagagtg | ccggtgtgga | 1380 |
| ggtgaccctg | gatcactttg | aggatggctt | tcacggatgt | atgatttca | ctagctggcc | 1440 |
| caccaacttc | tcagtgggaa | tccggactag | gaatagttac | atcaagtggc | tagatcaaaa | 1500 |
| cctgtaaagg | agcaaaactt | ccagaagcct | cgagcccctc | ttgacctcct | acacctgctt | 1560 |

```
tggaaagaca tgcactttt  agttgactaa ttcttcctcc cattccctc  tacttgcgag  1620
ttatggaatt tctattccat aactgaagtc tttatgataa cctaattttt aaaaatgaat  1680
ttgactaact taagtgcaaa acatgtaaat ttggttccca gagtgggcca atctctctgt  1740
tcttgttatc ttagccaact atactgatac ctacagctac agaaagcagg actaggaact  1800
ggaaataact ttgggtcctg ccttcattag gacgttcttt ttagaagcag ttcttccagc  1860
tctggatcat agagtgacct ttaataagtt aaaaaaacga ggactcctta attctgctag  1920
agttaacctt gagttcagag cagtattaaa tgcgtgcact ttcaggtcag tactggggac  1980
caagtaccct ctggtctttt gtgaatggat ggttttgttt cctatgggaa ttttggcaaa  2040
ggttttctgg aaagaacaag tttctcaaag gactttcttc ctctagaatg ttcattttat  2100
gagatcgcta tctgtaagtc cagttggatt acaggaatac ttgaaagtta ctttctacca  2160
ctattagaaa atatgaagtc gcatgcactg gatatctata tatcattagg ttttgttgt   2220
gttttggtt  atgctgtccc ccttctcctt ggggagatat ttgggagcaa acttatttag  2280
atttagagta aacttttcat tatagagcaa gtaaaaacag acaaatgaaa caacctagtg  2340
tttcacataa aaatacttct gacataaagt accaagagca gtgtgaatat acttggcata  2400
gtcaaaaag  aaaatacatt taatattagt tcaaaattgt taaaaatacc tttagaaggt  2460
ctagtctatt attgaaaact caattttttc acttatatgg ctttaaaatg gagctatttt  2520
gctacaatat aatgtattgt ttattttttt aagttattta atgttaatat acatagctag  2580
acttaaggtt tttcagaaag atgtccataa taaatattaa aaacaatggt atttttaaa   2640
aaactgcctt agggttttaa aaccttccct acagttataa ccacgtgtaa ttttgtggaa  2700
atgatataac agctattaat actactataa cataggcata aatattttcg tgtttatatg  2760
catatacaag ttaaataat  tagaaactat gactgcgcct agtaaagtca tctaggttta  2820
tagttcagta gcttaggcaa ggcacacact gctcatctcc gcttttagg  gtcagaggaa  2880
cacaagctca tgttctgagt gaagggcgta cactggcacc tggtgttgcc tagatccccc  2940
atctcctcct tccagccagg tctggaagtt tcaacagccc aagcttaact tcatgtaaag  3000
tcttcactgc cagtgggaac atctttgaca caacaagaca ctccaattgt gatttgagtt  3060
gaggatctct gcctgccttc ctgccgtcct tccttcttcc ccgatccatg ctacttttag  3120
gggctgcgga gagcagcagc agagctgagt aatgatacag ggcaccacgg agagaaagta  3180
gaaccatttc actcctggga agatgggggta tttcccactt ccagcaacga aataacaaat  3240
gaaaagttgc atacttattg atgtattgta tgagccagta gcattttatg tacaaaacag  3300
aagtcaatgc aacagtatgt atgtgtgcct gtgtgtgtat aaaataaccc attgaagcta  3360
acttgctaat gtacttaggc aagccacttc ccatctctgg gcctcgtctt tcctccctct  3420
aaaatcaaag agctgaatta tgtgatcctt gaggtctctt ccacttataa taccaactgt  3480
cttgtcagac tggcaaatta tattggcctc tccttatgtg gtggttttt  tggtaggtca  3540
tagttcctta tacacagaca cctgcatcat cgaaggtctt ttttttcctaa aaaaaaaaaa  3600
tgggatttta gttcttattc tgtgataact atcctcctca tataatacta ttcttttga   3660
caccatttga aggaaccaat atttggacct tattttgagg ttgtctgtct cgaagaaaaa  3720
gaaaataaaa tgtataggca gggttccttc aattggcatt ttccccagaa ttgtgagcca  3780
aagcctatag taattgcaga cagcaaatga ttccggatct ctaaaaggct ctctcagatg  3840
aaaagggagt aaaggaaaaa agaggtcaac cactgttttct gataatgtac ttgagtttca  3900
```

```
ttgttcttttt agtttgtatt cttataaaaa atgtttacac tctgcagatt gattttttt    3960 ttttagtact gtggctttct tttcctattt tatgaaaaaa atgataatct ttttgtaaaa    4020
ttgtctgtga aatataaaca ttaatatata aagaaaaacc ttgaagtgct gtatagtgaa    4080
gtataaatta atgttttatt gatttgtgaa gaatttaaga ctattatata attatcttgg    4140
tggatctatt ttatgcatga ccttttaacc tttgactttg cttatttccc actacgaagg    4200
ggaaggtaga ttttatgaat gatttttaata gcaaatatat tttataaagt gaaaatccag   4260
tgtggaggta gcaaagcatc tatctattct gaatcatgtt tggaaataaa attgctccat    4320
ctgggaatgt gctttcatt                                                 4339

<210> SEQ ID NO 61
<211> LENGTH: 4339
<212> TYPE: DNA
<213> ORGANISM: Homo sapiens

<400> SEQUENCE: 61
atgcagtaca aaccagtgtc ctccagagtc cgctgtgcct acggccagag cagcgacaga     60
gccttcctca aacctgtagt gactgccaca ctttgcaagg acaccgtaga gggggcatgt    120
ccgcgctcca acttcctccc gacgcagcct ctgattggct cctgggctta aagaaacgc    180 gtgaatgagc agctgccgcg ggcagaaagt tgccggaggc tccgggtgg tatcgccctt    240 tcctctttgc cagcccgctg gcgagccgag ccagggcaag atgaggtcgt cctgtgtcct    300
gctcaccgcc ctggtggcgc tggccgccta ttacgtctac atcccgctgc ctggctccgt    360
gtccgacccc tggaagctga tgctgctgga cgccactttc cggggtgcac agcaagtgag    420
taacctgatc cactacctgg gactgagcca tcacctgctg cactgaatt ttatcattgt    480 ttcttttggc aaaaaaagcg cgtggtcttc tgcccaagtg aaggtgaccg acacagactt    540
tgatggtgtg gaagtcagag tgtttgaagg ccctccgaag cccgaagagc cactgaaacg    600
cagcgtcgtt tatatccacg gaggaggctg ggccttggca agtgcaaaaa tcaggtatta    660
tgatgagctg tgtacagcaa tggctgagga attgaatgct gtcattgttt ccattgaata    720
caggctagtt ccaaaggttt attttcctga gcaaattcat gatgttgtac gggccacaaa    780
gtatttcctg aagccagaag tcttacagaa gtatatggtt gatccaggca gaatttgcat    840
ttctggtgac agtgctggtg gaaatctggc tgctgcccct ggacaacagt ttactcaaga    900
tgccagccta aaaataagc tcaaactaca agctttaatt tatccagttc ttcaagcttt    960 agatttttaac acaccatctt atcagcaaaa tgtgaacacc ccaatcctgc cccgctatgt   1020
catggtgaag tattgggtgg actacttcaa aggcaactat gactttgtgc aggcaatgat   1080
cgttaacaat cacacttcac ttgatgtgga agaggctgct gctgtcaggg cccgtctaaa   1140
ctggacatcc ctcttgcctg catccttcac aaagaactac aagcctgttg tacagaccac   1200
aggcaatgcc aggattgtcc aggagcttcc tcagttgctg gatgcccgct ccgccccact   1260
cattgcagac caggcagtgc tgcagctcct cccaaagacc tacattctga cgtgtgagca   1320
tgatgtcctc agagacgatg gcatcatgta tgccaagcgt ttggagagtg ccggtgtgga   1380
ggtgaccctg gatcactttg aggatggctt tcacggatgt atgattttca ctagctggcc   1440
caccaacttc tcagtgggaa tccgactag gaatagttac atcaagtggc tagatcaaaa   1500
cctgtaaagg agcaaaactt ccagaagcct cgagcccctc ttgacctcct acacctgctt   1560
tggaaagaca tgcactttt agttgactaa ttcttcctcc cattcccctc tacttgcgag   1620
ttatggaatt tctattccat aactgaagtc tttatgataa cctaattttt aaaaatgaat   1680
```

-continued

```
ttgactaact taagtgcaaa acatgtaaat ttggttccca gagtgggcca atctctctgt     1740
tcttgttatc ttagccaact atactgatac ctacagctac agaaagcagg actaggaact     1800
ggaaataact ttgggtcctg ccttcattag gacgttcttt ttagaagcag ttcttccagc     1860
tctggatcat agagtgacct ttaataagtt aaaaaaacga ggactcctta attctgctag     1920
agttaacctt gagttcagag cagtattaaa tgcgtgcact ttcaggtcag tactggggac     1980
caagtaccct ctggtctttt gtgaatggat ggttttgttt cctatgggaa ttttggcaaa     2040
ggttttctgg aaagaacaag tttctcaaag gactttcttc ctctagaatg ttcattttat     2100
gagatcgcta tctgtaagtc cagttggatt acaggaatac ttgaaagtta ctttctacca     2160
ctattagaaa atatgaagtc gcatgcactg gatatctata tatcattagg ttttttgttgt     2220 gttttttggtt atgctgtccc cctctccctt ggggagatat ttgggagcaa acttatttag     2280
atttagagta aactttttcat tatagagcaa gtaaaaacag acaaatgaaa caacctagtg     2340
tttcacataa aaatacttct gacataaagt accaagagca gtgtgaatat acttggcata     2400
gtcaaaaaag aaaatacatt taatattagt tcaaaattgt taaaaatacc tttagaaggt     2460
ctagtctatt attgaaaact caattttttc acttatatgg ctttaaaatg gagctatttt     2520
gctacaatat aatgtattgt ttatttttttt aagttattta atgttaatat acatagctag     2580
acttaaggtt tttcagaaag atgtccataa taaatattaa aaacaatggt atttttttaaa     2640 aaactgcctt agggttttaa aaccttccct acagttataa ccacgtgtaa ttttgtggaa     2700
atgatataac agctattaat actactataa cataggcata aatattttcg tgtttatatg     2760
catatacaag ttaaaataat tagaaaactat gactgcgcct agtaaagtca tctaggttta     2820
tagttcagta gcttaggcaa ggcacacact gctcatctcc gcttttagg gtcagaggaa     2880 cacaagctca tgttctgagt gaagggcgta cactggcacc tggtgttgcc tagatccccc     2940
atctcctcct tccagccagg tctggaagtt tcaacagccc aagcttaact tcatgtaaag     3000
tcttcactgc cagtgggaac atctttgaca caacaagaca ctccaattgt gatttgagtt     3060
gaggatctct gcctgccttc ctgccgtcct tccttcttcc ccgatccatg ctactttttag    3120 gggctgcgga gagcagcagc agagctgagt aatgatacag ggcaccacgg agagaaagta    3180
gaaccatttc actcctggga agatgggggta tttcccactt ccagcaacga aataacaaat    3240
gaaaagttgc atacttattg atgtattgta tgagccagta gcatttttatg tacaaaacag    3300 aagtcaatgc aacagtatgt atgtgtgcct gtgtgtgtat aaaaataacc attgaagcta    3360
acttgctaat gtacttaggc aagccacttc ccatctctgg gcctcgtctt tcctccctct    3420
aaaatcaaag agctgaatta tgtgatcctt gaggtctctt ccacttataa taccaactgt    3480
cttgtcagac tggcaaatta tattggcctc tccttatgtg gtggtttttt tggtaggtca    3540
tagttcctta tacacagaca cctgcatcat cgaaggtctt ttttttcctaa aaaaaaaaa    3600 tgggatttta gttcttattc tgtgataact atcctcctca tataatacta ttctttttga    3660
caccatttga aggaaccaat atttggacct tattttgagg ttgtctgtct cgaagaaaaa    3720
gaaaataaaa tgtataggca gggttccttc aattggcatt ttccccagaa ttgtgagcca    3780
aagcctatag taattgcaga cagcaaatga ttccggatct ctaaaaggct ctctcagatg    3840
aaaagggagt aaaggaaaaa agaggtcaac cactgtttct gataatgtac ttgagtttca    3900
ttgttctttt agtttgtatt cttataaaaa atgtttacac tctgcagatt gattttttttt    3960 ttttagtact gtggcttttct tttcctattt tatgaaaaaa atgataatct ttttgtaaaa    4020
```

| | |
|---|---|
| ttgtctgtga aatataaaca ttaatatata aagaaaaacc ttgaagtgct gtatagtgaa | 4080 |
| gtataaatta atgttttatt gatttgtgaa gaatttaaga ctattatata attatcttgg | 4140 |
| tggatctatt ttatgcatga cctttaacc tttgactttg cttatttccc actacgaagg | 4200 |
| ggaaggtaga ttttatgaat gattttaata gcaaatatat tttataaagt gaaaatccag | 4260 |
| tgtggaggta gcaaagcatc tatctattct gaatcatgtt tggaaataaa attgctccat | 4320 |
| ctgggaatgt gctttcatt | 4339 |

<210> SEQ ID NO 62
<211> LENGTH: 4339
<212> TYPE: DNA
<213> ORGANISM: Homo sapiens

<400> SEQUENCE: 62

| | |
|---|---|
| atgcagtaca aaccagtgtc ctccagagtc cgctgtgcct acggccagag cagcgacaga | 60 |
| gccttcctca aacctgtagt gactgccaca ctttgcaagg acaccgtaga gggggcatgt | 120 |
| ccgcgctcca acttcctccc gacgcagcct ctgattggct cctgggctta agaaaacgc | 180 |
| gtgaatgagc agctgccgcg ggcagaaagt tgccggaggc tccgggtgg tatcgccctt | 240 |
| tcctctttgc cagcccgctg gcgagccgag ccagggcaag atgaggtcgt cctgtgtcct | 300 |
| gctcaccgcc ctggtggcgc tggccgccta ttacgtctac atcccgctgc ctggctccgt | 360 |
| gtccgacccc tggaagctga tgctgctgga cgccactttc cggggtgcac agcaagtgag | 420 |
| taacctgatc cactacctgg gactgagcca tcacctgctg gcactgaatt ttatcattgt | 480 |
| ttctttttggc aaaaaaagcg cgtggtcttc tgcccaagtg aaggtgaccg acacagactt | 540 |
| tgatggtgtg gaagtcagag tgtttgaagg ccctccgaag cccgaagagc cactgaaacg | 600 |
| cagcgtcgtt tatatccacg gaggaggctg ggccttggca agtgcaaaaa tcaggtatta | 660 |
| tgatgagctg tgtacagcaa tggctgagga attgaatgct gtcattgttt ccattgaata | 720 |
| caggctagtt ccaaaggttt atttttcctga gcaaattcat gatgttgtac gggccacaaa | 780 |
| gtatttcctg aagccagaag tcttacgaa gtatatggtt gatccaggca gaatttgcat | 840 |
| ttctggtgac agtgctggtg gaaatctggc tgctgcccct ggacaacagt ttactcaaga | 900 |
| tgccagccta aaaataagc tcaaactaca agctttaatt tatccagttc ttcaagcttt | 960 |
| agattttaac acaccatctt atcagcaaaa tgtgaacacc ccaatcctgc cccgctatgt | 1020 |
| catggtgaag tattgggtgg actacttcaa aggcaactat gactttgtgc aggcaatgat | 1080 |
| cgttaacaat cacacttcac ttgatgtgga agaggctgct gctgtcaggg cccgtctaaa | 1140 |
| ctggacatcc ctcttgcctg catccttcac aaagaactac aagcctgttg tacagaccac | 1200 |
| aggcaatgcc aggattgtcc aggagcttcc tcagttgctg gatgcccgct ccgcccact | 1260 |
| cattgcagac caggcagtgc tgcagctcct cccaaagacc tacattctga cgtgtgagca | 1320 |
| tgatgtcctc agagacgatg gcatcatgta tgccaagcgt ttggagagtg ccggtgtgga | 1380 |
| ggtgacccctg gatcactttg aggatggctt tcacggatgt atgattttca ctagctggcc | 1440 |
| caccaacttc tcagtgggaa tccggactag gaatagttac atcaagtggc tagatcaaaa | 1500 |
| cctgtaaagg agcaaaactt ccagaagcct cgagcccctc ttgacctcct acacctgctt | 1560 |
| tggaaagaca tgcactttt agttgactaa ttcttcctcc cattccctc tacttgcgag | 1620 |
| ttatggaatt tctattccat aactgaagtc tttatgataa cctaattttt aaaatgaat | 1680 |
| ttgactaact taagtgcaaa acatgtaaat ttggttccca gagtgggcca atctctctgt | 1740 |
| tcttgttatc ttagccaact atactgatac ctacagctac agaaagcagg actaggaact | 1800 |

```
ggaaataact ttgggtcctg ccttcattag gacgttcttt ttagaagcag ttcttccagc   1860
tctggatcat agagtgacct ttaataagtt aaaaaaacga ggactcctta attctgctag   1920
agttaaccat gagttcagag cagtattaaa tgcgtgcact ttcaggtcag tactggggac   1980
caagtaccct ctggtctttt gtgaatggat ggttttgttt cctatgggaa ttttggcaaa   2040
ggttttctgg aaagaacaag tttctcaaag gactttcttc ctctagaatg ttcattttat   2100
gagatcgcta tctgtaagtc cagttggatt acaggaatac ttgaaagtta ctttctacca   2160
ctattagaaa atatgaagtc gcatgcactg gatatctata tatcattagg ttttgttgt   2220 gttttggtt atgctgtccc ccttctcctt ggggagatat ttgggagcaa acttatttag   2280
atttagagta aacttttcat tatagagcaa gtaaaaacag acaaatgaaa caacctagtg   2340
tttcacataa aaatacttct gacataaagt accaagagca gtgtgaatat acttggcata   2400
gtcaaaaaag aaaatacatt taatattagt tcaaaattgt taaaaatacc tttagaaggt   2460
ctagtctatt attgaaaact caattttttc acttatatgg ctttaaaatg gagctatttt   2520
gctacaatat aatgtattgt ttatttttt aagttattta atgttaatat acatagctag   2580
acttaaggtt tttcagaaag atgtccataa taaatattaa aaacaatggt attttttaaa   2640
aaactgcctt agggttttaa aaccttccct acagttataa ccacgtgtaa ttttgtggaa   2700
atgatataac agctattaat actactataa cataggcata aatattttcg tgtttatatg   2760
catatacaag ttaaaataat tagaaactat gactgcgcct agtaaagtca tctaggttta   2820
tagttcagta gcttaggcaa ggcacacact gctcatctcc gcttttagg gtcagaggaa   2880 cacaagctca tgttctgagt gaagggcgta cactggcacc tggtgttgcc tagatccccc   2940
atctcctcct tccagccagg tctggaagtt tcaacagccc aagcttaact tcatgtaaag   3000
tcttcactgc cagtgggaac atctttgaca caacaagaca ctccaattgt gatttgagtt   3060
gaggatctct gcctgccttc ctgccgtcct tccttcttcc ccgatccatg ctactttag    3120 gggctgcgga gagcagcagc agagctgagt aatgatacag ggcaccacgg agagaaagta   3180
gaaccatttc actcctggga agatgggggta tttcccactt ccagcaacga aataacaaat   3240
gaaaagttgc atacttattg atgtattgta tgagccagta gcatttatg tacaaaacag    3300 aagtcaatgc aacagtatgt atgtgtgcct gtgtgtgtat aaaaataacc attgaagcta   3360
acttgctaat gtacttaggc aagccacttc ccatctctgg gcctcgtctt tcctccctct   3420
aaaatcaaag agctgaatta tgtgatcctt gaggtctctt ccacttataa taccaactgt   3480
cttgtcagac tggcaaatta tattggcctc tccttatgtg gtggtttttt tggtaggtca   3540
tagttcctta tacacagaca cctgcatcat cgaaggtctt ttttcctaa aaaaaaaaa    3600 tgggatttta gttcttattc tgtgataact atcctcctca tataatacta ttcttttga   3660 caccatttga aggaaccaat atttggacct tattttgagg ttgtctgtct cgaagaaaaa   3720
gaaaataaaa tgtataggca gggttccttc aattggcatt ttccccagaa ttgtgagcca   3780
aagcctatag taattgcaga cagcaaatga ttccggatct ctaaaaggct ctctcagatg   3840
aaaagggagt aaaggaaaaa agaggtcaac cactgtttct gataatgtac ttgagtttca   3900
ttgttctttt agtttgtatt cttataaaaa atgtttacac tctgcagatt gatttttttt   3960
ttttagtact gtggctttct tttcctattt tatgaaaaaa atgataatct ttttgtaaaa   4020
ttgtctgtga aatataaaca ttaatatata agaaaaacc ttgaagtgct gtatagtgaa    4080
gtataaatta atgtttatt gatttgtgaa gaatttaaga ctattatata attatcttgg    4140
```

| | |
|---|---|
| tggatctatt ttatgcatga ccttttaacc tttgactttg cttatttccc actacgaagg | 4200 |
| ggaaggtaga ttttatgaat gattttaata gcaaatatat tttataaagt gaaaatccag | 4260 |
| tgtggaggta gcaaagcatc tatctattct gaatcatgtt tggaaataaa attgctccat | 4320 |
| ctgggaatgt gctttcatt | 4339 |

```
<210> SEQ ID NO 63
<211> LENGTH: 4116
<212> TYPE: DNA
<213> ORGANISM: Homo sapiens

<400> SEQUENCE: 63
```

| | |
|---|---|
| cggaggtctc cgggtggtat cgcccttttcc tctttgccag cccgctggcg agccgagccg | 60 |
| gggcaagatg aggtcgtcct gtgtcctgct caccgccctg gtggcgctgg ccacctatta | 120 |
| cgtctacatc ccgctgcctg gctccgtgtc cgacccctgg aagctgatgc tgctggacgc | 180 |
| cactttccgg ggtgcacagc aagtgagtaa cctgatccac tacctgggac tgagccatca | 240 |
| cctgctggca ctgaatttta tcattgtttc ttttggcaaa aaaagcgcgt ggtcttctgc | 300 |
| ccaagtgaag gtgaccgaca cagactttga tggtgtggaa gtcagagtgt ttgaaggccc | 360 |
| tccgaagccc gaagagccac tgaaacgcag cgtcgtttat atccacggag gaggctgggc | 420 |
| cttggcaagt gcaaaaatca ggtattatga tgagctgtgt acagcaatgg ctgaggaatt | 480 |
| gaatgctgtc attgtttcca ttgaatacag gctagttcca aaggtttatt tcctgagca | 540 |
| aattcatgat gttgtacggg ccacaaagta tttcctgaag ccagaagtct tacagaagta | 600 |
| tatggttgat ccaggcagaa tttgcatttc tggtgacagt gctggtggaa atctggctgc | 660 |
| tgcccttgga caacagttta ctcaagatgc cagcctaaaa aataagctca aactacaagc | 720 |
| tttaatttat ccagttcttc aagctttaga ttttaacaca ccatcttatc agcaaaatgt | 780 |
| gaacacccca atcctgcccc gctatgtcat ggtgaagtat tgggtggact acttcaaagg | 840 |
| caactatgac tttgtgcagg caatgatcgt taacaatcac acttcacttg atgtggaaga | 900 |
| ggctgctgct gtcagggccc gtctaaactg gacatccctc ttgcctgcat ccttcacaaa | 960 |
| gaactacaag cctgttgtac agaccacagg caatgccagg attgtccagg agcttcctca | 1020 |
| gttgctggat gcccgctccg ccccactcat tgcagaccag gcagtgctgc agctcctccc | 1080 |
| aaagacctac attctgacgt gtgagcatga tgtcctcaga gacgatggca tcatgtatgc | 1140 |
| caagcgtttg gagagtgccg gtgtggaggt gaccctggat cactttgagg atggctttca | 1200 |
| cggatgtatg attttcacta gctggcccac caacttctca gtgggaatcc ggactaggaa | 1260 |
| tagttacatc aagtggctag atcaaaacct gtaaaggagc aaaacttcca gaagcctcga | 1320 |
| gcccctcttg acctcctaca cctgctttgg aaagacatgc acttttttagt tgactaattc | 1380 |
| ttcctcccat tcccctctac ttgcgagtta tggaatttct attccataac tgaagtcttt | 1440 |
| atgataacct aattttttaaa aatgaatttg actaacttaa gtgcaaaaca tgtaaatttg | 1500 |
| gttcccagag tgggccaatc tctctgttct tgttatctta gccaactata ctcatacccta | 1560 |
| cagctacaga aagcaggact aggaactgga ataactttg ggtcctgcct tcattaggac | 1620 |
| gttcttttta gaagcagttc ttccagctct ggatcataga gtgaccttta ataagttaaa | 1680 |
| aaaacgagga ctccttaatt ctgctagagt taaccttgag ttcagagcag tattaaatgc | 1740 |
| gtgcactttc aggtcagtac tggggaccaa gtaccctctg gtcttttgtg aatggatggt | 1800 |
| tttgtttcct atgggaattt tggcaaaggt tttctggaaa gaacaagttt ctcaaaggac | 1860 |
| tttcttcctc tagaatgttc attttatgag atcgctatct gtaagtccag ttggattaca | 1920 |

```
ggaatacttg aaagttactt tctaccacta ttagaaaata tgaagtcgca tgcactggat   1980
atctatatat cattaggttt ttgttgtgtt tttggttatg ctgtcccct tctccttggg    2040 gagatatttg ggagcaaact tatttagatt tagagtaaac ttttcattat agagcaagta   2100
aaaacagaca aatgaaacaa cctagtgttt cacataaaaa tacttctgac ataaagtacc   2160
aagagcagtg tgaatatact tggcatagtc aaaaagaaa atacatttaa tattagttaa    2220
aaattgttaa aaatacccttt agaaggtcta gtctattatt gaaaactcaa ttttttcact  2280
tatatggctt taaaatggag ctattttgct acaatataat gtattgttta ttttttaag    2340 ttatttaatg ttaatataca tagctagact taaggttttt cagaaagatg tccataataa   2400
atattaaaaa caatggtatt tttaaaaaaa ctgccttagg gttttaaaac cttccctaca   2460
gttataacca cgtgtaattt tgtggaaatg atataacagc tattaatact actataacat   2520
aggcataaat atttcgtgt ttatatgcat atacaagtta aaataattag aaactatgac    2580
tgcgcctagt aaagtcatct aggtttatag ttcagtagct taggcaaggc acacactgct   2640
catctccgct ttttagggtc agaggaacac aagctcatgt tctgagtgaa gggcgtacac   2700
tggcacctgg tgttgcctag atcccccatc tcctccttcc agccaggtct ggaagtttca   2760
acagcccaag cttaacttca tgtaaagtct tcactgccag tgggaacatc tttgacacaa   2820
caagacactc caattgtgat ttgagttgag gatctctgcc tgccttcctg ccgtccttcc   2880 ttcttcccg atccatgcta cttttagggg ctgcggagag cagcagcaga gctgagtaat    2940
gatacagggc accacggaga gaaagtagaa ccatttcact cctgggaaga tggggtattt   3000
cccacttcca gcaacgaaat aacaaatgaa aagttgcata cttattgatg tattgtatga   3060
gccagtagca ttttatgtac aaaacagaag tcaatgcaac agtatgtatg tgtgcctgtg   3120
tgtgtataaa aataaccatt gaagctaact tgctaatgta cttaggcaag ccacttccca   3180
tctctgggcc tcgtctttcc tccctctaaa atcaaagagc tgaattatgt gatccttgag   3240
gtctcttcca cttataatac caactgtctt gtcagactgg caaattatat tggcctctcc   3300
ttatgtggtg gtttttttgg taggtcatag ttccttatac acggacacct gcatcatcga   3360
aggtcttttt ttcctaaaaa aaaaaaatgg gatttagtt cttattctgt gataactatc     3420
ctcctcatat aatactattc ttttgacac catttgaagg aaccaatatt tggaccttat     3480
tttgaggttg tctgtctcga agaaaagaa aatttaaatgt ataggcaggg ttccttcaat    3540
tggcattttc cccagaattg tgagccaaag cctatagtaa ttgcagacag caaatgattc   3600
cggatctcta aaaggctctc tcagatgaaa agggagtaaa ggaaaaaga gggaggtcaa    3660 ccactgtttc tgataatgta cttgagtttc attgttcttt tagtttgtat tcttataaaa   3720
aatgtttaca ctctgcagat tgattttttt ttttttagtac tgtggctttc ttttcctatt  3780
ttatgaaaaa aatgataatc ttttttgtaaa attgtctgtg aaatataaac attaatatat   3840
aaagaaaaac cttgaagtgc tgtatagtga agtataaatt aatgttttat tgatttgtga   3900
agaatttaag actattatat aattatcttg gtggatctat tttatgcatg accttttaac   3960
ctttgacttt gcttatttcc cactacgaag gggaaggtag attttatgaa tgattttaat   4020
agcaaatata ttttataaag tgaaaatcca gtgtggaggt agcaaagcat ctatctattc   4080
tgaatcatgt ttgaaataa aattgctcca tctggg                             4116
```

<210> SEQ ID NO 64  
<211> LENGTH: 526  
<212> TYPE: PRT

<213> ORGANISM: Homo sapiens

<400> SEQUENCE: 64

```
Met Arg Cys Ala Leu Ala Leu Ser Ala Leu Leu Leu Leu Ser Thr
 1               5                  10                  15
Pro Pro Leu Leu Pro Ser Ser Pro Ser Pro Ser Pro Ser Pro Ser Gln
            20                  25                  30
Asn Ala Thr Gln Thr Thr Thr Asp Ser Ser Asn Lys Thr Ala Pro Thr
        35                  40                  45
Pro Ala Ser Ser Val Thr Ile Met Ala Thr Asp Thr Ala Gln Gln Ser
    50                  55                  60
Thr Val Pro Thr Ser Lys Ala Asn Glu Ile Leu Ala Ser Val Lys Ala
65                  70                  75                  80
Thr Thr Leu Gly Val Ser Ser Asp Ser Pro Gly Thr Thr Leu Ala
            85                  90                  95
Gln Gln Val Ser Gly Pro Val Asn Thr Thr Val Ala Arg Gly Gly Gly
            100                 105                 110
Ser Gly Asn Pro Thr Thr Thr Ile Glu Ser Pro Lys Ser Thr Lys Ser
        115                 120                 125
Ala Asp Thr Thr Thr Val Ala Thr Ser Thr Ala Thr Ala Lys Pro Asn
    130                 135                 140
Thr Thr Ser Ser Gln Asn Gly Ala Glu Asp Thr Thr Asn Ser Gly Gly
145                 150                 155                 160
Lys Ser Ser His Ser Val Thr Thr Asp Leu Thr Ser Thr Lys Ala Glu
                165                 170                 175
His Leu Thr Thr Pro His Pro Thr Ser Pro Leu Ser Pro Arg Gln Pro
            180                 185                 190
Thr Ser Thr His Pro Val Ala Thr Pro Thr Ser Ser Gly His Asp His
        195                 200                 205
Leu Met Lys Ile Ser Ser Ser Ser Thr Val Ala Ile Pro Gly Tyr
    210                 215                 220
Thr Phe Thr Ser Pro Gly Met Thr Thr Thr Leu Pro Ser Ser Val Ile
225                 230                 235                 240
Ser Gln Arg Thr Gln Gln Thr Ser Ser Gln Met Pro Ala Ser Ser Thr
                245                 250                 255
Ala Pro Ser Ser Gln Glu Thr Val Gln Pro Thr Ser Pro Ala Thr Ala
            260                 265                 270
Leu Arg Thr Pro Thr Leu Pro Glu Thr Met Ser Ser Ser Pro Thr Ala
        275                 280                 285
Ala Ser Thr Thr His Arg Tyr Pro Lys Thr Pro Ser Pro Thr Val Ala
    290                 295                 300
His Glu Ser Asn Trp Ala Lys Cys Glu Asp Leu Glu Thr Gln Thr Gln
305                 310                 315                 320
Ser Glu Lys Gln Leu Val Leu Asn Leu Thr Gly Asn Thr Leu Cys Ala
                325                 330                 335
Gly Gly Ala Ser Asp Glu Lys Leu Ile Ser Leu Ile Cys Arg Ala Val
            340                 345                 350
Lys Ala Thr Phe Asn Pro Ala Gln Asp Lys Cys Gly Ile Arg Leu Ala
        355                 360                 365
Ser Val Pro Gly Ser Gln Thr Val Val Lys Glu Ile Thr Ile His
    370                 375                 380
Thr Lys Leu Pro Ala Lys Asp Val Tyr Glu Arg Leu Lys Asp Lys Trp
385                 390                 395                 400
```

```
Asp Glu Leu Lys Glu Ala Gly Val Ser Asp Met Lys Leu Gly Asp Gln
            405                 410                 415

Gly Pro Pro Glu Glu Ala Glu Asp Arg Phe Ser Met Pro Leu Ile Ile
            420                 425                 430

Thr Ile Val Cys Met Ala Ser Phe Leu Leu Val Ala Ala Leu Tyr
            435                 440                 445

Gly Cys Cys His Gln Arg Leu Ser Gln Arg Lys Asp Gln Gln Arg Leu
450                 455                 460

Thr Glu Glu Leu Gln Thr Val Glu Asn Gly Tyr His Asp Asn Pro Thr
465                 470                 475                 480

Leu Glu Val Met Glu Thr Ser Ser Glu Met Gln Glu Lys Lys Val Val
            485                 490                 495

Ser Leu Asn Gly Glu Leu Gly Asp Ser Trp Ile Val Pro Leu Asp Asn
            500                 505                 510

Leu Thr Lys Asp Asp Leu Asp Glu Glu Glu Asp Thr His Leu
            515                 520                 525

<210> SEQ ID NO 65
<211> LENGTH: 528
<212> TYPE: PRT
<213> ORGANISM: Homo sapiens

<400> SEQUENCE: 65

Met Arg Cys Ala Leu Ala Leu Ser Ala Leu Leu Leu Leu Leu Ser Thr
1               5                   10                  15

Pro Pro Leu Leu Pro Ser Ser Pro Ser Pro Ser Pro Ser Pro Ser Pro
            20                  25                  30

Ser Gln Asn Ala Thr Gln Thr Thr Thr Asp Ser Ser Asn Lys Thr Ala
            35                  40                  45

Pro Thr Pro Ala Ser Ser Val Thr Ile Met Ala Thr Asp Thr Ala Gln
        50                  55                  60

Gln Ser Thr Val Pro Thr Ser Lys Ala Asn Glu Ile Leu Ala Ser Val
65                  70                  75                  80

Lys Ala Thr Thr Leu Gly Val Ser Ser Asp Ser Pro Gly Thr Thr Thr
                85                  90                  95

Leu Ala Gln Gln Val Ser Gly Pro Val Asn Thr Thr Val Ala Arg Gly
            100                 105                 110

Gly Gly Ser Gly Asn Pro Thr Thr Thr Ile Glu Ser Pro Lys Ser Thr
        115                 120                 125

Lys Ser Ala Asp Thr Thr Thr Val Ala Thr Ser Thr Ala Thr Ala Lys
130                 135                 140

Pro Asn Thr Thr Ser Ser Gln Asn Gly Ala Glu Asp Thr Thr Asn Ser
145                 150                 155                 160

Gly Gly Lys Ser Ser His Ser Val Thr Thr Asp Leu Thr Ser Thr Lys
                165                 170                 175

Ala Glu His Leu Thr Thr Pro His Pro Thr Ser Pro Leu Ser Pro Arg
            180                 185                 190

Gln Pro Thr Leu Thr His Pro Val Ala Thr Pro Thr Ser Ser Gly His
        195                 200                 205

Asp His Leu Met Lys Ile Ser Ser Ser Ser Thr Val Ala Ile Pro
    210                 215                 220

Gly Tyr Thr Phe Thr Ser Pro Gly Met Thr Thr Thr Leu Pro Ser Ser
225                 230                 235                 240

Val Ile Ser Gln Arg Thr Gln Gln Thr Ser Ser Gln Met Pro Ala Ser
                245                 250                 255
```

Ser Thr Ala Pro Ser Ser Gln Glu Thr Val Gln Pro Thr Ser Pro Ala
            260                 265                 270

Thr Ala Leu Arg Thr Pro Thr Leu Pro Glu Thr Met Ser Ser Ser Pro
            275                 280                 285

Thr Ala Ala Ser Thr Thr His Arg Tyr Pro Lys Thr Pro Ser Pro Thr
            290                 295                 300

Val Ala His Glu Ser Asn Trp Ala Lys Cys Glu Asp Leu Glu Thr Gln
305                 310                 315                 320

Thr Gln Ser Glu Lys Gln Leu Val Leu Asn Leu Thr Gly Asn Thr Leu
            325                 330                 335

Cys Ala Gly Gly Ala Ser Asp Glu Lys Leu Ile Ser Leu Ile Cys Arg
            340                 345                 350

Ala Val Lys Ala Thr Phe Asn Pro Ala Gln Asp Lys Cys Gly Ile Arg
            355                 360                 365

Leu Ala Ser Val Pro Gly Ser Gln Thr Val Val Lys Glu Ile Thr
            370                 375                 380

Ile His Thr Lys Leu Pro Ala Lys Asp Val Tyr Glu Arg Leu Lys Asp
385                 390                 395                 400

Lys Trp Asp Glu Leu Lys Glu Ala Gly Val Ser Asp Met Lys Leu Gly
            405                 410                 415

Asp Gln Gly Pro Pro Glu Glu Ala Glu Asp Arg Phe Ser Met Pro Leu
            420                 425                 430

Ile Ile Thr Ile Val Cys Met Ala Ser Phe Leu Leu Leu Val Ala Ala
            435                 440                 445

Leu Tyr Gly Cys Cys His Gln Arg Leu Ser Gln Arg Lys Asp Gln Gln
            450                 455                 460

Arg Leu Thr Glu Glu Leu Gln Thr Val Glu Asn Gly Tyr His Asp Asn
465                 470                 475                 480

Pro Thr Leu Glu Val Met Glu Thr Ser Ser Glu Met Gln Glu Lys Lys
            485                 490                 495

Val Val Ser Leu Asn Gly Glu Leu Gly Asp Ser Trp Ile Val Pro Leu
            500                 505                 510

Asp Asn Leu Thr Lys Asp Asp Leu Asp Glu Glu Glu Asp Thr His Leu
            515                 520                 525

<210> SEQ ID NO 66
<211> LENGTH: 573
<212> TYPE: PRT
<213> ORGANISM: Homo sapiens

<400> SEQUENCE: 66

Met Cys Gly Ile Phe Ala Tyr Leu Asn Tyr His Val Pro Arg Thr Arg
  1               5                  10                  15

Arg Glu Ile Pro Gly Asp Pro Asn Gln Arg Pro Gln Arg Leu Glu Tyr
            20                  25                  30

Arg Ala His Asp Gly Leu Gly Val Gly Phe Asp Gly Gly Asn Asp Lys
            35                  40                  45

Asp Trp Glu Ala Asn Ala Cys Lys Ile Gln Leu Ile Lys Lys Lys Gly
        50                  55                  60

Lys Val Lys Ala Leu Asp Glu Glu Val His Lys Gln Gln Asp Met Asp
 65                  70                  75                  80

Leu Asp Ile Glu Phe Asp Val His Leu Gly Ile Ala His Thr Arg Trp
                85                  90                  95

Ala Thr His Gly Glu Pro Ser Pro Val Asn Ser His Pro Gln Arg Ser

-continued

```
                100                 105                 110
Asp Lys Asn Asn Glu Phe Ile Val Ile His Asn Gly Ile Ile Thr Asn
            115                 120                 125
Tyr Lys Asp Leu Lys Lys Phe Leu Glu Ser Lys Gly Tyr Asp Phe Glu
130                 135                 140
Ser Glu Thr Asp Thr Glu Thr Ile Ala Lys Leu Val Lys Tyr Met Tyr
145                 150                 155                 160
Asp Asn Arg Glu Ser Gln Asp Thr Ser Phe Thr Thr Leu Val Glu Arg
                165                 170                 175
Val Ile Gln Gln Leu Glu Gly Ala Phe Ala Leu Val Phe Lys Ser Val
            180                 185                 190
His Phe Pro Gly Gln Ala Val Gly Thr Arg Arg Gly Ser Pro Leu Leu
        195                 200                 205
Ile Gly Val Arg Ser Glu His Lys Leu Ser Thr Asp His Ile Pro Ile
    210                 215                 220
Leu Tyr Arg Thr Gly Lys Asp Lys Lys Gly Ser Cys Asn Leu Ser Arg
225                 230                 235                 240
Val Asp Ser Thr Thr Cys Leu Phe Pro Val Glu Glu Lys Ala Val Glu
                245                 250                 255
Tyr Tyr Phe Ala Ser Asp Ala Ser Ala Val Ile Glu His Thr Asn Arg
            260                 265                 270
Val Ile Phe Leu Glu Asp Asp Val Ala Ala Val Asp Gly Arg
275                 280                 285
Leu Ser Ile His Arg Ile Lys Arg Thr Ala Gly Asp His Pro Gly Arg
        290                 295                 300
Ala Val Gln Thr Leu Gln Met Glu Leu Gln Gln Ile Met Lys Gly Asn
305                 310                 315                 320
Phe Ser Ser Phe Met Gln Lys Glu Ile Phe Glu Gln Pro Glu Ser Val
                325                 330                 335
Val Asn Thr Met Arg Gly Arg Val Asn Phe Asp Asp Tyr Thr Val Asn
            340                 345                 350
Leu Gly Gly Leu Lys Asp His Ile Lys Glu Ile Gln Arg Cys Arg Arg
        355                 360                 365
Leu Ile Leu Ile Ala Cys Gly Thr Ser Tyr His Ala Gly Val Ala Thr
    370                 375                 380
Arg Gln Val Leu Glu Glu Leu Thr Glu Leu Pro Val Met Val Glu Leu
385                 390                 395                 400
Ala Ser Asp Phe Leu Asp Arg Asn Thr Pro Val Phe Arg Asp Asp Val
                405                 410                 415
Cys Phe Phe Leu Ser Gln Ser Gly Glu Thr Ala Asp Thr Leu Met Gly
            420                 425                 430
Leu Arg Tyr Cys Lys Glu Arg Gly Ala Leu Thr Val Gly Ile Thr Asn
        435                 440                 445
Thr Val Gly Ser Ser Ile Ser Arg Glu Thr Asp Cys Gly Val His Ile
    450                 455                 460
Asn Ala Gly Pro Glu Ile Gly Val Ala Ser Thr Lys Ala Tyr Thr Ser
465                 470                 475                 480
Gln Phe Val Ser Leu Val Met Phe Ala Leu Met Met Cys Asp Asp Arg
                485                 490                 495
Ile Ser Met Gln Glu Arg Arg Lys Glu Ile Met Leu Gly Leu Lys Arg
            500                 505                 510
Leu Pro Asp Leu Ile Lys Glu Val Leu Ser Met Asp Asp Glu Ile Gln
        515                 520                 525
```

```
Lys Leu Ala Thr Glu Leu Tyr His Gln Lys Ser Val Leu Ile Met Gly
            530                 535                 540

Arg Gly Tyr His Tyr Ala Thr Cys Leu Glu Gly Ala Leu Lys Ile Lys
545                 550                 555                 560

Glu Ile Thr Tyr Met His Ser Glu Gly Ile Leu Leu Cys
                565                 570

<210> SEQ ID NO 67
<211> LENGTH: 518
<212> TYPE: PRT
<213> ORGANISM: Homo sapiens

<400> SEQUENCE: 67

Met Arg Cys Ala Leu Ala Leu Ser Ala Leu Leu Leu Leu Leu Ser Thr
  1               5                  10                  15

Pro Pro Ser Pro Ser Pro Ser Gln Asn Ala Thr Gln Thr Thr Thr Asp
                 20                  25                  30

Ser Ser Asn Lys Thr Ala Pro Thr Pro Ala Ser Ser Val Thr Ile Met
             35                  40                  45

Ala Thr Asp Thr Ala Gln Gln Ser Thr Val Pro Thr Ser Lys Ala Asn
 50                  55                  60

Glu Ile Leu Ala Ser Val Lys Ala Thr Thr Leu Gly Val Ser Ser Asp
65                  70                  75                  80

Ser Pro Gly Thr Thr Thr Leu Ala Gln Gln Val Ser Gly Pro Val Asn
                 85                  90                  95

Thr Thr Val Ala Arg Gly Gly Gly Ser Gly Asn Pro Thr Thr Thr Ile
            100                 105                 110

Glu Ser Pro Lys Ser Thr Lys Ser Ala Asp Thr Thr Thr Val Ala Thr
        115                 120                 125

Ser Thr Ala Thr Ala Lys Pro Asn Thr Thr Ser Ser Gln Asn Gly Ala
    130                 135                 140

Glu Asp Thr Thr Asn Ser Gly Gly Lys Ser Ser His Ser Val Thr Thr
145                 150                 155                 160

Asp Leu Thr Ser Thr Lys Ala Glu His Leu Thr Thr Pro His Pro Thr
                165                 170                 175

Ser Pro Leu Ser Pro Arg Gln Pro Thr Ser Thr His Pro Val Ala Thr
            180                 185                 190

Pro Thr Ser Ser Gly His Asp His Leu Met Lys Ile Ser Ser Ser Ser
        195                 200                 205

Ser Thr Val Ala Ile Pro Gly Tyr Thr Phe Ala Ser Pro Gly Met Thr
    210                 215                 220

Thr Thr Leu Pro Ser Ser Val Ile Ser Gln Arg Thr Gln Gln Thr Ser
225                 230                 235                 240

Ser Gln Met Pro Ala Ser Ser Thr Ala Pro Ser Ser Gln Glu Thr Val
                245                 250                 255

Gln Pro Thr Ser Pro Ala Thr Ala Leu Arg Thr Pro Thr Leu Pro Glu
            260                 265                 270

Thr Met Ser Ser Ser Pro Thr Ala Ala Ser Thr Thr His Arg Tyr Pro
        275                 280                 285

Lys Thr Pro Ser Pro Thr Val Ala His Glu Ser Asn Trp Ala Lys Cys
    290                 295                 300

Glu Asp Leu Glu Thr Gln Thr Gln Ser Glu Lys Gln Leu Val Leu Asn
305                 310                 315                 320

Leu Thr Gly Asn Thr Leu Cys Ala Gly Gly Ala Ser Asp Glu Lys Leu
```

```
                        325                 330                 335
Ile Ser Leu Ile Cys Arg Ala Val Lys Ala Thr Phe Asn Pro Ala Gln
            340                 345                 350

Asp Lys Cys Gly Ile Arg Leu Ala Ser Val Pro Gly Ser Gln Thr Val
        355                 360                 365

Val Val Lys Glu Ile Thr Ile His Thr Lys Leu Pro Ala Lys Asp Val
    370                 375                 380

Tyr Glu Arg Leu Lys Asp Lys Trp Asp Glu Leu Lys Glu Ala Gly Val
385                 390                 395                 400

Ser Asp Met Lys Leu Gly Asp Gln Gly Pro Pro Glu Glu Ala Glu Asp
                405                 410                 415

Arg Phe Ser Met Pro Leu Ile Ile Thr Ile Val Cys Met Ala Ser Phe
            420                 425                 430

Leu Leu Leu Val Ala Ala Leu Tyr Gly Cys Cys His Gln Arg Leu Ser
        435                 440                 445

Gln Arg Lys Asp Gln Gln Arg Leu Thr Glu Glu Leu Gln Thr Val Glu
    450                 455                 460

Asn Gly Tyr His Asp Asn Pro Thr Leu Glu Val Met Glu Thr Ser Ser
465                 470                 475                 480

Glu Met Gln Glu Lys Lys Val Val Ser Leu Asn Gly Glu Leu Gly Asp
                485                 490                 495

Ser Trp Ile Val Pro Leu Asp Asn Leu Thr Lys Asp Asp Leu Asp Glu
            500                 505                 510

Glu Glu Asp Thr His Leu
        515

<210> SEQ ID NO 68
<211> LENGTH: 5880
<212> TYPE: DNA
<213> ORGANISM: Homo sapiens

<400> SEQUENCE: 68
agacgccgcc caggacgcag ccgccgccgc cgccgctcct ctgccactgg ctctgcgccc      60
cagcccggct ctgctgcagc ggcagggagg aagagccgcc gcagcgcgac tcgggagccc     120
cgggccacag cctggcctcc ggagccaccc acaggcctcc ccgggcggcg cccacgctcc     180
taccgcccgg acgcgcggat cctccgccgg caccgcagcc acctgctccc ggcccagagg     240
cgacgacacg atgcgctgcg cgctggcgct ctcggcgctg ctgctactgt tgtcaacgcc     300
gccgctgctg ccgtcgtcgc cgtcgccgtc gccgtcgccc tcccagaatg caacccagac     360
tactacggac tcatctaaca aaacagcacc gactccagca tccagtgtca ccatcatggc     420
tacagataca gcccagcaga gcacagtccc cacttccaag gccaacgaaa tcttggcctc     480
ggtcaaggcg accacccttg gtgtatccag tgactcaccg gggactacaa ccctggctca     540
gcaagtctca ggcccagtca cactaccgt ggctagagga ggcggctcag gcaaccctac     600
taccaccatc gagagcccca agagcacaaa aagtgcagac accactacag ttgcaacctc     660
cacagccaca gctaaaccta acaccacaag cagccagaat ggagcagaag atacaacaaa     720
ctctgggggg aaaagcagcc acagtgtgac cacagacctc acatccacta aggcagaaca     780
tctgacgacc cctcacccta caagtccact tagccccga caacccactt cgacgcatcc     840
tgtggccacc ccaacaagct cgggacatga ccatcttatg aaaatttcaa gcagttcaag     900
cactgtggct atccctggct acaccttcac aagcccgggg atgaccacca ccctaccgtc     960
atcggttatc tcgcaaagaa ctcaacagac ctccagtcag atgccagcca gctctacggc    1020
```

```
cccttcctcc caggagacag tgcagcccac gagcccggca acggcattga gaacacctac   1080
cctgccagag accatgagct ccagccccac agcagcatca actacccacc gatacccaa    1140
aacaccttct cccactgtgg ctcatgagag taactgggca aagtgtgagg atcttgagac   1200
acagacacag agtgagaagc agctcgtcct gaacctcaca ggaaacaccc tctgtgcagg   1260
gggcgcttcg gatgagaaat tgatctcact gatatgccga gcagtcaaag ccaccttcaa   1320
cccggcccaa gataagtgcg gcatacggct ggcatctgtt ccaggaagtc agaccgtggt   1380
cgtcaaagaa atcactattc acactaagct ccctgccaag gatgtgtacg agcggctgaa   1440
ggacaaatgg gatgaactaa aggaggcagg ggtcagtgac atgaagctag gggaccaggg   1500
gccaccggag gaggccgagg accgcttcag catgcccctc atcatcacca tcgtctgcat   1560
ggcatcattc ctgctcctcg tggcggccct ctatggctgc tgccaccagc gcctctccca   1620
gaggaaggac cagcagcggc taacagagga gctgcagaca gtggagaatg gttaccatga   1680
caacccaaca ctggaagtga tggagacctc ttctgagatg caggagaaga aggtggtcag   1740
cctcaacggg gagctggggg acagctggat cgtccctctg acaacctga ccaaggacga    1800
cctggatgag gaggaagaca cacacctcta gtccggtctg ccggtggcct ccagcagcac   1860
cacagagctc cagaccaacc accccaagtg ccgtttggat ggggaaggga aagactgggg   1920
agggagagtg aactccgagg ggtgtcccct cccaatcccc ccagggcctt aattttttccc   1980
ttttcaacct gaacaaatca cattctgtcc agattcctct tgtaaaataa cccactagtg   2040
cctgagctca gtgctgctgg atgatgaggg agatcaagaa aaagccacgt aagggacttt   2100
atagatgaac tagtggaatc ccttcattct gcagtgagat tgccgagacc tgaagagggt   2160
aagtgacttg cccaaggtca gagccacttg gtgacagagc caggatgaga acaaagattc   2220
catttgcacc atgccacact gctgtgttca catgtgcctt ccgtccagag cagtcccggg   2280
caggggtgaa actccagcag gtggctgggc tggaaaggag ggcagggcta catcctggct   2340
cggtgggatc tgacgacctg aaagtccagc tcccaagttt tccttctcct accccagcct   2400
cgtgtaccca tcttcccacc ctctatgttc ttacccctcc ctacactcag tgtttgttcc   2460
cacttactct gtcctggggc ctctgggatt agcacaggtt attcataacc ttgaacccct   2520
tgttctggat tcggattttc tcacatttgc ttcgtgagat gggggcttaa cccacacagg   2580
tctccgtgcg tgaaccaggt ctgcttaggg gacctgcgtg caggtgagga gagaagggga   2640
cactcgagtc caggctggta tctcagggca gctgatgagg ggtcagcagg aacactggcc   2700
cattgcccct ggcactcctt gcagaggcca cccacgatct tctttgggct tccatttcca   2760
ccagggacta aaatctgctg tagctagtga gagcagcgtt ttccttttgt tgttcactgc   2820
tcagctgatg ggagtgattc cctgagaccc agtatgaaag agcagtggct gcaggagagg   2880
ccttcccggg gccccccatc agcgatgtgt cttcagagac aatccattaa agcagccagg   2940
aaggacaggc tttcccctgt atatcatagg aaactcaggg acatttcaag ttgctgagag   3000
ttttgttata gttgttttct aacccagccc tccactgcca aaggccaaaa gctcagacag   3060
ttggcagacg tccagttagc tcatctcact cactctgatt ctcctgtgcc acaggaaaag   3120
agggcctgga aagcgcagtg catgctgggt gcatgaaggg cagcctgggg gacagactgt   3180
tgtgggaacg tcccactgtc ctggcctgga gctaggcctt gctgttcctc ttctctgtga   3240
gcctagtggg gctgctgcgg ttctcttgca gtttctggtg gcatctcagg gaacacaaa    3300
gctatgtcta ttccccaata taggactttt atgggctcgg cagttagctg ccatgtagaa   3360
```

```
ggctcctaag cagtgggcat ggtgaggttt catctgattg agaaggggga atcctgtgtg   3420
gaatgttgaa ctttcgccat ggtctccatc gttctgggcg taaattccct gggatcaagt   3480
aggaaaatgg gcagaactgc ttaggggaat gaaattgcca tttttcgggt gaaacgccac   3540
acctccaggg tcttaagagt caggctccgg ctgtagtagc tctgatgaaa taggctatcc   3600
actcgggatg gcttactttt taaaagggta ggggaggggg ctggggaaga tctgtcctgc   3660
accatctgcc taattccttc ctcacagtct gtagccatct gatatcctag gggaaaagga   3720
aggccagggg ttcacatagg gccccagcga gtttcccagg agttagaggg atgcgaggct   3780
aacaagttcc aaaaacatct gccccgatgc tctagtgttt ggaggtgggc aggatggaga   3840
acagtgcctg tttggggaa acaggaaat cttgttaggc ttgagtgagg tgtttgcttc   3900
cttcttgccc agcgctgggt tctctccacc cagtaggttt tctgttgtgg tcccgtggga   3960
gaggccagac tggattattc ctcctttgct gatcctgggt cacacttcac cagccagggc   4020
ttttgacgga gacagcaaat aggcctctgc aaatcaatca aaggctgcaa ccctatggcc   4080
tcttggagac agatgatgac tggcaaggac tagagagcag gagtgcctgg ccaggtcggt   4140
cctgactctc ctgactctcc atcgctctgt ccaaggagaa cccggagagg ctctgggctg   4200
attcagaggt tactgcttta tattcgtcca aactgtgtta gtctaggctt aggacagctt   4260
cagaatctga caccttgcct tgctcttgcc accaggacac ctatgtcaac aggccaaaca   4320
gccatgcatc tataaaggtc atcatcttct gccacccttta ctgggttcta aatgctctct   4380
gataattcag agagcattgg gtctgggaag aggtaagagg aacactagaa gctcagcatg   4440
acttaaacag gttgtagcaa agacagttta tcatcagctc tttcagtggt aaactgtggt   4500
ttccccaagc tgcacaggag gccagaaacc acaagtatga tgactaggaa gcctactgtc   4560
atgagagtgg ggagacaggc agcaaagctt atgaaggagg tacagaatat tctttgcgtt   4620
gtaagacaga atacgggttt aatctagtct aggcaccaga ttttttttccc gcttgataag   4680 gaaagctagc agaaagttta tttaaaccac ttcttgagct ttatcttttt tgacaatata   4740
ctggagaaac tttgaagaac aagttcaaac tgatacatat acacatattt ttttgataat   4800
gtaaatacag tgaccatgtt aacctaccct gcactgcttt aagtgaacat actttgaaaa   4860
agcattatgt tagctgagtg atggccaagt ttttctctg gacagtaatg taaatgtctt   4920
actggaaatg acaagttttt gcttgatttt tttttttaaa caaaaaatga aatataacaa   4980
gacaaactta tgataaagta tttgtcttgt agatcaggtg ttttgttttg ttttttttaat   5040 tttaaaatgc aaccctgccc cctccccagc aaagtcacag ctccatttca gtaaaggttg   5100
gagtcaatat gctctggttg gcaggcaacc ctgtagtcat ggagaaaggt atttcaagat   5160
ctagtccaat cttttttctag agaaaaagat aatctgaagc tcacaaagat gaagtgactt   5220
cctcaaaatc acatggttca ggacagaaac aagattaaaa cctggatcca cagactgtgc   5280
gcctcagaag gaataatcgg taaattaaga attgctactc gaaggtgcca gaatgacaca   5340
aaggacagaa ttcctttccc agttgttacc ctagcaaggc tagggagggc atgaacacaa   5400
acataagaac tggtcttcta cactttctct gaatcattta ggtttaagat gtaagtgaac   5460
aattctttct ttctgccaag aaacaaagtt ttggatgagc ttttatatat ggaacttact   5520
ccaacaggac tgagggacca aggaaacatg atggggagg cagagagggc aagagtaaaa   5580
ctgtagcata gcttttgtca cggtcactag ctgatccctc aggtctgctg caaacacagc   5640
atggaggaca cagatgactc tttggtgttg gtcttttttgt ctgcagtgaa tgttcaacag   5700
tttgcccagg aactggggga tcatatatgt cttagtggac agggtctga agtacactgg   5760
```

```
aatttactga gaaacttgtt tgtaaaaact atagttaata attattgcat tttcttacaa    5820
aaatatattt tggaaaattg tatactgtca attaaagtgt ttttgtgtaa actggttcaa    5880
```

<210> SEQ ID NO 69
<211> LENGTH: 5880
<212> TYPE: DNA
<213> ORGANISM: Homo sapiens

<400> SEQUENCE: 69

```
agacgccgcc caggacgcag ccgccgccgc cgccgctcct ctgccactgg ctctgcgccc      60
cagcccggct ctgctgcagc ggcagggagg aagagccgcc gcagcgcgac tcgggagccc     120
cgggccacag cctggcctcc ggagccaccc acaggcctcc ccgggcggcg cccacgctcc     180
taccgcccgg acgcgcggat cctccgccgg caccgcagcc acctgctccc ggcccagagg     240
cgacgacacg atgcgctgcg cgctggcgct ctcggcgctg ctgctactgt tgtcaacgcc     300
gccgctgctg ccgtcgtcgc cgtcgccgtc gccgtcgccc tcccagaatg caacccagac     360
tactacggac tcatctaaca aaacagcacc gactccagca tccagtgtca ccatcatggc     420
tacagataca gcccagcaga gcacagtccc cacttccaag gccaacgaaa tcttggcctc     480
ggtcaaggcg accaccccttg tgtatccag tgactcaccg ggactacaa ccctggctca     540 gcaagtctca ggcccagtca acactaccgt ggctagagga ggcggctcag gcaaccctac     600
taccaccatc gagagcccca agagcacaaa aagtgcagac accactacag ttgcaacctc     660
cacagccaca gctaaaccta acaccacaag cagccagaat ggagcagaag atacaacaaa     720
ctctgggggg aaaagcagcc acagtgtgac cacagacctc acatccacta aggcagaaca     780
tctgacgacc cctcacccta caagtccact tagcccccga caacccactt cgacgcatcc     840
tgtggccacc ccaacaagct cgggacatga ccatcttatg aaaatttcaa gcagttcaag     900
cactgtggct atccctggct acaccttcac aagcccgggg atgaccacca ccctaccgtc     960
atcggttatc tcgcaaagaa ctcaacagac ctccagtcag atgccagcca gctctacggc    1020
cccttcctcc caggagacag tgcagcccac gagcccggca acggcattga aacacctac    1080 cctgccagag accatgagct ccagccccac agcagcatca actacccacc gataccccaa    1140
aacaccttct cccactgtgg ctcatgagag taactgggca aagtgtgagg atcttgagac    1200
acagacacag agtgagaagc agctcgtcct gaacctcaca ggaaacaccc tctgtgcagg    1260
gggcgcttcg gatgagaaat tgatctcact gatatgccga gcagtcaaag ccaccttcaa    1320
cccggcccaa gataagtgcg gcatacggct ggcatctgtt ccaggaagtc agaccgtggt    1380
cgtcaaagaa atcactattc acactaagct ccctgccaag gatgtgtacg agcggctgaa    1440
ggacaaatgg gatgaactaa aggaggcagg ggtcagtgac atgaagctag ggaccaggg    1500 gccaccggag gaggccgagg accgcttcag catgccctc atcatcacca tcgtctgcat    1560
ggcatcattc ctgctcctcg tggcggccct ctatggctgc tgccaccagc gcctctccca    1620
gaggaaggac cagcagcggc taacagagga gctgcagaca gtggagaatg gttaccatga    1680
caacccaaca ctggaagtga tggagacctc ttctgagatg caggagaaga ggtggtcag    1740 cctcaacggg gagctggggg acagctggat cgtccctctg gacaacctga ccaaggacga    1800
cctggatgag gaggaagaca cacacctcta gtccggtctg ccggtggcct ccagcagcac    1860
cacagagctc cagaccaacc accccaagtc ccgtttggat ggggaaggga aagactgggg    1920
agggagagtg aactccgagg ggtgtcccct cccaatcccc ccagggcctt aattttcc    1980
```

```
ttttcaacct gaacaaatca cattctgtcc agattcctct tgtaaaataa cccactagtg    2040
cctgagctca gtgctgctgg atgatgaggg agatcaagaa aaagccacgt aagggacttt    2100
atagatgaac tagtggaatc ccttcattct gcagtgagat tgccgagacc tgaagagggt    2160
aagtgacttg cccaaggtca gagccacttg gtgacagagc caggatgaga acaaagattc    2220
catttgcacc atgccacact gctgtgttca catgtgcctt ccgtccagag cagtcccggg    2280
caggggtgaa actccagcag gtggctgggc tggaaaggag ggcagggcta catcctggct    2340
cggtgggatc tgacgacctg aaagtccagc tcccaagttt tccttctcct acccagcct    2400 cgtgtaccca tcttcccacc ctctatgttc ttacccctcc ctacactcag tgtttgttcc    2460
cacttactct gtcctggggc ctctgggatt agcacaggtt attcataacc ttgaacccct    2520
tgttctggat tcggattttc tcacatttgc ttcgtgagat gggggcttaa cccacacagg    2580
tctccgtgcg tgaaccaggt ctgcttaggg acctgcgtg caggtgagga gagaagggga    2640
cactcgagtc caggctggta tctcagggca gctgatgagg ggtcagcagg aacactggcc    2700
cattgcccct ggcactcctt gcagaggcca cccacgatct tctttgggct tccatttcca    2760
ccagggacta aaatcgctg tagctagtga gagcagcgtg ttccttttgt tgttcactgc    2820
tcagctgatg ggagtgattc cctgagaccc agtatgaaag agcagtggct gcaggagagg    2880
ccttcccggg gcccccatc agcgatgtgt cttcagagac aatccattaa agcagccagg    2940
aaggacaggc tttcccctgt atatcatagg aaactcaggg acatttcaag ttgctgagag    3000
ttttgttata gttgttttct aacccagccc tccactgcca aaggccaaaa gctcagacag    3060
ttggcagacg tccagttagc tcatctcact cactctgatt ctcctgtgcc acaggaaaag    3120
agggcctgga aagcgcagtg catgctgggt gcatgaaggg cagcctgggg gacagactgt    3180
tgtgggaacg tcccactgtc ctggcctgga gctaggcctt gctgttcctc ttctctgtga    3240
gcctagtggg gctgctgcgg ttctcttgca gtttctggtg gcatctcagg gaacacaaa    3300 gctatgtcta ttccccaata taggactttt atgggctcgg cagttagctg ccatgtagaa    3360
ggctcctaag cagtgggcat ggtgaggttt catctgattg agaaggggga atcctgtgtg    3420
gaatgttgaa cttttcgccat ggtctccatc gttctgggcg taaattccct gggatcaagt    3480
aggaaaatgg gcagaactgc ttaggggaat gaaattgcca tttttcgggt gaaacgccac    3540
acctccaggg tcttaagagt caggctccgg ctgtagtagc tctgatgaaa taggctatcc    3600 actcggatg gcttactttt taaaagggta gggggagggg ctgggaaaga tctgtcctgc    3660
accatctgcc taattccttc ctcacagtct gtagccatct gatatcctag gggaaaagga    3720
aggccagggg ttcacatagg gccccagcga gtttcccagg agttagaggg atgcgaggct    3780
aacaagttcc aaaaacatct gccccgatgc tctagtgttt ggaggtgggc aggatggaga    3840
acagtgcctg tttgggggaa aacaggaaat cttgttaggc ttgagtgagg tgtttgcttc    3900
cttcttgccc agcgctgggt tctctccacc cagtaggttt tctgttgtgg tcccgtggga    3960
gaggccagac tggattattc ctcctttgct gatcctgggt cacacttcac cagccagggc    4020
ttttgacgga gacagcaaat aggcctctgc aaatcaatca aaggctgcaa ccctatggcc    4080
tcttggagac agatgatgac tggcaaggac tagagagcag gagtgcctgg ccaggtcggt    4140
cctgactctc ctgactctcc atcgctctgt ccaaggagaa cccggagagg ctctgggctg    4200
attcagaggt tactgcttta tattcgtcca aactgtgtta gtctaggctt aggacagctt    4260
cagaatctga caccttgcct tgctcttgcc accaggacac ctatgtcaac aggccaaaca    4320
gccatgcatc tataaaggtc atcatcttct gccaccttta ctgggttcta aatgctctct    4380
```

```
gataattcag agagcattgg gtctgggaag aggtaagagg aacactagaa gctcagcatg    4440
acttaaacag gttgtagcaa agacagttta tcatcagctc tttcagtggt aaactgtggt    4500
ttccccaagc tgcacaggag gccagaaacc acaagtatga tgactaggaa gcctactgtc    4560
atgagagtgg ggagacaggc agcaaagctt atgaaggagg tacagaatat tctttgcgtt    4620
gtaagacaga atacgggttt aatctagtct aggcaccaga tttttttccc gcttgataag    4680
gaaagctagc agaaagttta tttaaaccac ttcttgagct ttatctttt tgacaatata    4740 ctggagaaac tttgaagaac aagttcaaac tgatacatat acacatattt ttttgataat    4800
gtaaatacag tgaccatgtt aacctaccct gcactgcttt aagtgaacat actttgaaaa    4860
agcattatgt tagctgagtg atggccaagt tttttctctg acagtaatg taaatgtctt    4920 actggaaatg acaagttttt gcttgatttt tttttttaaa caaaaatga aatataacaa    4980 gacaaactta tgataaagta tttgtcttgt agatcaggtg ttttgtttg ttttttaat    5040 tttaaaatgc aaccctgccc cctccccagc aaagtcacag ctccatttca gtaaaggttg    5100
gagtcaatat gctctggttg gcaggcaacc ctgtagtcat ggagaaaggt atttcaagat    5160
ctagtccaat cttttttctag agaaaaagat aatctgaagc tcacaaagat gaagtgactt    5220
cctcaaaatc acatggttca ggacagaaac aagattaaaa cctggatcca cagactgtgc    5280
gcctcagaag gaataatcgg taaattaaga attgctactc gaaggtgcca gaatgacaca    5340
aaggacagaa ttcctttccc agttgttacc ctagcaaggc tagggagggc atgaacacaa    5400
acataagaac tggtcttcta cactttctct gaatcattta ggtttaagat gtaagtgaac    5460 aattcttttct ttctgccaag aaacaaagtt ttggatgagc ttttatatat ggaacttact    5520
ccaacaggac tgagggacca aggaaacatg atgggggagg cagagagggc aagagtaaaa    5580
ctgtagcata gcttttgtca cggtcactag ctgatccctc aggtctgctg caaacacagc    5640
atggaggaca cagatgactc tttggtgttg gtcttttgt ctgcagtgaa tgttcaacag    5700
tttgcccagg aactggggga tcatatatgt cttagtggac aggggtctga agtacactgg    5760
aatttactga gaaacttgtt tgtaaaaact atagttaata attattgcat tttcttacaa    5820
aaatatattt tggaaaattg tatactgtca attaaagtgt ttttgtgtaa actggttcaa    5880
```

<210> SEQ ID NO 70
<211> LENGTH: 4734
<212> TYPE: DNA
<213> ORGANISM: Homo sapiens

<400> SEQUENCE: 70

```
cctggcctcg cgggccgtgt ctccggcatc atgtgtggta tatttgctta cttaaactac     60
catgttcctc gaacgagacg agaaattcct ggagaccta atcaaaggcc tcagagactg    120
gagtacagag ctcatgatgg tttaggtgtg ggatttgatg gaggcaatga taaagattgg    180
gaagccaatg cctgcaaaat ccagcttatt aagaagaaag gaaaagttaa ggcactggat    240
gaagaagttc acaagcaaca agatatggat ttggatatag aatttgatgt acaccttgga    300
atagctcata cccgttgggc aacacatgga gaacccagtc ctgtcaatag ccaccccag    360 cgctctgata aaataatga atttatcgtt attcacaatg gaatcatcac caactacaaa    420
gacttgaaaa agtttttgga agcaaaggc tatgacttcg aatctgaaac agacacagag    480
acaattgcca agctcgttaa gtatatgtat gacaatcggg aaagtcaaga taccagcttt    540
actaccttgg tggagagagt tatccaacaa ttggaaggtg cttttgcact tgtgtttaaa    600
```

```
agtgttcatt ttcccgggca agcagttggc acaaggcgag gtagccctct gttgattggt      660
gtacggagtg aacataaact ttctactgat cacattccta tactctacag aacaggcaaa      720
gacaagaaag gaagctgcaa tctctctcgt gtggacagca caacctgcct tttcccggtg      780
gaagaaaaag cagtggagta ttactttgct tctgatgcaa gtgctgtcat agaacacacc      840
aatcgcgtca tctttctgga agatgatgat gttgcagcag tagtggatgg acgtcttttct     900 atccatcgaa ttaaacgaac tgcaggagat caccccggac gagctgtgca aacactccag      960
atggaactcc agcagatcat gaagggcaac ttcagttcat ttatgcagaa ggaaatattt     1020
gagcagccag agtctgtcgt gaacacaatg agaggaagag tcaactttga tgactatact     1080
gtgaatttgg gtggtttgaa ggatcacata aaggagatcc agagatgccg gcgtttgatt     1140
cttattgctt gtggaacaag ttaccatgct ggtgtagcaa cacgtcaagt tcttgaggag     1200
ctgactgagt tgcctgtgat ggtggaacta gcaagtgact tcctggacag aaacacacca     1260
gtctttcgag atgatgtttg cttttttcctt agtcaatcag gtgagacagc agatactttg     1320
atgggtcttc gttactgtaa ggagagagga gctttaactg tggggatcac aaacacagtt     1380
ggcagttcca tatcacggga gacagattgt ggagttcata ttaatgctgg tcctgagatt     1440
ggtgtggcca gtacaaaggc ttataccagc cagtttgtat cccttgtgat gtttgcccttt     1500 atgatgtgtg atgatcggat ctccatgcaa gaaagacgca aagagatcat gcttggattg     1560
aaacggctgc ctgatttgat taaggaagta ctgagcatgg atgacgaaat tcagaaacta     1620
gcaacagaac tttatcatca gaagtcagtt ctgataatgg gacgaggcta tcattatgct     1680
acttgtcttg aaggggcact gaaaatcaaa gaaattactt atatgcactc tgaaggcatc     1740
cttctgtgct gagaggctat gatgttgatt tcccacggaa tcttgccaaa tctgtgactg     1800
tagagtgagg aatatctata caaaatgtac gaaactgtat gattaagcaa cacaagacac     1860
cttttgtatt taaaaccttg atttaaaata tcaccccttg aagcctttttt ttagtaaatc     1920 cttatttata tatcagttat aattattcca ctcaatatgt gattttttgtg aagttacctc     1980 ttacattttc ccagtaattt gtggaggact ttgaataatg gaatctatat tggaatctgt     2040
atcagaaaga ttctagctat tattttctttt aaagaatgct gggtgttgca tttctggacc     2100
ctccacttca atctgagaag acaatatgtt tctaaaaatt ggtacttgtt tcaccatact     2160
tcattcagac cagtgaaaga gtagtgcatt taattggagt atctaaagcc agtggcagtg     2220
tatgctcata cttggacagt tagggaaggg tttgccaagt tttaagagaa gatgtgattt     2280
attttgaaat ttgtttctgt tttgttttta aatcaaactg taaaacttaa aactgaaaaa     2340
ttttattggt aggatttata tctaagtttg gttagcctta gtttctcaga cttgttgtct     2400
attatctgta ggtggaagaa atttaggaag cgaaatatta cagtagtgca ttggtgggtc     2460
tcaatcctta acatatttgc acaatttttat agcacaaact ttaaattcaa gctgctttgg     2520
acaactgaca atatgatttt aaatttgaag atgggatgtg tacatgttgg gtatcctact     2580
actttgtgtt ttcatctcct aaaagtggtt tttatttcct tgtatctgta gtcttttatt     2640
ttttaaatga ctgctgaatg acatattttta tcttgttctt taaaatcaca acacagagct     2700
gctattaaat taatattgat atattcagta ttctcttcaa ctttgtcacg aggaagaatt     2760
tcctgtagtt aattttaact ttccttcatt acattgttgc ataaaactag tcccttagtg     2820
ccagtttgga agttacttgc aattgtttgg aagatttgca ggtcgctgac ctcatcattt     2880
cactctaagt atatgtggta ggctaagctc agaaaaaggt atgtatgctt tacactgata     2940
ggcaccaaat ttagtattgt atcctaagta tttttcctct tctgtatttt ctgtgctcta     3000
```

```
cccctgaaat atatttagga ataaagaaga tataaataaa gtgatattgg ggtatgttca  3060
gcttgtaagt gtcagaaatg gaagttgaca atttggatta aaatatttaa agtagaatgt  3120
tattatttga tacccccaaa attgtgagta ataatttctt aatggagctt ttctggccag  3180
atcttcaggg ctataggaga gtgtgtttgt ttttggtgaa gtccttcttt ttcaaaggtt  3240
tttactttta aattgtgaag ataagctatt tagcacaatt atttaagtaa gctgttttt   3300 cctttctttt ctttctttc ttgttttaac ttctgggtga ggttaagatt ttctaatagt   3360
tattgttgtt gccagagaag catagaattc tgcttgtgtc ttagggttag agaaagattt  3420
gttatatttt gaggtaattt ggaaggactt tcatacatgg tgactagaaa cctgatcttt  3480
ttaagaataa aatagggtca ctatttacat tatatataat atatggctat tatagctata  3540
ttaatctact ttaattgttt ctaagattat tttgtgtaag tcagctagcg tgtgtatagt  3600
gtcatttctt atgttttgta tattaacgtt ttacaaacac aatttgtgtg ggtttgtagc  3660
atttcttata gtttaaagta tgattcagca ttctaagtta aaactaatat gtgaagtcag  3720
tcattagtct gcataatctc tgtctccctc tgtgtgtgtc tttctataaa gcacatgtgt  3780
acacacacac acacaaatat actgaaagct agggtaagtt ctaaactgaa tatcaaaaac  3840
caaaatcaag aacaaagaag tgatattttc caaacaaaca tggattctct gccgggtgca  3900
gtggctcagc ctgtaatacc agcctccact ttgggagtct gaggtgggag tattgcttga  3960
gctcaagagt tggagaacat gctgggatta caggcatgag tcaccgtgtc ctgcccagac  4020
atatcaaatt tgacaggtat tgtatacct ttggatcttt aggaattaat ttttgcctct   4080
gtcactcagc tttgtatatt ttgaaatgga gataagtata gggaggtctt ggaaggaaaa  4140
ttgccagaat tcccaaacca tgtaacactc attgagaatt ccagatccat tatatctaaa  4200
gggcaagtga aggaaacagt attgtgaact gggtataact ccttggttct taactagtac   4260
attcttaatc tgtgagaccc aaaggttgat aaacaataat ttaagattgt acagtactct  4320
aaacgtctgc aaaggtctag atgttatcag tatcactagt ttttatttct gccagtagct  4380 ccctttagg ttacattgtt gtcctctttc cagtgtcgca tctgtcattg gttttttcact 4440 atggcaagtt cattaaaaag cttgctccat tgttatcttc aagtaatgcc cataaggaga  4500
tggaagatat ctgagacaat taaggcttta gcttctaggc aagagaaata acgttgcatt  4560
aaatttcaag tttctttctg ctagacttga atgtgtctag ccactctaat ttatgggggc  4620
ttttggtttt ttcctattgt actttgtatg tagaattgtt ttgaaatatc aagcatattt  4680
actttgaatt tgaactcttt cttaattttg tatttatcct ttgaataaaa tgta        4734
```

<210> SEQ ID NO 71
<211> LENGTH: 5880
<212> TYPE: DNA
<213> ORGANISM: Homo sapiens

<400> SEQUENCE: 71

```
agacgccgcc caggacgcag ccgccgccgc cgccgctcct ctgccactgg ctctgcgccc    60
cagcccggct ctgctgcagc ggcagggagg aagagccgcc gcagcgcgac tcgggagccc   120
cgggccacag cctggcctcc ggagccaccc acaggcctcc ccgggcggcg cccacgctcc   180
taccgcccgg acgcgcggat cctccgccgg caccgcagcc acctgctccc ggcccagagg   240
cgacgacacg atgcgctgcg cgctggcgct ctcgggcctg ctgctactgt tgtcaacgcc   300
gccgctgctg ccgtcgtcgc cgtcgccgtc gccgtcgccc tcccagaatg caacccagac   360
```

```
tactacggac tcatctaaca aaacagcacc gactccagca tccagtgtca ccatcatggc   420
tacagataca gcccagcaga gcacagtccc cacttccaag gccaacgaaa tcttggcctc   480
ggtcaaggcg accacccttg gtgtatccag tgactcaccg gggactacaa ccctggctca   540
gcaagtctca ggcccagtca acactaccgt ggctagagga ggcggctcag gcaaccctac   600
taccaccatc gagagcccca agagcacaaa aagtgcagac accactacag ttgcaacctc   660
cacagccaca gctaaaccta acaccacaag cagccagaat ggagcagaag atacaacaaa   720
ctctgggggg aaaagcagcc acagtgtgac cacagacctc acatccacta aggcagaaca   780
tctgacgacc cctcacccta caagtccact tagcccccga caacccactt cgacgcatcc   840
tgtggccacc ccaacaagct cgggacatga ccatcttatg aaaatttcaa gcagttcaag   900
cactgtggct atccctggct acaccttcac aagcccgggg atgaccacca ccctaccgtc   960
atcggttatc tcgcaaagaa ctcaacagac ctccagtcag atgccagcca gctctacggc  1020
cccttcctcc caggagacag tgcagcccac gagcccggca acggcattga gaacacctac  1080
cctgccagag accatgagct ccagccccac agcagcatca actacccacc gatacccaa   1140
aacaccttct cccactgtgg ctcatgagag taactgggca aagtgtgagg atcttgagac  1200
acagacacag agtgagaagc agctcgtcct gaacctcaca ggaaacaccc tctgtgcagg  1260
gggcgcttcg gatgagaaat tgatctcact gatatgccga gcagtcaaag ccaccttcaa  1320
cccggcccaa gataagtgcg gcatacggct ggcatctgtt ccaggaagtc agaccgtggt  1380
cgtcaaagaa atcactattc acactaagct ccctgccaag gatgtgtacg agcggctgaa  1440
ggacaaatgg gatgaactaa aggaggcagg ggtcagtgac atgaagctag ggaccaggg   1500
gccaccggag gaggccgagg accgcttcag catgcccctc atcatcacca tcgtctgcat  1560
ggcatcattc ctgctcctcg tggcggccct ctatggctgc tgccaccagc gcctctccca  1620
gaggaaggac cagcagcggc taacagagga gctgcagaca gtggagaatg gttaccatga  1680
caacccaaca ctggaagtga tggagacctc ttctgagatg caggagaaga ggtggtcag   1740
cctcaacggg gagctggggg acagctggat cgtccctctg gacaacctga ccaaggacga  1800
cctggatgag gaggaagaca cacacctcta gtccggtctg ccggtggcct ccagcagcac  1860
cacagagctc cagaccaacc accccaagtg ccgtttggat ggggaaggga aagactgggg  1920
agggagagtg aactccgagg ggtgtcccct cccaatcccc ccagggcctt aatttttccc  1980
ttttcaacct gaacaaatca cattctgtcc agattcctct tgtaaaataa cccactagtg  2040
cctgagctca gtgctgctgg atgatgaggg agatcaagaa aaagccacgt aagggacttt  2100
atagatgaac tagtggaatc ccttcattct gcagtgagat tgccgagacc tgaagagggt  2160
aagtgacttg cccaaggtca gagccacttg gtgacagagc caggatgaga acaaagattc  2220
catttgcacc atgccacact gctgtgttca catgtgcctt ccgtccagag cagtcccggg  2280
caggggtgaa actccagcag gtggctgggc tggaaaggag ggcagggcta catcctggct  2340
cggtgggatc tgacgacctg aaagtccagc tcccaagttt tccttctcct accccagcct  2400
cgtgtaccca tcttcccacc ctctatgttc ttacccctcc ctacactcag tgtttgttcc  2460
cacttactct gtcctggggc ctctgggatt agcacaggtt attcataacc ttgaacccct  2520
tgttctggat tcggattttc tcacatttgc ttcgtgagat gggggcttaa cccacacagg  2580
tctccgtgcg tgaaccaggt ctgcttaggg gacctgcgtg caggtgagga gagaagggga  2640
cactcgagtc caggctggta tctcaggca gctgatgagg ggtcagcagg aacactggcc   2700
cattgcccct ggcactcctt gcagaggcca cccacgatct tctttgggct tccatttcca  2760
```

```
ccagggacta aaatctgctg tagctagtga gagcagcgtg ttccttttgt tgttcactgc    2820
tcagctgatg ggagtgattc cctgagaccc agtatgaaag agcagtggct gcaggagagg    2880
ccttcccggg gcccccatc agcgatgtgt cttcagagac aatccattaa agcagccagg     2940
aaggacaggc tttcccctgt atatcatagg aaactcaggg acatttcaag ttgctgagag    3000
ttttgttata gttgttttct aacccagccc tccactgcca aaggccaaaa gctcagacag    3060
ttggcagacg tccagttagc tcatctcact cactctgatt ctcctgtgcc acaggaaaag    3120
agggcctgga aagcgcagtg catgctgggt gcatgaaggg cagcctgggg gacagactgt    3180
tgtgggaacg tcccactgtc ctggcctgga gctaggcctt gctgttcctc ttctctgtga    3240
gcctagtggg gctgctgcgg ttctcttgca gtttctggtg gcatctcagg gaacacaaa     3300 gctatgtcta ttccccaata taggactttt atgggctcgg cagttagctg ccatgtagaa    3360
ggctcctaag cagtgggcat ggtgaggttt catctgattg agaaggggga atcctgtgtg    3420
gaatgttgaa ctttcgccat ggtctccatc gttctgggcg taaattccct gggatcaagt    3480
aggaaaatgg gcagaactgc ttaggggaat gaaattgcca tttttcgggt gaaacgccac    3540
acctccaggg tcttaagagt caggctccgg ctgtagtagc tctgatgaaa taggctatcc    3600
actcgggatg gcttactttt taaaagggta gggggagggg ctggggaaga tctgtcctgc    3660
accatctgcc taattccttc ctcacagtct gtagccatct gatatcctag gggaaaagga    3720
aggccagggg ttcacatagg gccccagcga gtttcccagg agttagaggg atgcgaggct    3780
aacaagttcc aaaaacatct gccccgatgc tctagtgttt ggaggtgggc aggatggaga    3840
acagtgcctg tttgggggaa aacaggaaat cttgttaggc ttgagtgagg tgtttgcttc    3900
cttcttgccc agcgctgggt tctctccacc cagtaggttt tctgttgtgg tcccgtggga    3960
gaggccagac tggattattc ctcctttgct gatcctgggt cacacttcac cagccagggc    4020
ttttgacgga gacagcaaat aggcctctgc aaatcaatca aaggctgcaa ccctatggcc    4080
tcttggagac agatgatgac tggcaaggac tagagagcag gagtgcctgg ccaggtcggt    4140
cctgactctc ctgactctcc atcgctctgt ccaaggagaa cccggagagg ctctgggctg    4200
attcagaggt tactgcttta tattcgtcca aactgtgtta gtctaggctt aggacagctt    4260
cagaatctga caccttgcct tgctcttgcc accaggacac ctatgtcaac aggccaaaca    4320
gccatgcatc tataaaggtc atcatcttct gccacccttta ctgggttcta aatgctctct   4380
gataattcag agagcattgg gtctgggaag aggtaagagg aacactagaa gctcagcatg    4440
acttaaacag gttgtagcaa agacagttta tcatcagctc tttcagtggt aaactgtggt    4500
ttccccaagc tgcacaggag gccagaaacc acaagtatga tgactaggaa gcctactgtc    4560
atgagagtgg ggagacaggc agcaaagctt atgaaggagg tacagaatat tctttgcgtt    4620
gtaagacaga atacgggttt aatctagtct aggcaccaga ttttttttccc gcttgataag    4680 gaaagctagc agaaagttta tttaaaccac ttcttgagct ttatcttttt tgacaatata    4740
ctggagaaac tttgaagaac aagttcaaac tgatacatat acacatattt ttttgataat    4800
gtaaatacag tgaccatgtt aacctaccct gcactgcttt aagtgaacat actttgaaaa    4860
agcattatgt tagctgagtg atggccaagt ttttctctg dacagtaatg taaatgtctt     4920
actggaaatg acaagttttt gcttgatttt tttttttaaa caaaaaatga aatataacaa    4980
gacaaactta tgataaagta tttgtcttgt agatcaggtg ttttgttttg ttttttttaat   5040 tttaaaatgc aaccctgccc cctccccagc aaagtcacag ctccatttca gtaaaggttg    5100
```

-continued

```
gagtcaatat gctctggttg gcaggcaacc ctgtagtcat ggagaaaggt atttcaagat    5160
ctagtccaat cttttcttag agaaaaagat aatctgaagc tcacaaagat gaagtgactt    5220
cctcaaaatc acatggttca ggacagaaac aagattaaaa cctggatcca cagactgtgc    5280
gcctcagaag gaataatcgg taaattaaga attgctactc gaaggtgcca gaatgacaca    5340
aaggacagaa ttcctttccc agttgttacc ctagcaaggc tagggagggc atgaacacaa    5400
acataagaac tggtcttcta cactttctct gaatcattta ggtttaagat gtaagtgaac    5460
aattctttct ttctgccaag aaacaaagtt ttggatgagc ttttatatat ggaacttact    5520
ccaacaggac tgagggacca aggaaacatg atggggagg cagagagggc aagagtaaaa    5580
ctgtagcata gcttttgtca cggtcactag ctgatccctc aggtctgctg caaacacagc    5640
atggaggaca cagatgactc tttggtgttg gtcttttgt ctgcagtgaa tgttcaacag    5700
tttgcccagg aactggggga tcatatatgt cttagtggac aggggtctga agtacactgg    5760
aatttactga gaacttgtt tgtaaaaact atagttaata attattgcat tttcttacaa    5820
aaatatattt tggaaaattg tatactgtca attaaagtgt ttttgtgtaa actggttcaa    5880
```

<210> SEQ ID NO 72
<211> LENGTH: 160
<212> TYPE: PRT
<213> ORGANISM: Homo sapiens

<400> SEQUENCE: 72

```
Met Tyr Pro Ala Leu Leu Asn Ile Leu Asn Leu Ile Leu Gln Val Ser
  1               5                  10                  15

Arg Gly Gln Lys Val Thr Ser Leu Thr Ala Cys Leu Val Asp Gln Ser
             20                  25                  30

Leu Arg Leu Asp Cys Arg His Glu Asn Thr Ser Ser Ser Pro Ile Gln
         35                  40                  45

Tyr Glu Phe Ser Leu Thr Arg Glu Thr Lys Lys His Val Leu Phe Gly
     50                  55                  60

Thr Val Gly Val Pro Glu His Thr Tyr Arg Ser Arg Thr Asn Phe Thr
 65                  70                  75                  80

Ser Lys Tyr Asn Met Lys Val Leu Tyr Leu Ser Ala Phe Thr Ser Lys
                 85                  90                  95

Asp Glu Gly Thr Tyr Thr Cys Ala Leu His His Ser Gly His Ser Pro
            100                 105                 110

Pro Ile Ser Ser Gln Asn Val Thr Val Leu Arg Asp Lys Leu Val Lys
        115                 120                 125

Cys Glu Gly Ile Ser Leu Leu Ala Gln Asn Thr Ser Trp Leu Leu Leu
    130                 135                 140

Leu Leu Leu Ser Leu Ser Leu Leu Gln Ala Thr Asp Phe Met Ser Leu
145                 150                 155                 160
```

<210> SEQ ID NO 73
<211> LENGTH: 161
<212> TYPE: PRT
<213> ORGANISM: Homo sapiens

<400> SEQUENCE: 73

```
Met Asn Leu Ala Ile Ser Ile Ala Leu Leu Leu Thr Val Leu Gln Val
  1               5                  10                  15

Ser Arg Gly Gln Lys Val Thr Ser Leu Thr Ala Cys Leu Val Asp Gln
             20                  25                  30

Ser Leu Arg Leu Asp Cys Arg His Glu Asn Thr Ser Ser Ser Pro Ile
```

```
              35                  40                  45
Gln Tyr Glu Phe Ser Leu Thr Arg Glu Thr Lys Lys His Val Leu Phe
         50                  55                  60
Gly Thr Val Gly Val Pro Glu His Thr Tyr Arg Ser Arg Thr Asn Phe
 65                  70                  75                  80
Thr Ser Lys Tyr Asn Met Lys Val Leu Tyr Leu Ser Ala Phe Thr Ser
                 85                  90                  95
Lys Asp Glu Gly Thr Tyr Thr Cys Ala Leu His His Ser Gly His Ser
                100                 105                 110
Pro Pro Ile Ser Ser Gln Asn Val Thr Val Leu Arg Asp Lys Leu Val
            115                 120                 125
Lys Cys Glu Gly Ile Ser Leu Leu Ala Gln Asn Thr Ser Trp Leu Leu
        130                 135                 140
Leu Leu Leu Leu Ser Leu Ser Leu Leu Gln Ala Thr Asp Phe Met Ser
145                 150                 155                 160

Leu
```

<210> SEQ ID NO 74
<211> LENGTH: 1527
<212> TYPE: DNA
<213> ORGANISM: Homo sapiens

<400> SEQUENCE: 74

| | | | | | |
|---|---|---|---|---|---|
| ccggtgaaaa | ctgcgggctc | cgagctgggt | gcagcaaccg | gaggcggcgg | cgcgtctgga | 60 |
| ggaggctgca | gcagcggaag | accccagtcc | agatccagga | ctgagatccc | agaaccatga | 120 |
| acctggccat | cagcatcgct | ctcctgctaa | cagtcttgca | ggtctcccga | gggcagaagg | 180 |
| tgaccagcct | aacggcctgc | ctagtggacc | agagccttcg | tctggactgc | cgccatgaga | 240 |
| ataccagcag | ttcacccatc | cagtacgagt | tcagcctgac | ccgtgagaca | aagaagcacg | 300 |
| tgctctttgg | cactgtgggg | gtgcctgagc | acacataccg | ctcccgaacc | aacttcacca | 360 |
| gcaaatacaa | catgaaggtc | ctctacttat | ccgccttcac | tagcaaggac | gagggcacct | 420 |
| acacgtgtgc | actccaccac | tctggccatt | ccccacccat | ctcctcccag | aacgtcacag | 480 |
| tgctcagaga | caaactggtc | aagtgtgagg | gcatcagcct | gctggctcag | aacacctcgt | 540 |
| ggctgctgct | gctcctgctc | tccctctccc | tcctccaggc | cacggatttc | atgtccctgt | 600 |
| gactggtggg | gcccatggag | gagacaggaa | gcctcaagtt | ccagtgcaga | gatcctactt | 660 |
| ctctgagtca | gctgaccccc | tcccccaat  | ccctcaaacc | ttgaggagaa | gtggggaccc | 720 |
| caccctcat  | caggagttcc | agtgctgcat | gcgattatct | acccacgtcc | acgcggccac | 780 |
| ctcaccctct | ccgcacacct | ctggctgtct | ttttgtactt | tttgttccag | agctgcttct | 840 |
| gtctggttta | tttaggtttt | atccttcctt | ttctttgaga | gttcgtgaag | agggaagcca | 900 |
| ggattgggga | cctgatggag | agtgagagca | tgtgaggggt | agtgggatgg | tgggtaccca | 960 |
| gccactggag | gggtcatcct | tgcccatcgg | gaccagaaac | ctgggagaga | cttggatgag | 1020 |
| gagtggttgg | gctgtgcctg | ggcctagcac | ggacatggtc | tgtcctgaca | gcactcctcg | 1080 |
| gcaggcatgg | ctggtgcctg | aagacccag  | atgtgagggc | accaccaaga | atttgtggcc | 1140 |
| taccttgtga | gggagagaac | tgagcatctc | cagcattctc | agccacaacc | aaaaaaaaat | 1200 |
| aaaagggca  | gccctcctta | ccactgtgga | agtccctcag | aggccttggg | gcatgaccca | 1260 |
| gtgaagatgc | aggtttgacc | aggaaagcag | cgctagtgga | gggttggaga | aggaggtaaa | 1320 |
| ggatgagggt | tcatcatccc | tccctgcccc | cgcttcgctg | ggtctccac  | gggtgaggct | 1380 |

-continued

| | |
|---|---|
| gggaacgcc acctcttcct cttccctgac ttctccccaa ccacttagta gcaacgctac | 1440 |
| cccaggggct aatgactgca cactgggctt cttttcagaa tgaccctaac gagacacatt | 1500 |
| tgcccaaata aacgaacatc ccatgtc | 1527 |

<210> SEQ ID NO 75
<211> LENGTH: 1527
<212> TYPE: DNA
<213> ORGANISM: Homo sapiens

<400> SEQUENCE: 75

| | |
|---|---|
| ccggtgaaaa ctgcgggctc cgagctgggt gcagcaaccg gaggcggcgg cgcgtctgga | 60 |
| ggaggctgca gcagcggaag accccagtcc agatccagga ctgagatccc agaaccatga | 120 |
| acctggccat cagcatcgct ctcctgctaa cagtcttgca ggtctcccga ggcagaagg | 180 |
| tgaccagcct aacggcctgc ctagtggacc agagccttcg tctggactgc cgccatgaga | 240 |
| ataccagcag ttcacccatc cagtacgagt tcagcctgac ccgtgagaca agaagcacg | 300 |
| tgctctttgg cactgtgggg gtgcctgagc acacataccg ctcccgaacc aacttcacca | 360 |
| gcaaatacaa catgaaggtc ctctacttat ccgccttcac tagcaaggac gagggcacct | 420 |
| acacgtgtgc actccaccac tctggccatt ccccacccat ctcctcccag aacgtcacag | 480 |
| tgctcagaga caaactggtc aagtgtgagg catcagcct gctggctcag aacacctcgt | 540 |
| ggctgctgct gctcctgctc tccctctccc tcctccaggc cacggatttc atgtccctgt | 600 |
| gactggtggg gccatggag gagacaggaa gcctcaagtt ccagtgcaga gatcctactt | 660 |
| ctctgagtca gctgaccccc tccccccaat ccctcaaacc ttgaggagaa gtggggaccc | 720 |
| caccccctcat caggagttcc agtgctgcat gcgattatct acccacgtcc acgcggccac | 780 |
| ctcaccctct ccgcacacct ctggctgtct ttttgtactt tttgttccag agctgcttct | 840 |
| gtctggttta tttaggtttt atccttcctt tcctttgaga gttcgtgaag agggaagcca | 900 |
| ggattgggga cctgatggag agtgagagca tgtgagggt agtgggatgg tggggtacca | 960 |
| gccactggag gggtcatcct tgcccatcgg accagaaac ctgggagaga cttggatgag | 1020 |
| gagtggttgg gctgtgcctg gcctagcac ggacatggtc tgtcctgaca gcactcctcg | 1080 |
| gcaggcatgg ctggtgcctg aagaccccag atgtgagggc accaccaaga atttgtggcc | 1140 |
| taccttgtga gggagagaac tgagcatctc cagcattctc agccacaacc aaaaaaaat | 1200 |
| aaaaagggca gccctcctta ccactgtgga agtccctcag aggccttggg gcatgaccca | 1260 |
| gtgaagatgc aggtttgacc aggaaagcag cgctagtgga gggttggaga aggaggtaaa | 1320 |
| ggatgagggt tcatcatccc tccctgcccc cgcttcgctg gggtctccac gggtgaggct | 1380 |
| ggggaacgcc acctcttcct cttccctgac ttctccccaa ccacttagta gcaacgctac | 1440 |
| cccaggggct aatgactgca cactgggctt cttttcagaa tgaccctaac gagacacatt | 1500 |
| tgcccaaata aacgaacatc ccatgtc | 1527 |

<210> SEQ ID NO 76
<211> LENGTH: 2124
<212> TYPE: DNA
<213> ORGANISM: Homo sapiens

<400> SEQUENCE: 76

| | |
|---|---|
| aatcaagctg cccaaagtcc cccaatcact cctggaatac acagagagag gcagcagctt | 60 |
| gctcagcgga caaggatgct gggcgtgagg gaccaaggcc tgccctgcac tcgggcctcc | 120 |
| tccagccagt gctgaccagg gacttctgac ctgctggcca gccaggacct gtgtggggag | 180 |

```
gccctcctgc tgccttgggg tgacaatctc agctccaggc tacagggaga ccgggaggat    240
cacagagcca gcatgttaca ggatcctgac agtgatcaac ctctgaacag cctcgatgtc    300 aaaccctgc gcaaacccg tatccccatg gagaccttca gaaggtggg gatccccatc      360 atcatagcac tactgagcct ggcgagtatc atcattgtgg ttgtcctcat caaggtgatt    420
ctggataaat actacttcct ctgcgggcag cctctccact tcatcccgag gaagcagctg    480
tgtgacggag agctggactg tcccttgggg gaggacgagg agcactgtgt caagagcttc    540
cccgaagggc ctgcagtggc agtccgcctc tccaaggacc gatccacact gcaggtgctg    600
gactcggcca cagggaactg gttctctgcc tgtttcgaca acttcacaga agctctcgct    660
gagacagcct gtaggcagat gggctacagc agcaaaccca ctttcagagc tgtggagatt    720
ggcccagacc aggatctgga tgttgttgaa atcacagaaa acagccagga gcttcgcatg    780
cggaactcaa gtgggccctg tctctcaggc tccctggtct ccctgcactg tcttgcctgt    840
gggaagagcc tgaagacccc ccgtgtggtg ggtggggagg aggcctctgt ggattcttgg    900
ccttggcagg tcagcatcca gtacgacaaa cagcacgtct gtggagggag catcctggac    960
ccccactggg tcctcacggc agcccactgc ttcaggaaac ataccgatgt gttcaactgg    1020
aaggtgcggg caggctcaga caaactgggc agcttcccat ccctggctgt ggccaagatc    1080
atcatcattg aattcaaccc catgtacccc aaagacaatg acatcgccct catgaagctg    1140
cagttcccac tcactttctc aggcacagtc aggcccatct gtctgccctt ctttgatgag    1200
gagctcactc cagccacccc actctggatc attggatggg gctttacgaa gcagaatgga    1260
gggaagatgt ctgacatact gctgcaggcg tcagtccagg tcattgacag cacacggtgc    1320
aatgcagacg atgcgtacca gggggaagtc accgagaaga tgatgtgtgc aggcatcccg    1380 gaaggggtg tggacacctg ccagggtgac agtggtgggc ccctgatgta ccaatctgac    1440
cagtggcatg tggtgggcat cgttagctgg ggctatggct gcggggccc gagcacccca    1500 ggagtataca ccaaggtctc agcctatctc aactggatct acaatgtctg gaaggctgag    1560
ctgtaatgct gctgcccctt tgcagtgctg ggagccgctt ccttcctgcc ctgcccacct    1620
ggggatcccc caaagtcaga cacagagcaa gagtcccctt gggtacaccc ctctgcccac    1680
agcctcagca tttcttggag cagcaaaggg cctcaattcc tgtaagagac cctcgcagcc    1740
cagaggcgcc cagaggaagt cagcagccct agctcggcca cacttggtgc tcccagcatc    1800
ccagggagag acacagccca ctgaacaagg tctcaggggt attgctaagc caagaaggaa    1860
ctttcccaca ctactgaatg gaagcaggct gtcttgtaaa agcccagatc actgtgggct    1920
ggagaggaga aggaaagggt ctgcgccagc cctgtccgtc ttcacccatc ccaagcctat   1980
ctagagcaag aaaccagttg taatataaaa tgcactgccc tactgttggt atgactaccg    2040
ttacctactg ttgtcattgt tattacagct atggccacta ttattaaaga gctgtgtaac    2100
atctctggaa aaaaaaaaaa aaaa                                           2124

<210> SEQ ID NO 77
<211> LENGTH: 3162
<212> TYPE: DNA
<213> ORGANISM: Homo sapiens

<400> SEQUENCE: 77
gcgccctagc cctcttcgg ggatactggc cgaccccctc ttcctttcc cctttagtga     60 aggcctcccc cgtcgccgcg cggcttcccg gagccgactg cagactccct cagcccggtg    120
```

```
ttccccgcgt ccggacgccg aggtcgcggc ttcgcagaaa ctcgggcccc tccatccgcc      180
ctcagaaaag ggagcgatgt tgatctcagg aagcacaaag ggaccttcct agctctgact      240
gaaccacgga gctcaccctg gacagtatca ctccgtggag gaagactgtg agactgtggc      300
tggaagccag attgtagcca cacatccgcc cctgccctac cccagagccc tggagcagca      360
actggctgca gatcacagac acagtgagga tatgagtgta ggggtgagca cctcagcccc      420
tctttcccca acctcgggca caagcgtggg catgtctacc ttctccatca tggactatgt      480
ggtgttcgtc ctgctgctgg ttctctctct tgccattggg ctctaccatg cttgtcgtgg      540
ctggggccgg catactgttg gtgagctgct gatggcggac cgcaaaatgg gctgccttcc      600
ggtggcactg tccctgctgg ccaccttcca gtcagccgtg gccatcctgg gtgtgccgtc      660
agagatctac cgatttggga cccaatattg gttcctgggc tgctgctact ttctggggct      720
gctgatacct gcacacatct tcatccccgt tttctaccgc ctgcatctca ccagtgccta      780
tgagtacctg gagcttcgat tcaataaaac tgtgcgagtg tgtggaactg tgaccttcat      840
ctttcagatg gtgatctaca tgggagttgt gctctatgct ccgtcattgg ctctcaatgc      900
agtgactggc tttgatctgt ggctgtccgt gctggccctg gcattgtcct gtaccgtcta      960
tacagctctg ggtgggctga aggccgtcat ctggacagat gtgttccaga cactggtcat     1020
gttcctcggg cagctggcag ttatcatcgt ggggtcagcc aaggtgggcg gcttggggcg     1080
tgtgtgggcc gtggcttccc agcacggccg catctctggg tttgagctgg atccagaccc     1140
ctttgtgcgg cacaccttct ggaccttggc cttcggggt gtcttcatga tgctctcctt     1200
atacggggtg aaccaggctc aggtgcagcg gtacctcagt tcccgcacgg agaaggctgc     1260
tgtgctctcc tgttatgcag tgttcccctt ccagcaggtg tccctctgcg tgggctgcct     1320
cattggcctg gtcatgttcc gtattaccaa ggagtatccc atgagcattc agcaggctca     1380
ggcagcccca gaccagttcg tcctgtactt tgtgatggat ctcctgaagg gcctgccagg     1440
cctgccaggg ctcttcattg cctgcctctt cagcggctct ctcagcacta tatcctctgc     1500
ttttaattca ttggcaactg ttacgatgga agacctgatt cgaccttggt tccctgagtt     1560
ctctgaagcc cgggccatca tgcttttccag aggccttgcc tttggctatg ggctgctttg     1620
tctaggaatg gcctatattt cctcccagat gggacctgtg ctgcaggcag caatcagcat     1680
ctttggcatg gttggggac cgctgctggg actcttctgc cttggaatgt tctttccatg     1740
tgctaaccct cctggtgctg ttgtgggcct gttggctggg ctcgtcatgg ccttctggat     1800
tggcatcggg agcatcgtga ccagcatggg cttcagcatg ccaccctctc cctctaatgg     1860
gtccagcttc tccctgccca ccaatctaac cgttgccact gtgaccacac tgatgccctt     1920
gactaccttc tccaagccca cagggctgca gcggttctat tccttgtctt acttatggta     1980
cagtgctcac aactccacca cagtgattgt ggtgggcctg attgtcagtc tactcactgg     2040
gagaatgcga ggccggtccc tgaaccctgc aaccatttac ccagtgttgc aaagctcct      2100 gtccctcctt ccgttgtcct gtcagaagcg gctccactgc aggagctacg gccaggacca     2160
cctcgacact ggcctgtttc ctgagaagcc gaggaatggt gtgctggggg acagcagaga     2220
caaggaggcc atggccctgg atggcacagc ctatcagggg agcagctcca cctgcatcct     2280
ccaggagacc tccctgtgat gttgactcag gaccccgcct ctgtcctcac tgtgccaggc     2340
catagccaga ggccaccctg tagtacaggg atgagtcttg gtgtgttctg cagggacagg     2400
cctggatgat ctagctcata ccaaaggacc ttgttctgag aggttcttgc ctgcaggaga     2460
agctgtcaca tctcaagcat gtgaggcacc gttttttctcg tcgcttgcca atctgttttt     2520
```

| | |
|---|---|
| taaaggatca ggctcgtagg gagcaggatc atgccagaaa tagggatgga agtgcatcct | 2580 |
| ctgggaaaaa gataatggct tctgattcaa catagccata gtcctttgaa gtaagtggct | 2640 |
| agaaacagca ctctggttat aattgcccca gggcctgatt caggactgac tctccaccat | 2700 |
| aaaactggaa gctgcttccc ctgtagtccc catttcagta ccagttctgc cagccacagt | 2760 |
| gagcccctat tattactttc agattgtctg tgacactcaa gcccctctca tttttatctg | 2820 |
| tctacctcca ttctgaagag ggaggttttg gtgtccctgg tcctctggga atagaagatc | 2880 |
| catttgtctt tgtgtagagc aagcacgttt tccacctcac tgtctccatc ctccacctct | 2940 |
| gagatggaca cttaagagac ggggcaaatg tggatccaag aaaccagggc catgaccagg | 3000 |
| tccactgtgg agcagccatc tatctacctg actcctgagc caggctgccg tggtgtcatt | 3060 |
| tctgtcatcc gtgctctgtt tccttttgga gtttcttctc acattatct ttgttcctgg | 3120 |
| ggaataaaaa ctaccattgg acctaaaaaa aaaaaaaaaa aa | 3162 |

<210> SEQ ID NO 78
<211> LENGTH: 3779
<212> TYPE: DNA
<213> ORGANISM: Homo sapiens

<400> SEQUENCE: 78

| | |
|---|---|
| gcgtcgagct cgccgcggac tcaagatggc ggcgtgtgga cgtgtacgga ggatgttccg | 60 |
| cttgtcggcg gcgctgcatc tgctgctgct attcgcggcc ggggccgaga aactccccgg | 120 |
| ccagggcgtc cacagccagg gccagggtcc cggggccaac tttgtgtcct tcgtagggca | 180 |
| ggccggaggc ggcggcccgg cgggtcagca gctgccccag ctgcctcagt catcgcagct | 240 |
| tcagcagcaa cagcagcagc agcaacagca acagcagcct cagccgccgc agccgccttt | 300 |
| cccggcgggt gggcctccgg cccggcgggg aggagcgggg gctggtgggg gctggaagct | 360 |
| ggcggaggaa gagtcctgca gggaggacgt gacccgcgtg tgccctaagc acacctggag | 420 |
| caacaacctg gcggtgctcg agtgcctgca ggatgtgagg gagcctgaaa atgaaatttc | 480 |
| ttcagactgc aatcatttgt tgtggaatta taagctgaac ctaactacag atcccaaatt | 540 |
| tgaatctgtg gccagagagg tttgcaaatc tactataaca gagattaaag aatgtgctga | 600 |
| tgaaccggtt ggaaaaggtt acatggtttc ctgcttggtg gatcaccgag caacatcac | 660 |
| tgagtatcag tgtcaccagt acattaccaa gatgacggcc atcatttta gtgattaccg | 720 |
| tttaatctgt ggcttcatgg atgactgcaa aaatgacatc aacattctga aatgtggcag | 780 |
| tattcggctt ggagaaaagg atgcacattc acaaggtgag gtggtatcat gcttggagaa | 840 |
| aggcctggtg aaagaagcag aagaaagaga acccaagatt caagtttctg aactctgcaa | 900 |
| gaaagccatt ctccgggtgg ctgagctgtc atcggatgac tttcacttag accggcattt | 960 |
| atattttgct tgccgagatg atcgggagcg ttttttgtgaa atacacaag ctggtgaggg | 1020 |
| cagagtgtat aagtgcctct ttaaccataa atttgaagaa tccatgagtg aaaagtgtcg | 1080 |
| agaagcactt acaacccgcc aaaagctgat tgcccaggat tataaagtca gttattcatt | 1140 |
| ggccaaatcc tgtaaaagtg acttgaagaa ataccggtgc aatgtggaaa accttccgcg | 1200 |
| atcgcgtgaa gccaggctct cctacttgtt aatgtgcctg gagtcagctg tacacagagg | 1260 |
| gcgacaagtc agcagtgagt gccaggggga gatgctggat taccgacgca tgttgatgga | 1320 |
| agacttttct ctgagccctg agatcatcct aagctgtcgg ggggagattg aacaccattg | 1380 |
| ttccggatta catcgaaaag ggcggaccct acactgtctg atgaaagtag ttcgagggga | 1440 |

-continued

```
gaaggggaac cttggaatga actgccagca ggcgcttcaa acactgattc aggagactga    1500
ccctggtgca gattaccgca ttgatcgagc tttgaatgaa gcttgtgaat ctgtaatcca    1560
dacagcctgc aaacatataa gatctggaga cccaatgatc ttgtcgtgcc tgatggaaca    1620
tttatacaca gagaagatgg tagaagactg tgaacaccgt ctcttagagc tgcagtattt    1680
catctcccgg gattggaagc tggaccctgt cctgtaccgc aagtgccagg gagacgcttc    1740
tcgtctttgc cacacccacg gttggaatga gaccagtgaa tttatgcctc agggagctgt    1800
gttctcttgt ttatacagac acgcctaccg cactgaggaa cagggaagga ggctctcacg    1860
ggagtgccga gctgaagtcc aaaggatcct acaccagcgt gccatggatg tcaagctgga    1920
tcctgccctc caggataagt gcctgattga tctgggaaaa tggtgcagtg agaaaacaga    1980
gactggacag gagctggagt gccttcagga ccatctggat gacttggtgg tggagtgtag    2040
agatatagtt ggcaacctca ctgagttaga atcagaggat attcaaatag aagccttgct    2100
gatgagagcc tgtgagccca taattcagaa cttctgccac gatgtggcag ataaccagat    2160
agactctggg gacctgatgg agtgtctgat acagaacaaa caccagaagg acatgaacga    2220
gaagtgtgcc atcggagtta cccacttcca gctggtgcag atgaaggatt ttcggttttc    2280
ttacaagttt aaaatggcct gcaaggagga cgtgttgaag ctttgcccaa acataaaaaa    2340
gaaggtggac gtggtgatct gcctgagcac gaccgtgcgc aatgcactc tgcaggaagc    2400
caaggagcac agggtgtccc tgaagtgccg caggcagctc cgtgtggagg agctggagat    2460
gacgaggac atccgcttgg agccagatct atacgaagcc tgcaagagtg acatcaaaaa    2520
cttctgttcc gctgtgcaat atggcaacgc tcagattatc gaatgtctga agaaaacaa    2580
gaagcagcta agcacccgct gccaccaaaa agtatttaag ctgcaggaga cagagatgat    2640
ggacccagag ctagactaca ccctcatgag ggtctgcaag cagatgataa agaggttctg    2700
tccggaagca gattctaaaa ccatgttgca gtgcttgaag caaataaaa acagtgaatt    2760
gatggatccc aaatgcaaac agatgataac caagcgccag atcacccaga acacagatta    2820
ccgcttaaac cccatgttaa gaaaagcctg taaagctgac attcctaaat tctgtcacgg    2880
tatcctgact aaggccaagg atgattcaga attagaagga caagtcatct cttgcctgaa    2940
gctgagatat gctgaccagc gcctgtcttc agactgtgaa gaccagatcc gaatcattat    3000
ccaggagtcc gccctggact accgcctgga tcctcagctc cagctgcact gctcagacga    3060
gatctccagt ctatgtgctg aagaagcagc agcccaagag cagacaggtc aggtggagga    3120
gtgcctcaag gtcaacctgc tcaagatcaa aacagaattg tgtaaaaagg aagtgctaaa    3180
catgctgaag gaaagcaaag cagacatctt tgttgacccg gtacttcata ctgcttgtgc    3240
cctggacatt aaacaccact gcgcagccat cacccctggc cgcgggcgtc aaatgtcctg    3300
tctcatggaa gcactggagg ataagcgggt gaggttacag cccgagtgca aaaagcgcct    3360
caatgaccgg attgagatgt ggagttacgc agcaaaggtg gccccagcag atggcttctc    3420
tgatcttgcc atgcaagtaa tgacgtctcc atctaagaac tacattctct ctgtgatcag    3480
tgggagcatc tgtatattgt tcctgattgg cctgatgtgt ggacggatca ccaagcgagt    3540
gacacgagag ctcaaggaca ggctacaata caggtcagag acaatggctt ataaaggttt    3600
agtgtggtct caggatgtga caggcagtcc agcctgacct ttctgcacac tccagacaaa    3660
cttcccagac aagctccttt gtgcctctac gtggagaggg tgtggaaagt tatcacatta    3720
aaagatggag gatttaaaaa aaaaaaaaaa aaaaaaaaaa aaagaaaaaa aaaaaaaaa    3779
```

-continued

<210> SEQ ID NO 79
<211> LENGTH: 6367
<212> TYPE: DNA
<213> ORGANISM: Homo sapiens

<400> SEQUENCE: 79

| | | | | | | |
|---|---|---|---|---|---|---|
| cccgtggctg | agaagaagga | ggcctgagag | cgacatgtcc | ccggcggctc | aggcggagcg | 60 |
| gcccgtggcg | ctgttttttct | gagtccgggg | tggcctggca | gccggccgag | gacgagggtc | 120 |
| ggcgggggct | gccccccgtgg | tggtggccgc | catgctggga | gcctgggcgg | ttgagggaac | 180 |
| cgctgtggcc | ctcctgcgac | tgctgctgct | gctgctgccg | ccggcgatcc | ggggacccgg | 240 |
| gctcggcgtg | gccggcgtgg | ccggcgcggc | ggggccggg | ctgcccgaga | gcgtcatttg | 300 |
| ggcggtcaac | gcgggtggag | aggcgcatgt | ggacgtgcac | gggatccact | tccgcaagga | 360 |
| cccctttggaa | ggccgggtgg | gccgagcctc | agactatggc | atgaaactgc | caatcctgcg | 420 |
| ttccaaccct | gaggaccaga | tcctgtatca | aactgagcgg | tacaatgagg | agaccttttgg | 480 |
| ctacgaagtg | cccatcaaag | aggaggggga | ctacgtgctg | gtcttgaaat | ttgcagaggt | 540 |
| ctactttgca | cagtcccagc | aaaaggtatt | tgatgtacga | ttgaatggcc | acgtcgtggt | 600 |
| gaaggacttg | gatatctttg | atcgtgttgg | gcatagcaca | gctcacgatg | aaattatacc | 660 |
| tatgagcatc | agaaagggga | agctgagtgt | ccaggggag | gtgtccacct | tcacagggaa | 720 |
| actctacatt | gagtttgtca | ggggtacta | tgacaatccc | aaggtctgtg | cactctacat | 780 |
| catggctggg | acagtggatg | atgtaccaaa | gcttcagcct | catccgggat | tggagaagaa | 840 |
| agaagaggaa | gaagaagaag | aagaatatga | tgaagggtct | aatctcaaaa | aacagaccaa | 900 |
| taagaaccgg | gtgcagtcag | gccccccgcac | acccaaccc | tatgcctcgg | acaacagcag | 960 |
| cctcatgttt | cccatcctgg | tggccttcgg | agtcttcatt | ccaaccctct | tctgcctctg | 1020 |
| ccggttgtga | gaacaaatga | ctatcctgaa | cagggtggag | gggtgtggga | agaaaccag | 1080 |
| ccatattggt | tttggtttct | gtatttttca | caatgattaa | tgaacaaaaa | caagagaaa | 1140 |
| aaaacacaca | tcaattaaag | gagacaaaaa | gaggcagagc | gagtagagag | cagccctcat | 1200 |
| tcaccacctg | gtcccagacg | tgcttcagtc | ctcgtcctct | ctttgtggct | ggctcccagc | 1260 |
| cttctctttc | ctcttgagga | tacttagggt | aaactggatc | cttcctgctc | aaggatcctc | 1320 |
| atttgtatac | ctagtggaaa | ggactctgaa | ctcagaggag | tcactgttcc | ttttttttagg | 1380 |
| ttagaaatta | acagcaggga | aatgccatct | tattacctga | gacgaccagc | actgggagtt | 1440 |
| aggtacggtc | tgaagttatg | tctagataag | acttcagacg | tcctgggatt | gaaagaatgt | 1500 |
| gtgtgaaggg | gtagaatttg | tgcggtaaag | acttaaaaaa | aaagtaggg | agattaaaaa | 1560 |
| aaaagaaaga | aaatgcttcc | ttatctggaa | gcctttctgg | attaatccag | tgatggtccc | 1620 |
| acctttagtg | tttgagcttt | gtcattgctt | gtctccctgg | catgtgccag | ttatagactg | 1680 |
| tccagcatcc | aagacgtttc | ggttatgtcg | ggtcctcaga | tcgcctctga | cttgttacca | 1740 |
| caacaaatca | ttttgatttc | agtgcctgtt | ggggacttga | tttcttctca | gttttgtttg | 1800 |
| tttgtttgtt | tccttaatct | ggctcatttg | aaatttcttc | tccctctcaa | ccatcccact | 1860 |
| aagttatagc | caagaaggga | aggagacacg | gggatttggg | gttctctgct | tgaatgtctt | 1920 |
| ctcctttacc | acctcacctt | gttggtacct | ccctcccctgg | atctctgagc | cagcagccag | 1980 |
| gaggacctga | cccagcagtt | ctttactggc | ccctttgtag | ggccttgctg | ccaggggca | 2040 |
| gggatgcttt | ccagcctgca | gcaacagaac | acttgacctt | aaaagtctct | tctggtcttt | 2100 |
| ggattagaaa | aggcttatgt | tagcatagct | taagagcaac | ctcagagact | tgagccctac | 2160 |

| | |
|---|---|
| taagtgactg accactgttt agagtgtctg gtatctgatg ttcatttatt cccatgttct | 2220 |
| tgtgtgtcac agttcagcca gttttggttt atgcctagag ctacttcaag gaactagact | 2280 |
| aattagctat ataggcccag cgatgcttct tattgatctt aatagtatgc cctccttcc | 2340 |
| cctgtccttt catttctcta tccaagtagc agtcaggttc ttggtgtgat gggactgaaa | 2400 |
| gaattccagt cagccagagc cttggcagct ctgaagctaa ccttagcatc taagtgtcga | 2460 |
| tcttgaattc cctgaaaaaa tttctatagg aaatgaagct tccctggtcc cctcctttct | 2520 |
| ggccattgtc atccatttcc cagttagggc aacaatgaag gaggacccag ccaagctaga | 2580 |
| aggaattttg tggatgggag acagcaggat tagcttcagc ttgggctgga gcagtcaata | 2640 |
| taggatctca ggccaggccc gcttttctag aatgtgttta attttgagtt tgctttatta | 2700 |
| gatatgtttt ttaagagctc tgtatatttg aactgctcct tatgtgacaa aataggtagc | 2760 |
| tcttgggctc atgtcctggg ttttggctct ttaatgatta ctccaggcca gcatttagtc | 2820 |
| gtttgagaat tgtagcctgt tgttttcgct gtgacttggg tctcagtgct agggtattga | 2880 |
| gtcaggcagc tggagggttg tggcccgagg ctgcagtcag aggtatactt cccatagtgc | 2940 |
| ttcacacagc tcccctgctt ctaaaggata aggtactgta gccttggtcc tggggaccac | 3000 |
| ctgcctgggg cagtggacat cctaactaaa caggcttctg gcagtagctt tggttcctat | 3060 |
| cccatcgaaa ttccccaaag ccctgggcca ctgccattgg gttagtcaag atgaaggagg | 3120 |
| aggactggct gcctccattt tgccttgttt gttagtttgc ctgggtctgt ctgaggaagg | 3180 |
| aggggtccc gccttccacc tcaacacatc ccttcagtga ctcagagtct cagaaggaaa | 3240 |
| ccctgactcc tggggccatt tcctaatggt actgtaagcc aagcagcttt gcttctgcct | 3300 |
| ctgtttccaa gcccaccctt ttcccctgag ctcagggtta gggatgggcg cttctctc | 3360 |
| tggttgtgaa cgaaggaag gaacatctttt ctatggctaa caaaaactaa aggggaagtg | 3420 |
| aggaaacagg aagaagtatg gtgggggctg gggtagactc ccctggagcc aagcctatcc | 3480 |
| agctaacaag agctccctgg ggctggtcac agctggctca tgatgctgaa cttgaaagtt | 3540 |
| ttttgtttt tgttttttgtt ttgtggctcc tccaagatat aggtacatga agttaggtt | 3600 |
| aaaggggtgg gattctttat ttttatttt gtattgtatg tgtcaagaat tactctgttg | 3660 |
| ttcacccttt gcttttgtca ctgtttgttc tcttatctgt attttgagct tagtgctagg | 3720 |
| actgagaggc tgcaccatag ggaatgtatg ggagatggtg aggggtgcca gtgaggggtg | 3780 |
| cgtggaggag aggcctgggc tcctctactg gatctacact ctgtcccagg tttttagatc | 3840 |
| ccactgagcc cagctgactg aaaacaagga cagtcagggt gaaacttctt ttgccagaag | 3900 |
| tgtggcctga gttgaatttc tgggaggatg acgcagatgt ctgctgcaga gctgggctga | 3960 |
| gagttctgca gtctagctct gacttaggtc aggggcctgt tggtctctca ttggacgttt | 4020 |
| ttgggtctca ctcatgctta ctgaaacatt gtgccaagaa actctgtggg atttgtgtcc | 4080 |
| cttaaaccag actcactttt ctgaaaaatc tccattgttg aggagaggct gctcaatcga | 4140 |
| caccccgagt tctcatgact gggaagatag ttttcttcag gtgtcaatgg cgttagactc | 4200 |
| ccaggaagac tagccctgcc cacagggcca cctgttggtt tgagagcgtg ttcgtgttct | 4260 |
| cttgccctcc ctgcctaaga gctactggga tcacgttagc gggcatttag gctttgatga | 4320 |
| gagggcacag tttgagttag gtttacctcc ccctttctgt gcctgggaac tgtttggtcc | 4380 |
| agctttagaa ctgtggtttt gacttcctta tctcttggga gaagcttctg ttttaaggaa | 4440 |
| tttctcttcc ttcttctcct gcctctagcc tctcctggaa aggcctggat atggtttcta | 4500 |
| aaatctcagc tgagaacttc agaaaacagc agcagtattt tccttttcct agtgctaaaa | 4560 |

```
tcccttttccc tagaaattgg ctcaccttgg gaaacccagg gaaagaatca gcaggttctc    4620
tgccctccct aggggttggg gaaggaccca ccccggtcag cacagtgcct tttcctctcc    4680
tgctctgagc cagggtgggg cattccctct agattcaggt ttgggcaggg gtcctatagt    4740
ccctgccatg gggctgcttc cctgtccctt ccctccccct tgctggccta ctctggcata    4800
attcaagtgt cttcttgcct tggggatcct tagtggcatc aaatggcaac atggaatatt    4860
gtcctccatg cccctccaga aggacctagg agtaggtg agctttccaa agtgagagac     4920
gaatctttct ttcttttttt ttttaaaggg caggatgggg atgctttggg ctttctcctt    4980
ctgtggcccc ggaggaagga gagactgagg caaggcaaag tgatagtaca ctgaagcaga    5040
accggaaaca cccaggaact gttcagaaat ctcagaagaa atctgcttct cttcgatgga    5100
aagatataat taacgatcaa agagctctaa gaaaattgca agaagccttt aatgttcaag    5160
ctttagaaag atcagagcaa ttttctctt tcagtccaaa ctaagactct ctgtatttaa     5220
atctctctgg ggcaagaggg ctagatttcc tcattttgtt atgagactag attggtacca    5280
gtagatcagc tgcctagcga gggcaggttt cttctttgca tctgtgtggc ttgcttccag    5340
tctggcctgt cctttccagc tgcctttgt ctagcctgct atggggggcc agattatctt     5400
gataagagca ggtgatttgg ggactagctg ggttggcagg aaaagagcag gatggatctc    5460
ttgggacagg ttccccagg agtataaaca caaggagcca ggattgtgct ggcagccaag     5520
gaaacagtag tgcctgtttg agttggcaga gagggccttg gcacctcttg catccaggca    5580
gtcttgtgag atggggcac atagcactgg ggaaagcaga actccattct cacctctatt     5640
ttgagcttca gtgctttatt tcagtatgag gaaaacaac aacaaactga agtgcgcttt     5700
ccgtcctttc aaaggacaac tgtcgggaag ggagagccga gttgcgaggt aggagggag    5760 cactggcagg gagagacatt cttgactcct ctcttccctg gtgtgttgtg atccagggaa    5820
tgaaaagaaa tttgaccctg gattggttct ctccttggac ttaaggaatc ttaccttttc    5880
cttccacaaa gttctcccag gcaaggacca gctgcccatt ctgagcccag ggcagcctct    5940
tcaaccatta ttggtctaac ctggcttgtc aggaaaccaa gcccacccttt ccacattggg   6000 cctggctgct ctattctgta ccaagtactg gagaaaaagc atcaagttct tagcccttgt    6060
agcttctacc ctagtttccc atcctctctc tgtggaggcc aaaccaactc tttgccagca    6120
gccacaacat gcattgacag cggcacagtg agatataact gatgggcttt gaacctggtt    6180
ggccggggaa gctgtagggg tggatagagc tggctttcct tctgggctgt ctccatctga    6240
ccctacccct tccatgtccc accccactcc caccaaaaag tacaaaatca ggatgttttt    6300
cactgtccat tgctttgtgt tttaataaac aatttgcagt gacactctga aaaaaaaaaa   6360
aaaaaaa                                                              6367
```

<210> SEQ ID NO 80
<211> LENGTH: 3319
<212> TYPE: DNA
<213> ORGANISM: Homo sapiens

<400> SEQUENCE: 80

```
agcggagctg cagccggaga aagaggaaga gggagagaga gcgcgccagg gcagggcac       60 cgccgccggt cgggcgcgct gggcctgccc ggaatcccgc cgcctgcgcc ccgcgccccg     120
cgccctgcgg gccatgggag ccggccgccg gcagggacga cgcctgtgag acccgcgagc    180
ggcctcgggg accatgggga gcgatcgggc ccgcaagggc ggagggggcc cgaaggactt    240
```

-continued

```
cggcgcggga ctcaagtaca actcccggca cgagaaagtg aatggcttgg aggaaggcgt      300
ggagttcctg ccagtcaaca acgtcaagaa ggtggaaaag catggcccgg ggcgctgggt      360
ggtgctggca gccgtgctga tcggcctcct cttggtcttg ctggggatcg gcttcctggt      420
gtggcatttg cagtaccggg acgtgcgtgt ccagaaggtc ttcaatggct acatgaggat      480
cacaaatgag aattttgtgg atgcctacga gaactccaac tccactgagt ttgtaagcct      540
ggccagcaag gtgaaggacg cgctgaagct gctgtacagc ggagtcccat tcctgggccc      600
ctaccacaag gagtcggctg tgacggcctt cagcgagggc agcgtcatcg cctactactg      660
gtctgagttc agcatcccgc agcacctggt ggaggaggcc gagcgcgtca tggccgagga      720
gcgcgtagtc atgctgcccc cgcgggcgcg ctccctgaag tcctttgtgg tcacctcagt      780
ggtggctttc cccacggact ccaaaacagt acagaggacc caggacaaca gctgcagctt      840
tggcctgcac gcccgcggtg tggagctgat gcgcttcacc acgcccggct ccctgacag       900 cccctacccc gctcatgccc gctgccagtg ggccctgcgg gggacgccg actcagtgct       960 gagcctcacc ttccgcagct ttgaccttgc gtcctgcgac gagcgcggca gcgacctggt     1020
gacggtgtac aacaccctga gccccatgga gccccacgcc ctggtgcagt tgtgtggcac     1080
ctaccctccc tcctacaacc tgaccttcca ctcctcccag aacgtcctgc tcatcacact     1140
gataaccaac actgagcggc ggcatcccgg ctttgaggcc accttcttcc agctgcctag     1200
gatgagcagc tgtggaggcc gcttacgtaa agcccagggg acattcaaca gccccactac     1260
cccaggccac tacccacccac acattgactg cacatggaac attgaggtgc caacaacca    1320 gcatgtgaag gtgcgcttca aattcttcta cctgctggag cccggcgtgc ctgcgggcac     1380
ctgccccaag gactacgtgg agatcaacgg ggagaaatac tgcggagaga ggtcccagtt     1440
cgtcgtcacc agcaacagca acaagatcac agttcgcttc cactcagatc agtcctacac     1500
cgacaccggc ttcttagctg aatacctctc ctacgactcc agtgaccatg cccggggca     1560 gttcacgtgc cgcacggggc ggtgtatccg gaaggagctg cgctgtgatg ctgggccga     1620 ctgcaccgac cacagcgatg agctcaactg cagttgcgac gccggccacc agttcacgtg     1680
caagaacaag ttctgcaagc ccctcttctg ggtctgcgac agtgtgaacg actgcggaga     1740
caacagcgac gagcagggt gcagttgtcc ggcccagacc ttcaggtgtt ccaatgggaa      1800
gtgcctctcg aaaagccagc agtgcaatgg aaggacgac tgtggggacg ggtccgacga      1860
ggcctcctgc cccaaggtga acgtcgtcac ttgtaccaaa cacacctacc gctgcctcaa     1920
tgggctctgc ttgagcaagg gcaaccctga gtgtgacggg aaggaggact gtagcgacgg     1980
ctcagatgag aaggactgcg actgtgggct gcggtcattc acgagacagg ctcgtgttgt     2040
tgggggcacg gatgcggatg agggcgagtg gccctggcag gtaagcctgc atgctctggg     2100
ccagggccac atctgcggtg cttccctcat ctctcccaac tggctggtct ctgccgcaca     2160
ctgctacatc gatgacagag gattcaggta ctcagaccc acgcagtgga cggccttcct     2220
gggcttgcac gaccagagcc agcgcagcgc ccctggggtg caggagcgca ggctcaagcg     2280
catcatctcc cacccttct tcaatgactt caccttcgac tatgacatcg cgctgctgga     2340
gctggagaaa ccggcagagt acagctccat ggtgcggccc atctgcctgc cggacgcctc     2400
ccatgtcttc cctgccggca aggccatctg ggtcacgggc tggggacaca cccagtatgg     2460
aggcactggc gcgctgatcc tgcaaaaggg tgagatccgc gtcatcaacc agaccacctg     2520
cgagaacctc ctgccgcagc agatcacgcc gcgcatgatg tgcgtgggct tcctcagcgg     2580
cggcgtggac tcctgccagg gtgattccgg gggacccctg tccagcgtgg aggcggatgg     2640
```

-continued

| | |
|---|---|
| gcggatcttc caggccggtg tggtgagctg gggagacggc tgcgctcaga ggaacaagcc | 2700 |
| aggcgtgtac acaaggctcc ctctgtttcg ggactggatc aaagagaaca ctggggtata | 2760 |
| ggggccgggg ccacccaaat gtgtacacct gcggggccac ccatcgtcca ccccagtgtg | 2820 |
| cacgcctgca ggctggagac tggaccgctg actgcaccag cgcccccaga acatacactg | 2880 |
| tgaactcaat ctccagggct ccaaatctgc ctagaaaacc tctcgcttcc tcagcctcca | 2940 |
| aagtggagct gggaggtaga aggggaggac actggtggtt ctactgaccc aactgggggc | 3000 |
| aaaggtttga agacacagcc tccccgcca gccccaagct gggccgaggc gcgtttgtgc | 3060 |
| atatctgcct ccctgtctc taaggagcag cgggaacgga gcttcggggc ctcctcagtg | 3120 |
| aaggtggtgg ggctgccgga tctgggctgt ggggcccttg gccacgctc ttgaggaagc | 3180 |
| ccaggctcgg aggaccctgg aaaacagacg ggtctgagac tgaaattgtt ttaccagctc | 3240 |
| ccagggtgga cttcagtgtg tgtatttgtg taaatgagta aaacatttta tttcttttta | 3300 |
| aaaaaaaaaa aaaaaaaa | 3319 |

<210> SEQ ID NO 81
<211> LENGTH: 5903
<212> TYPE: DNA
<213> ORGANISM: Homo sapiens

<400> SEQUENCE: 81

| | |
|---|---|
| agacgccgcc caggacgcag ccgccgccgc cgccgctcct ctgccactgg ctctgcgccc | 60 |
| cagcccggct ctgctgcagc ggcagggagg aagagccgcc gcagcgcgac tcgggagccc | 120 |
| cgggccacag cctggcctcc ggagccaccc acaggcctcc ccgggcggcg cccacgctcc | 180 |
| taccgccccga acgcgcggat cctccgccgg caccgcagcc acctgctccc ggcccagagg | 240 |
| cgacgacacg atgcgctgcg cgctggcgct ctcggcgctg ctgctactgt tgtcaacgcc | 300 |
| gccgctgctg ccgtcgtcgc cgtcgccgtc gccgtcgccc tcccagaatg caacccagac | 360 |
| tactacggac tcatctaaca aaacagcacc gactccagca tccagtgtca ccatcatggc | 420 |
| tacagataca gcccagcaga gcacagtccc cacttccaag gccaacgaaa tcttggcctc | 480 |
| ggtcaaggcg accacccttg gtgtatccag tgactcaccg gggactacaa ccctggctca | 540 |
| gcaagtctca ggcccagtca acactaccgt ggctagagga ggcggctcag gcaaccctac | 600 |
| taccaccatc gagagcccca agagcacaaa aagtgcagac accactacag ttgcaacctc | 660 |
| cacagccaca gctaaaccta caccacaag cagccagaat ggagcagaag atacaacaaa | 720 |
| ctctgggggg aaaagcagcc acagtgtgac cacagacctc acatccacta aggcagaaca | 780 |
| tctgacgacc cctcaccta caagtccact tagcccccga caacccactt cgacgcatcc | 840 |
| tgtggccacc ccaacaagct cgggacatga ccatcttatg aaaatttcaa gcagttcaag | 900 |
| cactgtggct atccctggct acaccttcac aagcccgggg atgaccacca ccctaccgtc | 960 |
| atcggttatc tcgcaaagaa ctcaacagac ctccagtcag atgccagcca gctctacggc | 1020 |
| cccttcctcc caggagacag tgcagcccac gagcccggca acggcattga aacacctac | 1080 |
| cctgccagag accatgagct ccagccccac agcagcatca actacccacc gatacccaa | 1140 |
| aacaccttct cccactgtgg ctcatgagag taactgggca aagtgtgagg atcttgagac | 1200 |
| acagacacag agtgagaagc agctcgtcct gaacctcaca ggaaacaccc tctgtgcagg | 1260 |
| gggcgcttcg gatgagaaat tgatctcact gatatgccga gcagtcaaag ccaccttcaa | 1320 |
| cccggcccaa gataagtgcg gcatacggct ggcatctgtt ccaggaagtc agaccgtggt | 1380 |

```
cgtcaaagaa atcactattc acactaagct ccctgccaag gatgtgtacg agcggctgaa    1440
ggacaaatgg gatgaactaa aggaggcagg ggtcagtgac atgaagctag gggaccaggg    1500
gccaccggag gaggccgagg accgcttcag catgcccctc atcatcacca tcgtctgcat    1560
ggcatcattc ctgctcctcg tggcggccct ctatggctgc tgccaccagc gcctctccca    1620
gaggaaggac cagcagcggc taacagagga gctgcagaca gtggagaatg gttaccatga    1680
caacccaaca ctggaagtga tggagacctc ttctgagatg caggagaaga aggtggtcag    1740
cctcaacggg gagctggggg acagctggat cgtccctctg gacaacctga ccaaggacga    1800 cctgatgag gaggaagaca cacacctcta gtccggtctg ccggtggcct ccagcagcac    1860
cacagagctc cagaccaacc accccaagtg ccgtttggat ggggaaggga aagactgggg    1920
agggagagtg aactccgagg ggtgtcccct cccaatcccc ccagggcctt aattttccc    1980 ttttcaacct gaacaaatca cattctgtcc agattcctct tgtaaaataa cccactagtg    2040
cctgagctca gtgctgctgg atgatgaggg agatcaagaa aaagccacgt aagggacttt    2100
atagatgaac tagtggaatc ccttcattct gcagtgagat tgccgagacc tgaagagggt    2160
aagtgacttg cccaaggtca gagccacttg gtgacagagc caggatgaga acaaagattc    2220
catttgcacc atgccacact gctgtgttca catgtgcctt ccgtccagag cagtcccggg    2280
caggggtgaa actccagcag gtggctgggc tggaaaggag ggcagggcta catcctggct    2340
cggtgggatc tgacgacctg aaagtccagc tcccaagttt tccttctcct accccagcct    2400
cgtgtaccca tcttcccacc ctctatgttc ttaccctcc ctacactcag tgtttgttcc    2460
cacttactct gtcctggggc ctctgggatt agcacaggtt attcataacc ttgaacccct    2520
tgttctggat tcggattttc tcacatttgc ttcgtgagat gggggcttaa cccacacagg    2580
tctccgtgcg tgaaccaggt ctgcttaggg gacctgcgtg caggtgagga gagaagggga    2640
cactcgagtc caggctggta tctcagggca gctgatgagg ggtcagcagg aacactggcc    2700
cattgcccct ggcactcctt gcagaggcca cccacgatct tctttgggct tccatttcca    2760
ccagggacta aaatctgctg tagctagtga gagcagcgtg ttccttttgt tgttcactgc    2820
tcagctgatg ggagtgattc cctgagaccc agtatgaaag agcagtggct gcaggagagg    2880
ccttcccggg gcccccatc agcgatgtgt cttcagagac aatccattaa agcagccagg    2940
aaggacaggc tttcccctgt atatcatagg aaactcaggg acatttcaag ttgctgagag    3000
ttttgttata gttgttttct aacccagccc tccactgcca aaggccaaaa gctcagacag    3060
ttggcagacg tccagttagc tcatctcact cactctgatt ctcctgtgcc acaggaaaag    3120
agggcctgga aagcgcagtg catgctgggt gcatgaaggg cagcctgggg gacagactgt    3180
tgtgggaacg tcccactgtc ctggcctgga gctaggcctt gctgttcctc ttctctgtga    3240
gcctagtggg gctgctgcgg ttctcttgca gtttctggtg gcatctcagg gaacacaaa    3300 gctatgtcta ttccccaata taggactttt atgggctcgg cagttagctg ccatgtagaa    3360
ggctcctaag cagtgggcat ggtgaggttt catctgattg agaagggga atcctgtgtg    3420 gaatgttgaa ctttcgccat ggtctccatc gttctgggcg taaattccct gggatcaagt    3480
aggaaaatgg gcagaactgc ttaggggaat gaaattgcca ttttttcgggt gaaacgccac    3540 acctccaggt tcttaagagt caggctccgg ctgtagtagc tctgatgaaa taggctatcc    3600
actcgggatg gcttactttt taaaagggta gggggagggg ctggggaaga tctgtcctgc    3660
accatctgcc taattccttc ctcacagtct gtagccatct gatatcctag ggaaaagga    3720 aggccagggg ttcacatagg gccccagcga gtttcccagg agttagaggg atgcgaggct    3780
```

```
aacaagttcc aaaaacatct gccccgatgc tctagtgttt ggaggtgggc aggatggaga    3840
acagtgcctg tttggggaa aacaggaaat cttgttaggc ttgagtgagg tgtttgcttc     3900
cttcttgccc agcgctgggt tctctccacc cagtaggttt tctgttgtgg tcccgtggga    3960
gaggccagac tggattattc ctcctttgct gatcctgggt cacacttcac cagccagggc    4020
ttttgacgga gacagcaaat aggcctctgc aaatcaatca aaggctgcaa ccctatggcc    4080
tcttggagac agatgatgac tggcaaggac tagagagcag gagtgcctgg ccaggtcggt    4140
cctgactctc ctgactctcc atcgctctgt ccaaggagaa cccggagagg ctctgggctg    4200
attcagaggt tactgcttta tattcgtcca aactgtgtta gtctaggctt aggacagctt    4260
cagaatctga caccttgcct tgctcttgcc accaggacac ctatgtcaac aggccaaaca    4320
gccatgcatc tataaaggtc atcatcttct gccaccttta ctgggttcta aatgctctct    4380
gataattcag agagcattgg gtctgggaag aggtaagagg aacactagaa gctcagcatg    4440
acttaaacag gttgtagcaa agacagttta tcatcagctc tttcagtggt aaactgtggt    4500
ttccccaagc tgcacaggag gccagaaacc acaagtatga tgactaggaa gcctactgtc    4560
atgagagtgg ggagacaggc agcaaagctt atgaaggagg tacagaatat tctttgcgtt    4620
gtaagacaga atacgggttt aatctagtct aggcaccaga ttttttttccc gcttgataag    4680
gaaagctagc agaaagttta tttaaaccac ttccttgagct ttatcttttt tgacaatata    4740
ctggagaaac tttgaagaac aagttcaaac tgatacatat acacatattt ttttgataat    4800
gtaaatacag tgaccatgtt aacctaccct gcactgcttt aagtgaacat actttgaaaa    4860
agcattatgt tagctgagtg atggccaagt tttttctctg gacaggaatg taaatgtctt    4920
actgaaaatg acaagttttt gcttgatttt ttttttttaaa caaaaaatga aatataacaa    4980
gacaaactta tgataaagta tttgtcttgt agatcaggtg ttttgttttg ttttttttaat    5040
tttaaaatgc aaccctgccc cctccccagc aaagtcacag ctccatttca gtaaaggttg    5100
gagtcaatat gctctggttg gcaggcaacc ctgtagtcat ggagaaaggt atttcaagat    5160
ctagtccaat cttttttctag agaaaaagat aatctgaagc tcacaaagat gaagtgactt    5220
cctcaaaatc acatggttca ggacagaaac aagattaaaa cctggatcca cagactgtgc    5280
gcctcagaag gaataatcgg taaattaaga attgctactc gaaggtgcca gaatgacaca    5340
aaggacagaa ttcctttccc agttgttacc ctagcaaggc tagggagggc atgaacacaa    5400
acataagaac tggtcttcta cactttctct gaatcattta ggtttaagat gtaagtgaac    5460
aattctttct ttctgccaag aaacaaagtt ttggatgagc ttttatatat ggaacttact    5520
ccaacaggac tgagggacca aggaaacatg atggggagg cagagagggc aagagtaaaa    5580
ctgtagcata gcttttgtca cggtcactag ctgatccctc aggtctgctg caaacacagc    5640
atggaggaca cagatgactc tttggtgttg gtcttttttgt ctgcagtgaa tgttcaacag    5700
tttgcccagg aactggggga tcatatatgt cttagtggac aggggtctga agtacactgg    5760
aatttactga gaaacttgtt tgtaaaaact atagttaata attattgcat tttcttacaa    5820
aaatatattt tggaaaattg tatactgtca attaaagtgt ttttgtgtaa actggttcaa    5880
aaaaaaaaaa aaaaaaaaaa aaa                                            5903
```

<210> SEQ ID NO 82
<211> LENGTH: 1791
<212> TYPE: DNA
<213> ORGANISM: Homo sapiens

```
<400> SEQUENCE: 82
ggaggctgca gcagcggaag accccagtcc agatccagga ctgagatccc agaaccatga      60
acctggccat cagcatcgct ctcctgctaa cagtcttgca ggtctcccga gggcagaagg     120
tgaccagcct aacggcctgc ctagtggacc agagccttcg tctggactgc cgccatgaga     180
ataccagcag ttcacccatc cagtacgagt tcagcctgac ccgtgagaca agaagcacg      240
tgctctttgg cactgtgggg gtgcctgagc acacataccg ctcccgaacc aacttcacca     300
gcaaatacaa catgaaggtc ctctacttat ccgccttcac tagcaaggac gagggcacct     360
acacgtgtgc actccaccac tctggccatt ccccacccat ctcctcccag aacgtcacag     420
tgctcagaga caaactggtc aagtgtgagg gcatcagcct gctggctcag aacacctcgt     480
ggctgctgct gctcctgctc tccctctccc tcctccaggc cacggatttc atgtccctgt     540
gactggtggg gcccatggag agacaggaa gcctcaagtt ccagtgcaga gatcctactt      600
ctctgagtca gctgaccccc tcccgcaat ccctcaaacc ttgaggagaa gtggggaccc      660
caccctcat caggagttcc agtgctgcat gcgattatct acccacgtcc acgcggccac     720
ctcaccctct ccgcacacct ctggctgtct ttttgtactt tttgttccag agctgcttct     780
gtctggttta tttaggtttt atccttcctt ttctttgaga gttcgtgaag agggaagcca     840
ggattgggga cctgatggag agtgagagca tgtgagggggt agtgggatgg tggggtacca     900
gccactggag gggtcatcct tgcccatcgg gaccagaaac ctgggagaga cttggatgag     960
gagtggttgg gctgtgcctg gcctagcac ggacatggtc tgtcctgaca gcactcctcg     1020
gcaggcatgg ctggtgcctg aagaccccag atgtgagggc accaccaaga atttgtggcc    1080
taccttgtga gggagagaac tgagcatctc cagcattctc agccacaacc aaaaaaaaat    1140
aaaaagggca gccctcctta ccactgtgga agtccctcag aggccttggg gcatgaccca    1200
gtgaagatgc aggtttgacc aggaaagcag cgctagtgga gggttggaga aggaggtaag    1260
gatgagggtt catcatccct ccctgcctaa ggaagctaaa agcatggccc tgctgcccct    1320
ccctgcctcc acccacagtg gagagggcta caaaggagga caagaccctc tcaggctgtc    1380
ccaagctccc aagagcttcc agagctctga cccacagcct ccaagtcagg tggggtggag    1440
tcccagagct gcacagggtt tggcccaagt ttctaaggga ggcacttcct cccctcgccc    1500
atcagtgcca gcccctgctg gctggtgcct gagcccctca gacagccccc tgccccgcag    1560
gcctgccttc tcagggactt ctgcggggcc tgaggcaagc catggagtga gacccaggag    1620
ccggacactt ctcaggaaat ggcttttccc aaccccagc ccccacccgg tggttcttcc     1680
tgttctgtga ctgtgtatag tgccaccaca gcttatggca tctcattgag gacaaagaaa    1740
actgcacaat aaaaccaagc ctctggaatc taaaaaaaaa aaaaaaaaa a              1791

<210> SEQ ID NO 83
<211> LENGTH: 3512
<212> TYPE: DNA
<213> ORGANISM: Homo sapiens

<400> SEQUENCE: 83
gacatggcga gtgtagtgct gccgagcgga tcccagtgtg cggcggcagc ggcggcggcg      60
gcgcctcccg ggctccggct ccggcttctg ctgttgctct ctccgccgc ggcactgatc      120
cccacaggtg atgggcagaa tctgtttacg aaagacgtga cagtgatcga gggagaggtt     180
gcgaccatca gttgccaagt caataagagt gacgactctg tgattcagct actgaatccc     240
aacaggcaga ccatttattt cagggacttc aggcctttga aggacagcag gtttcagttg     300
```

-continued

```
ctgaattttt ctagcagtga actcaaagta tcattgacaa acgtctcaat ttctgatgaa      360
ggaagatact tttgccagct ctataccgat cccccacagg aaagttacac caccatcaca      420
gtcctggtcc caccacgtaa tctgatgatc gatatccaga gagacactgc ggtggaaggt      480
gaggagattg aagtcaactg cactgctatg ccagcaagc cagccacgac tatcaggtgg       540
ttcaaaggga acacagagct aaaaggcaaa tcggaggtgg aagagtggtc agacatgtac      600
actgtgacca gtcagctgat gctgaaggtg cacaaggagg acgatggggt cccagtgatc      660
tgccaggtgg agcaccctgc ggtcactgga aacctgcaga cccagcggta tctagaagta      720
cagtataagc cacaagtgca cattcagatg acttatcctc tacaaggctt aacccgggaa      780
ggggacgcgc ttgagttaac atgtgaagcc atcggaagc cccagcctgt gatggtaact       840
tgggtgagag tcgatgatga aatgcctcaa cacgccgtac tgtctgggcc caacctgttc      900
atcaataacc taaacaaaac agataatggt acataccgct gtgaagcttc aaacatagtg      960
gggaaagctc actcggatta tgctgtatgt atacgatc cccccacaac tatccctcct       1020
cccacaacaa ccaccaccac caccaccacc accaccacca ccatccttac catcatcaca     1080
gattcccgag caggtgaaga aggctcgatc agggcagtgg atcatgccgt gatcggtggc     1140
gtcgtggcgg tggtggtgtt cgccatgctg tgcttgctca tcattctggg gcgctatttt     1200
gccagacata aaggtacata cttcactcat gaagccaaag gagccgatga cgcagcagac     1260
gcagacacag ctataatcaa tgcagaagga ggacagaaca actccgaaga aaagaaagag     1320
tacttcatct agatcagcct ttttgtttca atgaggtgtc caactggccc tatttagatg     1380
ataaagagac agtgatattg gaacttgcga gaaattcgtg tgttttttta tgaatgggtg     1440
gaaaggtgtg agactgggaa ggcttgggat ttgctgtgta aaaaaaaaaa aaatgttct      1500 ttggaaagta cactctgctg tttgacacct cttttttcgt tgtttgttt gtttaatttt      1560 tatttcttcc taccaagtca aacttggata cttggattta gtttcagtag attgcagaaa     1620
attctgtgcc ttgttttttg tttgtttgtt gcgttccttt cttttccccc tttgtgcaca     1680
tttatttcct ccctctaccc caatttcgga ttttttccaa aatctcccat tttggaattt     1740
gcctgctggg attccttaga ctcttttcct tcccttttct gttctagttt tttacttttg     1800 tttatttta tggtaactgc tttctgttcc aaattcagtt tcataaagg agaaccagca      1860 cagcttagga tttcatagtt cagaatttag tgtatccata atgcattctt ctctgttgtc     1920
gtaaagattt gggtgaacaa acaatgaaaa ctctttgctg ctgcccatgt ttcaaatact     1980
tagagcagtg aagactagaa aattagactg tgattcagaa aatgttctgt ttgctgtgga     2040
actacattac tgtacagggt tatctgcaag tgaggtgtgt cacaatgaga ttgaatttca     2100
ctgtctttaa ttctgtatct gtagacggct cagtatagat accctacgct gtccagaaag     2160
gtttggggca gaaaggactc ctccttttc catgccctaa acagacctga caggtgaggt     2220
ctgttccttt tatataagtg gacaaatttt gagttgccac aggaggggaa gtaggagggg    2280
gggaaataca gttctgctct ggttgtttct gttccaaatg attccatcca cctttcccaa    2340
tcggccttac ttctcactaa tttgtaggaa aaagcaagtt cgtctgttgt gcgaatgact    2400
gaatgggaca gagttgattt ttttttttt tttcctttgt gcttagttag gaaggcagta    2460
ggatgtggcc tgcatgtact gtatattaca gatatttgtc atgctgggat ttccaactcg    2520
aatctgtgtg aaactttcat tccttcagat ttggcttgac aaaggcagga ggtacaaaag    2580
aagggctggt attgttctca cactggtctg ctgtcgctct cagttctcga taggtcagag    2640
```

```
cagaggtgga aaaacagcat gtacggattt tcagttactt aatcaaaact caaatgtgag    2700 tgttttatc tttttacctt tcatacacta gccttggcct ctttcctcag ccttaagaac     2760
catctgccaa aaattactga tcctcgcatg atggcagcca tagtgcatag ctactaaaat    2820
cagtgacctt gaacatatct tagatgggga gcctcgggaa aaggtagagg agtcacgtta    2880
ccatttacat gttttaaaga aagaagtgtg gggattttca ctgaaacgtc taggaaatct    2940
agaagtagtc ctgaaggaca gaaactaaac tcttaccata tgtttggtaa gactccagac    3000
tccagctaac agtccctatg gaaagatggc atcaaaaaag atagatctat atatatatat    3060
aaatatatat tctattacat tttcagtgag taattttgga ttttgcaagg tgcatttta     3120 ctattgttac attatgtgga aaacttatgc tgatttattt aaggggggaaa aagtgtcaac   3180 tctttgttat ttgaaaacat gtttattttt cttgtcttta ttttaacctt tgatagaacc   3240
attgcaatat gggggccttt tgggaacgga ctggtatgta aaagaaaatc cattatcgag   3300
cagcatttta tttacccctc ccctatccct aggcacttaa ccaagacaaa aagccacaat   3360
gaacatccct ttttcaatga attttataat ctgcagctct attccgagcc cttagcaccc   3420
attccgacca tagtataatc atatcaaagg gtgagaatca tttagcatgt tgttgaaagg   3480
ttttttttca gttgttcttt ttagaaaaaa ag                                  3512
```

METHODS AND COMPOSITIONS FOR DIAGNOSING AND TREATING DISEASES

FIELD OF THE INVENTION

This invention relates to the field of molecular biology. The invention provides compositions and methods for assessing and treating diseases, especially cancer. In particular, the invention provides the following targets and methods of using these targets: TMPRSS4, SLC5A6, ISGF4, ITGB6, GLG1, DB83, KIAA0152, Matriptase, AADACL1, Podocalyxin, and CD90 (Thy1) (see Figures), which are collectively referred to herein as "CAT" (cancer-associated targets).

BACKGROUND OF THE INVENTION

Cancer

Cancer is one of the leading causes of death worldwide, and cancer is difficult to diagnose and treat effectively. Accordingly, there is a need in the art for new compositions and methods for assessing and treating various cancers.

Targets

TMPRSS4 is a member of the serine protease family of proteins. TMPRSS4 is membrane-bound with an N-terminal anchor sequence and a glycosylated extracellular region containing the serine protease domain. The extracellular domain is typically larger than 300 amino acids in size. Two alternative transcripts encoding different isoforms have been described in the art.

SLC5A6 is a solute carrier with multiple extracellular domains (ECD). The largest ECD is greater than 70 amino acids in size.

ITGB6 (Integrin β6) associates with integrin αv and functions as a cell surface receptor for fibronectin, tenascin, vitronectin and TGF β1 latency-associated peptide (LAP). ITGB6 contains an ectodomain typically about 698 amino acids in size and typically recognizes RGD sequence in its ligand. ITGB6 induces protease activation and is associated with increased cell growth and motility.

GLG1 is a type I membrane protein with two isoforms that differ by 24 amino acids at the C-terminus. Isoform 1 is localized to Golgi, and the slightly longer isoform 2 is localized to the cell surface (*J Cell Science* (2005) 118:1725-1731). GLG1 has a single transmembrane domain, and one large extracellular domain that is typically more than 900aa in size. GLG1 is capably of binding E-selectin and mediating binding of neutrophils to endothelial cells; wherein fucosylation required (*Nature* (1995) 373:615-620). GLG1 binds to fibroblast growth factors and may chaperone to Golgi, suggesting the role in processing and targeting FGF in cells (*JBC* (2000) 275:15741-15748; *J Cell Physiol* (1997) 170:217-227). GLG1 is a component of the latent transforming growth factor-β (TGF-β) complex. This complex is thought to play a role in targeting TGF-β to specific locations on the cell surface/extracellular matrix (*Biochem J* (1997) 324:427-434).

KIAA0152 is a cell surface protein that has an extracellular domain that typically is larger than 250 amino acids in size.

Matriptase, also referred to as ST14, is an integral membrane protease that has an extracellular domain which is typically greater than 600 amino acids in size.

AADACL1 (arylacetamide deacetylase-like 1; exemplary sequences are shown in Genbank gi|46048176 and Swiss Prot Accession Number Q6PIU2) is a membrane-bound serine hydrolase expressed in the brain. AADACL1 has an extracellular domain that typically is 381 amino acids in size. AADACL1 binds the organophosphorous compound chlorpyrifos oxon (CPO). AADACL1 knockout mice demonstrate reduced levels of CPO labeling and hydrolytic metabolism. Thus, AADACL1 has been proposed to be an organophosphorous detoxification enzyme (Nomura et al. 2005. *PNAS* 102:6195-6200). Two discrete glycosylation states have been observed in AADACL1.

Podocalyxin-like protein (referred to herein simply as "podocalyxin") is an integral membrane glycoprotein which has a single transmembrane domain and a large extracellular domain (typically greater than 400 amino acid residues in size). Podocalyxin has highly conserved transmembrane and intracellular domains (~95%) with lower homology in ECD (~30%). Podocalyxin is heavily glycosylated and the extracellular domain contains five potential N-linked glycosylation sites and high Ser/Thr (39%) providing numerous potential O-linked sites. Podocalyxin has an anti-adhesive function which maintains slit diaphragms between foot processes through which urine is filtered (*Mol Biol Cell* (2000) 11, 3219-3232). Podocalyxin has a similar structure and sequence composition as stem-cell marker CD34. Podocalyxin is present on the luminal surface of high endothelial venules where it can serve as a ligand for leukocyte adhesion molecule, L-selectin (*J. Exp. Med.* (1998) 12, 1965-1975). A soluble form of podocalyxin has been detected in in vitro embryonal carcinoma culture and may be found in serum of patients with nonseminomatous germ cell tumors (*Arch Biochem Biophys* (1992) 298 538-543 and *Eur. J. Cancer* (1991) 27 300). Differentially sulfated forms of podocalyxin exist, and a sulfated form is present in HEV.

CD90 (also known as Thy1) (exemplary sequences are shown in Genbank P04216 and Swiss-Prot Accession Number P04216) is a 25-37 kDa GPI-anchored glycoprotein expressed on many cell types, including T cells and thymocytes in mice, and in neurons, endothelial cells, fibroblasts, and blood stem cells in humans (*Lab Invest.* (1986) 54, 122-135); *J. Exp. Med.* (1993) 177, 1331; *Oncogene* (2005) 24, 4710-4720). CD90 can promote T cell activation/inflammation. CD90 may play a role in cell-cell or cell-ligand interactions during synaptogenesis and other events in the brain.

ISGF4 (also referred to as IGSF4) is an integral membrane protein involved in cell adhesion. ISGF4 has a large extracellular domain that is typically greater than 300 amino acids in size.

DB83 is a multi-pass membrane protein. The largest extracellular domain of DB83 is typically greater than 50 amino acids in size (*DNA Research* (1998) 5:315-317).

DESCRIPTION OF THE SEQUENCE LISTING

The Sequence Listing discloses exemplary protein and nucleic acid sequences for each CAT (Cancer-Associated Target). Specifically, the Sequence Listing discloses amino acid sequences of CAT proteins and nucleic acid sequences of CAT transcripts that encode these CAT proteins, as set forth in the following table:

| Cancer-Associated Target (CAT) | Protein SEQ ID NO | Transcript SEQ ID NO |
|---|---|---|
| TMPRSS4 | 1-3 | 4-6 |
| SLC5A6 | 7-9 | 10-12 |
| ISGF4 | 13-17 | 18-22 |

-continued

| Cancer-Associated Target (CAT) | Protein SEQ ID NO | Transcript SEQ ID NO |
|---|---|---|
| ITGB6 | 23 | 24 |
| GLG1 | 25-33 | 34-42 |
| DB83 | 43-44 | 45-46 |
| KIAA0152 | 47-48 | 49-50 |
| Matriptase | 51-52 | 53-55 |
| AADACL1 | 56-59 | 60-63 |
| Podocalyxin | 64-67 | 68-71 |
| CD90 (Thy1) | 72-73 | 74-75 |

DESCRIPTION OF THE FIGURES

TMPRSS4

FIG. 1. TMPRSS4 is Over-Expressed in Multiple Tumor Types, as indicated by IHC.

Figure 2:
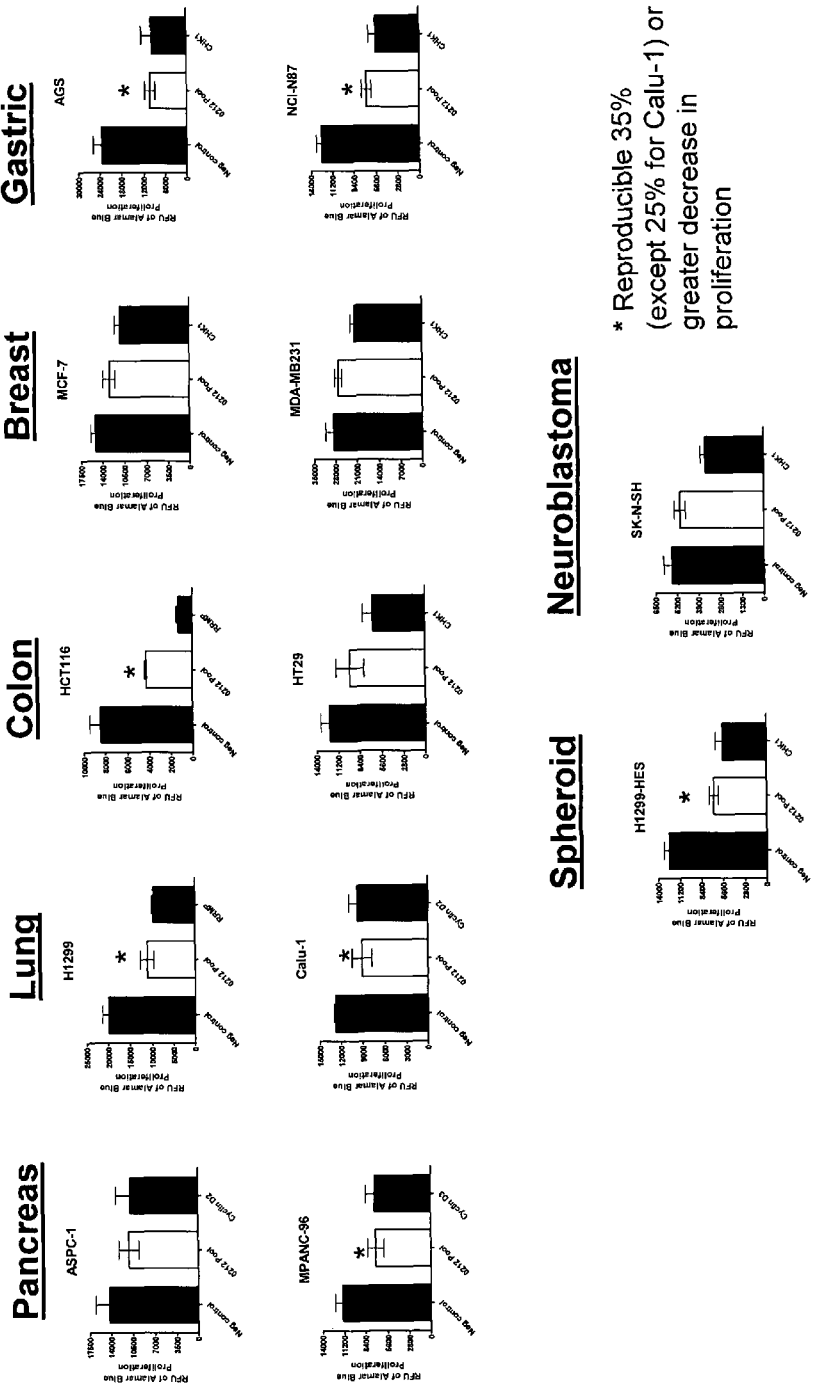

FIG. 2. Knockdown of TMPRSS4 mRNA Inhibits Proliferation in Multiple Cancer Cells.

Figure 3:
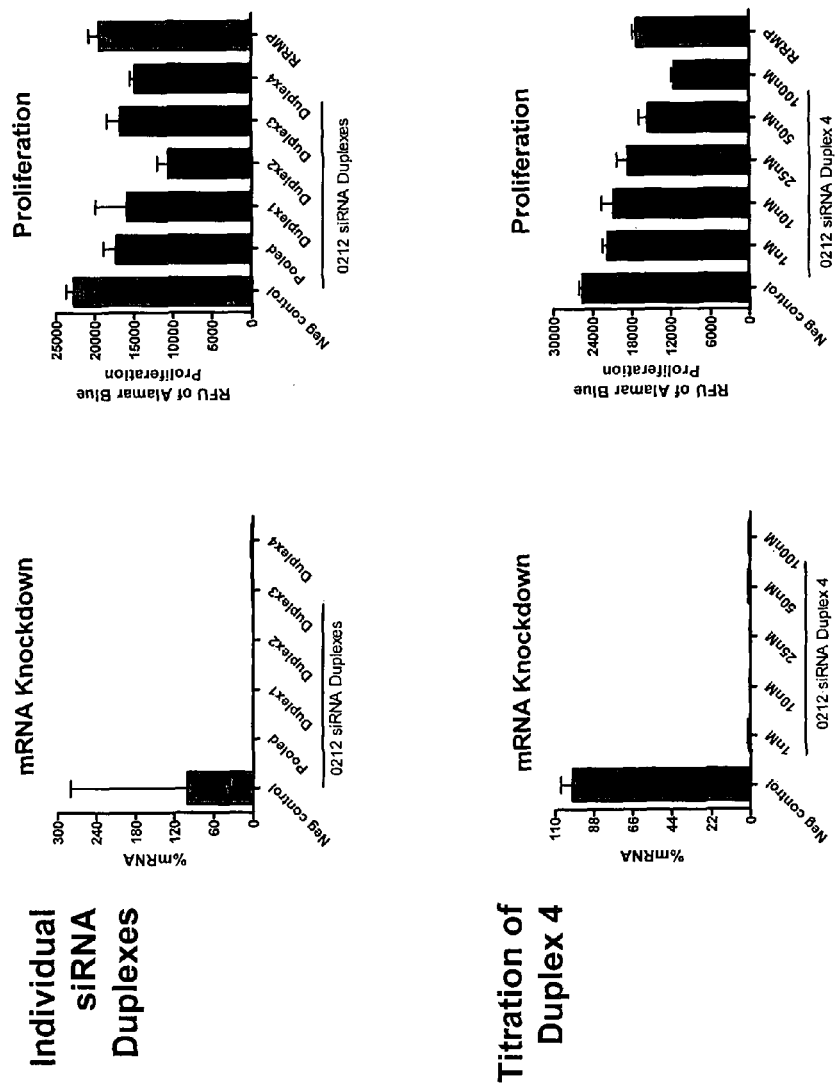

FIG. 3. Knockdown of TMPRSS4 mRNA Inhibits Proliferation in H1299 Lung Cancer Cells.

FIG. 4. Knockdown of TMPRSS4 mRNA Inhibits Proliferation in AGS Gastric Cancer Cells.

FIG. 5. TMPRSS4 mRNA Expression in Multiple Tumor Tissues.

FIG. 6. mRNA sequence of TMPRSS4, indicating siRNA target regions.

SLC5A6

FIG. 7. SLC5A6 is Overexpressed in Multiple Tumor Types, as indicated by IHC.

FIG. 8. SLC5A6 mRNA Expression Analysis in Multiple Tumor Tissues.

FIG. 9. Knockdown of SLC5A6 mRNA Inhibits Proliferation in Pancreatic and Gastric Cancer Cells.

FIG. 10. mRNA sequence of SLC5A6, indicating siRNA target regions.

ITGB6

FIG. 11. ITGB6 is Over-expressed in Multiple Tumor Types, as indicated by IHC.

Figure 12:
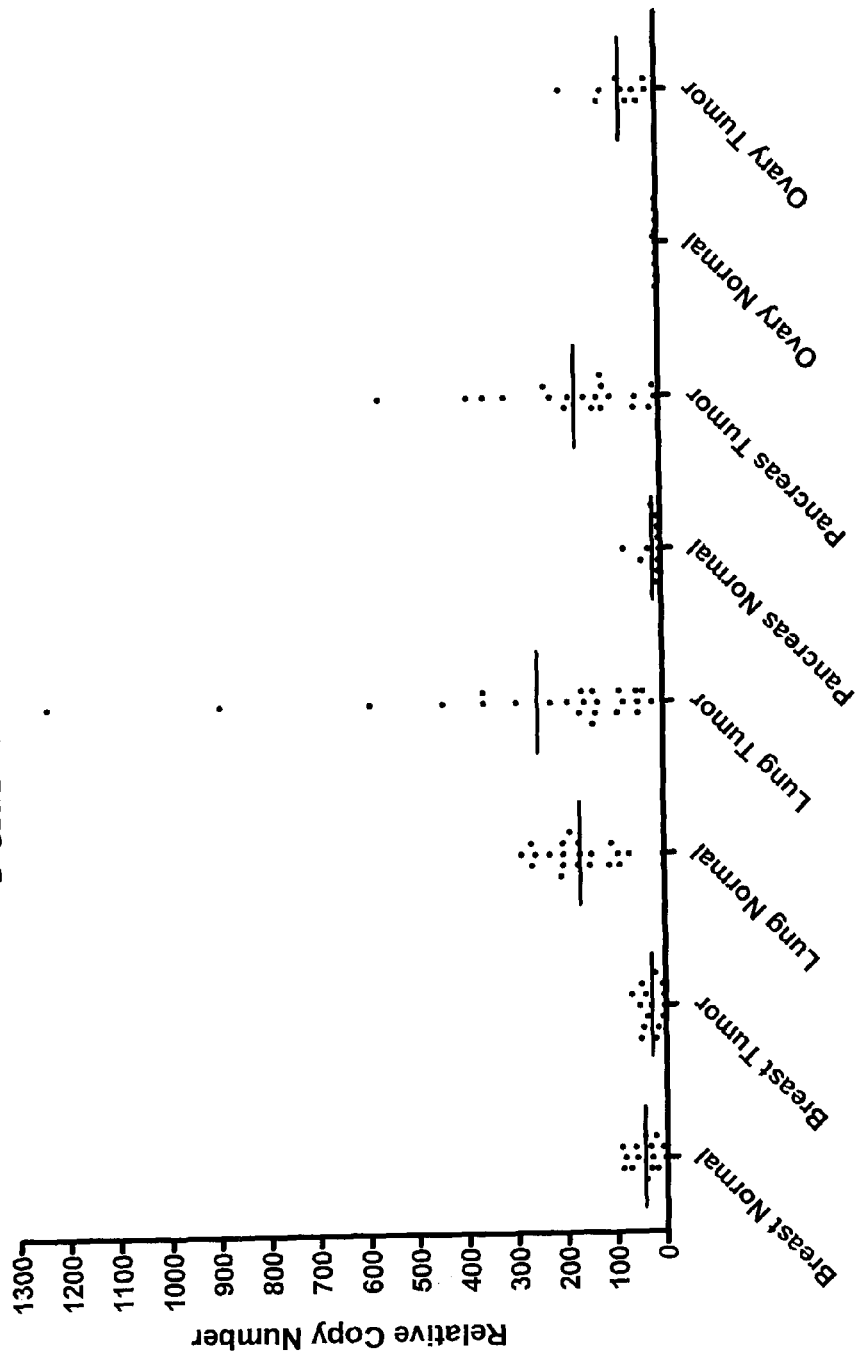

FIG. 12. ITGB6 mRNA Expression Analysis in Multiple Tumor Tissues.

Figure 13:
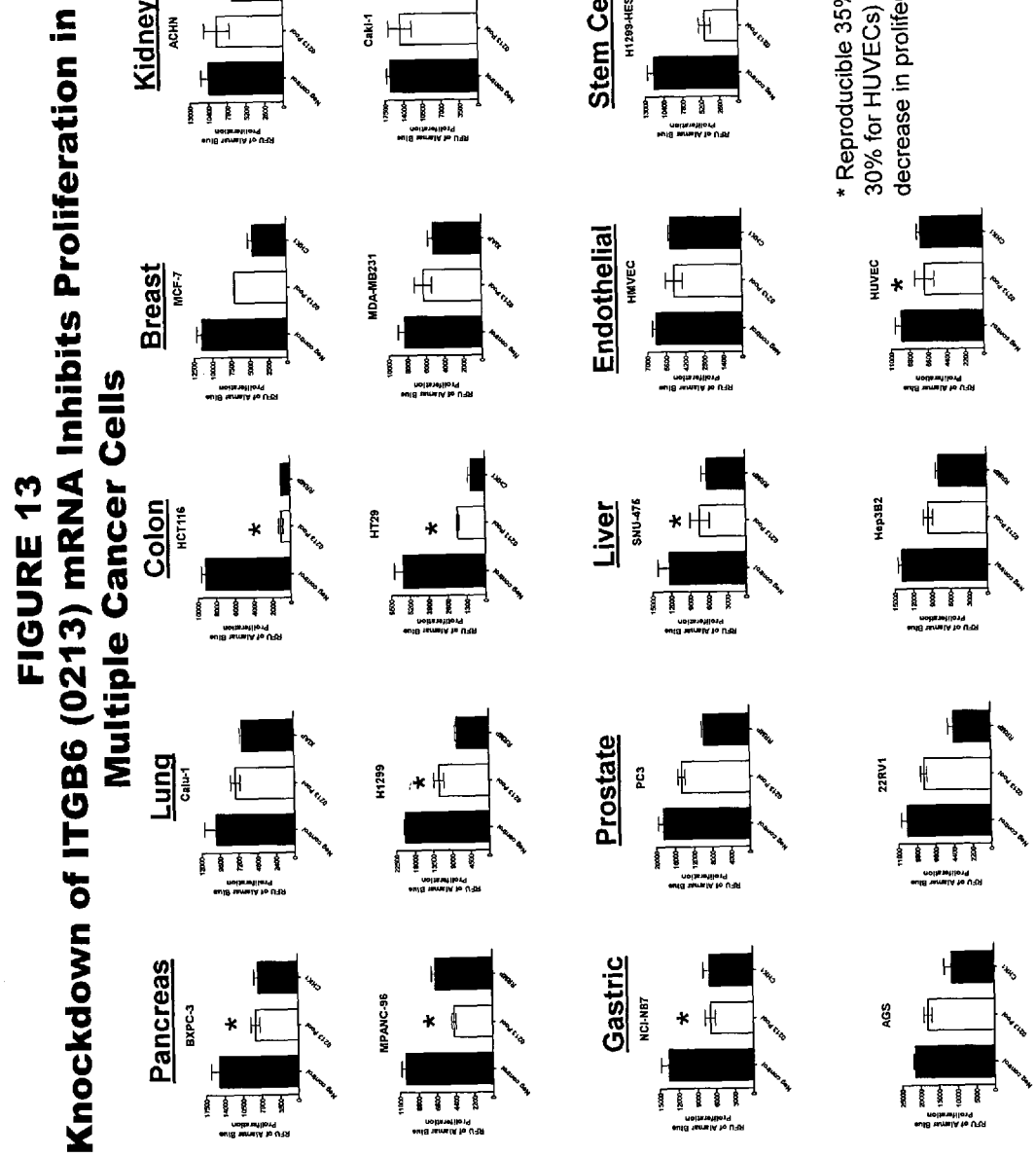

FIG. 13. Knockdown of ITGB6 mRNA Inhibits Proliferation in Multiple Cancer Cells.

Figure 14:
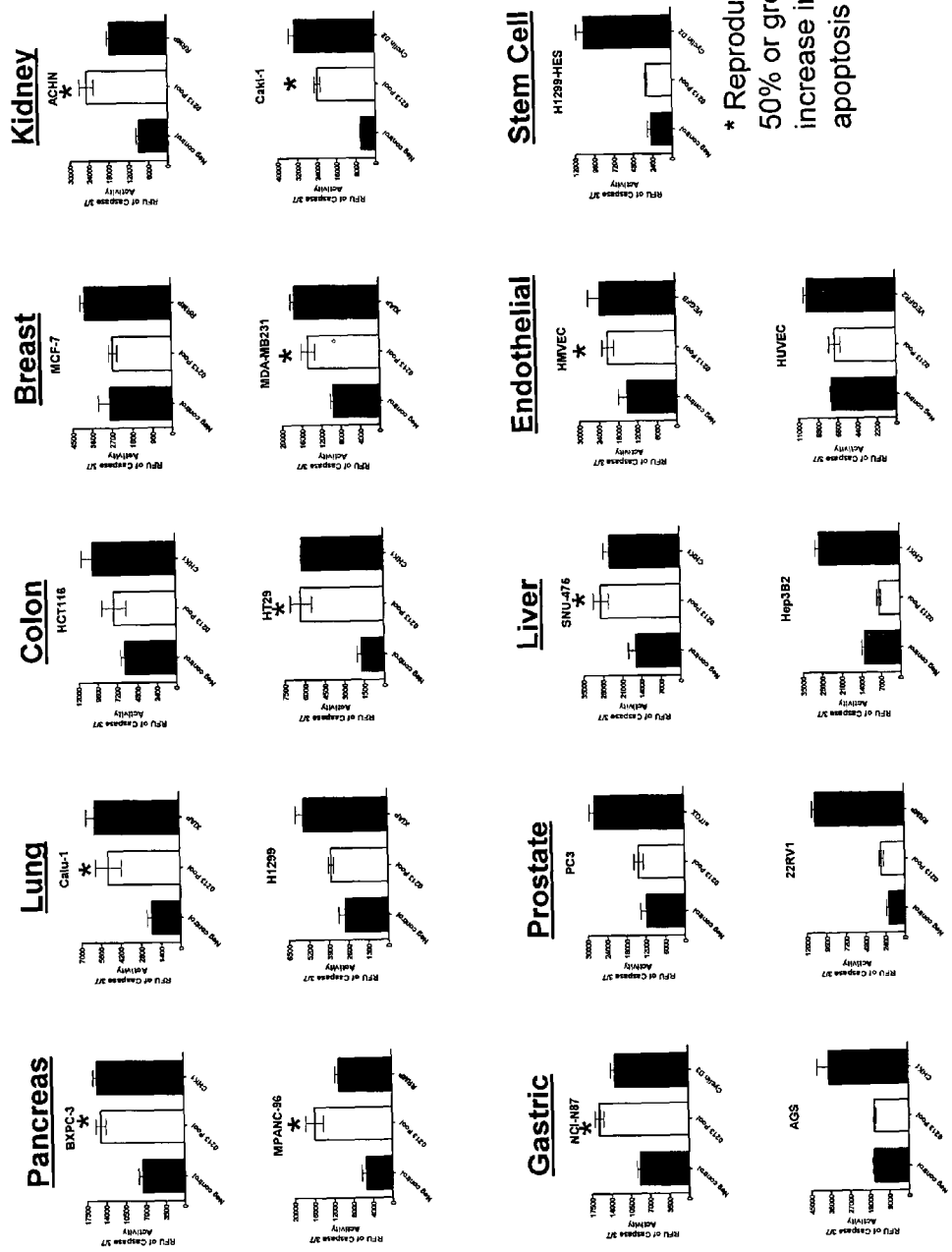

FIG. 14. Knockdown of ITGB6 mRNA Induces Apoptosis in Multiple Cancer Cells.

Figure 15:
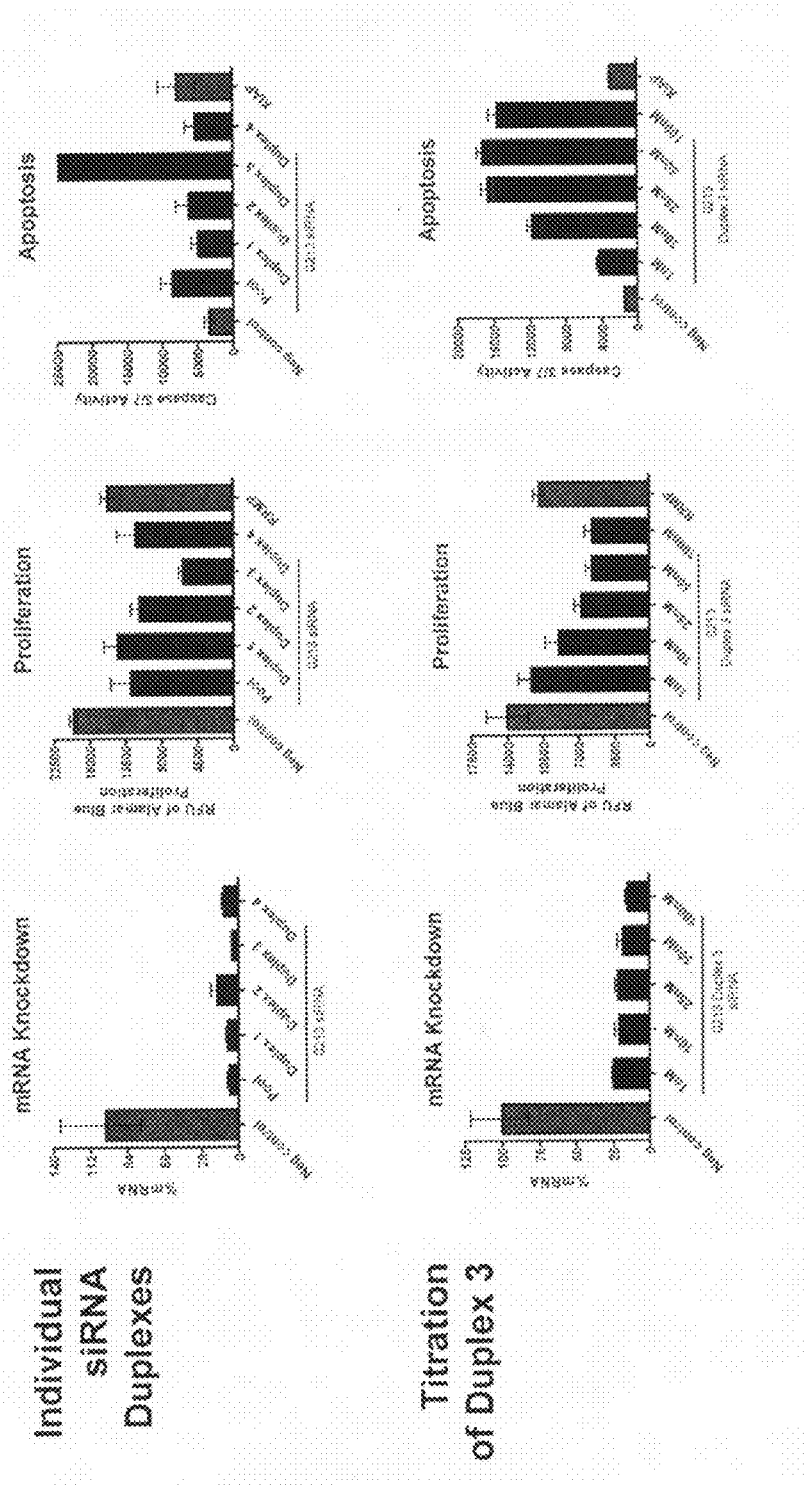

FIG. 15. Knockdown of ITGB6 mRNA Inhibits Proliferation and Induces Apoptosis in MPANC96 Pancreatic Cancer Cells.

Figure 16:
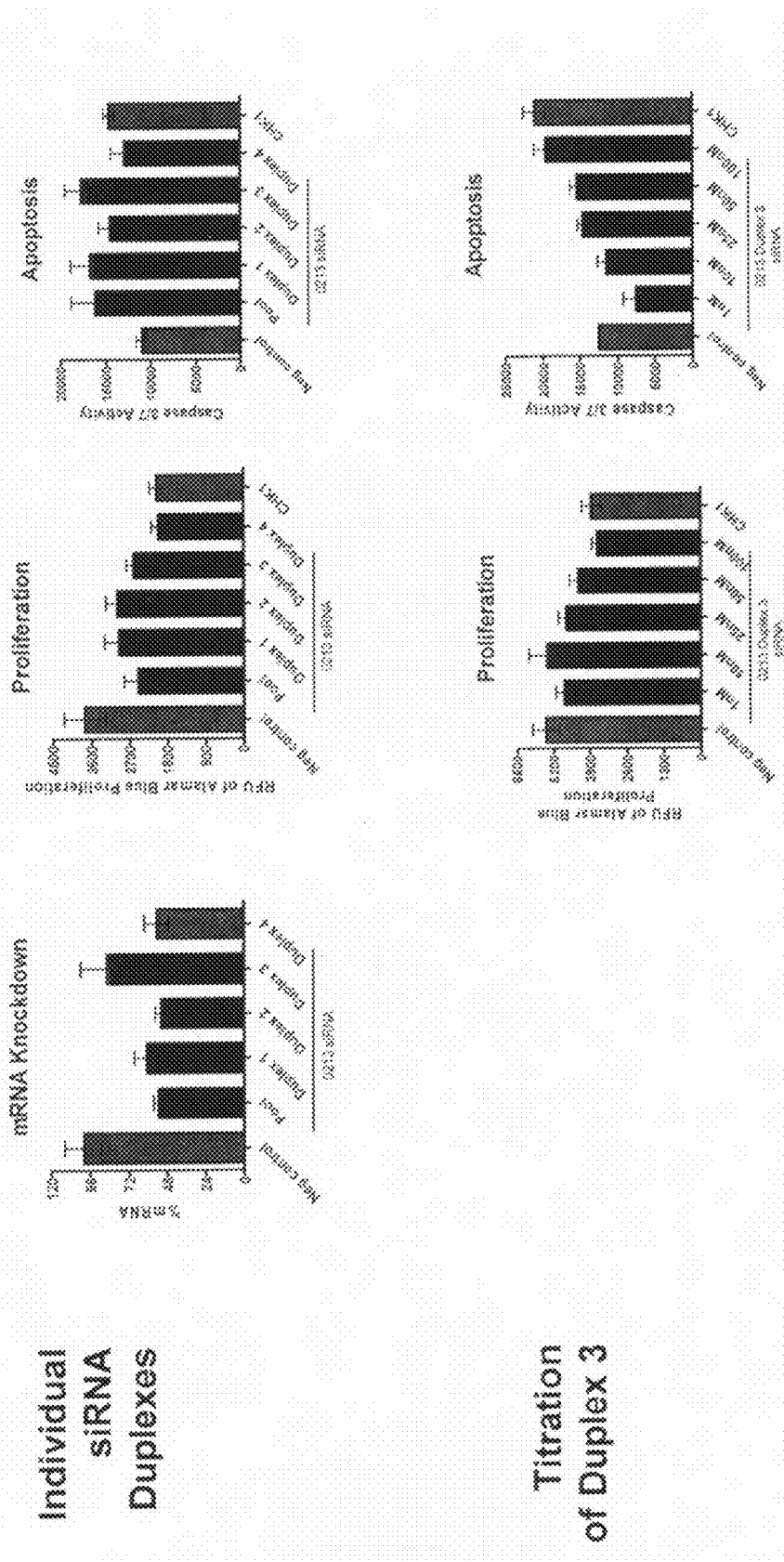

FIG. 16. Knockdown of ITGB6 mRNA Inhibits Proliferation and Induces Apoptosis in BXPC-3 Pancreatic Cancer Cells.

Figure 17:
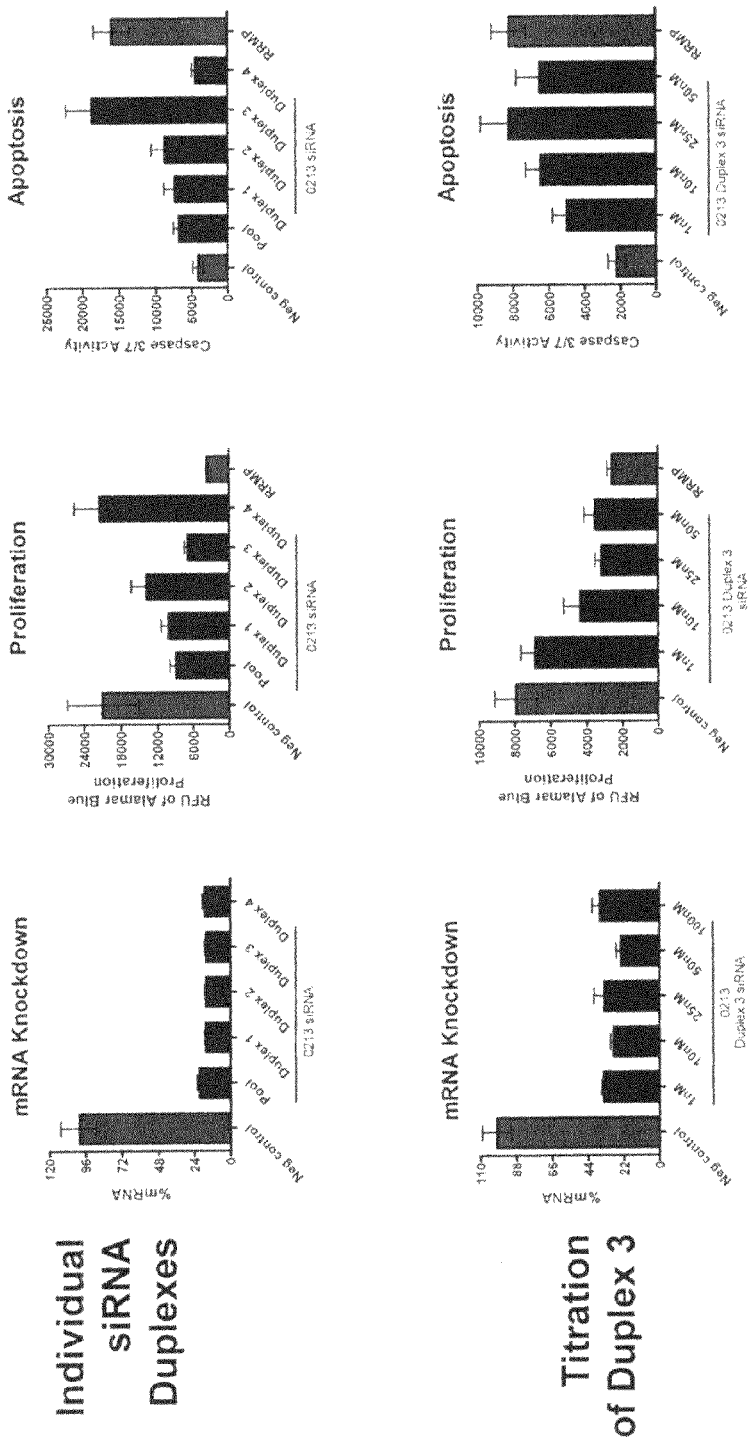

FIG. 17. Knockdown of ITGB6 mRNA Inhibits Proliferation and Induces Apoptosis in HT29 Colon Cancer Cells.

Figure 18:
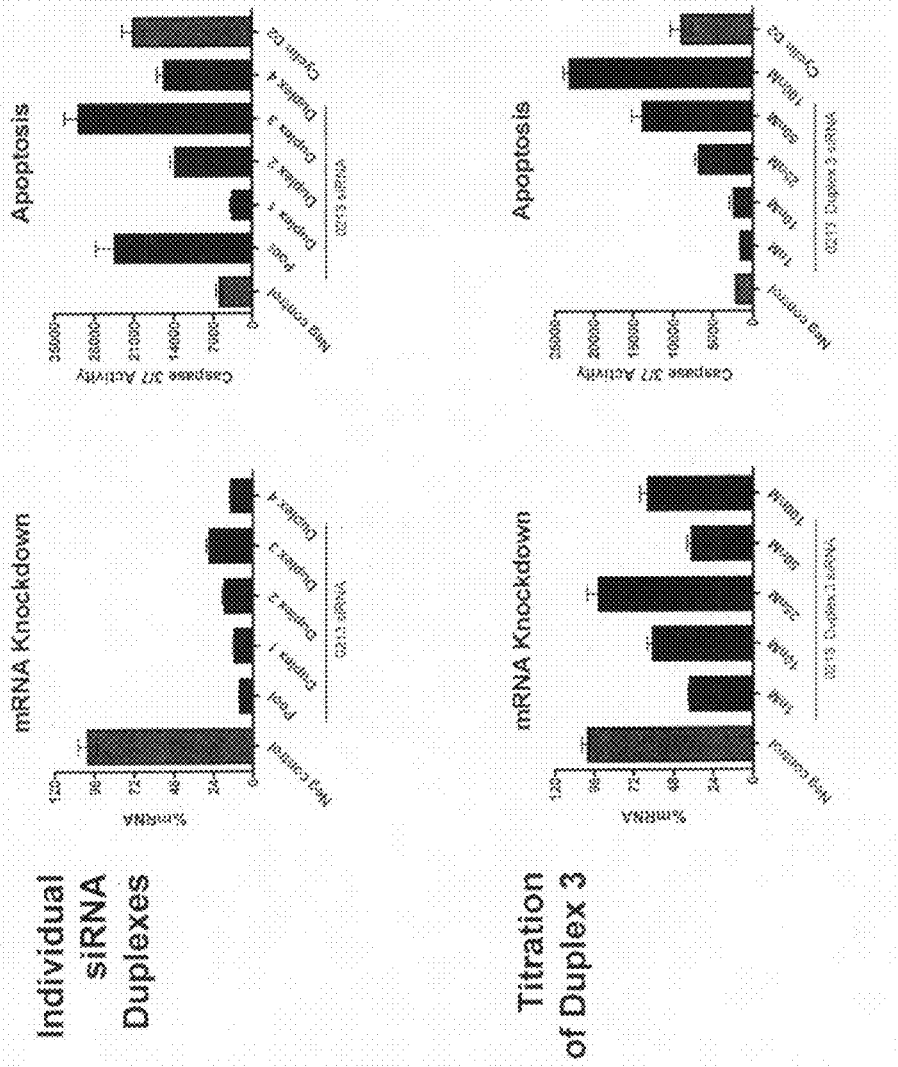

FIG. 18. Knockdown of ITGB6 mRNA Induces Apoptosis in Caki-1 Kidney Cancer Cells.

Figure 19:
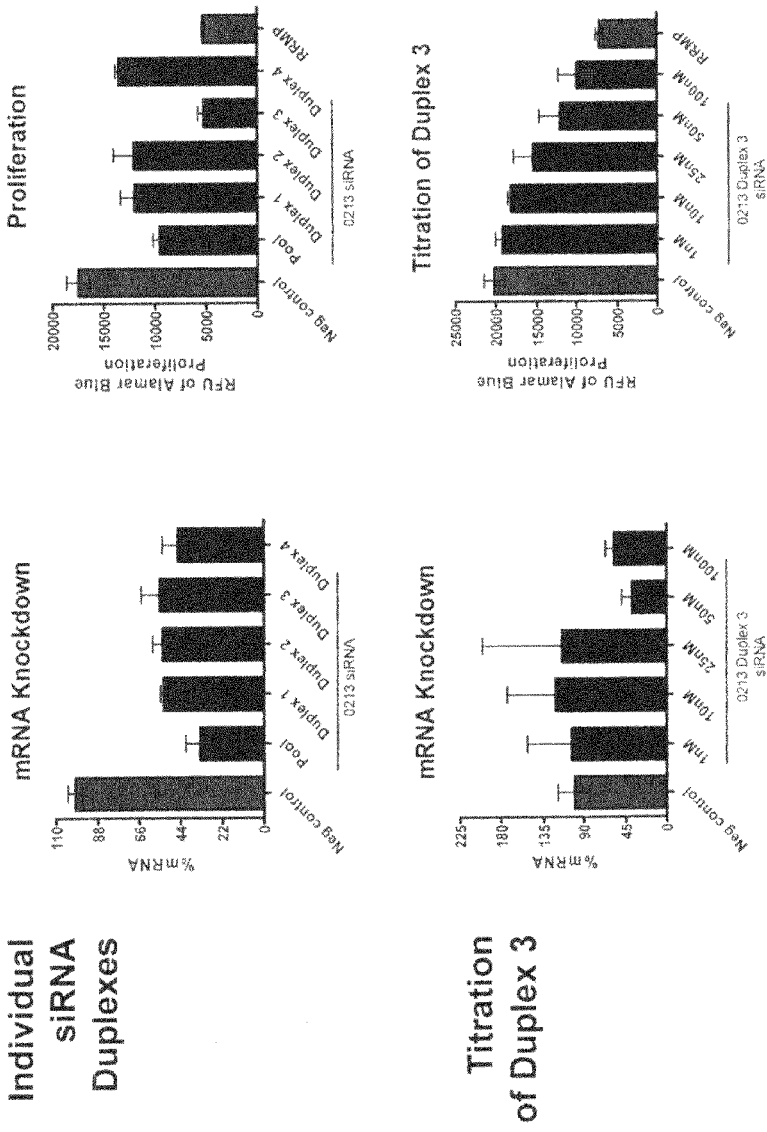

FIG. 19. Knockdown of ITGB6 mRNA Inhibits Proliferation in H1299 Lung Cancer Cells.

Figure 20:
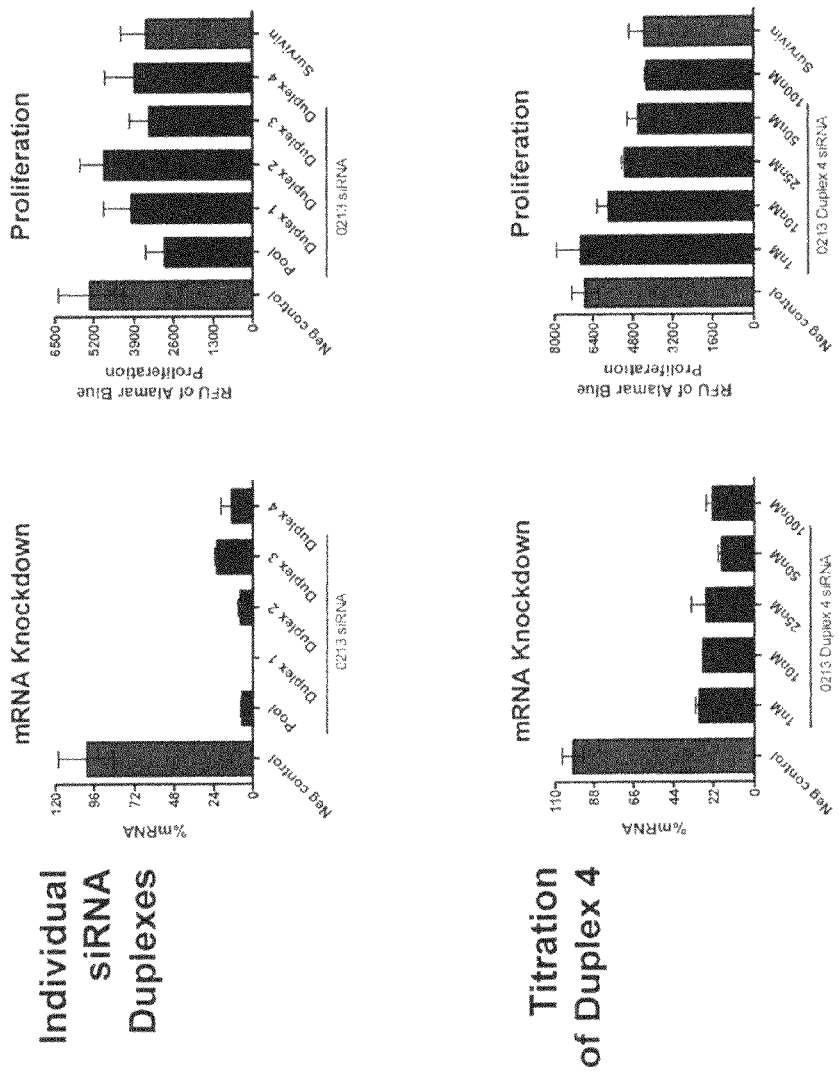

FIG. 20. Knockdown of ITGB6 mRNA Inhibits Proliferation in H1299-HES Spheroid Cancer Cells (Cancer Stem Cells).

Figure 21:
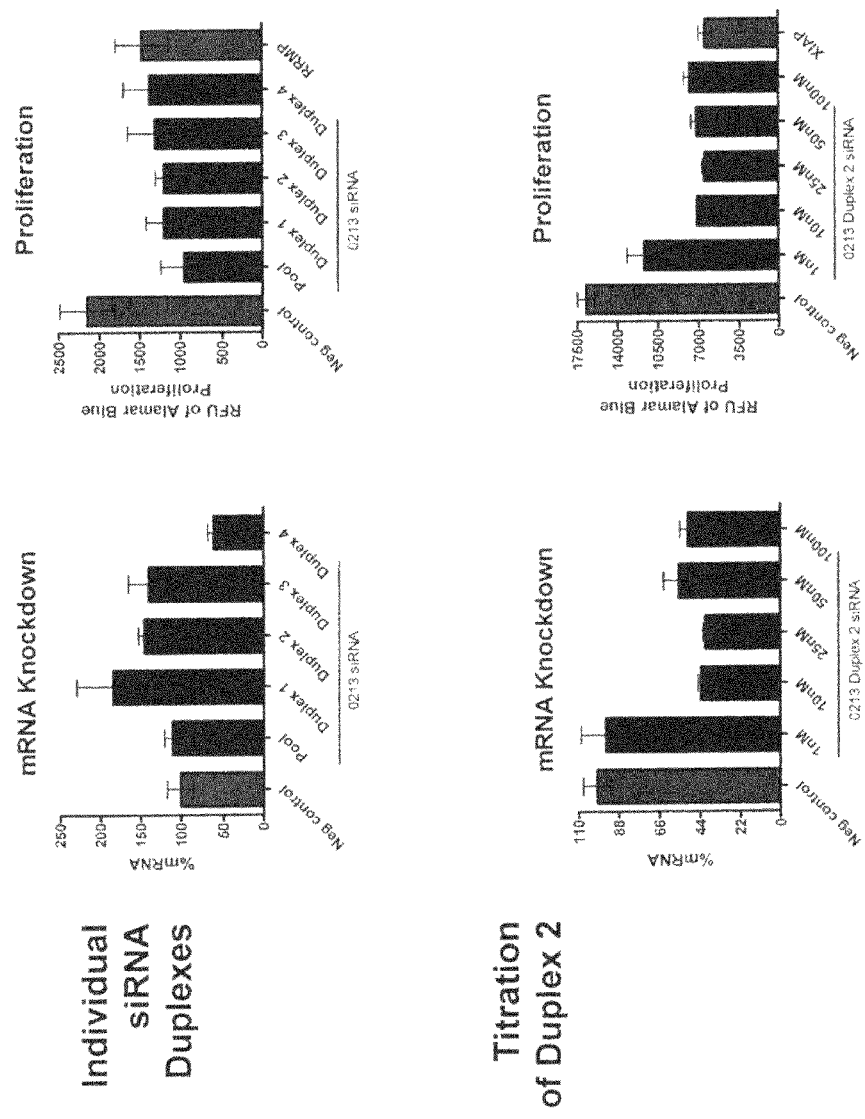

FIG. 21. Knockdown of ITGB6 mRNA Inhibits Proliferation in NCI-N87 Gastric Cancer Cells.

Figure 22:
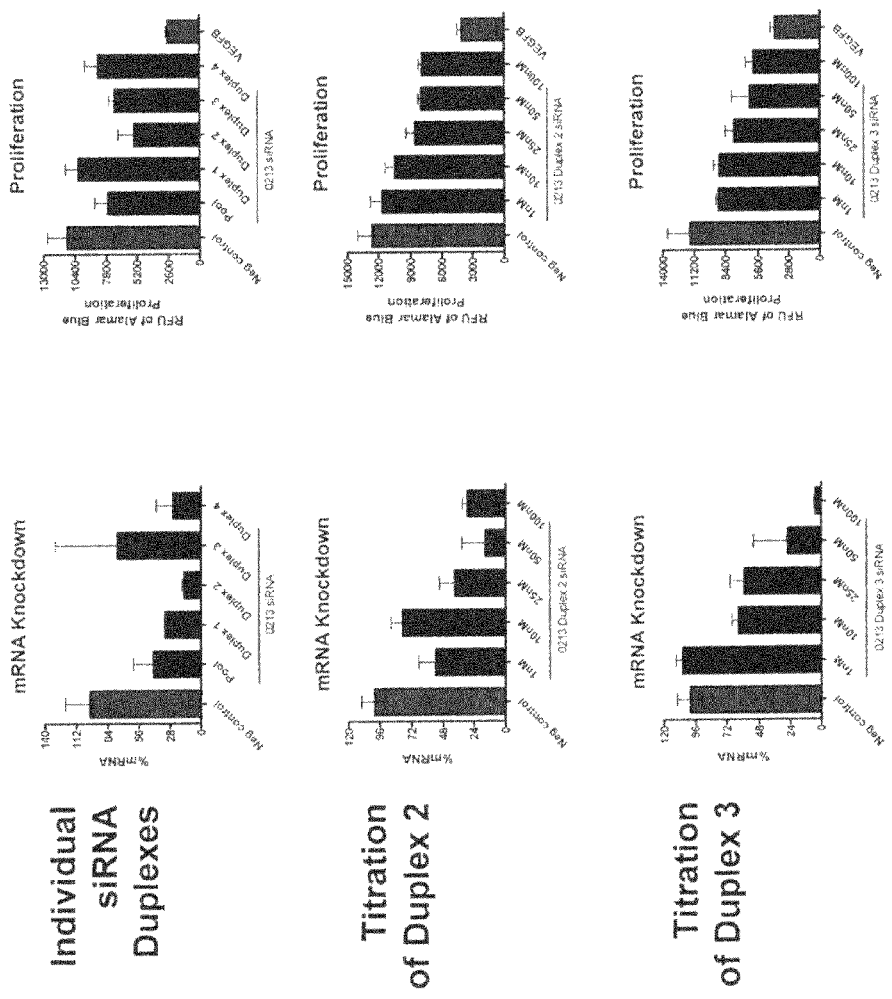

FIG. 22. Knockdown of ITGB6 mRNA Inhibits Proliferation in HUVEC Endothelial Cells.

Figure 23:
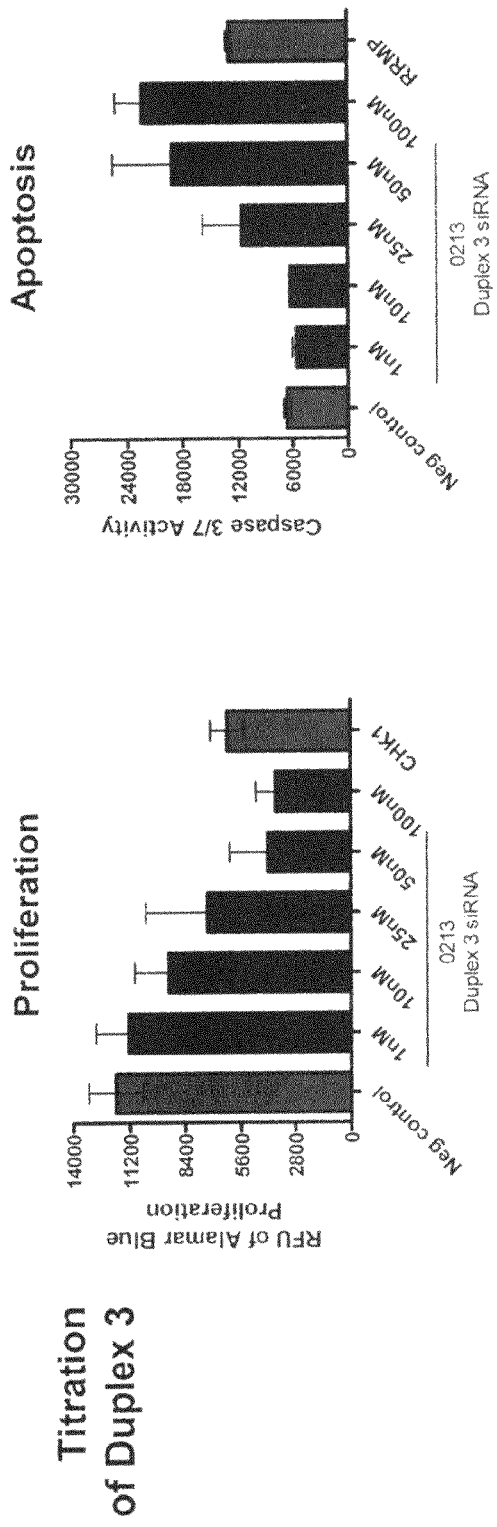

FIG. 23. Knockdown of ITGB6 mRNA Inhibits Proliferation and Induces Apoptosis in HMVEC Endothelial Cells.

Figure 24:
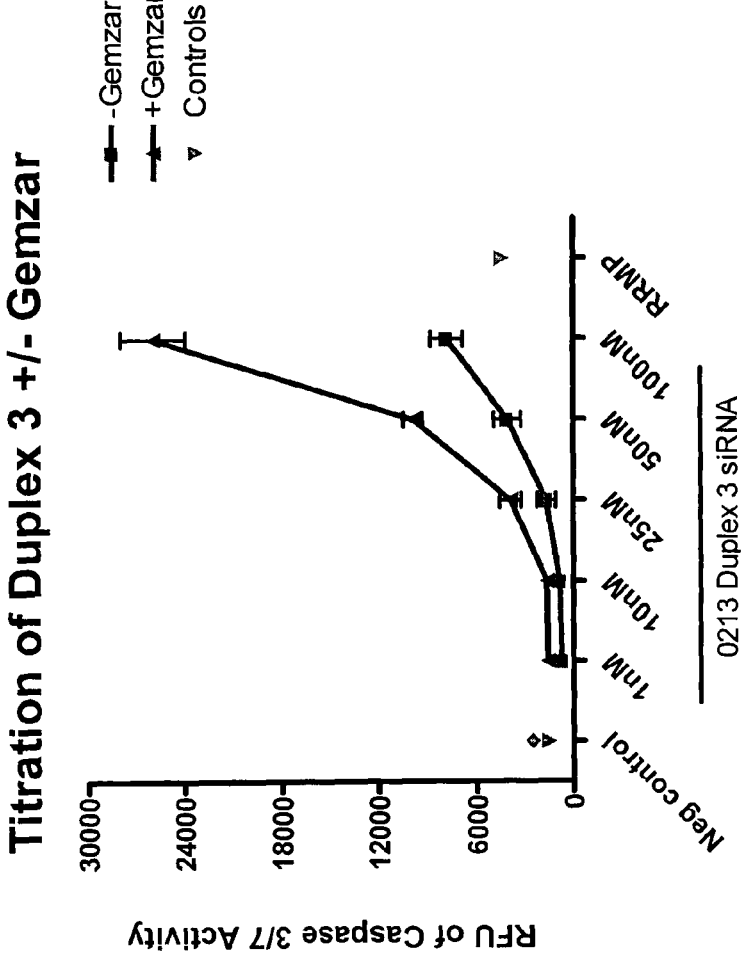

FIG. 24. Knockdown of ITGB6 mRNA in Combination with Gemzar Increases Apoptosis in Calu-1 Lung Cancer Cells.

Figure 25:
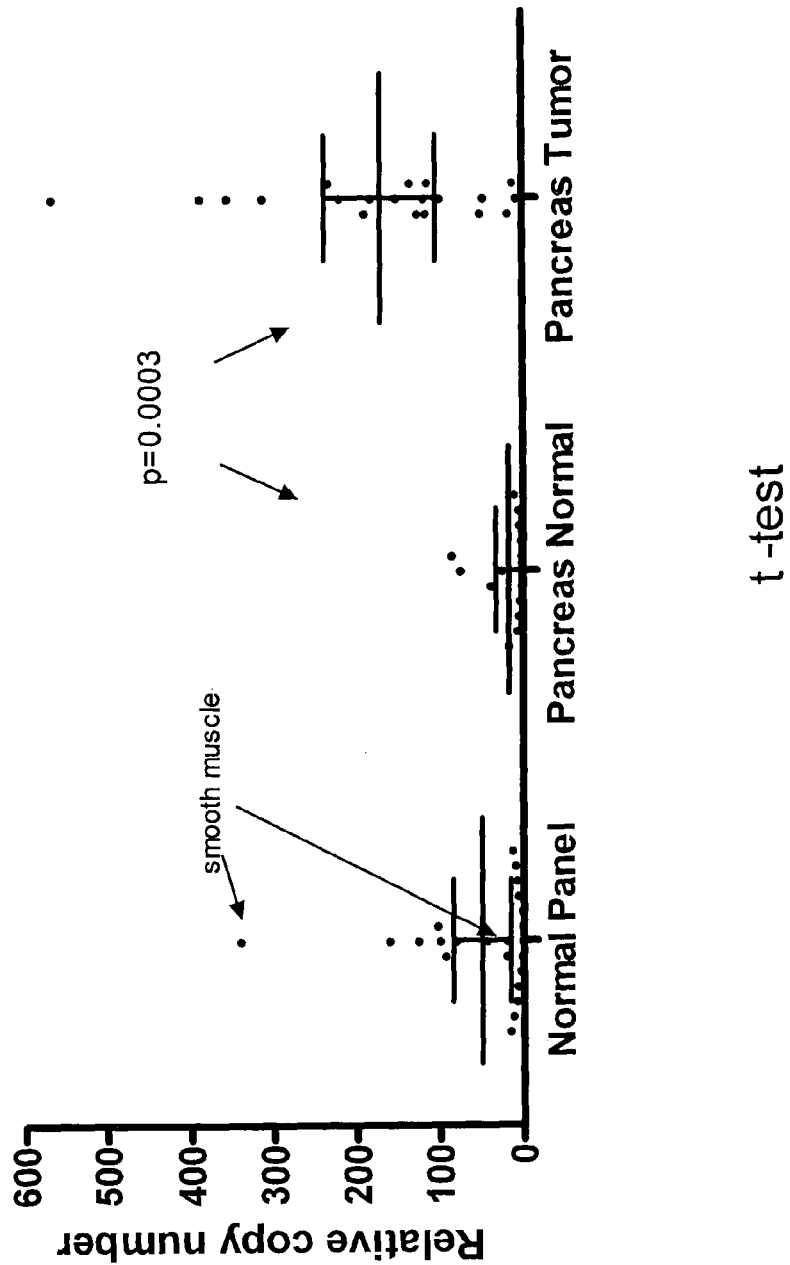

FIG. 25. ITGB6 mRNA in Pancreatic Tumor.

Figure 26:
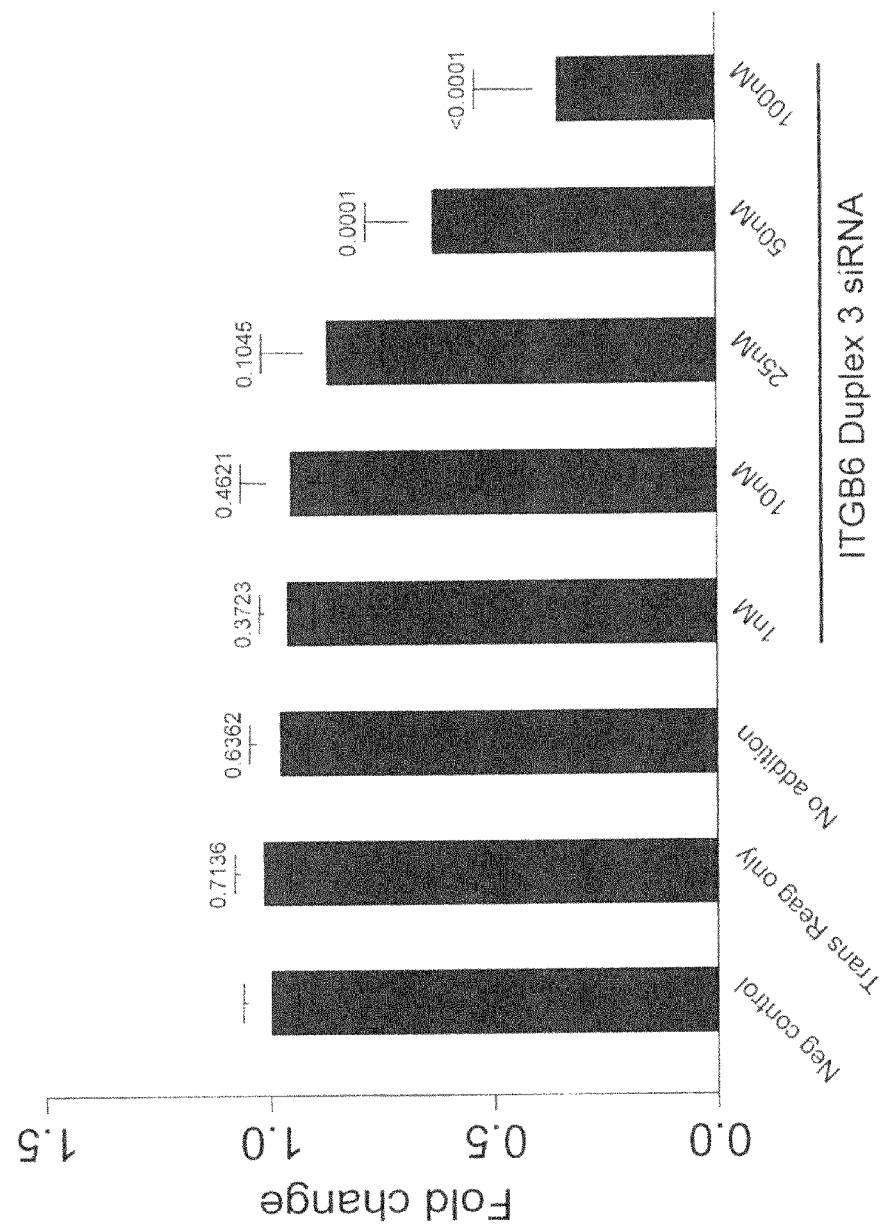

FIG. 26. Knockdown of ITGB63 Inhibits Proliferation in H1299 Lung Cancer cells (Normalized over 3 Experiments).

GLG1

FIG. 27. GLG1 is Overexpressed in Multiple Tumor Types, as indicated by IHC.

Figure 28:
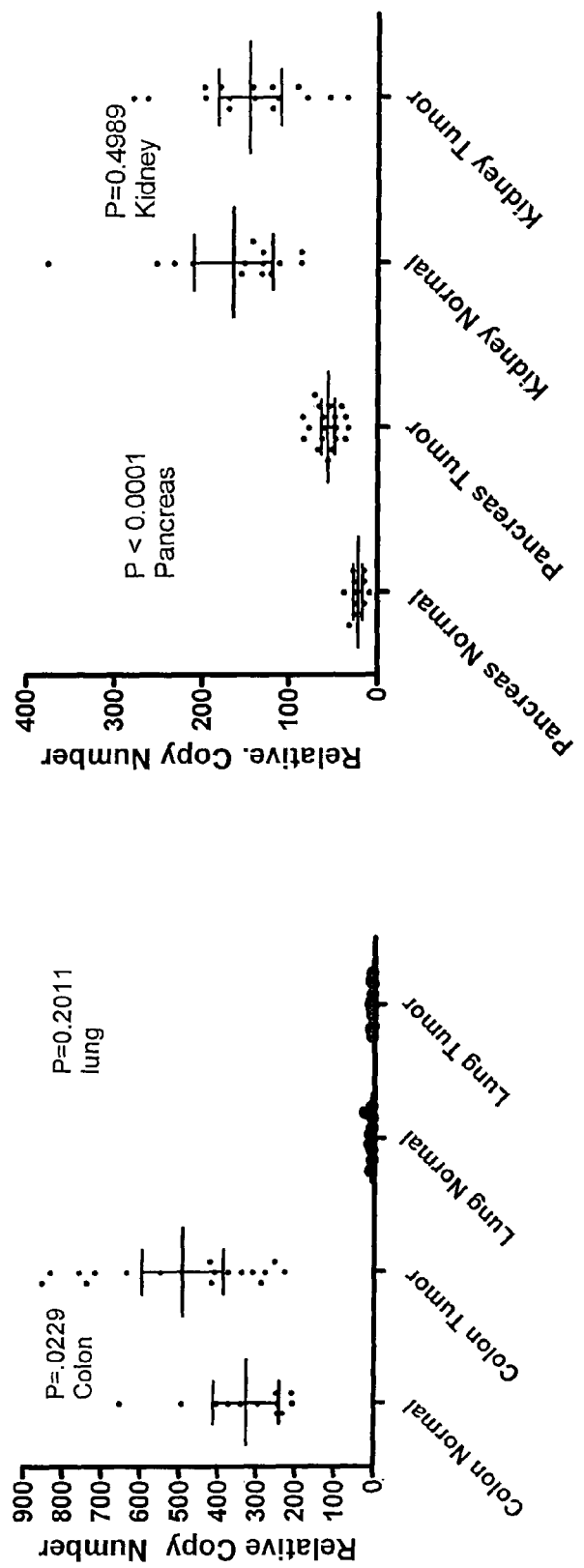

FIG. 28. GLG1 mRNA Expression Analysis in Multiple Tumor Tissues.

Figure 29:
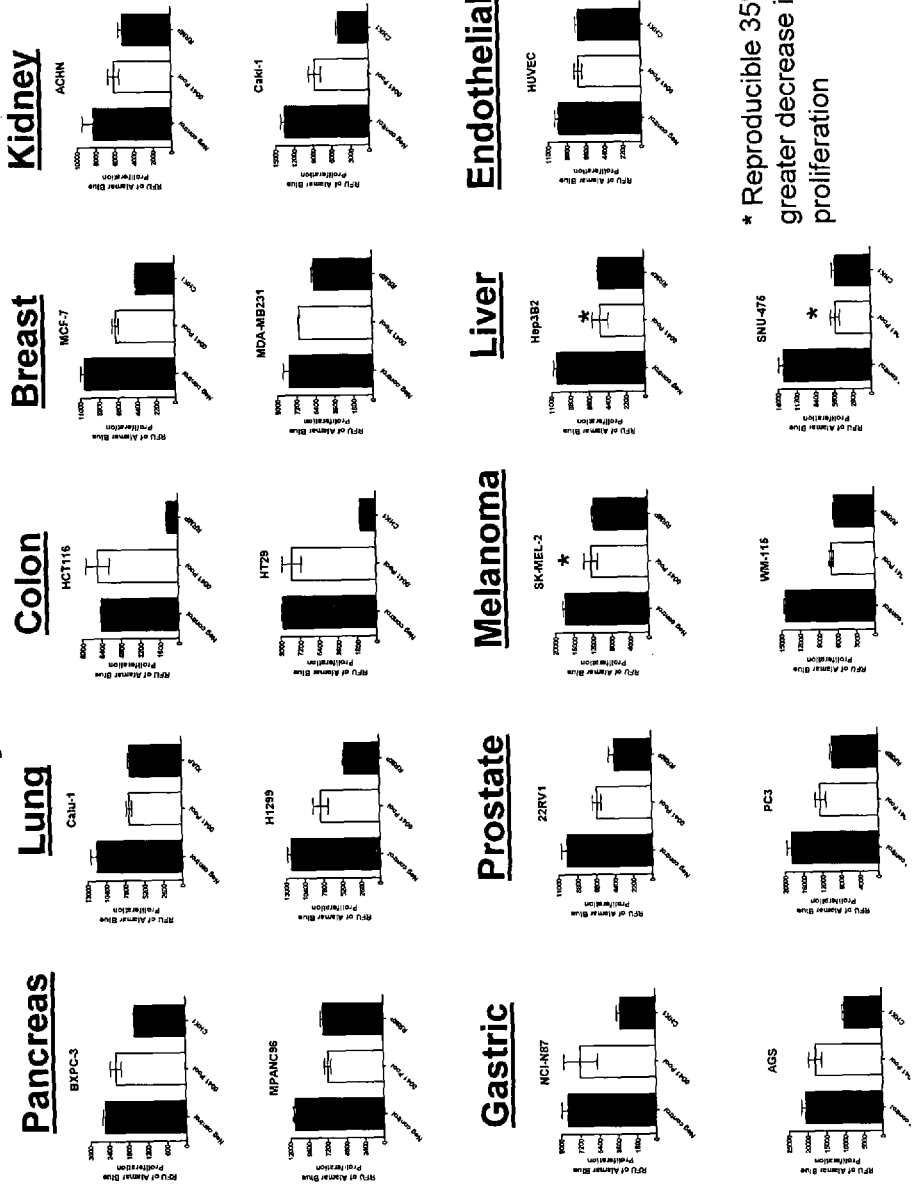

FIG. 29. Knockdown of GLG1 mRNA Inhibits Proliferation in Multiple Cancer Cells.

Figure 30:
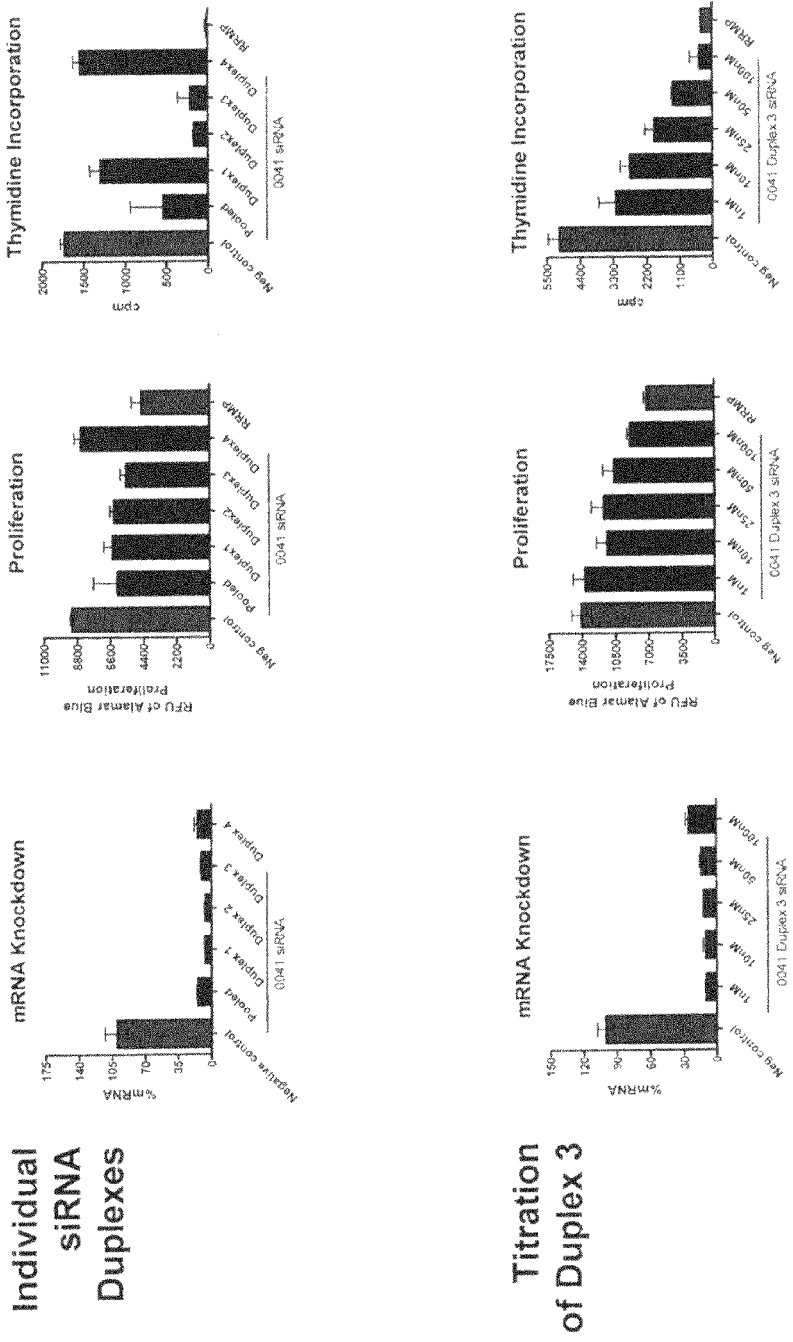

FIG. 30. Knockdown of GLG1 mRNA Inhibits Proliferation in SNU-475 Kidney Cancer Cells.

FIG. 31. mRNA sequence of GLG1, indicating siRNA target regions.

KIAA0152

FIG. 32. KIAA0152 is Over-Expressed in Multiple Tumor Types, as indicated by IHC.

Figure 33:
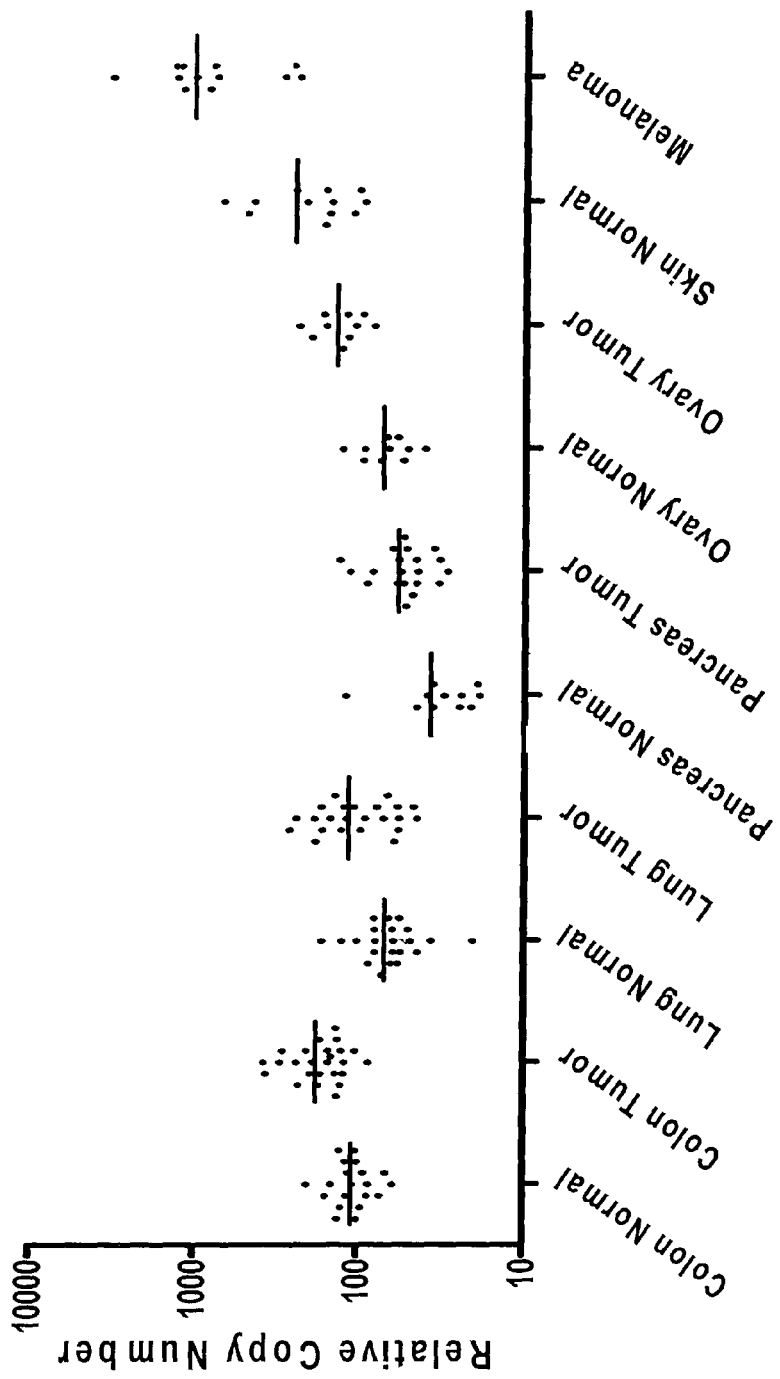

FIG. 33. KIAA0152 mRNA Expression Analysis in Multiple Tumor Tissues.

Figure 34:
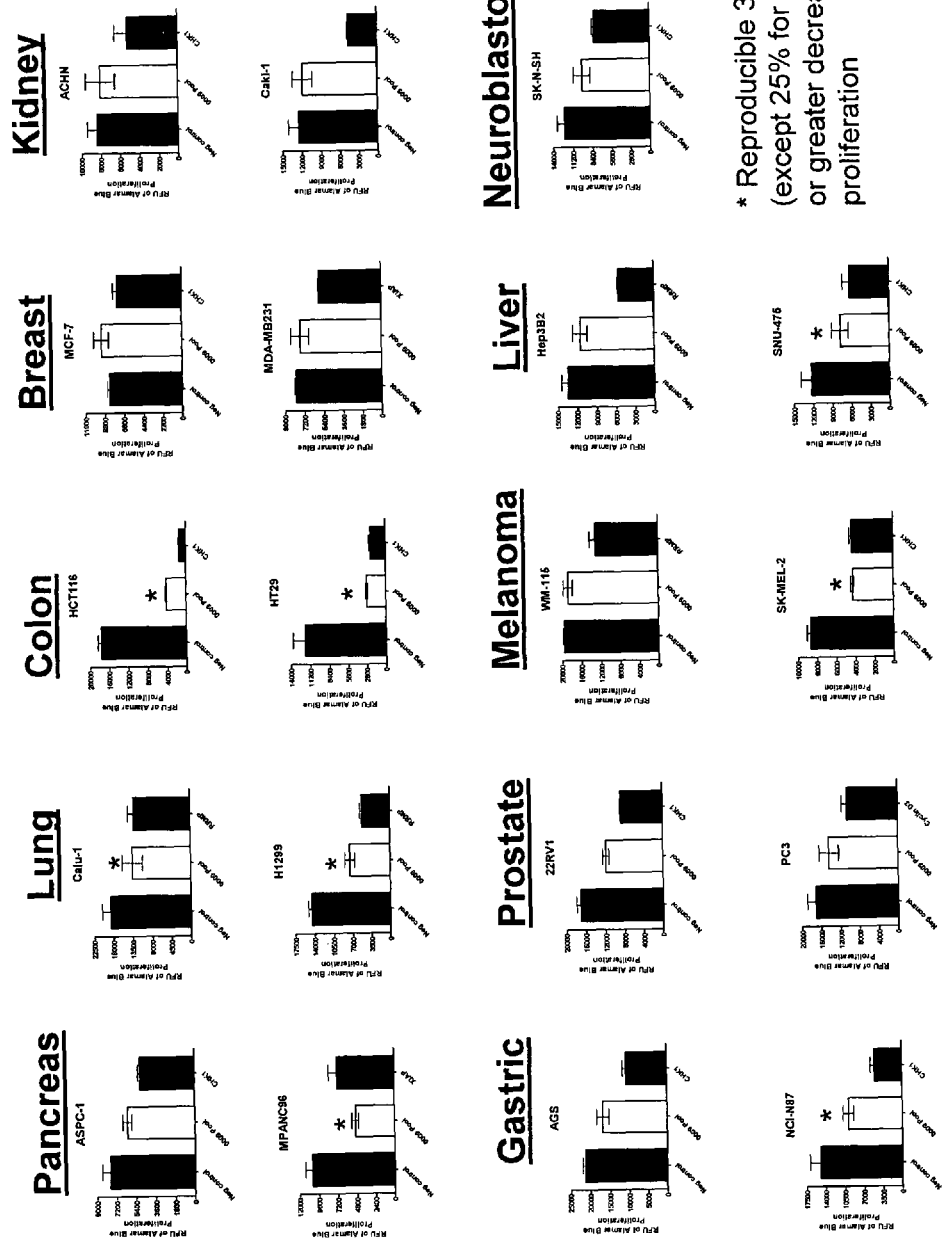

FIG. 34. Knockdown of KIAA0152 mRNA Inhibits Proliferation in Multiple Cancer Cells.

Figure 35:
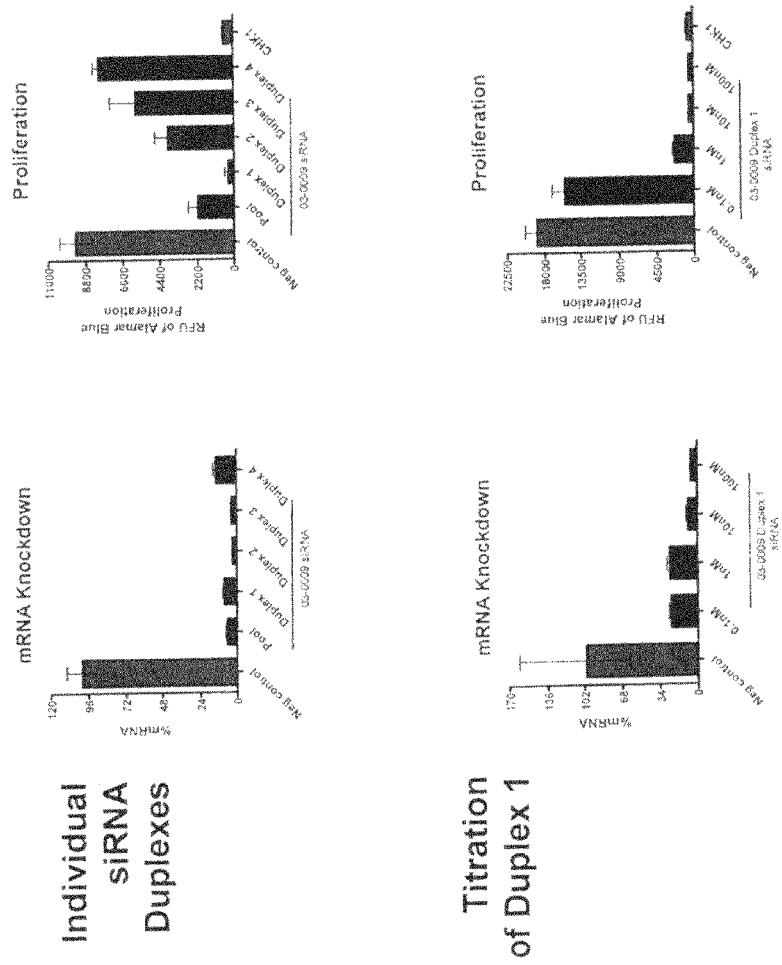

FIG. 35. Knockdown of KIAA0152 mRNA Inhibits Proliferation in HCT116 Colon Cancer Cells.

Figure 36:
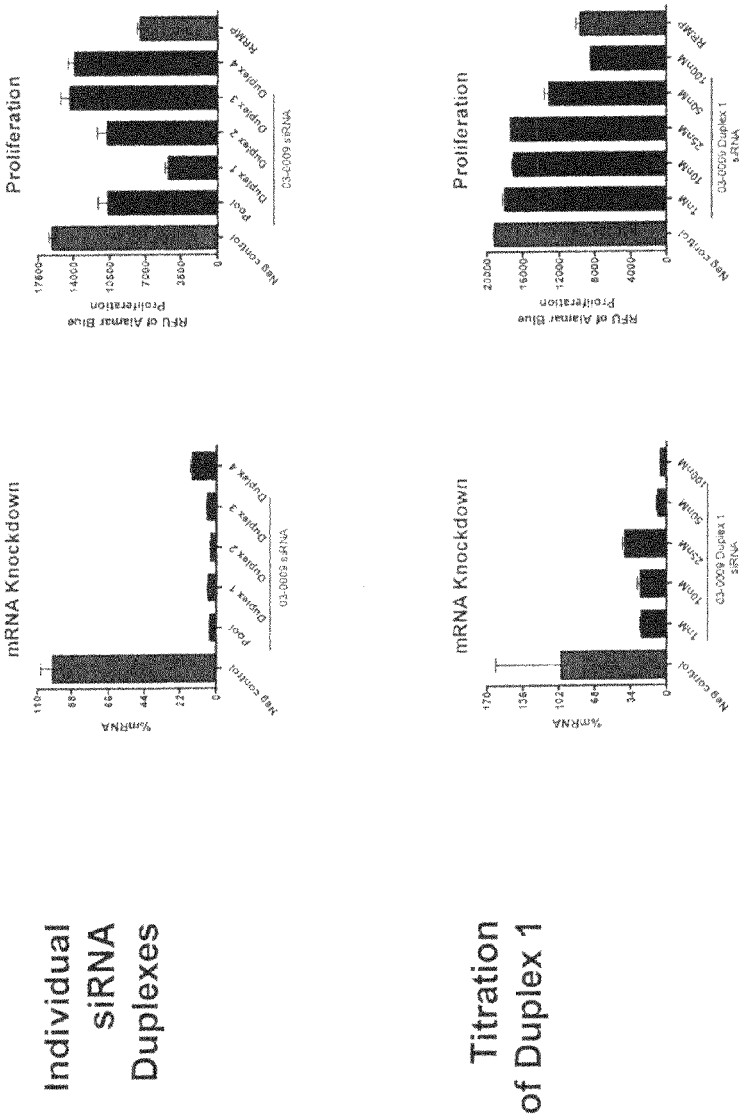

FIG. 36. Knockdown of KIAA0152 mRNA Inhibits Proliferation in H1299 Lung Cancer Cells.

Figure 37:
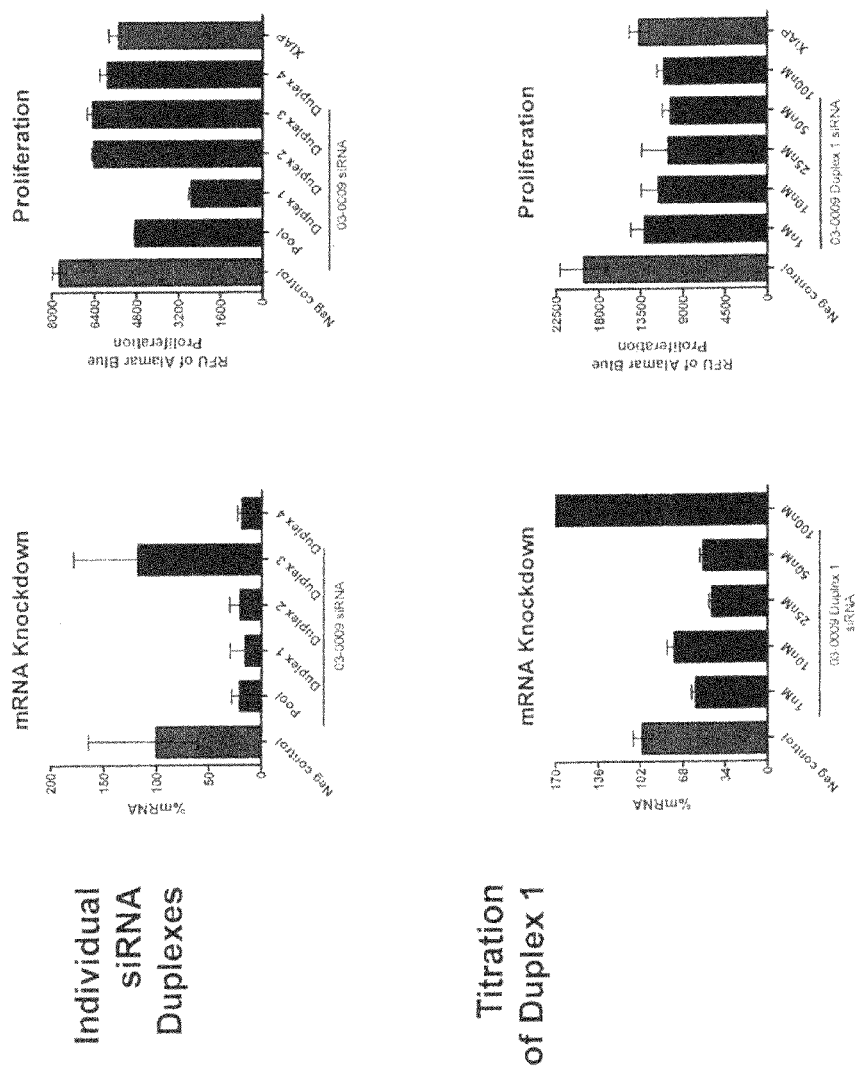

FIG. 37. Knockdown of KIAA0152 mRNA Inhibits Proliferation in MPANC96 Pancreatic Cancer Cells.

Figure 38:
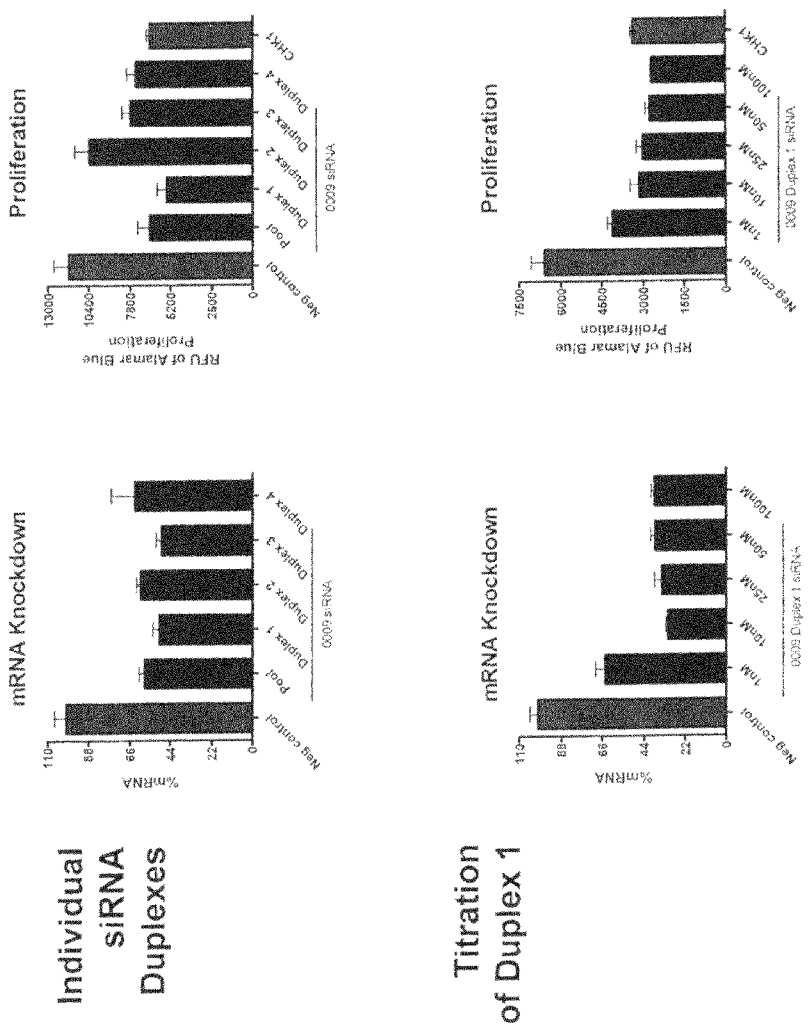

FIG. 38. Knockdown of KIAA0152 mRNA Inhibits Proliferation in NCI-N87 Gastric Cancer Cells.

Figure 39:
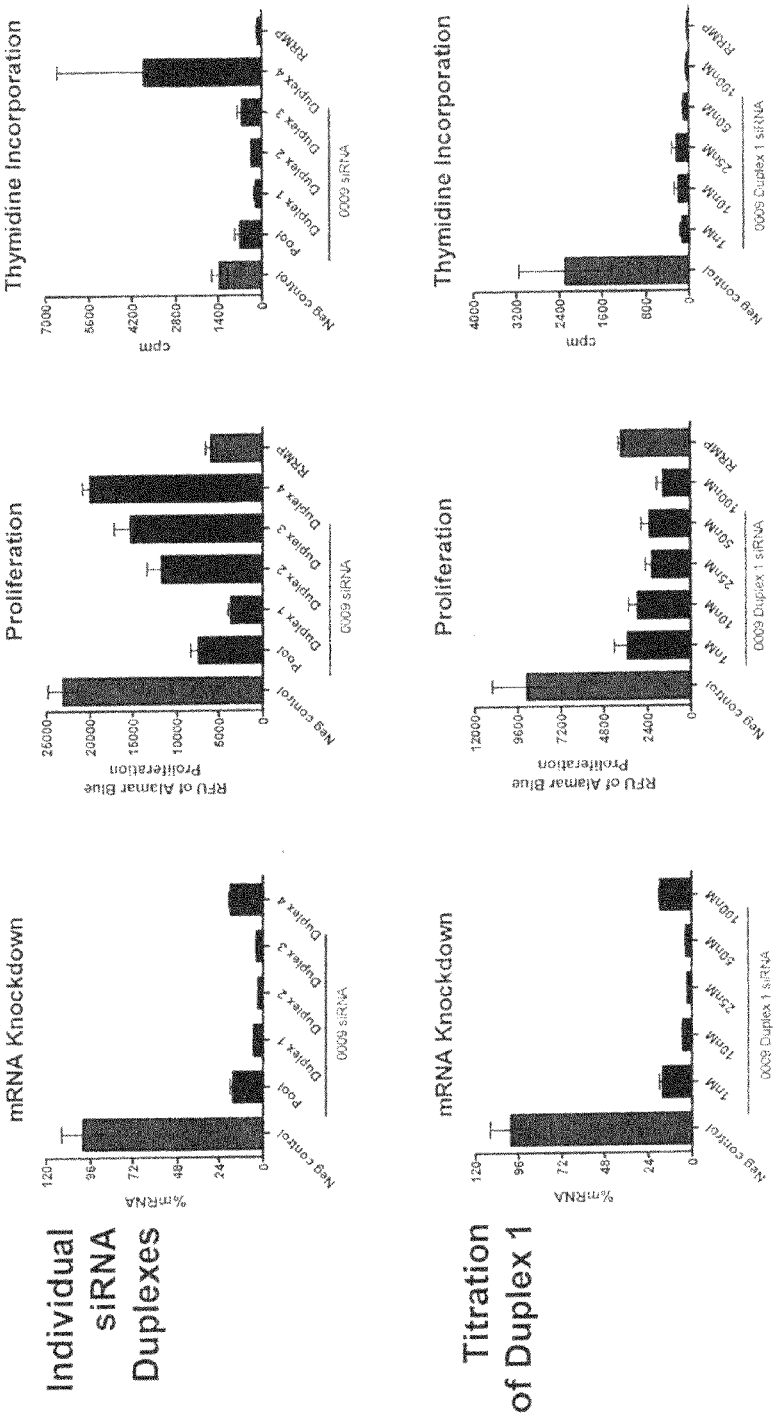

FIG. 39. Knockdown of KIAA0152 mRNA Inhibits Proliferation in SK-MEL-2 Melanoma Cancer Cells.

Figure 40:
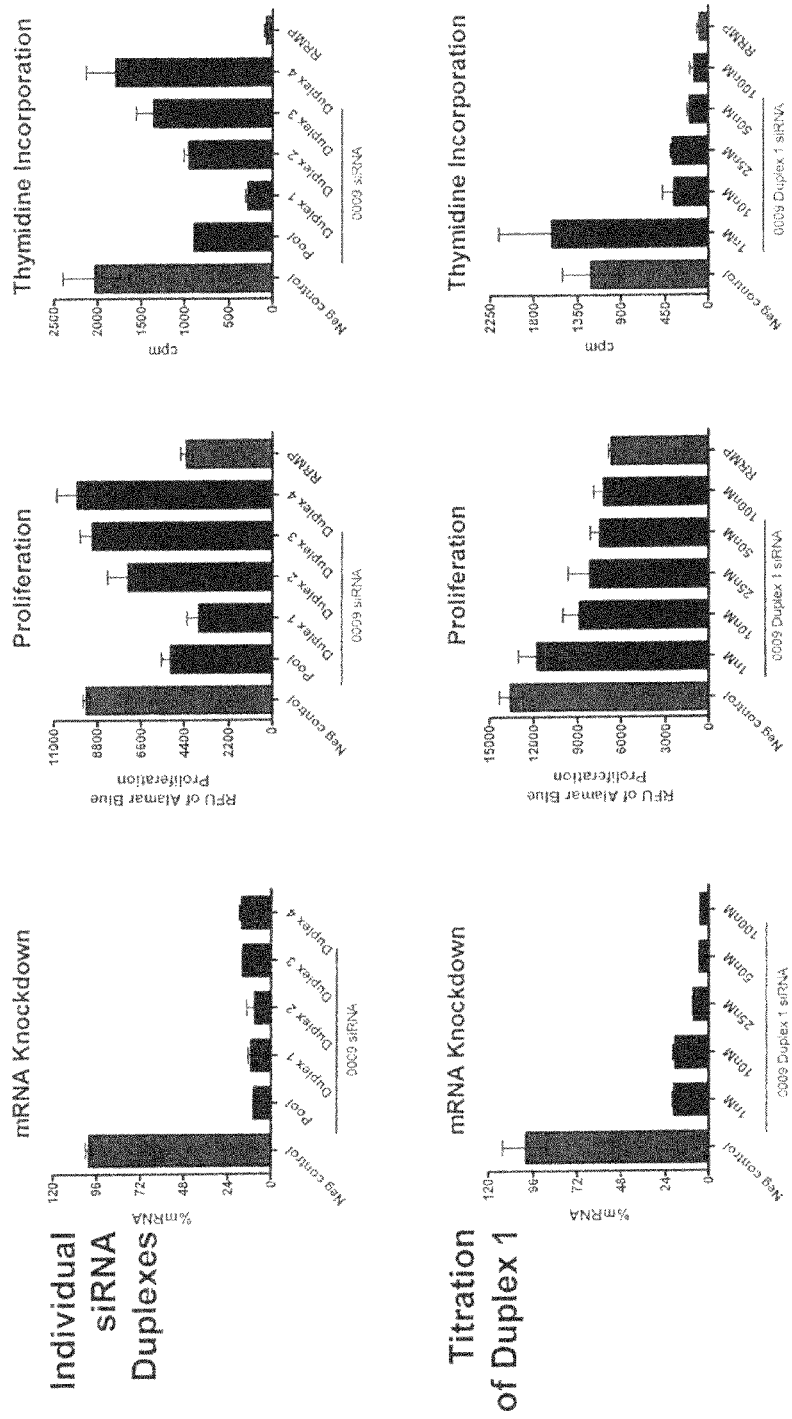

FIG. 40. Knockdown of KIAA0152 mRNA Inhibits Proliferation in SNU-475 Liver Cancer Cells.

Figure 41:
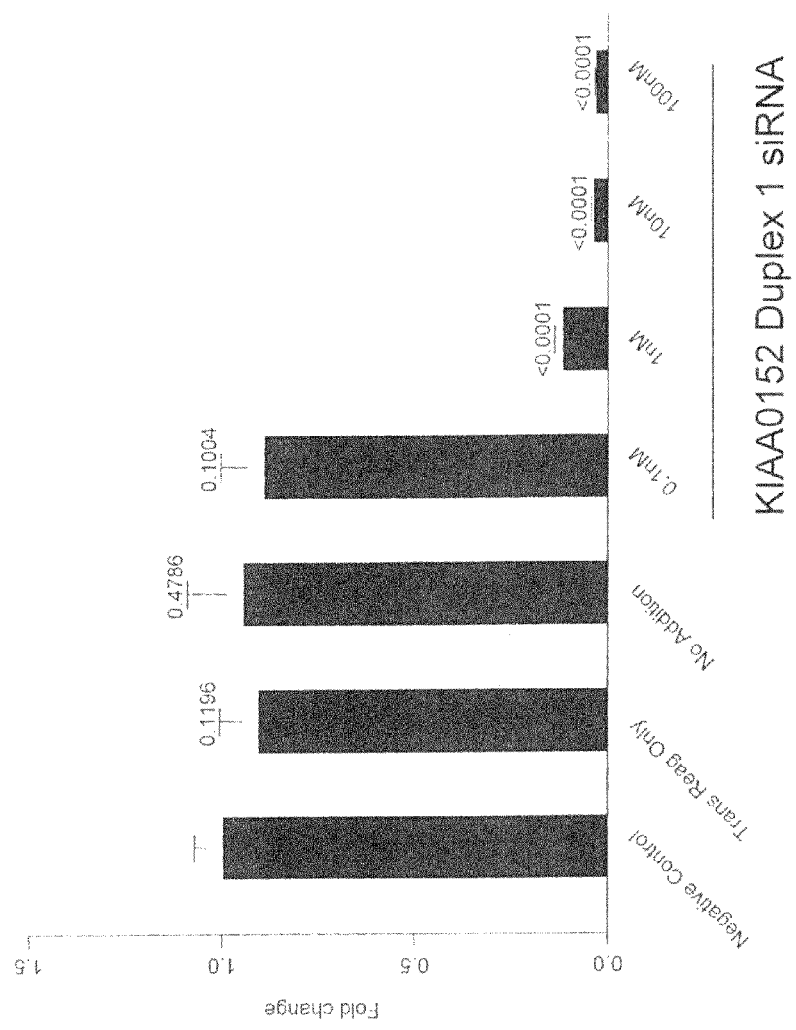

FIG. 41. Knockdown of KIAA0152 Inhibits Proliferation in HCT116 Colon Cancer Cells (normalized over 3 experiments).

Figure 42:
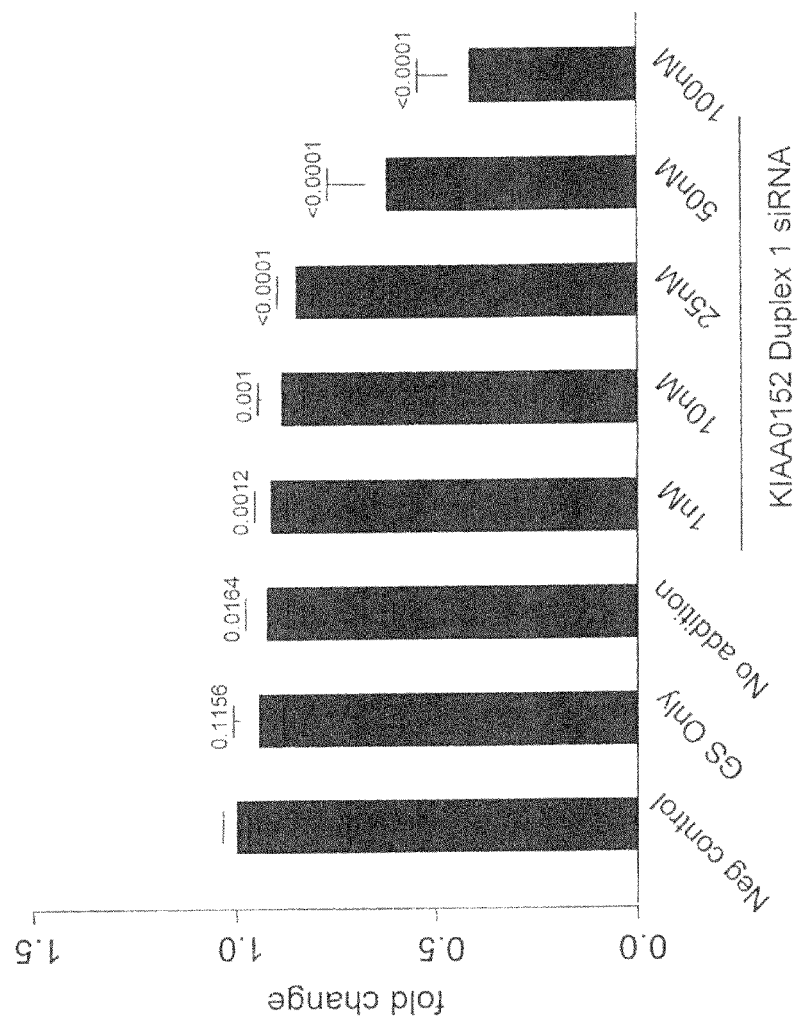

FIG. 42. Knockdown of KIAA0152 Inhibits Proliferation in H1299 Lung Cancer Cells (normalized over 3 experiments).

Figure 43:
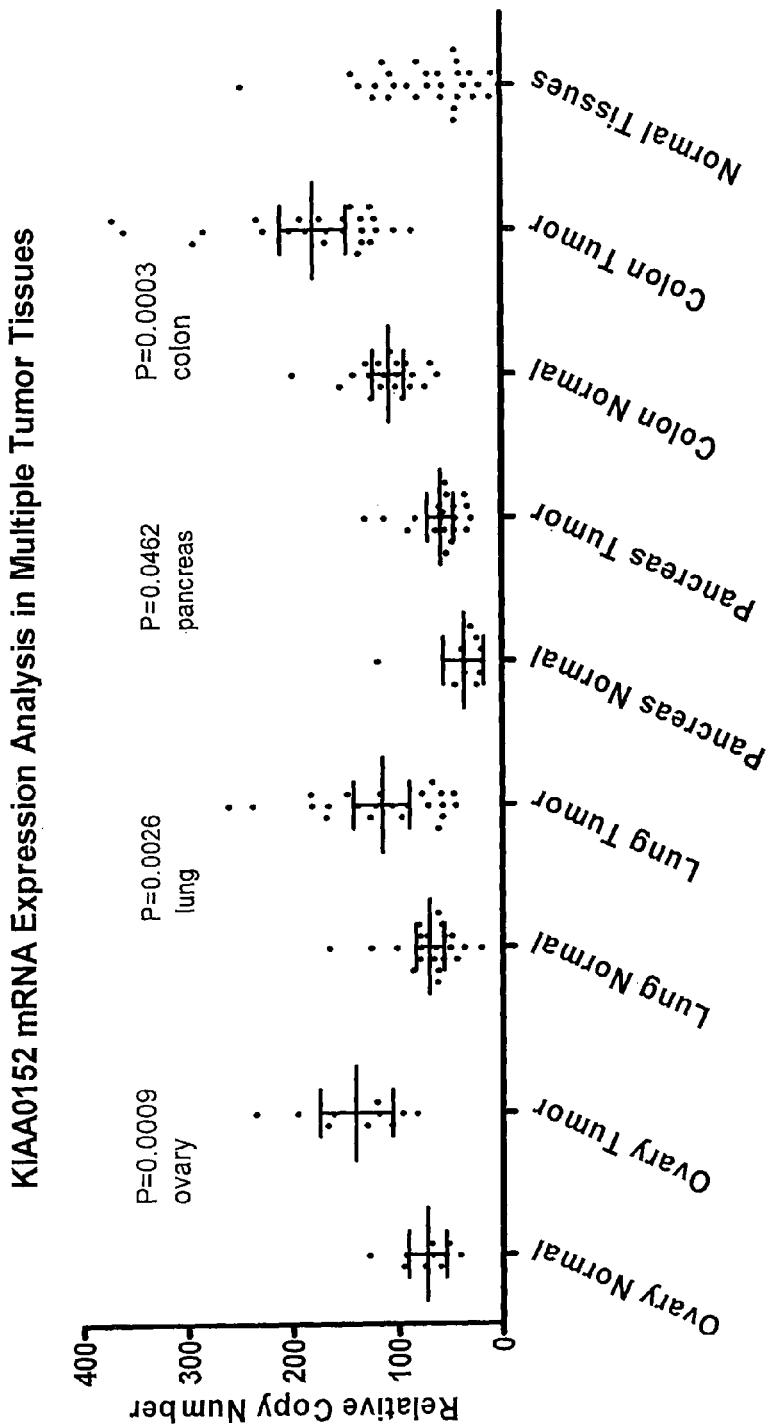

FIG. 43. KIAA0152 mRNA Expression Analysis in Multiple Tumor Tissues.

Figure 44:
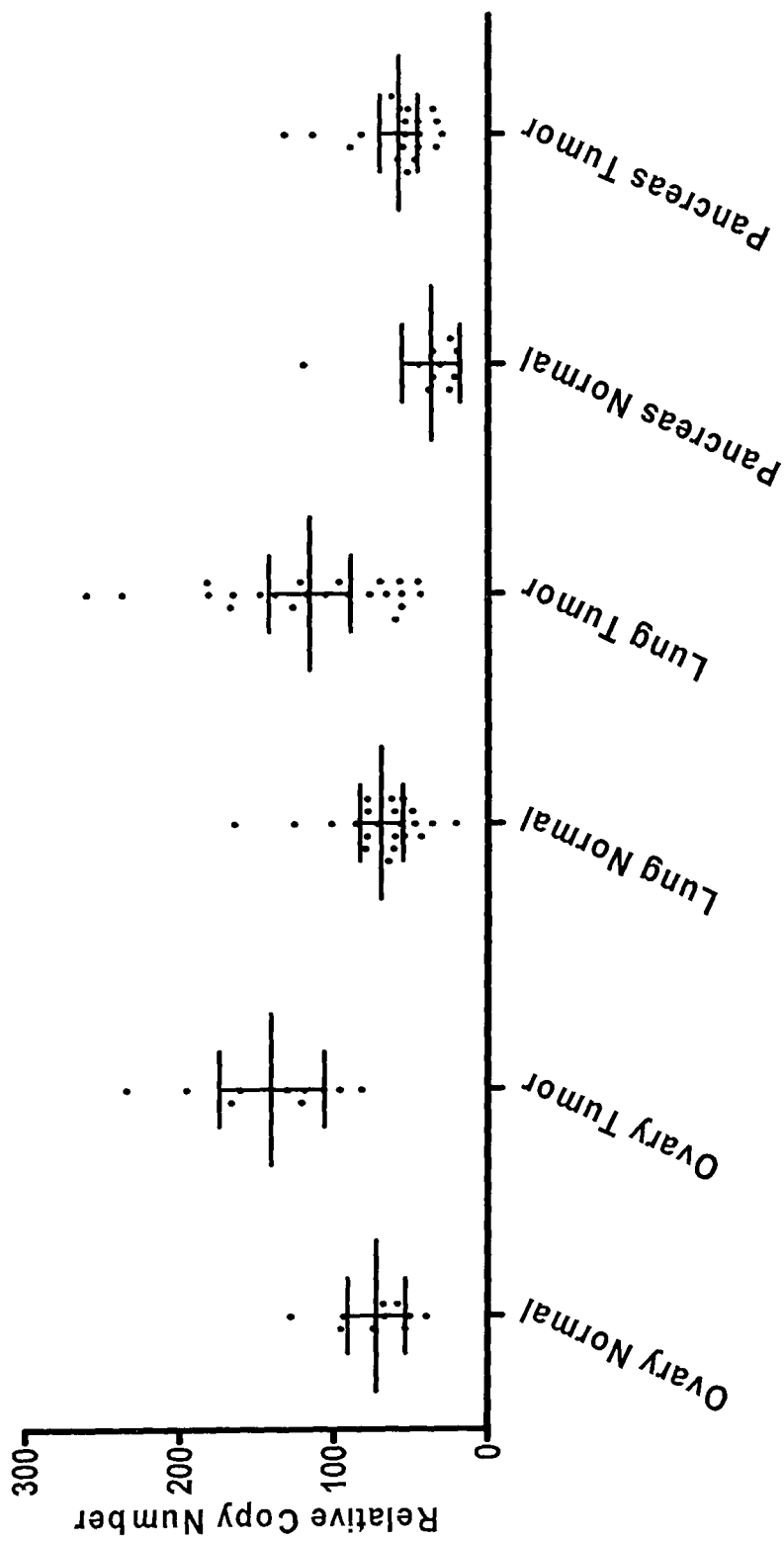

FIG. 44. KIAA0152 mRNA Expression Analysis in Multiple Tumor Tissues.

Figure 45:
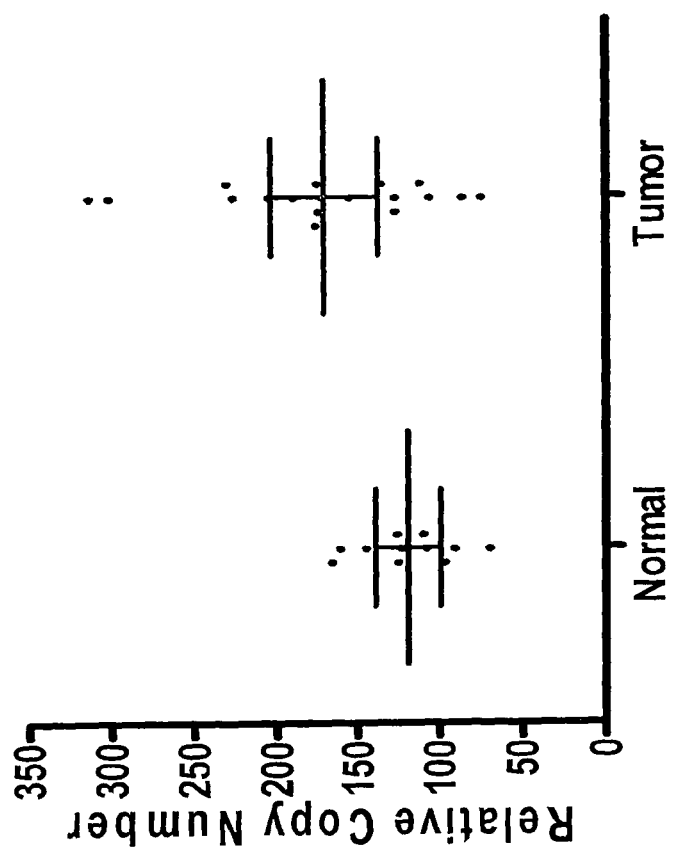

FIG. 45. KIAA0152 mRNA Expression in Colon Tumor Tissues.

FIG. 46. mRNA sequence of KIAA0152, indicating siRNA target regions.

Matriptase (ST14)

FIG. 47. Matriptase is Overexpressed in Multiple Tumor Types, as indicated by IHC.

Figure 48:
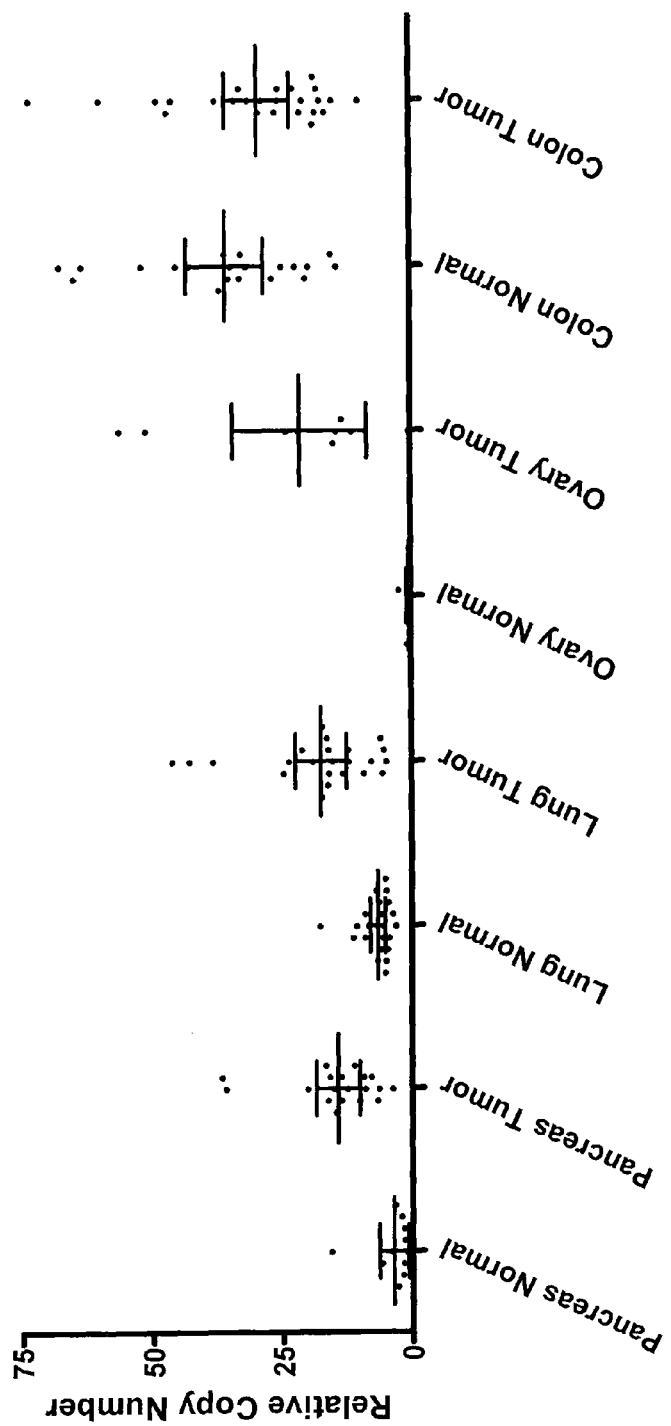

FIG. 48. Matriptase mRNA Expression Analysis Multiple Tumor Tissues.

Figure 49:
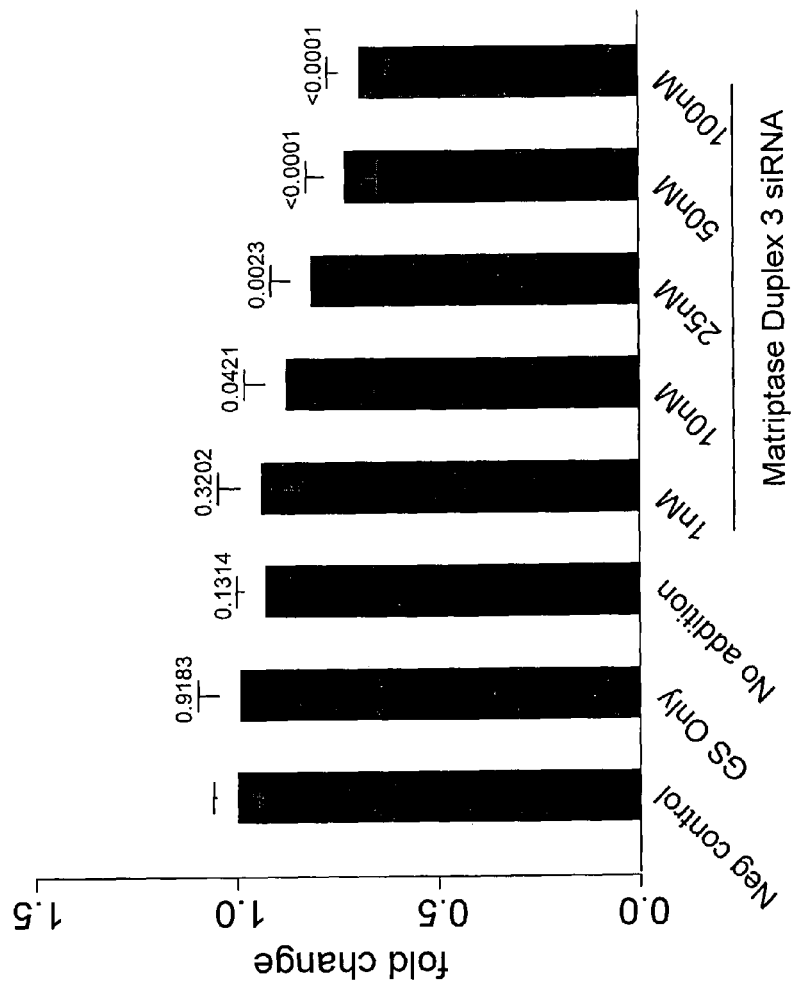

FIG. 49. Knockdown of Matriptase Inhibits Proliferation in H1299 Lung Cancer cells (normalized over 3 experiments).

Figure 50:
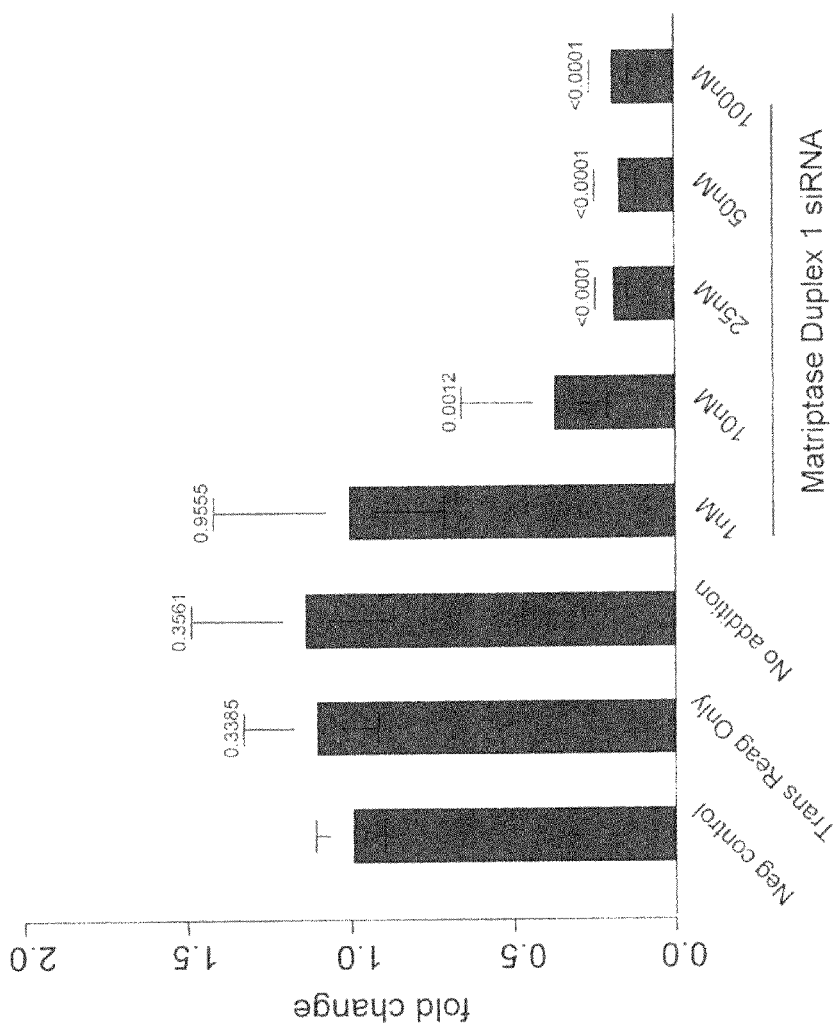

FIG. 50. Knockdown of Matriptase Inhibits Proliferation in HCT116 Colon Cancer cells (normalized over 3 experiments).

Figure 51:
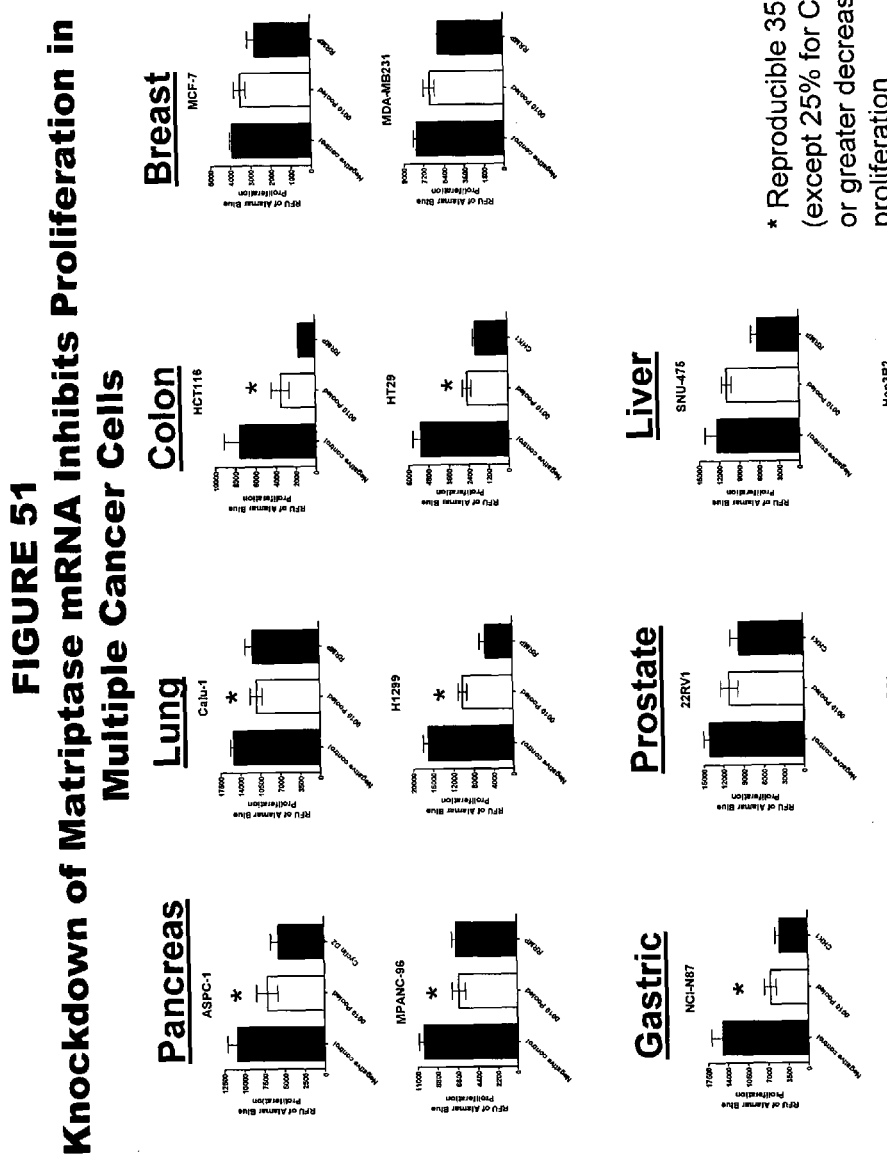

FIG. 51. Knockdown of Matriptase mRNA Inhibits Proliferation in Multiple Cancer Cells.

Figure 52:
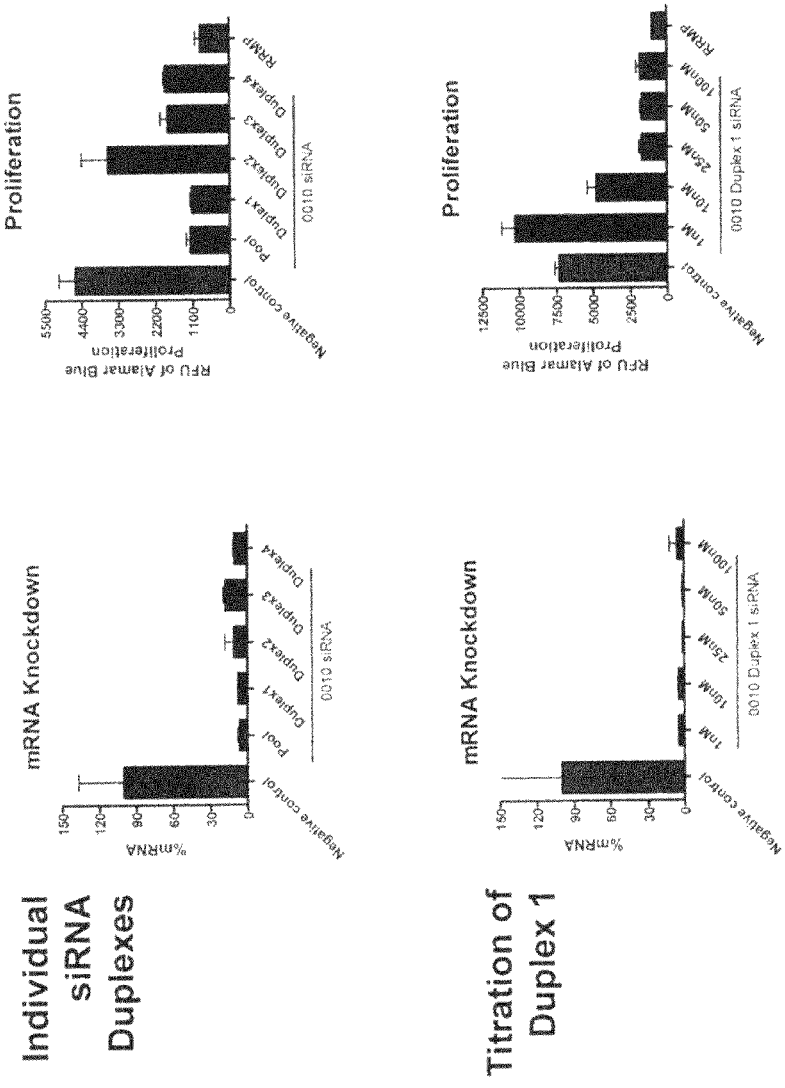

FIG. 52. Knockdown of Matriptase mRNA Inhibits Proliferation in HCT116 Colon Cancer Cells.

Figure 53:
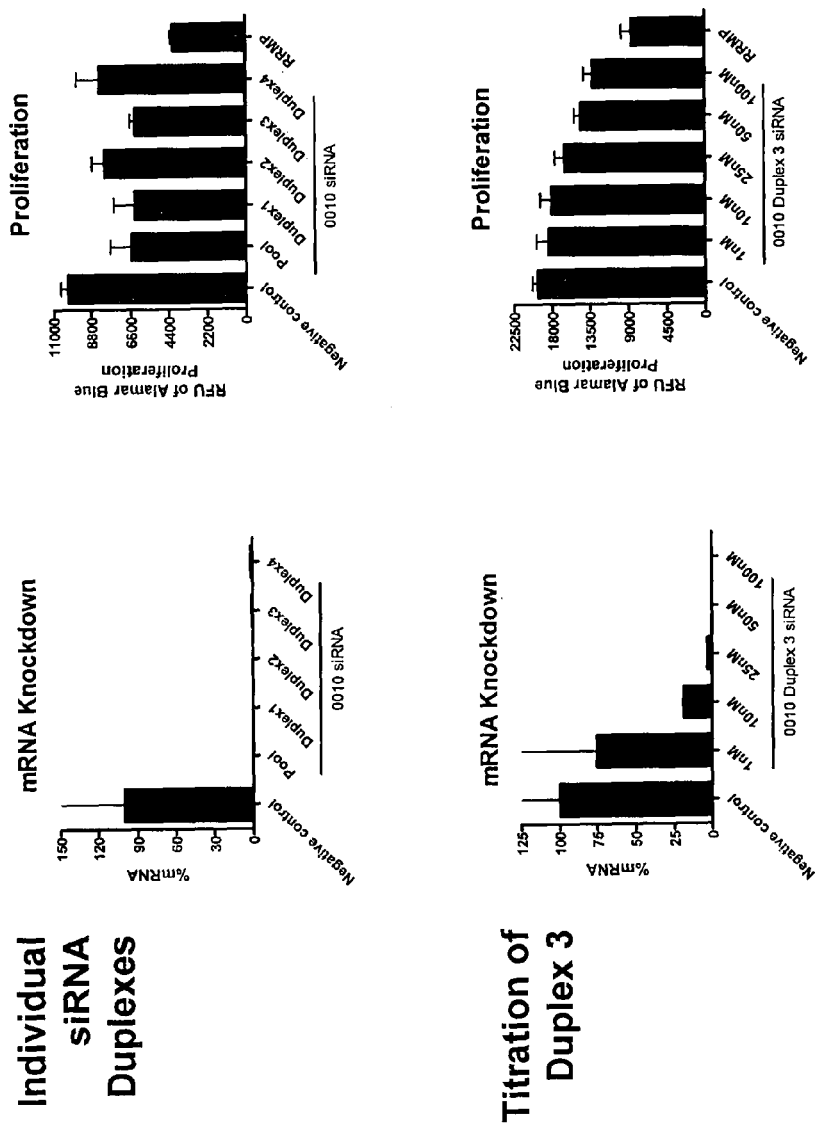

FIG. 53. Knockdown of Matriptase mRNA Inhibits Proliferation in H1299 Lung Cancer Cells.

Figure 54:
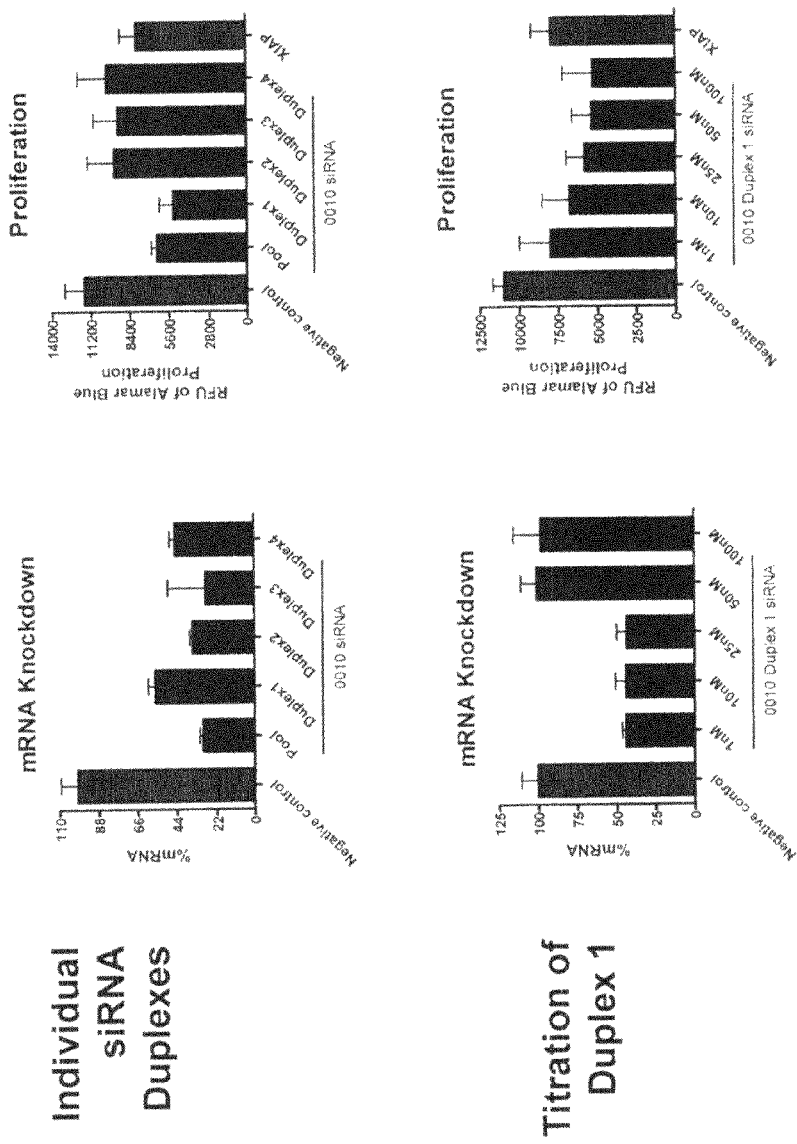

FIG. 54. Knockdown of Matriptase mRNA Inhibits Proliferation in ASPC-1 Pancreatic Cancer. Cells.

FIG. 55. mRNA sequence of Matriptase, indicating siRNA target regions.

AADACL1

FIG. 56. AADACL1 is Over-Expressed in Multiple Tumor Types, as Indicated by IHC.

Figure 57:
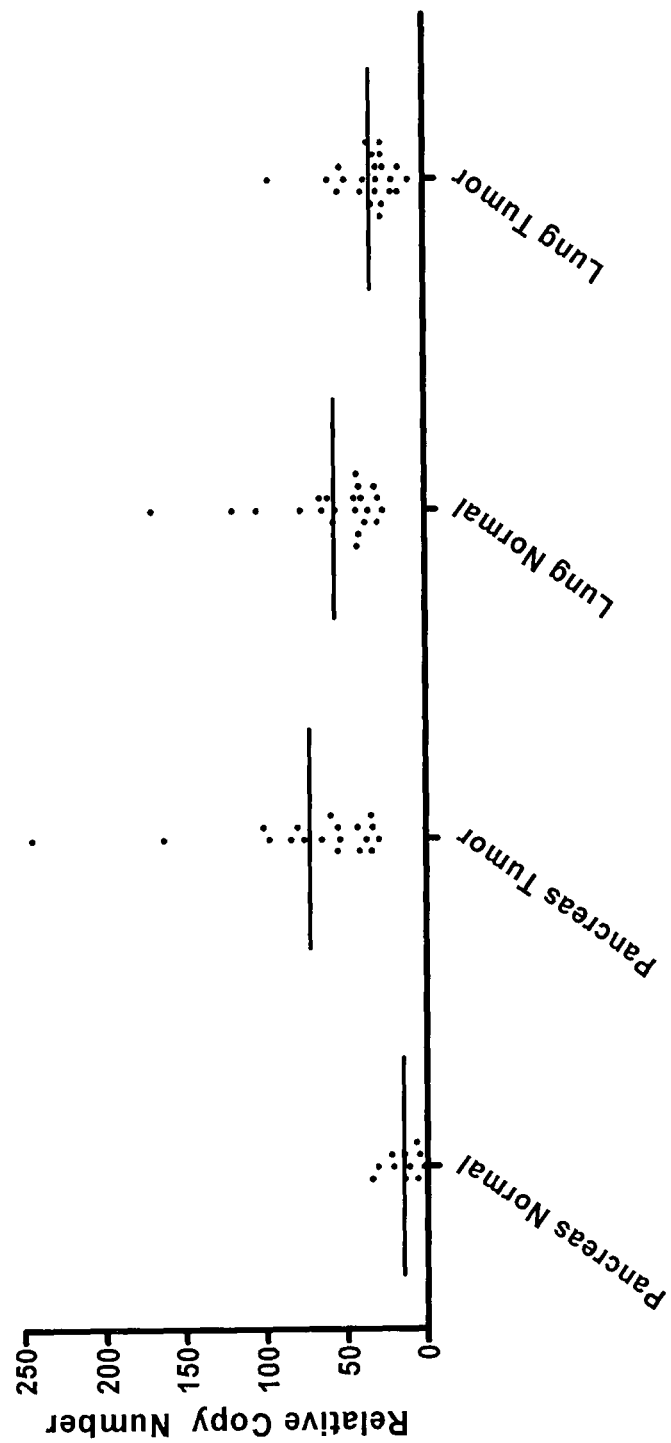

FIG. 57. AADACL1 mRNA Expression Analysis in Pancreatic and Lung Tumor Tissues.

Podocalyxin

FIG. 58. Podocalyxin is Overexpressed in Multiple Tumor Types, as Indicated by IHC.

Figure 59:
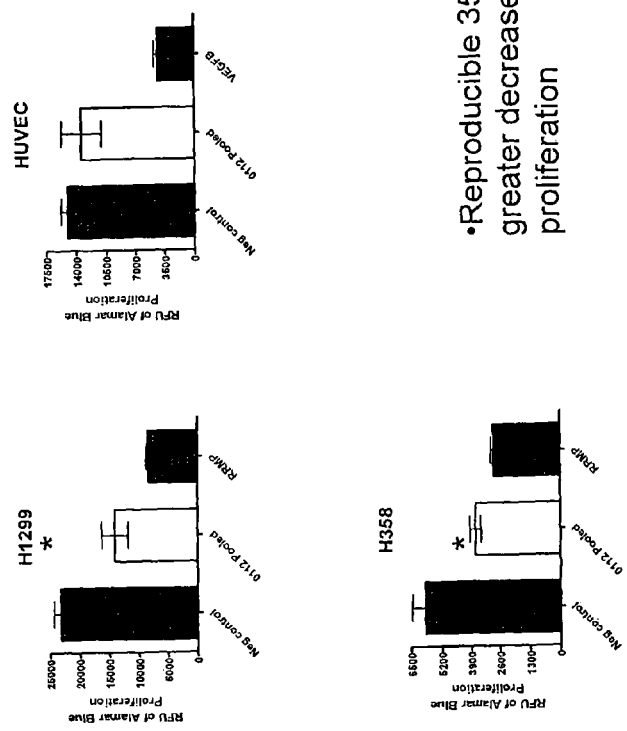

FIG. 59. Knockdown of Podocalyxin mRNA Inhibits Proliferation in Lung Cancer Cells.

Figure 60:
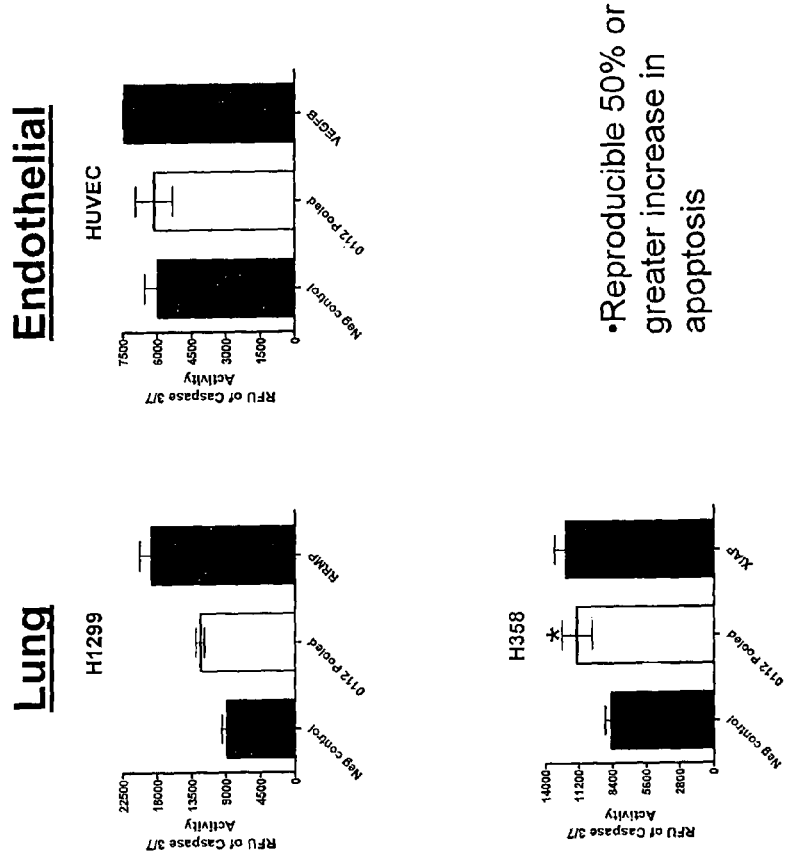

FIG. 60. Knockdown of Podocalyxin mRNA Increases Apoptosis in Lung Cancer Cells.

Figure 61:
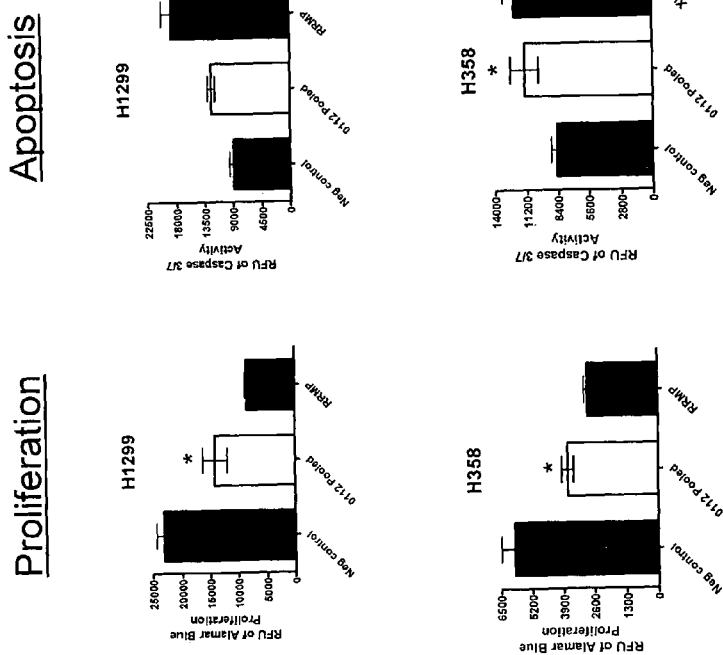

FIG. 61. Knockdown of Podocalyxin mRNA Inhibits Proliferation and induces apoptosis in Lung Cancer Cells.

Figure 62:
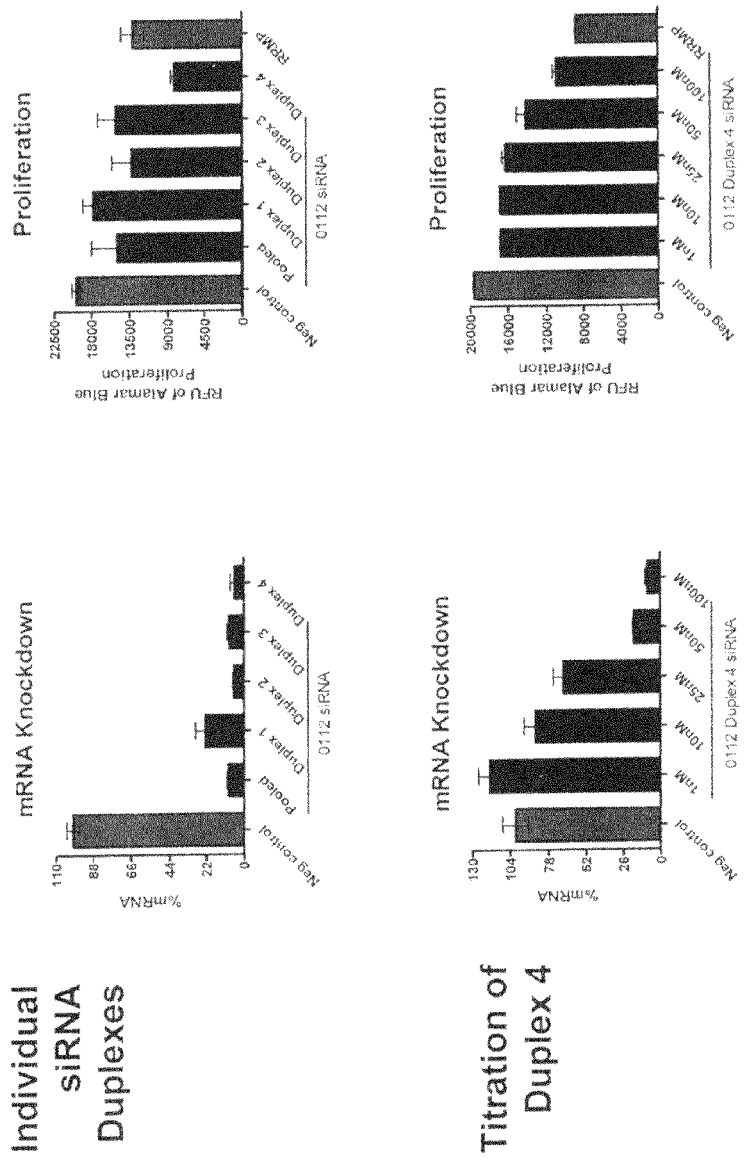

FIG. 62. Knockdown of Podocalyxin mRNA Inhibits Proliferation in H1299 Lung Cancer Cells.

Figure 63:
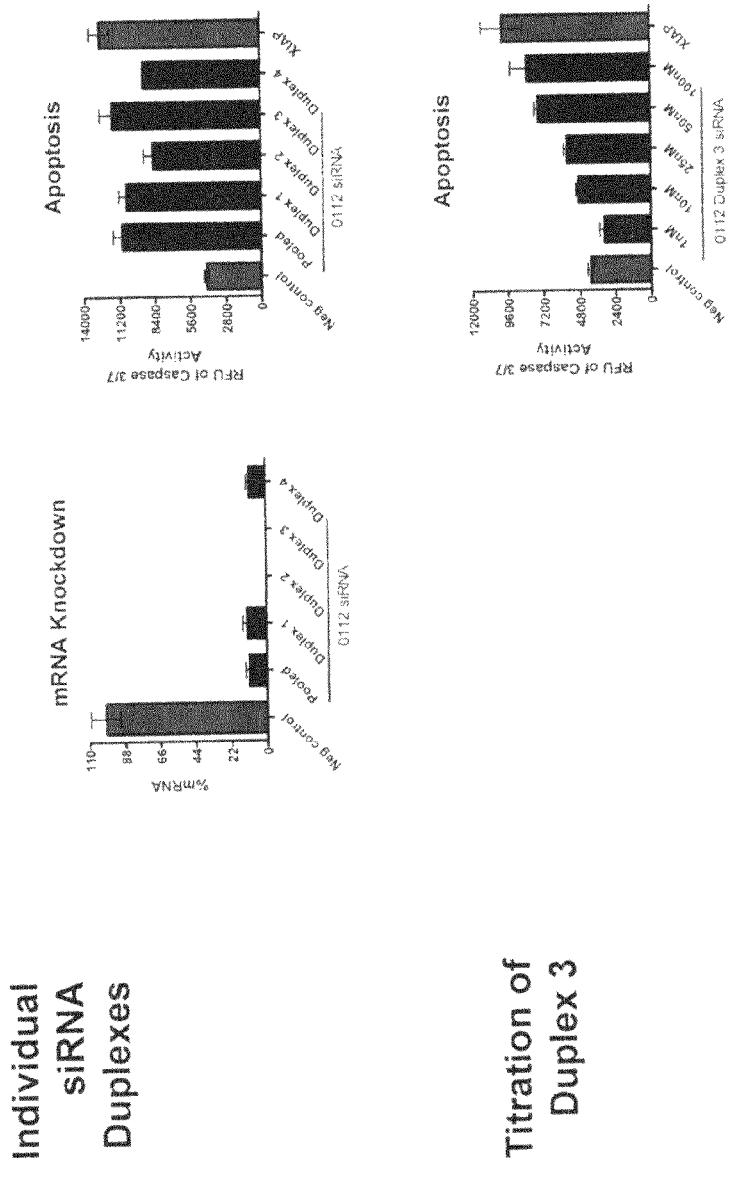

FIG. 63. Knockdown of Podocalyxin mRNA Induces Apoptosis H1229 Lung Cancer Cells.

Figure 64:
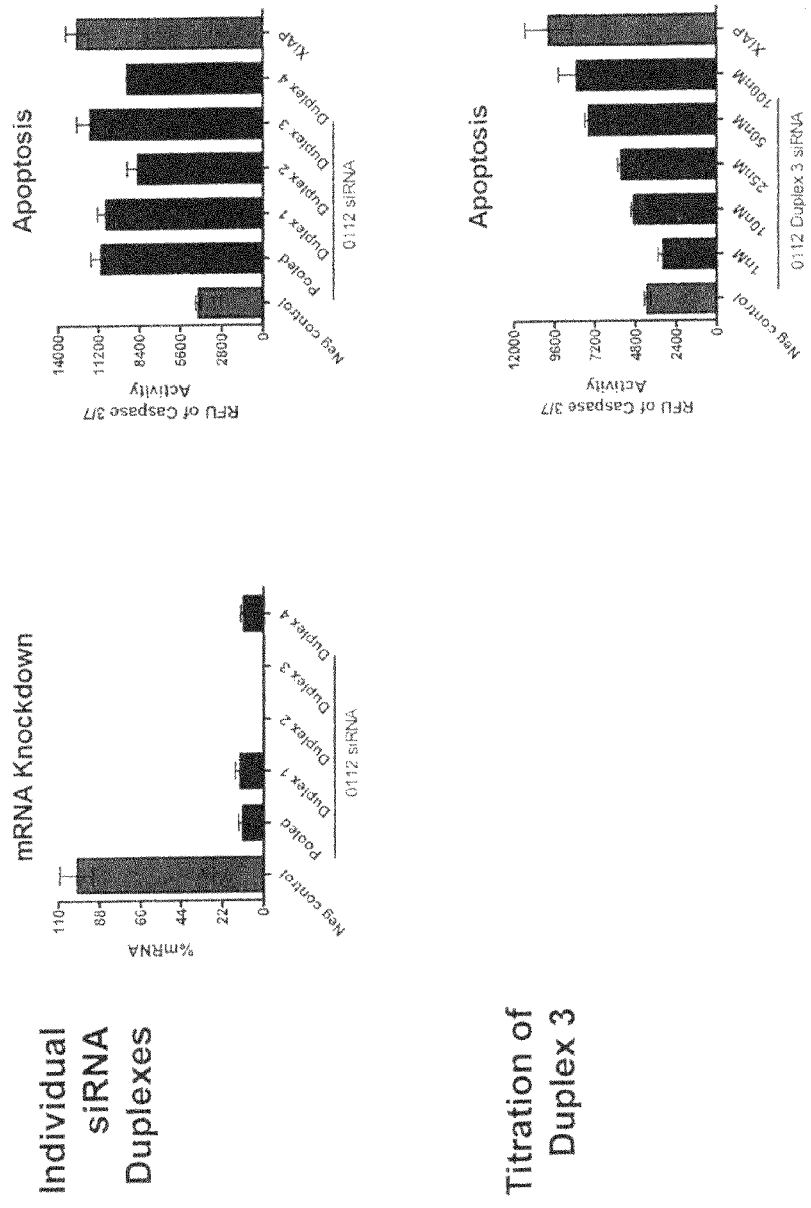

FIG. 64. Knockdown of Podocalyxin mRNA Induces Apoptosis in H358 Lung Cancer Cells.

Figure 65:
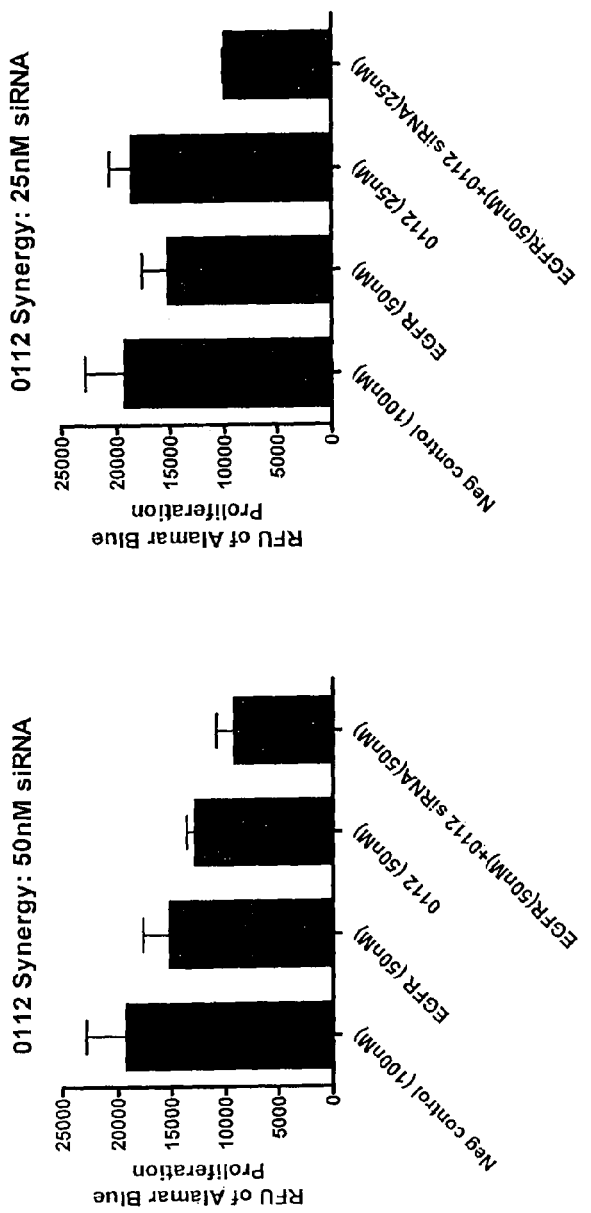

FIG. 65. Synergy of Podocalyxin siRNA with EGFR siRNA.

FIG. 66. mRNA sequence of Podocalyxin, indicating siRNA target regions.

CD90 (Thy1)

FIG. 67. CD90 is Over-expressed in Multiple Tumor Types, as indicated by IHC.

FIG. 68. CD90 is Over-expressed in Multiple Tumor Types, as indicated by IHC.

Figure 69:
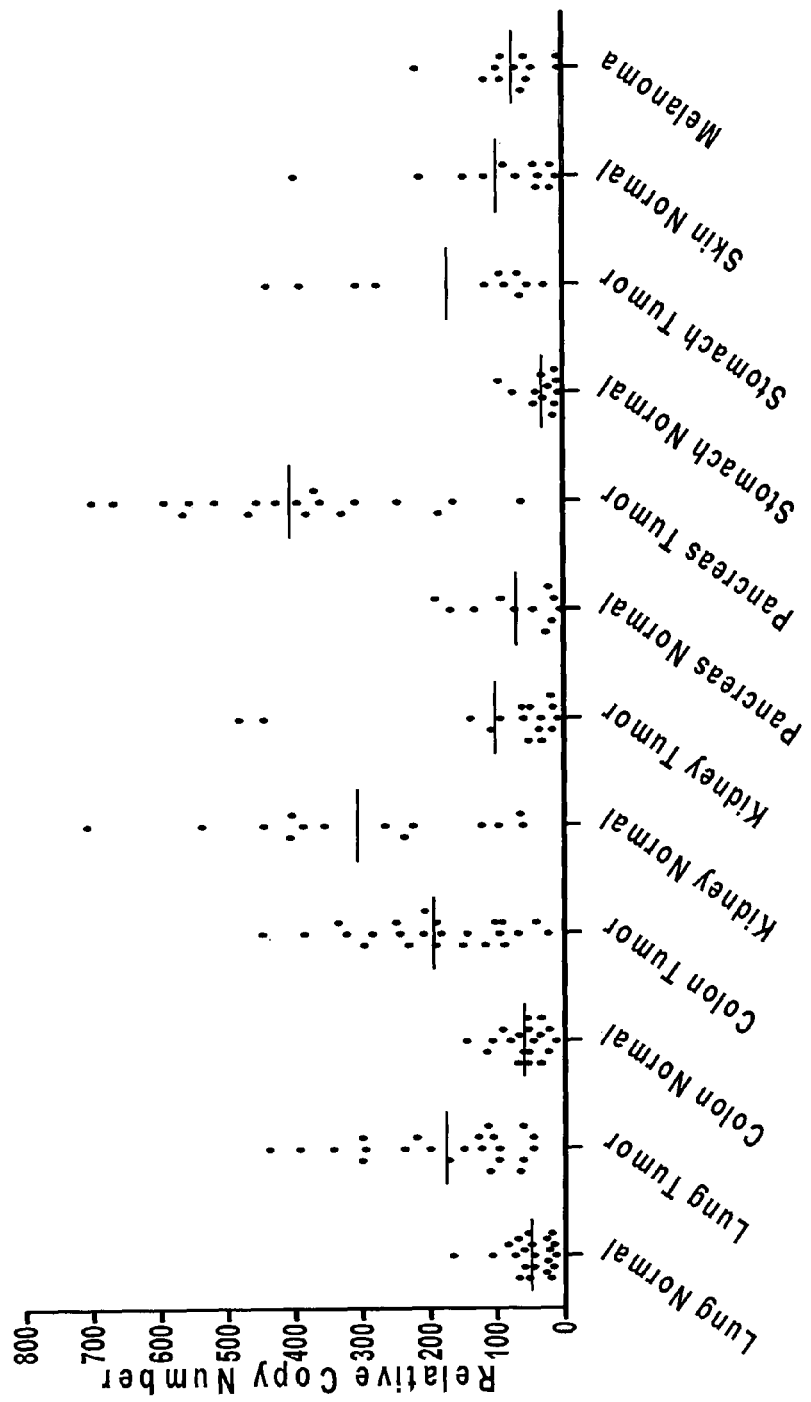

FIG. 69. CD90 mRNA Expression Analysis in Multiple Tumor Tissues.

Figure 70:
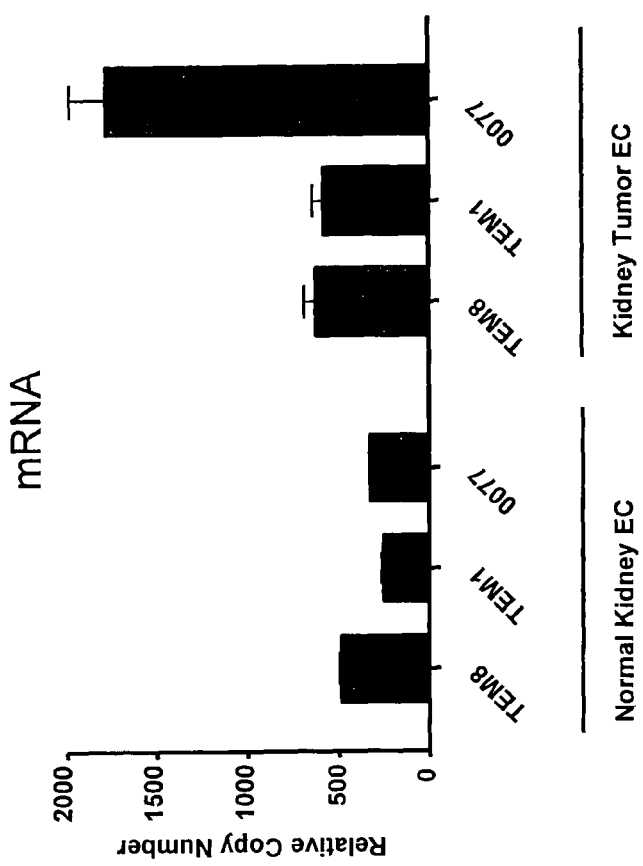

FIG. 70. CD90 mRNA Expression Analysis in Kidney Tumor Tissue Endothelial Cells.

Figure 71:
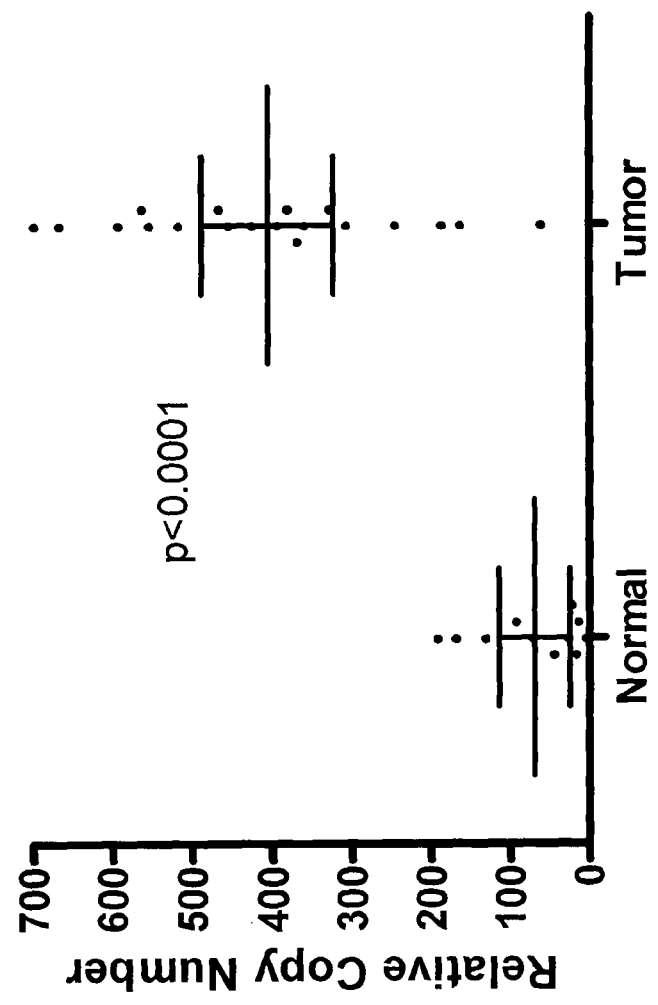

FIG. 71. CD90 mRNA Expression Analysis in Pancreas Tumor Tissues.

Figure 72:
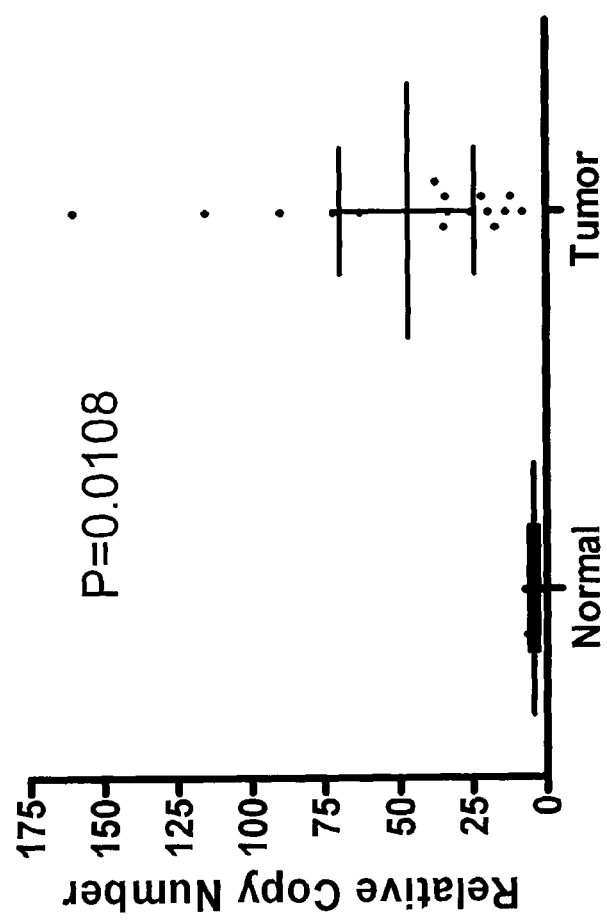

FIG. 72. CD90 mRNA Expression Analysis in Lung Tumor Tissues.

Figure 73:
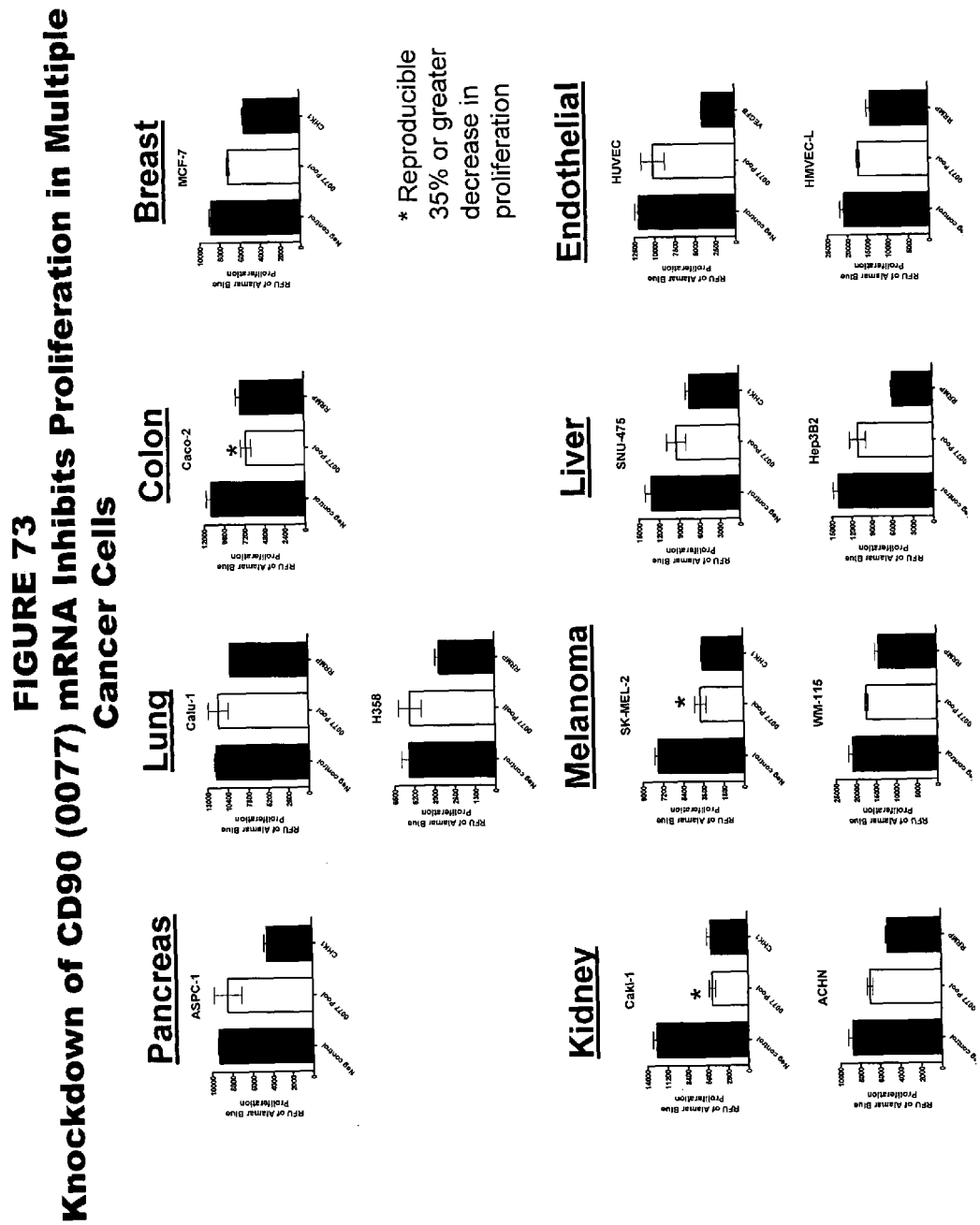

FIG. 73. Knockdown of CD90 mRNA Inhibits Proliferation in Multiple Cancer Cells.

Figure 74:
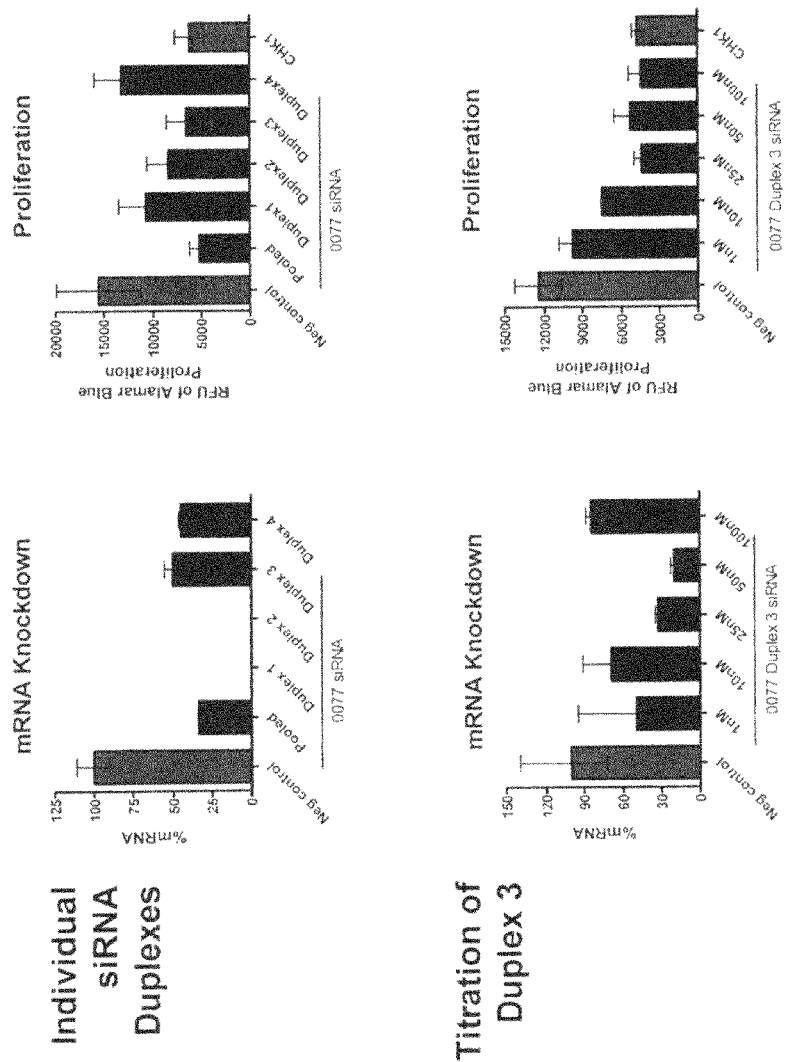

FIG. 74. Knockdown of CD90 mRNA Inhibits Proliferation in Caki-1 Kidney Cancer Cells.

Figure 75:
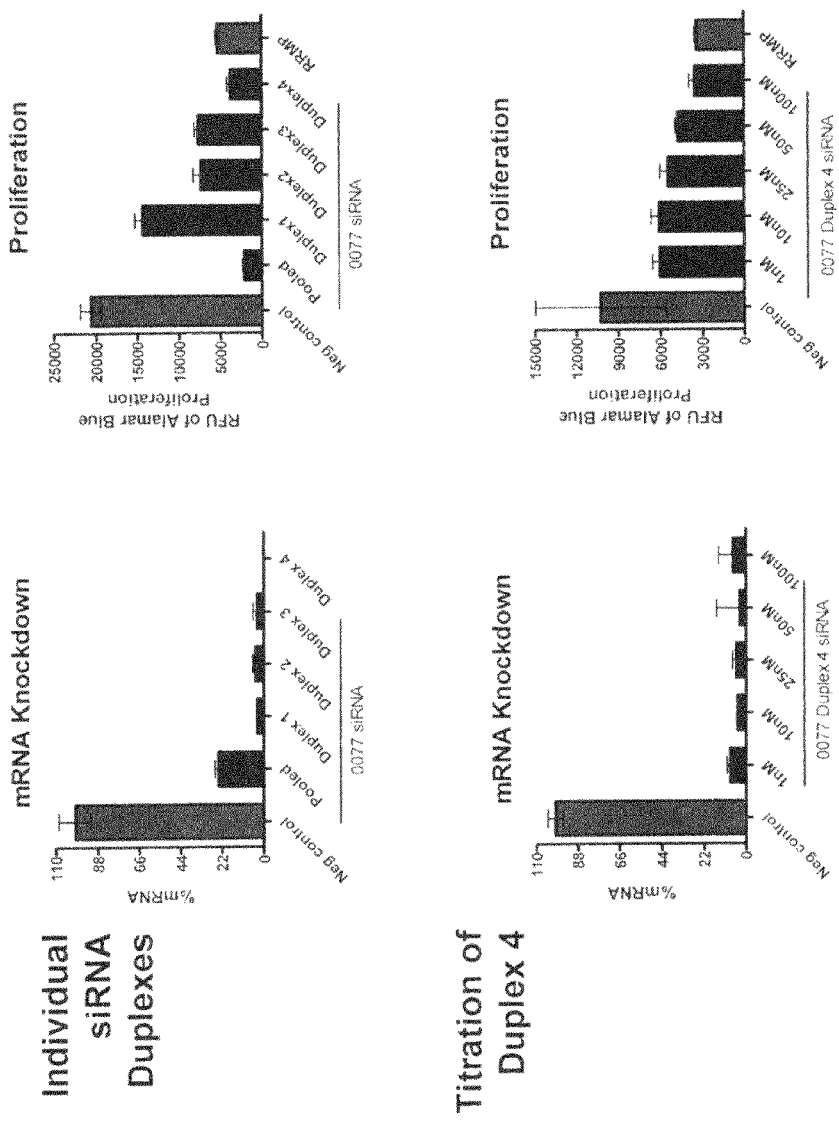

FIG. 75. Knockdown of CD90 mRNA Inhibits Proliferation in SK-MEL-2 Melanoma Cancer Cells.

Figure 76:
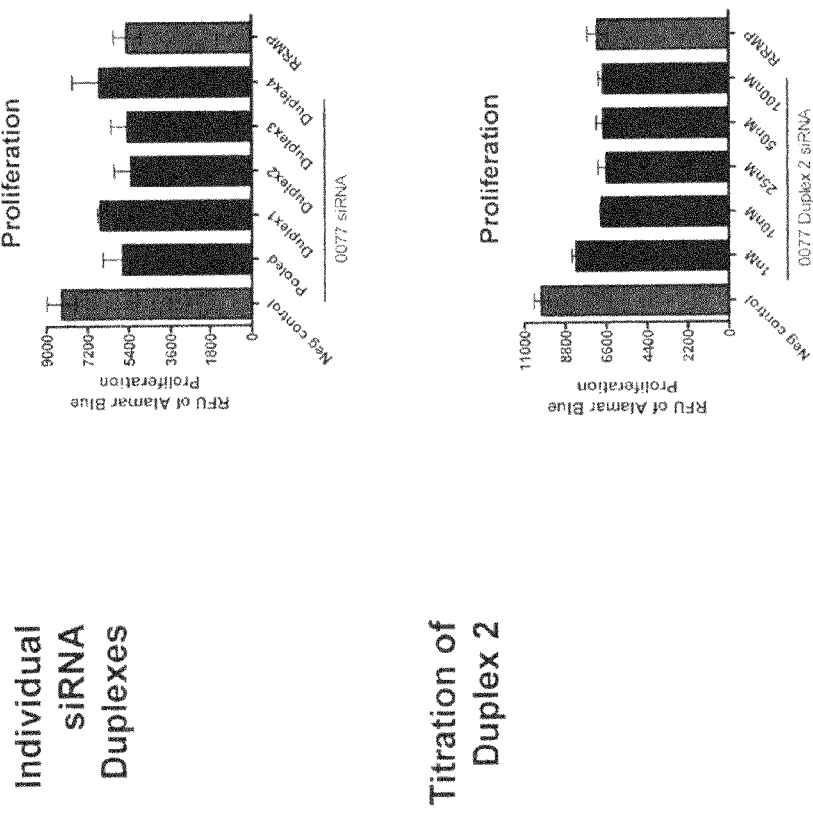

FIG. 76. Knockdown of CD90 mRNA Inhibits Proliferation in Caco-2 Colon Cancer Cells.

FIG. 77. mRNA sequence of CD90, indicating siRNA target regions.

ISGF4

FIG. 78. ISGF4 is Over-Expressed in Multiple Tumor Types, as-indicated by IHC.

Figure 79:
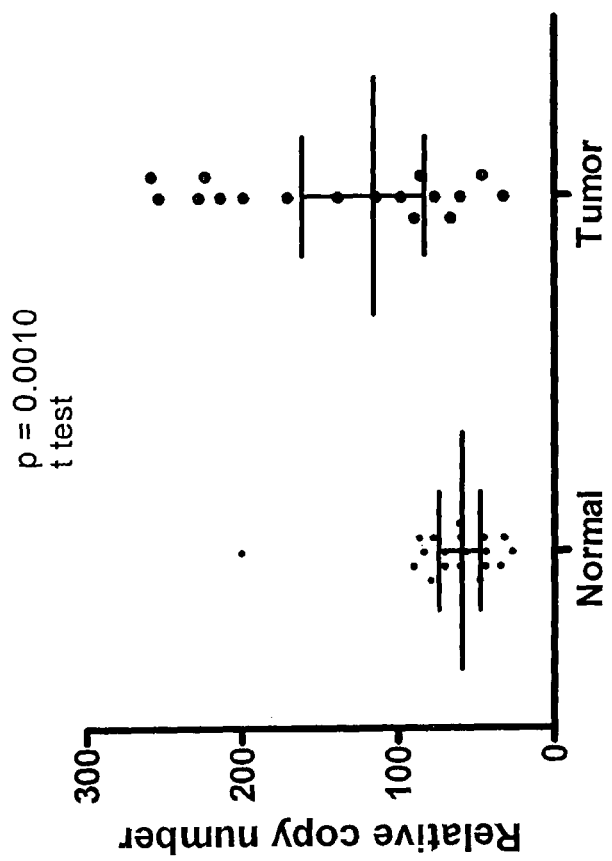

FIG. 79. ISGF4 mRNA Expression is Elevated in Breast Tumor Tissues.

Figure 80:
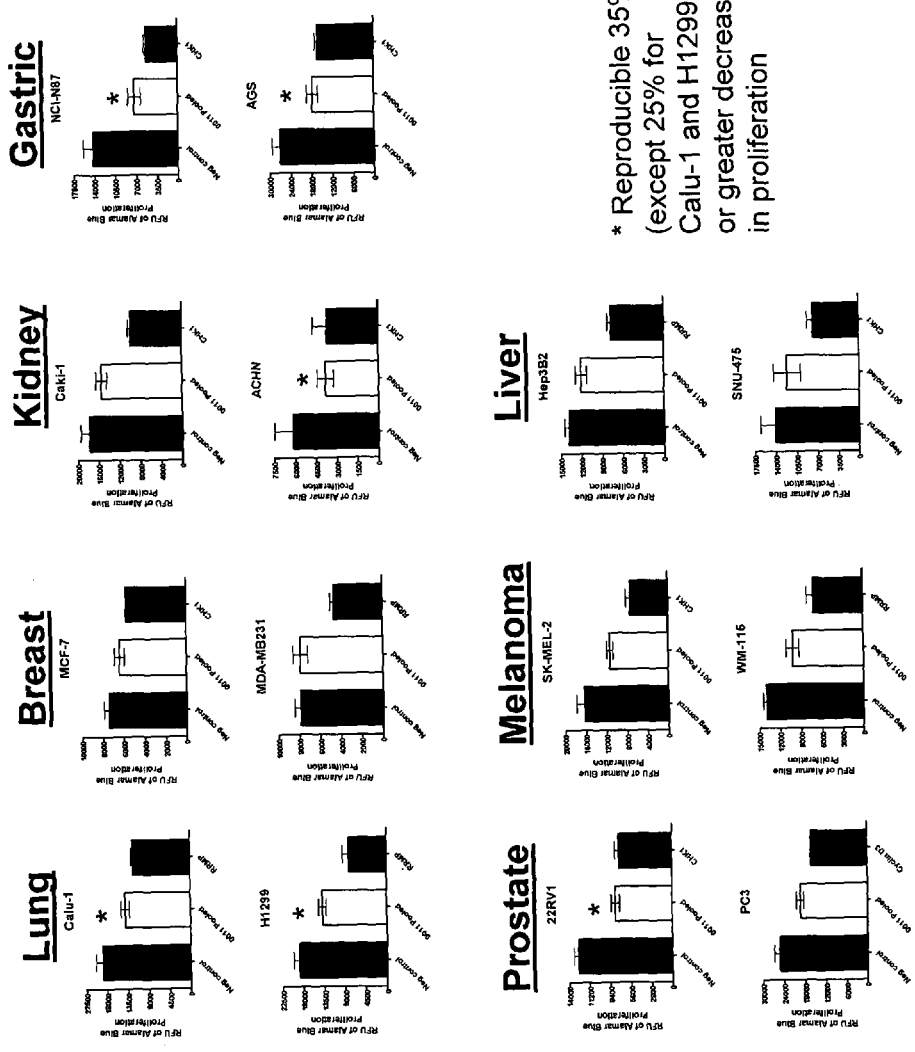

FIG. 80. Knockdown of ISGF4 mRNA Inhibits Proliferation in Multiple Cancer Cells.

Figure 81:
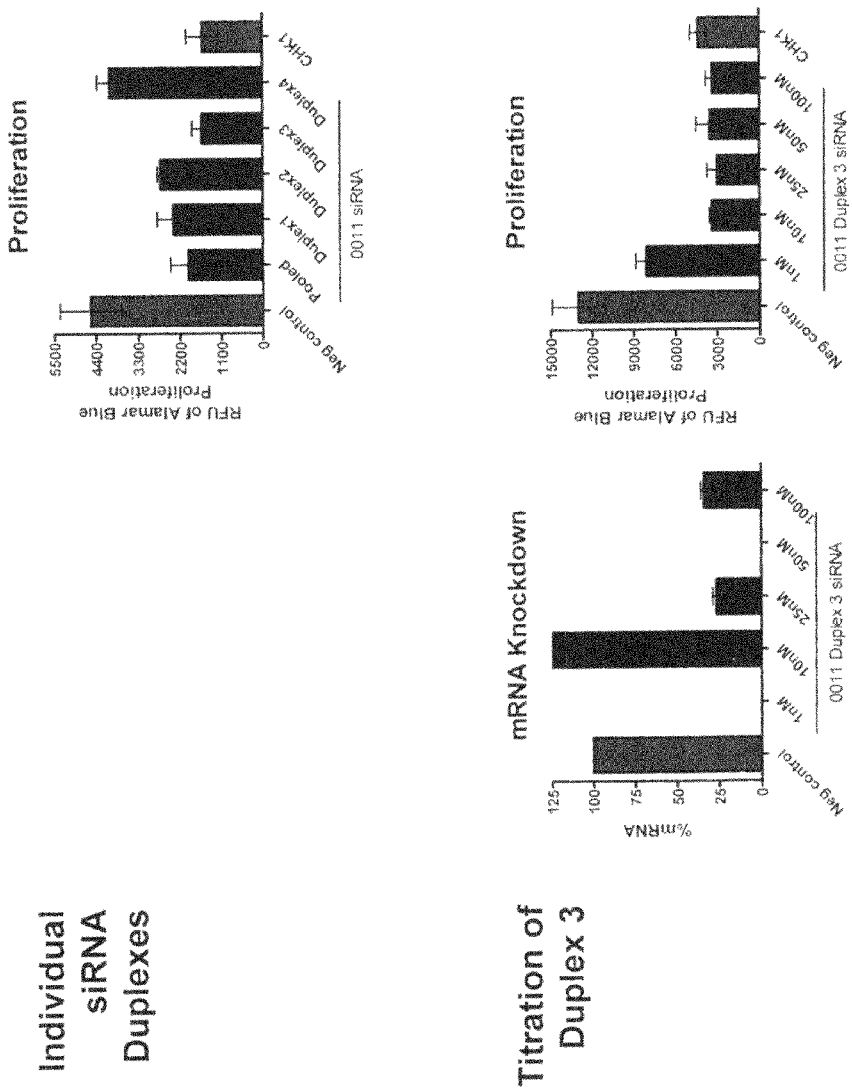

FIG. 81. Knockdown of ISGF4 mRNA Inhibits Proliferation in NCI-N87 Gastric Cancer Cells.

Figure 82:
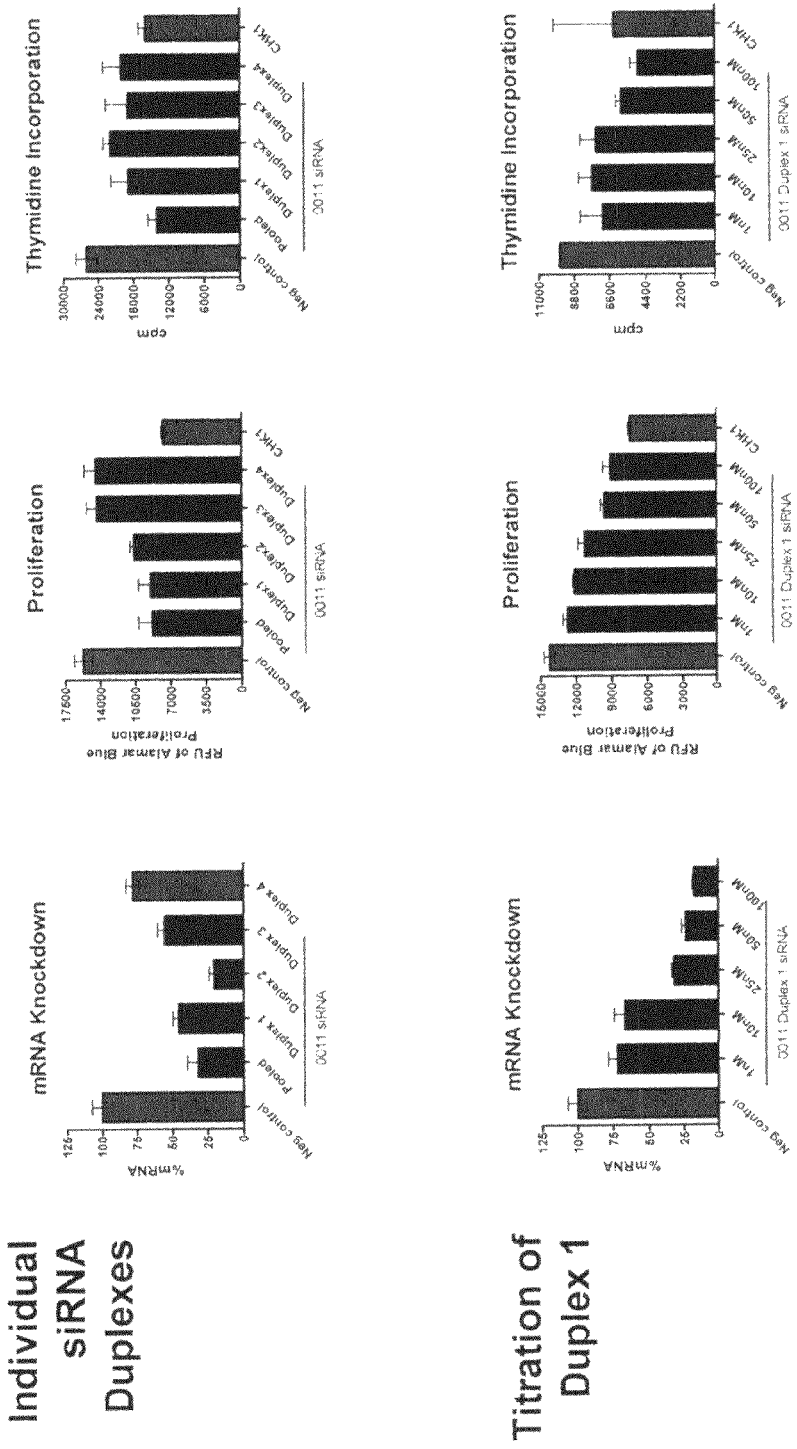

FIG. 82. Knockdown of ISGF4 mRNA Inhibits Proliferation in 22RV1 Prostate Cancer Cells.

FIG. 83. mRNA sequence of IGSF4, indicating siRNA target regions.

FIG. 84. mRNA Analysis for ISGF4 in Lung Cancer Cell Lines that are Increasingly Resistant to Cisplatin. FIG. 84 shows that increased ISGF4 expression correlates with increased resistance to cisplatin in lung cancer cells.

DB83

FIG. 85. DB83 is Over-expressed in Multiple Tumor Types, as indicated by IHC.

Figure 86:
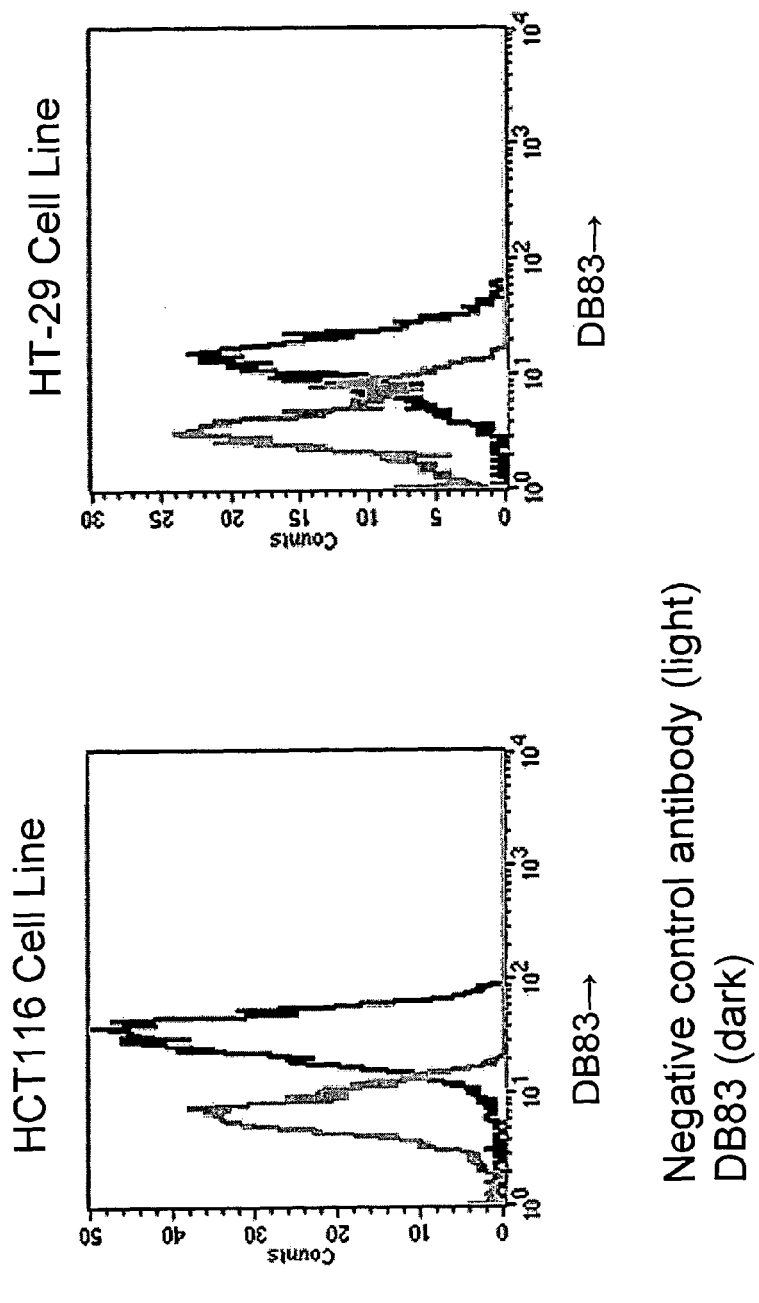

FIG. 86. DB83 Cell Surface Expression in Colon Cancer Cells, as indicated by FACS.

Figure 87:
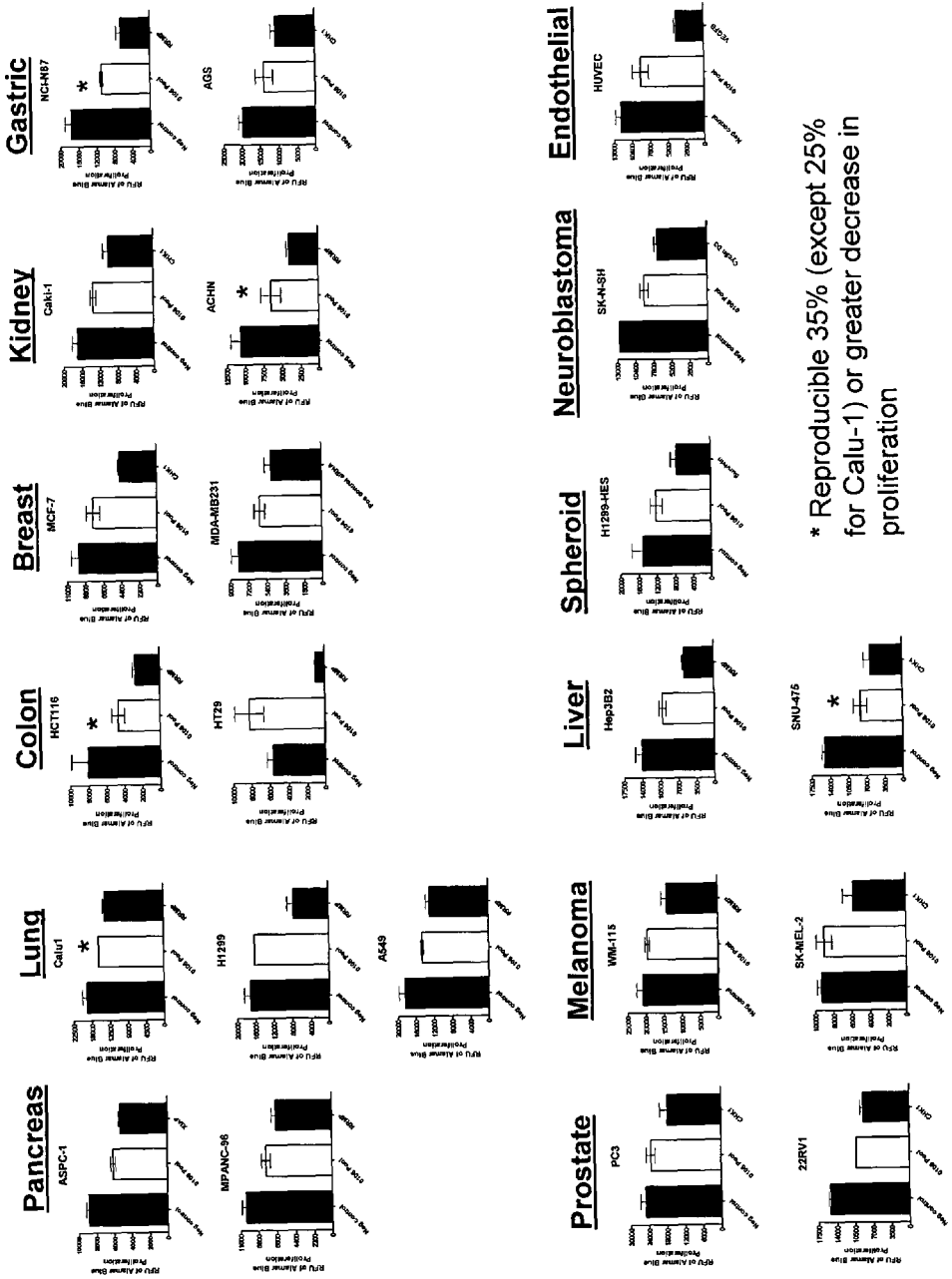

FIG. 87. Knockdown of DB83 mRNA Inhibits Proliferation in Multiple Cancer Cells.

Figure 88:
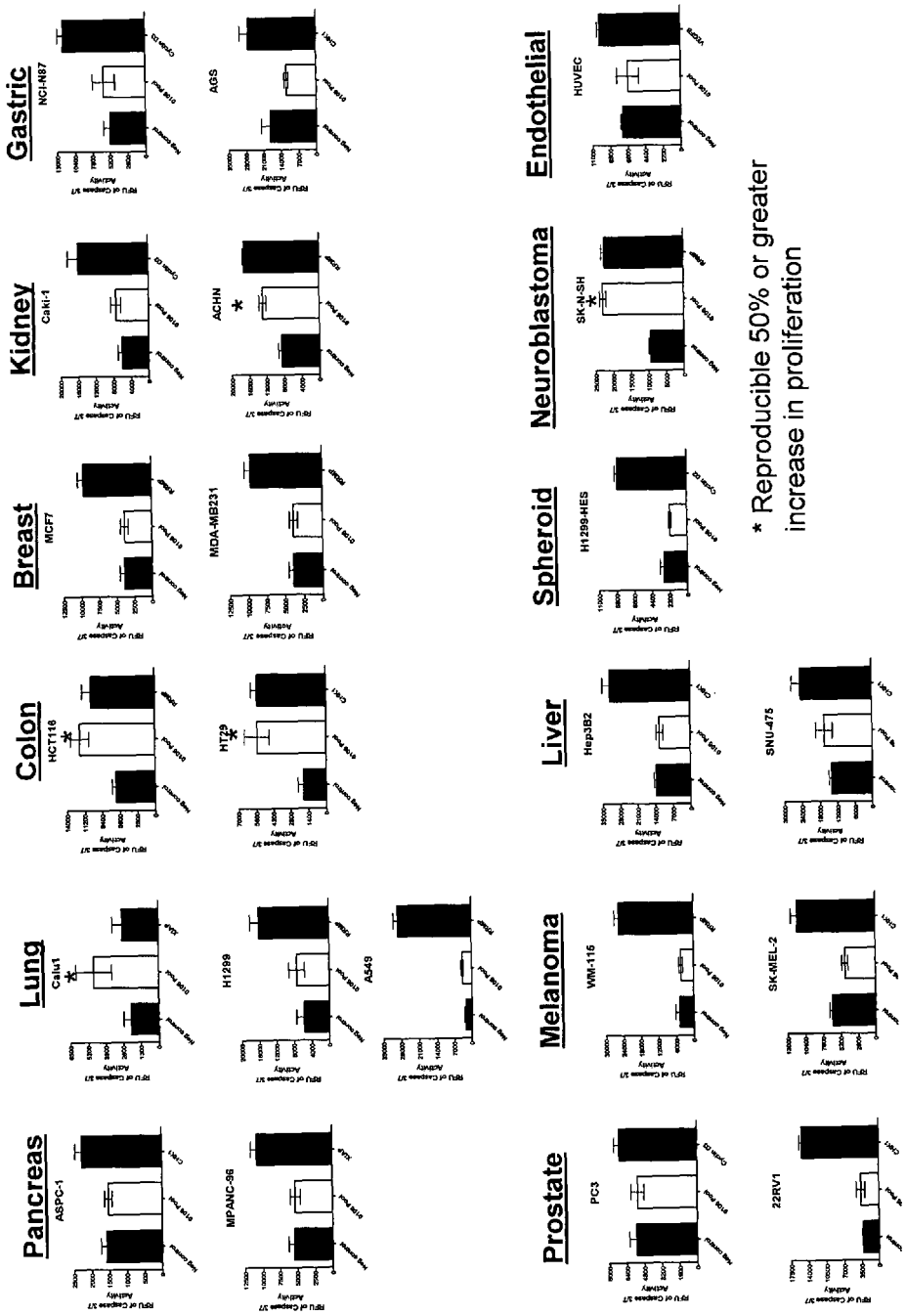

FIG. 88. Knockdown of DB83 mRNA Induces Apoptosis in Multiple Cancer Cells.

Figure 89:
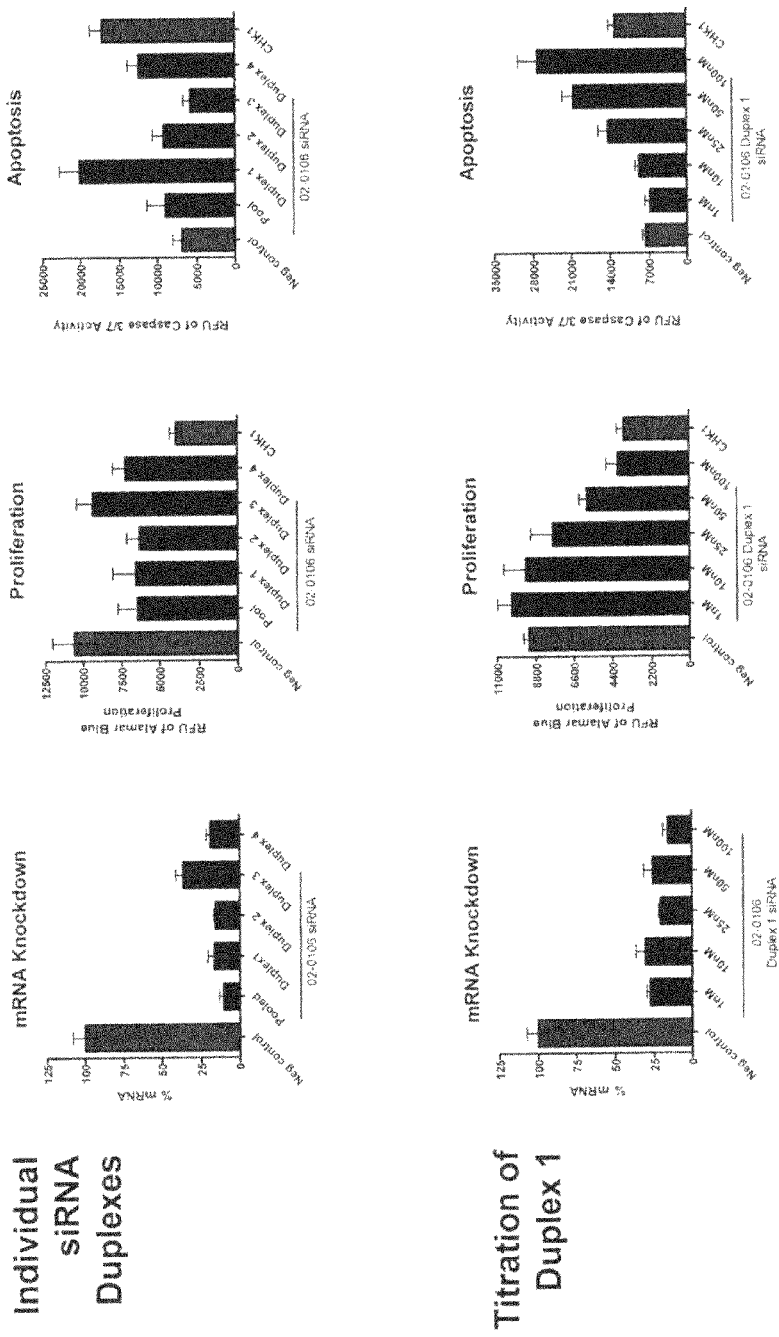

FIG. 89. Knockdown of DB83 mRNA Inhibits Proliferation and Induces Apoptosis in ACHN Kidney Cancer Cells.

Figure 90:
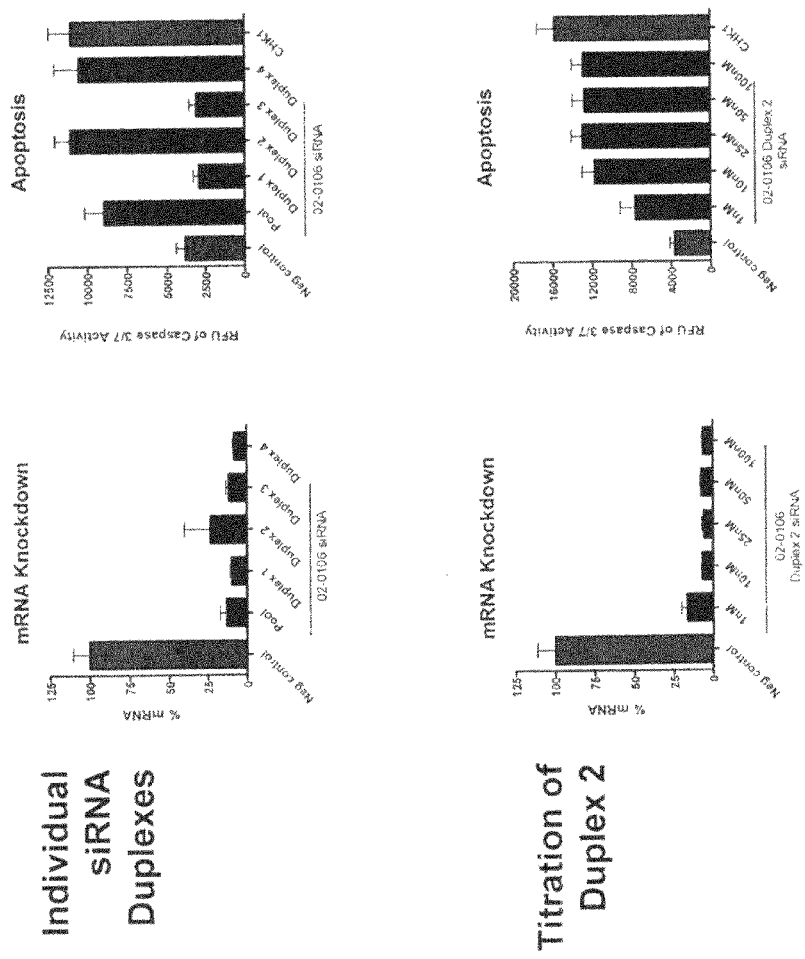

FIG. 90. Knockdown of DB83 mRNA Induces Apoptosis in HT29 Colon Cancer Cells.

Figure 91:
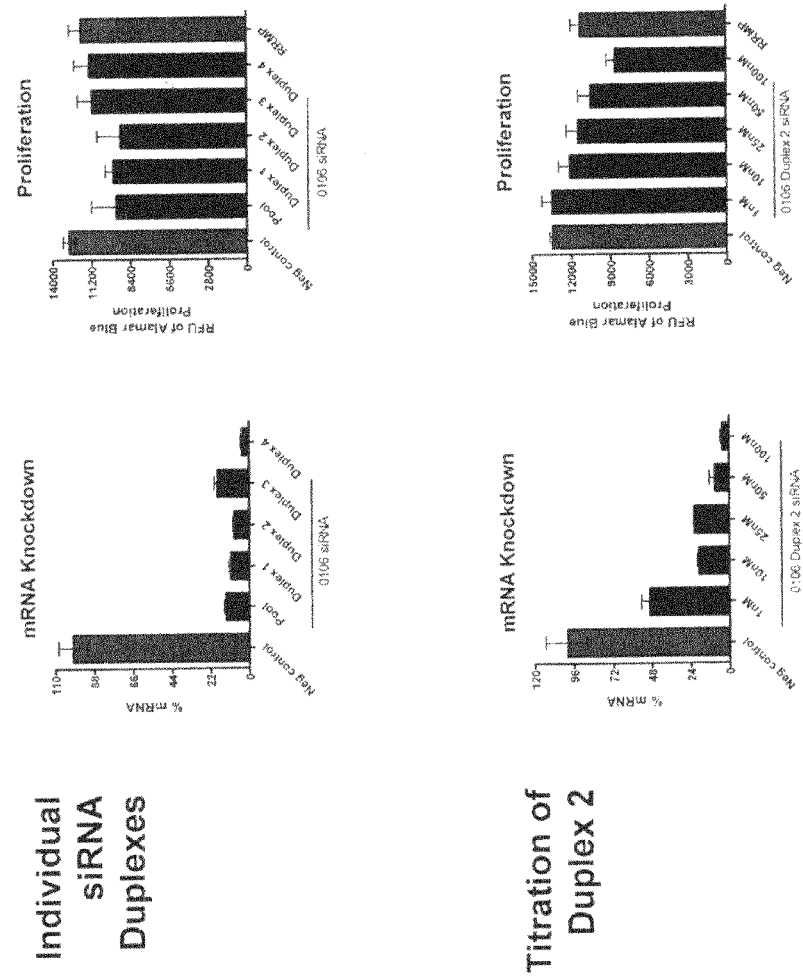

FIG. 91. Knockdown of DB83 mRNA Inhibits Proliferation in Calu-1 Lung Cancer Cells.

Figure 92:
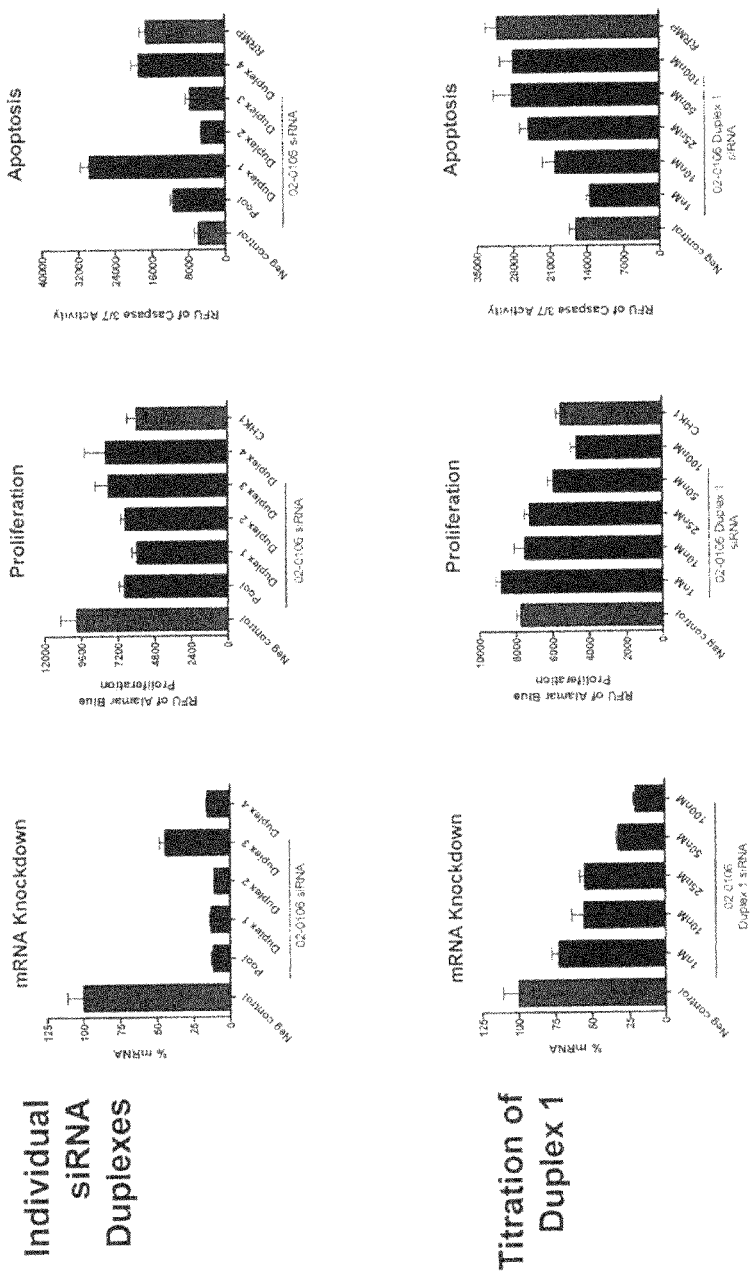

FIG. 92. Knockdown of DB83 mRNA Inhibits Proliferation and Induces Apoptosis in SK-N-SH Neuroblastoma Cancer Cells.

DETAILED DESCRIPTION OF EXEMPLARY EMBODIMENTS OF THE INVENTION

The invention will best be understood by reference to the following detailed description of the exemplary embodiments, taken in conjunction with the accompanying figure(s). The discussion below is exemplary and is not to be taken as limiting the scope defined by the claims.

The invention generally relates to molecules that have been identified using proteomic analysis techniques such as MALDI-TOF/TOF LC/MS-based protein expression analysis to determine the expression levels of proteins in disease tissues and/or disease cell lines (tissues and cell lines may be collectively referred to as "samples") and in normal tissues and/or normal cell lines, such that proteins that are differentially expressed (e.g., over- or under-expressed) in disease samples compared with normal samples are identified.

Exemplary embodiments of the invention provide the following targets and methods of using these targets: TMPRSS4, SLC5A6, ISGF4, ITGB6, GLG1, DB83, KIAA0152, Matriptase, AADACL1, Podocalyxin, and CD90 (Thy1) (see Figures), which are collectively referred to herein as "CAT" (cancer-associated targets). Each of these targets is associated with specific types of cancers in particular, as shown in the Figures and described in section 13 of the Examples section ("Specific Examples of Results from Experimental Validation").

Based on the finding that certain proteins, referred to herein as CAT proteins, are differentially expressed in cancer samples in comparison with normal samples, exemplary embodiments of the invention provide methods and compositions for assessing, treating, and preventing diseases, especially cancer, particularly the cancers identified in the Figures and section 13 of the Examples for each target, using CAT. Furthermore, the compositions and methods of the invention may be suitable for other types of cancer, particularly other epithelial cell-related cancers and solid tumors.

CAT proteins and fragments thereof, and CAT nucleic acid molecules and fragments thereof encoding CAT proteins, are collectively referred to as CAT or "targets" (which may be interchangeably referred to as "markers" or "biomarkers"). Exemplary CAT proteins are provided as SEQ ID NOS:1-3, 7-9, 13-17, 23, 25-33, 43-44, 47-48, 51-52, 56-59, 64-67, and 72-73 and exemplary CAT transcript sequences (which encode the CAT proteins of SEQ ID NOS:1-3, 7-9, 13-17, 23, 25-33, 43-44, 47-48, 51-52, 56-59, 64-67, and 72-73) are provided as SEQ ID NOS:4-6, 10-12, 18-22, 24, 34-42, 45-46, 49-50, 53-55, 60-63, 68-71, and 74-75. These targets can be, for example, cell surface proteins, cytosolic proteins, or secreted proteins, as well as nucleic acid molecules that encode these proteins.

The terms "protein" and "polypeptide" are used herein interchangeably. Exemplary CAT proteins/polypeptides are provided as SEQ ID NOS:1-3, 7-9, 13-17, 23, 25-33, 43-44, 47-48, 51-52, 56-59, 64-67, and 72-73. A "peptide" typically refers to a fragment of a protein/polypeptide. Thus, peptides are interchangeably referred to as fragments.

References herein to proteins, peptides, nucleic acid molecules, and antibodies typically are not limited to the full-size or full-length molecule, but also can encompass fragments of these molecules (unless a particular sequence or structure is explicitly stated).

Exemplary embodiments of the invention, which are discussed in greater detail below, provide antibodies, proteins, immunogenic peptides (e.g., peptides which induce a T-cell response), or other biomolecules, as well as small molecules, nucleic acid agents (e.g., RNAi and antisense nucleic acid agents), and other compositions that modulate the targets (e.g., agonists and antagonists), such as by binding to or otherwise interacting with or affecting the targets. These compositions can be used for assessing, treating, and preventing diseases, especially cancer, particularly the cancers identified in the Figures and section 13 of the Examples for each target, as well as other uses. Moreover, the invention provides methods for assessing, treating, and preventing diseases such as these based on CAT, such as by using these compositions. Further provided are methods of screening for agents that modulate CAT, such as by affecting the function, activity, and/or expression level ("expression level" may be interchangeably referred to as "abundance level" or "level") of CAT, and agents identified by these screening methods.

Exemplary embodiments of the invention also provide methods of modulating cell function. In particular, the invention provides methods of modulating cell proliferation and/or apoptosis. For example, for cancer/tumor cells, the invention provides methods of inhibiting cell proliferation and/or stimulating apoptosis. Such methods can be applied to the treatment of diseases, especially cancer.

Exemplary embodiments of the invention further provide methods of determining or predicting effectiveness or response to a particular treatment, and methods of selecting a treatment for an individual. For example, targets that are differentially expressed by cells that are more or less responsive or resistant to a particular treatment, such as a cancer treatment, are useful for determining or predicting effectiveness or response to the treatment or for selecting a treatment for an individual. Exemplary embodiments of the invention also provide methods of selecting individuals for a clinical trial of a therapeutic agent. For example, the targets can be used to identify individuals for inclusion in a clinical trial who are more likely to respond to a particular treatment. Alternatively, the targets can be used to exclude individuals from a clinical trial who are less likely to respond to a particular treatment or who are more likely to experience toxic or other undesirable side effects from a particular treatment.

Further exemplary embodiments of the invention are described in greater detail below.

1. CAT Proteins

Exemplary embodiments of the invention provide the following targets and methods of using these targets: TMPRSS4, SLC5A6, ISGF4, ITGB6, GLG1, DB83, KIAA0152, Matriptase, AADACL1, Podocalyxin, and CD90 (Thy1) (see Figures), which are collectively referred to herein as "CAT" (cancer-associated targets). In particular, the present invention provides methods of using these targets for diagnosing and treating cancer. Each of these targets is associated with specific types of cancers in particular, as shown in the Figures and described in section 13 of the Examples section ("Specific Examples of Results from Experimental Validation").

Exemplary embodiments of the invention provide isolated CAT proteins that consist of, consist essentially of, or comprise the amino acid sequences of SEQ ID NOS:1-3, 7-9, 13-17, 23, 25-33, 43-44, 47-48, 51-52, 56-59, 64-67, and 72-73 (which are encoded by the nucleotide sequences of SEQ ID NOS:4-6, 10-12, 18-22, 24, 34-42, 45-46, 49-50, 53-55, 60-63, 68-71, and 74-75, respectively), as well as all obvious variants of these proteins and nucleic acid molecules that are within the art to make and use. Examples of such obvious variants include, but are not limited to, naturally-occurring allelic variants, pre-processed or mature processed forms of a protein, non-naturally occurring recombinantly-derived variants, orthologs, and paralogs. Such variants can readily be generated using art-known techniques in the fields of recombinant nucleic acid technology and protein biochemistry.

A protein is said to be "isolated" or "purified" when it is substantially free of cellular material or free of chemical precursors or other chemicals. CAT proteins can be purified to homogeneity or other degrees of purity. The level of purification can be based on the intended use. The primary consideration is that the preparation allows for the desired function of the protein, even if in the presence of considerable amounts of other components.

In some uses, "substantially free of cellular material" includes preparations of a protein having less than about 30% (by dry weight) other proteins (i.e., contaminating protein), less than about 20% other proteins, less than about 10% other proteins, or less than about 5% other proteins. When the protein is recombinantly produced, it can also be substantially free of culture medium, i.e., culture medium represents less than about 20% of the volume of the protein preparation.

The language "substantially free of chemical precursors or other chemicals" includes preparations of a protein in which the protein is separated from chemical precursors or other chemicals that are involved in the protein's synthesis. In one embodiment, the language "substantially free of chemical precursors or other chemicals" includes preparations of a CAT protein having less than about 30% (by dry weight) chemical precursors or other chemicals, less than about 20% chemical precursors or other chemicals, less than about 10% chemical precursors or other chemicals, or less than about 5% chemical precursors or other chemicals.

Isolated CAT proteins can be purified from cells that naturally express it, purified from cells that have been altered to express it (recombinant), or synthesized using known protein synthesis methods (e.g., Sambrook et al., Molecular Cloning: A Laboratory Manual. 3rd. ed., Cold Spring Harbor Laboratory Press, Cold Spring Harbor, N.Y., (2001)). For example, a nucleic acid molecule encoding a CAT protein can be cloned into an expression vector, the expression vector introduced into a host cell, and the protein expressed in the host cell. The protein can then be isolated from the cells by an appropriate purification scheme using standard protein purification techniques.

A CAT protein or fragment thereof can be attached to heterologous sequences to form chimeric or fusion proteins. Such chimeric and fusion proteins comprise a protein operatively linked to a heterologous protein having an amino acid sequence not substantially homologous to the protein. "Operatively linked" indicates that the protein and the heterologous protein are fused in-frame. The heterologous protein can be fused to the N-terminus or C-terminus of the protein.

In some uses, the fusion protein does not affect the activity of the protein per se. For example, the fusion protein can include, but is not limited to, beta-galactosidase fusions, yeast two-hybrid GAL fusions, poly-His fusions, MYC-tagged, HI-tagged, and Ig fusions. Such fusion proteins, particularly poly-His fusions, can facilitate the purification of recombinant CAT proteins. In certain host cells (e.g., mammalian host cells), expression and/or secretion of a protein can be increased by using a heterologous signal sequence.

A chimeric or fusion CAT protein can be produced by standard recombinant DNA techniques. For example, DNA fragments coding for different protein sequences can be ligated together in-frame in accordance with conventional techniques. In another embodiment, a fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (Ausubel et al., Current Protocols in Molecular Biology, 1992-2006). Moreover, many expression vectors are commercially available that already encode a fusion moiety (e.g., a GST protein). A CAT-encoding nucleic acid can be cloned into such an expression vector such that the fusion moiety is linked in-frame to the CAT protein.

To determine the percent identity of two amino acid sequences or two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In an exemplary embodiment, at least 30%, 40%, 50%, 60%, 70%, 80%, or 90% or more of the length of a reference sequence can be aligned for comparison purposes. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, that are introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., Stockton Press, New York, 1991). In an exemplary embodiment, the percent identity between two amino acid sequences is determined using the Needleman and Wunsch (*J. Mol. Biol.* (48):444-453 (1970)) algorithm which has been incorporated into the GAP program in the GCG software package, using either a Blossom 62 matrix or a PAM250 matrix, a gap weight of 16, 14, 12, 10, 8, 6, or 4, and a length weight of 1, 2, 3, 4, 5, or 6. In another exemplary embodiment, the percent identity between two nucleotide sequences can be determined using the GAP program in the GCG software package (Devereux et al., *Nucleic Acids Res.* 12(1):387 (1984)) using a NWSgapdna.CMP matrix and a gap weight of 40, 50, 60, 70, or 80, and a length weight of 1, 2, 3, 4, 5, or 6. In another exemplary embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM 120 weight residue table, a gap length penalty of 12, and a gap penalty of 4.

The sequences of the proteins and nucleic acid molecules of the invention can further be used as a "query sequence" to perform a search against sequence databases to, for example, identify other protein family members or related sequences. Such searches can be performed using the NBLAST and XBLAST programs (version 2.0) of Altschul et al. (*J. Mol. Biol.* 215:403-10 (1990)). BLAST nucleotide searches can be performed with the NBLAST program, score=100, wordlength=12, to obtain nucleotide sequences homologous to the query nucleic acid molecule. BLAST protein searches can be performed with the XBLAST program, score=50, wordlength=3, to obtain amino acid sequences homologous to the query proteins. To obtain gapped alignments for comparison purposes, Gapped BLAST can be utilized as described in Altschul et al. (*Nucleic Acids Res.* 25(17):3389-3402 (1997)). When utilizing BLAST and gapped BLAST programs, the default parameters of the respective programs (e.g., XBLAST and NBLAST) can be used.

As used herein, two proteins (or a region or domain of the proteins) have significant homology/identity (also referred to as substantial homology/identity) when the amino acid sequences are typically at least about 70-80%, 80-90%, 90-95%, 96%, 97%, 98%, or 99% identical A significantly homologous amino acid sequence can be encoded by a nucleic acid molecule that hybridizes to a CAT protein-encoding nucleic acid molecule under stringent conditions, as more fully described below.

Orthologs of a CAT protein typically have some degree of significant sequence homology to at least a portion of a CAT protein and are encoded by a gene from another organism. Preferred orthologs are isolated from mammals, preferably non-human primates, for the development of human therapeutic targets and agents. Such orthologs can be encoded by a nucleic acid molecule that hybridizes to a CAT protein-encoding nucleic acid molecule under moderate to stringent conditions, as more fully described below, depending on the degree of relatedness of the two organisms yielding the proteins.

Non-naturally occurring variants of the CAT proteins can readily be generated using recombinant techniques. Such variants include, but are not limited to, deletions, additions, and substitutions in the amino acid sequence of the CAT protein. For example, one class of substitutions is conserved amino acid substitutions. Such substitutions are those that substitute a given amino acid in a CAT protein by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306-1310 (1990).

Variant CAT proteins can be fully functional or can lack function in one or more activities, e.g., ability to bind substrate, ability to phosphorylate substrate, ability to mediate signaling, etc. Fully functional variants typically contain only conservative variations or variation in non-critical residues or in non-critical regions.

Non-functional variants typically contain one or more non-conservative amino acid substitutions, deletions, insertions, inversions, or truncations, or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081-1085 (1989)). The latter procedure introduces single alanine mutations at every residue in the molecule. The resulting mutant molecules are then tested for biological activity or in assays such as in vitro proliferative activity. Sites that are critical for binding partner/substrate binding can also be determined by structural analysis such as crystallization, nuclear magnetic resonance, or photoaffinity labeling (Smith et al., *J. Mol. Biol.* 224:899-904 (1992); de Vos et al., *Science* 255:306-312 (1992)).

Exemplary embodiments of the invention provide fragments of a CAT, and peptides that comprise and consist of such fragments. An exemplary fragment typically comprises at least about 5, 6, 8, 10, 12, 14, 16, 18, 20 or more contiguous amino acid residues of a CAT protein. Such fragments can be chosen based on the ability to retain one or more of the biological activities of CAT or can be chosen for the ability to perform a function, e.g., bind a substrate or act as an immunogen. Particularly important fragments are biologically active fragments, such as peptides that are, for example, about 8 or more amino acids in length. Such fragments can include a domain or motif of a CAT, e.g., an active site, a transmembrane domain, or a binding domain. Further, possible fragments include, but are not limited to, soluble peptide fragments and fragments containing immunogenic structures. Domains and functional sites can readily be identified, for example, by computer programs well known and readily available to those of skill in the art (e.g., PROSITE analysis).

Proteins can contain amino acids other than the 20 amino acids commonly referred to as the 20 naturally-occurring amino acids. Further, many amino acids, including the terminal amino acids, can be modified by natural processes, such as processing and other post-translational modifications, or by chemical modification techniques well known in the art. Common modifications that occur naturally in proteins are well known to those of skill in the art.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, tRNA-mediated addition of amino acids to proteins such as arginylation, and ubiquitination.

Such modifications are well known to those of skill in the art and have been described in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins-Structure and Molecular Properties, 2nd Ed., T. E. Creighton, W. H. Freeman and Company, New York (1993). Many detailed reviews are available on this subject, such as by Wold (Post-translational Covalent Modification of Proteins, B. C. Johnson, Ed., Academic Press, New York 1-12 (1983)); Seifter et al. (Meth. Enzymol. 182: 626-646 (1990)); and Rattan et al. (Ann. N.Y. Acad. Sci. 663:48-62 (1992)).

Accordingly, exemplary CAT proteins and fragments thereof of the invention can also encompasses derivatives or analogs in which, for example, a substituted amino acid residue is not one encoded by the genetic code, in which a substituent group is included, in which a mature CAT is fused with another composition, such as a composition to increase the half-life of a CAT (e.g., polyethylene glycol or albumin), or in which additional amino acids are fused to a mature CAT, such as a leader or secretory sequence or a sequence for purification of a mature CAT or a pro-protein sequence.

2. Antibodies to CAT Proteins

Exemplary embodiments of the invention provide antibodies to CAT proteins, including, for example, monoclonal and polyclonal antibodies; chimeric, humanized, and fully human antibodies; and antigen-binding fragments and variants thereof, as well as other embodiments.

Antibodies that selectively bind to a CAT protein can be made using standard procedures known to those of ordinary skills in the art. The term "antibody" is used in the broadest sense, and specifically covers, for example, monoclonal antibodies, polyclonal antibodies, multispecific antibodies (e.g., bispecific antibodies), chimeric antibodies, humanized antibodies, fully human antibodies, and antibody fragments (e.g., Fab, F(ab')$_2$, Fv and Fv-containing binding proteins), so long as they exhibit the desired biological activity. Antibodies (Ab's) and immunoglobulins (Ig's) are glycoproteins typically having the same structural characteristics. While antibodies exhibit binding specificity to a specific antigen, immunoglobulins include both antibodies and other antibody-like molecules that lack antigen specificity. Antibodies can be of the IgG, IgE, IgM, IgD, and IgA class or subclass thereof (e.g., IgG1, IgG2, IgG3, IgG4, IgA1 and IgA2). Antibodies may be interchangeably referred to as "antigen-binding molecules".

The term "monoclonal antibody", as used herein, refers to an antibody obtained from a population of substantially homogeneous antibodies, i.e., the individual antibodies comprising the population are substantially identical except for possible naturally occurring mutations that may be present in minor amounts. Monoclonal antibodies are highly specific and are typically directed against a single antigenic site. Furthermore, in contrast to polyclonal antibody preparations, which typically include different antibodies directed against different determinants (epitopes), each monoclonal antibody is typically directed against a single determinant on an antigen. In addition to their specificity, monoclonal antibodies are advantageous in that substantially homogenous antibodies can be produced by a hybridoma culture which is uncontaminated by other immunoglobulins or antibodies. The modifier "monoclonal" antibody indicates the character of the antibody as being obtained from a substantially homogeneous population of antibodies, and is not to be construed as requiring production of the antibody by any particular method. For example, monoclonal antibodies can be made by hybridoma methods such as described by Kohler and Milstein, *Nature* 256: 495-497 (1975), by recombinant methods (e.g., as described in U.S. Pat. No. 4,816,567), or can be isolated from phage antibody libraries such as by using the techniques described in Clackson et al., *Nature* 352: 624-628 (1991) or Marks et al., *J. Mol. Biol.* 222: 581-597 (1991).

"Humanized" forms of non-human (e.g., murine or rabbit) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Typically, humanized antibodies are human immunoglobulins (a recipient antibody) in which residues from a complementarity determining regions ("CDR") of the recipient are replaced by residues from a CDR of a non-human species (a donor antibody) such as mouse, rat, or rabbit having the desired specificity, affinity, and capacity. In some instances, Fv framework residues of the human immunoglobulin are replaced by corresponding non-human residues. Furthermore, a humanized antibody may comprise residues which are found neither in the recipient antibody nor in the imported CDR or framework region (FR) sequences. These modifications can be made to further refine and optimize antibody performance. In general, a humanized antibody can comprise substantially all of at least one, and typically two, variable domains, in which all or substantially all of the CDRs correspond to those of a non-human immunoglobulin and all or substantially all of the FRs are those of a human immunoglobulin consensus sequence. A humanized antibody can also comprise at least a portion of an immunoglobulin constant region (Fc), typically that of a human immunoglobulin. For further details concerning humanized antibodies, see: Jones et al., *Nature* 321:522-525 (1986); Reichmann et al., *Nature* 332:323-327 (1988); Presta, *Curr. Op. Struct. Biol.* 2:593-596 (1992); Queen et al., U.S. Pat. Nos. 5,530,101; 5,585,089; 5,693,762; and 6,180,370; and Winter, U.S. Pat. No. 5,225,539.

Antibodies, as used herein, include antibody fragments, particularly antigen-binding fragments, as well as other modified antibody structures and antigen-binding scaffolds (such as modified antibody structures that are smaller or have less than all domains or chains compared with a typical naturally occurring, full-size human antibody). Examples of antibody fragments and other modified antibody structures and antigen-binding scaffolds are known in the art by such terms as minibodies (e.g., U.S. Pat. No. 5,837,821), Nanobodies (llama heavy chain antibodies; Ablynx, Ghent, Belgium), Adnectins (fibronectin domains; Adnexus Therapeutics, Waltham, Mass.), Affibodies (protein-binding domain of *Staphylococcus aureus* protein A; Affibody, Stockholm, Sweden), peptide aptamers (synthetic peptides; Aptanomics, Lyon, France), Avimers (A-domains derived from cell surface receptors; Avidia, Mountain View, Calif. (acquired by Amgen)), Transbodies (transferrin; BioRexis Pharmaceuticals, King of Prussia, Pa. (acquired by Pfizer)), trimerized tetranectin domains (Borean Pharma, Aarhus, Denmark), Domain antibodies (heavy or light chain antibodies; Domantis, Cambridge, UK (acquired by GlaxoSmithKline)), Evibodies (derived from V-like domains of T-cell receptors CTLA-4, CD28 and inducible T-cell costimulator; EvoGenix Therapeutics, Sydney, Australia), scFV fragments (stable single chain antibody fragments; ESBATech, Zurich, Switzerland), Unibodies (monovalent IgG4 mAbs fragments; Genmab, Copenhagen, Denmark), BiTEs (bispecific, T-cell activating single-chain antibody fragments; Micromet, Munich, Germany), DARPins (designed ankyrin repeat proteins; Molecular Partners, Zurich, Switzerland), Anticalins (derived from lipocalins; Pieris, Freising-Weihenstephan, Germany), Affilins (derived from human lens protein gamma crystalline; Scil Proteins, Halle, Germany), and SMIPs (small modular immunopharmaceuticals; Trubion Pharmaceuticals, Seattle, Wash.) (Sheridan, *Nature Biotechnology*, 2007 April; 25(4):365-6).

An "isolated" or "purified" antibody is one that has been identified and separated and/or recovered from a component of the environment in which it is produced. Contaminant components of its production environment are materials that would interfere with diagnostic or therapeutic uses for the antibody, and may include enzymes, hormones, and other proteinaceous or nonproteinaceous solutes. In exemplary embodiments, the antibody can be purified as measurable by any of at least three different methods: 1) to greater than 95% by weight of antibody as determined by the Lowry method, preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or silver stain. Isolated antibody can include an antibody in situ within recombinant cells since at least one component of the antibody's natural environment will not be present. Ordinarily, however, an isolated antibody can be be prepared by at least one purification step.

An "antigenic region", "antigenic determinant", or "epitope" includes any protein determinant capable of specific binding to an antibody. This is the site on an antigen to which each distinct antibody molecule binds. Epitopic determinants can be active surface groupings of molecules such as amino acids or sugar side chains and may have specific three-dimensional structural characteristics or charge characteristics.

"Antibody specificity" refers to an antibody that has a stronger binding affinity for an antigen from a first subject species than it has for a homologue of that antigen from a second subject species. Typically, an antibody "binds specifically" to a human antigen (e.g., has a binding affinity (Kd) value of no more than about $1\times10^{-7}$ M, preferably no more than about $1\times10^{-8}$ M, and most preferably no more than about $1\times10^{-9}$ M) but has a binding affinity for a homologue of the antigen from a second subject species which is at least about 50-fold, or at least about 500-fold, or at least about 1000-fold, weaker than its binding affinity for the human antigen. The antibodies can be of any of the various types of antibodies as described herein, such as humanized or fully human antibodies.

An antibody "selectively" or "specifically" binds a target protein when the antibody binds the target protein and does not significantly bind to unrelated proteins. An antibody can still be considered to selectively or specifically bind a target protein even if it also binds to other proteins that are not substantially homologous with the target protein as long as such proteins share homology with a fragment or domain of the target protein. In this case, it would be understood that antibody binding to the target protein is still selective despite some degree of cross-reactivity.

Exemplary embodiments of the invention provide an "antibody variant", which refers to an amino acid sequence variant of an antibody wherein one or more of the amino acid residues have been modified. Such variants necessarily have less than 100% sequence identity with the amino acid sequence of the antibody, and have at least 75%, 80%, 85%, 90%, 95%, 96%, 97%, 98%, or 99% amino acid sequence identity with the amino acid sequence of either the heavy or chain variable domain of the antibody.

The term "antibody fragment" refers to a portion of a full-length antibody, including the antigen binding or variable region or the antigen-binding portion thereof. Examples of antibody fragments include Fab, Fab', F(ab')$_2$ and Fv fragments. Papain digestion of antibodies typically produces two identical antigen binding fragments, called the Fab fragment, each with a single antigen binding site, and a residual "Fc" fragment. Pepsin treatment typically yields an F(ab')$_2$ fragment that has two antigen binding fragments which are capable of crosslinking antigen, and a residual other fragment (which is termed pFc').

Examples of additional antigen-binding fragments can include diabodies, triabodies, tetrabodies, single-chain Fv, single-chain Fv-Fc, SMIPs, and multispecific antibodies formed from antibody fragments. A "functional fragment", with respect to antibodies, typically refers to an Fv, F(ab), F(ab')$_2$ or other antigen-binding fragments comprising one or more CDRs that has substantially the same antigen-binding specificity as an antibody.

An "Fv" fragment is an example of an antibody fragment that contains a complete antigen recognition and binding site. This region typically consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen.

An "Fab" fragment (also designated as "F(ab)") also contains the constant domain of the light chain and the first constant domain (CH1) of the heavy chain. Fab' fragments differ from Fab fragments by the addition of a few residues at the carboxyl terminus of the heavy chain CH1 domain, including one or more cysteines from the antibody hinge region. Fab'-SH is the designation for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

A "single-chain Fv" or "scFv" antibody fragment contains $V_H$ and $V_L$ domains, wherein these domains are present in a single polypeptide chain. Typically, the Fv polypeptide further comprises a polypeptide linker between the $V_H$ and $V_L$ domains that enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). A single chain Fv-Fc is an scFv linked to a Fc region.

A "diabody" is a small antibody fragment with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., *Proc. Natl. Acad.*

Sci. USA 90:6444-6448 (1993). Triabodies, tetrabodies and other antigen-binding antibody fragments have been described by Hollinger and Hudson, 2005, *Nature Biotechnology* 23:1126.

A "small modular immunopharmaceutical" (or "SMIP") is a single-chain polypeptide including a binding domain (e.g., an scFv or an antigen binding portion of an antibody), a hinge region, and an effector domain (e.g., an antibody Fc region or a portion thereof). SMIPs are described in published U.S. Patent Application No. 20050238646.

Many methods are known for generating and/or identifying antibodies to a given target protein. Several such methods are described by Kohler et al., 1975, *Nature* 256: 495-497; Lane, 1985, *J. Immunol. Meth.* 81:223-228; Harlow et al., 1988, Antibodies: A Laboratory Manual. Cold Spring Harbor Laboratory Press; Harlow et al., 1998, Using Antibodies, Cold Spring Harbor Press; Zhong et al., 1997, *J. Indust. Microbiol. Biotech.* 19(1):71-76; and Berry et al., 2003, Hybridoma and Hybridomics 22(1): 23-31.

Polyclonal antibodies can be prepared by any known method or modifications of these methods, including obtaining antibodies from patients. In certain exemplary methods for generating antibodies such as polyclonal antibodies, an isolated protein can be used as an immunogen which is administered to a mammalian organism, such as a rat, rabbit, or mouse. For example, a complex of an immunogen such as a CAT protein (or fragment thereof) and a carrier protein can be prepared and an animal immunized by the complex. Serum or plasma containing antibodies against the protein can be recovered from the immunized animal and the antibodies separated and purified (in the same manner as for monoclonal antibodies, for example). The gamma globulin fraction or the IgG antibodies can be obtained, for example, by use of saturated ammonium sulfate or DEAE SEPHADEX, or other techniques known to those skilled in the art. The antibody titer in the antiserum can be measured in the same manner as in the supernatant of a hybridoma culture.

A full-length CAT protein, an antigenic peptide fragment, or a fusion protein thereof, can be used as an immunogen. A protein used as an immunogen is not limited to any particular type of immunogen. In one aspect, antibodies can be prepared from regions or discrete fragments (e.g., functional domains, extracellular domains, or portions thereof) of a CAT protein. Antibodies can be prepared from any region of a protein as described herein. In particular, the proteins can be selected from the group consisting of SEQ ID NOS:1-3, 7-9, 13-17, 23, 25-33, 43-44, 47-48, 51-52, 56-59, 64-67, and 72-73 and fragments thereof. An antigenic fragment can typically comprise at least 8, 10, 12, 14, 16, or more contiguous amino acid residues, for example. Such fragments can be selected based on a physical property, such as fragments that correspond to regions located on the surface of a protein (e.g., hydrophilic regions) or can be selected based on sequence uniqueness.

Antibodies can also be produced by inducing production in a lymphocyte population or by screening antibody libraries or panels of highly specific binding reagents, such as disclosed in Orlandi et al. (*Proc. Natl. Acad. Sci.* 86:3833-3837 (1989)) or Winter et al. (*Nature* 349:293-299 (1991)). A protein can be used in screening assays of phagemid or B-lymphocyte immunoglobulin libraries to identify antibodies having a desired specificity. Numerous protocols for competitive binding or immunoassays using either polyclonal or monoclonal antibodies with established specificities are well known in the art (e.g., Smith, *Curr. Opin. Biotechnol.* 2: 668-673 (1991)).

Antibodies can also be generated using various phage display methods known in the art. In representative phage display methods, functional antibody domains are displayed on the surface of phage particles which carry nucleic acid molecules that encode the antibody domains. In particular, such phage can be utilized to display antigen-binding domains expressed from a repertoire or combinatorial antibody library (e.g., human or murine). Phage expressing an antigen binding domain that binds an antigen of interest can be selected or identified with the antigen, e.g., using labeled antigen or antigen bound or captured to a solid surface or bead. Phage used in methods such as these can typically be filamentous phage including fd and M13 binding domains expressed from phage with Fab, Fv, or disulfide stabilized Fv antibody domains recombinantly fused to either the phage gene III or gene VIII protein. Examples of phage display methods that can be used to make antibodies include methods described in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187:9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Antibodies, antigen binding fragments, and/or antibody variants can be produced by recombinant and genetic engineering methods well known in the art. For example, methods of expressing heavy and light chain genes in *E. coli* are described in PCT publication numbers WO901443, WO901443, and WO9014424, and in Huse et al., 1989 *Science* 246:1275-1281. When using recombinant techniques, such as to produce an antibody variant, the antibody variant can be produced intracellularly, in the periplasmic space, or directly secreted into the medium. If an antibody variant is produced intracellularly, as a first step, the particulate debris, either host cells or lysed fragments, can be removed, for example, by centrifugation or ultrafiltration. Carter et al. (*Bio/Technology* 10: 163-167 (1992)) describe a procedure for isolating antibodies that are secreted to the periplasmic space of *E. coli*. Briefly, cell paste can be thawed in the presence of sodium acetate (pH 3.5), EDTA, and phenylmethylsulfonylfluoride (PMSF) over about 30 minutes. Cell debris can be removed by centrifugation. Where an antibody variant is secreted into the medium, supernatants from such expression systems can first be concentrated using a commercially available protein concentration filter (e.g., an Amicon or Millipore PELLICON ultrafiltration unit). A protease inhibitor such as PMSF can be included in any of the foregoing steps to inhibit proteolysis, and antibiotics can be included to prevent the growth of contaminating microorganisms.

An antibody composition prepared from cells can be purified using, for example, affinity chromatography, hydroxylapatite chromatography, gel electrophoresis, and/or dialysis. The suitability of protein A as an affinity ligand typically depends on the species and isotype of the immunoglobulin Fc domain of an antibody. Protein A can be used to purify antibodies that are based on human delta1, delta2, or delta4 heavy chains (Lindmark et al., *J. Immunol Meth.* 62: 1-13 (1983)). Protein G can be used for all mouse isotypes and for human delta3 (Guss et al., *EMBO J.* 5: 1567-1575 (1986)). The matrix to which the affinity ligand is attached can be, for example, agarose or mechanically stable matrices such as controlled pore glass or poly(styrenedivinyl)benzene. Where the antibody comprises a CH3 domain, the BAKERBOND ABX™ resin (J. T. Baker, Phillipsburg, N.J.) can be used for purification. Other exemplary techniques for antibody purification include, but are not limited to, fractionation on an ion-exchange column, ethanol precipitation, reverse phase HPLC, chromatography on silica, chromatography on heparin hepharos, chromatography on an anion or cation exchange resin (such as a polyaspartic acid column), chromatofocusing, SDS-PAGE, and ammonium sulfate precipitation.

Following any preliminary purification step(s), contaminants in a mixture containing an antibody of interest can be removed by low pH hydrophobic interaction chromatography using an elution buffer at a pH between about 2.5-4.5, preferably performed at low salt concentrations (e.g., from about 0-0.25M salt).

Full-length antibodies, as well as antibody fragments, can also be expressed and isolated from bacteria such as *E. coli*, such as described in Mazor et al., "Isolation of engineered, full-length antibodies from libraries expressed in *Escherichia coli*", *Nat. Biotechnol.* 2007 May; 25(5):563-5 and Sidhu, "Full-length antibodies on display", *Nat. Biotechnol.* 2007 May; 25(5):537-8.

Further details regarding antibodies are set forth in the following U.S. Pat. Nos. 6,248,516 (Winter et al.); 6,291,158 (Winter et al.); 5,885,793 (Griffiths et al.); 5,969,108 (McCafferty et al.); 5,939,598 (Kucherlapati et al.); 4,816,397 (Boss et al.); 4,816,567 (Cabilly et al.); 6,331,415 (Cabilly et al.); 5,770,429 (Lonberg et al.); 5,639,947 (Hiatt et al.); and 5,260,203 (Ladner et al.), each of which is incorporated herein by reference, and in the following published U.S. patent applications: US20040132101 (Lazar et al.), US20050064514 (Stavenhagen et al.), US20040261148 (Dickey et al.), and US20050014934 (Hinton et al.), each of which is incorporated herein by reference.

3. Antibody-Drug Conjugates to CAT Proteins

An antibody against CAT can be coupled (e.g., covalently bonded) to a suitable therapeutic agent (as further discussed herein) either directly or indirectly (e.g., via a linker group). A direct reaction between an antibody and a therapeutic agent is possible when each possesses a substituent capable of reacting with the other. For example, a nucleophilic group, such as an amino or sulfhydryl group, on one molecule may be capable of reacting with a carbonyl-containing group, such as an anhydride or an acid halide, or with an alkyl group containing a good leaving group (e.g., a halide) on the other molecule.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

A variety of bifunctional or polyfunctional reagents, both homo- and hetero-functional (such as those described in the catalog of the Pierce Chemical Co., Rockford, Ill.), can be employed as the linker group. Coupling can be effected, for example, through amino groups, carboxyl groups, sulfhydryl groups, or oxidized carbohydrate residues (e.g., U.S. Pat. No. 4,671,958).

Where a therapeutic agent is more potent when free from the antibody portion of an immunoconjugate, it may be desirable to use a linker group that is cleavable during or upon internalization into a cell. A number of different cleavable linker groups have been described. Mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), by protease cleavable linker (e.g., U.S. Pat. No. 6,214,345), and by acid-catalyzed hydrolysis (e.g., U.S. Pat. No. 4,569,789).

It may be desirable to couple more than one agent to an antibody. Multiple molecules of an agent can be coupled to one antibody molecule, and more than one type of agent can be coupled to the same antibody. For example, about 1, 2, 4, 6, 8, 10, 12, 14, 16, 18, 20, or 22 (or any other number in-between) molecules of therapeutic agents can be coupled to an antibody. The average number or quantitative distribution of therapeutic agent molecules per antibody molecule in a preparation of conjugation reactions can be determined by conventional means such as mass spectroscopy, ELISA, or HPLC. Separation, purification, and characterization of homogeneous antibody-drug conjugates having a certain number of therapeutic agents conjugated thereto can be achieved by means such as reverse phase HPLC or electrophoresis (see, e.g., Hamblett et al., *Clinical Cancer Res.* 10:7063-70 (2004).

Examples of suitable therapeutic agents that can be conjugated to an antibody include, but are not limited to, chemotherapeutic agents (e.g., cytotoxic or cytostatic agents or immunomodulatory agents), radiotherapeutic agents, therapeutic antibodies, small molecule drugs, peptide drugs, immunomodulatory agents, differentiation inducers, and toxins.

Examples of useful classes of cytotoxic or immunomodulatory agents include, but are not limited to, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Examples of individual cytotoxic or immunomodulatory agents include, but are not limited to, androgen, anthramycin (AMC), asparaginase, 5-azacytidine, azathioprine, bleomycin, busulfan, buthionine sulfoximine, calicheamicin or calicheamicin derivatives, camptothecin or camptothecins derivatives, carboplatin, carmustine (BSNU), CC-1065, chlorambucil, cisplatin, colchicine, cyclophosphamide, cytidine arabinoside (cytarabine), cytochalasin B, dacarbazine, dactinomycin (formerly actinomycin), daunorubicin, decarbazine, docetaxel, doxorubicin, etoposide, estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16, and VM-26.

Examples of other suitable cytotoxic agents include, but are not limited to, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, a maytansinoid, discodermolide, eleutherobin, and mitoxantrone.

Examples of other suitable agents include, but are not limited to, radionuclides, differentiation inducers, drugs, toxins, and derivatives thereof. Exemplary radionuclides include $^{90}$Y, $^{123}$I, $^{125}$I, $^{131}$I, $^{186}$Re, $^{188}$Re, $^{211}$At, and $^{212}$Bi. Exemplary drugs include methotrexate, and pyrimidine and purine analogs. Exemplary differentiation inducers include phorbol esters and butyric acid. Exemplary toxins include ricin, abrin, diptheria toxin, cholera toxin, gelonin, *Pseudomonas* exotoxin, *Shigella* toxin, and pokeweed antiviral protein.

In some embodiments, the therapeutic agent used in an antibody-drug conjugate is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs (e.g., epothilone A and B), nocodazole, colchicine and colcimid, estramustine, cryptophysins, cemadotin, maytansinoid, combretastatins, discodermolide, and eleutherobin.

In certain embodiments, the cytotoxic agent is a maytansinoid, another group of anti-tubulin agents. For example, in specific embodiments, the maytansinoid is maytansine, DM-1 (ImmunoGen, Inc.; see also Chari et al., *Cancer Res.* 52:127-131 (1992)) or DM-4. In some embodiments, the therapeutic agent is an auristatin, such as auristatin E (also known in the art as dolastatin-10) or a derivative thereof. Typically, an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP, MMAF, and MMAE. The synthesis and structure of auristatin derivatives are described in U.S. Patent Application Publication Nos. 2003-0083263, 2005-0238649 and 2005-0009751; PCT Publication Nos WO 04/010957 and WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

4. CAT Nucleic Acid Molecules

Exemplary isolated CAT nucleic acid molecules of the invention consist of, consist essentially of, or comprise a nucleotide sequence that encodes a CAT protein of the invention, an allelic variant thereof, or an ortholog or paralog thereof, for example. As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 kilobases (KB), 4 KB, 3 KB, 2 KB, or 1 KB or less, particularly contiguous protein-encoding sequences and protein-encoding sequences within the same gene but separated by introns in the genomic sequence, and flanking nucleotide sequences that contain regulatory elements. The primary consideration is that the nucleic acid is isolated from remote and unimportant flanking sequences such that it can be subjected to the specific manipulations described herein such as recombinant expression, preparation of probes and primers, and other uses specific to the nucleic acid molecules. Moreover, an "isolated" nucleic acid molecule, such as a transcript/cDNA molecule, can be substantially free of other cellular material, or culture medium when produced by recombinant techniques, or chemical precursors or other chemicals when chemically synthesized.

A nucleic acid molecule can be fused to other coding or regulatory sequences and still be considered isolated. Isolated nucleic acid molecules can include heterologous nucleotide sequences, such as heterologous nucleotide sequences that are fused to a nucleic acid molecule by recombinant techniques. For example, recombinant DNA molecules contained in a vector are considered isolated. Further examples of isolated DNA molecules include recombinant DNA molecules maintained in heterologous host cells, or purified (partially or substantially) DNA molecules in solution. Isolated RNA molecules include in vivo or in vitro RNA transcripts of isolated DNA molecules. Isolated nucleic acid molecules further include such molecules produced synthetically.

Isolated nucleic acid molecules can encode a mature protein plus additional amino or carboxyl-terminal amino acids, or amino acids interior to the mature protein (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, additional amino acids may be processed away from the mature protein by cellular enzymes.

Isolated nucleic acid molecules include, but are not limited to, sequences encoding a CAT protein alone, sequences encoding a mature protein with additional coding sequences (such as a leader or secretory sequence (e.g., a pre-pro or pro-protein sequence)), and sequences encoding a mature protein (with or without additional coding sequences) plus additional non-coding sequences (e.g., introns and non-coding 5' and 3' sequences such as transcribed but non-translated sequences that play a role in transcription, mRNA processing (including splicing and polyadenylation signals), ribosome binding, and/or stability of mRNA). In addition, nucleic acid molecules can be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. Nucleic acid molecules, especially DNA, can be double-stranded or single-stranded. Single-stranded nucleic acid can be the coding strand (sense strand) or the non-coding strand (anti-sense strand).

Exemplary embodiments of the invention further provide isolated nucleic acid molecules that encode fragments of a CAT protein as well as nucleic acid molecules that encode obvious variants of a CAT protein. Such nucleic acid molecules may be naturally occurring, such as allelic variants (same locus), paralogs (different locus), and orthologs (different organism), or can be constructed by recombinant DNA methods or by chemical synthesis. Such non-naturally occurring variants can be made by mutagenesis techniques, including those applied to nucleic acid molecules, cells, or organisms. Accordingly, nucleic acid molecule variants can contain nucleotide substitutions, deletions, inversions, and/or insertions. Variations can occur in either or both the coding and non-coding regions, and variations can produce conservative and/or non-conservative amino acid substitutions.

A fragment of a nucleic acid molecule typically comprises a contiguous nucleotide sequence at least 8, 10, 12, 15, 16, 18, 20, 22, 25, 30, 40, 50, 100, 150, 200, 250, 500 (or any other number in-between) or more nucleotides in length. The length of a fragment can be based on its intended use. For example, a fragment can encode epitope bearing regions of a protein, or can be used as DNA probes and primers. Isolated fragments can be produced by synthesizing an oligonucleotide probe using known techniques, for example, and can optionally be labeled and used to screen a cDNA library, genomic DNA, or mRNA, for example. Primers can be used in PCR reactions to clone specific regions of a gene.

A probe/primer typically comprises substantially a purified oligonucleotide or oligonucleotide pair. An oligonucleotide typically comprises a nucleotide sequence that hybridizes under stringent conditions to at least about 8, 10, 12, 14, 15, 16, 17, 18, 19, 20, 21, 22, 23, 24, 25, 30, 40, 50 (or any other number in-between) or more contiguous nucleotides.

Allelic variants, orthologs, and homologs can be identified using methods well known in the art. These variants can comprise a nucleotide sequence encoding a protein that is typically 60-70%, 70-80%, 80-90%, 90-95%, 96%, 97%, 98%, or 99% homologous to the nucleotide sequence. Such nucleic acid molecules can readily be identified as being able to hybridize under moderate to stringent conditions, to a nucleotide sequence shown in the Sequence Listing or a fragment thereof.

As used herein, the term "hybridizes under stringent conditions" is intended to describe conditions for hybridization and washing under which nucleotide sequences encoding a protein at least 60-70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in, for example, Current Protocols in Molecular Biology, John Wiley & Sons, N.Y. (1989-2006), 6.3.1-6.3.6. One example of stringent hybridization conditions is hybridization in 6× sodium chloride/sodium citrate (SSC) at about 45° C., followed by one or more washes in 0.2×SSC, 0.1% SDS at 50-65° C. Examples of moderate to low stringency hybridization conditions are well known in the art.

Exemplary embodiments of the invention also include kits for detecting the presence of CAT nucleic acid (e.g., DNA or mRNA) in a biological sample. For example, a kit can comprise reagents such as a labeled or labelable nucleic acid and/or other agents capable of detecting CAT nucleic acid in a biological sample; means for determining the amount of CAT nucleic acid in the sample; and means for comparing the amount of CAT nucleic acid in the sample with a standard. The nucleic acid and/or other agent can be packaged in one or more suitable containers. The kit can further comprise instructions for using the kit to detect CAT nucleic acid.

5. Vectors and Host Cells

Exemplary embodiments of the invention also provide vectors containing CAT ° nucleic acid molecules. The term "vector" refers to a vehicle, such as a nucleic acid molecule, which can transport the CAT nucleic acid molecules. When the vector is a nucleic acid molecule, the CAT nucleic acid molecules are covalently linked to the vector nucleic acid. A vector can be, for example, a plasmid, single or double stranded phage, a single or double stranded RNA or DNA viral vector, or artificial chromosome, such as a BAC, PAC, YAC, OR MAC.

A vector can be maintained in a host cell as an extrachromosomal element where it replicates and produces additional copies of the CAT nucleic acid molecules. Alternatively, a vector can integrate into a host cell genome and produce additional copies of the CAT nucleic acid molecules when the host cell replicates.

Exemplary embodiments of the invention provide vectors for maintenance (cloning vectors) and vectors for expression (expression vectors) of the nucleic acid molecules, for example. Expression vectors can express a portion of, or all of, a protein sequence. Vectors can function in prokaryotic or eukaryotic cells or in both (shuttle vectors). Vectors also include insertion vectors, which integrate a nucleic acid molecule into another nucleic acid molecule, such as into the cellular genome (such as to alter in situ expression of a gene and/or gene product). For example, an endogenous protein-coding sequence can be entirely or partially replaced via homologous recombination with a protein-coding sequence containing one or more specifically introduced mutations.

Expression vectors can contain cis-acting regulatory regions that are operably-linked in the vector to the nucleic acid molecules such that transcription of the nucleic acid molecules is allowed in a host cell. The nucleic acid molecules can be introduced into the host cell with a separate nucleic acid molecule capable of affecting transcription. The separate nucleic acid molecule may provide, for example, a trans-acting factor interacting with the cis-regulatory control region to allow transcription of the nucleic acid molecules from the vector. Alternatively, a trans-acting factor may be supplied by a host cell. Additionally, a trans-acting factor can be produced from a vector itself. It is understood, however, that transcription and/or translation of nucleic acid molecules can occur in cell-free systems.

Regulatory sequences to which CAT nucleic acid molecules can be operably linked include, for example, promoters for directing mRNA transcription. These include, but are not limited to, the left promoter from bacteriophage, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors can also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region, a ribosome binding site for translation. Other regulatory control elements for expression include initiation and termination codons as well as polyadenylation signals. Numerous regulatory sequences useful in expression vectors are well known in the art (e.g., Sambrook et al., Molecular Cloning: A Laboratory Manual. 3rd. ed., Cold Spring Harbor Laboratory Press, Cold Spring Harbor, N.Y. (2001)).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., Molecular Cloning: A Laboratory Manual. 3rd. ed., Cold Spring Harbor Laboratory Press, Cold Spring Harbor, N.Y. (2001).

A regulatory sequence can provide constitutive expression in one or more host cells (e.g., tissue specific) or can provide for inducible expression in one or more cell types such as by temperature, nutrient additive, or exogenous factors such as a hormone or other ligand. A variety of vectors providing for constitutive and inducible expression in prokaryotic and eukaryotic hosts are well known in the art.

Nucleic acid molecules can be inserted into vector nucleic acid by well-known methodology. For example, the DNA sequence that will ultimately be expressed can be joined to an expression vector by cleaving the DNA sequence and the expression vector with one or more restriction enzymes and then ligating the fragments together. Procedures for restriction enzyme digestion and ligation are well known in the art.

A vector containing a nucleic acid molecule of interest can be introduced into an appropriate host cell for propagation or expression using well-known techniques. Bacterial cells include, but are not limited to, *E. coli*, *Streptomyces*, and *Salmonella typhimurium*. Eukaryotic cells include, but are not limited to, yeast, insect cells such as *Drosophila*, animal cells such as COS and CHO cells (e.g., DG44 or CHO-s), and plant cells.

As described herein, it may be desirable to express a protein as a fusion protein. Accordingly, exemplary embodiments of the invention provide fusion vectors that allow for the production of fusion proteins. Fusion vectors can, for example, increase the expression of a recombinant protein; increase the solubility of a recombinant protein, and/or aid in the purification of a protein such as by acting as a ligand for affinity purification. A proteolytic cleavage site can be introduced at the junction of the fusion moiety so that the desired protein can ultimately be separated from the fusion moiety. Proteolytic enzymes include, but are not limited to, factor Xa, thrombin, and enteroenzyme. Typical fusion expression vectors include pGEX (Smith et al., Gene 67:31-40 (1988)), pMAL (New England Biolabs, Beverly, Mass.) and pRIT5 (Pharmacia, Piscataway, N.J.), which fuse glutathione S-transferase (GST), maltose E binding protein, or protein A, respectively, to a target recombinant protein. Examples of suitable inducible non-fusion *E. coli* expression vectors include pTrc (Amann et al., Gene 69:301-315 (1988)) and pET 11d (Studier et al., Gene Expression Technology: Methods in Enzymology 185:60-89 (1990)).

Recombinant protein expression can be maximized in host bacteria by providing a genetic background wherein the host cell has an impaired capacity to proteolytically cleave the recombinant protein (Gottesman, S., Gene Expression Technology: Methods in Enzymology 185, Academic Press, San Diego, Calif. (1990), pp. 119-128). Alternatively, the sequence of a nucleic acid molecule of interest can be altered to provide preferential codon usage for a specific host cell, such as *E. coli* (Wada et al., Nucleic Acids Res. 20:2111-2118 (1992)).

CAT nucleic acid molecules can, for example, be expressed by expression vectors in a yeast host. Examples of vectors for expression in yeast (e.g., *S. cerevisiae*) include pYepSec1 (Baldari, et al., EMBO J. 6:229-234 (1987)), pMFa (Kurjan et al., Cell 30:933-943 (1982)), pJRY88 (Schultz et al., Gene 54:113-123 (1987)), and pYES2 (Invitrogen Corporation, San Diego, Calif.). Nucleic acid molecules can also be expressed in insect cells using, for example, baculovirus expression vectors. Baculovirus vectors available for expression of proteins in cultured insect cells (e.g., Sf 9 cells) include the pAc series (Smith et al., Mol. Cell. Biol. 3:2156-2165 (1983)) and the pVL series (Lucklow et al., Virology 170:31-39 (1989)). Nucleic acid molecules can also be expressed in mammalian cells using mammalian expression vectors. Examples of mammalian expression vectors include pCDM8 (Seed, B. *Nature* 329:840 (1987)), pMT2PC (Kaufman et al., *EMBO J.* 6:187-195 (1987)), and CHEF (U.S. Pat. No. 5,888,809).

The expression vectors listed herein are provided by way of example only of well-known vectors available to those of ordinary skill in the art that would be useful to express CAT nucleic acid molecules. The person of ordinary skill in the art would be aware of other vectors suitable for maintenance, propagation, and/or expression of CAT nucleic acid molecules (e.g., Sambrook et al. Molecular Cloning: A Laboratory Manual. 3rd. ed., Cold Spring Harbor Laboratory Press, Cold Spring Harbor, N.Y. (2001).

Exemplary embodiments of the invention also encompasses vectors in which CAT nucleic acid molecules are cloned into a vector in reverse orientation, but operably linked to a regulatory sequence that permits transcription of antisense RNA. Thus, an antisense transcript can be produced to all, or to a portion, of a CAT nucleic acid molecule, including coding and non-coding regions. Expression of this antisense RNA may be subject to each of the parameters described above in relation to expression of the sense RNA (e.g., regulatory sequences, constitutive or inducible expression, tissue-specific expression).

Exemplary embodiments of the invention provide recombinant host cells containing the vectors described herein. Host cells include, for example, prokaryotic cells, lower eukaryotic cells such as yeast, other eukaryotic cells such as insect cells, and higher eukaryotic cells such as mammalian cells.

Recombinant host cells can be prepared by introducing vector constructs, such as described herein, into cells by techniques readily available to a person of ordinary skill in the art. These techniques include, but are not limited to, calcium phosphate transfection, DEAE-dextran-mediated transfection, cationic lipid-mediated transfection, electroporation, transduction, infection, lipofection, microinjection, and other techniques such as those found in Sambrook, et al. (Molecular Cloning: A Laboratory Manual. 3rd. ed., Cold Spring Harbor Laboratory Press, Cold Spring Harbor, N.Y. (2001).

For example, using techniques such as these, a retroviral or other viral vector can be introduced into mammalian cells. Examples of mammalian cells into which a retroviral vector can be introduced include, but are not limited to, primary mammalian cultures or continuous mammalian cultures, COS cells, NIH3T3, 293 cells (ATCC #CRL 1573), and dendritic cells.

Host cells can contain more than one vector. Thus, different nucleotide sequences can be introduced on different vectors of the same cell. Similarly, nucleic acid molecules of interest can be introduced either alone or with other unrelated nucleic acid molecules such as those providing trans-acting factors for expression vectors. When more than one vector is introduced into a cell, the vectors can be introduced independently, co-introduced, or joined to the nucleic acid molecule vector.

Bacteriophage and viral vectors can be introduced into cells as packaged or encapsulated virus by standard procedures for infection and transduction. Viral vectors can be replication-competent or replication-defective. If viral replication is defective, replication can occur in host cells that provide functions that complement the defects.

Vectors can include selectable markers that enable the selection of a subpopulation of cells that contain the recombinant vector constructs. Markers can be contained in the same vector that contains the nucleic acid molecules of interest or can be on a separate vector. Exemplary markers include tetracycline or ampicillin-resistance genes for prokaryotic host cells, and dihydrofolate reductase or neomycin resistance for eukaryotic host cells. However, any marker that provides selection for a phenotypic trait can be used.

While mature proteins can be produced in bacteria, yeast, mammalian cells, and other cells under the control of appropriate regulatory sequences, cell-free transcription and translation systems can also be used to produce these proteins using RNA derived from the DNA constructs described herein.

If secretion of a protein is desired, appropriate secretion signals can be incorporated into a vector. The signal sequence can be endogenous or heterologous to the protein.

If a protein is not secreted into a medium, the protein can be isolated from a host cell by standard disruption procedures, including freeze/thaw, sonication, mechanical disruption, use of lysing agents, and the like. A protein can then be recovered and purified by well-known purification methods including, for example, ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that, depending upon the host cell used in recombinant production of a protein, proteins can have various glycosylation patterns or can be non-glycosylated, such as when produced in bacteria. In addition, proteins can include an initial modified methionine in some instances as a result of a host-mediated process.

Recombinant host cells that express a CAT protein have a variety of uses. For example, such host cells are useful for producing CAT proteins, which can be further purified to produce desired amounts of the protein or fragments thereof. Thus, host cells containing expression vectors are useful for protein production.

Host cells are also useful for conducting cell-based assays involving a CAT protein or fragments thereof. For example, a recombinant host cell expressing a CAT protein can be used to assay compounds that stimulate or inhibit the protein's function.

Host cells are also useful for identifying mutant CAT proteins in which the protein's function is affected. Host cells expressing mutant proteins are useful for assaying compounds that have a desired effect on the mutant proteins (e.g., stimulating or inhibiting function), particularly if the mutant proteins naturally occur and give rise to a pathology.

6. Diagnosis and Treatment in General

The following terms, as used in the present specification and claims, are intended to have the meaning as defined below, unless indicated otherwise.

As used herein, a "biological sample" (or just "sample") can comprise, for example, tissue, blood, sera, cells, cell lines, or biological fluids such as plasma, interstitial fluid, urine, cerebrospinal fluid, and the like. A biological sample is typically, although not necessarily, obtained from an individual by a medical practitioner.

As used herein, a "subject" can be a mammalian subject or non-mammalian subject, preferably a mammalian subject. A mammalian subject can be a human or non-human, preferably a human. The terms "subject", "individual", and "patient" are used herein interchangeably.

A "healthy" or "normal" subject or biological sample is a subject or biological sample in which the disease of interest is not detectable, as ascertained by using conventional diagnostic methods (such a biological sample can interchangeably be referred to as a "control" sample).

As used herein, "disease(s)" include cancer, particularly the cancers identified in the Figures and section 13 of the Examples for each target, and associated diseases and pathologies.

The terms "diagnose" (or "diagnosing", etc.) and "assess" (or "assessing", etc.) are used herein interchangeably. Diagnosing or assessing diseases can include, for example, initially detecting a disease; determining a specific stage, subtype, or other classification of a disease; prognosing the future course of a disease; monitoring disease progression or remission (e.g., monitoring metastatic spread of a cancer); determining response to a treatment; determining or predicting recurrence of a disease; and/or determining the likelihood of developing a disease in the future.

"Treat", "treating", or "treatment" of a disease includes: (1) inhibiting the disease, i.e., arresting or reducing the development of the disease or its clinical symptoms, or (2) relieving the disease, i.e., causing regression of the disease or its clinical symptom(s).

The term "prophylaxis" is used to distinguish from "treatment," and to encompass both "preventing" and "suppressing." It is not always possible to distinguish between "preventing" and "suppressing," as the ultimate inductive event or events may be unknown, latent, or the patient is not ascertained until well after the occurrence of the event or events. Therefore, the term "protection", as used herein, is meant to include "prophylaxis."

A "therapeutically effective amount" means the amount of an agent that, when administered to a subject for treating a disease, is sufficient to effect such treatment for the disease. The "therapeutically effective amount" can vary depending on such factors as the agent, the disease and its severity, and the age, weight, etc., of the subject to be treated.

A "differential level" is a level of a target (e.g., CAT protein or nucleic acid) in a test sample (e.g., disease sample, or drug resistant cells) either above or below the level of the same target in a corresponding control or normal sample (e.g., a control cell line or a biological sample from a healthy individual, or cells responsive/sensitive to a drug).

Exemplary embodiments of the invention provide methods for treating diseases, especially cancer, particularly the cancers identified in the Figures and section 13 of the Examples for each target, comprising administering to a patient a therapeutically effective amount of an antagonist, agonist, or a pharmaceutical composition thereof. Exemplary embodiments of the invention further provide agonists and antagonists to CAT proteins, as well as pharmaceutical compositions that comprise an agonist or antagonist with a suitable carrier such as a pharmaceutically acceptable excipient.

Exemplary agonists or antagonists include antibodies that specifically bind to a CAT protein. Antibodies can be used alone or in combination with one or more other therapeutic agents (e.g., as an antibody-drug conjugate or a combination therapy). Further examples of molecules that can be used as antagonists include, but are not limited to, small molecules that inhibit the function or abundance level of CAT, and inhibitory nucleic acid molecules such as RNAi or antisense nucleic acid molecules that specifically hybridize to CAT nucleic acid.

Exemplary embodiments of the invention further encompass novel agents identified by screening assays using CAT, such as the screening assays described herein, as well as methods of using these agents, such as for treatment or diagnostic purposes. For example, an agent identified as described herein (e.g., a CAT-modulating agent, a CAT-specific nucleic acid molecule such as an RNAi or antisense molecule, a CAT-specific antibody, a CAT-specific antibody-drug conjugate, or a CAT-binding partner) can be used in an animal or other model, such as to determine efficacy, toxicity, or side effects of treatment with the agent.

Modulators of CAT protein activity, such as modulators identified according to the drug screening assays described herein, can be used to treat a subject with a disorder mediated by a CAT, e.g., by treating cells or tissues that express CAT at a differential level. Methods of treatment can include the step of administering a modulator of CAT activity in a pharmaceutical composition to a subject in need of such treatment.

In certain exemplary embodiments, if decreased expression or activity of a protein is desired, an antibody to the protein or an inhibitor/antagonist and the like, or a pharmaceutical agent containing one or more of these molecules, can be administered to an individual. In other exemplary embodiments, if increased expression or activity of a protein is desired, the protein itself or an agonist/enhancer and the like, or a pharmaceutical agent containing one or more of these molecules, can be administered. Administration can be effected by methods well known in the art and may include delivery by an antibody specifically targeted to the protein. Neutralizing antibodies, which inhibit dimer formation, can be used when decreased expression or activity of a protein is desired.

Although modulating agents can be administered in a pure or substantially pure form, modulating agents can also be administered as pharmaceutical compositions, formulations, or preparations with a carrier. Exemplary formulations of the invention, such as for human or veterinary use, comprise a suitable active CAT-modulating agent, together with one or more pharmaceutically acceptable carriers and, optionally, other therapeutic ingredients. The carrier(s) are "acceptable" in the sense of being compatible with other ingredients of a formulation and not deleterious to the recipient thereof. The formulations can be presented in unit dosage form and can be prepared by any method known to the skilled artisan.

Examples of suitable pharmaceutical carriers include proteins such as albumins (e.g., U.S. Pat. No. 4,507,234), peptides and polysaccharides such as aminodextran (e.g., U.S. Pat. No. 4,699,784), and water. A carrier can also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate can be formed from chelating compounds that include those containing nitrogen and sulfur atoms as the donor atoms for binding the metal, metal oxide, radionuclide. For example, U.S. Pat. No. 4,673,562 discloses representative chelating compounds and their synthesis.

Methods of preparing pharmaceutical formulations typically include the step of bringing into association the active ingredient with the carrier, which constitutes one or more accessory ingredients. Formulations can be prepared by uniformly and intimately bringing into association the active ingredient with liquid carriers or finely divided solid carriers, or both, and then, if necessary, shaping the product into the desired formulation.

Formulations suitable for intravenous, intramuscular, subcutaneous, or intraperitoneal administration can comprise sterile aqueous solutions of the active ingredient with solutions, which can be isotonic with the blood of the recipient. Such formulations can be prepared by dissolving solid active ingredient in water containing physiologically compatible substances such as sodium chloride (e.g., 0.1-2.0 M), glycine, and the like, and having a buffered pH compatible with physiological conditions to produce an aqueous solution, and rendering the solution sterile. These may be present in unit or multi-dose containers, for example, sealed ampoules or vials.

Exemplary formulations of the invention can incorporate a stabilizer. Exemplary stabilizers include polyethylene glycol, proteins, saccharides, amino acids, inorganic acids, detergents, and organic acids, which can be used either alone or as admixtures. These stabilizers can be incorporated in an amount of, for example, 0.11-10,000 parts by weight per part by weight of an agent. If two or more stabilizers are to be used, their total amount can be within the range specified above. These stabilizers can be used in aqueous solutions at an appropriate concentration and pH. The specific osmotic pressure of such aqueous solutions can be in the range of 0.1-3.0 osmoles, preferably in the range of 0.8-1.2. The pH of the aqueous solution can be adjusted to be within the range of 5.0-9.0, preferably within the range of 6-8. In formulating an antibody or antibody-drug conjugate, an anti-adsorption agent can be used.

Additional pharmaceutical methods can be employed to control duration of action. Controlled release can be achieved through the use of polymer to complex or absorb the proteins or their derivatives. Controlled delivery can be achieved by selecting appropriate macromolecules (e.g., polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate an anti-CAT antibody into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions can be combined with typical carriers, such as lactose, sucrose, starch, talc magnesium stearate, crystalline cellulose, methyl cellulose, carboxymethyl cellulose, glycerin, sodium alginate or gum arabic, among others.

Any of the therapeutic agents provided herein may be administered in combination with other therapeutic agents. Selection of agents for use in combination therapy can be made by one of ordinary skill in the art according to conventional pharmaceutical principles. A combination of therapeutic agents may act synergistically to affect treatment of a particular disorder at a lower dosage of each agent.

7. Methods of Detection and Diagnosis Based on CAT Proteins

CAT proteins are useful for diagnosing a disease, or predisposition to a disease, particularly diseases in which the protein is over- or under-expressed, especially cancer, particularly the cancers identified in the Figures and section 13 of the Examples for each target. The diagnostic methods may be further suitable for monitoring disease progression in patients undergoing treatment, or for testing for reoccurrence of disease in patients who were previously treated for a disease, for example. Accordingly, exemplary embodiments of the invention provide methods for detecting the presence of, or abundance levels of, a CAT protein in a biological sample.

In vitro techniques for detection of proteins include, but are not limited to, enzyme linked immunosorbent assays (ELISAs), Western blots, immunoprecipitations, and immunofluorescence using a detection reagent, such as an antibody or protein binding agent. Alternatively, a protein can be detected in vivo in a subject by introducing into the subject a labeled antibody (or other types of detection agent) specific for the protein target. For example, an antibody can be labeled with a radioactive marker whose presence and location in a subject can be detected by standard imaging techniques. Particularly useful are methods that detect variants of a protein (e.g., allelic variants or mutations) and methods that detect fragments of a protein in a sample.

Proteins can be isolated from a biological sample (such as from a patient having a disease) and assayed for the presence of a mutation. A mutation can include, for example, one or more amino acid substitutions, deletions, insertions, rearrangements (such as from aberrant splicing events), or inappropriate post-translational modifications. Examples of analytic methods useful for detecting mutations in a protein include, but are not limited to, altered electrophoretic mobility, altered tryptic peptide digest, altered protein activity in cell-based or cell-free assays, alteration in substrate or antibody-binding patterns, altered isoelectric point, and direct amino acid sequencing.

Information obtained by detecting a protein can be used, for example, to determine prognosis and appropriate course of treatment for a disease. For example, individuals with a particular CAT expression level or stage of disease may respond differently to a given treatment that individuals lacking CAT expression, or individuals over- or under-expressing CAT. Information obtained from diagnostic methods of the invention can provide for the personalization of diagnosis and treatment.

In exemplary embodiments, the invention provides methods for diagnosing disease (including, for example, monitoring treatment response or recurrence of disease following treatment) in a subject comprising: determining the abundance level of CAT (e.g., CAT protein or nucleic acid, or protein or nucleic acid fragments thereof) in a test sample from the subject; wherein a difference in the abundance level of CAT relative to the abundance level of CAT in a test sample from a healthy subject, or the level established for a healthy subject, is indicative of disease.

Exemplary embodiments of the invention provide methods for diagnosing diseases having differential protein expression. For example, normal, control, or standard values (e.g., that represent typical expression levels of a protein in healthy subjects) can be established, such as by combining body fluids, tissues, or cell extracts taken from a normal healthy mammalian or human subject with specific antibodies to a protein under conditions for complex formation. Standard values for complex formation in normal and disease tissues can be established by various methods, such as photometric means. Complex formation, as it is expressed in a test sample, can be compared with the standard values. Deviation from a normal standard and toward a disease standard can provide parameters for disease diagnosis or prognosis while deviation away from a disease standard and toward a normal standard can be used to evaluate treatment efficacy, for example.

Immunological methods for detecting and measuring complex formation as a measure of protein expression using either specific polyclonal or monoclonal antibodies are known in the art. Examples of such techniques include ELISAs, radio-immunoassays (RIAs), flow cytometry (also referred to as fluorescence-activated cell sorting, or FACS), and antibody arrays. Such immunoassays typically involve the measurement of complex formation between a protein and its specific antibody. These assays and their quantitation against purified, labeled standards are well known in the art (Ausubel, supra, unit 10.1-10.6). For example, a two-site, monoclonal-based immunoassay utilizing antibodies reactive to two non-interfering epitopes can be utilized, and competitive binding assay can also be utilized (Pound (1998) Immunochemical Protocols, Humana Press, Totowa N.J.).

For diagnostic applications, an antibody can be labeled with a detectable moiety (interchangeably referred to as a "label" or "detectable substance"), such as to facilitate detection by various imaging methods. Methods for detection of labels include, but are not limited to, fluorescence, light, confocal, and electron microscopy; magnetic resonance imaging and spectroscopy; fluoroscopy, computed tomography and positron emission tomography. Examples of suitable labels include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, labels may be bi- or multi-functional and be detectable by more than one of the methods listed. Antibodies may be directly or indirectly labeled. Attachment of labels to antibodies includes covalent attachment of a label, incorporation of a label into an antibody, and covalent attachment of a chelating compound for binding of a label, among others well known in the art.

Numerous detectable moieties are available for labeling antibodies, including, but not limited to, those in the following categories:

(a) Radioisotopes, such as $^{36}$S, $^{14}$C, $^{125}$I, $^{3}$H, and $^{131}$I. An antibody can be labeled with a radioisotope using the techniques described in Current Protocols in Immunology, vol 1-2, Coligen et al., Ed., Wiley-Interscience, New York, Pubs. (1991-2006), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. Fluorescent labels can be conjugated to an antibody using the techniques disclosed in Current Protocols in Immunology, supra, for example. Fluorescence can be quantified using a fluorometer.

(c) Various enzyme-substrate labels are available (e.g., U.S. Pat. Nos. 4,275,149 and 4,318,980). An enzyme generally catalyzes a chemical alteration of a chromogenic substrate which can be measured using various techniques. For example, an enzyme may catalyze a color change in a substrate, which can be measured spectrophotometrically. Alternatively, an enzyme may alter the fluorescence or chemiluminescence of a substrate. Techniques for quantifying a change in fluorescence are described herein and well known in the art A chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for Use in Enzyme Immunoassay, in Methods in Enzyme. (Ed. J. Langone & H. Van Vunakis), Academic press, New York, 73: 147-166 (1981).

A label can be indirectly conjugated with an antibody. The skilled artisan will be aware of various techniques for achieving this. For example, an antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of a label with an antibody, an antibody can be conjugated with a small hapten (e.g., digoxin) and one of the different types of labels mentioned above can be conjugated with an anti-hapten antibody (e.g., anti-digoxin antibody). Thus, indirect conjugation of a label with an antibody can be achieved.

Antibodies can be used to isolate CAT proteins by standard techniques, such as affinity chromatography or immunoprecipitation, and antibodies can facilitate the purification of the natural protein from cells and recombinantly-produced protein expressed in host cells. Biological samples can be tested directly for the presence of a CAT protein by assays (e.g., ELISA or radioimmunoassay) and format (e.g., microwells, dipstick, etc., as described in International Patent Publication WO 93/03367). Alternatively, proteins in a sample can be size separated (e.g., by polyacrylamide gel electrophoresis (PAGE)), in the presence or absence of sodium dodecyl sulfate (SDS), and the presence of a CAT detected by immunoblotting (e.g., Western blotting).

Antibody binding can also be detected by "sandwich" immunoassays, immunoradiometric assays, gel diffusion precipitation reactions, immunodiffusion assays, in situ immunoassays (e.g., using colloidal gold, enzyme or radioisotope labels, for example), precipitation reactions, agglutination assays (e.g., gel agglutination assays, hemagglutination assays, etc.), complement fixation assays, immunofluorescence assays, protein A assays, and immunoelectrophoresis assays, etc.

In certain exemplary embodiments, antibody binding can be detected by detecting a label on the primary antibody. In other exemplary embodiments, a primary antibody can be detected by detecting binding of a secondary antibody or reagent to the primary antibody. In further exemplary embodiments, the secondary antibody is labeled. Numerous means are known in the art for detecting binding in an immunoassay, and are within the scope of the invention. In some embodiments, an automated detection assay is utilized. Methods for the automation of immunoassays are well known in the art (e.g., U.S. Pat. Nos. 5,885,530: 4,981,785: 6,159,750: and 5,358,691, each of which is herein incorporated by reference). In some embodiments, the analysis and presentation of results are also automated. For example, in some embodiments, software that generates a prognosis based on the presence or absence of one or more antigens can be implemented.

Competitive binding assays typically rely on the ability of a labeled standard to compete with a test sample for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies can be separated from the standard and test sample that remain unbound.

Sandwich assays typically involve the use of two antibodies, each capable of binding to a different immunogenic portion, or epitope, of the protein to be detected. In typical sandwich assays, the test sample to be analyzed is bound by a first antibody, which is immobilized on a solid support, and thereafter a second antibody binds to the test sample, thus forming an insoluble three-part complex (e.g., U.S. Pat. No. 4,376,110). The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme.

Antibodies can also be used for in vivo diagnostic assays. Generally, an antibody can be labeled with a radionuclide (such as $^{111}$In, $^{99}$Tc, $^{14}$C, $^{131}$I, $^{3}$H, $^{32}$P or $^{35}$S) so that disease cells or tissues can be localized using immunoscintiography, for example. In certain embodiment, antibodies or fragments thereof bind to the extracellular domains of two or more CAT proteins and the affinity value (Kd) is less than $1 \times 10^8$ M.

For immunohistochemistry, a disease tissue sample may be, for example, fresh or frozen or may be embedded in paraffin and fixed with a preservative such as formalin. A fixed or embedded section can be contacted with a labeled primary antibody and secondary antibody, wherein the antibody is used to detect CAT protein expression in situ.

Antibodies can be used to detect a target protein in situ, in vitro, or in a cell lysate or supernatant in order to evaluate the abundance and pattern of expression. Also, antibodies can be used to assess abnormal tissue distribution or abnormal expression during development or progression of a biological condition. Antibodies against CAT proteins are useful for detecting the presence of the proteins in cells or tissues to determine the pattern of expression of the proteins among various tissues in an organism and over the course of the organism's development.

Further, antibodies can be used to assess expression in disease states such as in active stages of a disease or in an individual with a predisposition toward disease related to the protein's function. When a disorder is caused by inappropriate tissue distribution, developmental expression, or level of expression of a protein, or expressed/processed form, for example, an antibody can be prepared against the normal protein. If a disorder is characterized by a specific mutation in a protein, antibodies specific for the mutant protein can be used to assay for the presence of the specific mutant protein and to target the mutant protein for therapeutic purposes. Antibodies are also useful as diagnostic tools, as immunological markers for aberrant protein analyzed by electrophoretic mobility, isoelectric point, tryptic peptide digest, and other physical assays known in the art.

Certain exemplary diagnostic methods of the invention can also include monitoring a treatment modality. Accordingly, where treatment is ultimately aimed at correcting, for example, the function, activity, expression level, tissue distribution, or developmental expression of a protein, antibodies directed against the protein can be used to monitor therapeutic efficacy and to modify a treatment regimen as necessary.

Additionally, antibodies to a target protein are useful in pharmacogenomic analysis. For example, antibodies prepared against polymorphic proteins can be used to identify individuals that require modified treatment modalities. Moreover, the target proteins and antibodies thereto can be used for clinical trials, such as to identify individuals that should be included (e.g., individuals more likely to respond to a therapy) or excluded (e.g., individuals less likely to respond to a therapy, or individuals more likely to experience harmful side effects from a therapy) from a clinical trial.

The invention also encompasses kits for using antibodies to detect the presence of a target protein in a biological sample. An exemplary kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be configured to detect a single target protein or epitope or can be configured to detect one of a multitude of epitopes, such as in an antibody detection array.

LC/MS and ICAT

In certain exemplary embodiments, the invention provides detection or diagnostic methods of a CAT by using LC/MS. Proteins can be prepared from cells by methods known in the art (e.g., Zhang et al., *Nature Biotechnology* 21(6):660-666 (2003)). The differential expression of proteins in disease and healthy (or drug-resistant and drug-sensitive, for example) samples can be quantitated using mass spectrometry and ICAT (Isotope Coded Affinity Tag) labeling, which is known in the art. ICAT is an isotope label technique that allows for discrimination between two populations of proteins, such as a healthy and a disease sample. Over-expression or under-expression of a CAT protein, as measured by ICAT, can indicate, for example, the likelihood of having or developing a disease or an associated pathology.

LC/MS spectra can be collected for labeled samples and processed as follows. The raw scans from the LC/MS instrument can be subjected to peak detection and noise reduction software. Filtered peak lists can then be used to detect 'features' corresponding to specific peptides from the original sample(s). Features are characterized by their mass/charge ratio, charge, retention time, isotope pattern, and/or intensity, for example.

The intensity of a peptide present in both healthy and disease samples can be used to calculate the differential expression, or relative abundance, of the peptide. The intensity of a peptide found exclusively in one sample can be used to calculate a theoretical expression ratio for that peptide (singleton). Expression ratios can be calculated for each peptide in an assay or experiment.

Statistical tests can be performed to assess the robustness of the data and select statistically significant differentials. To ensure the accuracy of data, the following steps can be taken: a) ensure that similar features are detected in all replicates of an experiment; b) assess the distribution of the log ratios of all peptides (a Gaussian is expected); c) calculate the overall pair wise correlations between ICAT LC/MS maps to ensure that the expression ratios for peptides are reproducible across multiple replicates; and d) aggregate multiple experiments in order to compare the expression ratio of a peptide in multiple diseases or disease samples.

8. Methods of Treatment Based on CAT Proteins a. Antibody Therapy

Antibodies of the invention can be used for therapeutic purposes. It is contemplated that antibodies of the invention may be used to treat a mammal, preferably a human, with a disease, especially cancer, particularly the cancers identified in the Figures and section 13 of the Examples for each target. The antibodies can be delivered alone, in a pharmaceutical composition (such as with a carrier), or conjugated to one or more therapeutic agents, for example.

Antibodies can be useful for modulating (e.g., agonizing or antagonizing) protein function, such as for therapeutic purposes. Antibodies can also be useful for inhibiting protein function by, for example, blocking the binding of a CAT protein to a binding partner such as a substrate, which can be useful therapeutically. Antibodies can be prepared against, for example, specific portions of a protein that contain domains required for protein function, or against intact protein that is associated with a cell membrane.

Antibodies of the invention can also be used for enhancing the immune response. The antibodies can be administered in amounts similar to those used for other therapeutic administrations of antibodies. For example, pooled gamma globulin can be administered at a range of about 1 mg to about 100 mg per patient.

Antibodies reactive with CAT proteins can be administered alone or in conjunction with other therapies, such as anti-cancer therapies, to a mammal afflicted with cancer or other disease. Examples of anti-cancer therapies include, but are not limited to, chemotherapy, radiation therapy, and adoptive immunotherapy therapy with TIL (tumor infiltrating lymphocytes).

The selection of an antibody subclass for therapy may depend upon the nature of the antigen to be acted upon. For example, an IgM may be preferred in situations where the antigen is highly specific for the diseased target and rarely occurs on normal cells. However, where the disease-associated antigen is also expressed in normal tissues, although at lower levels, the IgG subclass may be preferred. The IgG subclass may be preferred in these instances because the binding of at least two IgG molecules in close proximity is typically required to activate complement, and therefore less complement-mediated damage may occur in normal tissues that express smaller amounts of the antigen and thus bind fewer IgG antibody molecules. Furthermore, IgG molecules, by being smaller, may be more able than IgM molecules to localize to a diseased tissue.

A mechanism for antibody therapy can be that a therapeutic antibody recognizes a cell surface, secreted, or cytosolic target protein that is expressed (preferably, over-expressed) in a disease cell. By NK cell or complement activation, or conjugation of the antibody with an immunotoxin or radiolabel, the interaction of the antibody with the target protein can abrogate ligand/receptor interaction or activation of apoptosis, for example.

Potential mechanisms of antibody-mediated cytotoxicity of diseased cells include phagocyte (antibody-dependent cellular cytotoxicity (ADCC)), complement (complement-dependent cytotoxicity (CDC)), naked antibody (receptor cross-linking apoptosis and growth factor inhibition), or targeted payload labeled with a therapeutic agent, such as a radionuclide, immunotoxin, or immunochemotherapeutic or other therapeutic agent.

In certain exemplary embodiments, an antibody is administered to a nonhuman mammal for the purposes of obtaining preclinical data, for example. Exemplary nonhuman mammals to be treated include nonhuman primates, dogs, cats, rodents, and other mammals in which preclinical studies are performed. Such mammals may be established animal models for a disease or may be used to study toxicity of an antibody of interest, for example. Dose escalation studies may be performed in the mammal, for example.

An antibody can be administered to an individual by any suitable means, including parenteral, subcutaneous, intraperitoneal, intrapulmonary, and intranasal, and, if desired for local immunomodulatory treatment, intralesional administration. Parenteral infusions include intramuscular, intravenous, intraarterial, intraperitoneal, or subcutaneous administration. In addition, an antibody can be administered by pulse infusion, particularly with declining doses of the antibody. The dosing can be given by injections, such as intravenous or subcutaneous injections, which may depend in part on whether the administration is brief or chronic.

For the prevention or treatment of a disease, the appropriate dosage of an antibody may depend on the type of disease to be treated, the severity and the course of the disease, whether the antibody is administered for preventive or therapeutic purposes, previous therapy, the patient's clinical history and response to the antibody, and the discretion of the attending physician.

Depending on the type and severity of disease, about 1 µg/kg to 150 mg/kg (e.g., 0.1-20 mg/kg) of antibody can be an initial candidate dosage for administration to a patient, whether, for example, by one or more separate administrations, or by continuous infusion. A typical daily dosage may range from about 1 µg/kg to 100 mg/kg or more, depending on such factors as those mentioned above. An antibody-drug conjugate can be administered from about 1 µg/kg to 50 mg/kg, typically from about 0.1-20 mg/kg, whether, for example, by one or more separate administrations, or by continuous infusion. A typical daily dosage may range from about 0.1 mg/kg to 10 mg/kg, or from about 0.3 mg/kg to about 7.5 mg/kg, depending on such factors as those mentioned above. For repeated administrations over several days or longer, depending on the condition, the treatment can be sustained until a desired suppression of disease symptoms occurs. However, other dosage regimens may be useful. Therapy progress can be monitored by conventional techniques and assays.

Antibody composition can be formulated, dosed, and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

An antibody may optionally be formulated with, or administered with, one or more therapeutic agents used to prevent or treat the disorder in question. For example, an antibody can be administered as a co-therapy with a standard of care therapeutic for the specific disease being treated.

b. Other Immunotherapy

An "immunogenic peptide" is a peptide that comprises an allele-specific motif such that the peptide will bind an MHC allele (HLA in human) and be capable of inducing a CTL (cytotoxic T-lymphocytes) response. Thus, immunogenic peptides are capable of binding to an appropriate class I or II MHC molecule and inducing a cytotoxic T cell or T helper cell response against the antigen from which the immunogenic peptide is derived.

Peptides derived from a CAT protein can be modified to increase their immunogenicity, such as by enhancing the binding of the peptide to the MHC molecules in which the peptide is presented. The peptide or modified peptide can be conjugated to a carrier molecule to enhance the antigenicity of the peptide. Examples of carrier molecules, include, but are not limited to, human albumin, bovine albumin, lipoprotein and keyhole limpet hemo-cyanin ("Basic and Clinical Immunology" (1991) Stites and Terr (eds) Appleton and Lange, Norwalk Conn., San Mateo, Calif.).

Further, amino acid sequence variants of a peptide can be prepared, such as by altering the nucleic acid sequence of the DNA which encodes the peptide, or by peptide synthesis. At the genetic level, these variants can be prepared by, for example, site-directed mutagenesis of nucleotides in the DNA encoding the peptide, thereby producing DNA encoding the variant, and thereafter expressing the DNA in recombinant cell culture. The variants can exhibit the same qualitative biological activity as the nonvariant peptide.

Exemplary embodiments of the invention provide peptides or modified peptides derived from a CAT protein that are differentially expressed in disease. Examples of peptide modifications include, but are not limited to, substitutions, deletions, or additions of one or more amino acids in a given immunogenic peptide sequence, or mutation of existing amino acids within a given immunogenic peptide sequence, or derivatization of existing amino acids within a given immunogenic peptide sequence. Any amino acid in an immunogenic peptide sequence may be modified. In some embodiments, at least one amino acid can be substituted or replaced within the given immunogenic peptide sequence. Any amino acid may be used to substitute or replace a given amino acid within the immunogenic peptide sequence. Modified peptides can include any immunogenic peptide obtained from differentially expressed proteins, which has been modified and exhibits enhanced binding to the MHC molecule with which it associates when presented to a T-cell. These modified peptides can be synthetically or recombinantly produced by conventional methods, for example.

In certain exemplary embodiments of the invention, the peptides comprise, or consist of, sequences of about 5-30 amino acids in length which are immunogenic (i.e., capable of inducing an immune response when injected into a subject).

In certain exemplary embodiments, the peptides may be used, for example, to treat T cell-mediated pathologies. The term "T cell-mediated pathologies" refers to any condition in which an inappropriate T cell response is a component of the pathology. The term is intended to encompass both T cell mediated diseases and diseases resulting from unregulated clonal T cell replication.

Modified (e.g., recombinant) or natural CAT proteins, or fragments thereof, can be used as a vaccine either prophylactically or therapeutically. When provided prophylactically, a vaccine can be provided in advance of any evidence of disease. The prophylactic administration of a disease vaccine may serve to prevent or attenuate a disease in a mammal such as a human.

An exemplary vaccine formulation can comprise an immunogen that induces an immune response directed against a disease-associated antigen such as a CAT protein. For example, a substantially or partially purified CAT protein or fragments thereof can be administered as a vaccine in a pharmaceutically acceptable carrier. An immunogen can be administered in a pure or substantially pure form, or can be administered as a pharmaceutical composition, formulation, or preparation. Exemplary doses of protein that can be administered are about 0.001 to about 100 mg per patient, or about 0.01 to about 100 mg per patient. Immunization can be repeated as necessary until a sufficient titer of anti-immunogen antibody or immune cells has been obtained.

Vaccine can be prepared using, for example, recombinant protein or expression vectors comprising a nucleic acid sequence encoding all or part of a CAT protein. Examples of vectors that can be used in vaccines include, but are not limited to, defective retroviral vectors, adenoviral vectors vaccinia viral vectors, fowl pox viral vectors, or other viral vectors (Mulligan, R. C., (1993) *Science* 260:926-932). The vectors can be introduced into a mammal (e.g., a human) either prior to any evidence of a disease or to mediate regression of a disease in a mammal afflicted with the disease. Examples of methods for administering a viral vector into mammals include, but are not limited to, exposure of cells to the virus ex vivo, or injection of the retrovirus or a producer cell line of the virus into the affected tissue, or intravenous administration of the virus. Alternatively, the vector can be administered locally by direct injection into a disease lesion or topical application in a pharmaceutically acceptable carrier. The quantity of viral vector to be administered can be based on the titer of virus particles. An exemplary range can be about $10^6$ to about $10^{11}$ virus particles per mammal.

After immunization, the efficacy of the vaccine can be assessed by, for example, the production of antibodies or immune cells that recognize the antigen, as assessed by specific lytic activity, specific cytokine production, or disease regression, which can be measured using conventional methods. If the mammal to be immunized is already afflicted with a disease, the vaccine can be administered in conjunction with other therapeutic treatments. Examples of other therapeutic treatments include, but are not limited to, adoptive T cell immunotherapy and coadministration of cytokines or other therapeutic drugs.

In certain embodiments, mammals, preferably humans, at high risk for disease, especially cancer, are prophylactically treated with vaccines of the invention. Examples include, but are not limited to, individuals with a family history of a disease, individuals who themselves have a history of disease (e.g., cancer that has been previously resected and at risk for reoccurrence), or individuals already afflicted with a disease. When provided therapeutically, a vaccine can be provided to enhance the patient's own immune response to a disease antigen. An exemplary vaccine, which acts as an immunogen, can be a cell, cell lysate from cells transfected with a recombinant expression vector, or a culture supernatant containing the expressed protein, for example. Alternatively, an immunogen can be, for example, a partially or substantially purified recombinant protein, peptide, or analog thereof, or a modified protein, peptide, or analog thereof. The proteins or peptides can be, for example, conjugated with lipoprotein or administered in liposomal form or with adjuvant.

Vaccination can be carried out using conventional methods. For example, an immunogen can be used in a suitable diluent such as saline or water, or complete or incomplete adjuvants. Further, an immunogen may or may not be bound to a carrier, including carriers to increase the immunogenicity of the immunogen. Examples of carrier molecules include, but are not limited to, bovine serum albumin (BSA), keyhole limpet hemocyanin (KLH), tetanus toxoid, and the like. An immunogen also may be coupled with lipoproteins or administered in liposomal form or with adjuvants. An immunogen can be administered by any route appropriate for antibody production such as intravenous, intraperitoneal, intramuscular, subcutaneous, and the like. An immunogen can be administered once or at periodic intervals until a significant titer of anti-CAT immune cells or anti-CAT antibody is produced. The presence of anti-CAT immune cells can be assessed by measuring the frequency of precursor CTL (cytotoxic T-lymphocytes) against CAT antigen prior to and after immunization by a CTL precursor analysis assay (Coulie et al., 1992, *International Journal Of Cancer* 50:289-297). An immunoassay can be used to detect antibody in serum.

The safety of a vaccine can be determined by examining the effect of immunization on the general health of an immunized animal (e.g., weight change, fever, change in appetite or behavior, etc.) and looking for pathological changes during autopsies. After initial testing in animals, a vaccine can be tested in patients having a disease of interest. Conventional methods can be used to evaluate the immune response of a patient to determine the efficiency of the vaccine.

In certain exemplary embodiments of the invention, a CAT protein or fragments thereof, or a modified CAT protein, can be exposed to dendritic cells cultured in vitro. The cultured dendritic cells provide a means of producing T-cell dependent antigens comprised of dendritic cell-modified antigen or dendritic cells pulsed with antigen, in which the antigen is processed and expressed on the antigen-activated dendritic cell. The antigen-activated dendritic cells or processed dendritic cell antigens can be used as immunogens for vaccines or for the treatment of diseases. The dendritic cells can be exposed to the antigen for sufficient time to allow the antigens to be internalized and presented on the surface of dendritic cells. The resulting dendritic cells or the dendritic cell-processed antigens can then be administered to an individual in need of therapy. Such methods are described in Steinman et al. (WO93/208185) and in Bancbereau et al. (EPO Application 0563485A1).

In certain exemplary embodiments of the invention, T-cells isolated from individuals can be exposed to a CAT protein or fragment thereof, or a modified CAT protein, in vitro and then administered in a therapeutically effective amount to a patient in need of such treatment. Examples of where T-lymphocytes can be isolated include, but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami et al., 1989, *J. Immunol.* 142: 2453-3461). Lymphocytes can be cultured in media such as RPMI or RPMI 1640 or AIM V for 1-10 weeks. Viability can be assessed by trypan blue dye exclusion assay. Examples of how these sensitized T-cells can be administered to a mammal include, but are not limited to, intravenously, intraperitoneally, or intralesionally. Parameters that can be assessed to determine the efficacy of these sensitized T-lymphocytes include, but are not limited to, production of immune cells in the mammal being treated or tumor regression. Conventional methods can be used to assess these parameters. Such treatment can be given in conjunction with cytokines or gene-modified cells, for example (Rosenberg et al., 1992, *Human Gene Therapy*, 3: 75-90; Rosenberg et al., 1992, *Human Gene Therapy*, 3: 57-73).

9. Screening Methods Using CAT Proteins

Exemplary embodiments of the invention provide methods of screening for agents (interchangeably referred to by such terms as candidate agents, compounds, or candidate compounds) that modulate CAT protein activity (interchangeably referred to as protein function). Examples of candidate agents include, but are not limited to, proteins, peptides, antibodies, nucleic acids (such as antisense and RNAi nucleic acid molecules), and small molecules. Exemplary embodiments of the invention further provide agents identified by these screening methods, and methods of using these agents, such as for treating diseases, especially cancer, particularly the cancers identified in the Figures and section 13 of the Examples for each target.

Exemplary screening methods can typically comprise the steps of (i) contacting a CAT protein with a candidate agent, and (ii) assaying for CAT protein activity, wherein a change in protein activity in the presence of the agent relative to protein activity in the absence of the agent indicates that the agent modulates CAT protein activity.

Other exemplary screening methods can determine a candidate agent's ability to modulate CAT expression. Exemplary methods can typically comprise the steps of (i) contacting a candidate agent with a system that is capable of expressing CAT protein or CAT mRNA, and (ii) assaying for the level of CAT protein or CAT mRNA, wherein a change in the level in the presence of the agent relative to the level in the absence of the agent indicates that the agent modulates CAT expression levels.

Exemplary embodiments of the invention further provide methods to screen for agents that bind to CAT proteins. Exemplary methods can typically comprise the steps of contacting a CAT protein with a test agent and measuring the extent of binding of the agent to the CAT protein.

CAT proteins can be used to identify agents that modulate activity of a protein in its natural state or an altered form that causes a specific disease or pathology. CAT proteins and appropriate variants and fragments can be used in high-throughput screens to assay candidate compounds for their ability to bind to CAT. These compounds can be further screened against functional CAT proteins to determine the effect of the compound on the protein's activity. Further, these compounds can be tested in animal or invertebrate systems to determine activity/effectiveness. Compounds can be identified that activate (agonist) or inactivate (antagonist) CAT proteins to a desired degree.

CAT proteins can be used to screen agents for their ability to stimulate or inhibit interaction between a CAT protein and a target molecule that normally interacts with the CAT protein (e.g., a substrate, an extracellular binding ligand, or a component of a signal pathway that a CAT protein normally interacts with such as a cytosolic signal protein). Exemplary assays can include the steps of combining a CAT protein or fragment thereof with a candidate compound under conditions that allow the CAT protein (or fragment thereof) to interact with a target molecule, and detecting the formation of a complex between the CAT protein and the target molecule or detecting the biochemical consequence of the interaction between the CAT protein and the target molecule, such as any of the associated effects of signal transduction (e.g., protein phosphorylation, cAMP turnover, adenylate cyclase activation, etc.). Any of the biological or biochemical functions mediated by a CAT protein can be used as an endpoint assay to identify an agent that modulates CAT activity.

Candidate compounds or agents include, but are not limited to, 1) peptides such as soluble peptides, including Ig-tailed fusion peptides and members of random peptide libraries (see, e.g., Lam et al., *Nature* 354:82-84 (1991); Houghten et al., *Nature* 354:84-86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767-778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

An exemplary candidate compound or agent is a soluble fragment of a CAT that competes for substrate binding. Other exemplary candidate compounds include mutant CAT proteins or appropriate fragments containing mutations that affect CAT function and thus compete for substrate. Accordingly, a fragment that competes for substrate, for example with a higher affinity, or a fragment that binds substrate but does not allow release, is encompassed by the invention.

Compounds can also be screened by using chimeric proteins in which any portion of a protein such as an amino terminal extracellular domain, a transmembrane domain (e.g., transmembrane segments or intracellular or extracellular loops), or a carboxy terminal intracellular domain can be replaced in whole or part by heterologous domains or subregions. For example, a substrate-binding region can be used that interacts with a different substrate than the substrate that is recognized by a native target protein. Accordingly, a different set of signal transduction components can be available as an end-point assay for activation, thereby allowing assays to be performed in other than the specific host cell from which a target is derived.

Competition binding assays can also be used to screen for compounds that interact with a target protein (e.g., binding partners and/or ligands). For example, a test compound can be exposed to a target protein under conditions that allow the test compound to bind or otherwise interact with the target protein. Soluble target protein can also be added to the mixture. If the test compound interacts with the soluble target protein, it can decrease the amount of complex formed or activity of the target protein. This type of assay is particularly useful in instances in which compounds are sought that interact with specific regions of a target protein. Thus, the soluble target protein that competes with the target protein can contain peptide sequences corresponding to the target region of interest.

To perform cell-free drug screening assays, it may be desirable to immobilize either a CAT protein (or fragment thereof) or a molecule that binds the CAT protein (referred to herein as a "binding partner") to facilitate separation of complexes from uncomplexed forms, as well as to facilitate automation of the assays.

Techniques for immobilizing proteins on matrices can be utilized in exemplary drug screening assays. In exemplary embodiments, a fusion protein can be provided which adds a domain that allows a protein to be bound to a matrix. For example, glutathione-S-transferase fusion proteins can be adsorbed onto glutathione SEPHAROSE beads (Sigma Chemical, St. Louis, Mo.) or glutathione derivatized microtitre plates, which are then combined with cell lysates (e.g., $^{35}$S-labeled) and a candidate compound, and the mixture incubated under conditions conducive to complex formation (e.g., at physiological conditions for salt and pH). Following incubation, the beads can be washed to remove any unbound label, and the matrix immobilized and radiolabel determined directly, or in the supernatant after the complexes are dissociated. Alternatively, the complexes can be dissociated from the matrix, separated by SDS-PAGE, and the level of a binding partner found in the bead fraction quantitated from the gel using standard electrophoretic techniques. For example, either a target protein or a binding partner can be immobilized by conjugation of biotin and streptavidin using techniques well known in the art. Alternatively, antibodies that are reactive with a target protein but do not interfere with binding of the target protein to its binding partner can be derivatized to the wells of a plate, and the target protein trapped in the wells by antibody conjugation. Preparations of a binding partner and a candidate compound can be incubated in target protein-presenting wells and the amount of complex trapped in the well can be quantitated. Methods for detecting such complexes, in addition to those described for GST-immobilized complexes, include immunodetection of complexes using antibodies reactive with a binding partner, or which are reactive with a target protein and compete with the binding partner, as well as target protein-linked assays which rely on detecting an enzymatic activity associated with a binding partner.

In exemplary embodiments of the invention, a CAT protein can be used as a "bait protein" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with a CAT protein and are involved in the protein's activity. The two-hybrid system is based on the modular nature of most transcription factors, which typically consist of separable DNA-binding and activation domains. In exemplary embodiments, the two-hybrid assay can utilize two different DNA constructs. In one construct, a gene that encodes a CAT protein can be fused to a gene encoding the DNA binding domain of a known transcription factor (e.g., GAL-4). In the other construct, a DNA sequence from a library of DNA sequences that encode an unidentified protein ("prey" or "sample") can be fused to a gene that encodes the activation domain of the known transcription factor. If the "bait" and the "prey" proteins are able to interact in vivo, forming a CAT-dependent complex, the DNA-binding and activation domains of the transcription factor are brought into close proximity. This proximity allows transcription of a reporter gene (e.g., LacZ), which can be operably linked to a transcriptional regulatory site responsive to the transcription factor. Expression of the reporter gene can be detected and cell colonies containing the functional transcription factor can be isolated and used to obtain the cloned gene that encodes the protein that interacts with the CAT protein.

Agents that modulate a CAT protein can be identified using one or more of the above assays, alone or in combination. For example, a cell-based or cell free system can be used for initial identification of agents, and then activity of the agents can be confirmed in an animal or other model system. Such model systems are well known in the art and can readily be employed in this context.

10. Diagnosis, Treatment, and Screening Methods Using CAT Nucleic Acid Molecules The nucleic acid molecules of the invention are useful, for example, as probes, primers, chemical intermediates, and in biological assays. The nucleic acid molecules are useful as hybridization probes for messenger RNA, transcript/cDNA, and genomic DNA to detect or isolate full-length cDNA and genomic clones encoding a CAT protein, or variants thereof. The nucleic acid molecules are also useful as primers for PCR to amplify any given region of a nucleic acid molecule and are useful to synthesize antisense molecules of desired length and sequence. The nucleic acid molecules are also useful for producing ribozymes corresponding to all, or a part, of the mRNA produced from the nucleic acid molecules described herein.

The nucleic acid molecules are also useful for constructing recombinant vectors. Exemplary vectors include expression vectors that express a portion of, or all of, a CAT protein. The nucleic acid molecules are also useful for expressing antigenic portions of the proteins. The nucleic acid molecules are also useful for constructing host cells expressing a part, or all, of the proteins. The nucleic acid molecules are also useful for constructing transgenic animals expressing all, or a part, of the proteins.

A primer or probe can correspond to any sequence along the entire length of a CAT-encoding nucleic acid molecule such as the nucleic acid molecules of SEQ ID NOS:4-6, 10-12, 18-22, 24, 34-42, 45-46, 49-50, 53-55, 60-63, 68-71, and 74-75. Accordingly, a primer or probe can be derived from 5' noncoding regions, coding regions, or 3' noncoding regions, for example.

Exemplary in vitro techniques for detection of mRNA include Northern hybridizations and in situ hybridizations. Exemplary in vitro techniques for detecting DNA include Southern hybridizations and in situ hybridization. Reverse transcriptase PCR amplification (RT-PCR) and the like can also be used for detecting RNA expression. A specific exemplary method of detection comprises using TaqMan technology (Applied Biosystems, Foster City, Calif.).

a. Methods of Diagnosis Using Nucleic Acids

Nucleic acid molecules of the invention are useful, for example, as hybridization probes for determining the presence, level, form, and/or distribution of nucleic acid expression. Exemplary probes can be used to detect the presence of, or to determine levels of, a specific nucleic acid molecule in cells, tissues, and in organisms. Accordingly, probes corresponding to a CAT described herein can be used to assess expression and/or gene copy number in a given cell, tissue, or organism, which can be applied to, for example, diagnosis of disorders involving an increase or decrease in CAT protein expression relative to normal CAT protein expression levels.

Probes can be used as part of a diagnostic test kit for identifying cells or tissues that express CAT protein differentially, such as by measuring a level of a CAT-encoding nucleic acid (e.g., mRNA or genomic DNA) in a sample of cells from a subject, or determining if a CAT-encoding nucleic acid is mutated.

Exemplary embodiments of the invention encompass kits for detecting the presence of CAT-encoding nucleic acid (e.g., mRNA or genomic DNA) in a biological sample. For example, an exemplary kit can comprise reagents such as a labeled or labelable nucleic acid or agent capable of detecting CAT nucleic acid in a biological sample; means for determining the amount of CAT nucleic acid in the sample; and means for comparing the amount of CAT nucleic acid in the sample with a standard. The compound or agent can be packaged in a suitable container. The kit can further comprise instructions for using the kit to detect CAT nucleic acid.

The nucleic acid molecules are useful in diagnostic assays for qualitative changes in CAT nucleic acid expression, and particularly in qualitative changes that lead to pathology. The nucleic acid molecules can be used to detect mutations in CAT genes and gene expression products such as mRNA. The nucleic acid molecules can be used as hybridization probes to detect naturally occurring genetic mutations in a CAT gene and to determine whether a subject with the mutation is at risk for a disorder caused by the mutation. Examples of mutations include deletions, additions, or substitutions of one or more nucleotides in a gene, chromosomal rearrangements (such as inversions or transpositions), and modification of genomic DNA such as aberrant methylation patterns or changes in gene copy number (such as amplification). Detection of a mutated form of a CAT gene associated with a dysfunction can provide a diagnostic tool for an active disease or susceptibility to disease in instances in which the disease results from overexpression, underexpression, or altered expression of a CAT protein, for example.

Mutations in a CAT gene can be detected at the nucleic acid level by a variety of techniques. For example, genomic DNA, RNA, or cDNA can be analyzed directly or can be amplified (e.g., using PCR) prior to analysis. In certain exemplary embodiments, detection of a mutation involves the use of a probe/primer in a PCR reaction (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077-1080 (1988) and Nakazawa et al., *PNAS* 91:360-364 (1994)), the latter of which can be particularly useful for detecting point mutations in a gene (see Abravaya et al., *Nucleic Acids Res.* 23:675-682 (1995)). Exemplary methods such as these can include the steps of collecting a sample of cells from a patient, isolating nucleic acid (e.g., genomic, mRNA, or both) from the cells of the sample, contacting the nucleic acid with one or more primers which specifically hybridize to a target nucleic acid under conditions such that hybridization and amplification of the target nucleic acid (if present) occurs, and detecting the presence or absence of an amplification product, or detecting the size of the amplification product and comparing the length to a control sample. Deletions and insertions can be detected by a change in size of the amplified product compared to a normal genotype. Point mutations can be identified by hybridizing amplified DNA to normal RNA or antisense DNA sequences, for example.

Alternatively, mutations in a CAT gene can be identified, for example, by alterations in restriction enzyme digestion patterns as determined by gel electrophoresis. Further, sequence-specific ribozymes (U.S. Pat. No. 5,498,531) can be used to identify the presence of specific mutations by development or loss of a ribozyme cleavage site. Perfectly matched sequences can be distinguished from mismatched sequences by nuclease cleavage digestion assays or by differences in melting temperature.

Sequence changes at specific locations can be assessed by nuclease protection assays such as RNase and 51 protection, or chemical cleavage methods. Furthermore, sequence differences between a mutant CAT gene and a corresponding wild-type gene can be determined by direct DNA sequencing. A variety of automated sequencing procedures can be utilized when performing diagnostic assays (Naeve, C. W., (1995) *Biotechniques* 19:448), including sequencing by mass spectrometry (e.g., PCT International Publication No. WO 94/16101; Cohen et al., *Adv. Chromatogr.* 36:127-162 (1996); and Griffin et al., *Appl. Biochem. Biotechnol.* 38:147-159 (1993)).

Other methods for detecting mutations in a nucleic acid include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286-295 (1992)), electrophoretic mobility of mutant and wild type nucleic acid is compared (Orita et al., *PNAS* 86:2766 (1989); Cotton et al., *Mutat. Res.* 285:125-144 (1993); and Hayashi et al., *Genet. Anal. Tech. Appl.* 9:73-79 (1992)), and movement of mutant or wild-type fragments in polyacrylamide gels containing a gradient of denaturant is assayed using denaturing gradient gel electrophoresis (DGGE) (Myers et al., *Nature* 313:495 (1985)). Examples of other techniques for detecting point mutations include selective oligonucleotide hybridization, selective amplification, and selective primer extension.

b. Methods of Monitoring Treatment and Pharmacogenomic Methods Using Nucleic Acids Nucleic acid molecules of the invention are also useful for monitoring the effectiveness of modulating agents on the expression or activity of a CAT gene, such as in clinical trials or in a treatment regimen. For example, the gene expression pattern of a CAT gene can serve as a barometer for the continuing effectiveness of treatment with a compound, particularly with compounds to which a patient can develop resistance. The gene expression pattern can also serve as a marker indicative of a physiological response of the affected cells to the compound. For example, based on monitoring nucleic acid expression, the administration of a compound can be increased or alternative compounds to which the patient has not become resistant can be administered instead. Similarly, if the level of nucleic acid expression falls below a desirable level, administration of the compound can be commensurately decreased.

The nucleic acid molecules are also useful for testing an individual for a genotype that, while not necessarily causing a disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules provided herein can be used to assess the mutation content of a target gene in an individual in order to select an appropriate compound or dosage regimen for treatment. For example, target nucleic acid molecules having genetic variations that affect treatment can provide diagnostic targets that can be used to tailor treatment to an individual. Accordingly, the production of recombinant cells and animals having these genetic variations allows effective clinical design of treatment compounds and dosage regimens, for example.

c. Methods of Treatment Using Nucleic Acids

Nucleic acid molecules of the invention are useful to design antisense constructs to control CAT gene expression in cells, tissues, and organisms. An antisense nucleic acid molecule typically blocks translation of mRNA into CAT protein by hybridizing to target mRNA in a sequence-specific manner. Nucleic acid molecules of the invention can also be used to specifically suppress gene expression by methods such as RNA interference (RNAi). RNAi and antisense-based gene suppression are well known in the art (e.g., Science 288:1370-1372, 2000). RNAi typically operates on a post-transcriptional level and is sequence specific. RNAi and antisense nucleic acid molecules are useful for treating diseases, especially cancer. RNAi fragments, particularly double-stranded (ds) RNAi, as well as antisense nucleic acid molecules can also be used to generate loss-of-function phenotypes by suppressing gene expression. Accordingly, exemplary embodiments of the invention provide RNAi and antisense nucleic acid molecules, and methods of using these RNAi and antisense nucleic acid molecules, such as for therapy or for modulating cell function. Nucleic acid molecules may also be produced that are complementary to a region of a gene involved in transcription, such as to hybridize to the gene to prevent transcription.

Exemplary embodiments of the invention relate to isolated RNA molecules (double-stranded; single-stranded) that are about 17 to about 29 nucleotides (nt) in length, and more particularly about 21 to about 25 nt in length, which mediate RNAi (e.g., degradation of mRNA, and such mRNA may be referred to herein as mRNA to be degraded). With respect to RNAi, the terms RNA, RNA molecule(s), RNA segment(s), and RNA fragment(s) are used interchangeably to refer to RNA that mediates RNAi. These terms include double-stranded RNA, single-stranded RNA, isolated RNA (e.g., partially purified RNA, essentially pure RNA, synthetic RNA, recombinantly produced RNA), as well as altered RNA that differs from naturally occurring RNA by the addition, deletion, substitution, and/or alteration of one or more nucleotides. Such alterations can include, for example, addition of non-nucleotide material, such as to the end(s) of a 21-25 nt RNA or internally (at one or more nucleotides of the RNA). Nucleotides in exemplary RNA molecules of the invention can also comprise non-standard nucleotides, including non-naturally occurring nucleotides or deoxyribonucleotides. Collectively, all such altered RNAs are referred to as analogs or analogs of naturally-occurring RNA. RNA of 21-25 nt typically need only be sufficiently similar to natural RNA that it has the ability to mediate RNAi. As used herein, the phrase "mediates RNAi" refers to the ability to distinguish which RNAs are to be degraded by RNAi processes. RNA that mediates RNAi directs degradation of particular mRNAs by RNAi processes. Such RNA may include RNAs of various structures, including short hairpin RNA.

In certain exemplary embodiments, the invention relates to RNA molecules of about 21 to about 25 nt that direct cleavage of specific mRNA to which their sequence corresponds. It is not necessary that there be a perfect correspondence (i.e., match) of the sequences, but the correspondence must be sufficient to enable the RNA to direct RNAi cleavage of the target mRNA (Holen et al., Nucleic Acids Res. 33:4704-4710 (2005)). In an exemplary embodiment, the 21-25 nt RNA molecules of the invention comprise a 3' hydroxyl group.

Certain exemplary embodiments of the invention relate to 21-25 nt RNAs of specific genes, produced by chemical synthesis or recombinant DNA techniques, that mediate RNAi. As used herein, the term "isolated RNA" includes RNA obtained by any means, including processing or cleavage of dsRNA, production by chemical synthetic methods, and production by recombinant DNA techniques, for example. Exemplary embodiments of the invention further relate to uses of the 21-25 nt RNAs, such as for therapeutic or prophylactic treatment and compositions comprising 21-25 nt RNAs that mediate RNAi, such as pharmaceutical compositions comprising 21-25 nt RNAs and an appropriate carrier.

Further exemplary embodiments of the invention relate to methods of mediating RNAi of genes of a patient. For example, RNA of about 21 to about 25 nt which targets a specific mRNA to be degraded can be introduced into a patient's cells. The cells can be maintained under conditions allowing degradation of the mRNA, resulting in RNA-mediated interference of the mRNA of the gene in the cells of the patient. Treatment of cancer patients, for example, with RNAi may inhibit the growth and spread of the cancer and reduce tumor size. Treatment of patients using RNAi can also be in combination with other therapies. For example, RNAi can be used in combination with other treatment modalities, such as chemotherapy, radiation therapy, and other treatments. In an exemplary embodiment, a chemotherapy agent is used in combination with RNAi. In a further exemplary embodiment, GEMZAR (gemcitabine HCl) chemotherapy is used with RNAi.

Treatment of certain diseases by RNAi may require introduction of the RNA into the disease cells. RNA can be directly introduced into a cell, or introduced extracellularly into a cavity, interstitial space, into the circulation of a patient, or introduced orally, for example. Physical methods of introducing nucleic acids, such as injection directly into a cell or extracellular injection into a patient, may also be used. RNA may be introduced into vascular or extravascular circulation, the blood or lymph system, or the cerebrospinal fluid, for example. RNA may be introduced into an embryonic stem cell or another multipotent cell, which may be derived from a patient. Physical methods of introducing nucleic acids include injection of a solution containing the RNA, bombardment by particles covered by the RNA, soaking cells or tissue in a solution of the RNA, or electroporation of cell membranes in the presence of the RNA. A viral construct packaged into a viral particle may be used to introduce an expression construct into a cell, with the construct expressing the RNA. Other methods known in the art for introducing nucleic acids to cells may be used, such as lipid-mediated carrier transport, chemical-mediated transport, and the like. The RNA may be introduced along with components that perform one or more of the following activities: enhance RNA uptake by the cell, promote annealing of the duplex strands, stabilize the annealed strands, or otherwise increase inhibition of the target gene.

Exemplary RNA of the invention can be used alone or as a component of a kit having at least one reagent for carrying out in vitro or in vivo introduction of the RNA to a cell, tissue/fluid, or patient. Exemplary components of a kit include dsRNA and a Vehicle that promotes introduction of the dsRNA. A kit may also include instructions for using the kit.

Certain exemplary embodiments of the invention provide compositions and methods for cleavage of mRNA by ribozymes having nucleotide sequences complementary to one or more regions in the mRNA, thereby attenuating the translation of the mRNA. Examples of regions in mRNA that can be targeted by ribozymes include coding regions, particularly coding regions corresponding to catalytic or other functional activities of a target protein, such as substrate binding. These compositions and methods may be used to treat a disorder characterized by abnormal or undesired target nucleic acid expression.

In certain exemplary embodiments, nucleic acid molecules of the invention may be used for gene therapy in individuals having cells that are aberrant in gene expression of a target. For example, recombinant cells that have been engineered ex vivo (which can include an individual's own cells) can be introduced into an individual where the cells produce the desired target protein to thereby treat the individual.

d. Methods of Screening Using Nucleic Acids

Nucleic acid expression assays are useful for drug screening to identify compounds that modulate CAT nucleic acid expression.

Exemplary embodiments of the invention thus provide methods for identifying a compound that can be used to treat a disease associated with differential expression of a CAT gene, especially cancer. Exemplary methods can typically include assaying the ability of a compound to modulate the expression of a target nucleic acid to thereby identify a compound that can be used to treat a disorder characterized by undesired target nucleic acid expression. The assays can be performed in cell-based or cell-free systems. Examples of cell-based assays include cells naturally expressing target nucleic acid or recombinant cells genetically engineered to express specific target nucleic acid sequences.

Assays for target nucleic acid expression can involve direct assay of target nucleic acid levels, such as mRNA levels, or on collateral compounds involved in a signal pathway. Further, the expression of genes that are up- or down-regulated in response to a signal pathway can also be assayed. In these embodiments, the regulatory regions of these genes can be operably linked to a reporter gene such as luciferase.

Thus, in exemplary embodiments, modulators of gene expression of a target can be identified in methods wherein a cell is contacted with a candidate agent and the expression of target mRNA determined. The level of expression of target mRNA in the presence of the candidate agent is compared to the level of expression of target mRNA in the absence of the candidate agent. The candidate agent can then be identified as a modulator of target nucleic acid expression based on this comparison and may be used, for example, to treat a disorder characterized by aberrant target nucleic acid expression. When expression of target mRNA is statistically significantly greater in the presence of the candidate agent than in its absence, the candidate agent is identified as a stimulator (agonist) of nucleic acid expression. When nucleic acid expression is statistically significantly less in the presence of the candidate agent than in its absence, the candidate compound is identified as an inhibitor (antagonist) of nucleic acid expression.

11. Arrays and Expression Analysis

"Array" (interchangeably referred to as "microarray") typically refers to an arrangement of at least one, but more typically at least two, nucleic acid molecules, proteins, or antibodies on a substrate. In certain exemplary arrangements, at least one of the nucleic acid molecules, proteins, or antibodies typically represents a control or standard, and other nucleic acid molecules, proteins, or antibodies are of diagnostic or therapeutic interest. In exemplary embodiments, the arrangement of nucleic acid molecules, proteins, or antibodies on the substrate is such that the size and signal intensity of each labeled complex (e.g., formed between each nucleic acid molecule and a complementary nucleic acid, or between each protein and a ligand or antibody, or between each antibody and a protein to which the antibody specifically binds) is individually distinguishable.

An "expression profile" is a representation of target expression in a sample. A nucleic acid expression profile can be produced using, for example, arrays, sequencing, hybridization, or amplification technologies for nucleic acids from a sample. A protein expression profile can be produced using, for example, arrays, gel electrophoresis, mass spectrometry, or antibodies (and, optionally, labeling moieties) which specifically bind proteins. Nucleic acids, proteins, or antibodies can be attached to a substrate or provided in solution, and their detection can be based on methods well known in the art.

A substrate includes, but is not limited to, glass, paper, nylon or other type of membrane, filter, chip, metal, or any other suitable solid or semi-solid (e.g., gel) support.

Exemplary arrays can be prepared and used according to the methods described in U.S. Pat. No. 5,837,832; PCT application WO95/11995; Lockhart et al., 1996, *Nat. Biotech.* 14: 1675-1680; Schena et al., 1996; *Proc. Natl. Acad. Sci.* 93: 10614-10619; and U.S. Pat. No. 5,807,522. Exemplary embodiments of the invention also provide antibody arrays (see, e.g., de Wildt et al. (2000) *Nat. Biotechnol.* 18:989-94).

Certain exemplary embodiments of the invention provide a nucleic acid array for assaying target expression, which can be composed of single-stranded nucleic acid molecules, usually either synthetic antisense oligonucleotides or fragments of cDNAs, fixed to a solid support. The oligonucleotides can be, for example, about 6-60 nucleotides in length, about 15-30 nucleotides in length, or about 20-25 nucleotides in length.

To produce oligonucleotides to a target nucleic acid molecule for an array, the target nucleic acid molecule of interest is typically examined using a computer algorithm to identify oligonucleotides of defined length that are unique to the nucleic acid molecule, have a GC content within a range suitable for hybridization, and lack predicted secondary structure that may interfere with hybridization. In certain instances, it may be desirable to use pairs of oligonucleotides on an array. In exemplary embodiments, the "pairs" can be identical, except for one nucleotide (which can be located in the center of the sequence, for example). The second oligonucleotide in the pair (mismatched by one) serves as a control. Any number of oligonucleotide pairs may be utilized.

Oligonucleotides can be synthesized on the surface of a substrate, such as by using a light-directed chemical process or by using a chemical coupling procedure and an ink jet application apparatus (e.g., PCT application WO95/251116).

In some exemplary embodiments, an array can be used to diagnose or monitor the progression of disease, for example, by assaying target expression.

For example, an oligonucleotide probe specific for a target can be labeled by standard methods and added to a biological sample from a patient under conditions that allow for the formation of hybridization complexes. After an incubation period, the sample can be washed and the amount of label (or signal) associated with hybridization complexes can be quantified and compared with a standard value. If complex formation in the patient sample is significantly altered (higher or lower) in comparison to a normal (e.g., healthy) standard, or is similar to a disease standard, this differential expression can be diagnostic of a disorder.

By analyzing changes in patterns of target expression, disease may be diagnosed at earlier stages before a patient is symptomatic. In exemplary embodiments of the invention, arrays or target expression analysis methods can be used to formulate a diagnosis or prognosis, to design a treatment regimen, and/or to monitor the efficacy of treatment. For example, a treatment dosage can be established that causes a change in target expression patterns indicative of successful treatment, and target expression patterns associated with the onset of undesirable side effects can be avoided. In further exemplary embodiments, assays of target expression can be repeated on a regular basis to determine if the level of target expression in a patient begins to approximate that which is observed in a normal subject. The results obtained from successive assays may be used to show the efficacy of treatment over a period ranging from several days to years, for example.

Exemplary arrays of the invention can also be used to screen candidate agents, such as to identify agents that produce a target expression profile similar to that caused by known therapeutic agents, with the expectation that agents that cause a similar expression profile of a target may have similar therapeutic effects and/or modes of action on the target.

EXAMPLES

Exemplary embodiments of the invention are further described in the following examples, which do not limit the scope of the invention.

1. Tissue Samples and Cell Lines

Tissue Processing and Preparation of Single Cell Suspensions from Tissue

Tissue samples (e.g., normal tissues or disease tissues such as surgically resected neoplastic or metastatic lesions) can be procured from clinical sites and transported in transport buffer. Tissues can be collected as remnant tissues following surgical resection of cancer (or other disease) tissues. Remnant tissues are supplied following processing for pathological diagnosis according to proper standards of patient care. Normal tissue specimens can be normal tissue adjacent to tumors (or other disease tissue) that is collected during tumor resection. Normal tissue from healthy patients not having cancer (or other disease of interest) can also be included, such as to reduce the contribution from pre-neoplastic changes that may exist in normal adjacent tissue. Procurement of tissue samples is carried out in an anonymous manner in compliance with federally mandated ethical and legal guidelines (HIPAA) and in accordance with clinical institution ethical review board and internal institutional review board guidelines.

Tissue can be crudely minced and incubated for 20-30 minutes with periodic agitation at 37° C. in Enzyme Combination #1 (200 units collagenase, cat# C5894 Sigma; 126 µg DNAse I, cat#D4513 Sigma (in 10 mM Tris/HCl pH7.5); 50 mM NaCl; 10 mM MgCl2; 0.05% elastase, cat# E7885 Sigma) (additionally, hyaluronidase enzyme may also be utilized). D-PBS is added at 3× the volume of the enzyme combination, the tissue finely minced, and disassociated cells passed through a 200 µm filter. The cells are washed twice with D-PBS. Red blood cells are lysed with PharMLyse (BD Biosciences) when necessary. Cell number and viability are determined by PI exclusion (GUAVA). Cells at a total cell number greater than $20 \times 10^6$ are sorted using a high-speed sorter (MoFlo Cytomation) for epithelial cells (EpCAM positive).

The remaining undigested tissue is incubated for 20-30 minutes with periodic agitation at 37° C. in Enzyme Combination #2 (1× Liberase Blendzyme 1, cat# 988-417 Roche; 1× Liberase Blendzyme 3, cat#814-184 Roche; 0.05% elastase, cat# E7885 Sigma). D-PBS is added at 3× the volume of the enzyme combination, and the tissue finely minced until tissue is completely disassociated. The cells are passed through a 200 µm filter, washed twice with D-PBS, and pooled with cells from the Enzyme Combination #1 digestion.

Cells are passed through a 70 µm filter for single cell suspension, and cell number and viability are determined by PI exclusion (GUAVA). When needed, red blood cells are lysed with PharMLyse (BD Biosciences). Cells are incubated in 20 ml of 1×PharMLyse in D-PBS for 30 seconds with gentle agitation and cells pelleted at 300×g for 5 minutes at 4° C. Cells are washed once in D-PBS and cell number and viability are recalculated by PI exclusion using the GUAVA. Cells at a total cell number greater than $20 \times 10^6$ are sorted using a high-speed sorter (MoFlo Cytomation) for epithelial cells (EpCAM positive).

Single cell suspensions can also be prepared from tissue samples as follows: specimens are washed in DTT for 15 min, digested with Dispase (30-60 min), then filtered twice (380 µm/74 µm) before red blood cells are removed through addition of ACK lysis buffer. Epithelial (EpCAM) and leukocyte (CD45) content and cellular viability (PI exclusion) can be determined through flow cytometry analysis (LSR I, BD Biosciences, San Jose, Calif.).

The epithelial content of both disease and normal specimens can be enriched through depletion of immune CD45-positive cells by flow cytometry or purification of Epithelial Cell Surface Antigen (ECSA/EpCam)-positive cells by bead capture.

Bead capture of epithelial cells can be performed using a Dynal CELLection Epithelial Enrich kit (Invitrogen, Carlsbad, Calif.) as follows. Dynal CELLection beads at a concentration of $2 \times 10^8$ beads are incubated with $1 \times 10^8$ cells in HBSS with 10% fetal calf serum for 30 minutes at 4° C. Cells and beads are placed in a magnet system Dynal MPC for 2 minutes. Bead/cell complexes are washed in RPMI 1640 media with 1% fetal calf serum. Cells are released from the bead complex with 15 minute incubation with DNase with agitation in RPMI with 1% fetal calf serum.

DynalBead cell depletion of CD45 cells can be carried out as follows. DynalBead M-450 CD45 beads and cells are incubated at a concentration of 250 µl beads per $2 \times 10^7$ cells for 30 minutes at 4° C. Bead/cell complexes are washed in DPBS buffer with 2% fetal bovine serum. Cells and beads are placed in a magnet system Dynal MPC for 2 minutes. The supernatant contains EpCAM enriched cells.

Cell Line Culture

Cell lines can be obtained from the American Type Culture Collection (ATCC, Manassas, Va.). Cell lines can be grown in a culturing medium that is supplemented as necessary with growth factors and serum, in accordance with the ATCC guidelines for each particular cell line. Cultures are established from frozen stocks in which the cells are suspended in a freezing medium (cell culture medium with 10% DMSO [v/v]) and flash frozen in liquid nitrogen. Frozen stocks prepared in this way are stored in liquid nitrogen vapor. Cell cultures are established by rapidly thawing frozen stocks at 37° C. Thawed stock cultures are slowly transferred to a culture vessel containing a large volume of supplemented culture medium. For maintenance of culture, cells are seeded at $1 \times 10^5$ cells/per ml in medium and incubated at 37° C. until confluence of cells in the culture vessel exceeds 50% by area. At this time, cells are harvested from the culture vessel using enzymes or EDTA where necessary. The density of harvested, viable cells is estimated by hemocytometry and the culture reseeded as above. A passage of this nature is repeated no more than 25 times, at which point the culture is destroyed and reestablished from frozen stocks as described above.

Alternatively, cells (e.g., adipocytes such as differentiated subcutaneous or visceral adipocytes) can be obtained from commercial sources, which may provide the cells seeded into T-75 tissue culture flasks. Upon arrival in the laboratory, the media is removed and replaced with DMEM/Ham's F-12 medium (1:1 v/v) supplemented with HEPES pH 7.4, FBS, biotin, pantothenate, human insulin, dexamethasone, penicillin-streptomycin, and Amphotercin B. The cells are cultured for two days and then harvested with versene before enrichment of proteins.

Alternatively, for secreted protein analysis, cells can be grown under routine tissue culture conditions in 490 $cm^2$ roller bottles at an initial seeding density of approximately 15 million cells per roller bottle. When the cells reach ~70-80% confluence, the culturing media is removed, the cells are washed 3 times with D-PBS and once with CD293 protein-free media (Invitrogen cat# 11913-019), and the culturing media is replaced with CD293 for generating conditioned media. Cells are incubated for 72 hours in CD293 and the media is collected for analysis, such as mass spectrometry analysis of secreted proteins (30-300 ml). Cell debris is removed from the conditioned media by centrifugation at 300 g for 5 minutes and filtering through a 0.2 micron filter prior to analysis.

Alternatively, for secreted protein analysis, conditioned media collected from differentiated cells (e.g., visceral or subcutaneous adipocytes), can be obtained (e.g., from a commercial source). Conditioned medium is shipped on dry ice and maintained at −80° C. ahead of protein capture. Cells are isolated from tissue and expanded to passage 2 (P2) to passage 4 (P4) prior to differentiation. Media is changed and cells are grown in conditioned medium for three days prior to harvesting. Enriching for proteins such as secreted proteins can then be carried out.

2. Cloning and Expression of Target Proteins cDNA Retrieval

Peptide sequences can be searched using the BLAST algorithm against relevant protein sequence databases to identify the corresponding full-length protein (reference sequence). Each full-length protein sequence can then be searched using the BLAST algorithm against a human cDNA clone collection. For each sequence of interest, clones can be pulled and streaked onto LB/Ampicillin (100 μg/ml) plates. Plasmid DNA is isolated using Qiagen spin mini-prep kit and verified by restriction digest. Subsequently, the isolated plasmid DNA is sequence verified against the reference full-length protein sequence. Sequencing reactions are carried out using Applied Biosystems BigDye Terminator kit followed by ethanol precipitation. Sequence data is collected using the Applied Biosystems 3700 Genetic Analyzer and analyzed by alignment to the reference full-length protein sequence using the Clone Manager alignment tool.

PCR

PCR primers are designed to amplify the region encoding the full-length protein and/or any regions of the protein that are of interest for expression (e.g., antigenic or hydrophilic regions as determined by the Clone Manager sequence analysis tool). Primers also contain 5' and 3' overhangs to facilitate cloning (see below). PCR reactions contain 2.5 units Platinum Taq DNA Polymerase High Fidelity (Invitrogen), 50 ng cDNA plasmid template, 1 μM forward and reverse primers, 800 μM dNTP cocktail (Applied Biosystems), and 2 mM $MgSO_4$. After 20-30 cycles (94° C. for 30 seconds, 55° C. for 1 minute, and 73° C. for 2 minutes), the resulting product is verified by sequence analysis and quantitated by agarose gel electrophoresis.

Construction of Entry Clones

PCR products are cloned into an entry vector for use with the Gateway recombination based cloning system (Invitrogen). These vectors include pDonr221, pDonr201, pEntr/D-TOPO, or pEntr/SD/D-TOPO and are used as described in the cloning methods below.

TOPO Cloning into pEntr/D-TOPO or pEntr/SD/D-TOPO

For cloning using this method, the forward PCR primer contains a 5' overhang containing the sequence "CACC". PCR products are generated as described above and cloned into the entry vector using the Invitrogen TOPO® cloning kit. Reactions are typically carried out at room temperature for 10 minutes and subsequently transformed into TOP10 chemically competent cells (Invitrogen, CA). Candidate clones are picked, and plasmid DNA is prepared using a Qiagen spin mini-prep kit and screened by restriction enzyme digestion. Inserts are subsequently sequence-verified as described above.

Gateway Cloning into pDonr201 or pDonr221

For cloning using this method, PCR primers contain forward and reverse 5' overhangs. PCR products are generated as described above. Protein-encoding nucleic acid molecules are recombined into the entry vector using the Invitrogen Gateway BP Clonase enzyme mix. Reactions are typically carried out at 25° C. for 1 hour, treated with Proteinase K at 37° C. for 10 minutes, and transformed into Library Efficiency DH5α chemically competent cells (Invitrogen, CA). Candidate clones are picked, plasmid DNA is prepared using a Qiagen spin mini-prep kit, and screened by restriction enzyme digestion. Inserts are subsequently sequence-verified as described above.

Construction of Expression Clones

Protein-encoding nucleic acid molecules are transferred from the entry construct into a series of expression vectors using the Gateway LR Clonase enzyme mix. Reactions are typically carried out for 1 hour at 25° C., treated with Proteinase K at 37° C. for 10 minutes, and subsequently transformed into Library Efficiency DH5a chemically competent cells (Invitrogen). Candidate clones are picked, plasmid DNA is prepared using a Qiagen spin mini-prep kit, and screened by restriction enzyme digestion. Expression vectors include, but are not limited to, pDest14, pDest15, pDest17, pDest8, pDest10 and pDest20. These vectors allow expression in systems such as *E. coli* and recombinant baculovirus. Other vectors not listed here allow expression in yeast, mammalian cells, or in vitro.

Expression of Recombinant Proteins in *E. coli*

Constructs are transformed into one or more of the following host strains: BL21 SI, BL21 AI, (Invitrogen), Origami B (DE3), Origami B (DE3) pLysS, Rosetta (DE3), Rosetta (DE3) pLysS, Rosetta-Gami (DE3), Rosetta-Gami (DE3) pLysS, or Rosetta-Gami B (DE3) pLysS (Novagen). The transformants are grown in LB with or without NaCl and with appropriate antibiotics, at temperatures in the range of 20-37° C., with aeration. Expression is induced with the addition of IPTG (0.03-0.30 mM) or NaCl (75-300 mM) when the cells are in mid-log growth. Growth is continued for one to 24 hours post-induction. Cells are harvested by centrifugation in a Sorvall RC-3C centrifuge in a H6000A rotor for 10 minutes at 3000 rpm at 4° C. Cell pellets are stored at −80° C.

Expression of Recombinant Proteins using Baculovirus

Recombinant proteins are expressed using baculovirus in Sf21 fall army worm ovarian cells. Recombinant baculoviruses are prepared using the Bac-to-Bac system (Invitrogen)

per the manufacturer's instructions. Proteins are expressed on the large scale in Sf900II serum-free medium (Invitrogen) in a 10 L bioreactor tank (27° C., 130 rpm, 50% dissolved oxygen for 48 hours).

3. Recombinant Protein Purification

Recombinant proteins can be purified from *E. coli* and/or insect cells using a variety of standard chromatography methods. Briefly, cells are lysed using sonication or detergents. The insoluble material is pelleted by centrifugation at 10,000×g for 15 minutes. The supernatant is applied to an appropriate affinity column. For example, His-tagged proteins are separated using a pre-packed chelating sepharose column (Pharmacia) or GST-tagged proteins are separated using a glutathione sepharose column (Pharmacia). After using the affinity column, proteins are further separated using various techniques, such as ion exchange chromatography (columns from Pharmacia) to separate on the basis of electrical charge or size exclusion chromatography (columns from Tosohaas) to separate on the basis of molecular weight, size, and shape.

Expression and purification of the protein can also be achieved using either a mammalian cell expression system or an insect cell expression system. The pUB6/V5-His vector system (Invitrogen, CA) can be used to express cDNA in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen, CA). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6×His which enables purification as described above. Purified proteins can be used to produce antibodies.

4. Chemical Synthesis of Proteins

Proteins or portions thereof can be produced not only by recombinant methods (such as described above), but also by using chemical methods well known in the art. Solid phase peptide synthesis can be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-a-protected by acid labile Boc (t-butyloxycarbonyl) or base-labile Fmoc (9-fluorenylmethoxycarbonyl) groups. The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full-length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1-S20).

Automated synthesis can also be carried out on machines such as the 431A peptide synthesizer (Applied Biosystems, Foster City, Calif.). A protein or portion thereof can be purified by preparative high performance liquid chromatography and its composition confirmed by amino acid analysis or by sequencing (Creighton, 1984, Proteins, Structures and Molecular Properties, W H Freeman, New York N.Y.).

5. Antibody Production

Polyclonal Antibodies

Polyclonal antibodies against recombinant proteins can be raised in rabbits (Green Mountain Antibodies, Burlington, Vt.). Briefly, two New Zealand rabbits are immunized with 0.1 mg of antigen in complete Freund's adjuvant. Subsequent immunizations are carried out using 0.05 mg of antigen in incomplete Freund's adjuvant at days 14, 21, and 49. Bleeds are collected and screened for recognition of the antigen by solid phase ELISA and Western blot analysis. The IgG fraction is separated by centrifugation at 20,000×g for 20 minutes followed by a 50% ammonium sulfate cut. The pelleted protein is resuspended in 5 mM Tris and separated by ion exchange chromatography. Fractions are pooled based on IgG content. Antigen-specific antibody is affinity purified using Pierce AminoLink resin coupled to the appropriate antigen.

Isolation of Antibody Fragments Directed Against a Protein Target from a Library of scFvs Naturally occurring V-genes isolated from human PBLs can be constructed into a library of antibody fragments which contain reactivities against a target protein to which the donor may or may not have been exposed (see, for example, U.S. Pat. No. 5,885,793, incorporated herein by reference in its entirety).

Rescue of the library: A library of scFvs is constructed from the RNA of human PBLs, as described in PCT publication WO 92/01047. To rescue phage displaying antibody fragments, approximately $10^9$ *E. coli* harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, $2×10^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 rpm. for 10 min. and the pellet resuspended in 2 liters of 2×TY containing 100 μg/ml ampicillin and 50 μg/ml kanamycin and grown overnight. Phage are prepared as described in PCT publication WO 92/01047.

Preparation of M13 delta gene III: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 rpm for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 2001, Molecular Cloning: A Laboratory Manual. 3rd. ed., Cold Spring Harbor Laboratory Press, Cold Spring Harbor, N.Y.), resuspended in 2 ml PBS and passed through a 0.45 μm filter (Minisart NML; Sartorius) to give a final concentration of approximately $10^{13}$ transducing units/ml (ampicillin-resistant clones).

Panning of the library: Immunotubes (Nunc) are coated overnight in PBS with 4 ml of either 100 μg/ml or 10 μg/ml of a protein target of interest. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over-and-under turntable and then left to stand for another 1.5 hours. Tubes are washed 10 times with PBS 0.1% Tween-20 and 10 times with PBS. Phage are eluted by adding. 1 ml of 100 mM triethylamine and rotating 15 minutes on an under-and-over turntable after which the solution is immediately neutralized with 0.5 ml of 1.0 M Tris-HCl, pH 7.4. Phages are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of binders: Eluted phage from the 3rd and 4th rounds of selection are used to infect *E. coli* HB 2151 and soluble scFv is produced (Marks et al., 1991, *J. Mol. Biol.* 222: 581-597) from single colonies for assay. ELISAs are performed with microtitre plates coated with either 10 μg/ml of the protein target of interest in 50 mM bicarbonate pH 9.6. Clones positive in ELISA are further characterized by PCR fingerprinting (see, e.g., PCT publication WO 92/01047) and then by sequence analysis.

Monoclonal Antibodies a) Materials:

1. Complete Media No Sera (CMNS) for washing of the myeloma and spleen cells; Hybridoma medium CM-HAT (Cell Mab (BD), 10% FBS (or HS); 5% Origen HCF (hybridoma cloning factor) containing 4 mM L-glutamine and antibiotics) to be used for plating hybridomas after the fusion.

2. Hybridoma medium CM-HT (no aminopterin) (Cell Mab (BD), 10% FBS 5% Origen HCF containing 4 mM L-glutamine and antibiotics) to be used for fusion maintenance is stored in the refrigerator at 4-6° C. The fusions are fed on days 4, 8, and 12, and subsequent passages. Inactivated and pre-filtered commercial fetal bovine serum (FBS) or horse serum (HS) are thawed and stored in the refrigerator at 4° C. and is pretested for myeloma growth from single cells prior to use.

3. The L-glutamine (200 mM, 100× solution), which is stored at −20° C., is thawed and warmed until completely in solution. The L-glutamine is dispensed into media to supplement growth. L-glutamine is added to 2 mM for myelomas and 4 mM for hybridoma media. Further, the penicillin, streptomycin, amphotericin (antibacterial-antifungal stored at −20° C.) is thawed and added to Cell Mab Media to 1%.

4. Myeloma growth media is Cell Mab Media (Cell Mab Media, Quantum Yield, from BD, which is stored in the refrigerator at 4° C. in the dark), to which is added L-glutamine to 2 mM and antibiotic/antimycotic solution to 1% and is called CMNS.

5. One bottle of PEG 1500 in Hepes (Roche, N.J.) is prepared.

6. 8-Azaguanine is stored as the dried powder supplied by SIGMA at −700° C. until needed. One vial/500 ml of media is reconstituted and the entire contents are added to 500 ml media (e.g., 2 vials/liter).

7. Myeloma Media is CM which has 10% FBS (or HS) and 8-Aza (1×) stored in the refrigerator at 4° C.

8. Clonal cell medium D (Stemcell, Vancouver) contains HAT and methyl cellulose for semi-solid direct cloning from the fusion. This comes in 90 ml bottles with a CoA and is melted at 37° C. in a waterbath in the morning of the day of the fusion. The cap is loosened and the bottle is left in a $CO_2$ incubator to sufficiently gas the medium D and bring the pH down.

9. Hybridoma supplements HT [hypoxanthine, thymidine] to be used in medium for the section of hybridomas and maintenance of hybridomas through the cloning stages, respectively.

10. Origen HCF can be obtained directly from Igen and is a cell supernatant produced from a macrophage-like cell-line. It can be thawed and aliqouted to 15 ml tubes at 5 ml per tube and stored frozen at −20° C. Positive hybridomas are fed HCF through the first subcloning and are gradually weaned (individual hybridomas can continue to be supplemented, as needed). This and other additives are typically more effective in promoting new hybridoma growth than conventional feeder layers.

b) Procedure:

To generate monoclonal antibodies, mice are immunized with 5-50 μg of antigen, either intra-peritoneally (i.p.) or by intravenous injection in the tail vein (i.v.). The antigen used can be a recombinant target protein of interest, for example. The primary immunization takes place two months prior to the harvesting of splenocytes from the mouse, and the immunization is typically boosted by i.v. injection of 5-50 μg of antigen every two weeks. At least one week prior to the expected fusion date, a fresh vial of myeloma cells is thawed and cultured. Several flasks of different densities can be maintained so that a culture at the optimum density is ensured at the time of fusion. An optimum density can be $3-6\times10^5$ cells/ml, for example. 2-5 days before the scheduled fusion, a final immunization of approximately 5 m of antigen in PBS is administered (either i.p. or i.v).

Myeloma cells are washed with 30 ml serum free media by centrifugation at 500 g at 4° C. for 5 minutes. Viable cell density is determined in resuspended cells using hemocytometry and vital stains. Cells resuspended in complete growth medium are stored at 37° C. during the preparation of splenocytes. Meanwhile, to test aminopterin sensitivity, $1\times10^6$ myeloma cells are transferred to a 15 ml conical tube and centrifuged at 500 g at 4° C. for 5 minutes. The resulting pellet is resuspended in 15 ml of HAT media and cells plated at 2 drops/well on a 96-well plate.

To prepare splenocytes from immunized mice, the animals are euthanised and submerged in 70% ethanol. Under sterile conditions, the spleen is surgically removed and placed in 10 ml of RPMI medium supplemented with 20% fetal calf serum in a petri dish. Cells are extricated from the spleen by infusing the organ with medium >50 times using a 21 g syringe.

Cells are harvested and washed by centrifugation (at 500 g at 4° C. for 5 minutes) with 30 ml of medium. Cells are resuspended in 10 ml of medium and the density of viable cells determined by hemocytometry using vital stains. The splenocytes are mixed with myeloma cells at a ratio of 5:1 (spleen cells: myeloma cells). Both the myeloma and spleen cells are washed twice more with 30 ml of RPMI-CMNS, and the cells are spun at 800 rpm for 12 minutes.

Supernatant is removed and cells are resuspended in 5 ml of RPMI-CMNS and are pooled to fill volume to 30 ml and spun down as before. Then, the pellet is broken up by gently tapping on the flow hood surface and resuspending in 1 ml of BMB REG1500 (prewarmed to 37° C.) dropwise with a 1 cc needle over 1 minute.

RPMI-CMNS to the PEG cells and RPMI-CMNS are added to slowly dilute out the PEG. Cells are centrifuged and diluted in 5 ml of Complete media and 95 ml of Clonacell Medium D (HAT) media (with 5 ml of HCF). The cells are plated out 10 ml per small petri plate.

Myeloma/HAT control is prepared as follows: dilute about 1000 P3X63 Ag8.653 myeloma cells into 1 ml of medium D and transfer into a single well of a 24-well plate. Plates are placed in an incubator, with two plates inside of a large petri plate, with an additional petri plate full of distilled water, for 10-18 days under 5% $CO_2$ overlay at 37° C. Clones are picked from semisolid agarose into 96-well plates containing 150-200 μl of CM-HT. Supernatants are screened 4 days later in ELISA, and positive clones are moved up to 24-well plates. Heavy growth requires changing of the media at day 8 (+/− 150 ml). The HCF can be further decreased to 0.5% (gradually—2%, then 1%, then 0.5%) in the cloning plates.

6. Liquid Chromatography and Mass Spectrometry (LC/MS)

For LC/MS analysis, proteins are reduced in 2.5 mM DTT for 1 hour at 37° C., and alkylated with ICAT™ reagent according to the procedures recommended by the manufacturer (Applied Biosystems, Framingham, Mass.). The reaction is quenched by adding excess DTT. Proteins are digested using sequencing grade modified trypsin overnight at 37° C. followed by desalting using 3 cc Oasis HLB solid phase extraction columns (Waters, Milford, Mass.) and vacuum drying. Cysteine-containing peptides are purified by avidin column (Applied Biosystems, Framingham, Mass.). The peptides are reconstituted in buffer A (0.1% formic acid in water) and separated over a C18 monomeric column (150 mm, 150 μm i.d., Grace Vydac 238EV5, 5 μm) at a flow rate of 1.5 μl/min with a trap column. Peptides are eluted from the column using a gradient, 3%-30% buffer B (0.1% formic acid in 90% acetonitrile) in 215 min, 30%-90% buffer B in 30 min. Eluted peptides are analyzed using an online QSTAR XL system (MDS/Sciex, Toronto, ON). Peptide ion peaks from the map are automatically detected with RESPECT™ (PPL Inc., UK).

The sequence-composition of peptides detected, for example, at higher levels in disease samples (or drug-resistant samples) relative to adjacent normal tissue (or drug-sensitive samples) can be resolved through tandem mass spectrometry and database analysis. For data analysis, peptide ion peaks of LC/MS maps from normal and disease samples can be aligned based on mass to charge ratio (m/z), retention time (Rt), and charge state (z). The list of aligned peptide ions is loaded into Spotfire™ (Spotfire Inc. Somerville, Mass.). Intensities can be normalized before further differential analysis between disease and normal samples. Differentially expressed ions are manually verified before LC-MS/MS-based peptide sequencing and database searching for protein/protein identification.

For intensity normalization and expression analysis, a heat map can be constructed by sorting the rows by the ratio of the mean intensity in the disease samples to the mean intensity of the normal samples. Rows are included if there is at least one MS/MS identification of an ion in the row. The display colors are determined for each row separately by assigning black to the median intensity in the row, green to the lowest intensity in the row, and red to the highest intensity.

Using a mass spectrometry procedure such as this, a comprehensive analysis of proteins differentially expressed by disease cells (or drug resistant cells, for example) compared with normal cells (or cells responsive/sensitive to a drug, for example) can be carried out.

7. mRNA Expression Analysis

Expression of target mRNA can be quantitated by RT-PCR using TaqMan® technology. The Taqman® system couples a 5' fluorogenic nuclease assay with PCR for real-time quantitation. A probe is used to monitor the formation of the amplification product.

Total RNA can be isolated from disease model cell lines using an RNEasy Kit® (Qiagen, Valencia, Calif.) with DNase treatment (per the manufacturer's instructions). Normal human tissue RNAs can be acquired from commercial vendors (e.g., Ambion, Austin, Tex.; Stratagene, La Jolla, Calif.; BioChain Institute, Newington, N.H.), as well as RNAs from matched disease/normal tissues.

Target transcript sequences can be identified for differentially expressed peptides by database searching using a search algorithm such as BLAST. TaqMan® assays (PCR primer/probe sets) specific for those transcripts can be obtained from Applied Biosystems (AB) as part of the Assays on Demand™ product line or by custom design through the AB Assays by Design$^{SM}$ service. If desired, the assays can be designed to span exon-exon borders so as not to amplify genomic DNA.

RT-PCR can be accomplished using AmpliTaq Gold® and MultiScribe™ reverse transcriptase in the One Step RT-PCR Master Mix reagent kit (AB) (according to the manufacturer's instructions). Probe and primer concentrations are 250 nM and 900 nM, respectively, in a 15 μl reaction. For each experiment, a master mix of the above components is made and aliquoted into each optical reaction well. Eight nanograms of total RNA is used as template. Quantitative RT-PCR can be performed using the ABI Prism® 7900HT Sequence Detection System (SDS). The following cycling parameters are used: 48° C. for 30 min. for one cycle; 95° C. for 10 min for one cycle; and 95° C. for 15 sec, 60° C. for 1 min. for 40 cycles.

SDS software can be utilized to calculate the threshold cycle ($C_T$) for each reaction, and $C_T$ values are used to quantitate the relative amount of starting template in the reaction. The $C_T$ values for each set of reactions can be averaged for all subsequent calculations Data can be analyzed to determine estimated copy number per cell. Gene expression can be quantitated relative to 18S rRNA expression and copy number estimated assuming $5 \times 10^6$ copies of 18S rRNA per cell. Alternatively, data can be analyzed for fold difference in expression using an endogenous control for normalization and expressed relative to a normal tissue or normal cell line reference. The choice of endogenous control can be determined empirically by testing various candidates against the cell line and tissue RNA panels and selecting the one with the least variation in expression. Relative changes in expression can be quantitated using the $2^{-\Delta\Delta C_T}$ method (Livak et al., 2001, Methods 25: 402-408; User bulletin #2: ABI Prism 7700 Sequence Detection System). Alternatively, total RNA can be quantitated using a RiboGreen RNA Quantitation Kit according to manufacturer's instructions and the percentage mRNA expression calculated using total RNA for normalization. Percentage knockdown can then be calculated relative to a no addition control.

8. Flow Cytometry (FACS) Analysis

Flow cytometry is interchangeably referred to as fluorescence-activated cell sorting (FACS). Quantitative flow cytometry can be used to compare the level of expression of a protein on disease cells to the level found on normal cells, for example.

Expression levels of a target protein on primary tissue samples can be quantified using the Quantum Simply Cellular System (Bangs Laboratories, Fishers, Ind.) and a target-specific antibody. Normal adjacent and disease tissues can be processed into single cell suspensions, as described above, which can be stained for various markers (e.g., the epithelial marker EpCam) and the target-specific antibody. At least $0.5\times10^6$ cells are typically used for each analysis. Cells are washed once with Flow Staining Buffer (0.5% BSA, 0.05% $NaN_3$ in D-PBS). To the cells, 20 µl of each target-specific antibody are added. An additional 5 µl of anti-EpCam antibody conjugated to APC can be added when unsorted cells are used. Cells are incubated with antibodies for 30 minutes at 4° C. Cells are washed once with Flow Staining Buffer and either analyzed immediately on an LSR flow cytometry apparatus or fixed in 1% formaldehyde and stored at 4° C. until LSR analysis. Antibodies used to detect a target can be PE-conjugated. PE-conjugated mouse IgG1k can used as an isotype control antibody. Cells are analyzed by flow cytometry and epitope copy number and the percentage of viable epithelial cells positive for target expression can be measured. Cell numbers and viability can be determined by PI exclusion (GUAVA) for cells isolated from both normal and disease tissue. Standard curve and samples can be analyzed on a LSR I (BDBiosciences, San Jose Calif.) flow cytometer. Antibody binding capacity for each lineage population can be calculated using geometric means and linear regression.

Expression levels of a target protein can be quantified in cell lines with QIFIKIT flow cytometric indirect immunofluorescence assay (Dako A/S) using a primary antibody to the target. Briefly, cells are detached with versene or trypsin and washed once with complete media and then PBS. $5\times10^5$ cells/sample are incubated with saturating concentration (10 µg/ml) of primary antibody for 60 minutes at 4° C. After washes, a FITC-conjugated secondary antibody (1:50 dilution) is added for 45 minutes at 4° C. QIFIKIT standard beads are simultaneously labeled with the secondary antibody. Binding of antibodies is analyzed by flow cytometry and specific antigen density is calculated by subtracting background antibody equivalent from antibody-binding capacity based on a standard curve of log mean fluorescence intensity versus log antigen binding capacity.

Cells can also be prepared for flow cytometry analysis (as well as other types of analysis) as follows: cells are incubated with 1:100 dilution of BrdU in culturing media for 2-4 hours (BrdU Flow Kit, cat# 559619 BD Biosciences). Cells are washed 3 times with D-PBS and disassociated from the flask with versene. Cell numbers and viability can be determined by PI exclusion (GUAVA). Cells are washed once with Flow Staining Buffer (0.5% BSA, 0.05% $NaN_3$ in D-PBS). Cells are incubated with 400 µA of Cytofix/Cytoperm Buffer (BrdU Flow Kit, BD Biosciences) for 15-30 minutes at 4° C. Cells are washed once with Flow Staining Buffer and resuspended in 400 µl Cytoperm Plus Buffer (BrdU Flow Kit BD Biosciences). Cells are incubated for 10 minutes at 4° C. and washed once with 1× Perm/Wash Buffer (BrdU Flow Kit, BD Biosciences). Cells are incubated for 1 hour at 37° C. protected from light in DNAse solution (BrdU Flow Kit, BD Biosciences). Cells are washed once with lx Perm/Wash Buffer and incubated for 20 min at room temperature with anti-BrdU FITC-conjugated antibody (BrdU Flow Kit, BD Biosciences), PE-conjugated active caspase 3 (BD Biosciences cat# 550821), and PE mouse IgG2β isotype control. Cells are washed once with 1× Perm/Wash Buffer and resuspended in DAPI for LSR flow cytometry analysis.

9. Immunohistochemistry (IHC)

IHC of Tissue Sections

Paraffin embedded, fixed tissue sections (e.g., from disease tissue samples such as solid tumors or other cancer tissues) can be obtained from a panel of normal tissues as well as tumor (or other disease) samples with matched normal adjacent tissues, along with replicate sections (if desired). For example, for an initial survey of target expression, a panel of common cancer formalin-fixed paraffin-embedded (FFPE) tissue microarrays (TMAs) can be used for analysis, and such TMAs can be obtained from commercial sources (TriStar, Rockville, Md.; USBiomax, Rockville, Md.; Imgenex, San Diego, Calif.; Petagen/Abxis, Seoul, Korea). Sections can be stained with hemotoxylin and eosin and histologically examined to ensure adequate representation of cell types in each tissue section.

An identical set of tissues can be obtained from frozen sections for use in those instances where it is not possible to generate antibodies that are suitable for fixed sections. Frozen tissues do not require an antigen retrieval step.

Paraffin Fixed Tissue Sections

An exemplary protocol for hemotoxylin and eosin staining of paraffin embedded, fixed tissue sections is as follows. Sections are deparaffinized in three changes of xylene or xylene substitute for 2-5 minutes each. Sections are rinsed in two changes of absolute alcohol for 1-2 minutes each, in 95% alcohol for 1 minute, followed by 80% alcohol for 1 minute. Slides are washed in running water and stained in Gill solution 3 hemotoxylin for 3-5 minutes. Following a vigorous wash in running water for 1 minute, sections are stained in Scott's solution for 2 minutes. Sections are washed for 1 minute in running water and then counterstained in eosin solution for 2-3 minutes, depending upon the desired staining intensity. Following a brief wash in 95% alcohol, sections are dehydrated in three changes of absolute alcohol for 1 minute each and three changes of xylene or xylene substitute for 1-2 minutes each. Slides are coverslipped and stored for analysis.

Optimization of Antibody Staining

For each antibody, a positive and negative control sample can be generated using data from ICAT analysis of disease cell lines or tissues. Cells can be selected that are known to express low levels of a particular target as determined from the ICAT data, and this cell line can be used as a reference normal control. Similarly, a disease cell line that is determined to over-express the target can also be selected.

Antigen Retrieval

Sections are deparaffinized and rehydrated by washing 3 times for 5 minutes in xylene, two times for 5 minutes in 100% ethanol, two times for 5 minutes in 95% ethanol, and once for 5 minutes in 80% ethanol. Sections are then placed in endogenous blocking solution (methanol+2% hydrogen peroxide) and incubated for 20 minutes at room temperature. Sections are rinsed twice for 5 minutes each in deionized water and twice for 5 minutes in phosphate buffered saline (PBS), pH 7.4.

Alternatively, where necessary, sections are de-parrafinized by High Energy Antigen Retrieval as follows: sections are washed three times for 5 minutes in xylene, two times for 5 minutes in 100% ethanol, two times for 5 minutes in 95% ethanol, and once for 5 minutes in 80% ethanol. Sections are placed in a Coplin jar with dilute antigen retrieval solution (10 mM citrate acid, pH 6). The Coplin jar containing slides is placed in a vessel filled with water and microwaved on high for 2-3 minutes (700 watt oven). Following cooling for 2-3 minutes, steps 3 and 4 are, repeated four times (depending on the tissue), followed by cooling for 20 minutes at room temperature. Sections are then rinsed in deionized water (two times for 5 minutes), placed in modified endogenous oxidation blocking solution (PBS+2% hydrogen peroxide), and rinsed for 5 minutes in PBS.

Alternatively, formalin fixed paraffin embedded tissues can be deparaffinized and processed for antigen retrieval using the EZ-retriever system (BioGenex, San Ramon, Calif.). EZ-antigen Retrieval common solution is used for deparaffinization and EZ-retrieval citrate-based buffer used for antigen retrieval. Samples are pre-blocked with non-serum protein block (Dako A/S, Glostrup, Denmark) for 15 min. Primary antibodies (at 2.5-5.0 µg/ml, for example) are incubated overnight at room temperature. Envision Plus system HRP (Dako A/S) is used for detection with diaminobenzidine (DAB) as substrate for horseradish peroxidase.

Blocking and Staining

Sections are blocked with PBS/1% bovine serum albumin (PBA) for 1 hour at room temperature followed by incubation in normal serum diluted in PBA (2%) for 30 minutes at room temperature to reduce non-specific binding of antibody. Incubations are performed in a sealed humidity chamber to prevent air-drying of the tissue sections. The choice of blocking serum is typically the same as the species of the biotinylated secondary antibody. Excess antibody is gently removed by shaking and sections covered with primary antibody diluted in PBA and incubated either at room temperature for 1 hour or overnight at 4° C. (care is taken that the sections do not touch during incubation). Sections are rinsed twice for 5 minutes in PBS, shaking gently. Excess PBS is removed by gently shaking. The sections are covered with diluted biotinylated secondary antibody in PBA and incubated for 30 minutes to 1 hour at room temperature in the humidity chamber. If using a monoclonal primary antibody, addition of 2% rat serum can be used to decrease the background on rat tissue sections. Following incubation, sections are rinsed twice for 5 minutes in PBS, shaking gently. Excess PBS is removed and sections incubated for 1 hour at room temperature in Vectastain ABC reagent (as per kit instructions). The lid of the humidity chamber is secured during all incubations to ensure a moist environment. Sections are rinsed twice for 5 minutes in PBS, shaking gently.

Developing and Counterstaining

Sections are incubated for 2 minutes in peroxidase substrate solution that is made up immediately prior to use as follows: 10 mg diaminobenzidine (DAB) dissolved in 10 ml of 50 mM sodium phosphate buffer, pH 7.4; 12.5 microliters 3% $CoCl_2/NiCl_2$ in deionized water; and 1.25 microliters hydrogen peroxide.

Slides are rinsed well three times for 10 minutes in deionized water and counterstained with 0.01% Light Green acidified with 0.01% acetic acid for 1-2 minutes, depending on the desired intensity of counterstain.

Slides are rinsed three times for 5 minutes with deionized water and dehydrated two times for 2 minutes in 95% ethanol; two times for 2 minutes in 100% ethanol; and two times for 2 minutes in xylene. Stained slides are mounted for visualization by microscopy.

Slides are scored manually using a microscope such as the Zeiss Axiovert 200M microscope (Carl Zeiss Microimaging, Thornwood, N.Y.). Representative images are acquired using 40× objective (400× magnification).

IHC Staining of Frozen Tissue Sections

For IHC staining of frozen tissue sections, fresh tissues are embedded in OCT in plastic mold, without trapping air bubbles surrounding the tissue. Tissues are frozen by setting the mold on top of liquid nitrogen until 70-80% of the block turns white at which point the mold is placed on dry ice. The frozen blocks are stored at −80° C. Blocks are sectioned with a cryostat with care taken to avoid warming to greater than −10° C. Initially, the block is equilibrated in the cryostat for about 5 minutes and 6-10 mm sections are cut sequentially. Sections are allowed to dry for at least 30 minutes at room temperature. Following drying, tissues are stored at 4° C. for short term and −80° C. for long term storage.

Sections are fixed by immersing in an acetone jar for 1-2 minutes at room temperature, followed by drying at room temperature. Primary antibody is added (diluted in 0.05 M Tris-saline [0.05 M Tris, 0.15 M NaCl, pH 7.4], 2.5% serum) directly to the sections by covering the section dropwise to cover the tissue entirely. Binding is carried out by incubation in a chamber for 1 hour at room temperature. Without letting the sections dry out, the secondary antibody (diluted in Tris-saline/2.5% serum) is added in a similar manner to the primary antibody and incubated as before (at least 45 minutes).

Following incubation, the sections are washed gently in Tris-saline for 3-5 minutes and then in Tris-saline/2.5% serum for another 3-5 minutes. If a biotinylated primary antibody is used, in place of the secondary antibody incubation, slides are covered with 100 µl of diluted alkaline phosphatase conjugated streptavidin, incubated for 30 minutes at room temperature and washed as above. Sections are incubated with alkaline phosphatase substrate (1 mg/ml Fast Violet; 0.2 mg/ml Napthol AS-MX phosphate in Tris-Saline pH 8.5) for 10-20 minutes until the desired positive staining is achieved at which point the reaction is stopped by washing twice with Tris-saline. Slides are counter-stained with Mayer's hematoxylin for 30 seconds and washed with tap water for 2-5 minutes. Sections are mounted with Mount coverslips and mounting media.

10. RNAi Assays in Cell Lines

RNAi Transfections

Expression of a target can be knocked down by transfection with small interfering RNA (siRNA) to that target. Synthetic siRNA oligonucleotides can be obtained from Dharmacon (Lafayette, Colo.) or Qiagen (Valencia, Calif.). For siRNA transfection, cells (e.g., disease cells) can be seeded into 96 well tissue culture plates at a density of 2,500 cells per well 24 hours before transfection. Culture medium is removed and 500 of reaction mix containing siRNA (final concentration 1 to 100 nM) and 0.4 µl of DharmaFECT4 (Dharmacon, Lafayette, Colo.) diluted in Opti-MEM is added to each well. An equal volume of complete medium follows and the cells are then incubated at 5% $CO_2$ at 37° C. for 1 to 4 days.

Alternatively, in the initial screening phase, RNAi can be performed using 100 nM (final) of Smartpools (Dharmacon, Lafayette, Colo.), pool of 4-for Silencing siRNA duplexes (Qiagen, Valencia, Calif.), or non-targeting negative control siRNA (Dharmacon or Qiagen). In the breakout phase, each individual duplex is used at 100 nM (final). In the titration phase, individual duplex is used at 0.1-100 nM (final). Transient transfections are carried out using either Lipofectamine 2000 from Invitrogen (Carlsbad, Calif.) or GeneSilencer from Gene Therapy Systems (San Diego, Calif.) (see below). One day after transfections, total RNA is isolated using the RNeasy 96 Kit (Qiagen) according to manufacturer's instructions and expression of mRNA is quantitated using TaqMan technology. Apoptosis and cell proliferation assays can be performed daily using Apop-one homogeneous caspase-3/7 kit and Alamar Blue or CellTiter 96 AQueous One Solution Cell Proliferation Assays (see below).

RNAi Transfections—Lipofectamine 2000 and GeneSilencer

Transient RNAi transfections can be carried out using Lipofectamine 2000 (Invitrogen, Carlsbad, Calif.) or GeneSilencer (Gene Therapy Systems, San Diego, Calif.), such as on sub-confluent disease cell lines, as described elsewhere (Elbashir et al., 2001, *Nature* 411: 494-498; Caplen et al., 2001, *Proc Natl Acad Sci USA* 98: 9742-9747; Sharp, 2001, *Genes and Development* 15: 485-490). Synthetic RNA to a gene of interest or non-targeting negative control siRNA are transfected using Lipofectamine 2000 or GeneSilencer according to manufacturer's instructions. Cells are plated in 96-well plates in antibiotic-free medium. The next day, the transfection reagent and siRNA are prepared for transfections as follows.

0.1-100 nM siRNA is resuspended in 20-25 μl serum-free media in each well (with Plus for Lipofectamine 2000) and incubated at room temperature for 15 minutes. 0.1-1 μl of Lipofectamine 2000 or 1-1.5 μl of GeneSilencer is also resuspended in serum-free medium to a final volume of 20-25 μl per well. After incubation, the diluted siRNA and either the Lipofectamine 2000 or the GeneSilencer are combined and incubated for 15 minutes (Lipofectamine 2000) or 5-20 minutes (GeneSilencer) at room temperature. Media is then removed from the cells and the combined siRNA-Lipofectamine 2000 reagent or siRNA-GeneSilencer reagent is added to a final volume of 50 μl per well. After further incubation at 37° C. for 4 hours, 50 μl serum-containing medium is added back to the cells. 1-4 days after transfection, expression of mRNA can be quantitated by RT-PCR using TaqMan technology, and protein expression levels can be measured by flow cytometry. Apoptosis and proliferation assays can be performed daily using Apop-one homogeneous caspase-3/7 kit and Alamar Blue or CellTiter 96 AQueous One Solution Cell Proliferation Assays (see below).

mRNA and Protein Knockdowns

Knockdown of target mRNA levels can be monitored by Q-PCR one day after siRNA transfection by using a TaqMan® assay (Applied Biosystems, Foster City, Calif.). RT-PCR is accomplished in a one-step reaction by using M-MLV reverse transcriptase (Promega, Madison, Wis.) and AmpliTaq Gold® (ABI) and analyzed on the ABI Prism® 7900HT Sequence Detection System (ABI). Relative gene expression can be quantitated by the ΔΔCt method (User Bulletin #2, ABI) with 18S rRNA serving as the endogenous control.

Protein knockdown can be monitored by FACS four days after transfection by using an antibody to the target. The samples can be run on a LSR flow cytometer (BD Biosciences, San Jose, Calif.) and live cells monitored by using PI exclusion (50 μg/ml PI, 2.5 units/ml RNase A, 0.1% Triton X-100 in D-PBS). The data can be analyzed using CellQuest software.

Cell Proliferation—Alamar Blue

Cell growth can be assessed four days after transfection by adding a 1:10 dilution of Alamar blue reagent (Invitrogen, Carlsbad, Calif. or Biosource, Camarillo, Calif.) and incubated for 2 hours at 37° C. Analysis can be performed on a Spectrafluor Plus (Tecan, Durham, N.C.) set at excitation wavelength of 530 nm and emission wavelength of 595 nm.

Cell Proliferation—MTS

Alternatively, cell proliferation assays can be performed using a CellTiter 96 AQueous One Solution Cell Proliferation Assay kit (Promega, Madison, Wis.). 20 μl of CellTiter 96 AQueous One Solution is added to 100 μl of culture medium. The plates are then incubated for 1-4 hours at 37° C. in a humidified 5% $CO_2$ incubator. After incubation, the change in absorbance is read at 490 nm.

Apoptosis

Apoptosis assays can be performed using the Apop-one homogeneous caspase-3/7 kit (Promega, Madison, Wis.). Briefly, the caspase-3/7 substrate is thawed to room temperature and diluted 1:100 with buffer. The diluted substrate is then added 1:1 to cells, control, or blank. The plates are then placed on a plate shaker for 30 minutes to 18 hours at 300-500 rpm. The fluorescence of each well is then measured using an excitation wavelength of 485+/−20 nm and an emission wavelength of 530+/−25 nm.

11. Antibody Assays in Cell Lines

Cytotoxicity Assays

Cytotoxicity can be measured using a Resazurin (Sigma, Mo.) dye reduction assay (McMillian et al., 2002, *Cell Biol. Toxicol.* 18:157-173). Briefly, cells are plated at 1,000-5,500 cells/well in 96 well plates, allowed to attach to the plates for 18 hours before addition of fresh media with or without antibody. After 96-144 hours of exposure to antibody, resazurin is added to cells to a final concentration of 50 μM. Cells are incubated for 2-6 hours depending on dye conversion of cell lines, and dye reduction is measured on a Fusion HT fluorescent plate reader (Packard Instruments, Meridien, Conn.) with excitation and emission wavelengths of 530 nm and 590 nm, respectively. The $IC_{50}$ value is defined here as the drug concentration that results in 50% reduction in growth or viability as compared with untreated control cultures.

Assays for Antibody-Dependent Cellular Cytotoxicity

Antibody-dependent cellular cytotoxicity (ADCC) assays can be carried out as follows. Cultured disease cells (e.g., tumor cells) are labeled with 100 μCi $^{51}Cr$ for 1 hour (Livingston et al., 1997, *Cancer Immunol. Immunother.* 43, 324-330). After being washed three times with culture medium, cells are resuspended at $10^5$/ml, and 100 μl/well are plated onto 96-well round-bottom plates. A range of antibody concentrations are applied to the wells, including an isotype control together with donor peripheral blood mononuclear cells that are plated at a 100:1 and 50:1 ratio. After an 18 hour incubation at 37° C., supernatant (30 μl/well) is harvested and transferred onto Lumaplate 96 (Packard), dried, and read in a Packard Top-Count NXT γ counter. Spontaneous release is determined by cpm of disease cells incubated with medium and maximum release by cpm of disease cells plus 1% Triton X-100 (Sigma). Specific lysis is defined as: % specific lysis= [(experimental release−spontaneous release)/(maximum release−spontaneous release)]×100. The percent ADCC is expressed as peak specific lysis postimmune subtracted by preimmune percent specific lysis. A doubling of the ADCC to >20% can typically be considered significant.

Assays for Complement Dependent Cytotoxicity

Chromium release assays to assess complement dependent cytotoxicity (CDC) can be carried out as follows (Dickler et al., 1999, *Clin. Cancer Res.* 5, 2773-2779). Cultured disease cells (e.g., tumor cells) are washed in FCS-free media two times, resuspended in 500 μl of media, and incubated with 100 μCi $^{51}Cr$ per 10 million cells for 2 hours at 37° C. The cells are then shaken every 15 min for 2 hours, washed 3 times in media to achieve a concentration of approximately 20,000 cells/well, and then plated in round-bottom plates. The plates contain either 50 μl cells plus 50 μl monoclonal antibody, 50 μl cells plus serum (pre- and post-therapy), or 50 μl cells plus mouse serum as a control. The plates are incubated in a cold room on a shaker for 45 min. Human complement of a 1:5 dilution (resuspended in 1 ml of ice-cold water and diluted with 3% human serum albumin) is added to each well at a volume of 100 μl. Control wells include those for maximum release of isotope in 10% Triton X-100 (Sigma) and for spontaneous release in the absence of complement with medium alone. The plates are incubated for 2 hours at 37° C., centrifuged for 3 min, and then 100 μl of supernatant is removed for radioactivity counting. The percentage of specific lysis is calculated as follows: % cytotoxicity=[(experimental release−spontaneous release)/(maximum release−spontaneous release)]×100. A doubling of the CDC to >20% can typically be considered significant.

Cell Proliferation Assays

To measure cell proliferation, cells can be plated, grown and treated as for the cytotoxicity assay (above) in 96 well plates. After 96-144 hours of treatment, 0.5 µCi/well $^3$H-Thymidine (PerkinElmer, 6.7 Ci/mmol) is added to cells and incubated for 4-6 hours at 37° C., 5% $CO_2$ in an incubator. To lyse cells, plates are frozen overnight at −20° C. and then cell lysates are harvested using FilterMate (Packard Instrument, Meridien, Conn.) into 96 well filter plates. Radioactivity associated with cells is measured on a TopCount (Packard) scintillation counter.

Other cell assays (e.g., proliferation assays such as Alamar blue and MTS, and apoptosis assays) can be carried out using antibodies, as described above for RNAi.

Testing of Function-Blocking Antibodies

For testing of function-blocking antibodies, sub-confluent disease cell lines are serum-starved overnight. The next day, serum-containing media is added back to the cells in the presence of 5-50 ng/ml of function-blocking antibodies. After 2 or 5 days incubation at 37° C. 5% $CO_2$, antibody binding is examined by flow cytometry, and apoptosis and proliferation are measured.

Cell Invasion

Cell invasion assays can be performed using a 96-well cell invasion assay kit (Chemicon). After the cell invasion chamber plates are adjusted to room temperature, 100 µl serum-free media is added to the interior of the inserts. 1-2 hours later, cell suspensions of $1\times10^6$ cells/ml are prepared. Media is then carefully removed from the inserts and 100 µl of prepared cells are added into the insert +/−0 to 50 ng function blocking antibodies. The cells are pre-incubated for 15 minutes at 37° C. before 150 µl of media containing 10% FBS is added to the lower chamber. The cells are then incubated for 48 hours at 37° C. After incubation, the cells from the top side of the insert are discarded and the invasion chamber plates are then placed on a new 96-well feeder tray containing 150 µl of pre-warmed cell detachment solution in the wells. The plates are incubated for 30 minutes at 37° C. and are periodically shaken. Lysis buffer/dye solution (4 µl CyQuant Dye/300 µl 4× lysis buffer) is prepared and added to each well of dissociation buffer/cells on feeder tray. The plates are incubated for 15 minutes at room temperature before 150 µl is transferred to a new 96-well plate. Fluorescence of invading cells is then read at 480 nm excitation and 520 nm emission.

Receptor Internalization

For quantification of receptor internalization, ELISA assays can be performed essentially as described by Daunt et al. (Daunt et al., 1997, *Mol. Pharmacol.* 51, 711-720). Cell lines are plated at $6\times10^5$ cells per in a 24-well tissue culture dishes that have previously been coated with 0.1 mg/ml poly-L-lysine. The next day, the cells are washed once with PBS and incubated in DMEM at 37° C. for several minutes. Agonist to the cell surface target of interest is then added to the wells at a pre-determined concentration in prewarmed DMEM. The cells are then incubated for various times at 37° C. and reactions are stopped by removing the media and fixing the cells in 3.7% formaldehyde/TBS for 5 min at room temperature. The cells are then washed three times with TBS and nonspecific binding blocked with TBS containing 1% BSA for 45 min at room temperature. The first antibody is added at a pre-determined dilution in TBS/BSA for 1 hr at room temperature. Three washes with TBS follow, and cells are briefly reblocked for 15 min at room temperature. Incubation with goat anti-mouse conjugated alkaline phosphatase (Bio-Rad) diluted 1:1000 in TBS/BSA is carried out for 1 hr at room temperature. The cells are washed three times with TBS and a colorimetric alkaline phosphatase substrate is added. When the adequate color change is reached, 100 µl samples are taken for colorimetric readings.

12. Treatment with Antibodies

Treatment of Disease Cells with Monoclonal Antibodies.

Disease cells (e.g., cancer cells), or cells such as NIH 3T3 cells that express a target of interest, are seeded at a density of $4\times10^4$ cells per well in 96-well microtiter plates and allowed to adhere for 2 hours. The cells are then treated with different concentrations of monoclonal antibody (Mab) specific for the protein target of interest, or irrelevant isotype matched (e.g., anti-rHuIFN-gamma) Mab, at 0.05, 0.5 or 5.0 µg/ml. After a 72 hour incubation, the cell monolayers are stained with crystal violet dye for determination of relative percent viability (RPV) compared to control (untreated) cells. Each treatment group can have replicates. Cell growth inhibition is monitored.

In Vivo Treatment with Monoclonal Antibodies.

NIH 3T3 cells transfected with either an expression plasmid that expresses the target of interest or a neo-DHFR vector are injected into nu/nu (athymic) mice subcutaneously at a dose of $10^6$ cells in 0.1 ml of phosphate-buffered saline. On days 0, 1, 5, and every 4 days thereafter, 100 µg (0.1 ml in PBS) of a Mab specific for the protein target of interest, or an irrelevant Mab, of the IgA2 subclass is injected intraperitoneally. Disease progression (e.g., tumor occurrence and size) can be monitored for a one month period of treatment, for example.

13. Specific Examples of Results from Experimental Validation

Exemplary results of experimental validation studies for each target are provided in the Figures and are set forth below:

TMPRSS4

A TMPRSS4 peptide was observed by mass-spec as over expressed in a pancreatic cancer cell line.

IHC indicated over-expression of TMPRSS4 in multiple tumor types, as follows: kidney (over-expressed in 100% of tumors evaluated); brain, glioblastoma (85%); lung, adenocarcinoma (70%); melanoma, lymph node (60%); liver (50%); pancreas (43%); lung, squamous (40%); pancreas, metastatic (33%); and colon (20%) (FIG. 1). TMPRSS4 was expressed in 8/10 lung tumor specimens evaluated, and TMPRSS4 was over-expressed by two pathology grades in 70% of the lung tumor samples evaluated. TMPRSS4 was expressed in 7/10 pancreatic tumor specimens evaluated, and TMPRSS4 was over-expressed by two pathology grades in 40% of the pancreatic tumor samples evaluated. TMPRSS4 was expressed in 10/10 kidney tumor specimens evaluated, and TMPRSS4 was over-expressed by two pathology grades in 100% of the renal tumor samples evaluated.

RNAi knockdown of TMPRSS4 inhibits proliferation in H1299 (lung) and AGS (gastric) cancer cell lines, as well as other cancer cell lines (FIGS. 2-4; "spheroid cells" shown in FIG. 2 are cancer stem cells).

TMPRSS4 mRNA levels over-expressed in lung and pancreas tumor tissues (FIG. 5).

SLC5A6

SLC5A6 peptides were identified by mass-spec as overexpressed in 6 breast cancer cell-lines (3.1-8.2 fold over-expressed), 5 colon tumor tissues (4.3-15.9 fold), and 1 gastric cancer cell line (4.8 fold).

IHC indicates over-expression of SLC5A6 in multiple tumor types, as follows: 100% renal (i.e., over-expressed in 100% of tumors evaluated), 90% breast, 70% lung (squamous), 63% liver, 60% lung (adenocarcinoma), 50% metastatic pancreas, 30% colon, and 20% ovary (FIG. 7). IHC confirmed expression of SLC5A6 in 6 out of 10 gastric tumor specimens, 9 out of 10 breast tumor specimens, 2 out of 10 colon tumor specimens, 10 out of 10 kidney tumors specimens, 4 out of 8 liver tumor specimens, 7 out of 10 lung carcinoma specimens, 2 out of 10 ovary tumor specimens, 2 out of 8 pancreatic tumor specimens, and 7 out of 10 lung carcinoma specimens.

SLC5A6 mRNA overexpression observed in colorectal, lung, and kidney tumor tissue (FIG. 8).

Knockdown of SLC5A6 mRNA inhibits proliferation of pancreatic cancer cells (MPANC-96 cell line) (30%) and gastric cancer cells (NCI-N87 cells) (39%), as well as other cancer cells (FIG. 9; "spheroid cells" are cancer stem cells).

ITGB6

ITGB6 peptides were observed by mass spec as over-expressed in pancreatic, lung, breast, and gastric tumor cell lines, and in breast cancer conditioned medium, as well as in a colon cancer stem cell line. Degree of ITGB6 over-expression was as follows: 3-21 fold over-expressed in pancreatic cell lines, 15-20 fold in lung cell lines, 5-100 fold in breast cell lines, 12 fold in a gastric cell line, 9 fold in a breast cell line conditioned medium, and 4 fold in a colon cancer stem cell line.

IHC indicates over-expression of ITGB6 in multiple tumor types, as follows: pancreas, metastatic (over-expressed in 67% of tumors evaluated); pharyngeal (60%); pancreas (57%); lung NSC (50%); skin melanoma (40%); melanoma, lymph node (40%); liver (38%); breast (30%); and lung, squamous (10%) (FIG. 11). As indicated by IHC, ITGB6 was expressed in 4 out of 7 pancreatic tumor specimens, in 5 out of 10 lung tumor specimens, and in 3 out of 10 breast tumor specimens.

ITGB6 mRNA over-expression was observed in pancreatic tumor tissue (FIGS. 12 and 25).

Knockdown of ITGB6 mRNA inhibits proliferation in the following cancer cells: gastric (47%), pancreas (52 and 52%), lung (50%), colon (64 and 84%), liver (42%), cancer stem cells (51%), and endothelial cells (31%) (FIGS. 13, 15-17, 19-23, and 26).

Knockdown of ITGB6 induced apoptosis in the following cancer cells: gastric (1.7 fold), pancreas (1.7 and 1.9 fold), lung (2.8 fold), colon (3.6 fold), breast (1.5 fold), kidney (2.7 and 4.6 fold), liver (1.9 fold), and endothelial cells (3.1 fold) (FIGS. 14-18 and 23).

Knockdown of ITGB6 mRNA in combination with Gemzar increases apoptosis in Calu-1 lung cancer cells (FIG. 24).

GLG1

GLG1 peptides were observed by mass spec as over-expressed in 4 breast cell lines, 1 breast tumor tissue, 2 colon cell lines, 10 colon tumor tissues, 3 lung cell lines, 6 lung tumor tissues, 2 pancreatic cell lines, 3 gastric cell lines and 1 gastric tumor tissue. GLG1 was over-expressed by 2.2-9.2 fold in breast cell lines and tissues, 2.1-100 fold in colon cell lines and tissues, 4.6 fold in kidney tissue, 2.4-100 fold in lung cell lines and tissues, 2.7-100 fold in pancreatic cell lines, 5-7.9 fold in stomach lines, and 20.9 fold in stomach tissue.

IHC confirmed the mass spec results and indicated expression of GLG1 in multiple tumor types, as follows: 80% melanoma (over-expressed in 80% of melanoma tumors evaluated); 50% melanoma, lymph nodes; 43% pancreas; 30% lung (squamous); and 17% non-Hodgkin's lymphoma (FIG. 27).

mRNA over-expression observed in pancreatic tumor tissues (FIG. 28).

Further ectopic expression of non-cell surface targets in tumor cell populations (for example, A549 lung cancer cell line vs. Beas-2B non-cancer lung cell line) showed that GLG1 is overexpressed in the tumor cell line.

Knockdown of GLG1 mRNA inhibits proliferation in multiple cancer cells (FIG. 29), including SNU-475 kidney cancer cells (FIG. 30).

KIAA0152

A KIAA0152 peptide was identified by mass spec as over-expressed (by 7-fold) in colon tumor tissue.

As indicated by IHC, KIAA0152 was overexpressed in multiple tumor types, as follows: brain, glioblastoma (over-expressed in 100% of tumors evaluated); pancreas (57%); liver (38%); pancreas, metastatic (33%); and bladder (30%) (FIG. 32). As indicated by IHC, KIAA0152 was expressed in 6 out of 7 pancreatic tumor specimens, in 8 out of 10 melanoma specimens, in 6 out of 6 glioblastoma specimens, in 10 out of 10 colon tumor specimens, in 9 out of 10 lung tumor specimens, and in 7 out of 10 prostate tumor specimens.

Over-expression of KIAA0152 was confirmed by FACS in primary and lymph node metastatic colon tumor tissues.

Elevated KIAA0152 mRNA expression was observed in colon tumors by TaqMan (FIG. 45), which correlated with elevated protein expression observed by mass-spec and IHC.

KIAA0152 mRNA knockdown inhibits proliferation in the following cancer cell lines: colon (91% and 82%) (FIGS. 35 and 41), lung (64% and 28%) (FIGS. 36 and 42), pancreas (53%) (FIG. 37), melanoma (44%) (FIG. 39), gastric (35%) (FIG. 38), and liver (FIG. 40). Expression of KIAA0152 was observed by FACS in the following cancer cell lines: breast (MDA MB 231 and MCF-7 cell lines), colon (HCT116 cell line), pancreas (BXPC3 cell line), and prostate (LnCAP and RWPE-2 cell lines). Expression of KIAA0152 was also observed in hormone-dependent and refractory prostate xenografts (LnCAP cell line—LnCAP hormone-dependent xenograft and LnCAP hormone-independent xenograft).

KIAA0152 is under-expressed in 3D spheroid cells (cancer stem cells) derived from kidney and lung cancer cell lines (ACHN kidney cell line and H1299 lung cell line).

Matriptase (ST14)

Matriptase peptides were identified by mass spec as over-expressed in breast, pancreatic, gastric, colon, and melanoma cancer cell lines, and in conditioned medium from lung and breast tumor cell lines. The degree of matriptase over-expression was as follows: 4.5-46.1 fold in breast cancer cell lines, 5.8 fold in breast conditioned medium, 4.7-17.7 fold in gastric cancer cell lines, 4.3 fold in lung conditioned medium, and 5.4-7.1 fold in pancreatic cancer cell lines.

IHC indicates over expression of matriptase in multiple tumors types, as follows: non-Hodgkins lymphoma ("NHL") (lymph node) (over-expressed in 83% of tumors evaluated), colon (70%), ovary (60%), pancreas (38%), and lung (squamous) (20%) (FIG. 47). IHC indicated expression of matriptase in 7 out of 10 lung tumor specimens that were evaluated, in 5 out of 6 NHL tumor specimens, in 6 out of 10 ovary tumor specimens, in 7 out of 10 colon tumor specimens, and in 4 out of 8 pancreatic tumor specimens.

Over-expression of matriptase mRNA was observed in pancreatic, lung, and ovarian tumor tissues (FIG. 48), as well as breast tumor tissues.

Knockdown of matriptase mRNA leads to inhibition of proliferation in pancreatic (38-53%) (FIG. 54), lung (31-35%) (FIGS. 49 and 53), colon (47-75%) (FIGS. 50 and 52), and gastric (50%) cancer cell lines.

AADACL1

AADACL1 peptides were observed by mass spec as overexpressed in colon tumor tissues and in breast, colon, pancreatic, and prostate cancer cell lines. The degree of AADACL1 over-expression was as follows: 2.3 fold in breast cancer cell line, 3 fold in colon cancer cell line, 4.4-13.3 fold in colon tumor tissues, 2.2-5.7 fold in pancreatic cancer cell line, and 5.5-12.1 fold in prostate cancer cell line.

IHC indicates over-expression of AADACL1 in multiple tumor types, as follows: pancreas (over-expressed in 100% of tumors evaluated); melanoma, lymph node (80%); melanoma (80%); metastatic pancreas (75%); colon (60%); and non-Hodgkin's lymphoma (NHL) (33%) (FIG. 56). AADACL1 was expressed in 6 out of 6 pancreatic tumor specimens, in 8 out of 10 melanoma specimens, in 8 out of 10 melanoma lymph node specimens, in 6 out of 10 colon carcinoma specimens, and in 2 out of 6 NHL tumor specimens.

AADACL1 mRNA over-expression was observed in pancreatic tumor tissues and pancreatic tumor cell lines (FIG. 57).

Podocalyxin

Podocalyxin peptides were observed by mass spec as overexpressed in breast and lung tumor tissue samples and in breast, esophageal, hepatocellular, liver, lung, ovarian, prostate, melanoma, and gastric cancer cell lines. Podocalyxin peptides were also observed in conditioned medium collected from colon tumor cell lines. Degree of podocalyxin over-expression, as measured by mass spec, was as follows: 3.9-100 fold in breast tumor tissues, 3.4-36.6 fold in breast cancer cell lines, 10.3-10.6 fold in esophageal cancer cell line, 27.3-60.7 fold in gastric cancer cell lines, 21.3-44.7 fold in gastric tumor tissues, 8.4-8.6 fold in ovarian cancer cell lines, 12.8-13.1 fold in lung cancer cell lines, 3.5-100 fold in lung tumor tissues, 7.2-12.6 fold in melanoma cell lines, 8.8-12.6 fold in prostate cancer cell lines, 7.8-20.5 fold in liver cancer cell lines, and 3.4-11.8 fold in conditioned medium from colon cancer cells.

IHC confirms expression of podocalyxin in colon, lung, gastric, and breast tumor samples. IHC indicates that podocalyxin is over-expressed in multiple tumor types, as follows: pancreatic (over-expressed in 40% of tumors evaluated), ovarian (20%), breast (10%), and colon (10%) (FIG. 58). As measured by IHC, podocalyxin was expressed in 4 out of 10 pancreatic tumor specimens and in 2 out of 10 ovary tumor specimens.

RNAi knockdown of podocalyxin mediates a decrease in proliferation and induction of apoptosis in lung cancer cells (FIGS. 59-64).

mRNA analysis confirms elevated expression of podocalyxin in pancreatic tumor tissues.

Cell surface expression of podocalyxin was confirmed by FACS in lung and breast cancer cell lines.

Podocalyxin siRNA is synergistic with EGFR siRNA (FIG. 65).

CD90 (Thy1)

CD90 peptides were observed by mass spec as over-expressed in colon, lung, breast, kidney, and stomach tumor tissues, in liver, lung, and skin tumor cell lines, in kidney and colon tumor endothelium, and in adipose tissue. Degree of CD90 over-expression, as measured by mass spec, was as follows: 3-70 fold in 6 kidney tumor endothelia, 15-74 fold in colon tumor derived endothelial cell line, 4-10 fold in 2 breast tumor tissues, 4-14 fold in 4 colon tumor tissues, 3-6 fold in 2 kidney tumor tissues, 4-22 fold in 3 lung tumor tissues, 6 fold in 1 stomach tumor tissue, 7-13 fold in 2 liver tumor cell lines, 5-48 fold in 2 lung tumor cell lines, 37-153 fold in 1 skin cell line, and 66 fold in 1 adipose tissue.

IHC indicated over-expression of CD90 in multiple tumor types, as follows: pancreas (over-expressed in 38% of tumors evaluated), liver (25%), prostate (20%), skin (melanoma) (20%), gastric (20%), breast (20%), bladder (20%), and non-Hodgkin's Lymphoma (17%) (FIGS. 67-68). IHC confirms expression of CD90 in 2 out of 10 melanoma specimens that were evaluated, in 3 out of 8 pancreatic tumor specimens, in 2 out of 10 breast carcinoma specimens, in 2 out of 10 gastric tumor specimens, in 2 out of 10 prostate tumor specimens, and in 5 out of 10 kidney tumor specimens.

CD90 is over-expressed in tumor endothelium, as indicated by IHC, including kidney, pancreas, and lung tumor endothelium.

CD90 is over-expressed in colorectal tumor tissues, as indicated by QFACS. FACS also indicates that CD90 is over-expressed in kidney tumors.

CD90 is expressed by kidney tumor endothelial cells and lung tumor tissue endothelial cells.

mRNA analysis shows marked over-expression of CD90 in pancreas, lung, stomach and colon tumor tissues, and in kidney tumor tissue endothelial cells (FIGS. 69-72).

Knockdown of CD90 mRNA inhibits proliferation in cancer cell lines, particularly in kidney (61%), melanoma (43%) and colon (38%) cancer cell lines (FIGS. 73-76).

ISGF4

ISGF4 peptides were identified by mass spectrometry as over-expression in 3 breast cancer cell lines, 1 kidney cancer cell line, 3 liver cancer cell lines, 4 lung cancer cell lines, 2 prostate cancer cell lines, 3 melanoma cell lines, and 1 gastric cancer cell line. The magnitude of ISGF4 overexpression, as indicated by mass spec, was as follows: 26.9-100 fold over-expression in breast cell lines, 3.6-fold in a kidney cell line, 4-7.4 fold in liver cell lines, 4.9-377.6 fold in lung cell lines, 7.5-73.4 fold in prostate cell lines, 5.1-13.9 fold in melanoma cell lines, and 11.2-fold in gastric cell line.

ISGF4 is over-expressed in multiple tumor types, as indicated by IHC, as follows: 100% kidney (over-expressed in 100% of kidney tumors evaluated), 80% ovary, 60% bladder, 50% lung (NSC), 50% lung (Squamous), 50% liver, 50% stomach, 33% metastatic pancreatic, 30% colon, 20% prostate, and 10% breast (FIG. 78). As indicated by IHC, ISGF4 was expressed in 10 out of 10 kidney tumor specimens, 6 out of 10 lung tumor specimens, and 9 out of 10 ovarian tumor specimens that were evaluated.

Over-expression of ISGF4 mRNA was observed in breast tumor tissues (FIG. 79).

Knockdown of ISGF4 mRNA inhibited proliferation in multiple types of cancer cells, particularly in lung, kidney, gastric, and prostate cancer cells, as well as other types of cancer (FIGS. 80-82).

Both mass spec and mRNA analysis of ISGF4 in lung cancer cell lines indicates an increase in ISGF4 expression in lung cancer cell lines that are increasingly resistant to the drug cisplatin (results of mRNA analysis are shown in FIG. 84). Thus, increased ISGF4 expression correlates with increased resistance to cisplatin in lung cancer cells.

DB83

DB83 peptides were identified by mass-spec as over-expressed in 7 lung tumor tissues, 1 breast tumor tissue and 1 colon cancer cell line. DB83 peptides were over-expressed 4.6-100 fold in lung tissues, 2.6 fold in breast tumor tissue, 3.6 fold in colon cancer cell line.

DB83 is over-expressed, as indicated by IHC, in multiple tumor types as follows: 100% renal (over-expressed in 100% of kidney tumors evaluated), 80% lung (adenocarcinoma), 80% melanoma, 66% glioblastoma, 50% lung (squamous), 33% metastatic pancreas, 29% pancreas, 20% colon (FIG. 85).

Mass-spec cross tissue analysis of DB83 reveals elevated levels of DB83 in lung tumors.

DB83 is expressed on the cell surface of colon cancer cells (HCT116 and HT29 cells), as indicated by FACS (FIG. 86).

Over-expression of DB83 mRNA was observed in kidney, breast, colon and lung tumors.

Knockdown of DB83 mRNA inhibits proliferation and induces apoptosis in multiple types of cancer cells (FIGS. 87-88), such as in ACHN kidney cancer cells (FIG. 89) and SK-N-SH neuroblastoma cancer cells (FIG. 92). Knockdown of DB83 mRNA induces apoptosis in HT29 colon cancer cells (FIG. 90) and inhibits proliferation in Calu-1 lung cancer cells (FIG. 91).

RNAi knockdown of DB83 inhibits proliferation in the following cancer cell lines: in NCI-N87 gastric cells by 39%, in ASPC-1 pancreatic cells by 30%, in HCT116 colon cells by 36%, and in Calu-1 lung cells by 20%.

RNAi knockdown of DB83 induces apoptosis in the following cancer cell lines: in HT29 and HCT116 colon cells by 3.2 and 2.4 fold, in Calu-1 lung cells by 1.9 fold, and in ACHN kidney cells by 3.2 fold.

All publications and patents mentioned in the above specification are herein incorporated by reference. Various modifications and variations of the described methods and compositions of the invention will be apparent to those skilled in the art without departing from the scope and spirit of the invention. Although the invention has been described in connection with specific exemplary embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. A method of inhibiting proliferation of pancreatic cancer cells, the method comprising contacting the pancreatic cancer cells with an isolated antibody that selectively binds to a SLC5A6 protein to thereby inhibit proliferation of the pancreatic cancer cells, wherein the amino acid sequence of the SLC5A6 protein comprises a sequence selected from the group consisting of SEQ ID NOS:7-9.

2. The method of claim 1, wherein the antibody is coupled to at least one agent selected from the group consisting of drugs, toxins, differentiation inducers, and radionuclides.

3. The method of claim 1, wherein the contacting step comprises administering a therapeutically effective amount of the isolated antibody to an individual harboring the pancreatic cancer cells.

4. The method of claim 2, wherein the contacting step comprises administering a therapeutically effective amount of the isolated antibody to an individual harboring the pancreatic cancer cells.

* * * * *